US006727269B1

(12) United States Patent
Moinet et al.

(10) Patent No.: US 6,727,269 B1
(45) Date of Patent: Apr. 27, 2004

(54) 2-ARYLIMINO-2,3-DIHYDROTHIAZOLES, AND THEIR USE THEREOF AS SOMATOSTATIN RECEPTOR LIGANDS

(75) Inventors: Christophe Moinet, Montreal (CA); Carole Sackur, Paris (FR); Christophe Thurieau, Paris (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 1 day.

(21) Appl. No.: 10/031,429

(22) PCT Filed: Jul. 21, 2000

(86) PCT No.: PCT/FR00/02095

§ 371 (c)(1), (2), (4) Date: Jan. 15, 2002

(87) PCT Pub. No.: WO01/07424

PCT Pub. Date: Feb. 1, 2001

(30) Foreign Application Priority Data

Jul. 22, 1999 (FR) ........................................ 99 09496

(51) Int. Cl.$^7$ ..................... A61K 31/426; C07D 277/08
(52) U.S. Cl. ..................... 514/370; 548/195; 546/270.7
(58) Field of Search ..................... 546/270.7; 548/195; 514/370

(56) References Cited

U.S. PATENT DOCUMENTS 4,421,757 A * 12/1983 Lang et al. ................. 514/331

* cited by examiner

*Primary Examiner*—Joseph K. McKane
*Assistant Examiner*—Golam M M Shameem
(74) *Attorney, Agent, or Firm*—Muserlian, Lucas and Mercanti

(57) ABSTRACT

The invention concerns novel 2-arylimino-2,3-dihydrothiazole derivatives of general formula (I), their preparation methods and their use as medicines, in particular for treating pathological conditions or diseases wherein one (or several) somatostatin receptors is/are involved. Said pathological conditions include in particular acromegaly, pituitary adenoma or endocrine gastroenteropanceatic tumors including the carcinoid syndrome, and gastrointestinal bleeding. In general formula (I), R1 represents in particular an alkyl, aralkyl, cyclohexyl radical optionally substituted by an amino radical or R1 represents a —C(R11)(R12)—CO—R10 radical wherein R11 represents H, R12 represents in particular H, carbocyclic or heterocyclic alkyl, cycloalkyl or aralkyl and R10 represents in particular an aminoalkylamino radical; R2 represents a carcyclic or heterocyclic aryl radical optionally substituted; R3 represents in particular COR5 or a carbocyclic or heterocyclic alkyl, adamantyl, aryl radical optionally substituted, carbocyclic or heterocyclic aralkyl optionally substituted on the aryl group; and R5 represents a radical fixed by a nitrogen atom to the group CO.

(I)

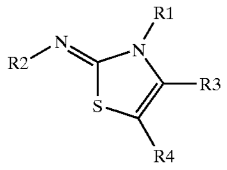

7 Claims, No Drawings

2-ARYLIMINO-2,3-DIHYDROTHIAZOLES, AND THEIR USE THEREOF AS SOMATOSTATIN RECEPTOR LIGANDS

This application is a 371 of PCT/FR00/02095 filed Jul. 21, 2000.

A subject of the present Application is new derivatives of 2-arylimino-2,3-dihydrothiazoles and their preparation processes. These products have a good affinity with certain sub-types of somatostatin receptors and therefore have useful pharmacological properties. The invention also relates to these same products as medicaments, the pharmaceutical compositions containing them and their use for the preparation of a medicament intended to treat pathological states or diseases in which one (or more) somatostatin receptors are involved.

Somatostatin (SST) is a cyclic tetradecapeptide which was isolated for the first time from the hypothalamus as a substance which inhibits the growth hormone (Brazeau P. et al., *Science* 1973, 179, 77–79). It also operates as a neurotransmitter in the brain (Reisine T. et al., *Neuroscience* 1995, 67, 777–790; Reisine T. et al., *Endocrinology* 1995, 16, 427–442). Molecular cloning has allowed it to be shown that the bioactivity of somatostatin depends directly on a family of five receptors linked to the membrane.

The heterogeneity of the biological functions of somatostatin has lead to studies which try to identify the structure-activity relationships of peptide analogues on somatostatin receptors, which has led to the discovery of 5 sub-types of receptors (Yamada et al., *Proc. Natl. Acad. Sci. U.S.A,* 89, 251–255, 1992; Raynor, K. et al, *Mol. Pharmacol.,* 44, 385–392, 1993). The functional roles of these receptors are currently being actively studied. The affinities with different sub-types of somatostatin receptors have been associated with the treatment of the following disorders/diseases. Activation of sub-types 2 and 5 has been associated with suppression of the growth hormone (GH) and more particularly with that of adenomas secreting GH (acromegalia) and those secreting hormone TSH. Activation of sub-type 2 but not sub-type 5 has been associated with the treatment of adenomas secreting prolactin. Other indications associated with the activation of sub-types of somatostatin receptors are the recurrence of stenosis, inhibition of the secretion of insulin and/or of glucagon and in particular diabetes mellitus, hyperlipidemia, insensiblity to insulin, Syndrome X, angiopathy, proliferative retinopathy, dawn phenomenon and nephropathy; inhibition of the secretion of gastric acid and in particular peptic ulcers, enterocutaneous and pancreaticocutaneous fistulae, irritable colon syndrome, dumping syndrome, aqueous diarrhea syndrome, diarrhea associated with AIDS, diarrhea induced by chemotherapy, acute or chronic pancreatitis and secretory gastrointestinal tumors; the treatment of cancer such as hepatomas; the inhibition of angiogenesis, the treatment of inflammatory disorders such as arthritis; chronic rejection of allografts; angioplasty; the prevention of bleeding of grafted vessels and gastrointestinal bleeding. The agonists of somatostatin can also be used to reduce the weight of a patient.

Among the pathological disorders associated with somatostatin (Moreau J. P. et al., Life Sciences 1987, 40, 419; Harris A. G. et al., *The European Journal of Medicine,* 1993, 2, 97–105), there can be mentioned for example: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, hyperthyroidism, gigantism, endocrinic gastroenteropancreatic tumors including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, gastroesophageal reflux, gastroduodenal reflux, pancreatitis, enterocutaneous and pancreatic fistulae but also diarrheas, refractory diarrheas of acquired immunodeficiency syndrome, chronic secretary diarrhea, diarrhea associated with irritable bowel syndrome, disorders linked with gastrin releasing peptide, secondary pathologies with intestinal grafts, portal hypertension as well as hemorrhages of the varices in patients with cirrhosis, gastro-intestinal hemorrhage, hemorrhage of the gastroduodenal ulcer, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and other therapeutic fields such as, for example, cephaleas including cephalea associated with hypophyseal tumors, pain, panic attacks, chemotherapy, cicatrization of wounds, renal insufficiency resulting from delayed development, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of *H pylori,* psoriasis, as well as Alzheimer's disease. Osteoporisis can also be mentioned. The Applicant found that the compounds of general formula (I) described hereafter have an affinity and a selectivity for the somatostatin receptors. As somatostatin and its peptide analogues often have a poor bioavailability by oral route and a low selectivity (Robinson, C., Drugs of the Future, 1994, 19, 992; Reubi, J. C. et al., TIPS, 1995, 16, 110), said compounds, non-peptide agonists or antagonists of somatostatin, can be advantageously used to treat pathological states or illnesses as presented above and in which one (or more) somatostatin receptors are involved. Preferably, said compounds can be used for the treatment of acromegalia, hypophyseal adenomas or endocrine gastroenteropancreatic tumors including carcinoid syndrome.

The compounds of the present invention correspond to general formula (I)

(I)

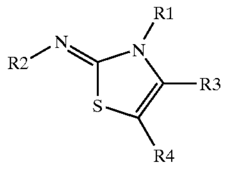

in racemic, enantiomeric form or all combinations of these forms, in which:

R1 represents an amino($C_2$–$C_7$)alkyl, aminoalkylarylalkyl, aminoalkylcycloalkylalkyl, ($C_1$–$C_{15}$)alkyl, ($C_3$–$C_7$)cycloalkyl, ($C_1$–$C_6$)alkyl ($C_3$–$C_6$)cycloalkyl, ($C_3$–$C_6$)cycloalkylalkyl, cyclohexenylalkyl, alkenyl, alkynyl, carbocyclic aryl radical containing at least two rings of which at least one is not aromatic, carbocyclic or heterocyclic aralkyl radical optionally substituted on the aryl group, bis-arylalkyl, alkoxyalkyl, furannylalkyl, tetrahydrofurannylalkyl, dialkylaminoalkyl, N-acetamidoalkyl, cyanoalkyl, alkylthioalkyl, arylhydroxyalkyl, aralkoxyalkyl, morpholinoalkyl, pyrrolidinoalkyl, piperidinoalkyl, N-alkylpyrrolidinoalkyl, N-alkylpiperazinylalkyl or oxopyrrolidinoalkyl radical, or R1 represents one of the radicals represented below:

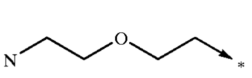

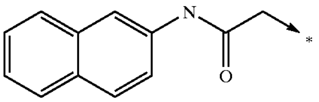

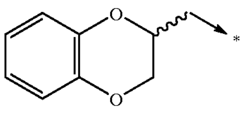

or also R1 represents a —C(R11)(R12)—CO—R10 radical;

R2 represents an optionally substituted carbocyclic or heterocyclic aryl radical, R2 represents one of the radicals represented below:

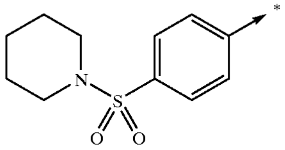

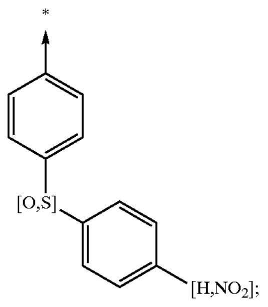

R3 represents an alkyl, adamantyl, optionally substituted carbocyclic or heterocyclic aryl radical, carbocyclic or heterocyclic aralkyl optionally substituted on the aryl group, or R3 represents one of the radicals represented below:

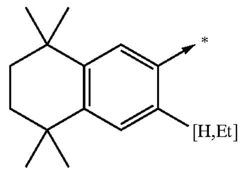

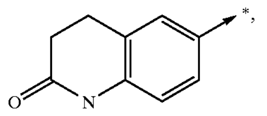

or also R3 represents a —CO—R5 radical;

R4 represents H, alkyl, carbocyclic or heterocyclic aralkyl optionally situated on the aryl radical;

or then the

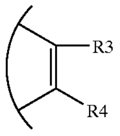

radical represents a radical of general formula

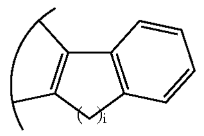

in which i represents an integer from 1 to 3;

R5 represents the N(R6)(R7) radical;

R6 represents a ($C_1$–$C_{16}$)alkyl, cycloalkylalkyl, hydroxyalkyl, aryloxyalkyl radical, carbocyclic or heterocyclic aralkyl radical optionally substituted on the aryl group, aralkoxyalkykl, arylhydroxyalkyl, alkoxyalkyl, alkylthioalkyl, alkenyl, alkynyl, cyclohexenyl, cyclohexenylalkyl, alkylthiohydroxyalkyl, cyanoalkyl, N-acetamidoalkyl radical, bis-arylalkyl radical optionally substituted on the aryl groups, di-arylalkyl radical optionally substituted on the aryl groups, morpholinoalkyl, pyrrolidinoalkyl, piperidinoalkyl, N-alkylpyrrolidinoalkyl, oxopyrrolidinoalkyl, tetrahydrofurannylalkyl, N-benzylpyrrolidinoalkyl, N-alkylpiperazinylalkyl, N-benzylpiperazinylalkyl, N-benzylpiperidinylalkyl or N-alkoxycarbonylpiperidinyl radical, or R6 represents a ($C_3$–$C_8$)cycloalkyl radical optionally substituted by a radical chosen, from the group comprising the hydroxy radical and an alkyl radical, or R6 represents one of the radicals represented below:

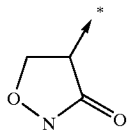

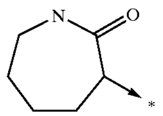

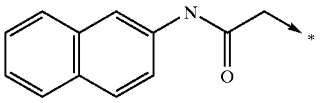

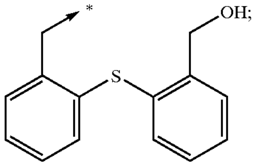

R7 represents H or an alkyl, hydroxyalkyl, mono- or di-aminoalkyl or aralkyl radical;

or the —N(R6)(R7) radical represents the radical of the following general formula:

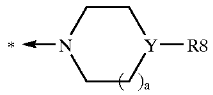

in which:

R8 represents H, alkyl, hydroxyalkyl, optionally substituted carbocyclic or heterocyclic aryl, aralkyl optionally substituted on the aryl group, alkenyl, alkoxyalkyl, cycloalkyl, cycloalkylalkyl, bis-arylalkyl, piperidinyl, pyrrolidinyl, hydroxy, arylalkenyl, or R8 represents —X—$(CH_2)_b$—R9;

R9 represents H or an alkyl, alkoxy, aryloxy, optionally substituted carbocyclic or heterocyclic aryl, morpholinyl, pyrrolidinyl, alkylamino or N,N'-(alkyl)(aryl)amino radical;

X represents CO, CO—NH or $SO_2$;

Y represents CH or N;

a represents 1 or 2;

b represents an integer from 0 to 6;

or the N(R6)(R7) radical represents a radical of general formula

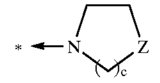

in which:

Z represents CH, O or S;

c represents an integer from 0 to 4;

or the N(R6)(R7) radical represents one of the radicals represented below:

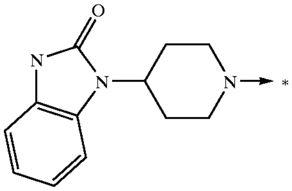
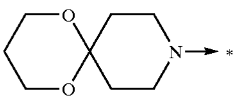
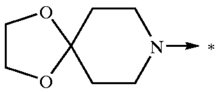
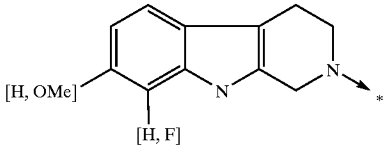
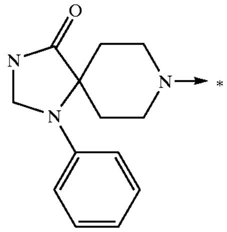
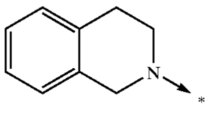
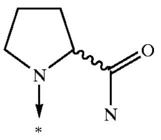
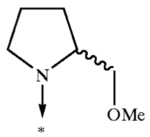
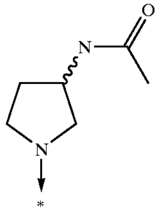
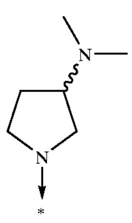
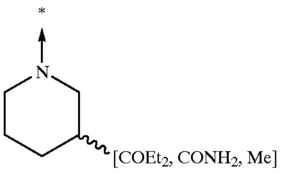

-continued

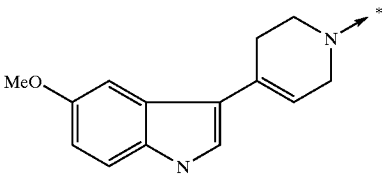
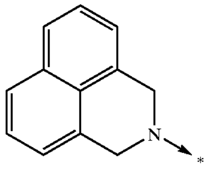
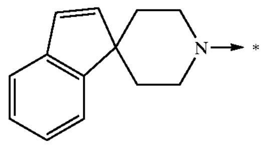
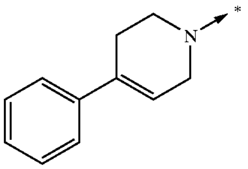
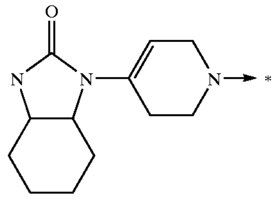

R10 represents an amino($C_2$–$C_7$)alkylamino, ((aminoalkyl)aryl)alkylamino, ((aminoalkyl)cycloalkyl)alkylamino, piperazinyl, homopiperazinyl radical, or R10 represents the radical represented below:

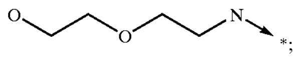

R11 represents H;

R12 represents H or an alkyl, ($C_3$–$C_7$)cycloalkyl, optionally substituted carbocyclic or heterocyclic aralkyl, propargyl, allyl, hydroxyalkyl, alkylthioalkyl, arylalkylalkoxyalkyl, arylalkylthioalkoxyalkyl radical;

or the compounds of the invention are salts of the compounds of general formula (I).

When the compounds of general formula (I) contain the R1, R2, R3, R4, R6, R8 or R9 radicals including an substituted aryl radical or an aralkyl substituted on the aryl group, said aryl or aralkyl radicals are preferably such that:

For R1, when the aryl group is substituted, it can be from 1 to 5 times (other than the bond which links it with the remainder of the molecule) by the radicals chosen independently from the group comprising a halogen atom and an alkyl, alkoxy, alkylthio, haloalkyl, haloalkoxy, aryl, aralkoxy or $SO_2NH_2$ radical. Two substituents can, if appropriate, be linked together and form a ring, for example by representing together a methylenedioxy or propylene radical.

For R2, when the aryl group is substituted, it can be from 1 to 5 times (other than the bond which links it with the remainder of the molecule) by the radicals chosen independently from the group comprising a halogen atom and an alkyl, alkoxy, alkylthio, haloalkyl, alkenyl, haloalkoxy, nitro, cyano, azido, $SO_2N$, mono- or di-alkylamino, aminoalkyl, aralkoxy or aryl radical. Two substituents can, if appropriate, be linked together and form a ring, for example by representing together a methylenedioxy, ethylenedioxy or propylene radical.

For R3, when the aryl group or groups (originating from an aryl or aralkyl radical) are substituted, they can be, according to the case, from 1 to 5 times (other than the bond which links them with the remainder of the molecule). The carbocyclic aryl or aralkyl radicals can be substituted from 1 to 5 times on the aryl ring by the radicals chosen independently from the group comprising a halogen atom and an alkyl, hydroxy, alkoxy, haloalkyl, haloalkoxy, nitro, cyano, azido, mono- or di-alkylamino, pyrrolidinyl, morpholinyl, aralkoxy or aryl radical. Two substituents can, if appropriate, be linked together and form a ring, for example by representing together an alkylenedioxy radical containing 1 to 3 carbon atoms. The heterocyclic aryl or aralkyl radicals of R3 can be substituted 1 to 2 times on the ring by the radicals chosen independently from the group comprising a halogen atom and an alkyl radical.

For R4, when the aryl group is substituted, it can be from 1 to 5 times (other than the bond which links it with the remainder of the molecule). The aryl radical can be substituted by the radicals chosen independently from the group comprising a halogen atom and an alkyl or alkoxy radical.

For R6, when the aryl group or groups are substituted, they can be from 1 to 5 times (other than the bond which links them with the remainder of the molecule). The optional substituents on the aryl groups are chosen independently from the group comprising a halogen atom and an alkyl, alkoxy, alkylthio, haloalkyl, haloalkoxy, aryl, aryloxy or $SO_2NH_2$ radical.

For R8, when the aryl group or groups are substituted, they can be from 1 to 5 times (other than the bond which links them with the remainder of the molecule). The optional substituents on the aryl groups are chosen independently from the group comprising a halogen atom and an alkyl, haloalkyl, alkoxy, hydroxy, cyano, nitro or alkylthio radical.

For R9, when the carbocyclic or heterocyclic aryl radical is substituted, it can be from 1 to 5 times (other than the bond which links it with the remainder of the molecule). The optional substituents on the aryl group are chosen independently from the group comprising a halogen atom and an alkyl, haloalkyl, alkoxy, haloalkoxy, alkylthio, carbocyclic aryl, hydroxy, cyano or nitro radical.

For R12, when the carbocyclic or heterocyclic aryl radical is substituted, it can be from 1 to 5 times (other than the bond which links it with the remainder of the molecule). The optional substituents on the aryl group are chosen independently from the group comprising a halogen atom and an alkyl, alkoxy, carbocyclic aryl, aralkoxy, hydroxy, cyano or nitro radical.

By alkyl, unless specified otherwise, is meant a linear or branched alkyl radical containing 1 to 6 carbon atoms. By cycloalkyl, unless specified otherwise, is meant a monocyclic carbon system containing 3 to 7 carbon atoms. By alkenyl, unless specified otherwise, is meant a linear or branched alkyl radical containing 1 to 6 carbon atoms and having at least one unsaturation (double bond). By alkynyl, unless specified otherwise, is meant a linear or branched alkyl radical containing 1 to 6 carbon atoms and having at least one double unsaturation (triple bond). By carbocyclic or heterocyclic aryl, is meant a carbocyclic or heterocyclic system containing at least one aromatic ring, a system referred to as heterocyclic when at least one of the rings which comprise it contains a heteroatom (O, N or S). By haloalkyl, is meant an alkyl radical of which at least one of the hydrogen atoms (and optionally all) is replaced by a halogen atom.

By alkylthio, alkoxy, haloalkyl, haloalkoxy, aminoalkyl, alkenyl, alkynyl and aralkyl radicals, is meant respectively the alkylthio, alkoxy, haloalkyl, haloalkoxy, aminoalkyl, alkenyl, alkynyl and aralkyl radicals the alkyl radical of which has the meaning indicated previously.

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By cycloalkyl, is meant in particular the cyclopropanyl, cyclobutanyl, cyclopentanyl, cyclohexyl and cycloheptanyl radicals. By carbocyclic or heterocyclic aryl, is meant in particular the phenyl, naphthyl, pyridinyl, furannyl, thiophenyl, indanyl, indolyl, imidazolyl, benzofurannyl, benzothiophenyl, phthalimidyl radicals. By carbocyclic or heterocyclic aralkyl, is meant in particular the benzyl, phenylethyl, phenylpropyl, phenylbutyl, indolylalkyl, phthalimidoalkyl, naphthylalkyl, furannylalkyl, thiophenylalkyl, benzothiophenylalkyl, pyridinylalkyl and imidazolylalkyl radicals.

When an arrow emanates from a chemical structure, said arrow indicates the attachment point. For example:

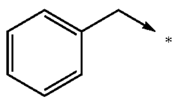

represents the benzyl radical.

Preferably, the compounds of general formula (I) are such that:

R1 represents —C(R11)(R12)—CO—R10 or one of the following radicals:

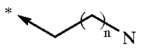

n = 1–6

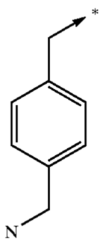

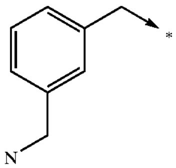

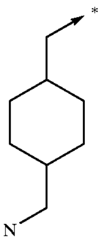

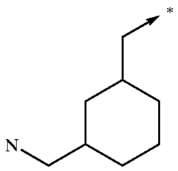

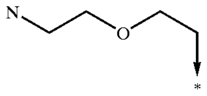

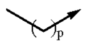

p = 0–15

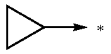

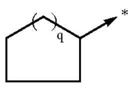

q = 0–4

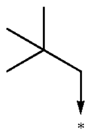

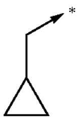

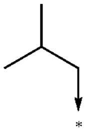

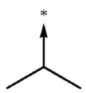

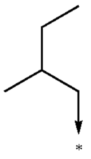

-continued
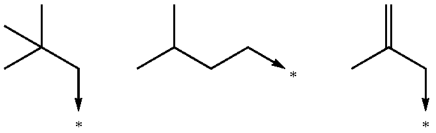
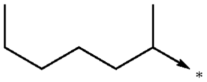
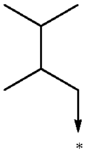
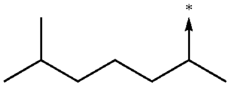
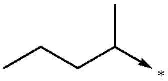
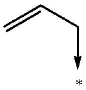
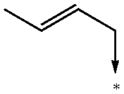
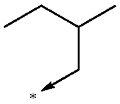
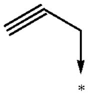
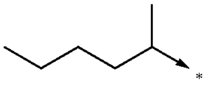
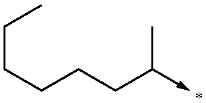
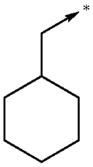
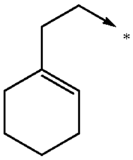
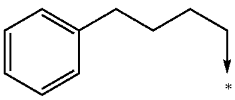
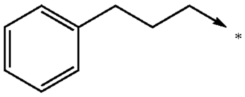
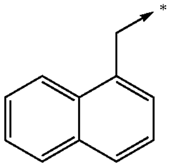
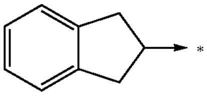
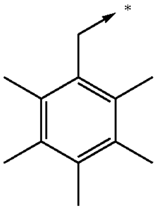
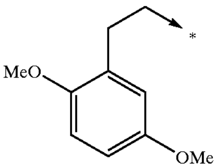
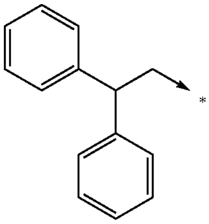
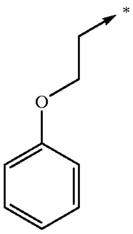
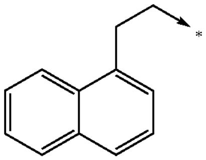
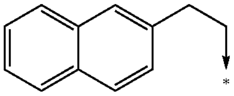
-continued
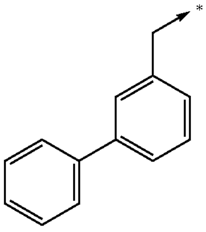
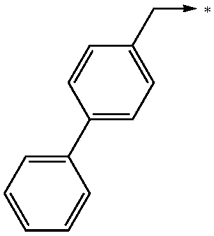
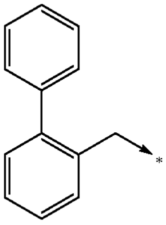
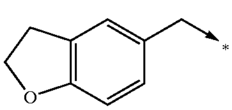
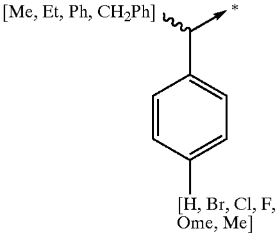
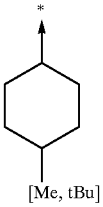
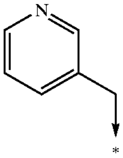
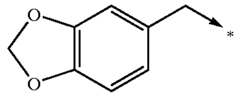
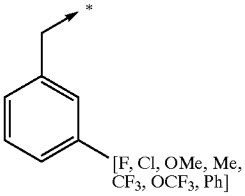
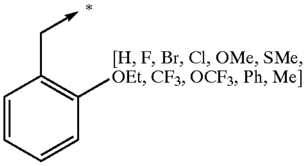
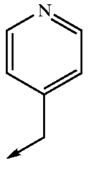
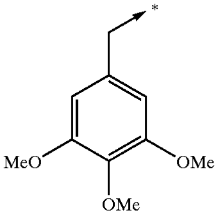
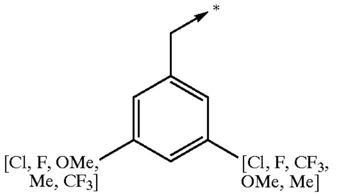
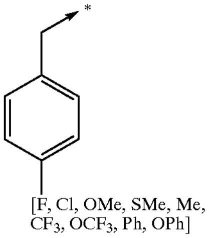
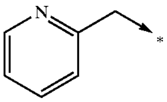
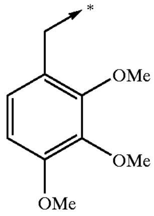

-continued
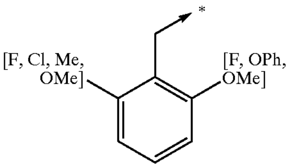
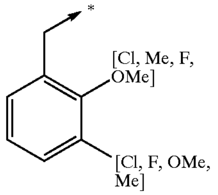
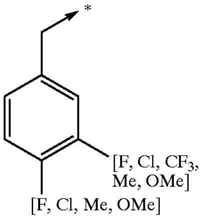
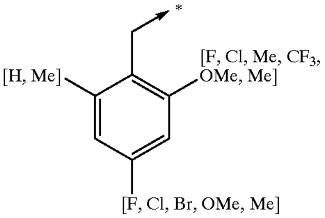
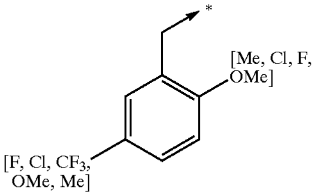
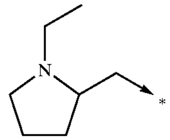
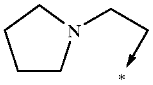
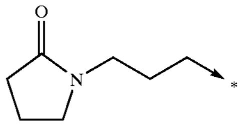
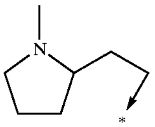
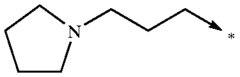
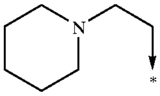
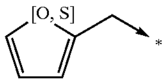
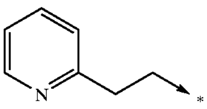
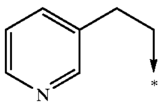
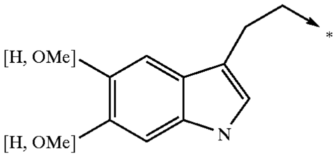
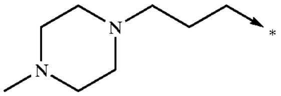
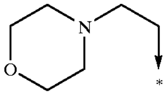
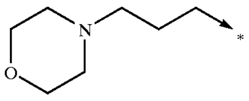
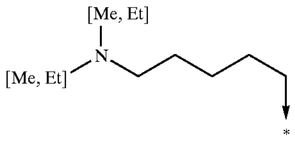
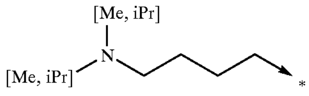
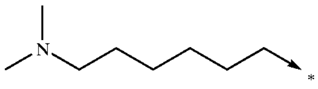
-continued
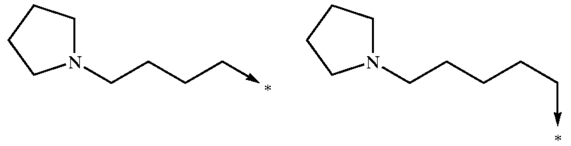
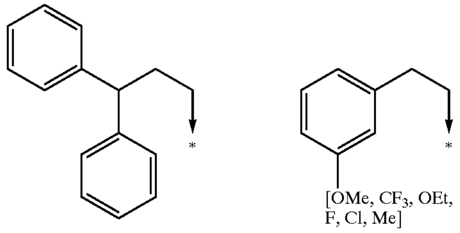
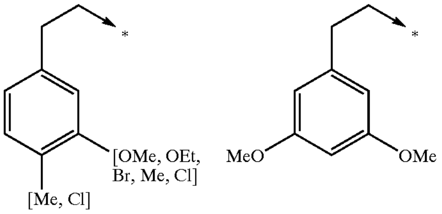
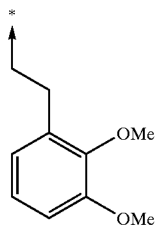
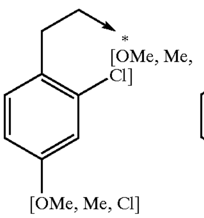
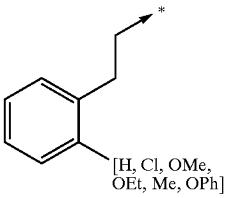
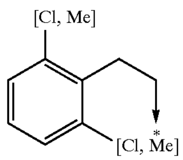
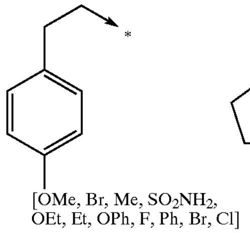
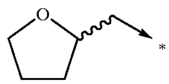
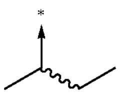
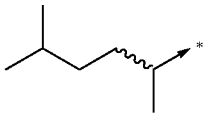
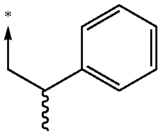
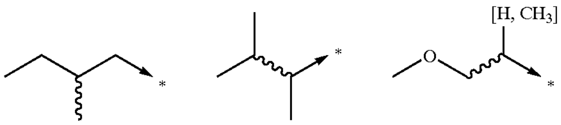
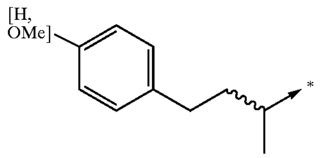
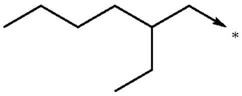
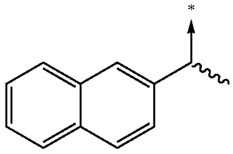
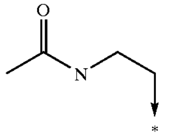
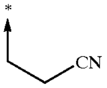

-continued
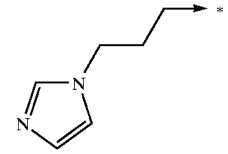
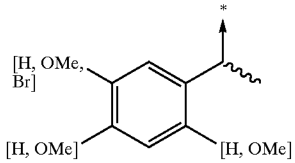
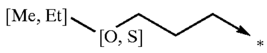
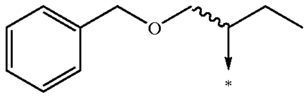
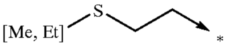
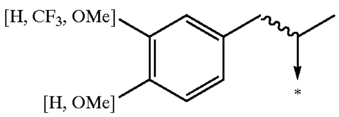
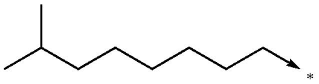
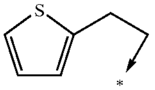
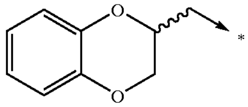
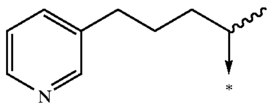
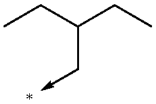
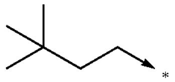
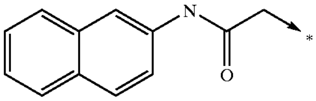
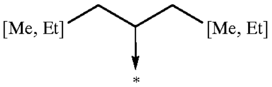
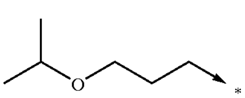
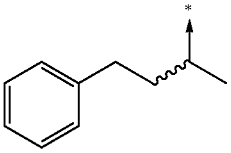
;
R2 represents one of the following radicals:
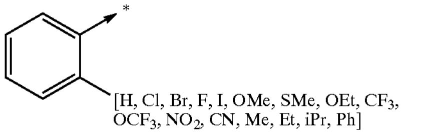
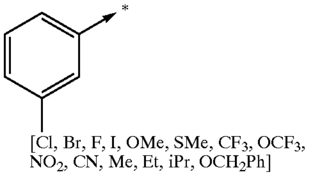
-continued
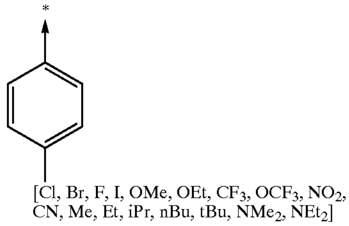
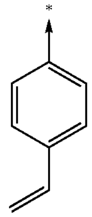
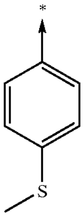
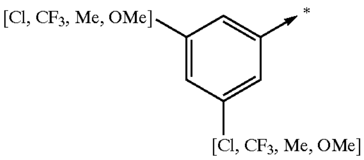
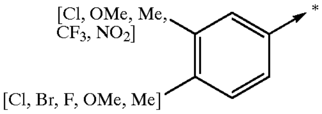
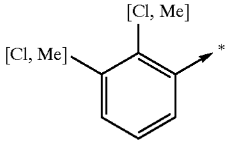
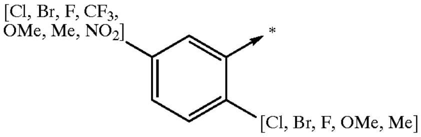
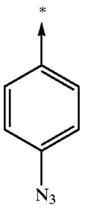
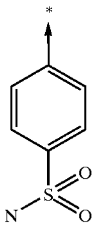
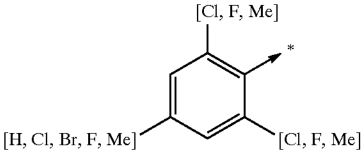
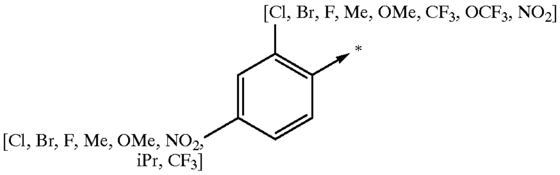
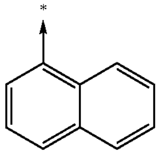

-continued
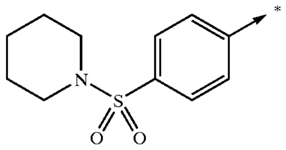
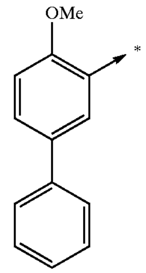
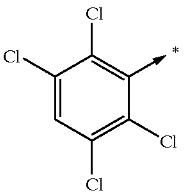
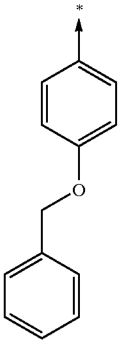
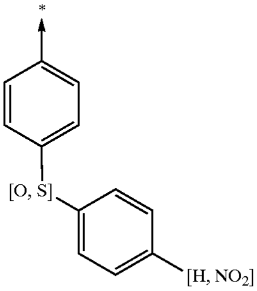
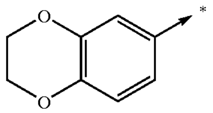
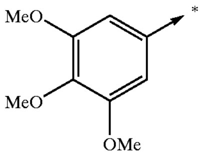
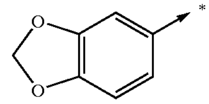
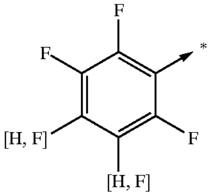
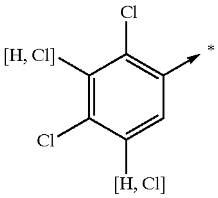
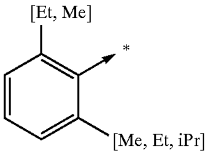
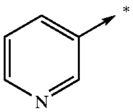
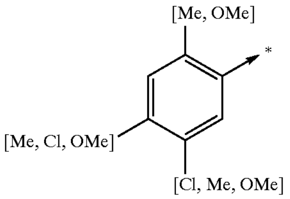
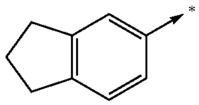
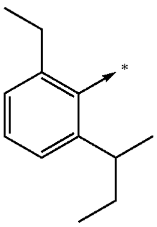
-continued
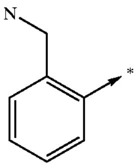
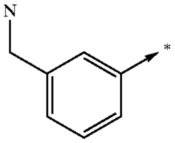
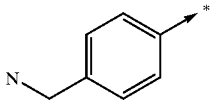
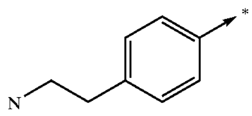
;
R3 represents CO—R5 or one of the following radicals:
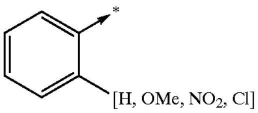
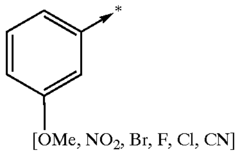
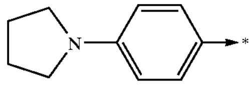
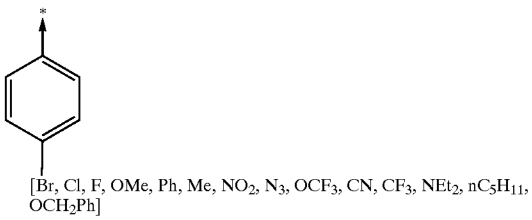
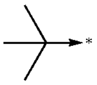
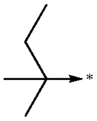
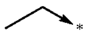
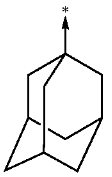
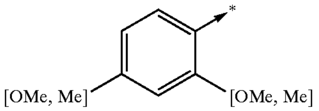
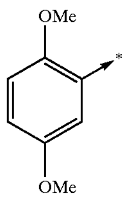
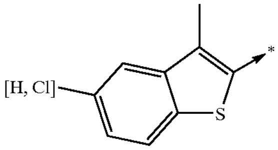
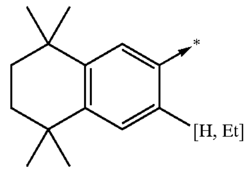
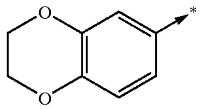
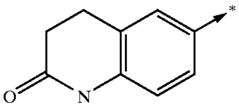

-continued
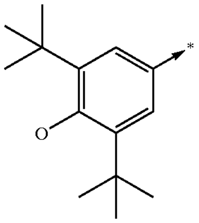
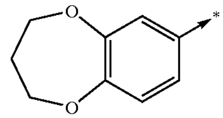
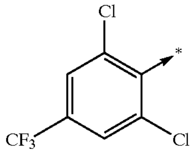
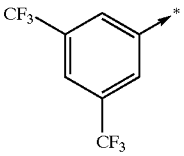
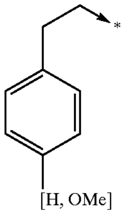
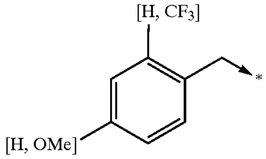
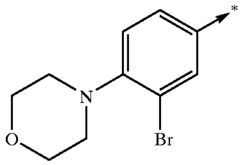
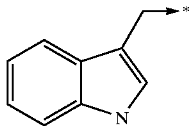
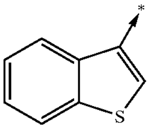
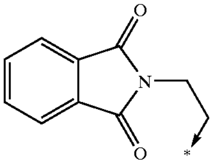
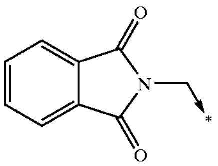
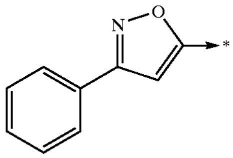
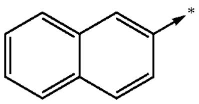
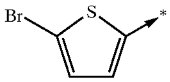
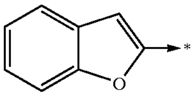
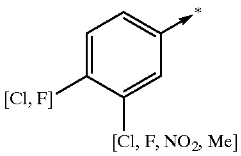
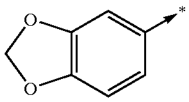
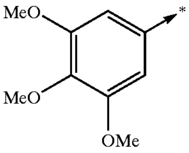
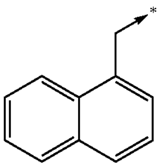
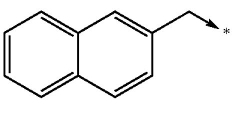
;
R4 represents H, alkyl, carbocyclic or heterocyclic aralkyl optionally substituted on the aryl radical;
or then the
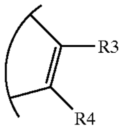
radical represents a radical of general formula
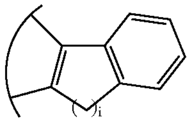
in which i represents an integer from 1 to 3;
R5 represents one of the following radicals:
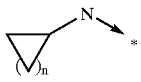
n = 1–6
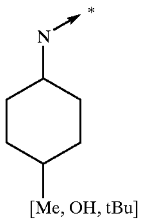
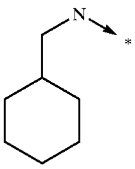
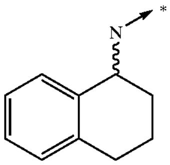
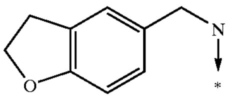
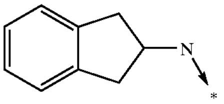
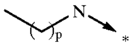
p = 0–15
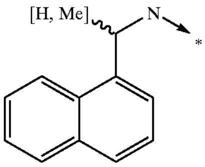
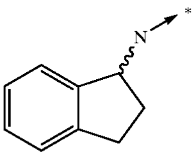
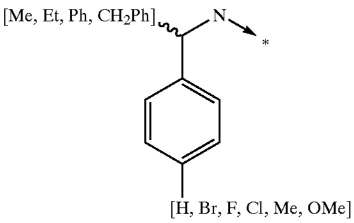
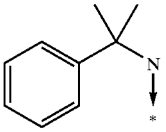
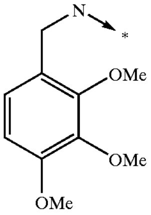
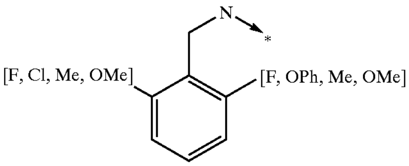

-continued
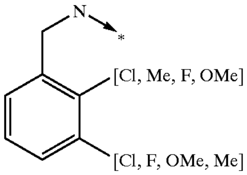
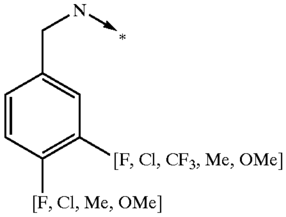
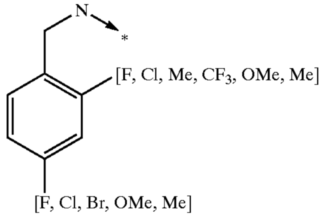
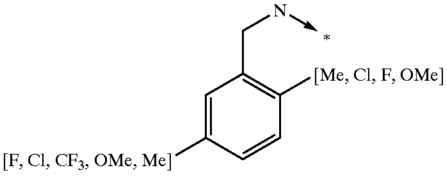
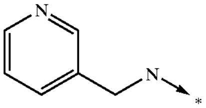
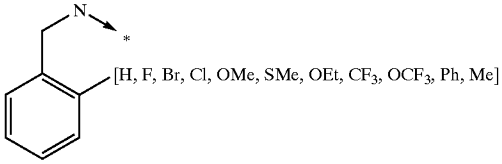
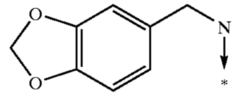
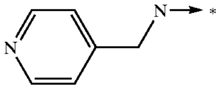
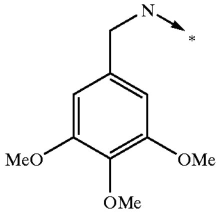
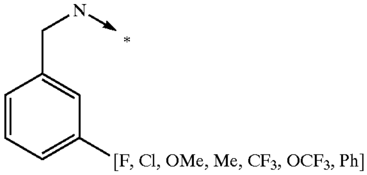
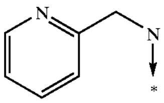
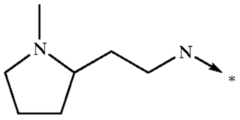
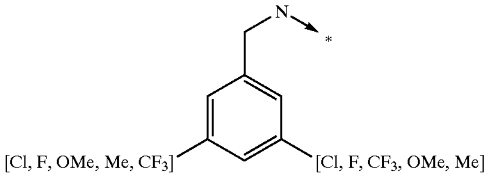
-continued
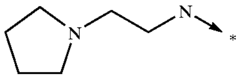
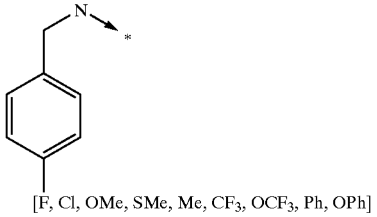
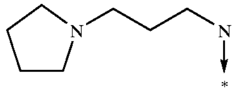
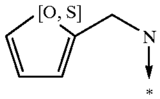
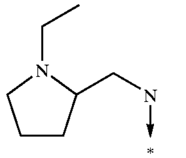
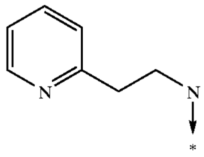
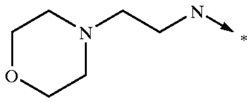
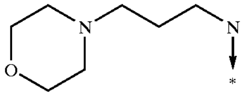
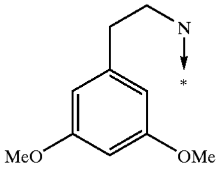
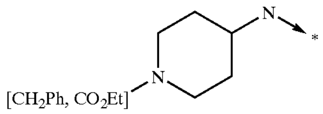
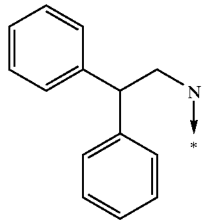
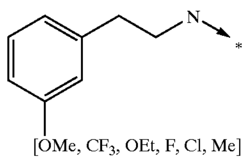
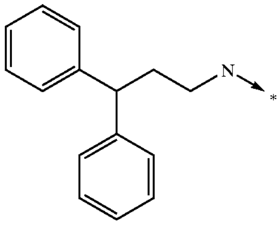
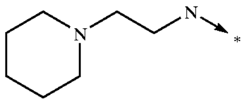
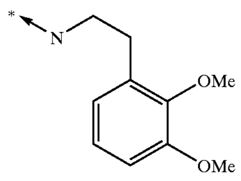
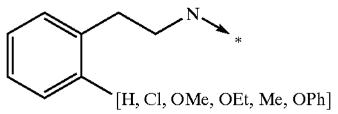
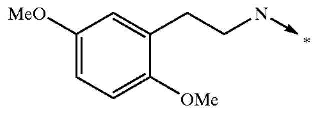

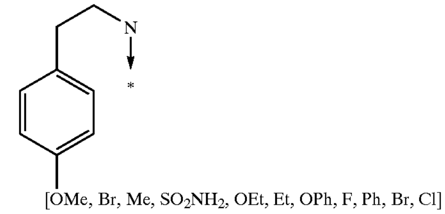
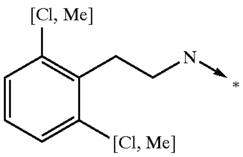
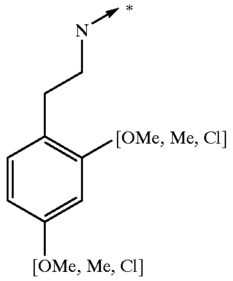
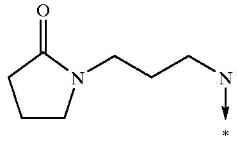
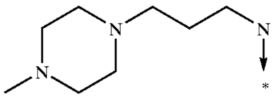
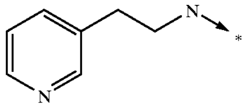
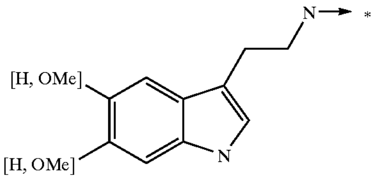
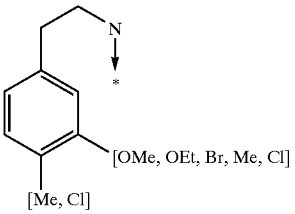
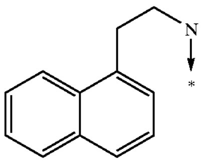
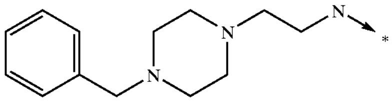
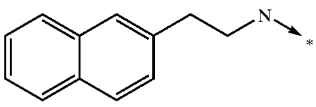
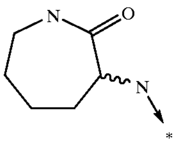
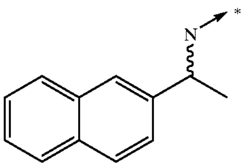
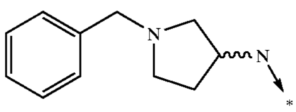
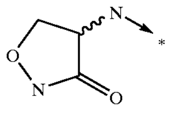
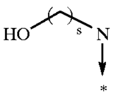
s = 2–6
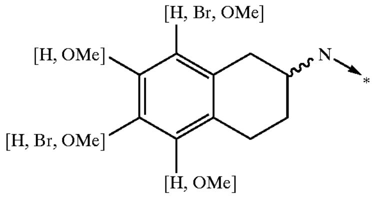
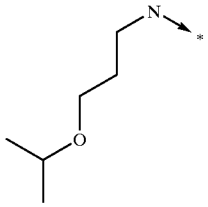
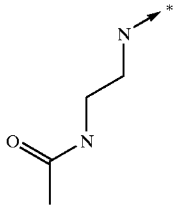
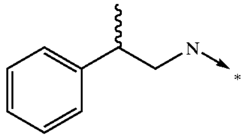
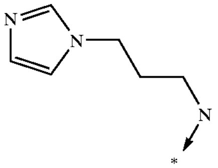
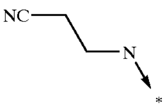
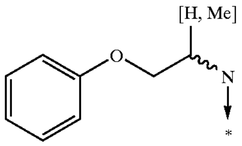
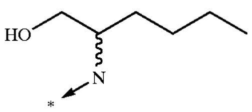
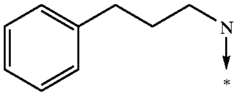
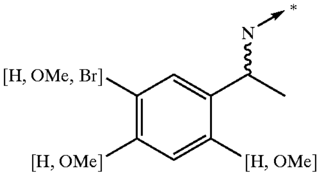
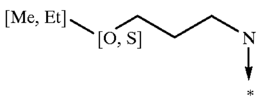
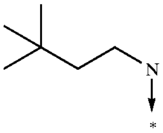
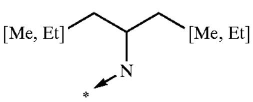
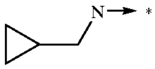
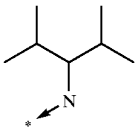
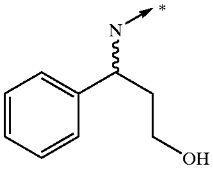
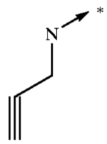
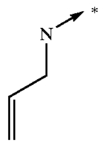
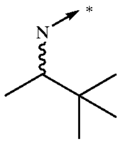
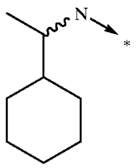
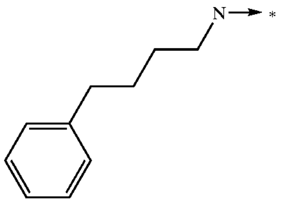

-continued
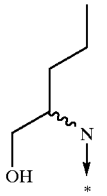
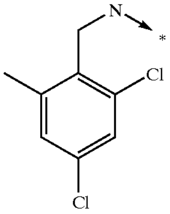
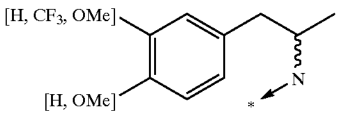
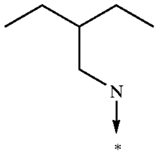
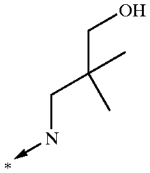
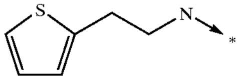
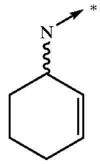
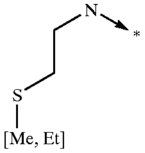
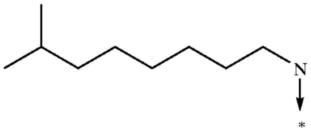
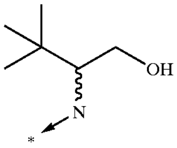
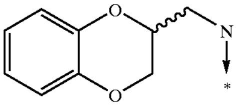
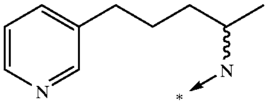
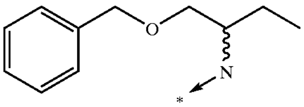
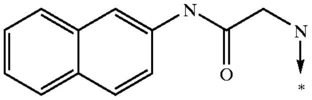
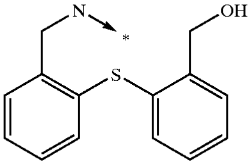
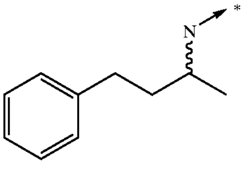
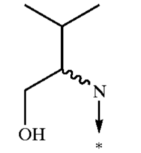
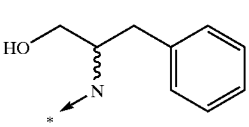
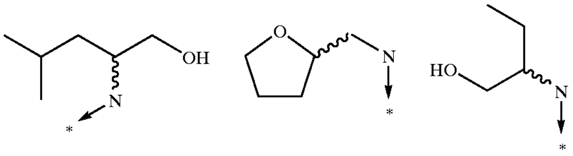
-continued
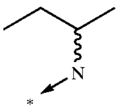
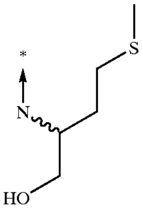
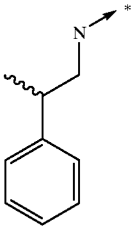
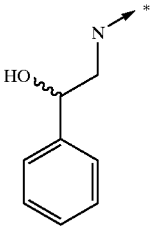
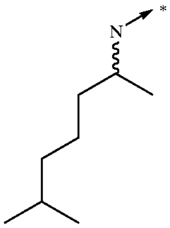
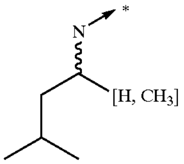
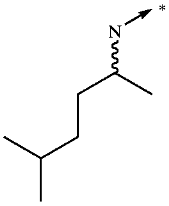
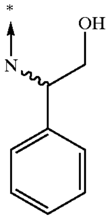
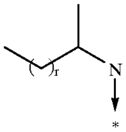
r = 0–6
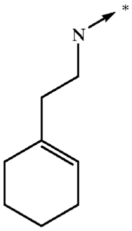
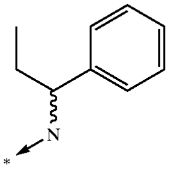
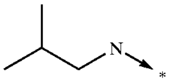
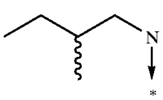
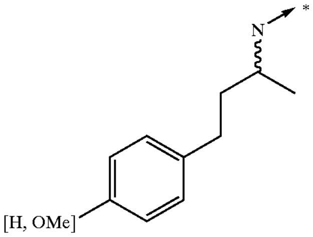
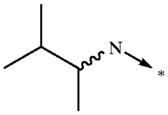
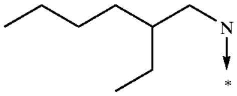
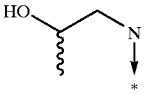
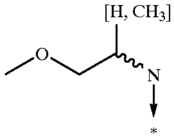
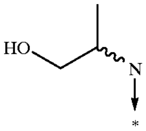
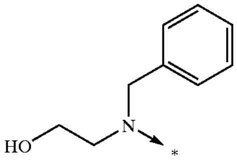
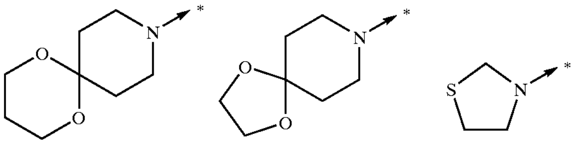

-continued
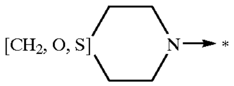
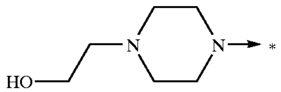
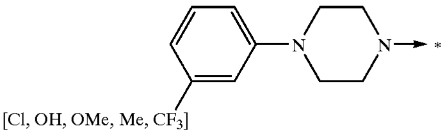
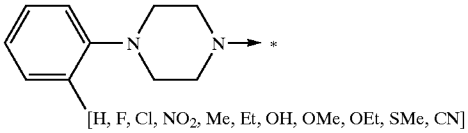
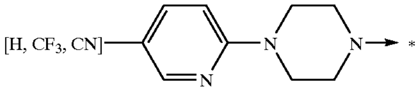
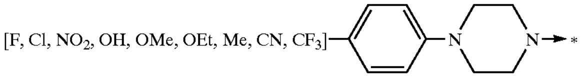
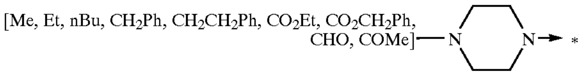
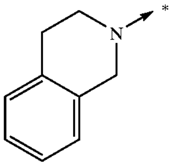
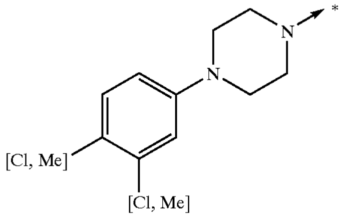
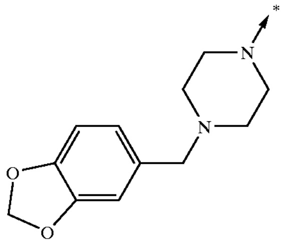
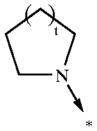
t = 0–4
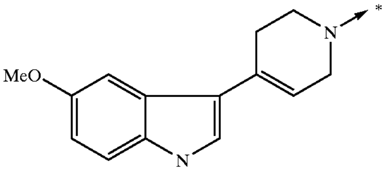
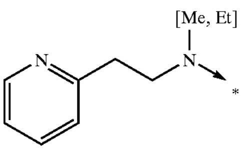
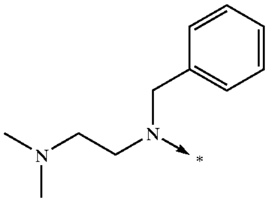
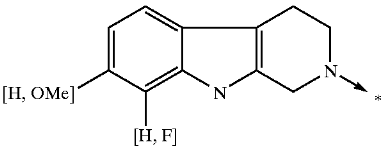
-continued
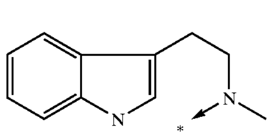
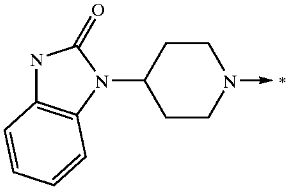
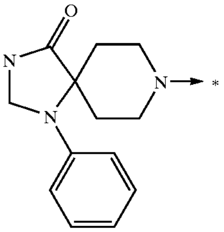
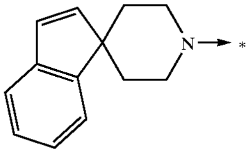
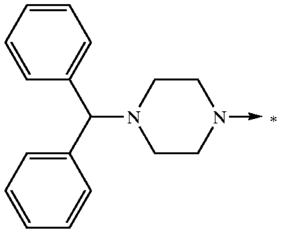
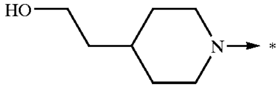
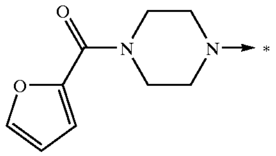
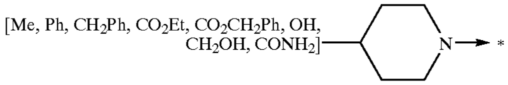
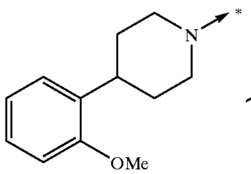
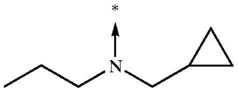
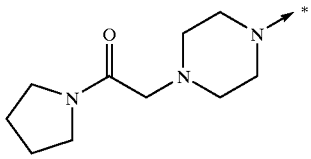
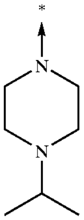
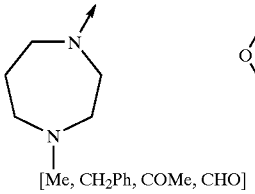
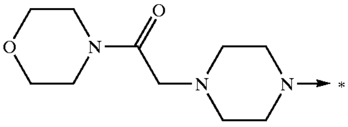
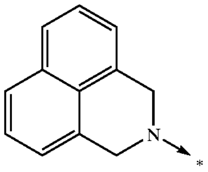

-continued
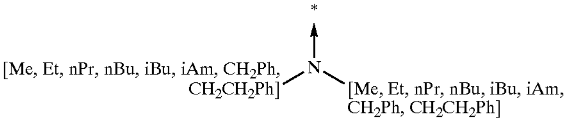
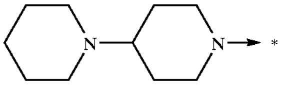
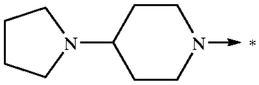
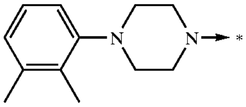
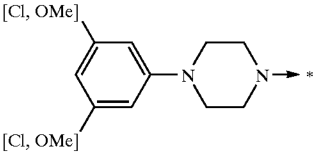
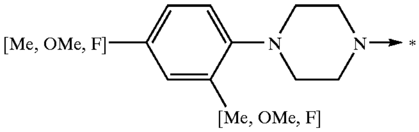
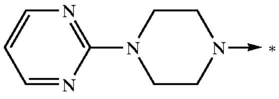
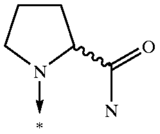
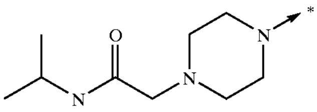
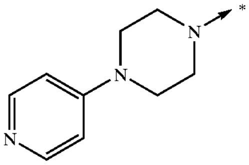
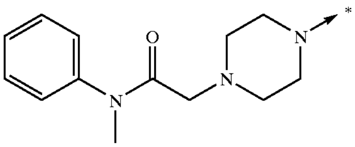
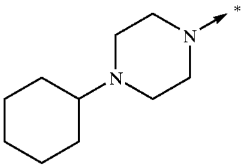
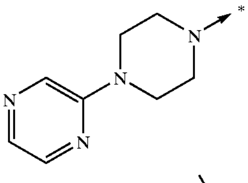
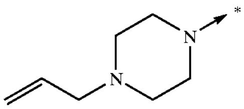
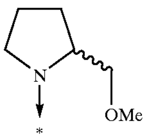
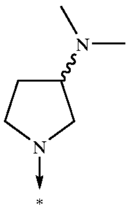
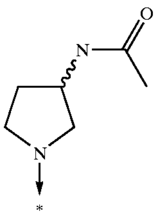
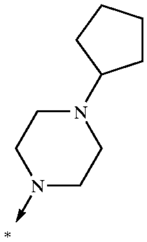
-continued
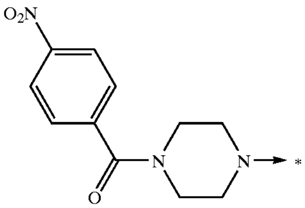
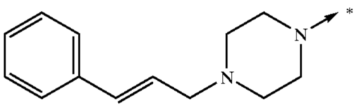
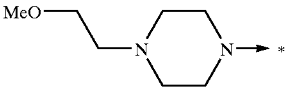
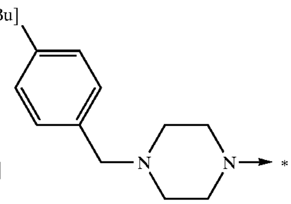
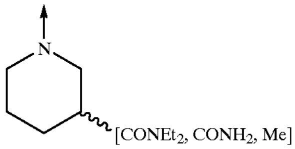
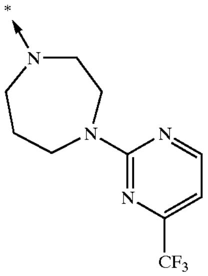
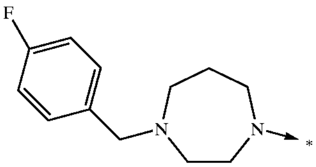
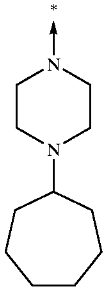
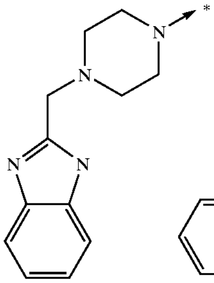
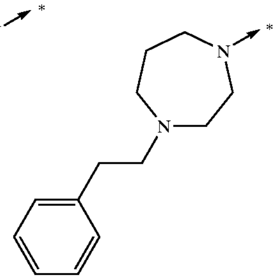
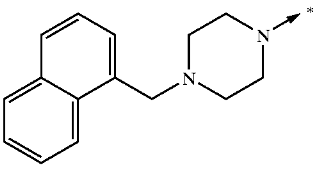
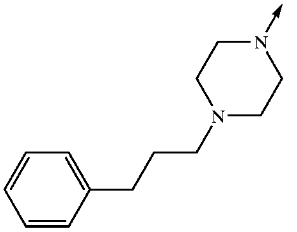
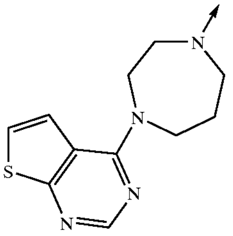

-continued
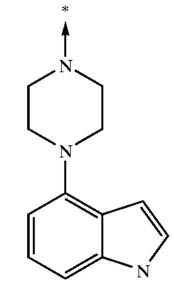
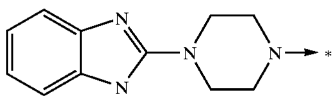
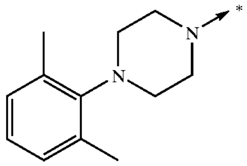
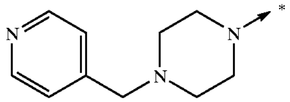
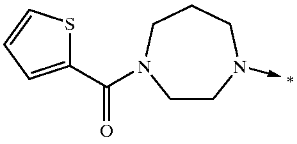
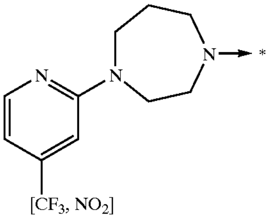
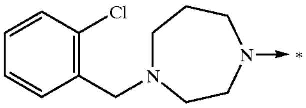
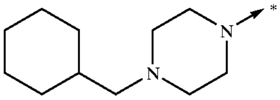
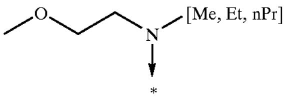
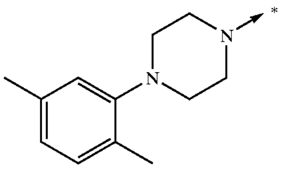
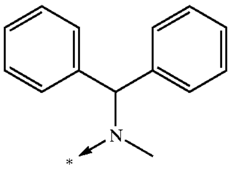
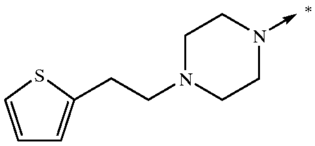
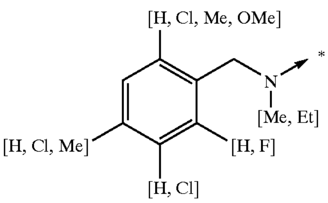
-continued
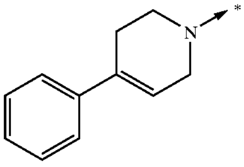
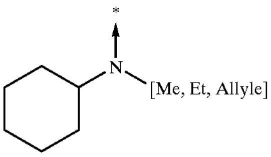
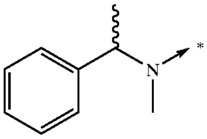
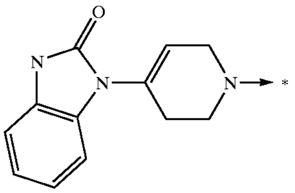
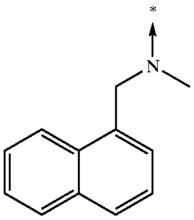
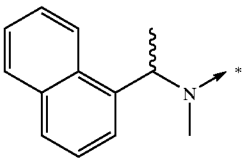
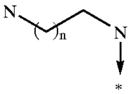
n = 1–6
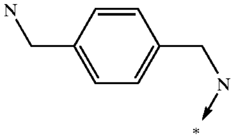
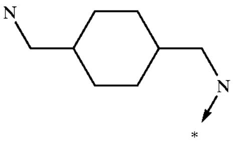
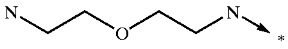
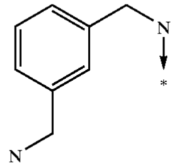
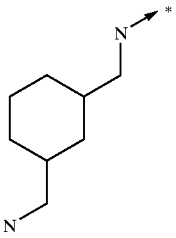
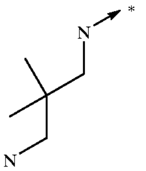
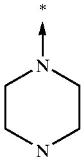
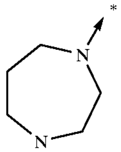
;
R10 represents one of the following radicals:
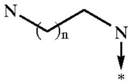
n = 1–6
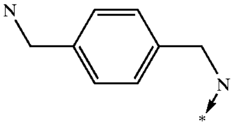
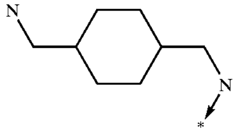
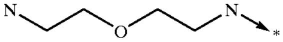

-continued

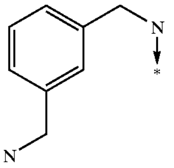
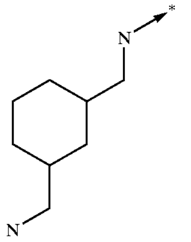
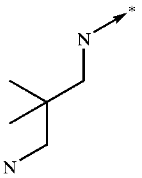
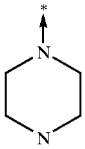
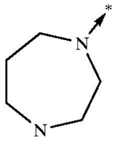
;

R11 represents H;

R12 represents one of the following radicals:

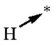
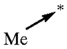
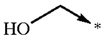
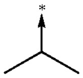
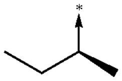
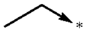
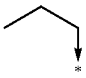
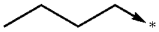
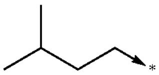
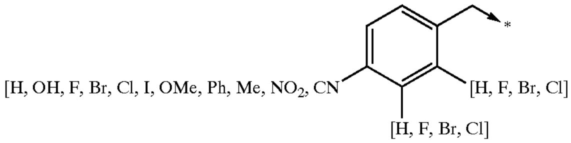
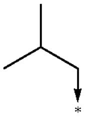
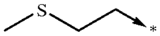
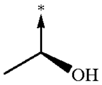
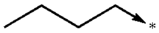
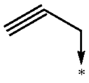
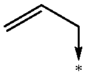
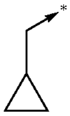
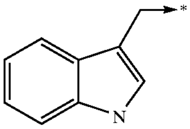
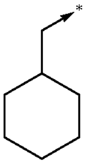
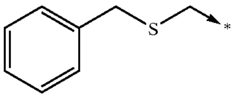
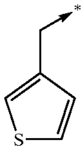
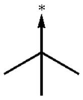

-continued

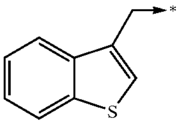
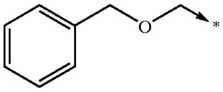
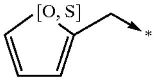
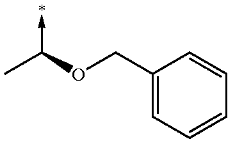
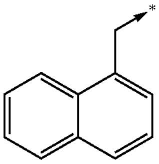
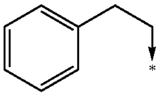
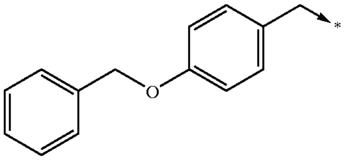
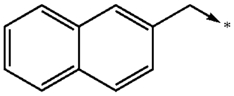
;

it being understood that for R4, when the aryl group is substituted, it can be from 1 to 5 times (other than the bond which links it with the remainder of the molecule) by the radicals chosen independently from the group comprising a halogen atom and an alkyl or alkoxy radical.

The compounds of the invention are preferably such that R4 represents H.

More preferentially, the compounds according to the invention correspond to general formula (II)

(II)

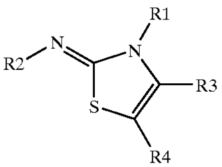

in which:

either R1 represents one of the radicals below

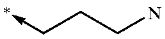
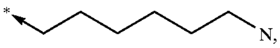

R2 represents one of the radicals below

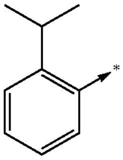
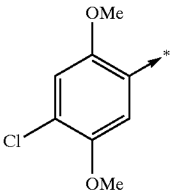
,

R3 represents one of the radicals below

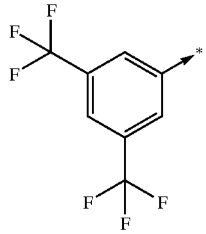

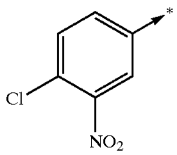
, and R4 represents H;

or also R1 represents one of the radicals below

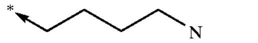

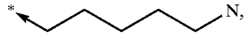

R2 represents one of the radicals below

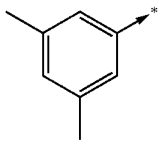

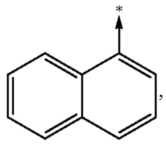
,

R3 represents COR5,

R4 represents H, and R5 represents one of the radicals below

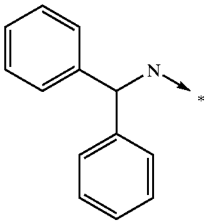

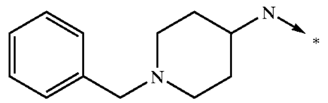

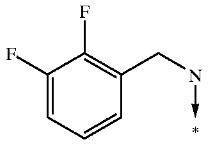

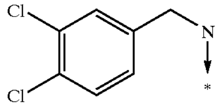

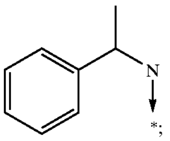

or finally R1 represents the —C(R11)(R12)—CO—R10 radical in which

R10 represents the radical

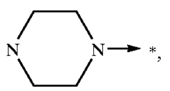

R11 represents H and R12 represents the radical

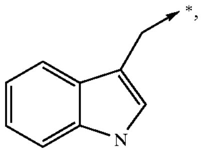

R2 represents the radical

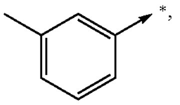

R3 represents the radical

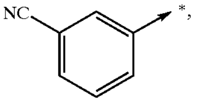

and R4 represents H.

Moreover, the invention relates to preparation processes on a solid support for the compounds of general formula (I) described previously (also applicable to the corresponding compounds of general formula (II)).

According to the invention, the compounds of general formula (I)a (I)a

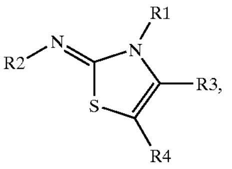

in which:

R1 represents a $—CH_2—Al—NH_2$ radical, in which Al represents a $—(CH_2)_n—$, $—(CH_2)_n—O—(CH_2)_p—$, aralkylene or cycloalkylalkylene radical, n and p represent integers from 1 to 6;

R2 and R4 represent the same radicals as in general formula (I);

and R3 represents the same radicals as in general formula (I), with the exception of the —CO—R5 radicals;

can be prepared for example according to a process characterized in that it comprises the following successive stages:

1) treatment, in an aprotic solvent such as dichloromethane or dimethylformamide, of a p-nitrophenylcarbonate Wang resin with a large excess of $R1—NH_2$ symmetrical diamine;

2) treatment, in an aprotic solvent such as dichloromethane or dimethylformamide, of the resin isolated after stage 1) with an aromatic isothiocyanate of general formula R2—N=C=S in which the R2 radical has the same meaning as in general formula (I)a;

3) treatment, in an aprotic solvent such as dioxane or dimethylformamide, of the resin obtained in Stage 2) with the compound of general formula (III)

(III)

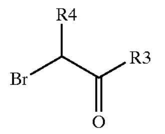

in which the R3 and R4 radicals have the same meaning as in general formula (I)a;

4) cleavage of the resin under acid conditions;

5) treatment under basic conditions of the product obtained after Stage 4).

The preparation of the p-nitrophenylcarbonate Wang resin is described further on in the part entitled "PREPARATION OF THE COMPOUNDS OF THE INVENTION".

Preferably, for the above process, in order to have the large excess in Stage 1), of the order of 10 to 20 equivalents of diamine R1—$NH_2$ will be used. Stage 1) is preferably carried out at ambient temperature. Stage 3) is carried out at a temperature greater than ambient temperature, for example at a temperature comprised between 60 and 90° C., using of the order of 2 to 5 equivalents of the compound of general formula (III). In Stage 4), the acid conditions can for example be created by using a dichloromethane/trifluoroacetic acid mixture at 50%, said acid conditions being preferably maintained for a duration of the order of 1 to 2 hours. In Stage 5), the basic conditions can for example be created by using a saturated solution of sodium hydrogen carbonate or by elution on a basic alumina cartridge.

According to a variant of the invention, the compounds of general formula (I)b (I)b

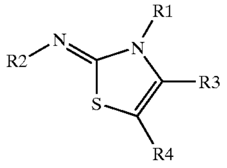

in which:

R1 represents the same radicals as in general formula (I), with the exception of the —$CH_2$—Al—$NH_2$ type radicals, in which Al represents a —$(CH_2)_n$—, —$(CH_2)_n$—O—$(CH_2)_p$—, aralkylene or cycloalkylalkylene radical, n and p representing integers from 1 to 6, and also with the exception of the —C(R11)(R12)—CO—R10 radicals;

R2 represents an aminoalkylphenyl radical;

R3 represents the same radicals as in general formula (I), with the exception of the —CO—R5 radicals;

and R4 represents the same radicals as in general formula (I);

can be prepared for example according to a process characterized in that it comprises the following successive stages:

1) treatment, in an aprotic solvent such as dichloromethane or dimethylformamide, of a p-nitrophenylcarbonate Wang resin with an excess of aminoalkylaniline of general formula R2—$NH_2$ in which the R2 radical has the same meaning as in general formula (I)b;

2) treatment, in an aprotic solvent such as dichloromethane or dimethylformamide, of the resin isolated after Stage 1) with an isothiocyanate of general formula R1—N═C═S in which the R1 radical has the same meaning as in general formula (I)b;

3) treatment, in an aprotic solvent such as dioxane or dimethylformamide, of the resin obtained in Stage 2) with the compound of general formula (III)

(III)

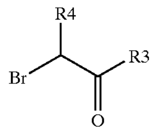

in which the R3 and R4 radicals have the same meaning as in general formula (I)b;

4) cleavage of the resin under acid conditions;

5) treatment under basic conditions of the product obtained after Stage 4).

Preferably, for the above process, in order to have the excess in Stage 1), of the order of 5 to 10 equivalents of aminoalkylaniline will be used. Stage 1) is preferably carried out at ambient temperature. Stage 3) is carried out at a temperature greater than ambient temperature, for example at a temperature comprised between 60 and 90° C., using of the order of 2 to 5 equivalents of the compound of general formula (III). In Stage 4), the acid conditions can for example be created by using a dichloromethane/trifluoroacetic acid mixture at 50%, said acid conditions being preferably maintained for a duration of the order of 1 to 2 hours. In Stage 5), the basic conditions can for example be created by using a saturated solution of sodium hydrogen carbonate or by elution on a basic alumina cartridge.

According to another variant of the invention, the compounds of general formula (I)c (I)c

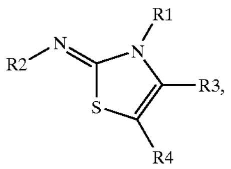

in which:

R1 represents a —$CH_2$—Al—$NH_2$ radical, in which Al represents a —$(CH_2)_n$—, —$(CH_2)_n$—O—$(CH_2)_p$—, aralkylene or cycloalkylalkylene radical, n and p representing integers from 1 to 6;

R2 represents the same radicals as in general formula (I);

R3 represents a —CO—R5 radical; and R4 and R5 represent the same radicals as in general formula (I);

can be prepared according to a process characterized in that it comprises the following successive stages:

1) treatment, in an aprotic solvent such as dichloromethane or dimethylformamide, of a p-nitrophenylcarbonate Wang resin with a large excess of symmetrical diamine of formula R1—$NH_2$ in which the R1 radical has the same meaning as in general formula (I)c;

2) treatment, in an aprotic solvent such as dichloromethane or dimethylformamide, of the resin isolated after Stage 1) with an aromatic isothiocyanate of formula R2—N═C═S in which the R2 radical has the same meaning as in general formula (I)c;

3) treatment, in an aprotic solvent such as dioxane or dimethylformamide, of the resin obtained in Stage 2) with the acid of general formula (IV)

(IV)

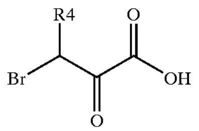

in which the R4 radical has the same meaning as in the general formula (I)c;

4) peptide coupling;

5) cleavage of the resin under acid conditions;

6) treatment under basic conditions of the product obtained after Stage 5).

Preferably, for the above process, in order to have the large excess in Stage 1) of the order of 10 to 20 equivalents of symmetrical diamine will be used. Stage 1) is preferably carried out at ambient temperature. Stage 3) is carried out at a temperature greater than ambient temperature, for example at a temperature comprised between 60 and 90° C., using of the order of 2 to 5 equivalents of the acid of general formula (IV). The peptide coupling of Stage 4) is carried out for example in DMF with coupling agents such as for example dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1.1,3,3-tetramethyluronium hexafluorophosphate (HBTU) or 2-(1H-benzotriazol-1-yl)-1.1,3,3-tetramethyluronium tetrafluoroborate (TBTU) and aminated compounds. Preferably, the coupling agents are used in proportions of 4 to 5 equivalents, as with the aminated compounds, and the reaction will take place at a temperature of the order of ambient temperature for a duration of the order of 1 to 24 hours. In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

According to yet another variant, the compounds of general formula (I)d (I)d

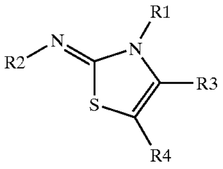

in which:

R1 represents the same radicals as in general formula (I) as defined in claim 1, with the exception of the $—CH_2—Al—NH_2$ type radicals, in which Al represents a $—(CH_2)_n—$, $—(CH_2)_n—O—(CH_2)_p—$, aralkylene or cycloalkylalkylene radical, n and p represent integers from 1 to 6, and also with the exception of the —C(R11)(R12)—CO—R10 radicals;

R2 represents an aminoalkylphenyl radical;

R3 represents a —CO—R5 radical;

and R4 and R5 represent the same radicals as in general formula (I);

can be prepared according to a process characterized in that it comprises the following successive stages:

1) treatment, in an aprotic solvent such as dichloromethane or dimethylformamide, of a p-nitrophenylcarbonate Wang resin with an excess of aminoalkylaniline of general formula $R2—NH_2$ in which the R2 radical has the same meaning as in general formula (I)d;

2) treatment, in an aprotic solvent such as dichloromethane or dimethylformamide, of the resin isolated after Stage 1) with an isothiocyanate of general formula R1—N═C═S in which the R1 radical has the same meaning as in general formula (I)d;

3) treatment, in an aprotic solvent such as dioxane or dimethylformamide, of the resin obtained in Stage 2) with the acid of general formula (IV)

(IV)

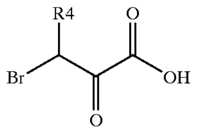

in which the R4 radical has the same meaning as in general formula (I)d;

4) peptide coupling;

5) cleavage of the resin under acid conditions;

6) treatment under basic conditions of the product obtained after Stage 5).

Preferably, for the above process, in order to have the excess in Stage 1), of the order of 5 to 10 equivalents of aminoalkylaniline will be used. Stage 1) is preferably carried out at ambient temperature. Stage 3) is carried out at a temperature greater than ambient temperature, for example at a temperature comprised between 60 and 90° C., using of the order of 2 to 5 equivalents of the acid of general formula (IV). The peptide coupling of Stage 4) is carried out for example in DMF with coupling agents such as for example dicyclohexylcarbodiimide (DCC), diisopropylcarbodiimide (DIC), a DIC/N-hydroxybenzotriazole (HOBt) mixture, benzotriazolyloxytris(dimethylamino) phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds. Preferably, the coupling agents are used in proportions of 4 to 5 equivalents, as with the aminated compounds, and the reaction will take place at a temperature of the order of ambient temperature for a duration of the order of 1 to 24 hours. In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

According to another variant, the compounds of general formula (I)e (I)e

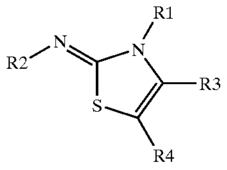

in which:

R1 represents the same radicals as in general formula (I), with the exception of the $—CH_2—Al—NH_2$ radicals, in which Al represents a $—(CH_2)_n—$, $—(CH_2)_n—O—(CH_2)_p—$, aralkylene or cycloalkylalkylene radical, n and p representing integers from 1 to 6, and also with the exception of the —C(R11)(R12)—CO—R10 radicals;

R2 represents the same radicals as in general formula (I);

R3 represents a —CO—R5 radical;

R4 represents H;

R5 represents a $—CH_2—Al—NH_2$ radical, in which Al represents a linear or branched alkylene radical containing 1 to 6 carbon atoms, $—(CH_2)_n—O—(CH_2)_p—$, aralkylene or cycloalkylalkylene, n and p representing integers from 1 to 6, or also R5 represents the N(R6)(R7) radical corresponding to the following general formula:

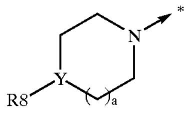

in which:

R8 represents H;

Y represents N;

a represents 1 or 2;

can be prepared by a process characterized in that it comprises the following successive stages:

1) treatment, in an aprotic solvent such as dichloromethane or dimethylformamide, of a p-nitrophenylcarbonate Wang resin with a large excess of symmetrical diamine of general formula R5—H;

2) peptide coupling with the acid of general formula (IV) on the resin obtained in Stage 1)

(IV)

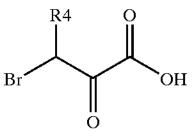

in which the R4 radical has the same meaning as that in the general formula (I)e;

3) reaction of the primary amine of general formula $R1—NH_2$ with the isothiocyanate of general formula R2—NCS in a solvent such as dimethylformamide or dioxane, R1 and R2 having the same meanings as in general formula (I)e;

4) addition of the thiourea obtained in Stage 3) to the resin obtained in Stage 2) and heating the mixture;

5) cleavage of the resin under acid conditions;

6) treatment under basic conditions of the product obtained after Stage 5).

Preferably, for the above process, in order to have the large excess in Stage 1), of the order of 10 to 20 equivalents of diamine $R5—NH_2$ will be used. Stage 1) is preferably carried out at ambient temperature. The peptide coupling of Stage 2) is carried out in DMF with a coupling agent such as for example a DIC/N-hydroxybenzotriazole (HOBt) mixture. Preferably, the reaction of Stage 3) is carried out in a solvent such as dimethylformamide or dioxane. During the addition of Stage 4), 2 to 5 equivalents of thiourea will be used per equivalent of resin; preferably, heating will be carried out at a at a temperature greater than ambient temperature, for example at a temperature from 40 to 100° C. (in particular at a temperature of approximately 80° C.) and for a duration of the order of 2 to 24 hours. In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

According to yet another variant, the compounds of general formula (I)f (I)f

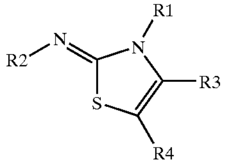

in which:

R1 represents a —C(R11R12)—CO—R10 radical;

R2, R3 and R4 represent the same radicals as in general formula (I);

R10 represents an amino($C_2$–$C_7$)alkylamino, ((aminoalkyl)aryl)alkylamino, ((aminoalkyl)cycloalkyl)alkylamino, piperazinyl, homopiperazinyl radical, or R10 represents the radical represented below:

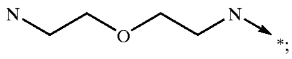

R11 represents H;

R12 represents H or an alkyl, ($C_3$–$C_7$)cycloalkyl, optionally substituted carbocyclic or heterocyclic aralkyl, propargyl, allyl, hydroxyalkyl, alkylthioalkyl, arylalkylalkoxyalkyl, arylalkylthioalkoxyalkyl radical;

can be prepared by a process characterized in that it comprises the following successive stages:

1) treatment, in an aprotic solvent such as dichloromethane or dimethylformamide, of a p-nitrophenylcarbonate Wang resin with a large excess of symmetrical diamine of general formula R10—H in which R10 has the same meaning as in general formula (I)f;

2) peptide coupling of the resin obtained in Stage 1) with an amino acid of general formula HOOC—C(R11)(R12)—NH—Fmoc in which R11 and R12 have the same meaning as in general formula (I)f;

3) cleavage of the Fmoc group of the resin obtained in Stage 2);

4) reaction of the resin obtained in Stage 3) with an isothiocyanate of general formula R2—NCS in which R2 has the same meaning as in general formula (I)f;

5) cleavage of the resin under acid conditions;

6) treatment under basic conditions of the product obtained after Stage 5).

Preferably, for the above process, in order to have the large excess in Stage 1), of the order of 10 to 20 equivalents of diamine R10—H will be used. Stage 1) is preferably carried out at ambient temperature. The peptide coupling of Stage 2) is carried out for example in DMF with coupling agents such as for example dicyclohexylcarbodiimide (DCC), diisopropylcarbodiimide (DIC), a DIC/N-hydroxybenzotriazole (HOBt) mixture, benzotriazolyloxytris(dimethylamino) phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU). Preferably, the reaction of Stage 2) is carried out at ambient temperature and for a duration of 1 to 24 hours. The deprotection of Stage 3) can be carried out, for example, by means of a mixture of DMF containing 20% piperidine. Stage 4) will preferably be carried out in a solvent such as dimethylformamide or dichloromethane, the isothiocyanate preferably being added in a proportion of 5 to 10 equivalents per equivalent of the resin obtained in Stage 3). In Stage 5), the acid conditions can for example be created by using a dichloromethane/trifluoroacetic acid mixture at 50%, said acid conditions being preferably maintained for a duration of the order of 1 to 2 hours. In Stage 6), the basic conditions can for example be created by using a saturated solution of sodium hydrogen carbonate or by elution on a basic alumina cartridge.

A subject of the invention is also, as medicaments, the compounds of general formulae (I) and (II) described previously or their pharmaceutically acceptable salts. It also relates to the pharmaceutical compositions containing said compounds or their pharmaceutically acceptable salts, and their use for the preparation of a medicament intended to treat the pathological states or the diseases in which one (or more) of the somatostatin receptors are involved.

In particular, the compounds of general formulae (I) and (II) described previously or their pharmaceutically acceptable salts can be used for the preparation of a medicament intended to treat the pathological states or the diseases chosen from the group comprising the following pathological states or diseases: acromegalia, hypophyseal adenomas, Cushing's disease, gonadotrophinomas and prolactinomas, catabolic side-effects of glucocorticoids, insulin dependent diabetes, diabetic retinopathy, diabetic nephropathy, syndrome X, dawn phenomena, angiopathy, angioplasty, hyperthyroidism, gigantism, endocrinic gastroenteropancreatic tumors including carcinoid syndrome, VIPoma, insulinoma, nesidioblastoma, hyperinsulinemia, glucagonoma, gastrinoma and Zollinger-Ellison's syndrome, GRFoma as well as acute bleeding of the esophageal varices, ulcers, gastroesophageal reflux, gastroduodenal reflux, pancreatitis, enterocutaneous and pancreatic fistulae but also diarrheas, refractory diarrheas of acquired immunodeficiency syndrome, chronic secretary diarrhea, diarrhea associated with irritable bowel syndrome, diarrheas induced by chemotherapy, disorders linked with gastrin releasing peptide, secondary pathologies with intestinal grafts, portal hypertension as well as hemorrhages of the varices in patients with cirrhosis, gastro-intestinal hemorrhage, hemorrhage of the gastroduodenal ulcer, bleeding of grafted vessels, Crohn's disease, systemic scleroses, dumping syndrome, small intestine syndrome, hypotension, scleroderma and medullar thyroid carcinoma, illnesses linked with cell hyperproliferation such as cancers and more particularly breast cancer, prostate cancer, thyroid cancer as well as pancreatic cancer and colorectal cancer, fibroses and more particularly fibrosis of the kidney, fibrosis of the liver, fibrosis of the lung, fibrosis of the skin, also fibrosis of the central nervous system as well as that of the nose and fibrosis induced by chemotherapy, and in other therapeutic fields such as, for example, cephaleas including cephalea associated with hypophyseal tumors, pain, inflammatory disorders such as arthritis, panic attacks, chemotherapy, cicatrization of wounds, renal insufficiency resulting from delayed development, hyperlipidemia, obesity and delayed development linked with obesity, delayed uterine development, dysplasia of the skeleton, Noonan's syndrome, sleep apnea syndrome, Graves' disease, polycystic disease of the ovaries, pancreatic pseudocysts and ascites, leukemia, meningioma, cancerous cachexia, inhibition of *H pylori,* psoriasis, chronic rejection of allografts as well as Alzheimer's disease and finally osteoporisis.

Preferably, the compounds of general formulae (I) and (II) described previously or their pharmaceutically acceptable salts can be used for the preparation of a medicament intended to treat the pathological states or diseases chosen from the group comprising the following pathological states or diseases: acromegalia, hypophyseal adenomas or endocrinic gastroenteropancreatic tumors including carcinoid syndrome, and gastrointestinal bleeding.

By pharmaceutically acceptable salt is meant in particular addition salts of inorganic acids such as hydrochloride, sulphate, phosphate, diphosphate, hydrobromide and nitrate, or of organic acids, such as acetate, maleate, fumarate, tartrate, succinate, citrate, lactate, methanesulphonate, p-toluenesulphonate, pamoate, oxalate and stearate. The salts formed from bases such as sodium or potassium hydroxide also fall within the scope of the present invention, when they can be used. For other examples of pharmaceutically acceptable salts, reference can be made to "Pharmaceutical salts", *J. Pharm. Sci.* 66:1 (1977).

The pharmaceutical composition can be in the form of a solid, for example powders, granules, tablets, capsules, liposomes or suppositories. Appropriate solid supports can be for example calcium phosphate, magnesium stearate, talc, sugars, lactose, dextrin, starch, gelatin, cellulose, methyl cellulose, sodium carboxymethyl cellulose, polyvinylpyrrolidine and wax. The suspensions contain in particular suspensions of sustained release microparticles loaded with active ingredient (in particular microparticles of polylactide-co-glycolide or PLGA—cf. for example the Patents U.S. Pat. No. 3,773,919, EP 52 510 or EP 58 481 or the Patent Application PCT WO 98/47489), which allow the administration of a determined daily dose over a period of several days to several weeks.

The pharmaceutical compositions containing a compound of the invention can also be presented in the form of a liquid, for example, solutions, emulsions, suspensions or syrups. Appropriate liquid supports can be, for example, water, organic solvents such as glycerol or the glycols, as well as their mixtures, in varying proportions, in water.

The administration of a medicament according to the invention can be done by topical, oral, parenteral route, by intramuscular injection, etc.

The administration dose envisaged for a medicament according to the invention is comprised between 0.1 mg to 10 g according to the type of active compound used.

These compounds can be prepared according to the methods described below.

PREPARATION OF THE COMPOUNDS OF THE INVENTION

I) Preparation of α-bromoketones

First Method

This method is inspired by the protocols described in the following publications: Macholan, L.; Skursky, L. *Chem. Listy* 1955, 49, 1385–1388; Bestman, H. J.; Seng, F. *Chem. Ber.* 1963, 96, 465–469; Jones, R. G.; Kornfeld, E. C.; McLaughlin, K. C. *J. Am. Chem. Soc.* 1950, 72, 4526–4529; Nimgirawath, S.; Ritchie, E.; Taylor, W. C. *Aust. J. Chem.* 1973, 26, 183–193).

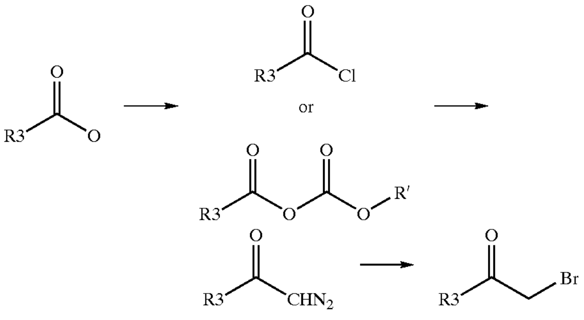

A carboxylic acid is firstly converted to an acid by using oxalyl or thionyl chloride, or by activating it in the form of an anhydride using an alkyl chloroformate (for example isobutyl chloroformate, cf. Krantz, A.; Copp, L. J. *Biochemistry* 1991, 30, 4678–4687; or ethyl chloroformate, cf. Podlech, J.; Seebach, D. *Liebigs Ann.* 1995, 1217–1228) in the presence of a base (triethylamine or N-methylmorpholine).

The activated carboxyl group is then converted to diazoketone using diazomethane in an ethereal solution or a commercial solution of trimethylsilyldiazomethane (Aoyama, T.; Shiori, T. *Chem. Pharm. Bull.* 1981, 29, 3249–3255) in an aprotic solvent such as diethyl ether, tetrahydrofuran (THF) or acetonitrile.

The bromination is then carried out using a bromination agent such as hydrobromic acid in acetic acid, aqueous hydrobromic acid in diethyl ether or dichloromethane.

Preparation 1

2-(4-bromo-3-oxobutyl)-1H-isoindole-1,3(2H)-dione ($C_{12}H_{10}BrNO_3$, MM=296.12):

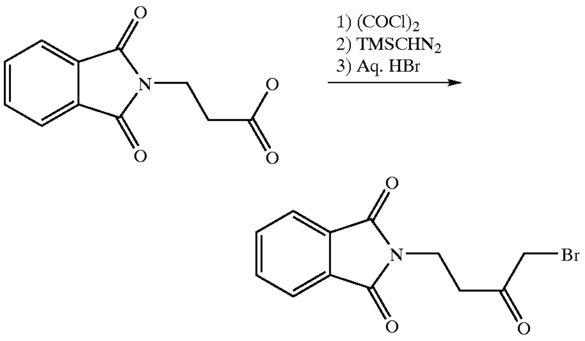

Oxalyl chloride (5.8 ml; 66.7 mmol) is added to Pht-β-Ala-OH (9.96 g; 44.5 mmol) dissolved in dichloromethane (120 ml) and 3 drops of dimethylformamide (DMF). The mixture is stirred for 3 hours at ambient temperature. After elimination of the solvent, the white solid is taken up in a 1:1 mixture of anhydrous tetrahydrofuran and acetonitrile (200 ml) then 49 ml of a 2 M solution of (trimethylsilyl) diazomethane in hexane (97.9 mmol) are added dropwise at 0° C. The solvents are eliminated after one night of stirring at 0° C. The pale yellow solid is then dissolved in dichloromethane (60 ml) and 12 ml of aqueous hydrobromic acid (48%) is added dropwise at 0° C. The mixture is stirred until the temperature reaches 15° C. and 50 ml of a saturated solution of sodium bicarbonate is added. The organic phase is washed with salt water then dried over sodium sulphate. Crystallization from diethyl ether allows a white solid to be obtained (11.39 g; yield=86%).

NMR $^1H$ (DMSO D6, 100 MHz, δ): 7.83 (s, 4H); 4.36 (s, 2H, $CH_2Br$); 3.8 (t, 2H, J=7.1 Hz, $NCH_2$); 2.98 (t, 2H, J=6.9 Hz, $CH_2CO$).

Preparations 2–11

The following compounds were prepared in a similar fashion to the procedure described in Preparation 1:

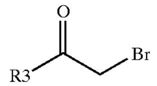

| Prep. | R3 | Yield (%) |
|---|---|---|
| 2* | 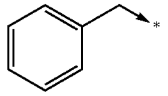 | 78 |
| 3* | 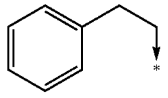 | 60 |
| 4* | 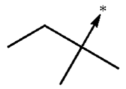 | 10 |
| 5* | 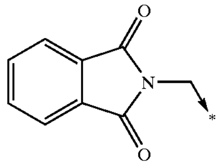 | 69 |
| 6* | 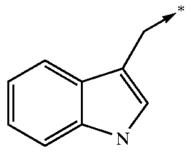 | 41 |
| 7 | 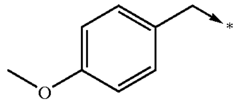 | 67 |
| 8 | 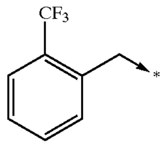 | 51 |

-continued

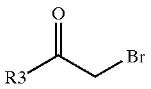

| Prep. | R3 | Yield (%) |
| --- | --- | --- |
| 9 | 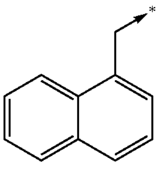 | 38 |
| 10 | 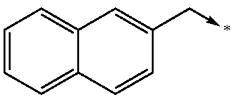 | 22 |
| 11 | 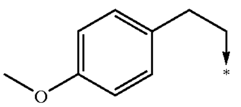 | 67 |

*Compounds already described in the literature.

Second Method

The starting product is an arylmethylketone or a heteroarylmethylketone.

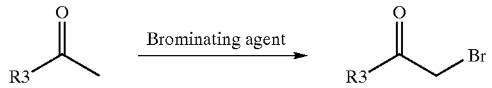

The starting arylmethylketone or heteroarylmethylketone is converted to the corresponding α-bromoketone by using different brominating agents:

- $CuBr_2$ (King, L. C.; Ostrum, G. K. *J. Org. Chem.* 1964, 29, 3459–3461) heated in ethyl acetate or dioxane;
- the N-bromosuccinimide in $CCl_4$ or aqueous acetonitrile, (Morton, H. E.; Leanna, M. R. *Tetrahedron Lett.* 1993, 34, 4481–4484);
- the bromine in glacial acetic acid or sulphuric acid;
- phenyltrimethylammonium tribromide (Sanchez, J. P.; Parcell, R. P. *J. Heterocyclic Chem,* 1988, 25, 469–474) at 20–80° C. in an aprotic solvent such as THF or tetrabutylammonium tribromide (Kajigaeshi, S.; Kakinami, T.; Okamoto, T.; Fujisaki, *S. Bull Chem. Soc. Jpn.* 1987, 60, 1159–1160) in a dichloromethane/methanol mixture at ambient temperature;
- brominating agent on a polymer support such as perbromide on an Amberlyst A-26 resin, poly(perbromide of vinylpyridinium hydrobromide) (Frechet, J. M. J.; Farrall, M. J. *J Macromol. Sci. Chem.* 1977, 507–514) in a protic solvent such as methanol at approximately 20–35° C. for approximately 2–10 hours.

Preparation 12

1-(1-benzofuran-2-yl)-2-bromo-1-ethanone ($C_{10}H_7BrO_2$, MM=239.06):

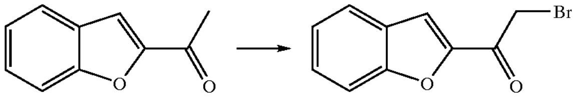

A polymer of perbromide of pyridine hydrobromide (8.75 g; 17.5 mmol; 1.4 equivalent) is added to a solution of (benzofuran-2-yl)methylketone (2 g; 12.5 mmol) in methanol (40 ml). The resulting mixture is stirred at ambient temperature for 7 hours and the reaction is stopped by filtration. The methanol is eliminated under reduced pressure and an additional addition of diethyl ether allows crystallization of the expected product (3.6 g; yield=60%).

NMR $^1H$ (DMSO D6, 100 MHz, δ): 8.09 (s, 1H); 7.98 (d, 1H, J=6.6 Hz); 7.75 (d, 1H, J=8.4 Hz); 7.58 (t, 1H, J=8.4 Hz); 7.4 (t, 1H, J=7 Hz); 4.83 (s, 2H, $CH_2Br$).

Preparations 8–12

The following compounds have been prepared in similar fashion to the procedure described in Preparation 12:

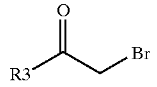

| Prep. | R3 | Duration of reaction (hrs) | Yield (%) |
| --- | --- | --- | --- |
| 13* | 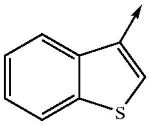 | 8 | 78 |
| 14* | 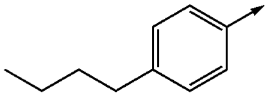 | 2 | 62 |
| 15* | 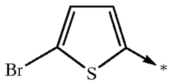 | 10 | 56 |
| 16* | 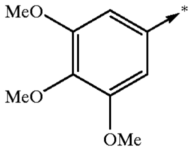 | 2 | 53 |
| 17* | 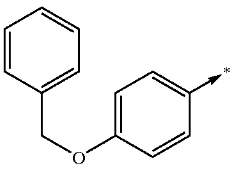 | 3 | 95 |

-continued

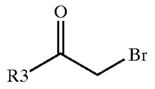

| Prep. | R3 | Duration of reaction (hrs) | Yield (%) |
|---|---|---|---|
| 18 | 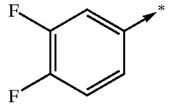 | 8 | 27 |

*Compound already described in the literature.

II) Synthesis of 2-arylimino-2,3-dihydrothiazoles via Synthesis on Solid Phase

Preparation of p-nitrophenylcarbonate Wang Resin

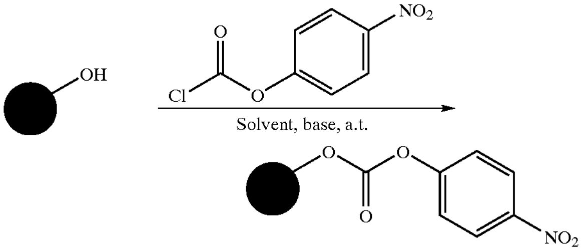

This resin was prepared from Wang resin, acquired from Bachem or Novabiochem with a load greater than 0.89 mmol/g, by a well described general procedure (cf. Bunin, B. A. *The Combinatorial Index,* Academic Press, 1998, p. 62–63; Dressman, B. A.; Spangle, L. A.; Kaldor, S. W. *Tetrahedron Lett.* 1996, 37, 937–940; Hauske, J. R.; Dorff, P. *Tetrahedron Lett.* 1995, 36, 1589–1592; Cao, J.; Cuny, G. D.; Hauske, J. R. *Molecular Diversity* 1998, 3, 173–179): N-methylmorpholine or pyridine as base and 4-nitrophenylchloroformate are successively added to a Wang resin pre-swollen in dichloromethane (DCM) or tetrahydrofuran (THF) at ambient temperature. The mixture is stirred overnight. The resin is then washed successively with THF, diethyl ether and DCM then dried overnight under reduced pressure at 50° C.

Method A

Preparation of Monoprotected Symmetrical Diamines

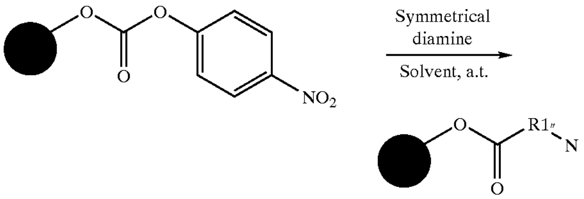

General procedure: as already described in the literature (Dixit, D. M.; Leznoff, C. C. *J. C. S. Chem. Comm.* 1977, 798–799; Dixit, D. M.; Leznoff, C. C. *Israel J. Chem.* 1978, 17, 248–252; Kaljuste K.; Unden, A. *Tetrahedron Lett.* 1995, 36, 9211–9214; Munson, M. C.; Cook, A. W.; Josey, J. A.; Rao, C. *Tetrahedron Lett.* 1998, 39, 7223–7226), a p-nitrophenylcarbonate Wang resin is treated with a large excess of symmetrical diamine (10–20 equivalents), in an aprotic solvent such as DCM or DMF, in order to produce a monoprotected diamine resin after stirring overnight.

Preparation of Thiourea Resins

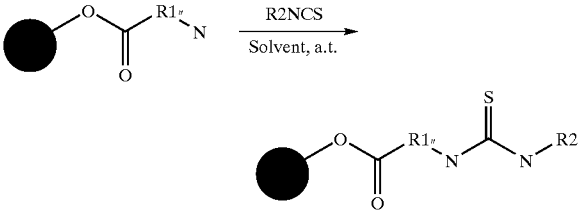

General procedure: aromatic and heteroaromatic isothiocyanates (5–10 equivalents) are added (Smith, J.; Liras, J. L.; Schneider, S. E.; Anslyn, E. V. *J. Org. Chem.* 1996, 61, 8811–8818) to monoprotected symmetrical diamines in a solvent such as DCM or DMF stirred overnight at ambient temperature. Washed successively with DMF and DCM, the thiourea resin is isolated then dried overnight under reduced pressure at 50° C.

Preparation 19

(phenylaminothioyl)ethyl Carbamate Wang Resin

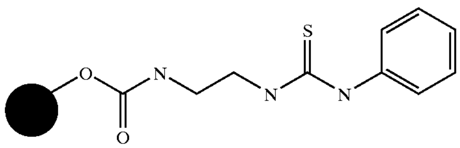

Phenylisothiocyanate (1 ml; 8.5 mmol; 5 eq.) is added to an ethylene diamine N-carbamate Wang resin (2 g; 1.72 mmol; 0.86 mmol/g) swollen in DCM (50 ml). After stirring overnight at ambient temperature, the resin is washed successively with DMF (5x20 ml) and DCM (5x20 ml). The success of the coupling is monitored using the Kaiser ninhydrin test (Kaiser, E.; Colescott, R. L.; Bossinger, C. D.; Cook, P. I. *Anal. Biochem.* 1970, 34, 595–598). A pale yellow resin (1.79 g) is obtained with a load of 0.648 mmol/g calculated from the elemental analysis of sulphur.

Synthesis of 2-arylimino-2,3-dihydrothiazoles

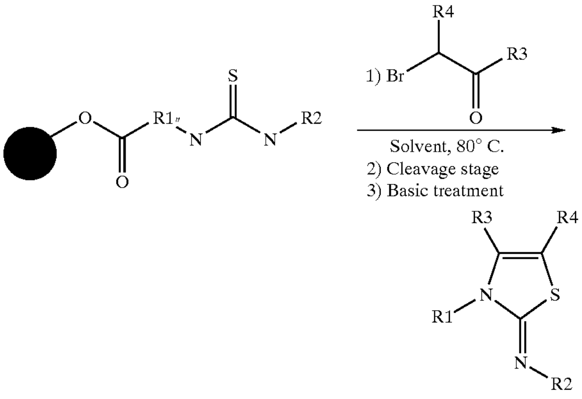

General procedure: regioselective cyclization stage (Korohoda, M. J.; Bojarska, A. B. *Polish J. Chem.* 1984, 58, 447–453; Ragab, F. A.; Hussein, M. M.; Hanna, M. M.; Hassan, G. S.; Kenawy, S. A. *Egypt. J. Pharm. Sci.* 1993, 34, 387–400; Hassan, H. Y.; El-Koussi, N. A.; Farghaly, Z. S. *Chem. Pharm. Bull.* 1998, 46, 863–866) takes place in aprotic solvents such as dioxane or DMF at 80° C. for 2–3 hours between the thiourea resin and the α-bromoketone (2–5 equivalents). The resin is then washed successively with DMF, methanol and DCM then dried under reduced pressure. The 2-arylimino-2,3-dihydrothiazole resin is cleaved under acid conditions (DCM/trifluoroacetic acid at 50%) for 1–2 hours then rinsed with DCM. The solvent is evaporated off and the free base is isolated after treatment under basic conditions (saturated solution of sodium hydrogen carbonate), extraction with DCM or elution with methanol in a basic alumina cartridge (500 mg, Interchim).

EXAMPLE 1

N-[3-(2-aminoethyl)-4-(4-chlorophenyl)-1,3-thiazol-2(3H)-ylidene]aniline ($C_{17}H_{16}ClN_3S$, MM=329.86):

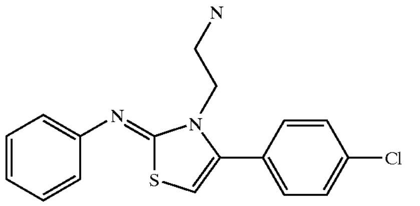

2-bromo-4'-chloroacetophenone (30.2 mg; 129 μmol; 2 eq.) dissolved in DMF (1 ml) is added to a thiourea resin prepared above (100 mg; 64.8 μmol; load of 0.648 mmol/g). The mixture is stirred for 2 hours at 80° C. The resin is then successively washed with DMF (3x2 ml), methanol (3x2 ml) and DCM (3x2 ml). The release stage, carried out in 1 ml of mixture of DCM/trifluoroacetic acid at 50%, produces an oil after one hour 30 minutes of stirring which is eluted with methanol in a basic alumina cartridge (500 mg, Interchim). The free base is isolated in a quantitative fashion (21.3 mg) in the form of a yellow oil having a purity measured by UV spectrophotometry of 98% at 220 nm.

NMR $^1H$ (DMSO D6, 100 MHz) δ: 7.55 (s, 5H); 7.3 (d, 2H, J=7.1 Hz); 6.99 (d, 2H, J=7.1 Hz); 6.21 (s, 1H, H azole); 3.74 (t, 2H, J=6.2 Hz, $NCH_2$); 3.32 (broad s, 2H, $NH_2$); 2.72 (t, 2H, J=6.2 Hz, $NCH_2$). SM/LC: m/z=330 $(M+H)^+$.

A series of 2-arylimino-2,3-dihydrothiazoles was synthesized according to method A using our robotic system (ACT MOS 496):

R1 groups:

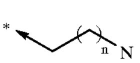

n = 1–6

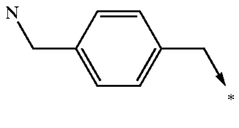

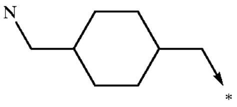

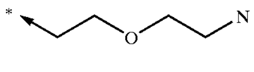

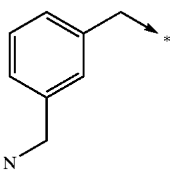

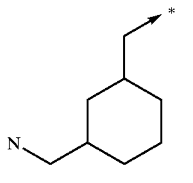

R2 groups:

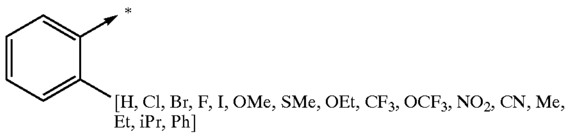

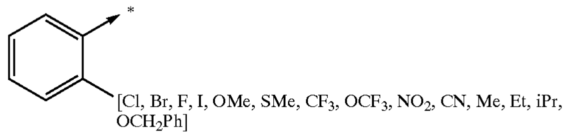

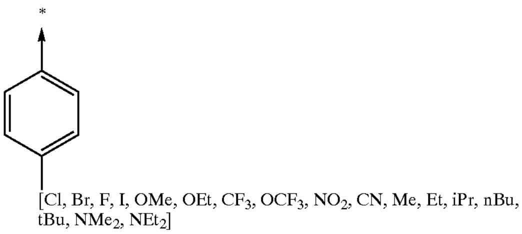

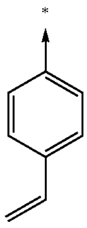

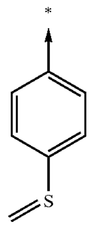

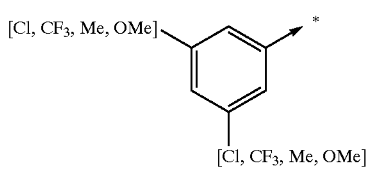

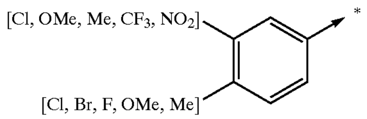

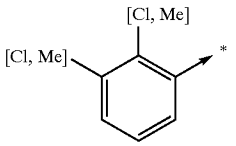

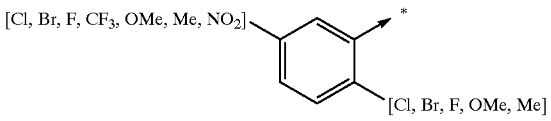

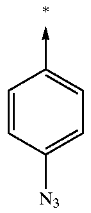

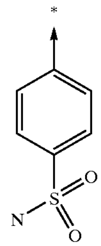

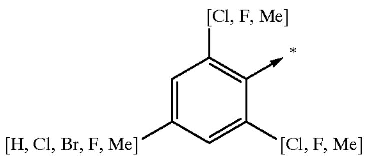

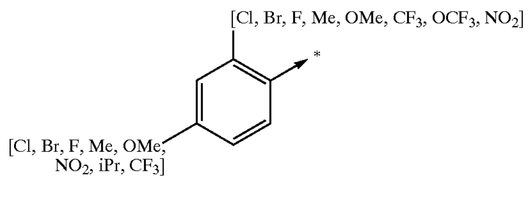

-continued
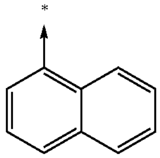
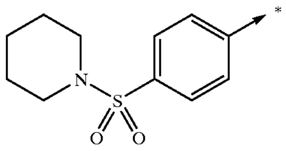
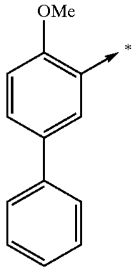
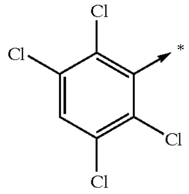
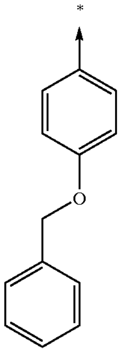
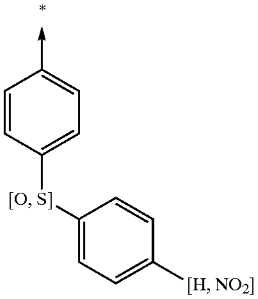
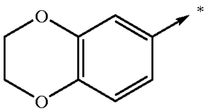
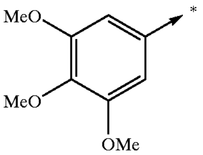
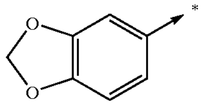
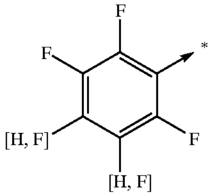
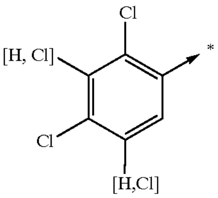
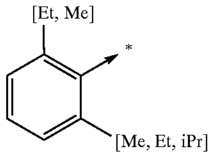
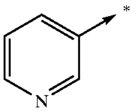
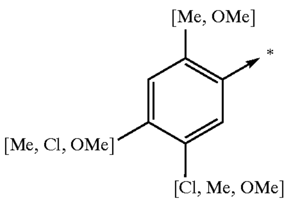
-continued
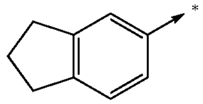
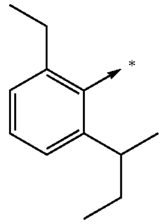
R3 groups:
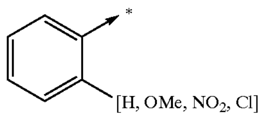
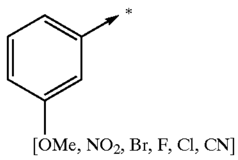
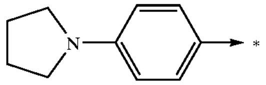
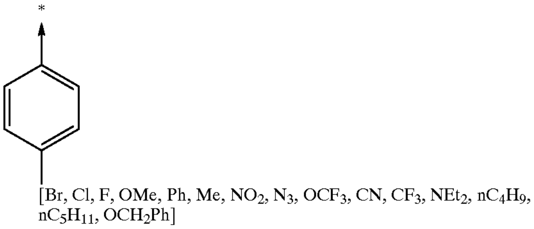
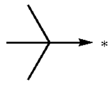
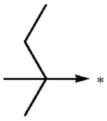
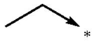
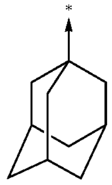
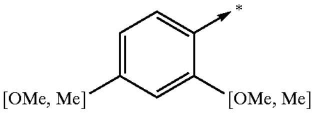
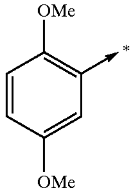
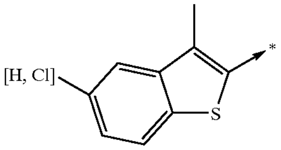
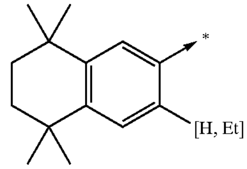
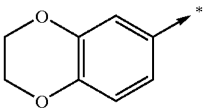
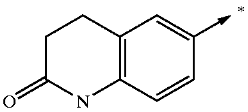
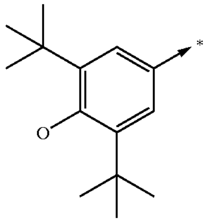
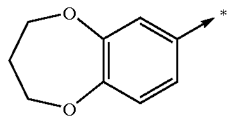

-continued

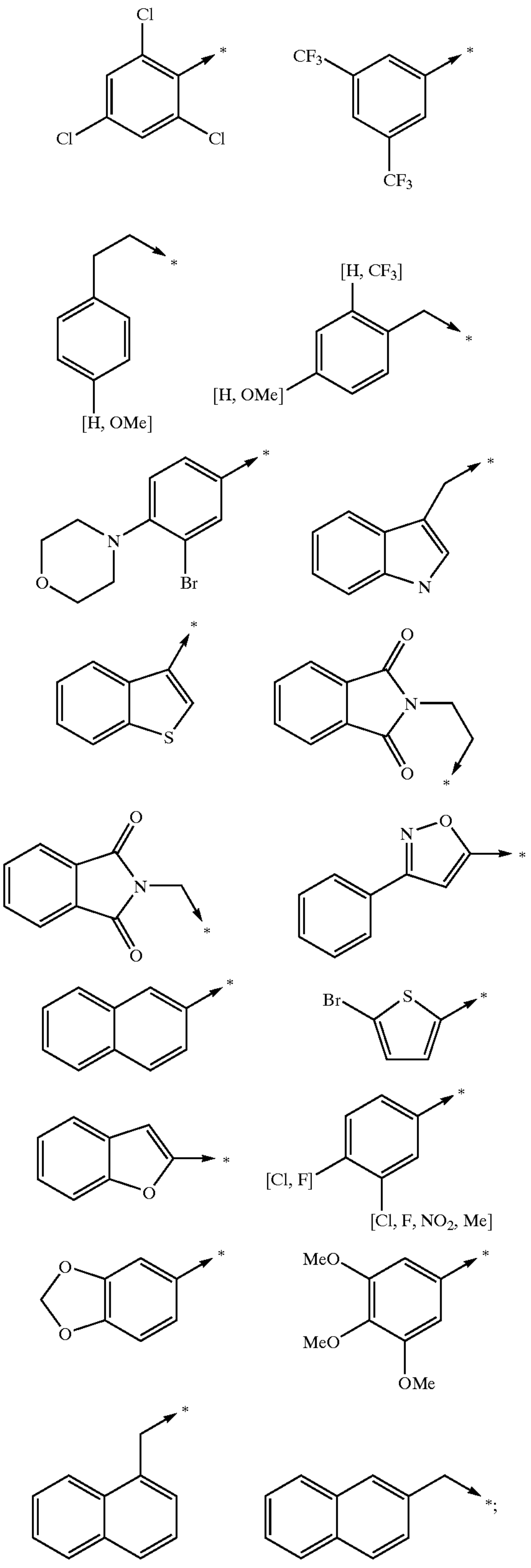

R4 represents H, alkyl, carbocyclic or heterocyclic aralkyl optionally situated on the aryl radical;

or then the

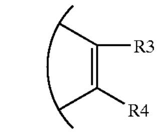

radical represents a radical of general formula

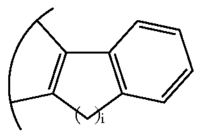

in which i represents an integer from 1 to 3;

it being understood that for R4, when the aryl group is substituted, it can be 1 to 5 times (other than the bond which links it to the remainder of the molecule) by radicals chosen independently from the group composed of a halogen atom and an alkyl or alkoxy radical.

Method B

Preparation of carbamate Wang resins from aminoalkylanilines

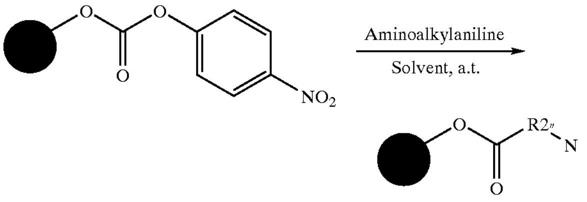

General procedure: as already described (Hulme, C.; Peng, J.; Morton, G.; Salvino, J. M.; Herpin, T.; Labaudiniere, R. *Tetrahedron Lett.* 1998, 39, 7227–7230), a p-nitrophenylcarbonate Wang resin is treated with an excess of aminoalkylaniline (5–10 eq.) in DCM or DMF and stirred at ambient temperature overnight. The resin is washed successively with DMF, methanol and DCM then dried overnight under reduced pressure at 50° C.

Preparation 20

4-aminophenylethyl Carbamate Wang Resin

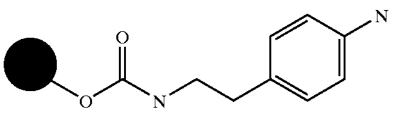

A solution of 2-(4-aminophenyl)ethylamine (2.48 g; 17.3 mmol; 5 eq.) in 30 ml of anhydrous DMF is added to a p-nitrophenylcarbonate Wang resin (4.05 g; 3.47 mmol; load of 0.857 mmol/g) pre-swollen in 50 ml of anhydrous DMF. The mixture is stirred at ambient temperature overnight and filtered. The resin is washed successively with DMF (10×30 ml), methanol (5×30 ml) and DCM (5×30 ml). 3.7 g of yellow resin (load of 0.8 mmol/g calculated from the elemental analysis of the nitrogen), giving a positive Kaiser ninhydrin test, is isolated after drying overnight under reduced pressure at 50° C.

Preparation of Thiourea Resins with Aliphatic Isothiocyanates

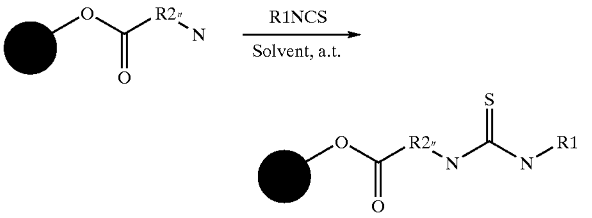

General procedure: aliphatic isothiocyanates (5–10 equivalents) are added to an aminoalkylaniline resin in a solvent such as DCM or DMF and stirring is carried out overnight at ambient temperature. After washing successively with DMF and DCM, the thiourea resin is isolated and dried overnight under reduced pressure at 50° C.

Preparation 21

4-{[(phenylethylamino)carbothioyl]amino}-phenylethyl Carbamate Wang Resin

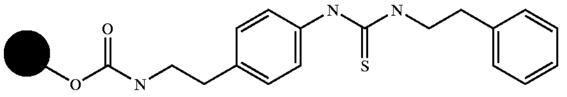

10 ml of anhydrous DMF and phenylethylisothiocyanate (624 μl, 4 mmol, 10 eq.) are added under an argon atmosphere to the resin described previously (0.5 g; 0.4 mmol; load of 0.8 mmol/g). The reaction medium is stirred overnight at ambient temperature and produces a negative Kaiser ninhydrin test. The resin is then washed successively with DMF (5×20 ml) and DCM (5×20 ml). Drying under reduced pressure at 50° C. produces 488 mg of resin with a load of 0.629 mmol/g calculated from elemental analysis of the sulphur.

Synthesis of 2-arylimino-2,3-dihydrothiazoles

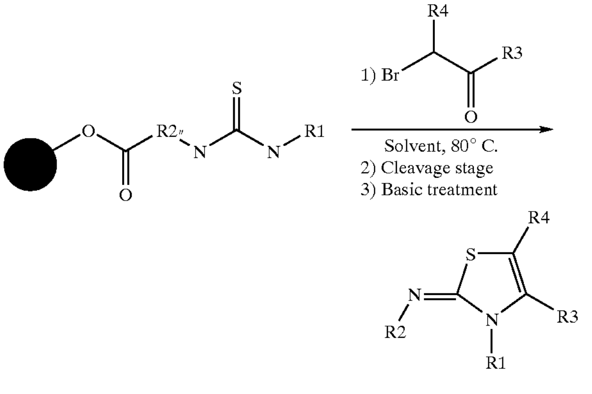

General procedure: the cyclization stage takes place in aprotic solvents such as dioxane or DMF at 80° C. for 2 hours between the thiourea resin and the α-bromoketone (2–5 equivalents). The resin is then washed successively with DMF, methanol and DCM then dried under reduced pressure. The iminothiazole resin is cleaved by treatment under acid conditions (DCM/trifluoroacetic acid at 50%) for 1–2 hours then rinsed with DCM. The solvent is evaporated off and the free base isolated after extraction under basic conditions (saturated solution of sodium hydrogen carbonate), extraction with DCM or elution with methanol in a basic alumina cartridge (500 mg, Interchim).

EXAMPLE 2

4-(2-aminoethyl)-N-[4-(4-chlorophenyl)-3-phenethyl-1,3-thiazol-2(3H)-ylidene]aniline ($C_{25}H_{24}ClN_3S$, MM=434.01):

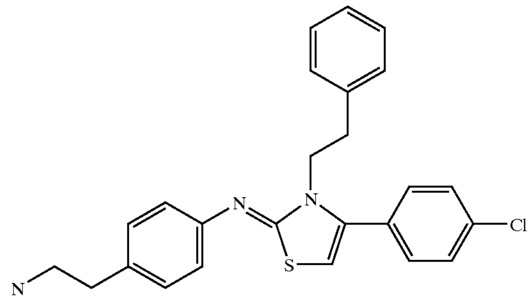

100 mg (62.9 μmol, load of 0.629 mmol/g) of thiourea resin and 2-bromo-4'-chloroacetophenone (30 mg; 125.8 μmol; 2 eq.) are dissolved in 1 ml of DMF and heated to 80° C. for 2 hours. The resin is then washed successively with DMF (5×1 ml), methanol (5×1 ml) and DCM (5×1 ml). The resin is stirred in 1 ml of a DCM/trifluoroacetic acid mixture at 50% for one hour and 30 minutes at ambient temperature. The resin is rinsed with DCM (5×1 ml) and the filtrate evaporated under reduced pressure. The residue, dissolved in methanol, is eluted in a basic alumina cartridge (500 mg, Interchim) in order to quantitatively produce (27.3 mg) the expected product in the form of a solid (UV purity: 97%).

NMR $^1H$ (DMSO D6, 100 MHz) δ: 7.9 (broad s, 2H, $NH_2$); 7.53 (d, 2H, J=8.5 Hz); 7.32–7.15 (m, 7H); 7.08–6.9 (m, 4H); 6.37 (s, 1H, H azole); 4.07 (m, 2H, $NCH_2$); 3.03 (m, 2H, $NCH_2$); 2.88 (m, 4H). MS/LC: m/z=435 $(M+H)^+$.

A series of 2-arylimino-2,3-dihydrothiazoles was synthesized according to method B with our robotic system (ACT MOS 496):

R1 groups

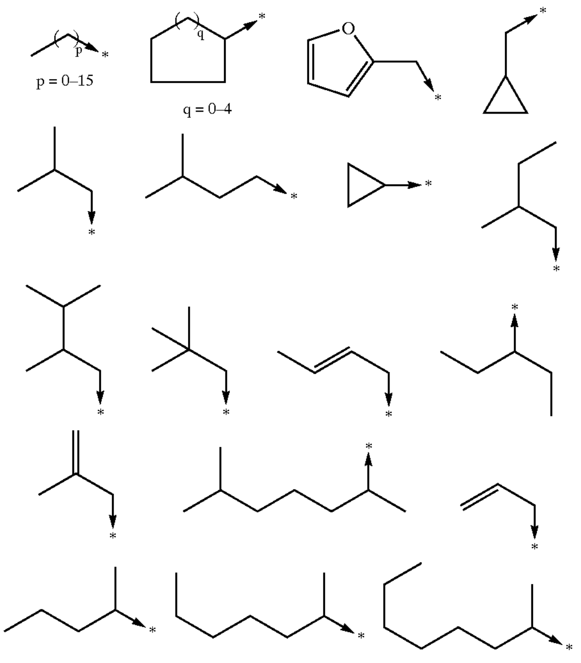

-continued
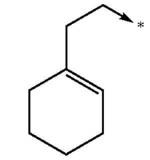
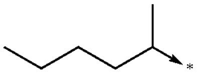
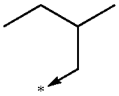
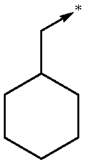
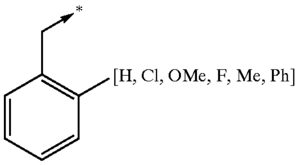
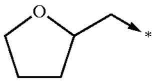
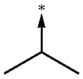
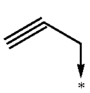
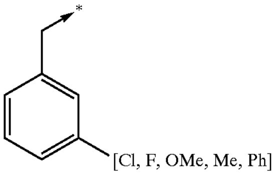
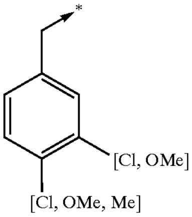
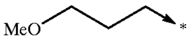
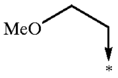
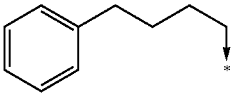
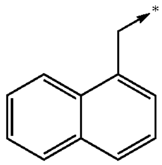
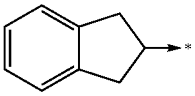
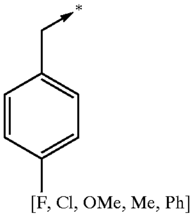
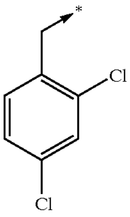
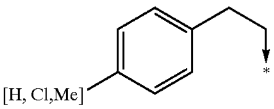
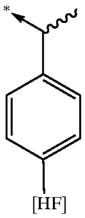
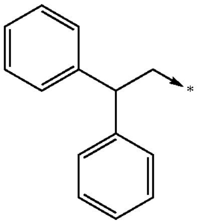
-continued
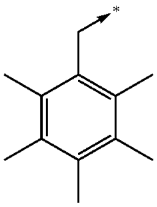
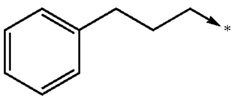
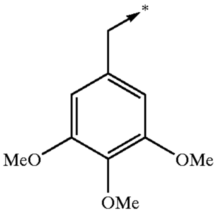
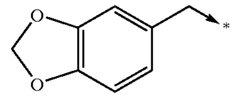
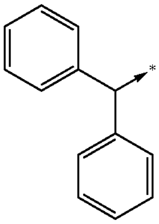
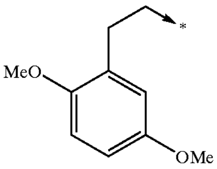
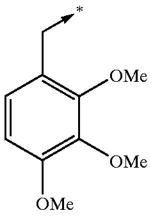
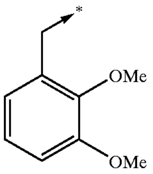
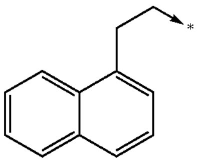
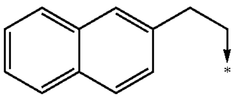
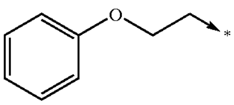
R2 groups
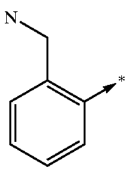
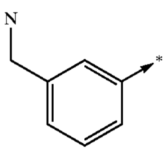
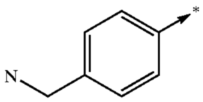
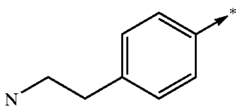
R3 and R4 groups such as those of method A Method C Synthesis of 2-arylimino-1,3-thiazole-4(3H)-carboxamides

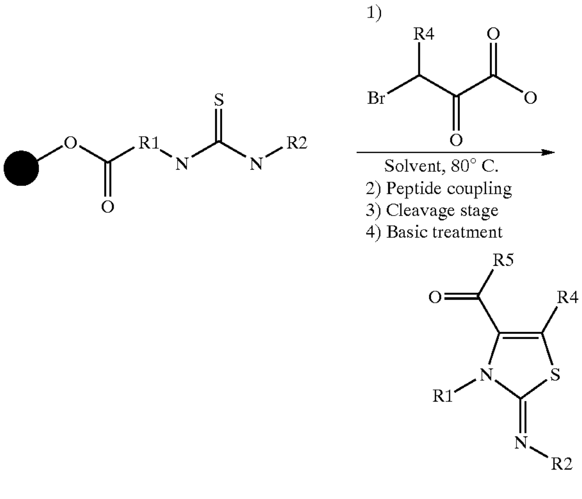

General procedure: a regioselective cyclization stage using α-bromopyruvic acid (2–5 eq.) is carried out starting from the thiourea resin prepared in the method A in aprotic solvents such as dioxane or DMF at 80° C. for 2–3 hours. The resin is then washed successively with DMF, methanol and DCM then dried under reduced pressure. The peptide coupling (Knorr, R.; Trzeciak, A.; Bannwarth, W.; Gillessen, D. *Tetrahedron Lett.* 989, 30, 1927–1930) takes place in DMF at ambient temperature for 1–24 hours with different standard coupling agents (4–5 eq.) such as dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds (4–5 eq.). The 2-arylimino-1,3-thiazole-4(3H)-carboxamide resin is cleaved by treatment under acid conditions (DCM/trifluoroacetic acid to 50%) for 1–2 hours then rinsed with DCM. The solvent is evaporated off and the free base is isolated after treatment under basic conditions (saturated solution of sodium hydrogen carbonate), extraction is carried out with DCM or elution with methanol in a basic alumina cartridge (500 mg, Interchim).

EXAMPLE 3

3-(4-aminobutyl)-N-benzhydryl-2-[(4-bromophenyl)imino]-1,3-thiazole-4(3H)-carboxamide ($C_{27}H_{27}BrN_4OS$, MM=535.51):

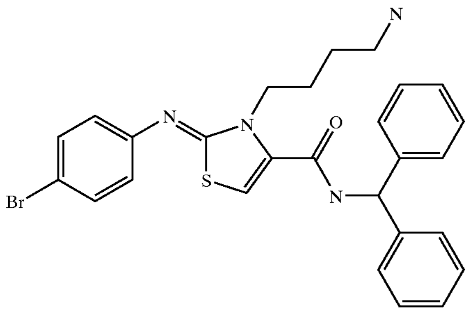

50 mg (27.5 μmol, load of 0.55 mmol/g) of carboxylic acid resin is activated for 15 minutes with 14.8 mg (0.11 mmol, 4 eq.) of N-hydroxybenzotriazole and 35.3 mg (0.11 mmol, 4 eq.) of TBTU in 800 μl of anhydrous DMF. 20.7 mg (0.11 mmol, 4 eq.) of aminodiphenylmethane dissolved in 200 μl of anhydrous DMF is then added and the resin is filtered after stirring overnight at ambient temperature. A sequential washing with DMF (5×1 ml), methanol (5×1 ml) and DCM (5×1 ml) produces a resin which is treated for one hour and 30 minutes under acid conditions (DCM/trifluoroacetic acid at 50%). The resin is rinsed with DCM (5×1 ml) and the filtrate evaporated under reduced pressure. The residue, taken up in methanol, is eluted in a basic alumina cartridge (500 mg, Interchim) in order to produce a pale yellow solid (8.2 mg; yield of 55.7%; UV purity of 94% at 220 nm).

NMR $^1H$ (DMSO D6, 100 MHz, δ): 9.6 (d; 1H; J=8.6 Hz; NH); 7.49 (d; 2H; J=8.6 Hz); 7.35 (s; 10H); 6.92 (s; 1H; H azole); 6.91 (d; 2H; J=8.5 Hz); 6.27 (d; 1H; J=8.5 Hz; NHCH); 4.02 (m; 2H; $NCH_2$); 3.45 (broad m; 2H+2H; $NH_2$ and $NCH_2$); 1.55–1.24 (broad m; 4H). MS/LC: m/z=535 (M+H).

A series of 2-arylimino-1,3-thiazole-4(3H)-carboxamides was synthesized according to method C using our robotic system (ACT MOS 496):

R1 and R2 groups already described in method A;

R3=—CO—R5;

R4=H;

R5 groups

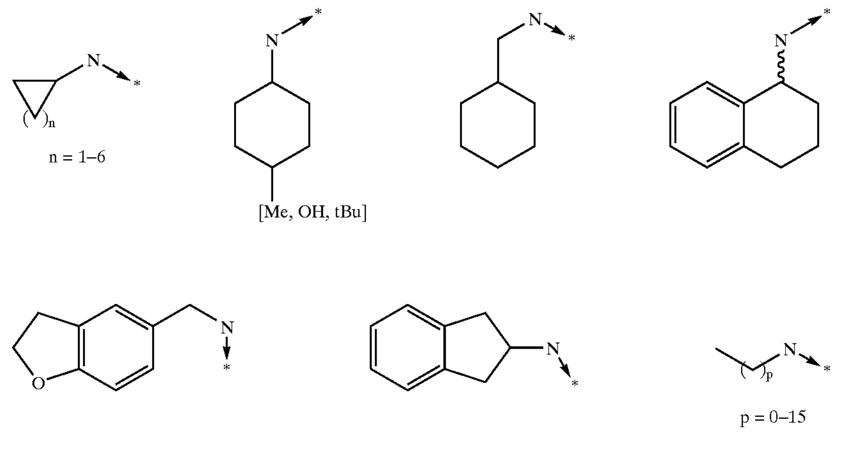

-continued
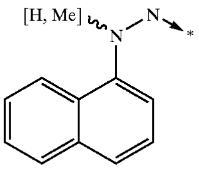
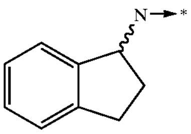
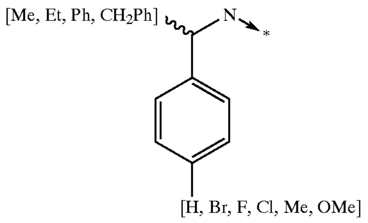
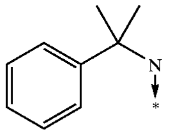
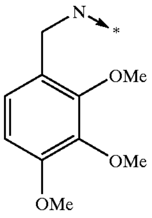
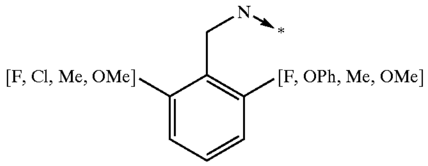
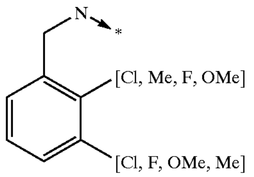
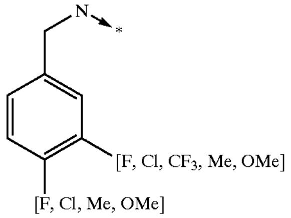
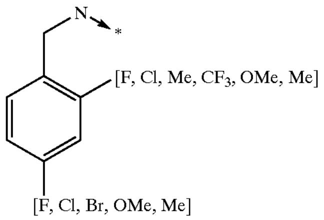
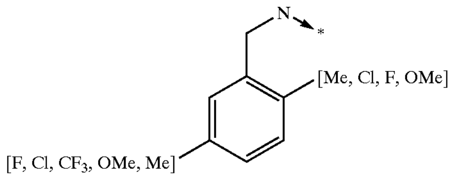
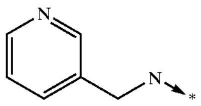
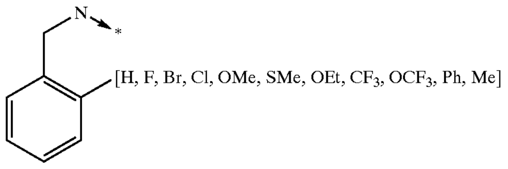
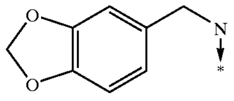
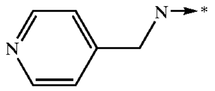
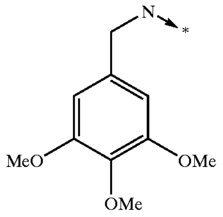
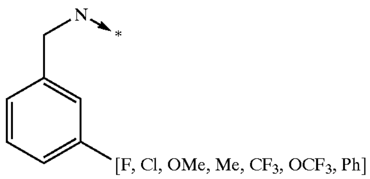
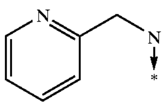
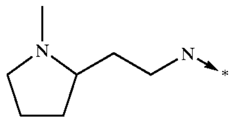
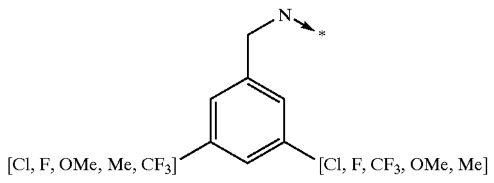
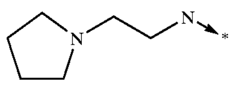

-continued
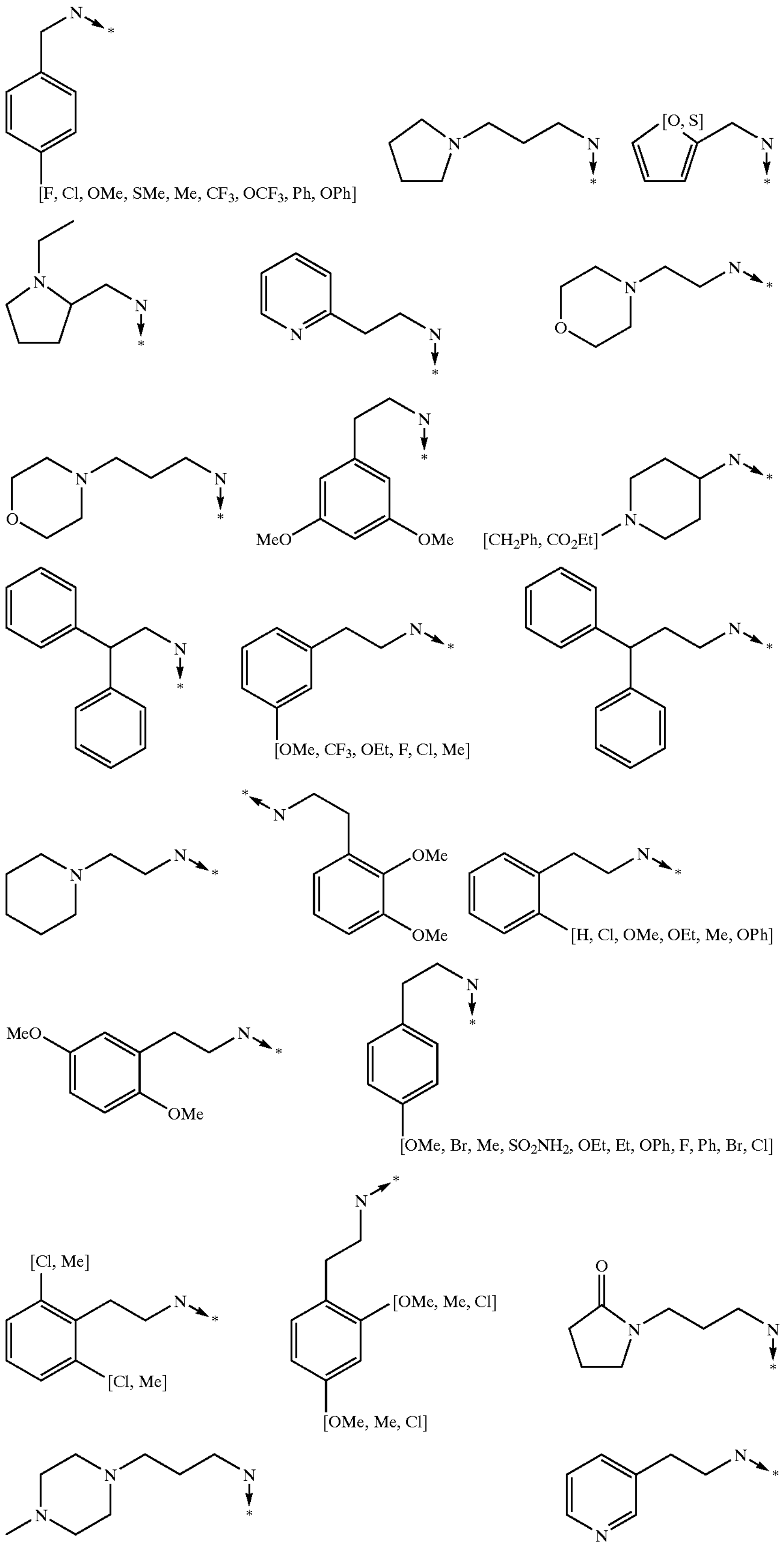

-continued
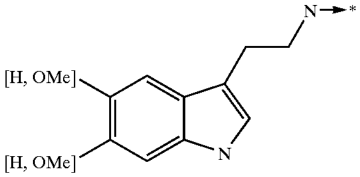
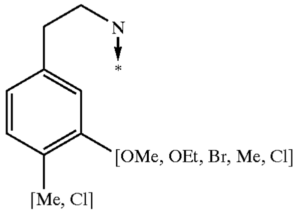
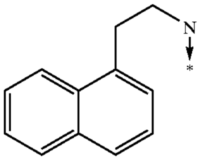
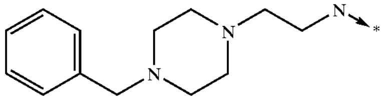
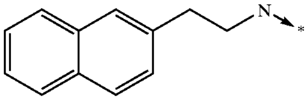
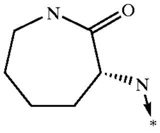
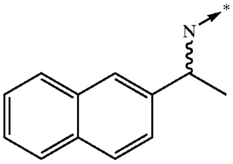
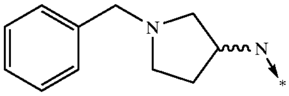
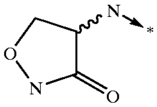
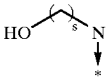
s = 2–6
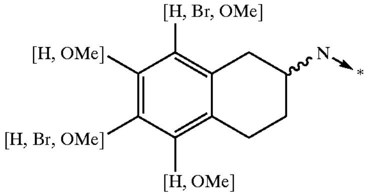
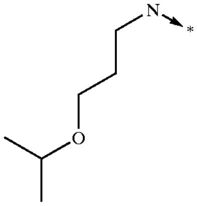
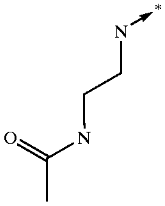
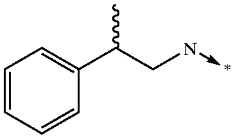
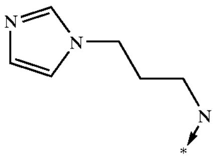
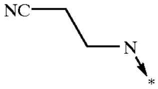
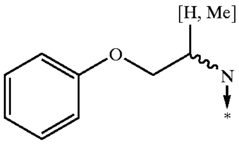
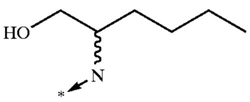
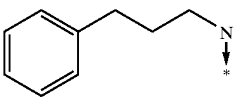
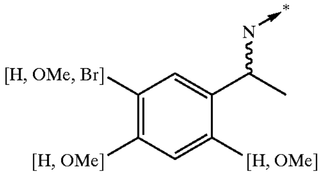
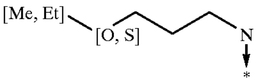
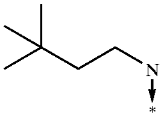
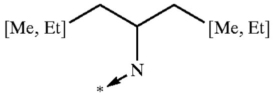
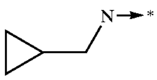
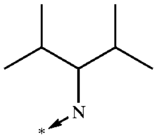

-continued
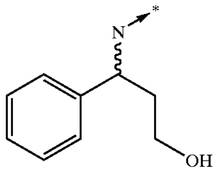
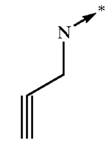
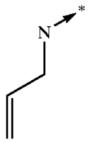
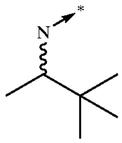
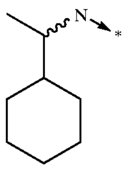
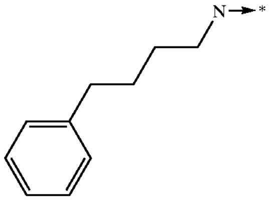
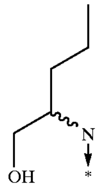
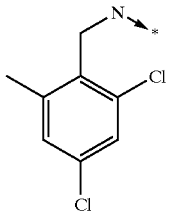
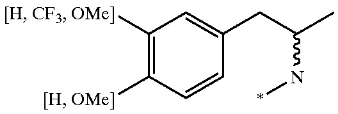
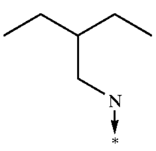
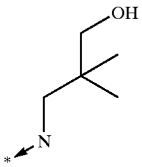
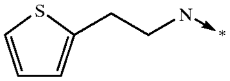
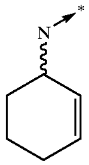
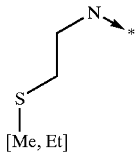
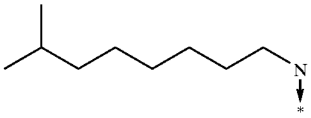
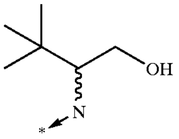
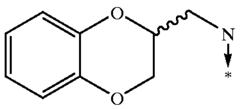
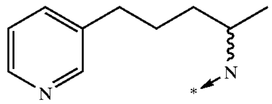
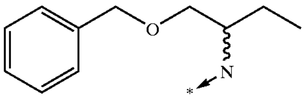
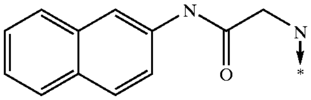
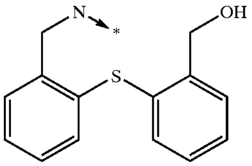
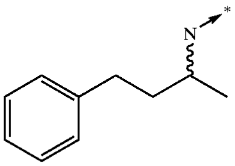
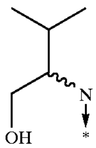
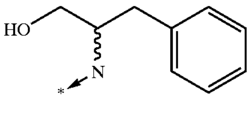
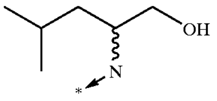
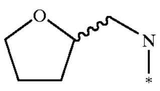
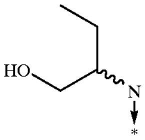
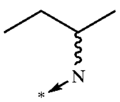
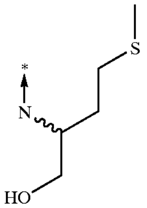
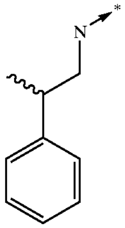

-continued
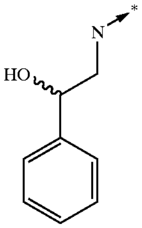
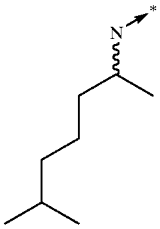
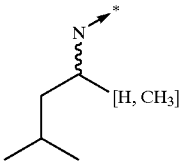
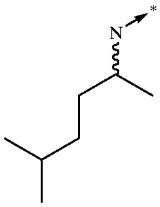
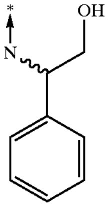
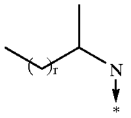
r = 0–6
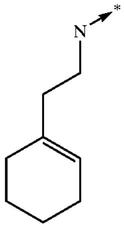
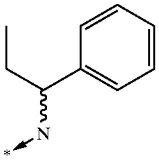
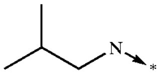
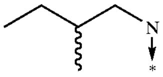
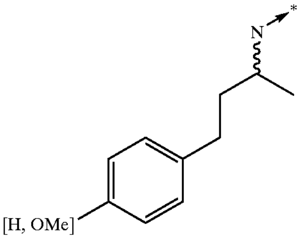
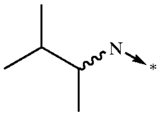
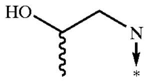
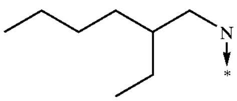
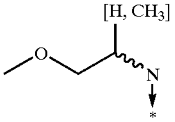
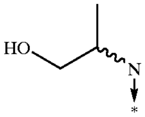
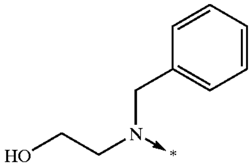
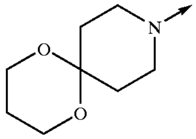
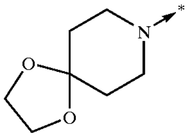
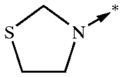
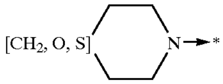
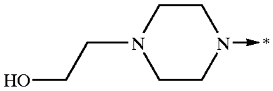
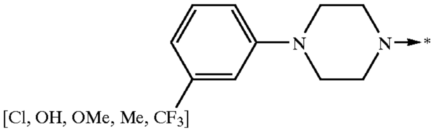
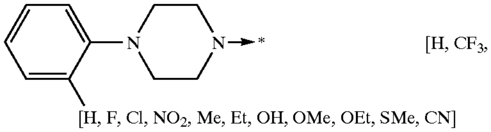
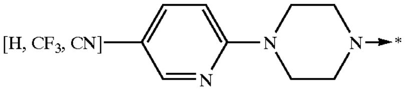
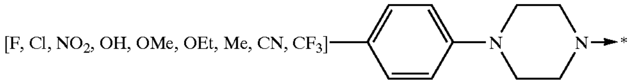
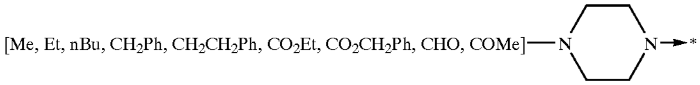

-continued
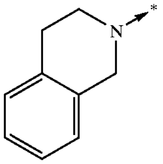
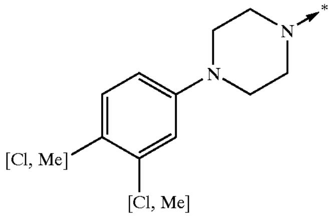
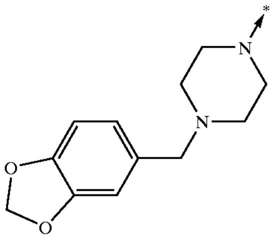
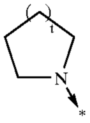
t = 0–4
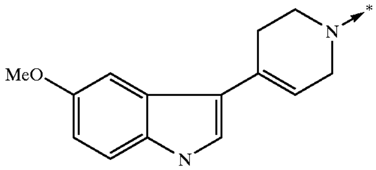
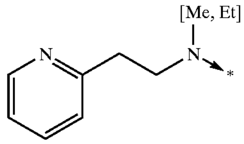
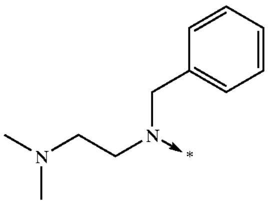
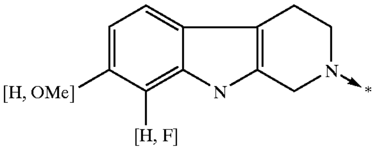
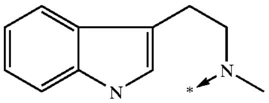
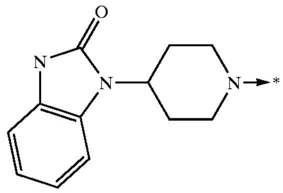
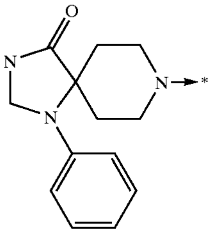
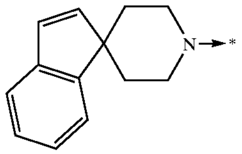
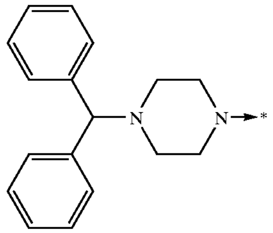
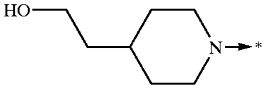
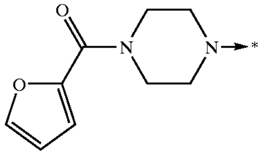
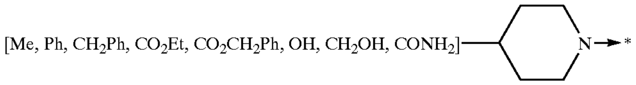
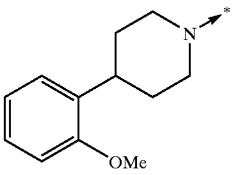
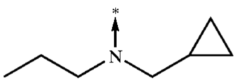
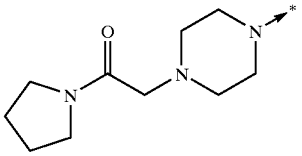
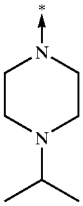
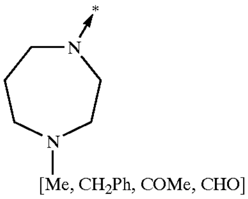
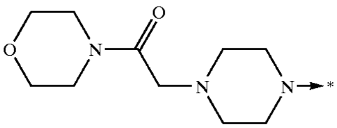

-continued
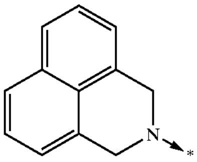
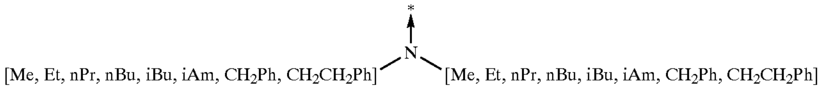
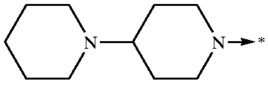
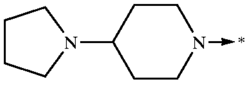
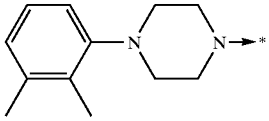
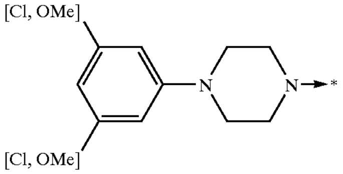
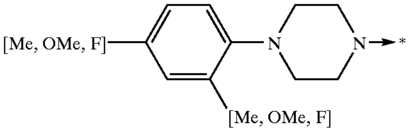
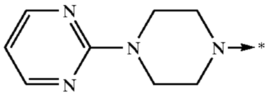
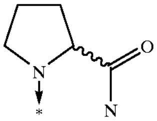
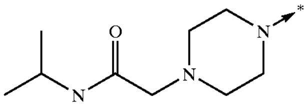
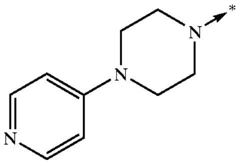
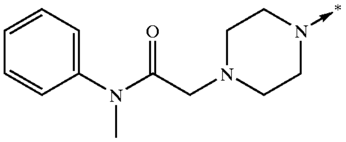
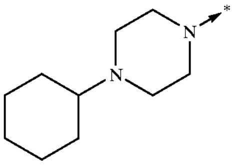
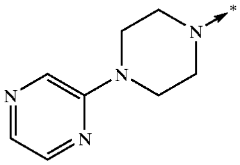
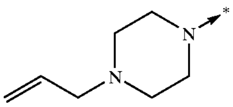
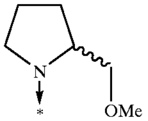
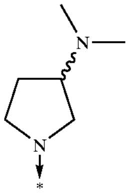
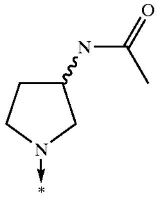
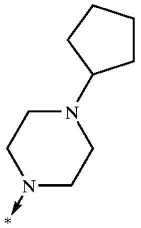
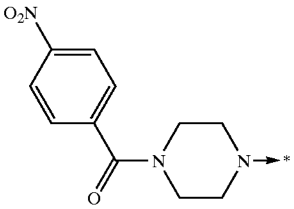
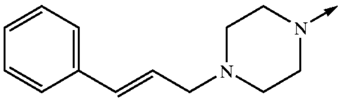
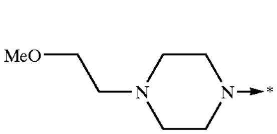
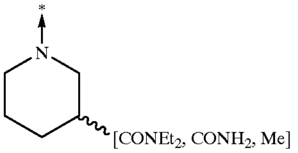

-continued
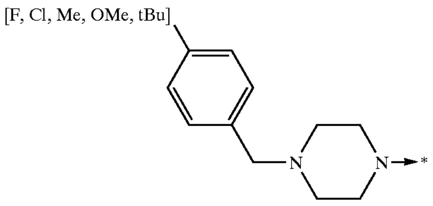
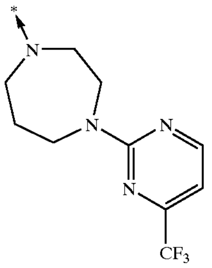
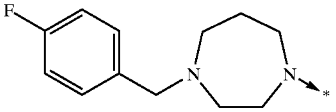
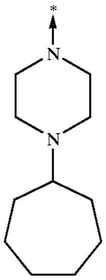
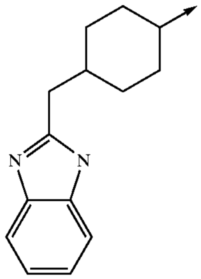
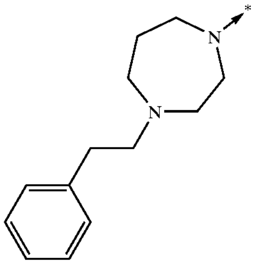
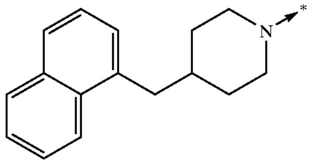
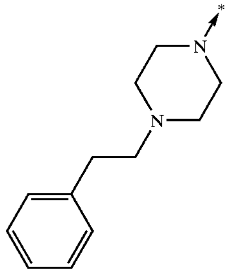
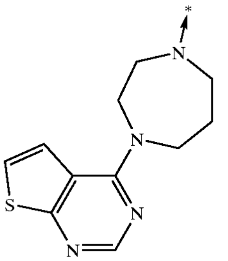
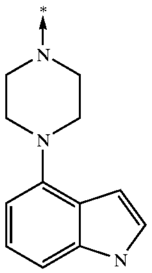
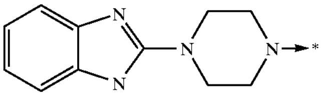
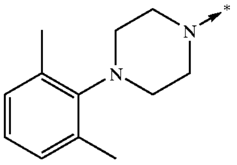
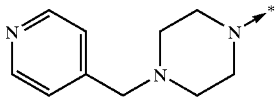
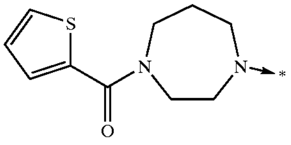
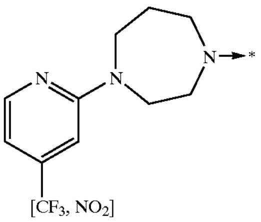
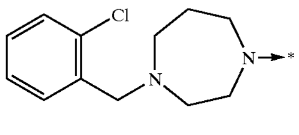
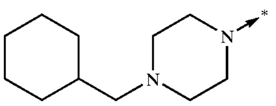
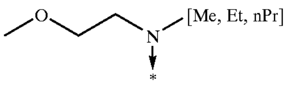

-continued

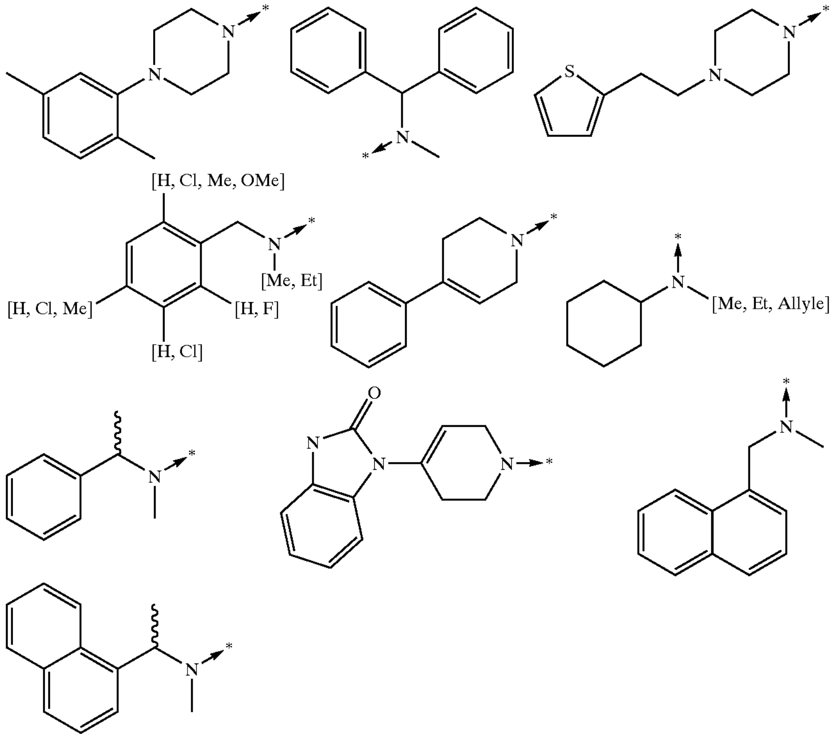

Method D
Synthesis of 2-arylimino-1,3-thiazole-4(3H)-carboxamides

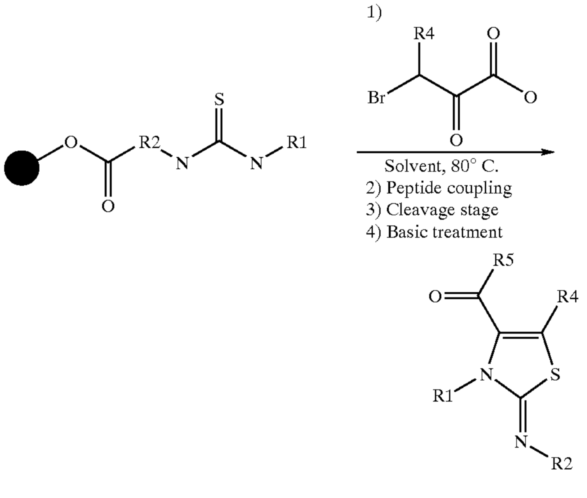

General procedure: a regioselective cyclization stage using α-bromopyruvic acid (2–5 eq.) is carried out starting from the thiourea resin prepared in method B in aprotic solvents such as dioxane or DMF at 80° C. for 2–3 hours. The resin is then successively washed with DMF, methanol and DCM then dried under reduced pressure. The peptide coupling (Knorr, R.; Trzeciak, A.; Bannwarth, W.; Gillessen, D. *Tetrahedron Lett.* 1989, 30, 1927–1930) takes place in DMF at ambient temperature for 1–24 hours with different standard coupling agents (4–5 eq.) such as dicyclohexylcarbodiimide (DCC), diisopropylcarbodiimide (DIC), a DIC/N-hydroxybenzotriazole (HOBt) mixture, benzotriazolyloxytris(dimethylamino)phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU) and aminated compounds (4–5 eq.). The 2-arylimino-1,3-thiazole-4(3H)-carboxamide resin is cleaved by treatment under acid conditions (DCM/trifluoroacetic acid at 50%) for 1–2 hours then rinsed with DCM. The solvent is evaporated off and the free base is isolated after treatment under basic conditions (saturated solution of sodium hydrogen carbonate) followed by an extraction with DCM or elution with methanol in a basic alumina cartridge (500 mg, Interchim).

EXAMPLE 4

(2Z)-2 {[4-(2-aminoethyl)phenyl]imino}-N-(4-chlorobenzyl)-3-(2-phenylethyl)-2,3-dihydro-1,3-thiazole-4-carboxamide ($C_{27}H_{27}ClN_4OS$, MM=491.05):

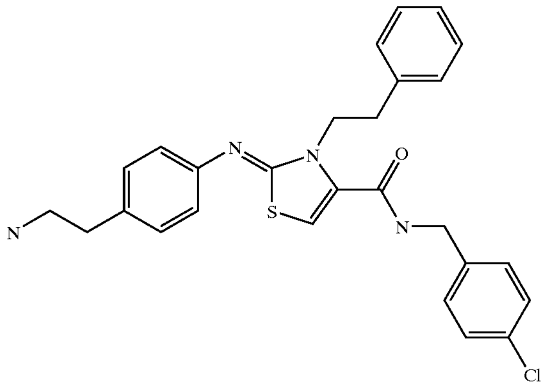

Phenylethylisothiocyanate (310 mg; 1.9 mmol; 10 eq.) in 3 ml of dimethylformamide is added to 200 mg (190 μmol, load of 0.946 mmol/g) of aminated resin (see Preparation 20). Stirring overnight at ambient temperature produces a negative Kaiser ninhydrin test. The resin is then successively washed with DMF (5×3 ml) and DCM (5×3 ml) then dried under vacuum for one hour before adding bromopyruvic acid (63.4 mg; 380 μmol; 2 eq.) diluted beforehand in 3 ml of dimethylformamide. The mixture is stirred for 2.5 hours at 80° C. The resin is filtered and washed with DMF (5×3 ml), methanol (3×3 ml) then DCM (5×3 ml). The carboxylic acid resin is preactivated for 1 hour with 244 mg (0.76 mmol; 4 eq.) of TBTU diluted in 2 ml of anhydrous DMF. 110 mg (0.76 mmol; 4 eq.) of 4-chlorobenzylamine dissolved in 1 ml of anhydrous DMF is then added and the resin is filtered after stirring overnight at ambient temperature. Sequential washing with DMF (5×3 ml), methanol (3×3 ml) and DCM (3×3 ml) produces a resin which is treated for one hour and 30 minutes under acid conditions (DCM/trifluoroacetic acid at 50%). The resin is rinsed with DCM (5×1 ml) and the filtrate evaporated under reduced pressure. The residue, taken up in DCM, is neutralized with a saturated solution of sodium hydrogen carbonate in order to produce after evaporation a solid (38.2 mg; yield of 41%; UV purity of % to).

NMR $^1$H (DMSO D6, 400 MHz, δ): 9.1 (m, 1H); 7.39 (d, 2H, J=8.4 Hz); 7.33 (d, 2H, J=8.4 Hz); 7.25 (q, 2H, J=6.8 Hz); 7.19 (q, 1H, J=7.2 Hz); 7.11 (m, 4H); 6.8 (d, 2H, J=8 Hz); 6.75 (s, 1H, H azole); 4.34 (d, 2H, J=6 Hz); 4.27 (t, 2H, J=6.8 Hz); 3.14 (m, 1H); 2.89 (t, 2H, J=6.8 Hz); 2.73 (t, 1H, J=7.2 Hz); 2.62 (m, 2H). MS/LC: m/z=491.24 $(M+H)^{30}$ .

A series of 2-arylimino-1,3-thiazole-4(3H)-carboxamides was synthesized according to method D using our robotic system (ACT MOS 496):

R1 and R2 groups already described in method B

R3=—CO—R5

R4=H

R5 groups already described in method C.

Method E

Preparation of Monoprotected Diamine Resin Functionalized with α-bromopyruvic Acid

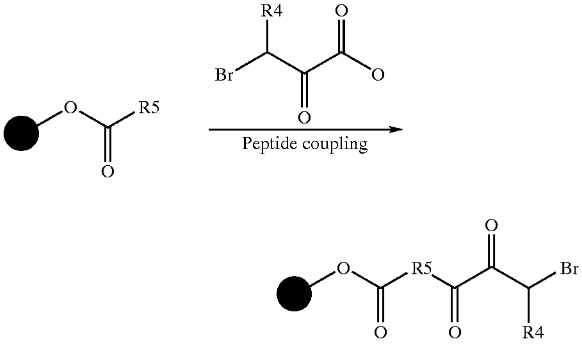

General procedure: the monoprotected symmetrical primary or secondary diamine resin (the preparation of which is already described in method A) is functionalized by peptide coupling with α-bromopyruvic acid (10 eq.), DIC (10 eq.) and HOBt (10 eq.) in a solvent such as DMF at ambient temperature. The resin is washed successively with DMF then with DCM after 2 to 24 hours of stirring before being dried under vacuum. The negative Kaiser ninhydrin test indicates a complete functionalization.

Preparation 22

N-carbamate of 2-[(3-bromo-2-oxopropanoyl)amino]ethyl Wang Resin

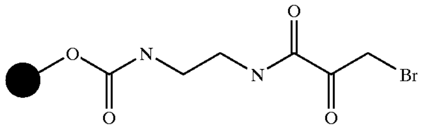

HOBt (0.93 g, 6.88 mmol) and α-bromopyruvic acid (1.18 g, 6.88 mmol) are dissolved in 28 ml of DMF (0.5 M). DIC (1.07 ml; 6.88 mmol) is then added by syringe to activate the acid. The mixture is stirred for approximately 15 minutes at ambient temperature before adding it to the N-carbamate of ethylene diamine Wang resin (0.8 g; 0.688 mmol; load rate 0.86 mmol/g). After stirring for 3 hours at ambient temperature, the Kaiser ninhydrin test being negative, the resin is filtered and washed successively with DMF (5×20 ml) then with DCM (5×20 ml) before being dried under vacuum. An ochre resin (0.812 g) is obtained with a load rate of 0.525 mmol/g calculated from elemental analysis of the bromine.

Synthesis of 2-arylimino-1,3-thiazole-4(3H)-carboxamides

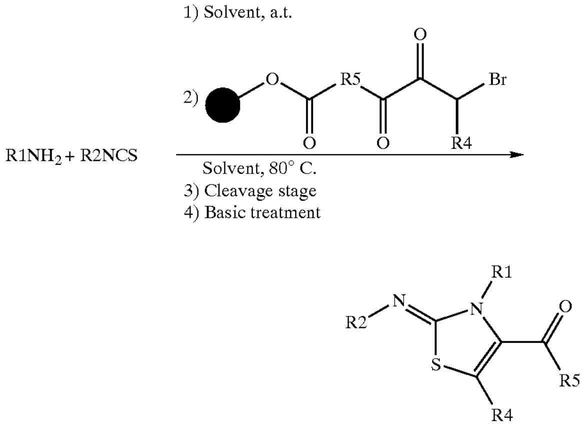

General procedure: formation of the thiourea is carried out in a solvent such as DMF or dioxane by mixing an equimolar quantity of primary amine and aromatic or heteroaromatic isothiocyanate. After stirring for 2 to 24 hours at ambient temperature, the thiourea (2 to 5 eq.) is added to the functionalized resin then heated at 80° C. for 2 to 4 hours. The 2-arylimino-1,3-thiazole-4(3H)-carboxamide resin is cleaved by treatment under acid conditions (DCM/trifluoroacetic acid at 50%) for 1–2 hours then rinsing with DCM. The solvent is evaporated off and the free base isolated after treatment under basic conditions (saturated solution of sodium hydrogen carbonate), extraction with DCM or elution with methanol in a basic alumina cartridge (500 mg, Interchim).

EXAMPLE 5

(2Z)-N-(2-aminoethyl)-3-[2-(3,4-dimethoxyphenyl)ethyl]-2-(phenylimino)-2,3-dihydro-1,3-thiazole-4-carboxamide ($C_{22}H_{26}N_4O_3S$, MM=426.54):

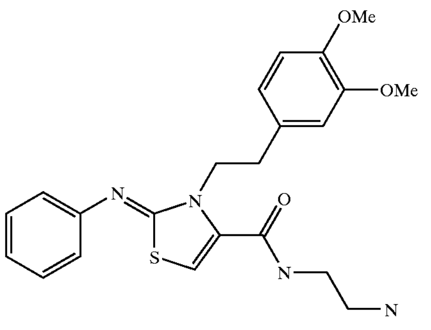

18 μl (105 μmol; 2 eq.) of β-(3,4-dimethoxyphenyl)ethylamine and 12.6 μl (105 μmol; 2 eq.) of phenylisothiocyanate are stirred in 1 ml of DMF for 18 hours. The thiourea is added to 100 mg (52.5 μmol; load rate of 0.525 mmol/g) of resin (Preparation 22) and the mixture heated at 80° C. for 3 hours. The resin is then filtered then washed successively with DMF (5×1 ml), methanol (5×1 ml) then DCM (5×1 ml). The resin is dried under vacuum before adding 1 ml of a 50% DCM/TFA mixture. Stirring is carried out for 1.5 hours at ambient temperature, the resin is filtered and rinsed with DCM. The residue recovered after evaporation is then eluted with methanol in a basic alumina cartridge in order to isolate 22.2 mg (quantitative yield; UV purity of 93.4% at 230 nm) of a brown solid corresponding to the free amine.

NMR $^1H$ (DMSO D6, 100 MHz, δ): 8.42 (m, 1H, NH); 7.32 (t, 2H, J=7.1 Hz); 7.08–6.63 (m, 6H); 5.76 (s, 1H, H azole); 4.31 (t, 2H, J=6.6 Hz); 3.72 (s, 6H, $OCH_3$); 3.32 (broad s, 2H); 3.17 (mn, 2H); 2.89 (m, 2H); 2.62 (m, 2H). MS/LC: m/z=427.17 $(M+H)^+$.

A series of 2-arylimino-1,3-thiazole-4(3H)-carboxamides was synthesized according to method E using our robotic system (ACT MOS 496):

R1 groups:

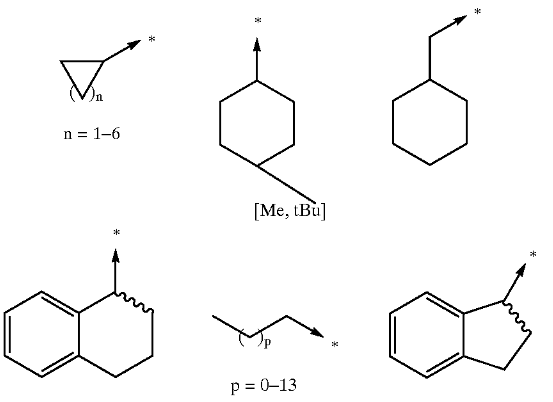

-continued

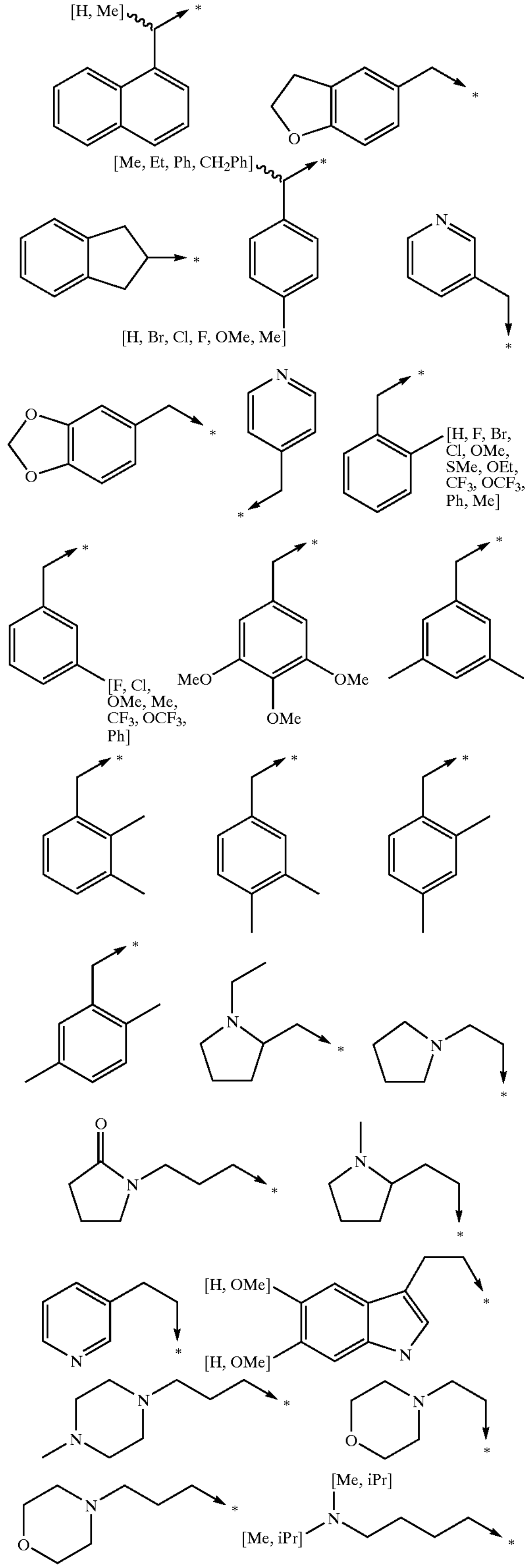

-continued
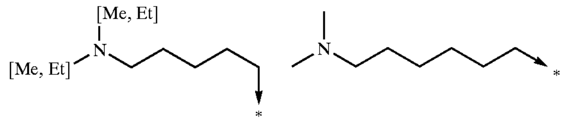
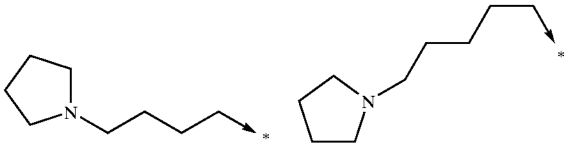
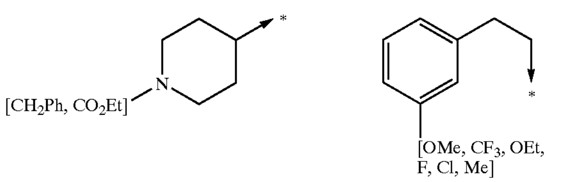
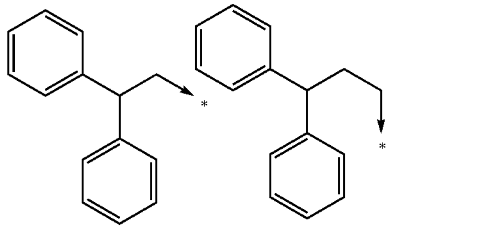
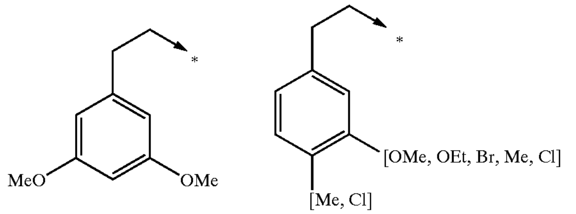
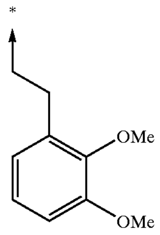
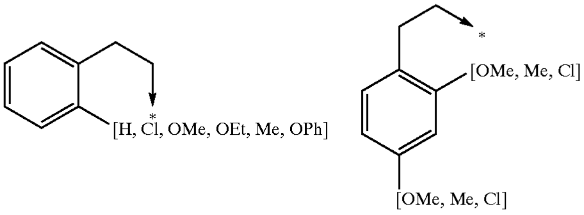
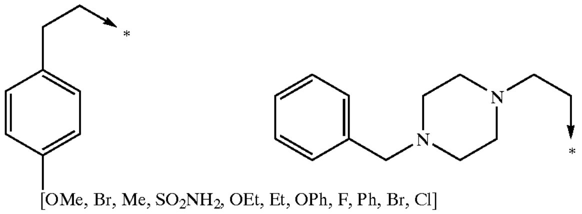
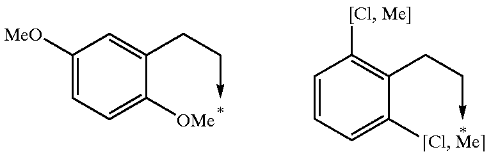
-continued
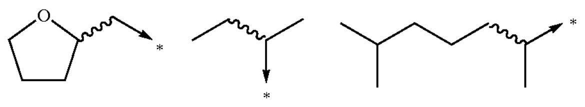
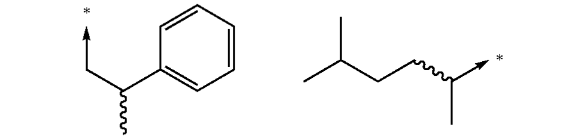
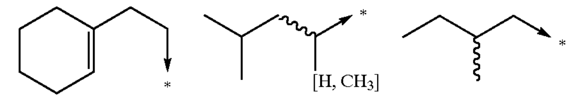
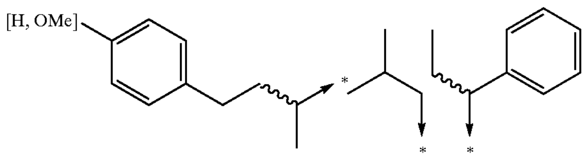
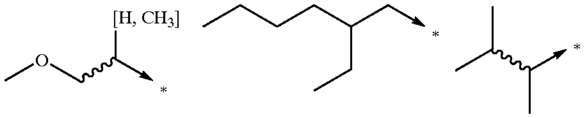
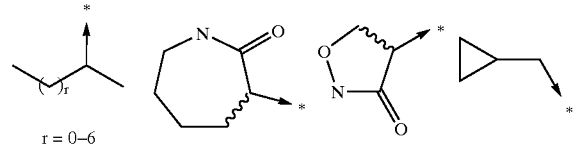
r = 0–6
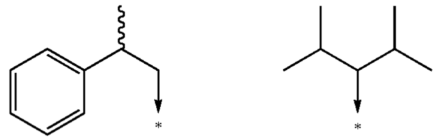
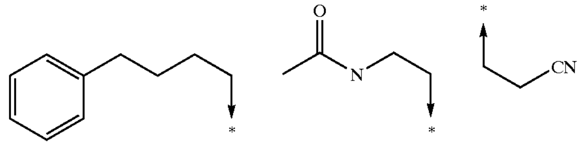
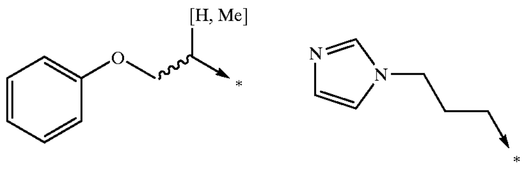
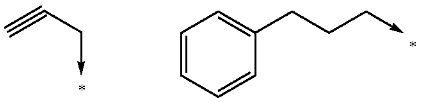
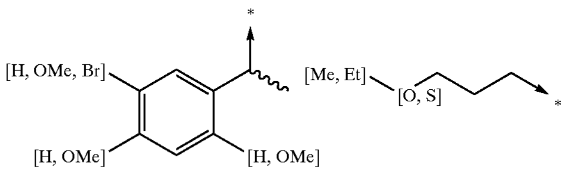
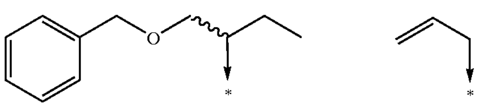

-continued

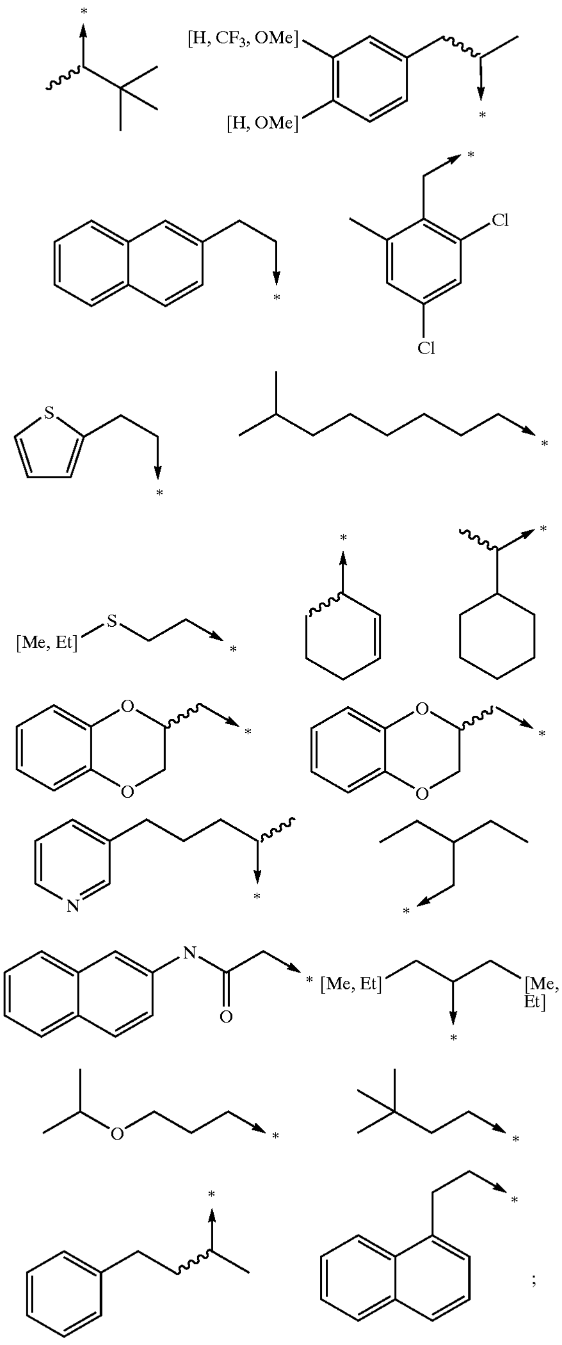

R2 groups already described in method A

R3=—CO—R5

R4=H

R5 groups:

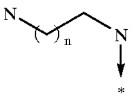

n = 1–6

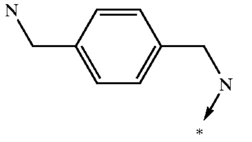

-continued

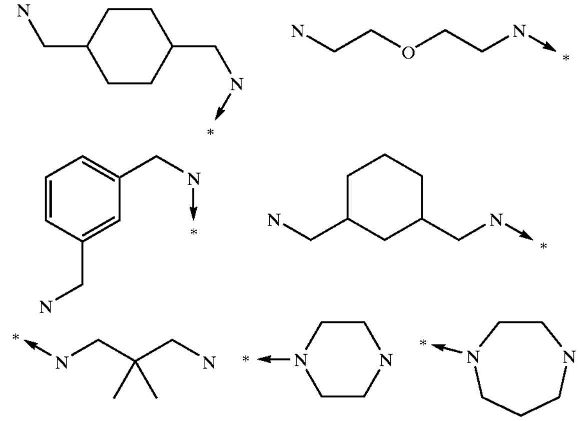

Method F

Preparation of Monoprotected Diamine Resins Functionalized with N-protected Amino Acids (Fmoc)

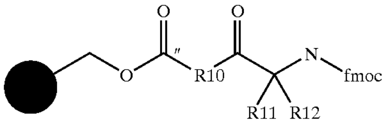

General procedure: the peptide coupling of the monoprotected diamine resins with N-Fmoc amino acids (4 to 10 eq.) which are commercially available (Bunin, B. A. *The Conmbinatorial Index,* Academic Press, 1998, p. 77–82) is carried out in DMF at ambient temperature for 1 to 24 hours with different standard coupling agents (4 to 10 eq.) such as dicyclohexylcarbodiimide (DCC), diisopropylcarbodiimide (DIC), a DIC/N-hydroxybenzotriazole (HOBt) mixture, benzotriazolyloxytris(dimethylamino) phosphonium hexafluorophosphate (PyBOP), 2-(1H-benzotriazol-1-yl)-1,1,3,3-tetramethyluronium hexafluorophosphate (HBTU) or 2-(1H-benzotriazol-1-yl)-1,1,3,3-tetramethyluronium tetrafluoroborate (TBTU). The resin is then washed successively with DMF and DCM. The coupling sequence can be repeated (1 to two times) until the Kaiser ninhydrin test is negative.

Preparation 23

N-carbamate of 4-[({[(9H-fluoren-9-ylmethoxy)carbonyl]amino}acetyl)amino]butyl Wang Resin

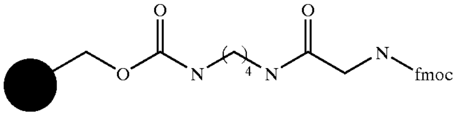

The Fmoc-Gly-OH acid (2.36 g, 7.94 mmol) is activated with HOBt (1.07 g, 7.94 mmol) and of the DIC (1.25 ml, 7.94 mmol) in 22 ml of DMF for 5 minutes before adding the mixture to butylamine N-carbamate Wang resin (1 g, load rate of 0.794 mmol/g) preswollen in 10 ml of DMF. After stirring for 18 hours at ambient temperature, the resin is washed successively with DMF (5x20 ml) then with DCM (5x20 ml ) before being dried under vacuum. 1.27 g of pale yellow resin is thus obtained presenting a negative Kaiser ninhydrin test.

Preparation of the Thiourea Resins

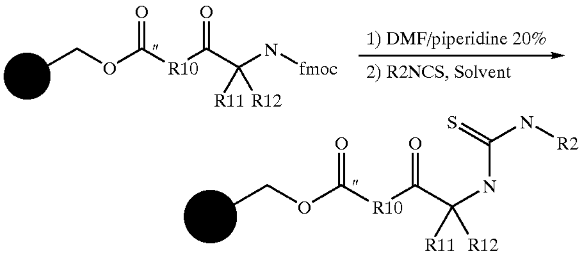

General procedure: a resin described above is deprotected with a 20% DMF/piperidine mixture. After stirring for one hour at ambient temperature, the resin is filtered and washed successively with DMF then with DCM. The deprotection/washing sequence is repeated a second time and the resin is dried under vacuum. The latter is preswollen in a solvent such as DMF or DCM then an aromatic or heteroaromatic isothiocyanate (5 to 10 eq.) is added. The mixture is stirred for 2 to 24 hours at ambient temperature before the resin is filtered and washed successively with DMF then with DCM. The resin is then dried under vacuum and a negative Kaiser ninhydrin test confirms that the substitution reaction is complete.

Preparation 24

4-[({[(1-naphthylamino)carbothioyl]amino}acetyl)amino] butyl N-carbamate Wang Resin

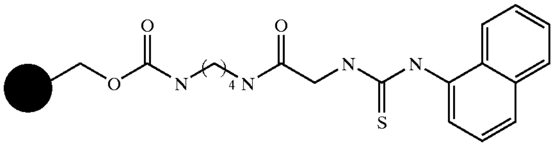

1.27 g of the above resin (see Preparation 23) is deprotected with 14 ml of DMF/piperidine at 20%. The mixture is stirred for one hour at ambient temperature. The resin is then filtered then washed with DMF (5x30 ml) then with DCM (5x30 ml). The deprotection/washing sequence is repeated once before the resin is dried under vacuum. 0.781 g of pale yellow resin was thus obtained with a load rate of 0.758 mmol/g calculated after elemental analysis of the sulphur. 416 mg (2.2 mmol, 10 eq.) of 1-naphthylisothiocyanate diluted in 6 ml of DMF is added to 0.3 g (0.22 mmol) of this thiourea resin. The mixture is stirred for 18 hours at ambient temperature. The resin is filtered then washed successively with DMF (5x20 ml) then with DCM (5x20 ml). 310 mg of a pale resin yellow is isolated after drying under vacuum with a load rate of 0.66 mmol/g calculated after elemental analysis of the nitrogen.

Synthesis of 2-arylimino-2,3-dihydrothiazoles

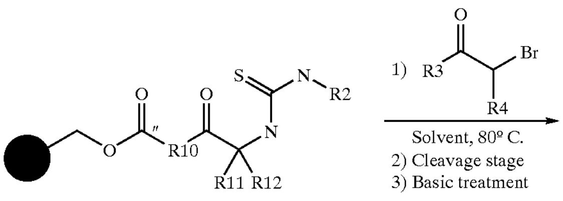

-continued

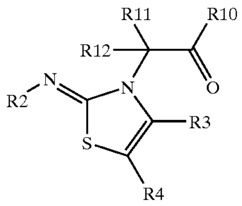

General procedure: the regioselective cyclization stage is carried out in aprotic solvents such as dioxane, DMF or N-methylpyrrolidinone at 80° C. for 2 to 3 hours between the thiourea resin and the α-bromoketone (2 to 5 eq.). The resin is then washed successively with DMF, methanol and DCM then dried under reduced pressure. The 2-arylimino-2,3-dihydrothiazole resin is cleaved under acid conditions (DCM/trifluoroacetic acid at 50%) for 1 to 2 hours then rinsed with DCM. The solvent is evaporated off and the free base isolated after treatment under basic conditions (saturated solution of sodium hydrogen carbonate) followed by an extraction with DCM or elution with methanol in a basic alumina cartridge (500 mg, Interchim).

EXAMPLE 6

N-(4-aminobutyl)-2-((2Z)-4-(4-chlorophenl)-2-(1-naphthylimino)-1,3-thiazol-3-thiazol-3(2H)-yl) acetamide ($C_{25}H_{25}ClN_4OS$, MM=465.02):

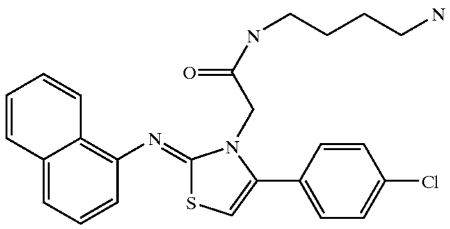

80 mg (52.8 μmol, load rate of 0.66 mmol/g) of thiourea resin (Preparation 24) and 25.1 mg (105.6 mmol, 2 eq.) of 2-bromo-4'-chloroacetophenone are diluted in 1 ml of DMF. The mixture is heated at 80° C. for 2 hours. The resin is filtered then washed with DMF (5x1 ml), methanol (5x1 ml) then DCM (5x1 ml) before being dried under vacuum. 1 ml of a 50% DCM/TFA mixture is added followed by stirring for 1 hour 30 minutes. The resin is filtered and rinsed with DCM. The filtrate is evaporated then rediluted in methanol for elution on basic alumina. 20.6 mg (yield of 84%; UV purity of 94.2% at 220 nm) of yellow solid is thus isolated after evaporation corresponding to the free base.

NMR $^1H$ (DMSO D6, 100 MHz, δ): 8.36 (t, 1H, J=4.7 Hz, NH); 8.12 (dd, 1H, J=2.1 and 7.3 Hz); 7.87 (dd, 1H, J=2.7 and 6.3 Hz); 7.63–7.34 (m, 8H); 7.13 (dd, 1H, J=1.61 and 6.7 Hz); 6.33 (s, 1H, H azole); 4.44 (broad s, 2H); 3.14 (m, 2H); 2.7 (m, 2H); 1.5 (m, 4H). MS/LC: m/z=465.21 $(M+H)^+$.

A series of 2-arylimino-2,3-dihydrothiazoles was synthesized according to method F using our robotic system (ACT MOS 496):

R1=—C(R11R12)—CO—R10

R2, R3 and R4 groups already described in method A

R10 groups:

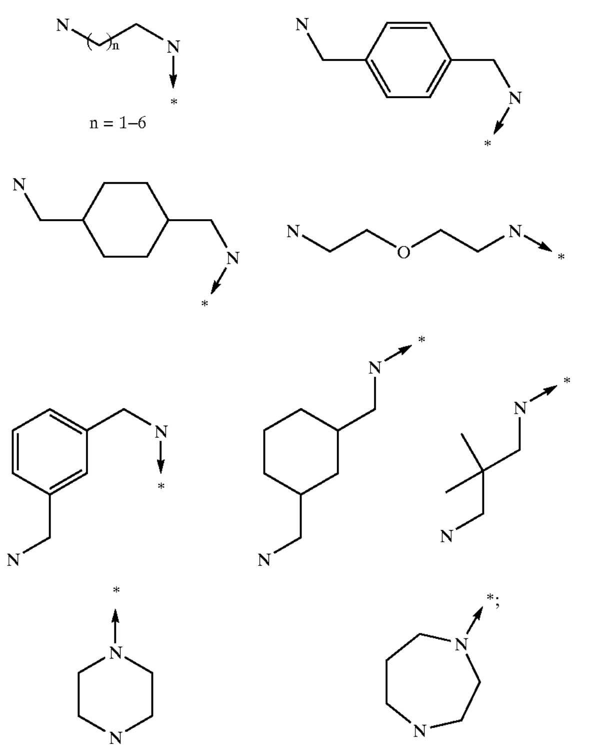

R11=H

R12 groups:

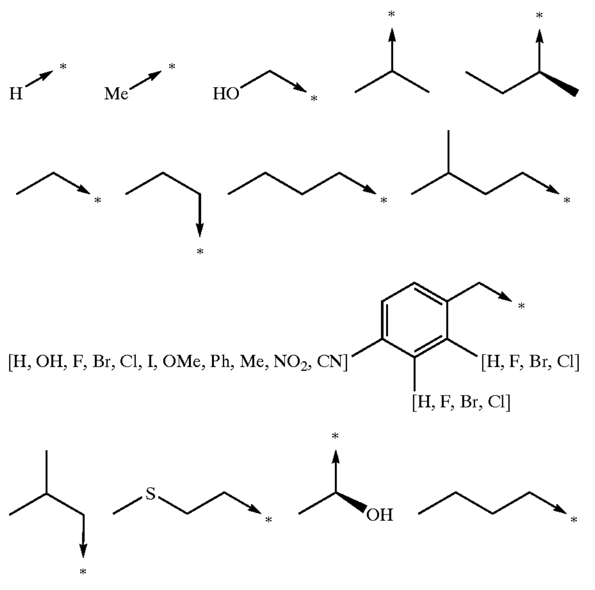

-continued

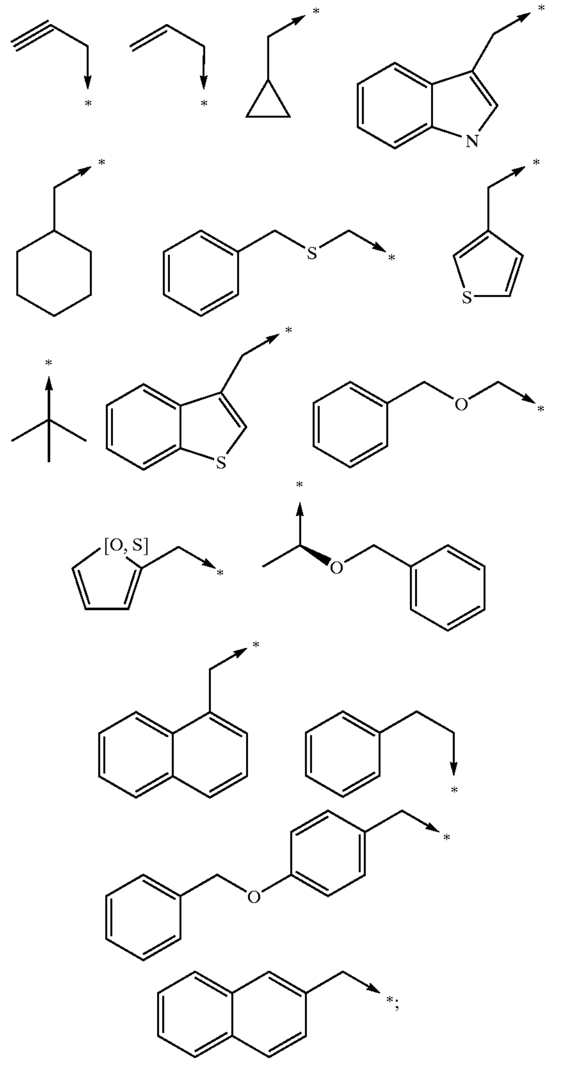

EXAMPLES

Examples obtained according to methods A, B, C, D, E and F described above are shown below. These examples are presented to illustrate the above procedures and must in no case be considered as a limit to the scope of the invention.

The compounds obtained have been characterized by their retention times (rt) and by mass spectrometry $(M+H)^+$.

| Ex. | R2 | R3 | Purity (%) | rt (min.) | [M + H]$^+$ |
|---|---|---|---|---|---|
| | | 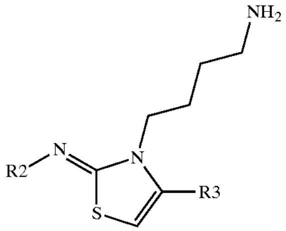 | | | |
| 7 | 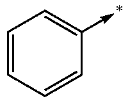 | 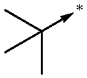 | 91.2 | 3.09 | 304.2 |
| 8 | 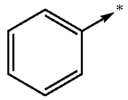 | 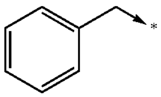 | 93.1 | 3.38 | 338.2 |
| 9 | 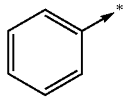 | 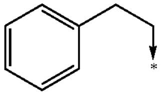 | 94 | 3.56 | 352.2 |
| 10 | 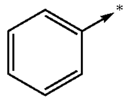 | 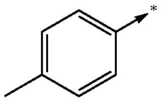 | 93.3 | 3.42 | 338.2 |
| 11 | 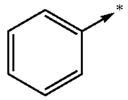 | 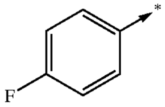 | 96.6 | 3.25 | 342.2 |
| 12 | 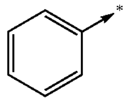 | 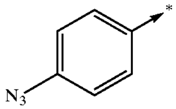 | 96.4 | 3.46 | 365.2 |

-continued
| | | | | | |
|---|---|---|---|---|---|
| 13 | 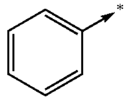 | 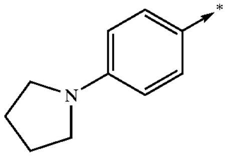 | 91.9 | 3.86 | 393.2 |
| 14 | 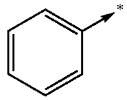 | 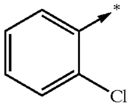 | 96.4 | 3.44 | 358.2 |
| 15 | 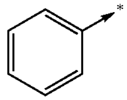 | 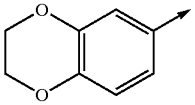 | 95.6 | 3.34 | 382.2 |
| 16 | 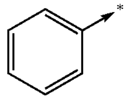 | 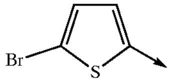 | 94.5 | 3.7 | 408 |
| 17 | 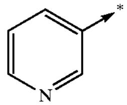 | 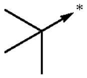 | 54.43 | 2.9 | 305.2 |
| 18 | 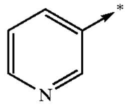 | 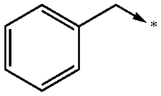 | 50.4 | 3.14 | 339.2 |
| 19 | 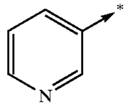 | 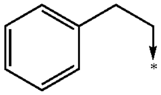 | 48.9 | 3.38 | 535.2 |
| 20 | 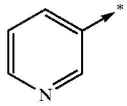 | 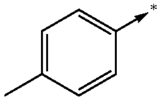 | 39.3 | 3.26 | 339.2 |

-continued
| | | | | | |
|---|---|---|---|---|---|
| 21 | 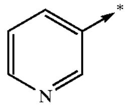 | 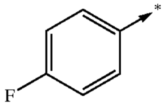 | 49.5 | 3.06 | 343.2 |
| 22 | 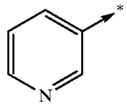 | 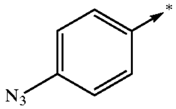 | 42.3 | 3.29 | 366.2 |
| 23 | 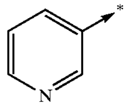 | 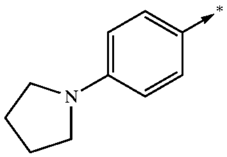 | 43.4 | 3.7 | 394.3 |
| 24 | 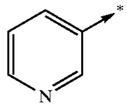 | 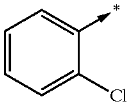 | 56.7 | 3.16 | 359.2 |
| 25 | 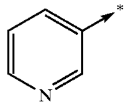 | 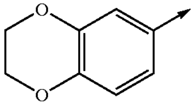 | 45.3 | 3.09 | 383.2 |
| 26 | 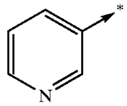 | 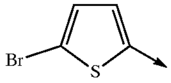 | 45.7 | 3.3 | 409 |
| 27 | 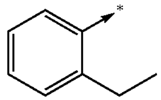 | 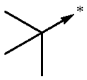 | 96.8 | 3.41 | 332.3 |
| 28 | 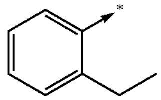 | 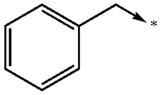 | 92.8 | 3.7 | 366.3 |

-continued
| | | | | | |
|---|---|---|---|---|---|
| 29 | 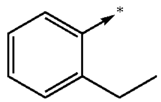 | 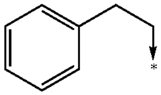 | 90.6 | 3.84 | 380.3 |
| 30 | 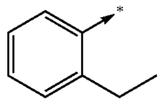 | 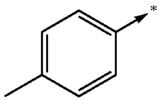 | 93.7 | 3.76 | 366.3 |
| 31 | 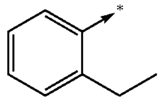 | 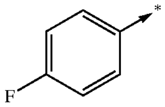 | 94.4 | 3.63 | 370.2 |
| 32 | 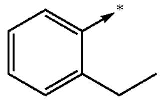 | 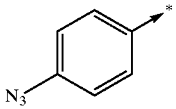 | 89.1 | 3.82 | 393.2 |
| 33 | 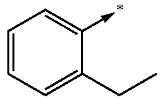 | 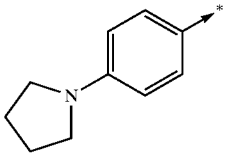 | 90.1 | 4.12 | 410.2 |
| 34 | 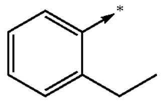 | 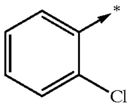 | 96.7 | 3.83 | 386.2 |
| 35 | 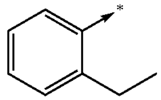 | 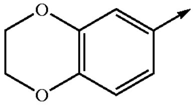 | 95.8 | 3.67 | 410.2 |
| 36 | 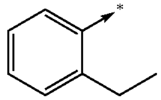 | 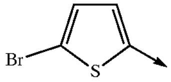 | 93.4 | 4.17 | 436.1 |

-continued
| | | | | | |
|---|---|---|---|---|---|
| 37 | 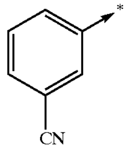 | 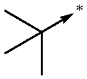 | 88.4 | 3.64 | 329.25 |
| 38 | 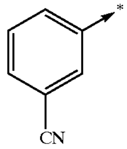 | 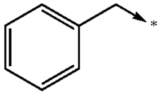 | 91.8 | 4.03 | 363.2 |
| 39 | 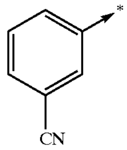 | 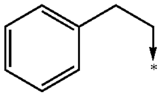 | 88.6 | 4.15 | 377.2 |
| 40 | 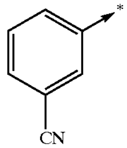 | 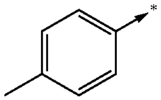 | 94.1 | 4.22 | 363.2 |
| 41 | 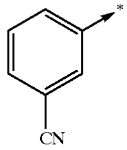 | 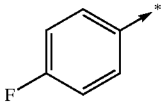 | 95.2 | 4.1 | 376.2 |
| 42 | 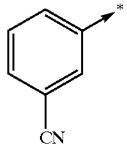 | 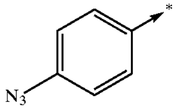 | 92.8 | 4.35 | 390.2 |

-continued
| | | | | | |
|---|---|---|---|---|---|
| 43 | 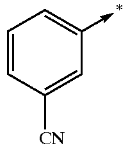 | 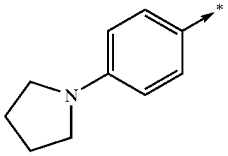 | 94.1 | 4.54 | 418.2 |
| 44 | 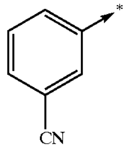 | 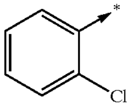 | 95 | 4.34 | 383.1 |
| 45 | 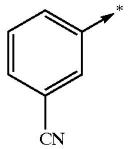 | 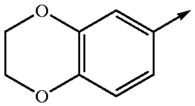 | 95.1 | 4.06 | 407.2 |
| 46 | 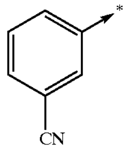 | 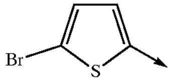 | 93 | 4.7 | 433.1 |
| 47 | 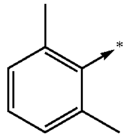 | 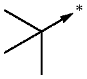 | 96.4 | 3.32 | 332.3 |
| 48 | 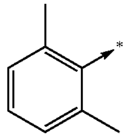 | 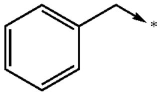 | 92.9 | 3.62 | 366.3 |

-continued
| | | | | | |
|---|---|---|---|---|---|
| 49 | 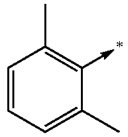 | 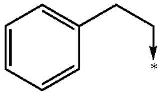 | 95.6 | 3.76 | 380.3 |
| 50 | 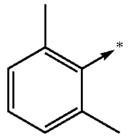 | 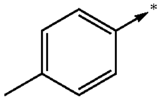 | 95.6 | 3.64 | 366.33 |
| 51 | 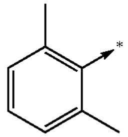 | 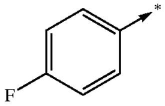 | 96 | 3.51 | 370.2 |
| 52 | 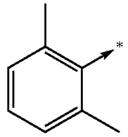 | 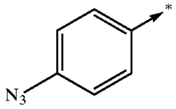 | 87 | 3.69 | 390.2 |
| 53 | 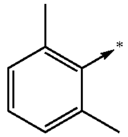 | 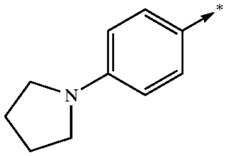 | 80.9 | 4.04 | 421.3 |
| 54 | 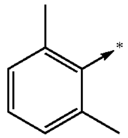 | 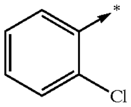 | 97.1 | 3.7 | 436.1 |
| 55 | 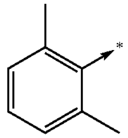 | 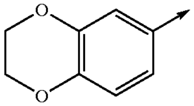 | 94.6 | 3.59 | 410.2 |

-continued
| | | | | | |
|---|---|---|---|---|---|
| 56 | 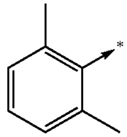 | 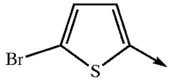 | 95.6 | 3.92 | 436.1 |
| 57 | 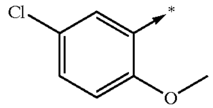 | 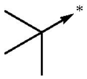 | 82.1 | 3.66 | 368.2 |
| 58 | 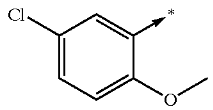 | 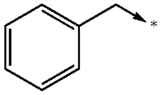 | 90.7 | 3.94 | 402.2 |
| 59 | 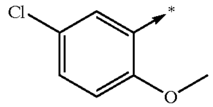 | 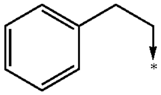 | 85.5 | 4.06 | 416.2 |
| 60 | 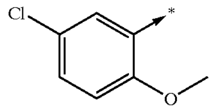 | 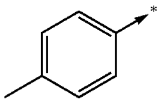 | 94.4 | 4.09 | 402.2 |
| 61 | 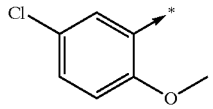 | 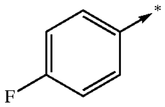 | 95.1 | 3.99 | 406.2 |
| 62 | 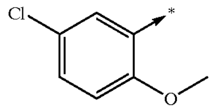 | 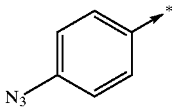 | 93.6 | 4.21 | 429.2 |
| 63 | 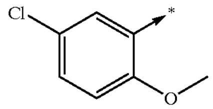 | 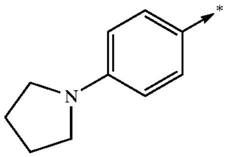 | 93.6 | 4.39 | 457.2 |

-continued
| | | | | | |
|---|---|---|---|---|---|
| 64 | 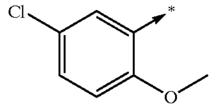 | 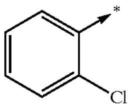 | 96 | 4.22 | 422.1 |
| 65 | 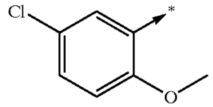 | 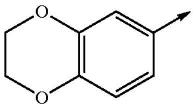 | 91.6 | 3.96 | 446.2 |
| 66 | 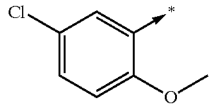 | 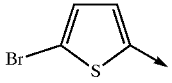 | 94.5 | 4.65 | 472 |
| 67 | 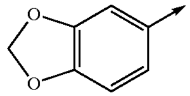 | 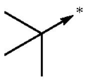 | 97 | 3.07 | 348.2 |
| 68 | 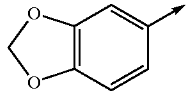 | 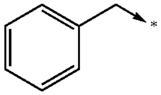 | 93.6 | 3.36 | 382.2 |
| 69 | 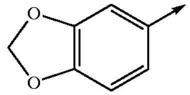 | 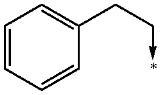 | 93.4 | 3.54 | 396.2 |
| 70 | 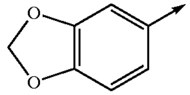 | 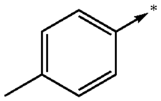 | 94.7 | 3.41 | 382.1 |
| 71 | 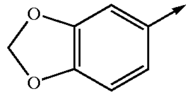 | 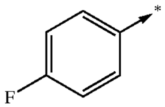 | 96.3 | 3.24 | 386.2 |
| 72 | 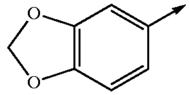 | 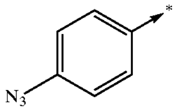 | 94.5 | 3.44 | 409.1 |

-continued
| | | | | | |
|---|---|---|---|---|---|
| 73 | 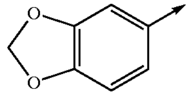 | 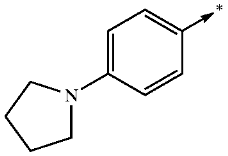 | 93.4 | 3.83 | 437.2 |
| 74 | 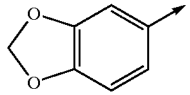 | 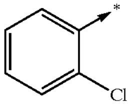 | 95.4 | 3.41 | 402.1 |
| 75 | 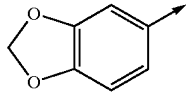 | 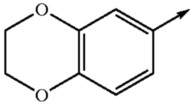 | 95.7 | 3.32 | 426.2 |
| 76 | 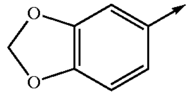 | 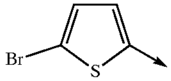 | 92.4 | 3.64 | 452.2 |
| 77 | 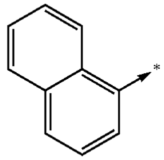 | 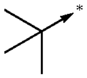 | 98.1 | 3.66 | 324.2 |
| 78 | 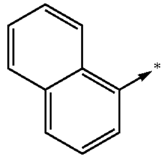 | 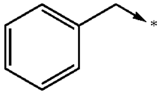 | 91.2 | 3.98 | 388.2 |
| 79 | 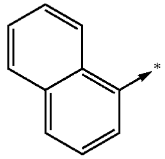 | 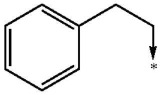 | 81.9 | 4.09 | 402.2 |

-continued
| | | | | | |
|---|---|---|---|---|---|
| 80 | 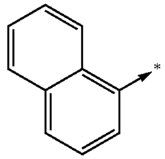 | 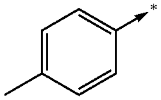 | 96.1 | 4.12 | 388.2 |
| 81 | 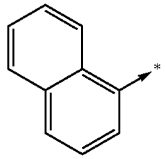 | 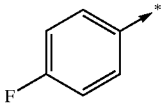 | 96.1 | 4.03 | 392.2 |
| 82 | 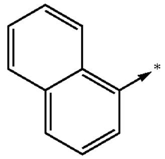 | 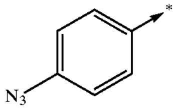 | 94.2 | 4.24 | 415.2 |
| 83 | 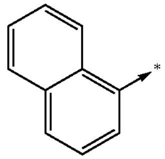 | 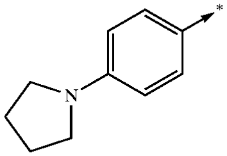 | 93.3 | 4.39 | 443.3 |
| 84 | 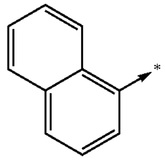 | 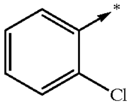 | 96.3 | 4.28 | 408.1 |
| 85 | 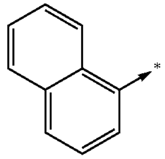 | 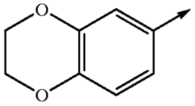 | 94.2 | 4.0 | 432.2 |

-continued
| | | | | | |
|---|---|---|---|---|---|
| 86 | 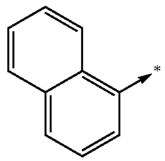 | 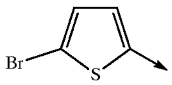 | 95.6 | 4.7 | 458.1 |
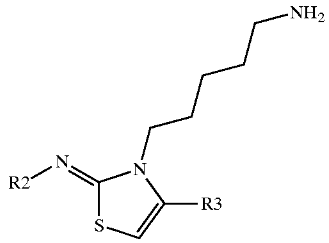
| | | | | | |
|---|---|---|---|---|---|
| 87 | 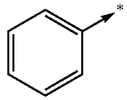 | 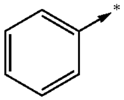 | 97 | 3.35 | 338.2 |
| 88 | 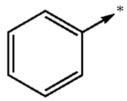 | 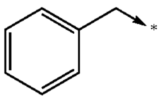 | 94 | 3.51 | 352.3 |
| 89 | 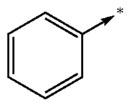 | 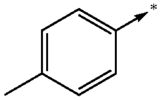 | 94 | 3.58 | 352.3 |
| 90 | 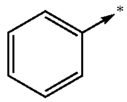 | 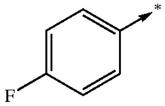 | 97 | 3.42 | 356.2 |
| 91 | 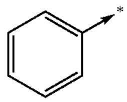 | 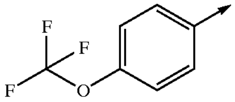 | 86 | 4.01 | 422.2 |

-continued
| | | | | | |
|---|---|---|---|---|---|
| 92 | 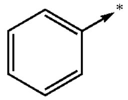 | 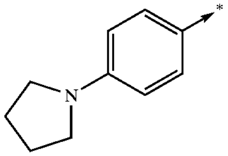 | 96 | 3.99 | 407.3 |
| 93 | 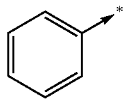 | 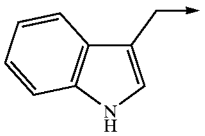 | 7 | 3.65 | 391.3 |
| 94 | 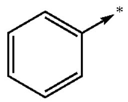 | 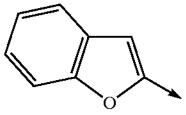 | 92 | 4.11 | 378.2 |
| 95 | 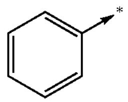 | 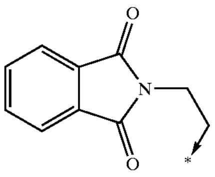 | 95 | 3.43 | 435.2 |
| 96 | 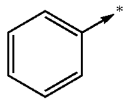 | 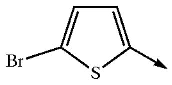 | 97 | 3.91 | 422.1 |
| 97 | 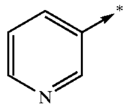 | 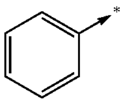 | 43 | 3.19 | 339.2 |
| 98 | 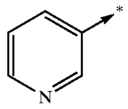 | 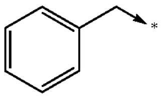 | 32 | 3.33 | 353.2 |

-continued
| | | | | | |
|---|---|---|---|---|---|
| 99 | 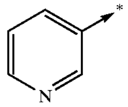 | 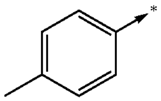 | 39 | 3.45 | 353.2 |
| 100 | 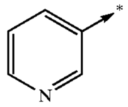 | 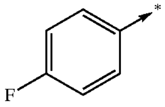 | 39 | 3.28 | 357.2 |
| 101 | 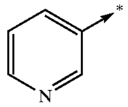 | 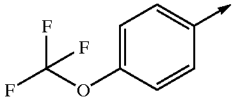 | 42 | 3.8 | 423.2 |
| 102 | 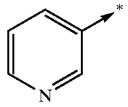 | 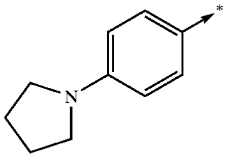 | 41 | 3.89 | 408.2 |
| 103 | 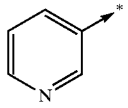 | 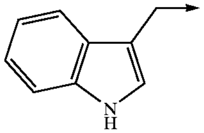 | 14 | 3.43 | 392.2 |
| 104 | 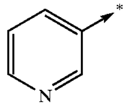 | 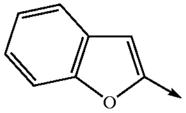 | 39 | 3.62 | 379.2 |
| 105 | 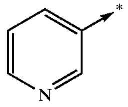 | 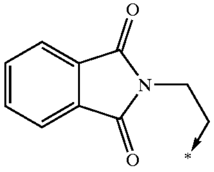 | 28 | 3.2 | 436.2 |

-continued
| | | | | | |
|---|---|---|---|---|---|
| 106 | 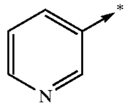 | 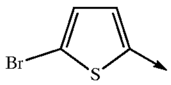 | 35 | 3.56 | 423.1 |
| 107 | 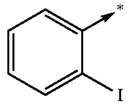 | 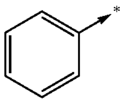 | 95 | 4.65 | 464.1 |
| 108 | 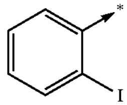 | 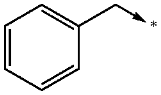 | 89 | 4.64 | 478.2 |
| 109 | 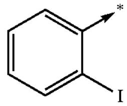 | 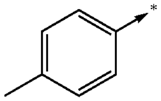 | 82 | 4.88 | 478.1 |
| 110 | 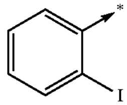 | 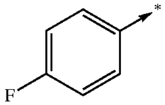 | 92 | 4.76 | 482.1 |
| 111 | 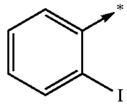 | 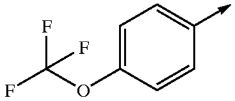 | 90 | 5.41 | 548.1 |
| 112 | 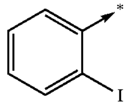 | 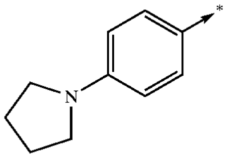 | 86 | 5.13 | 533.2 |
| 113 | 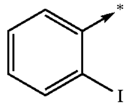 | 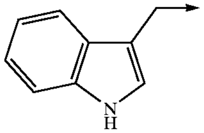 | 9 | 4.5 | 517.1 |

-continued
| | | | | | |
|---|---|---|---|---|---|
| 114 | 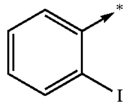 | 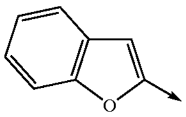 | 95 | 5.49 | 504.1 |
| 115 | 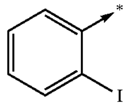 | 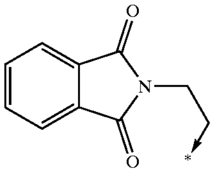 | 80 | 4.4 | 561.1 |
| 116 | 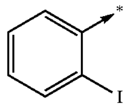 | 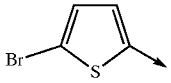 | 89 | 5.4 | 548.0 |
| 117 | 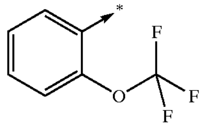 | 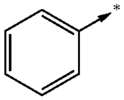 | 96 | 4.85 | 422.2 |
| 118 | 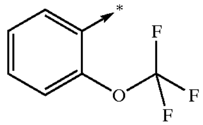 | 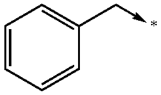 | 91 | 4.86 | 436.2 |
| 119 | 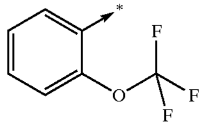 | 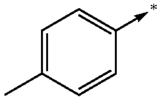 | 88 | 5.08 | 436.2 |
| 120 | 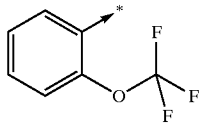 | 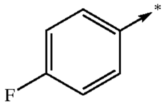 | 95 | 4.96 | 440.2 |

-continued
| | | | | | |
|---|---|---|---|---|---|
| 121 | 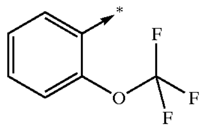 | 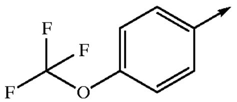 | 81 | 5.56 | 506.2 |
| 122 | 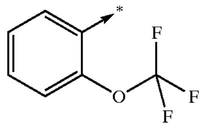 | 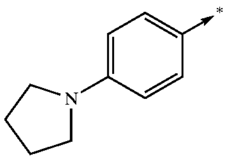 | 83 | 5.34 | 491.2 |
| 123 | 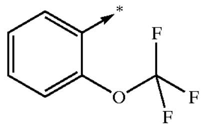 | 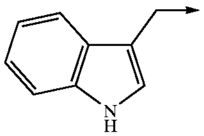 | 3 | 4.7 | 475.3 |
| 124 | 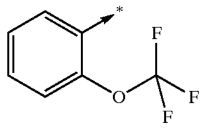 | 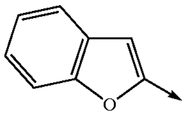 | 91 | 5.59 | 462.2 |
| 125 | 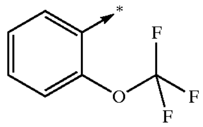 | 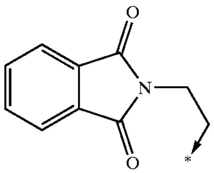 | 92 | 4.61 | 519.2 |
| 126 | 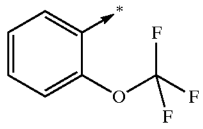 | 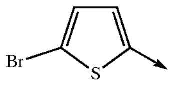 | 92 | 5.52 | 506.1 |
| 127 | 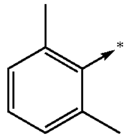 | 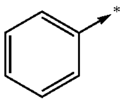 | 98 | 3.63 | 366.3 |

-continued
| | | | | | |
|---|---|---|---|---|---|
| 128 | 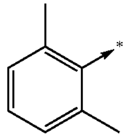 | 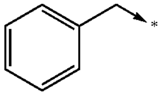 | 97 | 3.76 | 380.3 |
| 129 | 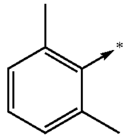 | 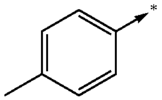 | 98 | 3.82 | 380.3 |
| 130 | 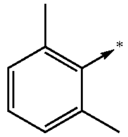 | 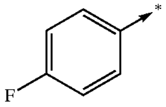 | 98 | 3.67 | 384.2 |
| 131 | 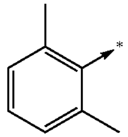 | 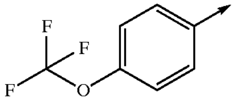 | 97 | 4.16 | 450.2 |
| 132 | 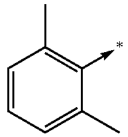 | 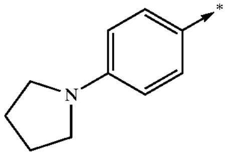 | 96 | 4.2 | 435.3 |
| 133 | 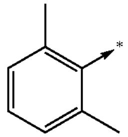 | 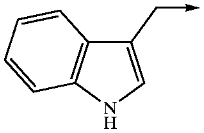 | 21 | 3.9 | 419.3 |

-continued
| | | | | | |
|---|---|---|---|---|---|
| 134 | 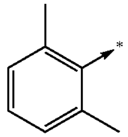 | 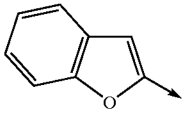 | 88 | 4.28 | 406.2 |
| 135 | 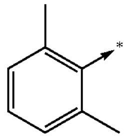 | 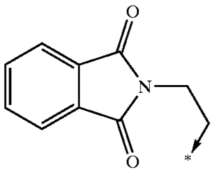 | 97 | 3.68 | 463.3 |
| 136 | 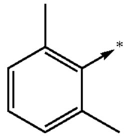 | 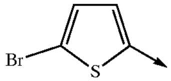 | 82 | 4.09 | 450.1 |
| 137 | 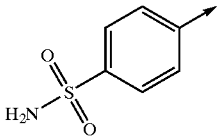 | 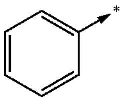 | 93 | 3.44 | 417.2 |
| 138 | 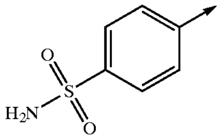 | 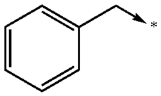 | 94 | 3.5 | 431.2 |
| 139 | 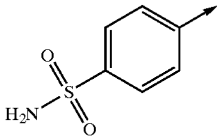 | 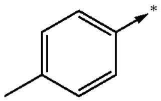 | 95 | 3.71 | 431.2 |

-continued
| | | | | | |
|---|---|---|---|---|---|
| 140 | 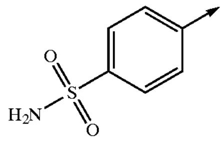 | 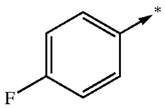 | 95 | 3.58 | 435.2 |
| 141 | 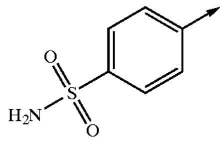 | 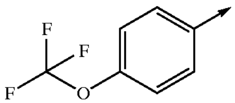 | 94 | 4.27 | 501.2 |
| 142 | 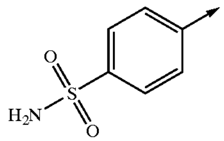 | 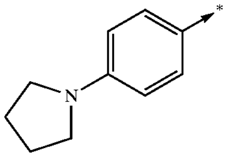 | 93 | 4.05 | 486.6 |
| 143 | 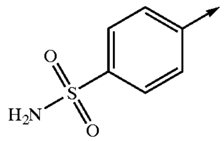 | 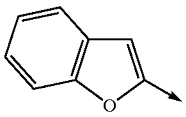 | 94 | 4.28 | 457.2 |
| 144 | 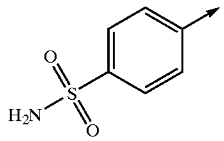 | 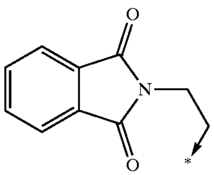 | 92 | 3.39 | 514.2 |
| 145 | 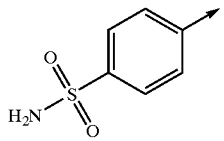 | 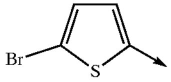 | 85 | 4.16 | 501.1 |
| 146 | 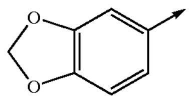 | 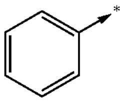 | 97 | 3.36 | 382.2 |

-continued
| | | | | | |
|---|---|---|---|---|---|
| 147 | 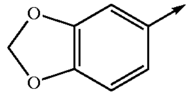 | 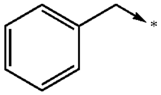 | 94 | 3.53 | 396.2 |
| 148 | 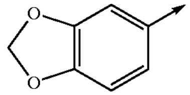 | 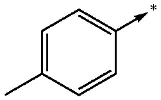 | 97 | 3.6 | 396.2 |
| 149 | 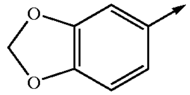 | 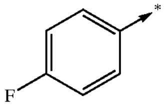 | 97 | 3.43 | 400.2 |
| 150 | 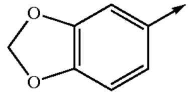 | 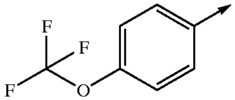 | 97 | 3.95 | 466.2 |
| 151 | 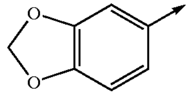 | 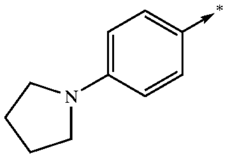 | 95 | 4.01 | 451.3 |
| 152 | 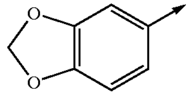 | 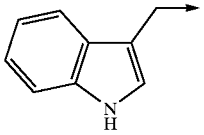 | 15 | 3.57 | 435.2 |
| 153 | 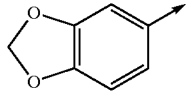 | 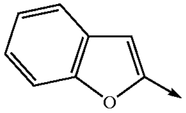 | 94 | 4.0 | 422.2 |

-continued
| | | | | | |
|---|---|---|---|---|---|
| 154 | 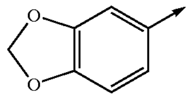 | 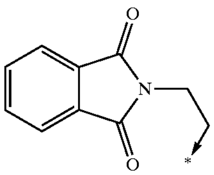 | 95 | 3.45 | 479.3 |
| 155 | 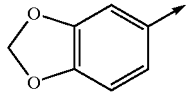 | 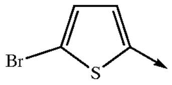 | 95 | 3.84 | 466.1 |
| 156 | 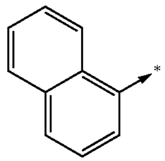 | 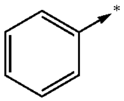 | 96 | 4.11 | 388.2 |
| 157 | 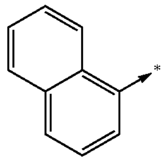 | 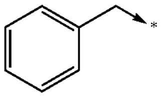 | 90 | 4.14 | 402.2 |
| 158 | 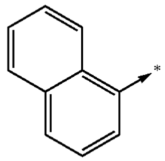 | 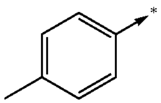 | 96 | 4.31 | 402.2 |
| 159 | 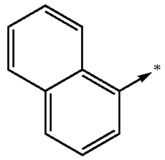 | 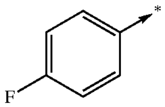 | 96 | 4.21 | 406.2 |

-continued
| | | | | | |
|---|---|---|---|---|---|
| 160 | 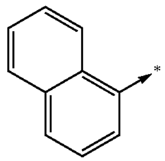 | 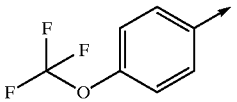 | 97 | 4.83 | 472.3 |
| 161 | 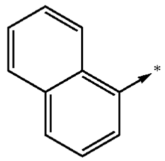 | 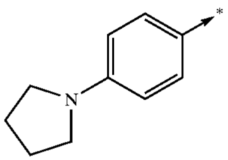 | 95 | 4.57 | 457.3 |
| 162 | 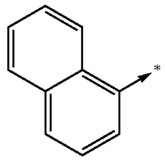 | 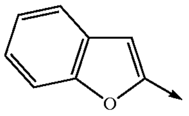 | 96 | 5.12 | 428.2 |
| 163 | 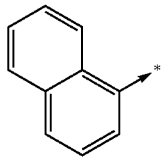 | 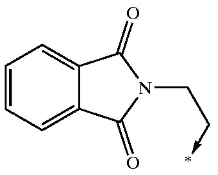 | 88 | 4.01 | 485.3 |
| 164 | 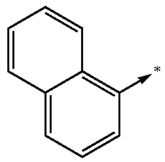 | 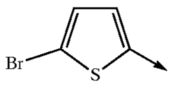 | 97 | 4.91 | 472.1 |

-continued
| | | | | | |
|---|---|---|---|---|---|
| | | 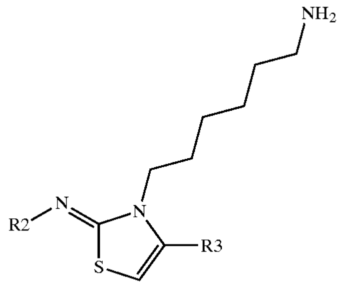 | | | |
| 165 | 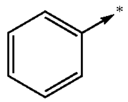 | 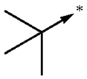 | 93 | 3.52 | 332.3 |
| 166 | 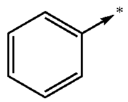 | 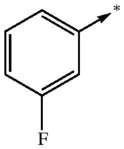 | 99 | 3.76 | 370.3 |
| 167 | 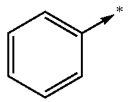 | 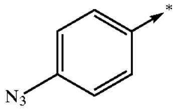 | 97 | 3.9 | 393.3 |
| 168 | 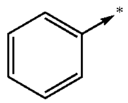 | 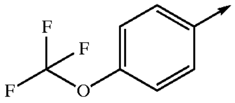 | 98 | 4.25 | 436.2 |
| 169 | 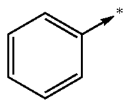 | 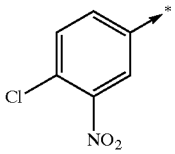 | 98 | 4.14 | 431.2 |

-continued
| | | | | | |
|---|---|---|---|---|---|
| 170 | 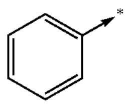 | 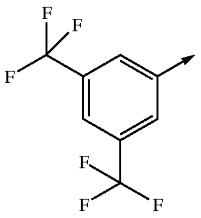 | 99 | 4.79 | 488.2 |
| 171 | 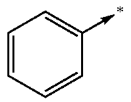 | 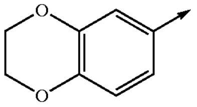 | 98 | 3.74 | 410.2 |
| 172 | 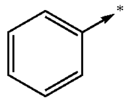 | 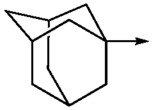 | 98 | 4.28 | 410.3 |
| 173 | 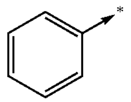 | 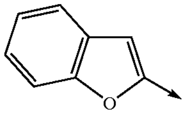 | 98 | 4.38 | 392.2 |
| 174 | 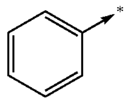 | 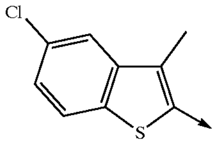 | 98 | 4.73 | 456.2 |
| 175 | 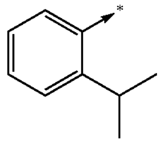 | 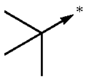 | 98 | 4.06 | 374.3 |
| 176 | 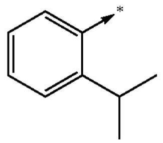 | 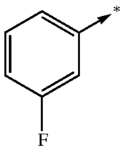 | 98 | 4.37 | 412.3 |

-continued
| | | | | | |
|---|---|---|---|---|---|
| 177 | 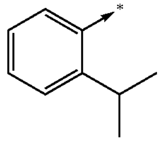 | 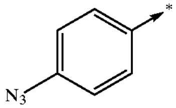 | 97 | 4.46 | 435.3 |
| 178 | 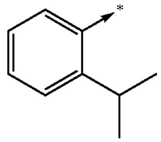 | 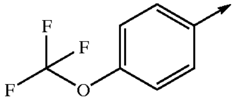 | 98 | 4.8 | 478.3 |
| 179 | 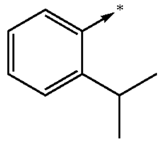 | 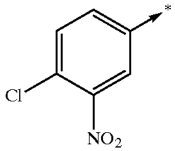 | 99 | 4.78 | 473.3 |
| 180 | 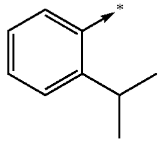 | 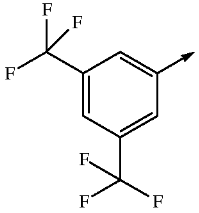 | 94 | 5.43 | 530.3 |
| 181 | 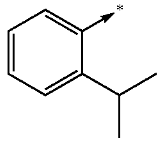 | 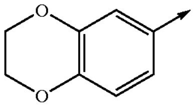 | 97 | 4.27 | 452.3 |
| 182 | 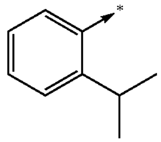 | 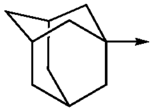 | 85 | 4.73 | 452.4 |

-continued
| | | | | | |
|---|---|---|---|---|---|
| 183 | 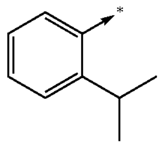 | 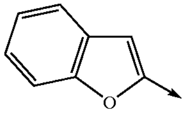 | 98 | 5.07 | 434.3 |
| 184 | 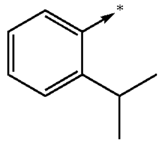 | 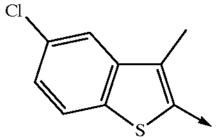 | 93 | 5.33 | 498.3 |
| 185 | 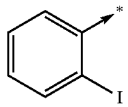 | 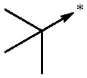 | 98 | 4.61 | 458.2 |
| 186 | 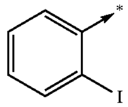 | 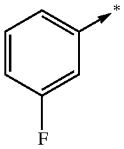 | 97 | 5.23 | 496.1 |
| 187 | 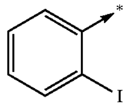 | 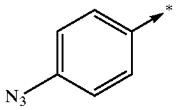 | 96 | 5.34 | 519.1 |
| 188 | 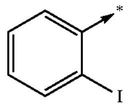 | 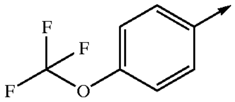 | 97 | 5.72 | 562.1 |
| 189 | 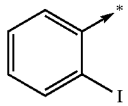 | 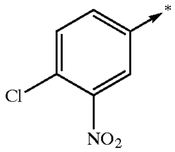 | 98 | 5.57 | 557.1 |

-continued
| | | | | | |
|---|---|---|---|---|---|
| 190 | 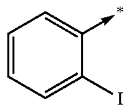 | 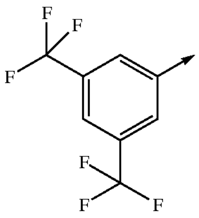 | 96 | 6.16 | 614.1 |
| 191 | 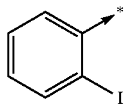 | 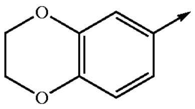 | 96 | 4.97 | 536.1 |
| 192 | 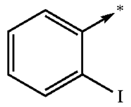 | 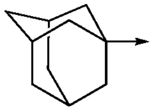 | 85 | 5.67 | 536.2 |
| 193 | 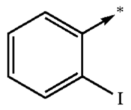 | 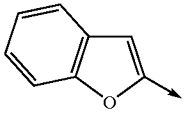 | 96 | 5.86 | 518.1 |
| 194 | 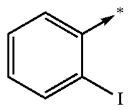 | 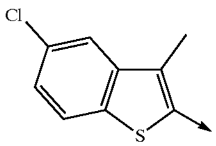 | 97 | 6.32 | 582.1 |
| 195 | 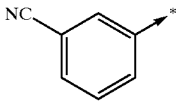 | 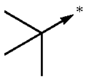 | 96 | 4.16 | 357.3 |
| 196 | 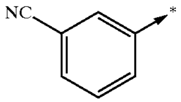 | 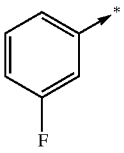 | 98 | 4.74 | 395.2 |

-continued
| | | | | | |
|---|---|---|---|---|---|
| 197 | 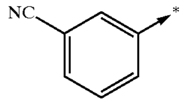 | 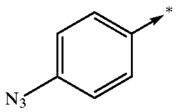 | 97 | 4.86 | 418.2 |
| 198 | 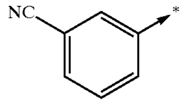 | 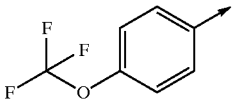 | 98 | 5.26 | 461.2 |
| 199 | 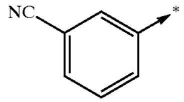 | 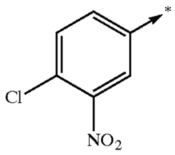 | 98 | 5.12 | 456.2 |
| 200 | 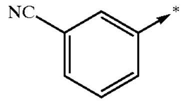 | 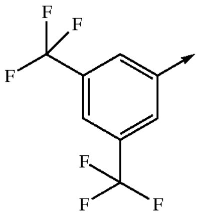 | 97 | 5.72 | 513.2 |
| 201 | 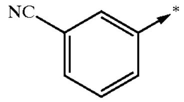 | 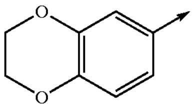 | 96 | 4.51 | 435.2 |
| 202 | 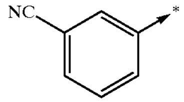 | 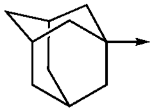 | 98 | 5.18 | 435.3 |
| 203 | 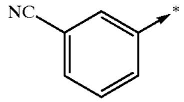 | 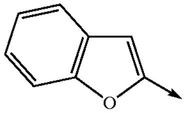 | 95 | 5.37 | 417.2 |

-continued
| | | | | | |
|---|---|---|---|---|---|
| 204 | 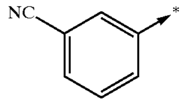 | 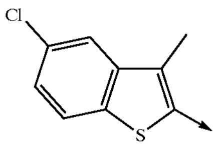 | 95 | 5.84 | 481.2 |
| 205 | 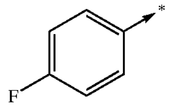 | 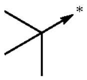 | 96 | 3.63 | 350.3 |
| 206 | 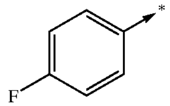 | 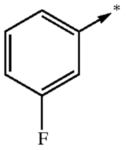 | 98 | 3.95 | 388.2 |
| 207 | 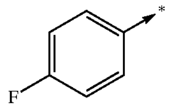 | 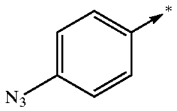 | 95 | 4.07 | 411.2 |
| 208 | 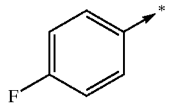 | 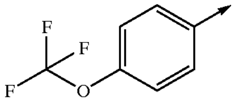 | 98 | 4.44 | 454.2 |
| 209 | 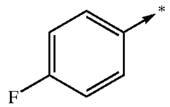 | 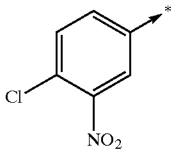 | 97 | 4.38 | 449.2 |
| 210 | 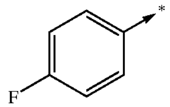 | 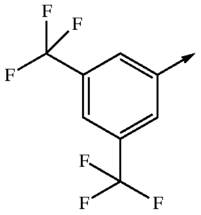 | 89 | 5.03 | 506.2 |

-continued
| | | | | | |
|---|---|---|---|---|---|
| 211 | 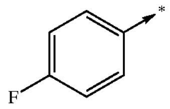 | 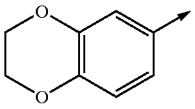 | 96 | 3.87 | 428.2 |
| 212 | 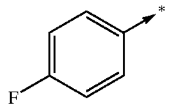 | 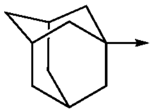 | 97 | 4.4 | 428.3 |
| 213 | 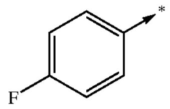 | 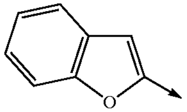 | 96 | 4.63 | 410.2 |
| 214 | 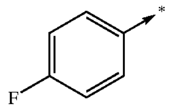 | 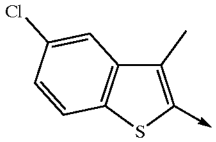 | 96 | 4.96 | 474.2 |
| 215 | 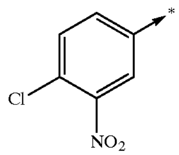 | 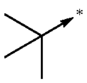 | 94 | 5.38 | 411.2 |
| 216 | 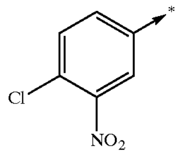 | 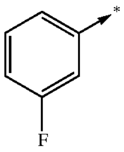 | 98 | 5.63 | 449.2 |
| 217 | 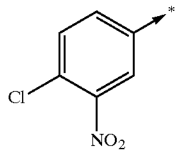 | 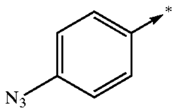 | 96 | 5.77 | 472.2 |

-continued
| | | | | | |
|---|---|---|---|---|---|
| 218 | 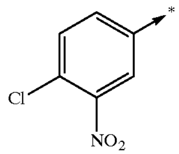 | 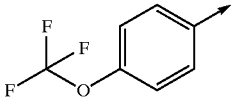 | 98 | 6.04 | 515.2 |
| 219 | 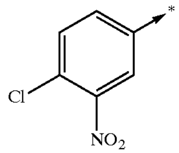 | 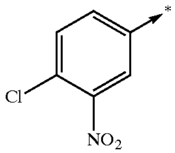 | 98 | 5.74 | 510.1 |
| 220 | 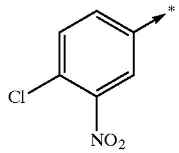 | 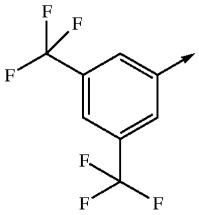 | 91 | 6.29 | 567.2 |
| 221 | 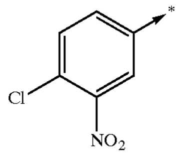 | 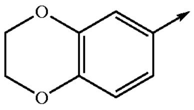 | 98 | 5.53 | 489.2 |
| 222 | 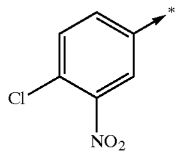 | 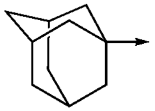 | 96 | 6.38 | 489.3 |
| 223 | 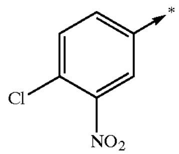 | 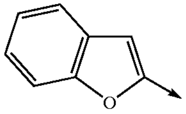 | 97 | 6.0 | 471.2 |

-continued
| | | | | | |
|---|---|---|---|---|---|
| 224 | 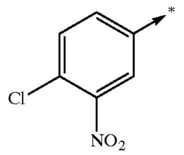 | 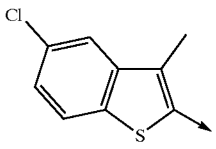 | 98 | 6.49 | 535.1 |
| 225 | 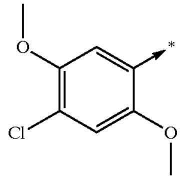 | 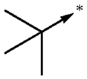 | 98 | 3.99 | 426.3 |
| 226 | 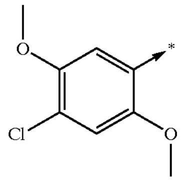 | 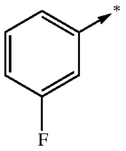 | 98 | 4.34 | 464.2 |
| 227 | 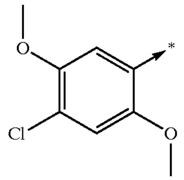 | 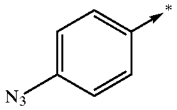 | 96 | 4.43 | 487.3 |
| 228 | 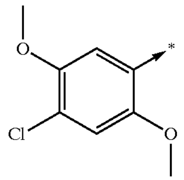 | 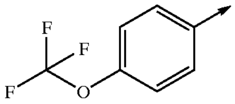 | 97 | 4.78 | 530.2 |

-continued
| | | | | | |
|---|---|---|---|---|---|
| 229 | 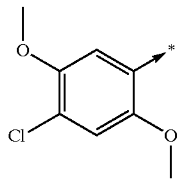 | 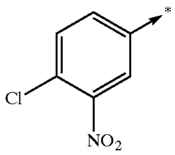 | 98 | 4.76 | 525.2 |
| 230 | 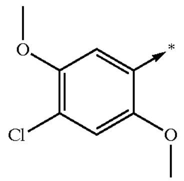 | 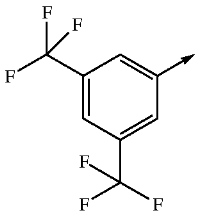 | 96 | 5.36 | 582.2 |
| 231 | 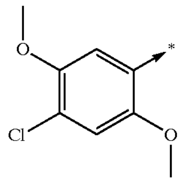 | 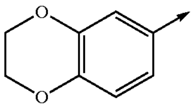 | 95 | 4.23 | 504.3 |
| 232 | 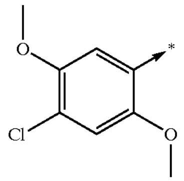 | 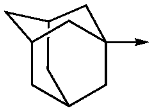 | 97 | 4.7 | 504.3 |
| 233 | 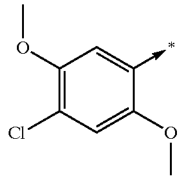 | 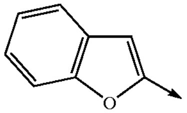 | 98 | 4.99 | 486.2 |

-continued
| | | | | | |
|---|---|---|---|---|---|
| 234 | 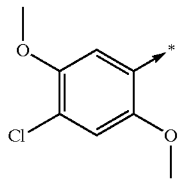 | 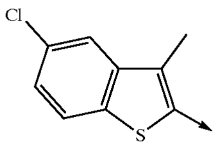 | 97 | 5.3 | 550.2 |
| 235 | 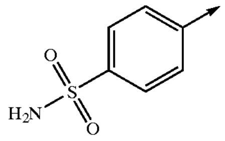 | 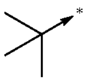 | 96 | 3.44 | 411.2 |
| 236 | 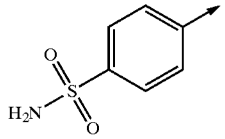 | 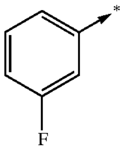 | 95 | 3.94 | 449.2 |
| 237 | 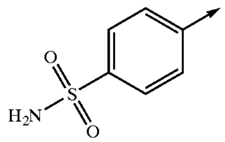 | 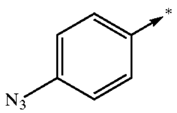 | 96 | 4.11 | 472.3 |
| 238 | 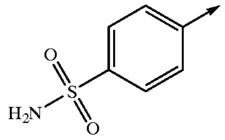 | 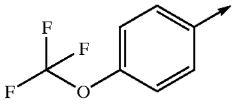 | 95 | 4.52 | 515.2 |
| 239 | 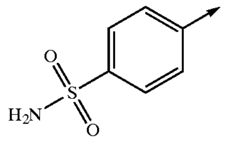 | 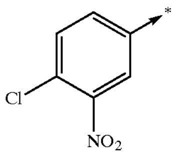 | 95 | 4.39 | 510.2 |

-continued
| | | | | | |
|---|---|---|---|---|---|
| 240 | 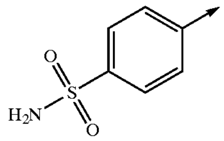 | 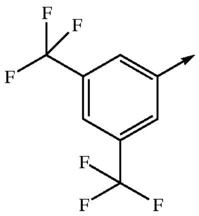 | 94 | 5.01 | 567.2 |
| 241 | 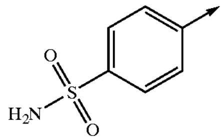 | 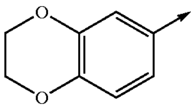 | 96 | 3.74 | 489.2 |
| 242 | 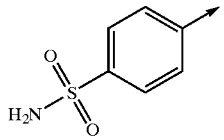 | 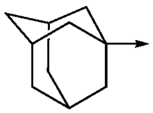 | 96 | 4.41 | 489.3 |
| 243 | 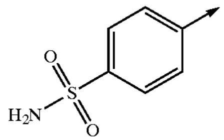 | 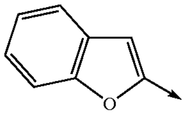 | 96 | 4.56 | 471.2 |
| 244 | 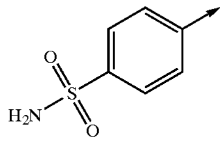 | 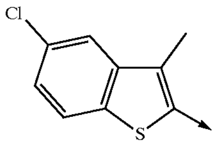 | 97 | 5.01 | 535.2 |

-continued
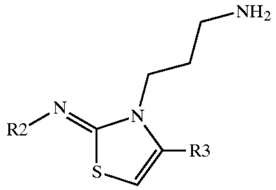
| | | | | | |
|---|---|---|---|---|---|
| 245 | 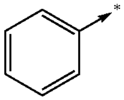 | 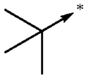 | 98.1 | 3.2 | 290.2 |
| 246 | 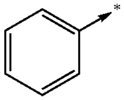 | 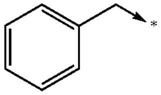 | 96.9 | 3.78 | 324.2 |
| 247 | 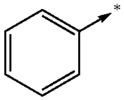 | 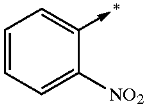 | 69.3 | 3.88 | 355.2 |
| 248 | 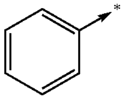 | 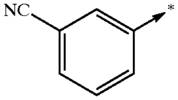 | 99.3 | 3.79 | 335.2 |
| 249 | 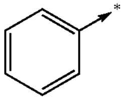 | 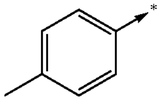 | 99.4 | 3.86 | 324.2 |
| 250 | 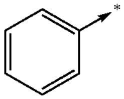 | 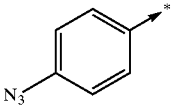 | 98 | 3.97 | 351.2 |
| 251 | 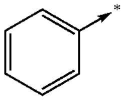 | 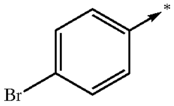 | 98.7 | 4.14 | 388.1 |

-continued
| | | | | | |
|---|---|---|---|---|---|
| 252 | 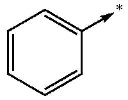 | 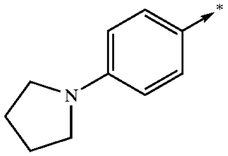 | 93.5 | 4.24 | 379.3 |
| 253 | 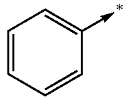 | 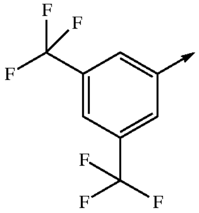 | 82.4 | 5.16 | 446.2 |
| 254 | 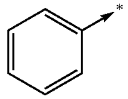 | 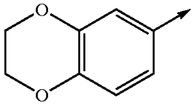 | 98.8 | 3.7 | 368.2 |
| 255 | 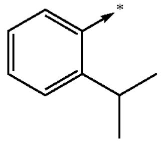 | 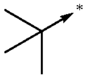 | 98.5 | 3.9 | 332.3 |
| 256 | 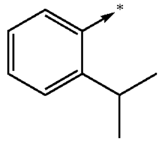 | 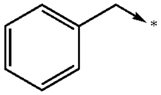 | 92.3 | 4.4 | 366.3 |
| 257 | 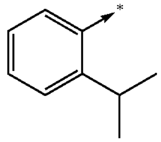 | 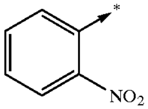 | 82.3 | 4.55 | 397.2 |

-continued
| | | | | | |
|---|---|---|---|---|---|
| 258 | 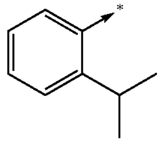 | 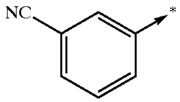 | 98.4 | 4.48 | 377.3 |
| 259 | 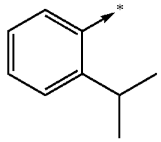 | 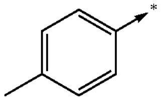 | 97.3 | 4.49 | 366.3 |
| 260 | 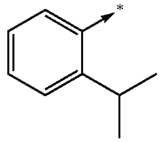 | 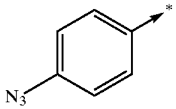 | 95.4 | 4.59 | 393.3 |
| 261 | 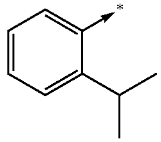 | 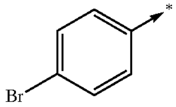 | 98.7 | 4.77 | 430.2 |
| 262 | 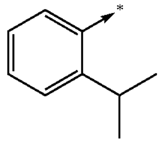 | 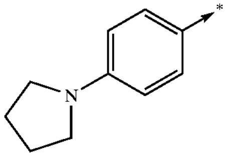 | 90.9 | 4.76 | 421.3 |
| 263 | 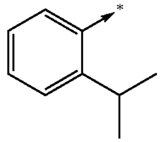 | 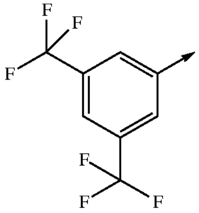 | 98.7 | 5.72 | 488.2 |

-continued
| | | | | | |
|---|---|---|---|---|---|
| 264 | 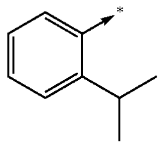 | 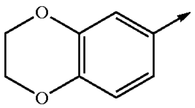 | 97.7 | 4.33 | 410.3 |
| 265 | 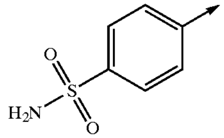 | 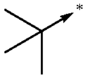 | 98.5 | 3.42 | 369.2 |
| 266 | 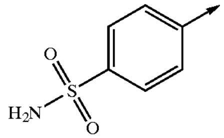 | 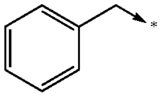 | 94.9 | 3.91 | 403.2 |
| 267 | 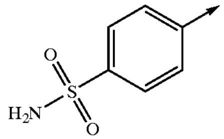 | 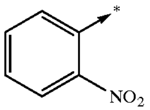 | 98.1 | 3.81 | 434.2 |
| 268 | 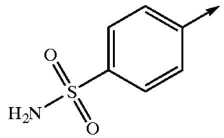 | 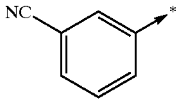 | 97.9 | 3.78 | 414.1 |
| 269 | 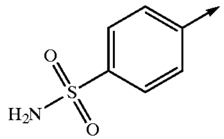 | 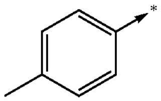 | 98.1 | 4.06 | 403.2 |
| 270 | 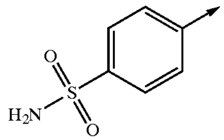 | 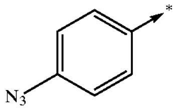 | 96.2 | 4.14 | 430.2 |

-continued
| | | | | | |
|---|---|---|---|---|---|
| 271 | 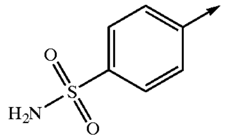 | 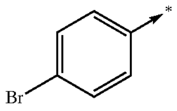 | 98.3 | 4.28 | 467.1 |
| 272 | 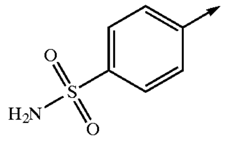 | 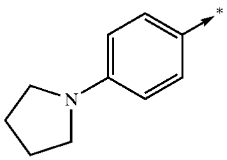 | 96.8 | 4.5 | 458.2 |
| 273 | 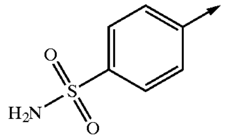 | 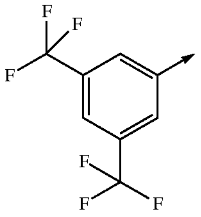 | 98.3 | 4.92 | 525.2 |
| 274 | 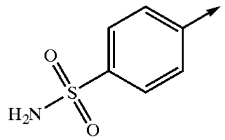 | 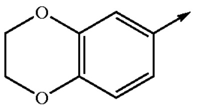 | 97.1 | 3.84 | 447.2 |
| 275 | 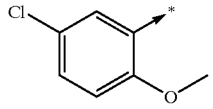 | 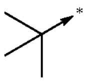 | 96.5 | 4.28 | 354.2 |
| 276 | 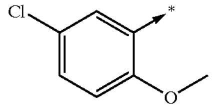 | 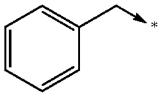 | 93.3 | 5.02 | 388.2 |

-continued
| | | | | | |
|---|---|---|---|---|---|
| 277 | 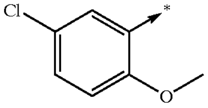 | 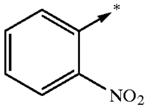 | 68.7 | 4.96 | 419.2 |
| 278 | 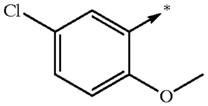 | 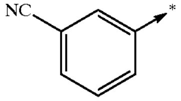 | 97.8 | 4.86 | 399.2 |
| 279 | 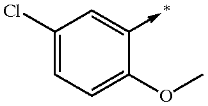 | 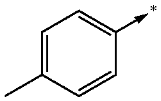 | 96 | 5.13 | 388.2 |
| 280 | 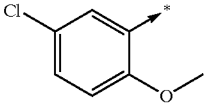 | 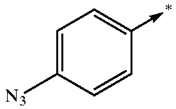 | 96.9 | 5.18 | 415.2 |
| 281 | 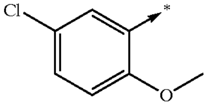 | 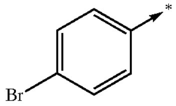 | 98.6 | 5.31 | 452.1 |
| 282 | 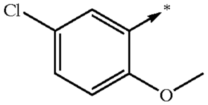 | 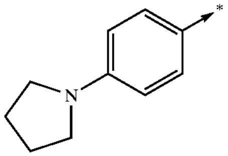 | 89.5 | 5.54 | 443.2 |
| 283 | 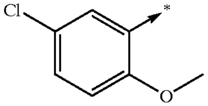 | 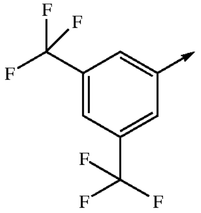 | 65.5 | 5.89 | 510.2 |

-continued
| | | | | | |
|---|---|---|---|---|---|
| 284 | 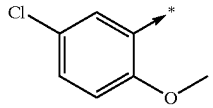 | 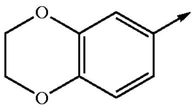 | 97.8 | 4.89 | 432.2 |
| 285 | 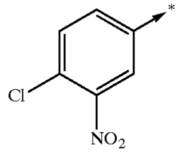 | 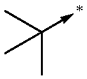 | 93.2 | 5.08 | 369.2 |
| 286 | 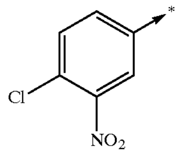 | 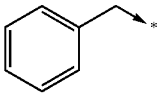 | 94.6 | 5.31 | 403.1 |
| 287 | 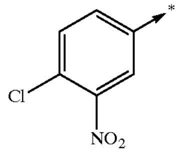 | 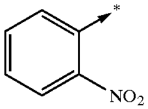 | 97.6 | 5.07 | 434.1 |
| 288 | 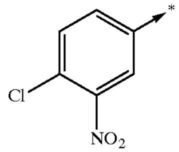 | 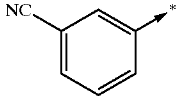 | 99.1 | 5.05 | 414.1 |
| 289 | 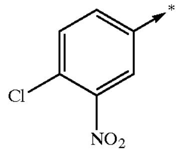 | 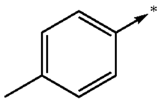 | 99.1 | 5.39 | 403.1 |

-continued
| | | | | | |
|---|---|---|---|---|---|
| 290 | 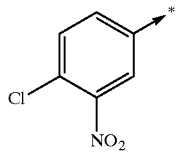 | 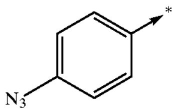 | 98.3 | 5.44 | 430.2 |
| 291 | 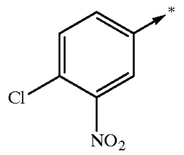 | 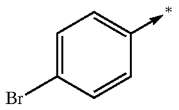 | 99.4 | 5.47 | 467.1 |
| 292 | 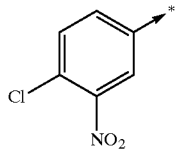 | 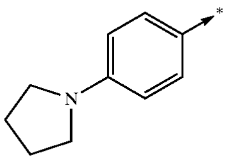 | 97.4 | 5.86 | 458.2 |
| 293 | 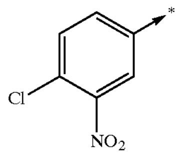 | 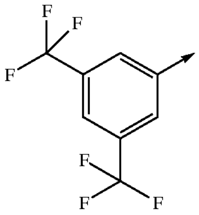 | 99.5 | 5.87 | 525.1 |
| 294 | 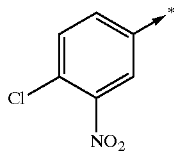 | 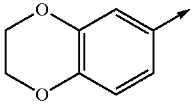 | 98.5 | 5.21 | 447.2 |

-continued
| | | | | | |
|---|---|---|---|---|---|
| 295 | 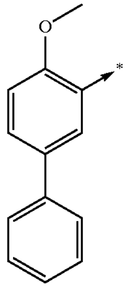 | 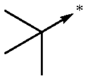 | 95.7 | 4.41 | 396.3 |
| 296 | 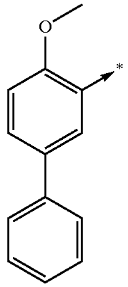 | 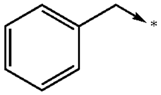 | 92.9 | 5.06 | 430.3 |
| 297 | 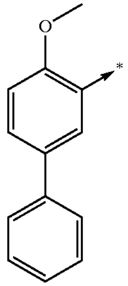 | 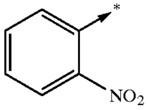 | 54 | 5.19 | 461.2 |

-continued
| | | | | | |
|---|---|---|---|---|---|
| 298 | 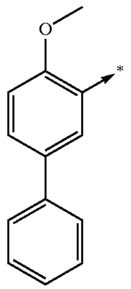 | 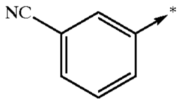 | 91.8 | 5.07 | 441.2 |
| 299 | 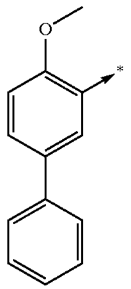 | 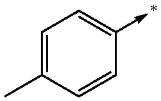 | 95.8 | 5.18 | 430.3 |
| 300 | 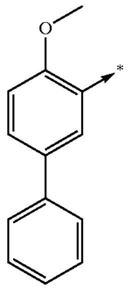 | 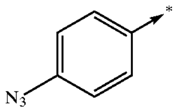 | 96 | 5.28 | 457.3 |

-continued
| | | | | | |
|---|---|---|---|---|---|
| 301 | 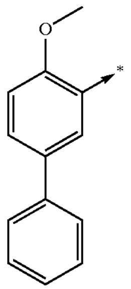 | 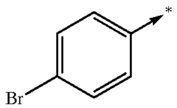 | 96.9 | 5.45 | 494.2 |
| 302 | 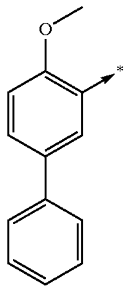 | 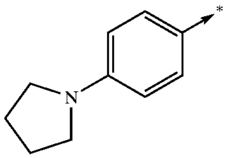 | 87 | 5.49 | 485.3 |
| 303 | 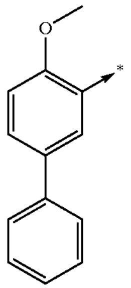 | 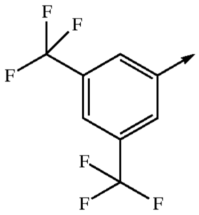 | 35.6 | 6.18 | 552.2 |

-continued
| | | | | | |
|---|---|---|---|---|---|
| 304 | 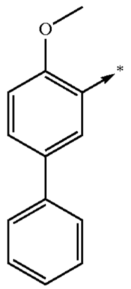 | 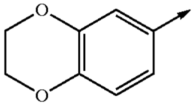 | 96.7 | 4.97 | 474.3 |
| 305 | 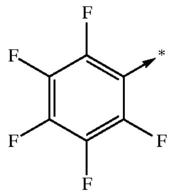 | 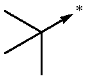 | 83.9 | 5.24 | 380.2 |
| 306 | 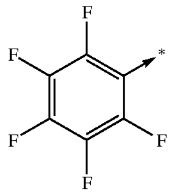 | 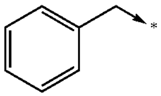 | 92.8 | 5.39 | 414.2 |
| 307 | 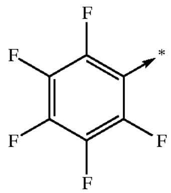 | 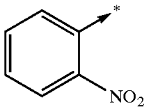 | 92 | 5.14 | 445.2 |

-continued
| | | | | | |
|---|---|---|---|---|---|
| 308 | 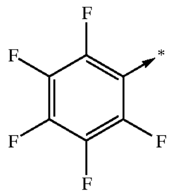 | 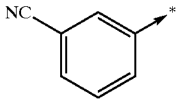 | 97.4 | 5.11 | 425.1 |
| 309 | 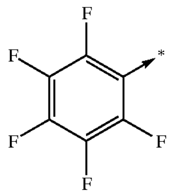 | 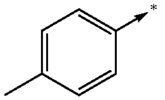 | 98.1 | 5.47 | 414.2 |
| 310 | 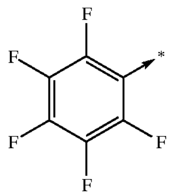 | 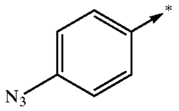 | 97.2 | 5.47 | 441.1 |
| 311 | 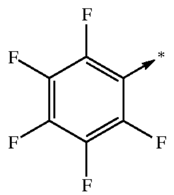 | 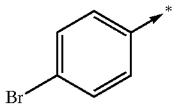 | 97 | 5.52 | 478.1 |
| 312 | 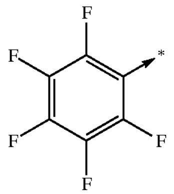 | 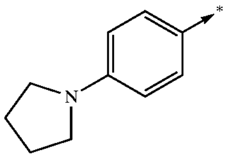 | 93.3 | 5.99 | 469.2 |

-continued
| | | | | | |
|---|---|---|---|---|---|
| 313 | 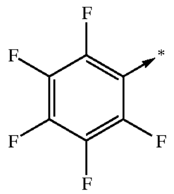 | 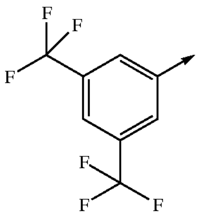 | 98.3 | 5.91 | 536.1 |
| 314 | 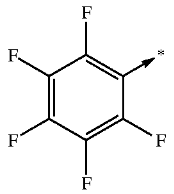 | 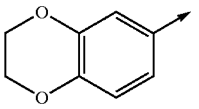 | 96.5 | 5.31 | 458.2 |
| 315 | 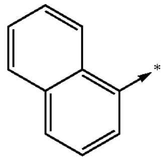 | 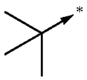 | 98.7 | 4.12 | 340.3 |
| 316 | 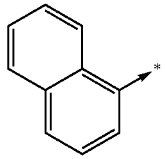 | 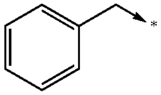 | 93.4 | 4.66 | 374.2 |
| 317 | 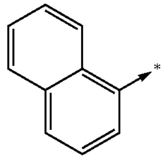 | 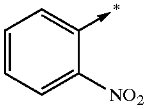 | 98.9 | 4.78 | 405.2 |

-continued
| | | | | | |
|---|---|---|---|---|---|
| 318 | 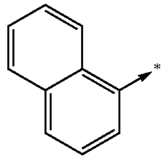 | 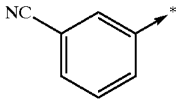 | 97.8 | 4.71 | 385.2 |
| 319 | 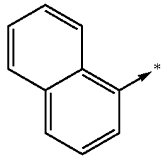 | 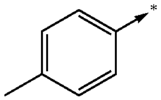 | 98.1 | 4.78 | 374.2 |
| 320 | 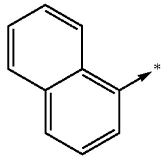 | 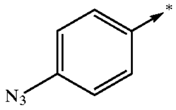 | 97.2 | 4.9 | 401.2 |
| 321 | 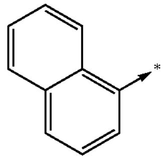 | 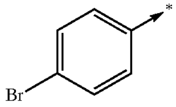 | 98.8 | 5.09 | 438.1 |
| 322 | 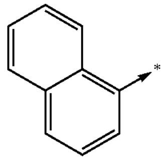 | 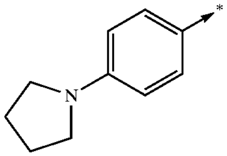 | 95.8 | 5.07 | 429.3 |
| 323 | 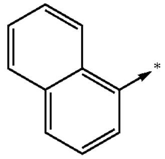 | 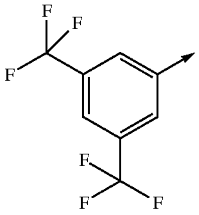 | 98.5 | 5.82 | 496.2 |

-continued
| | | | | | |
|---|---|---|---|---|---|
| 324 | 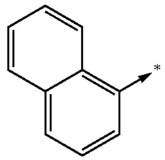 | 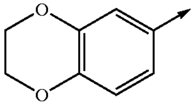 | 97.5 | 4.59 | 418.2 |
| | | 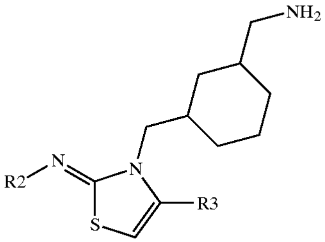 | | | |
| 325 | 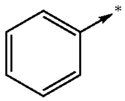 | 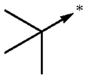 | 93 | 3.71 | 358.2 |
| 326 | 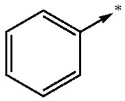 | 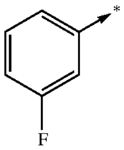 | 68 + 30 | 4.0 + 4.1 | 396.2 |
| 327 | 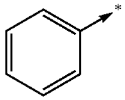 | 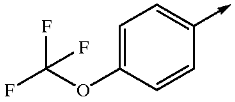 | 69 + 31 | 4.5 + 4.6 | 462.2 |
| 328 | 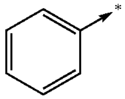 | 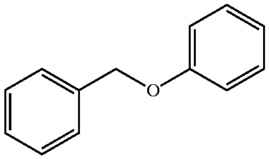 | 66 + 27 | 4.7 + 4.8 | 484.3 |

-continued
| | | | | | |
|---|---|---|---|---|---|
| 329 | 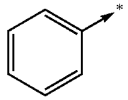 | 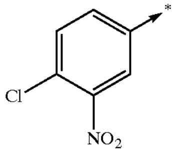 | 67 + 31 | 4.4 + 4.6 | 457.2 |
| 330 | 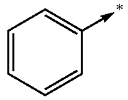 | 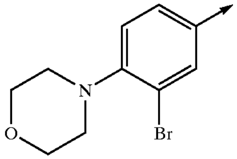 | 67 + 30 | 4.3 + 4.5 | 541.2 |
| 331 | 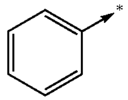 | 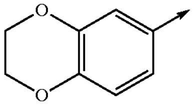 | 62 + 33 | 3.9 + 4.0 | 436.2 |
| 332 | 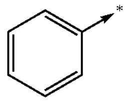 | 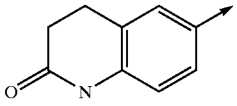 | 64 + 30 | 3.5 + 3.6 | 447.3 |
| 333 | 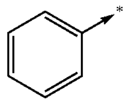 | 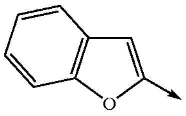 | 65 + 30 | 4.7 + 4.9 | 418.2 |
| 334 | 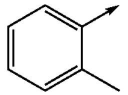 | 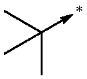 | 68 + 29 | 3.8 + 3.9 | 372.3 |
| 335 | 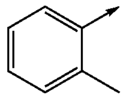 | 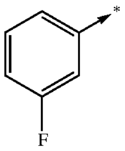 | 69 + 29 | 4.2 + 4.3 | 410.2 |

-continued
| | | | | | |
|---|---|---|---|---|---|
| 336 | 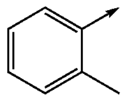 | 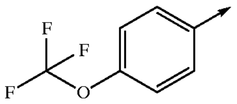 | 68 + 30 | 4.6 + 4.8 | 476.2 |
| 337 | 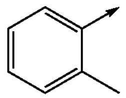 | 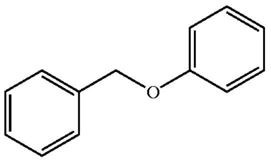 | 61 + 32 | 4.8 + 4.89 | 498.3 |
| 338 | 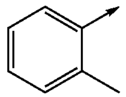 | 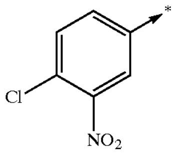 | 66 + 30 | 4.55 + 4.71 | 471.2 |
| 339 | 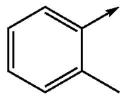 | 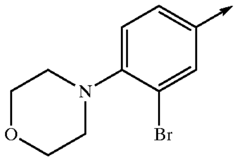 | 68 + 29 | 4.46 + 4.58 | 555.2 |
| 340 | 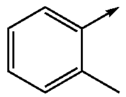 | 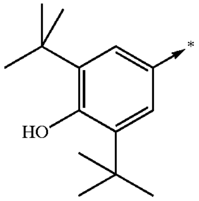 | 22 + 11 | 5.13 + 5.22 | 520.4 |
| 341 | 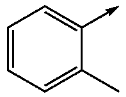 | 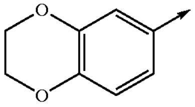 | 67 + 24 | 4.09 + 4.14 | 450.3 |
| 342 | 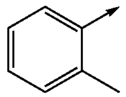 | 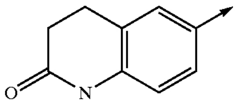 | 71 + 23 | 3.7 + 3.74 | 461.3 |

-continued
| | | | | | |
|---|---|---|---|---|---|
| 343 | 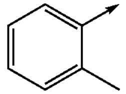 | 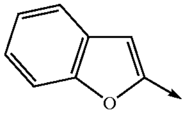 | 67 + 31 | 4.82 + 5.02 | 432.2 |
| 344 | 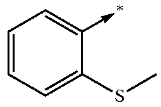 | 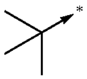 | 66 + 31 | 4.14 + 4.39 | 404.3 |
| 345 | 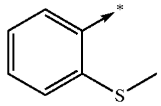 | 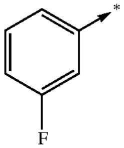 | 65 + 31 | 4.74 + 4.94 | 442.2 |
| 346 | 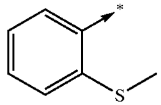 | 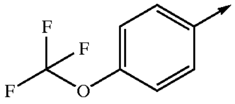 | 65 + 31 | 5.25 + 5.47 | 508.2 |
| 347 | 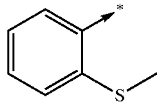 | 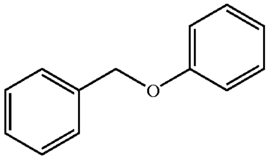 | 62 + 29 | 5.28 + 5.5 | 530.3 |
| 348 | 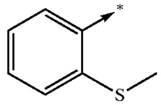 | 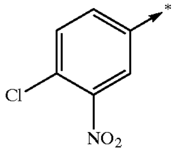 | 65 + 30 | 5.21 + 5.38 | 503.2 |
| 349 | 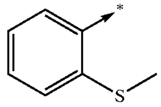 | 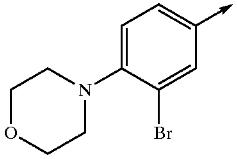 | 63 + 30 | 5.03 + 5.24 | 587.2 |

-continued
| | | | | | |
|---|---|---|---|---|---|
| 350 | 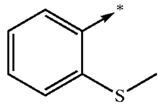 | 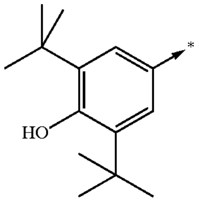 | 64 + 30 | 5.59 + 5.84 | 552.3 |
| 351 | 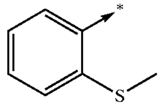 | 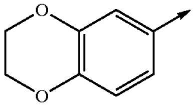 | 58 + 28 | 4.49 + 4.66 | 482.3 |
| 352 | 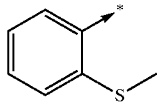 | 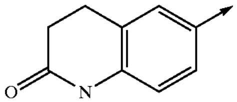 | 64 + 26 | 4.01 + 4.11 | 493.3 |
| 353 | 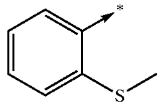 | 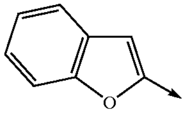 | 65 + 31 | 5.54 + 5.71 | 464.2 |
| 354 | 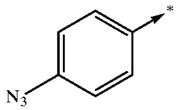 | 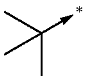 | 57 + 24 | 4.08 + 4.19 | 399.3 |
| 355 | 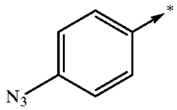 | 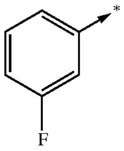 | 62 + 28 | 4.52 + 4.7 | 437.2 |
| 356 | 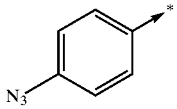 | 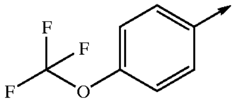 | 62 + 28 | 5 + 5.2 | 503.2 |

-continued
| | | | | | |
|---|---|---|---|---|---|
| 357 | 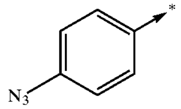 | 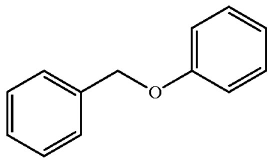 | 58 + 26 | 5.08 + 5.25 | 525.3 |
| 358 | 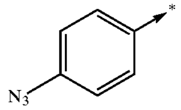 | 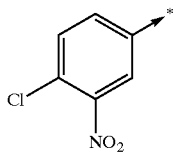 | 62 + 29 | 4.98 + 5.19 | 498.2 |
| 359 | 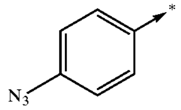 | 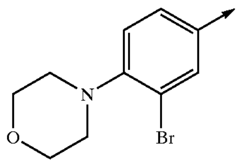 | 62 + 29 | 4.82 + 4.99 | 582.2 |
| 360 | 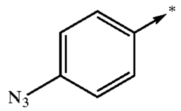 | 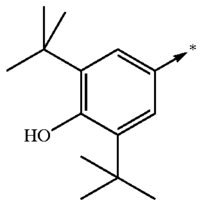 | 62 + 28 | 5.39 + 5.58 | 547.3 |
| 361 | 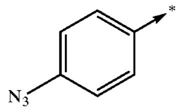 | 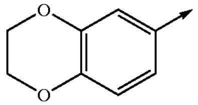 | 56 + 26 | 4.37 + 4.49 | 477.3 |
| 362 | 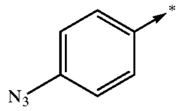 | 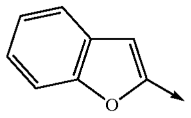 | 64 + 32 | 5.32 + 5.55 | 459.2 |

-continued
| | | | | | |
|---|---|---|---|---|---|
| 363 | 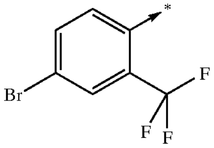 | 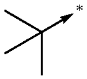 | 94 | 6.36 | 505.2 |
| 364 | 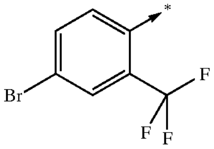 | 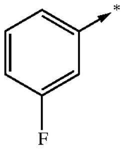 | 98 | 6.39 | 542.1 |
| 365 | 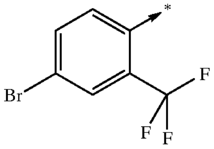 | 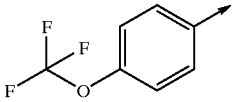 | 25 + 72 | 6.74 + 6.77 | 608.1 |
| 366 | 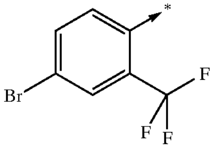 | 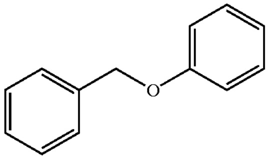 | 92 | 7.07 | 630.2 |
| 367 | 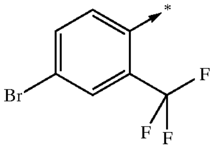 | 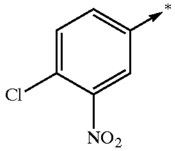 | 23 + 73 | 6.38 + 6.42 | 603.1 |
| 368 | 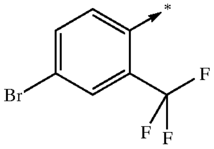 | 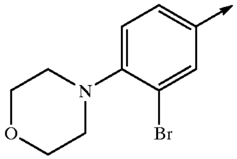 | 26 + 69 | 6.73 + 6.76 | 687.1 |

-continued
| | | | | | |
|---|---|---|---|---|---|
| 369 | 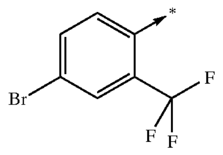 | 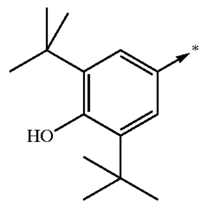 | 60 | 7.55 | 652.3 |
| 370 | 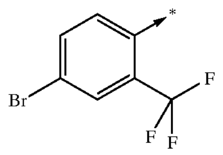 | 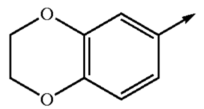 | 82 | 6.39 | 582.1 |
| 371 | 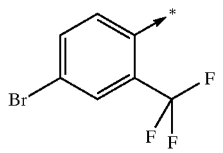 | 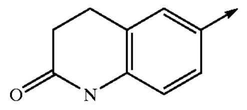 | 94 | 5.74 | 593.2 |
| 372 | 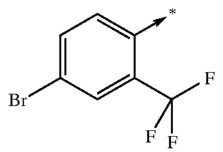 | 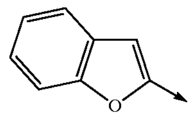 | 22 + 73 | 6.68 + 6.74 | 564.1 |
| 373 | 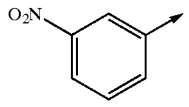 | 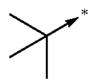 | 59 + 27 | 4.88 + 5.13 | 403.3 |
| 374 | 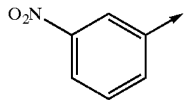 | 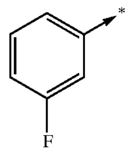 | 67 + 30 | 5.35 + 5.44 | 441.2 |

-continued
| | | | | | |
|---|---|---|---|---|---|
| 375 | 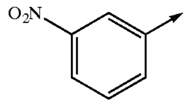 | 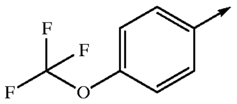 | 64 + 34 | 5.84 + 5.92 | 507.2 |
| 376 | 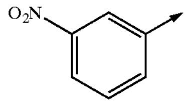 | 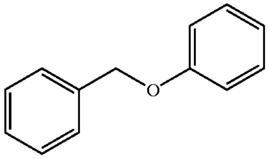 | 62 + 28 | 6 + 6.13 | 529.3 |
| 377 | 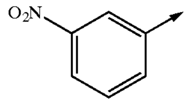 | 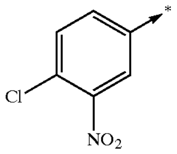 | 97 | 5.58 | 502.2 |
| 378 | 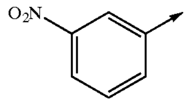 | 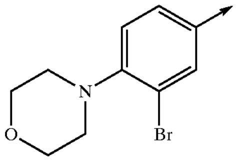 | 65 + 32 | 5.71 + 5.8 | 586.2 |
| 379 | 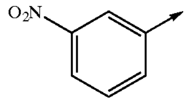 | 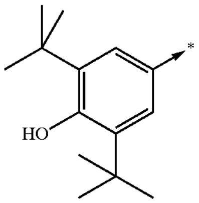 | 49 + 23 | 6.45 + 6.58 | 551.3 |
| 380 | 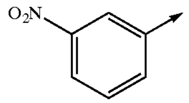 | 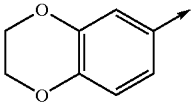 | 61 + 26 | 5.18 + 5.3 | 481.2 |
| 381 | 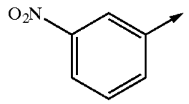 | 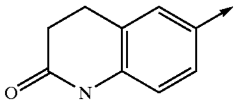 | 45 + 21 | 4.57 + 4.68 | 492.3 |

-continued
| | | | | | |
|---|---|---|---|---|---|
| 382 | 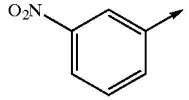 | 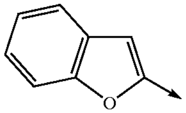 | 84 | 5.9 | 463.2 |
| 383 | 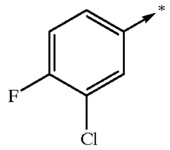 | 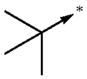 | 56 + 26 | 4.65 + 4.89 | 410.2 |
| 384 | 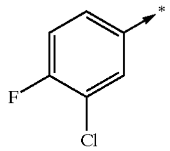 | 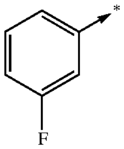 | 64 + 30 | 5.29 + 5.47 | 448.2 |
| 385 | 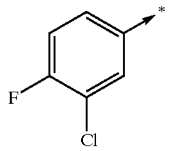 | 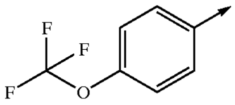 | 65 + 30 | 5.78 + 5.95 | 514.2 |
| 386 | 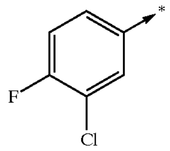 | 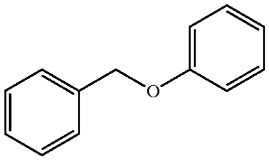 | 63 + 27 | 5.8 + 6.02 | 536.2 |
| 387 | 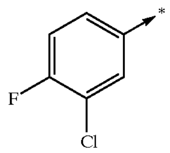 | 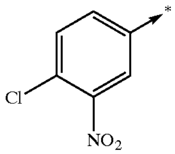 | 65 + 31 | 5.71 + 5.81 | 509.1 |

-continued
| | | | | | |
|---|---|---|---|---|---|
| 388 | 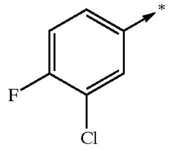 | 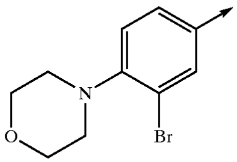 | 62 + 32 | 5.59 + 5.79 | 593.1 |
| 389 | 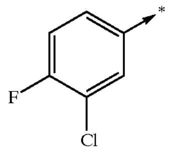 | 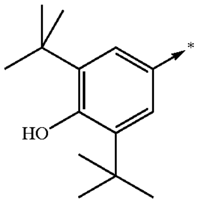 | 30 + 14 | 6.22 + 6.45 | 558.3 |
| 390 | 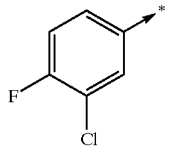 | 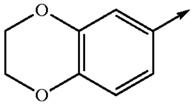 | 57 + 26 | 5.01 + 5.2 | 488.2 |
| 391 | 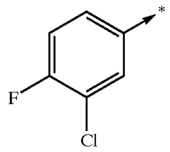 | 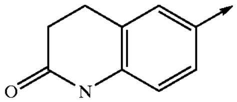 | 54 + 26 | 4.46 + 4.61 | 499.2 |
| 392 | 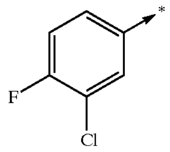 | 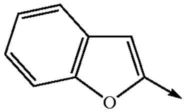 | 27 + 11 | 6.09 + 6.18 | 470.2 |

-continued
| | | | | | |
|---|---|---|---|---|---|
| 393 | 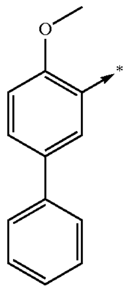 | 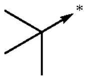 | 63 + 29 | 4.53 + 4.6 | 464.3 |
| 394 | 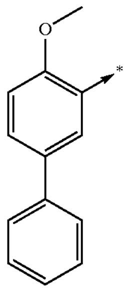 | 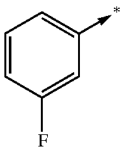 | 65 + 30 | 4.78 + 4.93 | 502.3 |
| 395 | 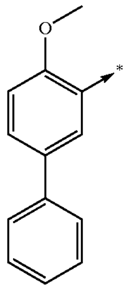 | 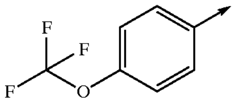 | 61 + 28 | 5.16 + 5.35 | 568.2 |

-continued
| | | | | | |
|---|---|---|---|---|---|
| 396 | 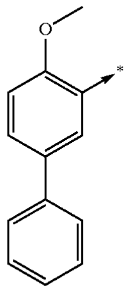 | 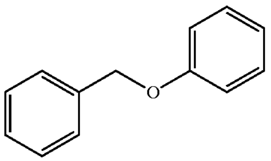 | 59 + 25 | 5.3 + 5.42 | 590.3 |
| 397 | 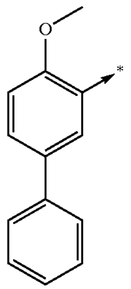 | 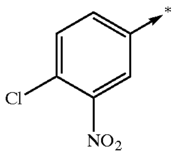 | 60 + 30 | 5.12 + 5.34 | 563.2 |
| 398 | 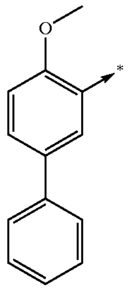 | 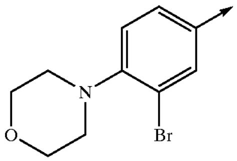 | 63 + 32 | 5.01 + 5.17 | 647.2 |

-continued
| | | | | | |
|---|---|---|---|---|---|
| 399 | 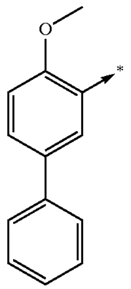 | 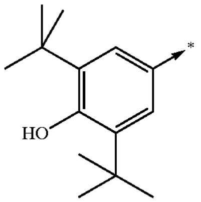 | 59 + 26 | 5.55 + 5.7 | 612.4 |
| 400 | 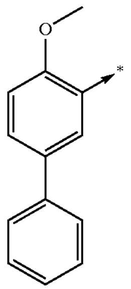 | 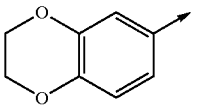 | 52 + 14 | 4.35 + 4.4 | 553.3 |
| 401 | 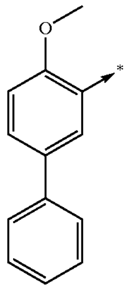 | 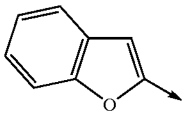 | 61 + 29 | 5.36 + 5.64 | 524.3 |

-continued
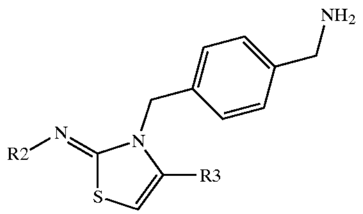
| | | | | | |
|---|---|---|---|---|---|
| 402 | 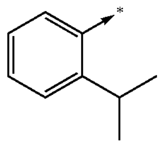 | 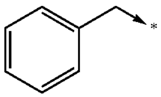 | 88.5 | 4.52 | 442.1 |
| 403 | 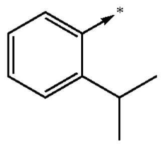 | 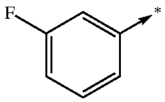 | 94.6 | 4.72 | 432.15 |
| 404 | 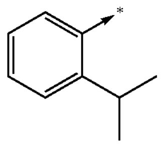 | 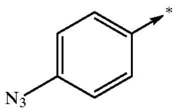 | 95 | 4.78 | 455.16 |
| 405 | 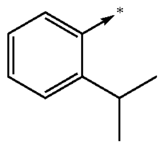 | 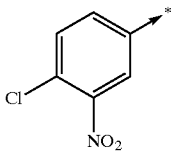 | 98.6 | 5.19 | 493.12 |
| 406 | 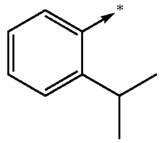 | 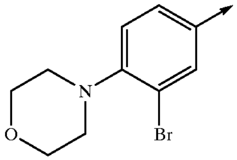 | 95.8 | 4.99 | 577.11 |

-continued
| | | | | | |
|---|---|---|---|---|---|
| 407 | 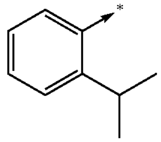 | 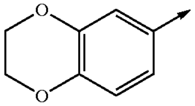 | 95.1 | 4.44 | 472.19 |
| 408 | 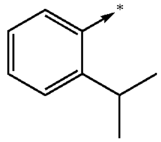 | 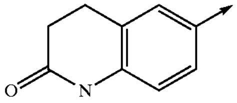 | 96.3 | 4.0 | 483.21 |
| 409 | 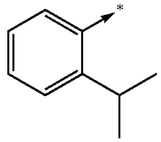 | 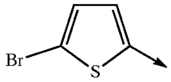 | 94.5 | 5.35 | 498.04 |
| 410 | 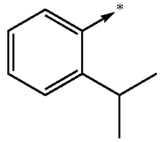 | 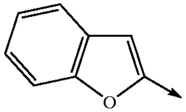 | 94.1 | 5.61 | 454.15 |
| 411 | 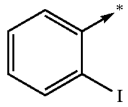 | 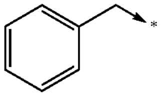 | 83 | 5.43 | 526.03 |
| 412 | 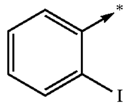 | 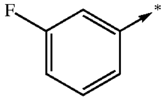 | 94.9 | 5.4 | 515.97 |
| 413 | 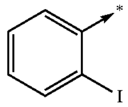 | 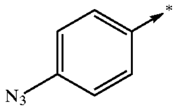 | 93.4 | 5.52 | 539.00 |

-continued
| | | | | | |
|---|---|---|---|---|---|
| 414 | 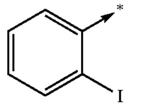 | 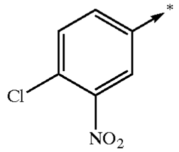 | 97.1 | 5.48 | 576.95 |
| 415 | 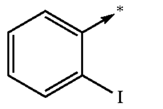 | 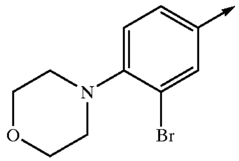 | 92.7 | 5.69 | 660.99 |
| 416 | 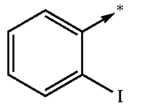 | 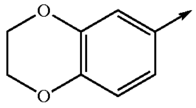 | 92.2 | 5.27 | 555.98 |
| 417 | 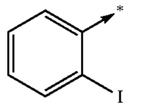 | 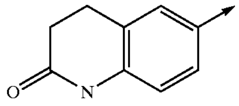 | 92 | 4.7 | 567.00 |
| 418 | 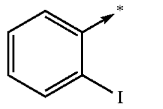 | 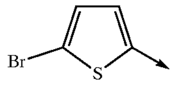 | 89.7 | 5.73 | 581.87 |
| 419 | 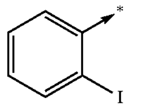 | 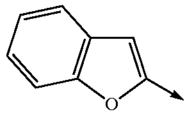 | 87.8 | 5.77 | 538.00 |
| 420 | 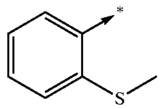 | 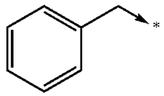 | 84.4 | 4.74 | 446.14 |
| 421 | 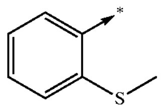 | 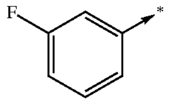 | 92.6 | 4.9 | 436.08 |

-continued
| | | | | | |
|---|---|---|---|---|---|
| 422 | 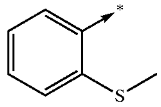 | 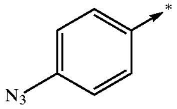 | 91.2 | 5.0 | 459.10 |
| 423 | 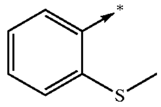 | 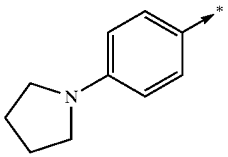 | 72.4 | 5.0 | 487.16 |
| 424 | 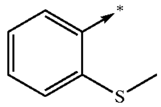 | 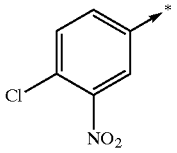 | 94.9 | 5.19 | 497.07 |
| 425 | 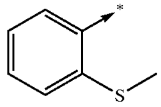 | 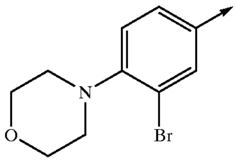 | 91.7 | 5.18 | 581.05 |
| 426 | 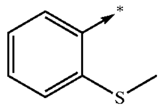 | 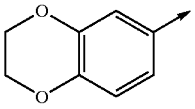 | 91.5 | 4.67 | 476.12 |
| 427 | 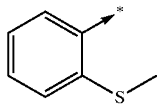 | 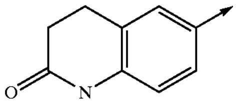 | 89.6 | 4.16 | 487.13 |
| 428 | 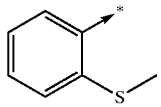 | 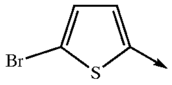 | 91.7 | 5.38 | 501.96 |

-continued
| | | | | | |
|---|---|---|---|---|---|
| 429 | 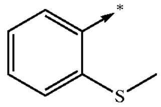 | 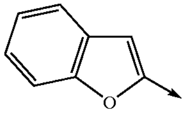 | 89.9 | 5.48 | 458.10 |
| 430 | 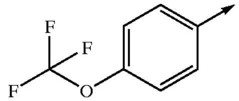 | 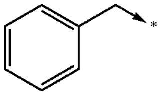 | 87.1 | 5.26 | 484.14 |
| 431 | 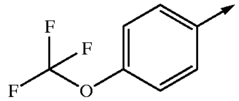 | 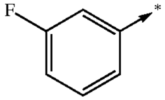 | 95.7 | 5.41 | 474.10 |
| 432 | 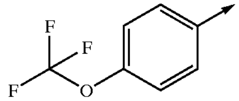 | 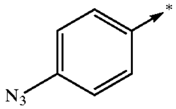 | 94.6 | 5.51 | 497.12 |
| 433 | 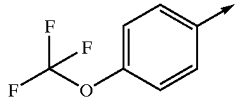 | 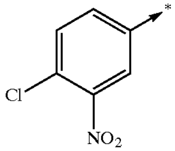 | 97.4 | 5.64 | 535.01 |
| 434 | 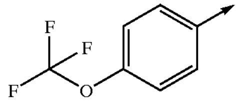 | 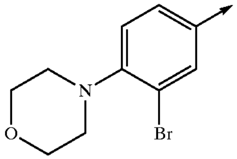 | 96.2 | 5.69 | 619.04 |
| 435 | 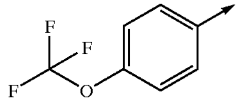 | 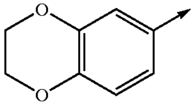 | 94.4 | 5.21 | 514.10 |
| 436 | 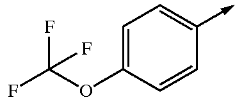 | 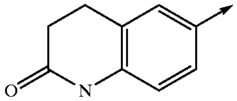 | 94.7 | 4.67 | 525.11 |

-continued
| | | | | | |
|---|---|---|---|---|---|
| 437 | 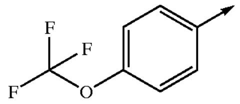 | 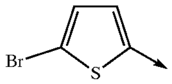 | 92.7 | 5.84 | 539.94 |
| 438 | 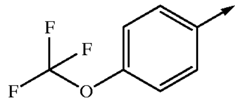 | 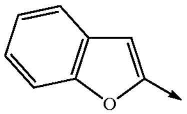 | 91 | 5.93 | 496.09 |
| 439 | 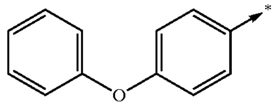 | 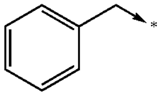 | 82.4 | 4.82 | 492.18 |
| 440 | 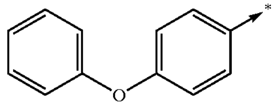 | 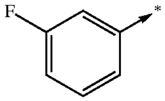 | 92.2 | 5.03 | 482.14 |
| 441 | 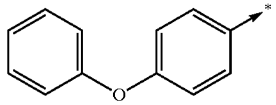 | 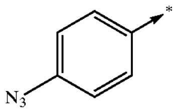 | 90.4 | 5.08 | 505.15 |
| 442 | 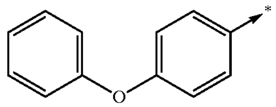 | 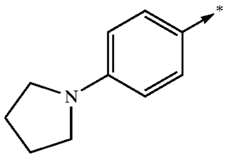 | 33.4 | 5.14 | 533.18 |
| 443 | 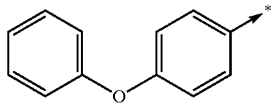 | 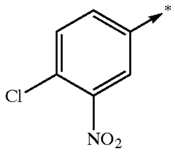 | 97.6 | 5.45 | 543.07 |

-continued
| | | | | | |
|---|---|---|---|---|---|
| 444 | 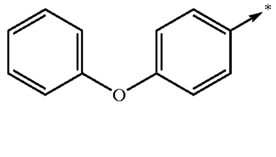 | 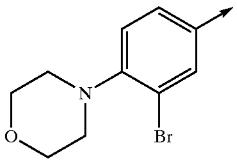 | 93.9 | 5.26 | 627.10 |
| 445 | 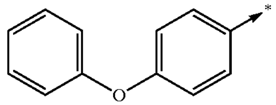 | 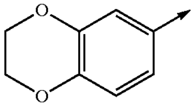 | 93.6 | 4.78 | 522.14 |
| 446 | 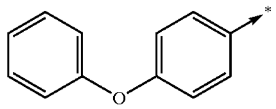 | 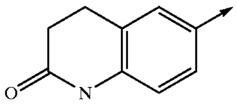 | 94 | 4.34 | 533.15 |
| 447 | 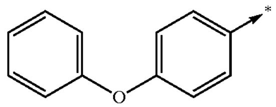 | 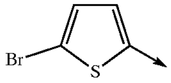 | 91.6 | 5.6 | 547.98 |
| 448 | 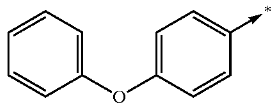 | 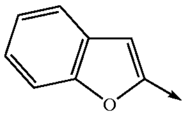 | 92.6 | 5.82 | 504.14 |
| 449 | 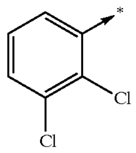 | 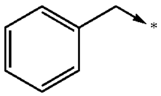 | 84.9 | 5.76 | 468.08 |
| 450 | 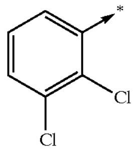 | 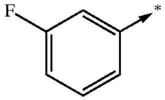 | 95.4 | 5.54 | 458.03 |

-continued
| | | | | | |
|---|---|---|---|---|---|
| 451 | 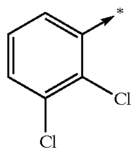 | 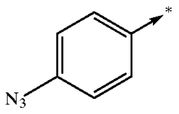 | 93.3 | 5.74 | 481.03 |
| 452 | 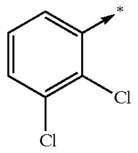 | 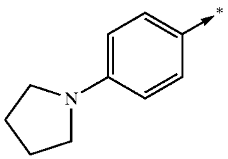 | 85.3 | 6.21 | 509.06 |
| 453 | 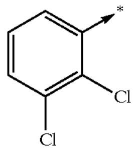 | 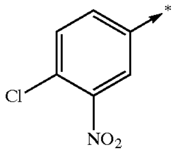 | 97.4 | 5.62 | 518.97 |
| 454 | 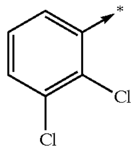 | 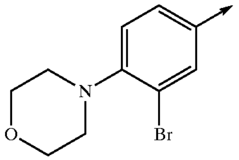 | 92 | 5.91 | 602.90 |
| 455 | 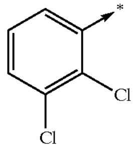 | 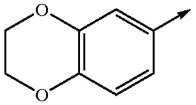 | 91.4 | 5.54 | 498.06 |
| 456 | 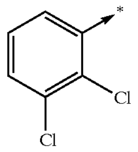 | 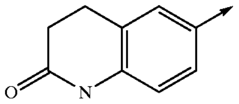 | 91.4 | 4.98 | 509.06 |

-continued
| | | | | | |
|---|---|---|---|---|---|
| 457 | 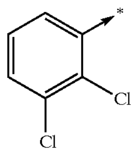 | 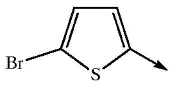 | 88.7 | 5.9 | 523.88 |
| 458 | 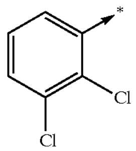 | 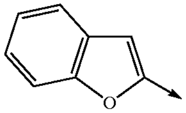 | 88.5 | 5.88 | 480.05 |
| 459 | 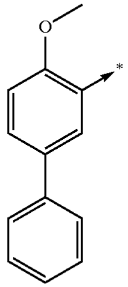 | 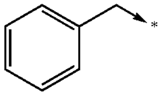 | 88.2 | 4.69 | 506.18 |
| 460 | 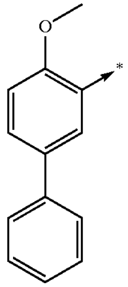 | 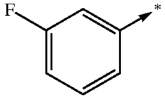 | 93.1 | 4.87 | 496.15 |

-continued
| | | | | | |
|---|---|---|---|---|---|
| 461 | 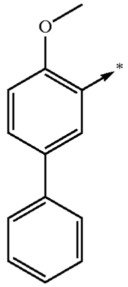 | 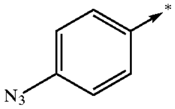 | 91.2 | 4.92 | 519.15 |
| 462 | 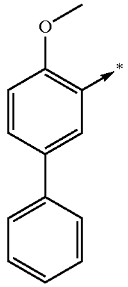 | 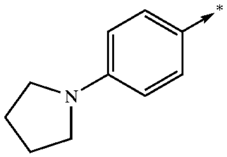 | 26.9 | 5.01 | 547.17 |
| 463 | 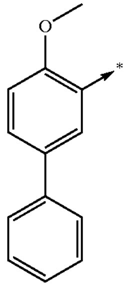 | 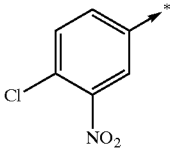 | 93.9 | 5.26 | 557.08 |

-continued
| | | | | | |
|---|---|---|---|---|---|
| 464 | 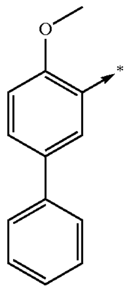 | 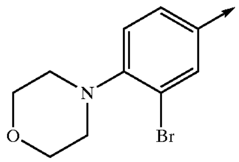 | 93.2 | 5.08 | 641.13 |
| 465 | 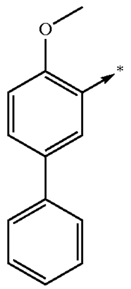 | 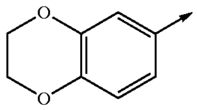 | 95.7 | 4.64 | 536.15 |
| 466 | 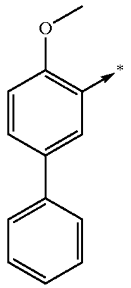 | 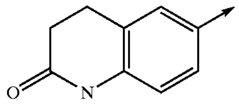 | 95.3 | 4.24 | 547.15 |

-continued
| | | | | | |
|---|---|---|---|---|---|
| 467 | 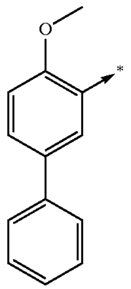 | 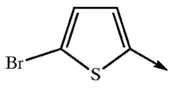 | 92.3 | 5.39 | 562.00 |
| 468 | 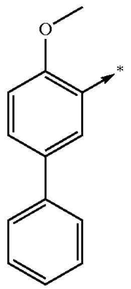 | 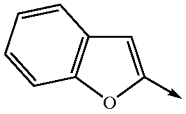 | 92 | 5.6 | 518.14 |
| 469 | 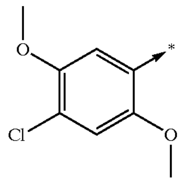 | 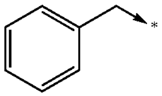 | 75.3 | 4.59 | 494.13 |
| 470 | 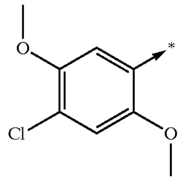 | 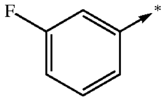 | 97.1 | 4.73 | 484.11 |

-continued
| | | | | | |
|---|---|---|---|---|---|
| 471 | 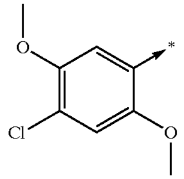 | 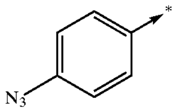 | 95.4 | 4.81 | 507.11 |
| 472 | 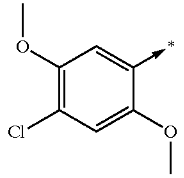 | 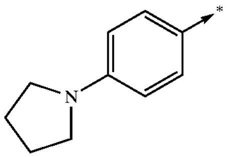 | 10.7 | 4.9 | 535.14 |
| 473 | 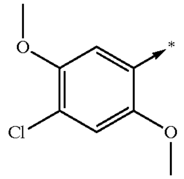 | 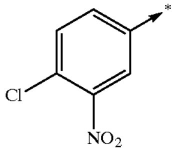 | 96.4 | 5.07 | 545.02 |
| 474 | 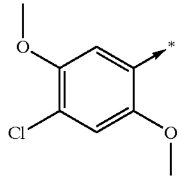 | 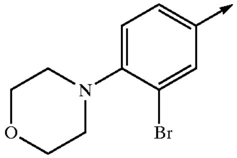 | 96.5 | 4.98 | 629.05 |
| 475 | 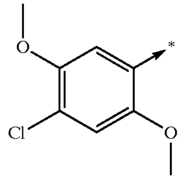 | 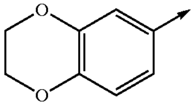 | 95.2 | 4.5 | 524.08 |

-continued
| | | | | | |
|---|---|---|---|---|---|
| 476 | 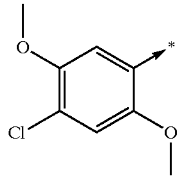 | 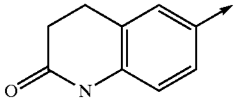 | 96 | 4.06 | 535.09 |
| 477 | 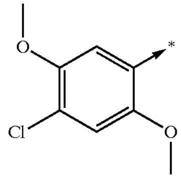 | 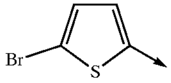 | 95.3 | 5.22 | 549.95 |
| 478 | 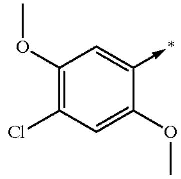 | 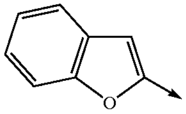 | 94.1 | 5.36 | 506.08 |
| | | 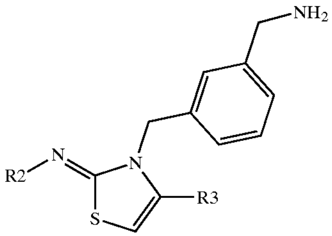 | | | |
| 479 | 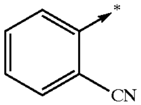 | 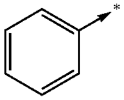 | 45.6 | 4.95 | 377.14 |
| 480 | 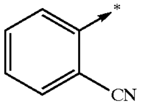 | 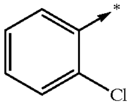 | 79 | 5.17 | 431.07 |

-continued
| | | | | | |
|---|---|---|---|---|---|
| 481 | 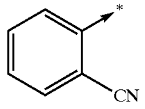 | 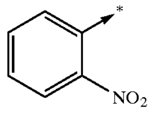 | 56.8 | 4.84 | 442.08 |
| 482 | 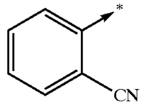 | 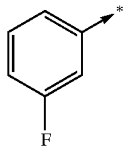 | 79.2 | 5.04 | 415.07 |
| 483 | 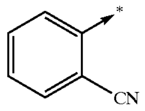 | 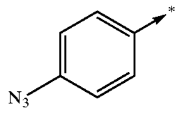 | 78.4 | 5.25 | 438.11 |
| 484 | 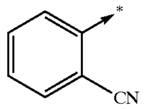 | 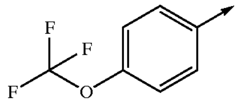 | 82.6 | 5.47 | 481.10 |
| 485 | 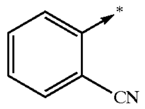 | 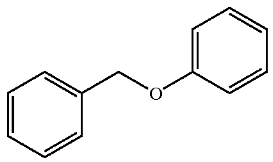 | 72.6 | 5.81 | 503.17 |
| 486 | 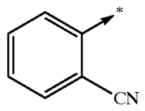 | 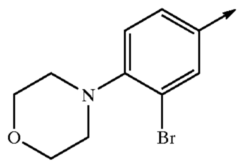 | 79 | 5.36 | 560.04 |
| 487 | 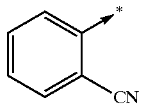 | 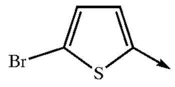 | 72.1 | 5.34 | 480.98 |

-continued
| | | | | | |
|---|---|---|---|---|---|
| 488 | 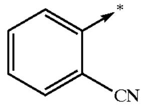 | 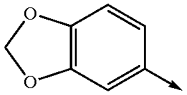 | 76.9 | 5.0 | 441.09 |
| 489 | 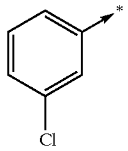 | 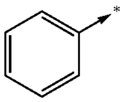 | 94.5 | 4.6 | 386.09 |
| 490 | 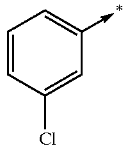 | 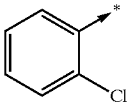 | 95.4 | 5.34 | 440.04 |
| 491 | 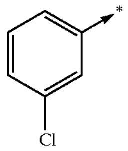 | 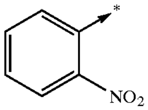 | 95.3 | 5.05 | 451.06 |
| 492 | 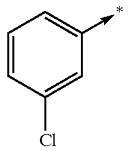 | 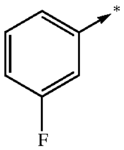 | 95.2 | 5.23 | 424.07 |
| 493 | 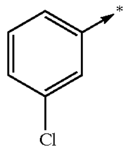 | 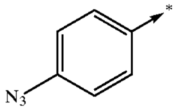 | 93.4 | 5.35 | 447.07 |

-continued
| | | | | | |
|---|---|---|---|---|---|
| 494 | 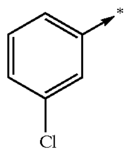 | 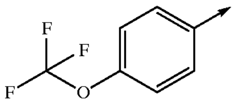 | 96.1 | 5.67 | 490.07 |
| 495 | 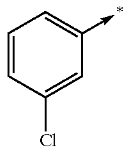 | 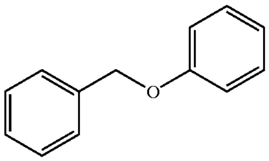 | 88.5 | 5.84 | 512.12 |
| 496 | 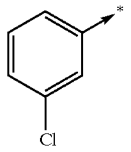 | 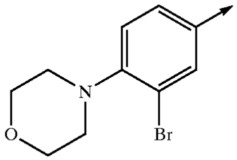 | 92.9 | 5.55 | 569.00 |
| 497 | 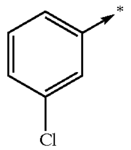 | 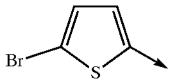 | 92.8 | 5.64 | 489.95 |
| 498 | 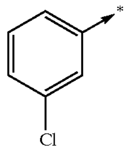 | 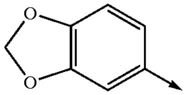 | 92 | 5.03 | 450.08 |
| 499 | 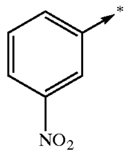 | 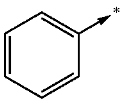 | 96.5 | 4.87 | 397.11 |

-continued
| | | | | | |
|---|---|---|---|---|---|
| 500 | 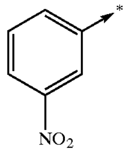 | 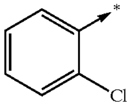 | 96.1 | 5.26 | 451.06 |
| 501 | 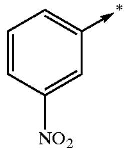 | 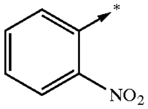 | 96.1 | 4.95 | 462.07 |
| 502 | 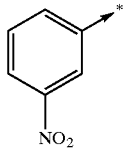 | 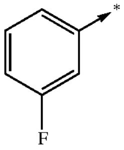 | 96.3 | 5.15 | 435.08 |
| 503 | 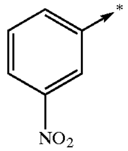 | 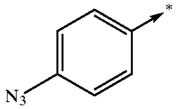 | 96.2 | 5.31 | 458.11 |
| 504 | 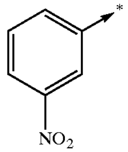 | 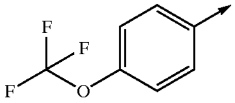 | 96.5 | 5.57 | 501.08 |
| 505 | 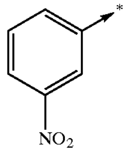 | 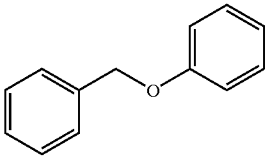 | 89.3 | 5.86 | 523.15 |

-continued
| | | | | | |
|---|---|---|---|---|---|
| 506 | 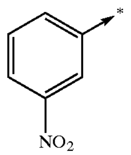 | 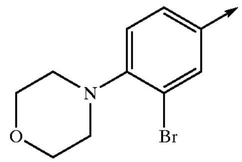 | 95.8 | 5.46 | 580.03 |
| 507 | 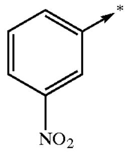 | 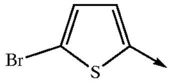 | 94.2 | 5.45 | 500.96 |
| 508 | 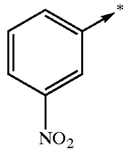 | 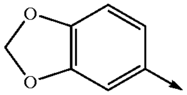 | 93.5 | 5.07 | 461.08 |
| 509 | 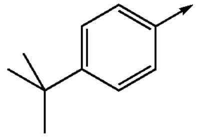 | 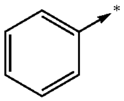 | 98.5 | 4.29 | 408.18 |
| 510 | 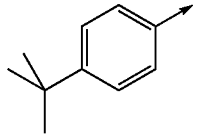 | 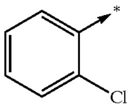 | 97.2 | 4.98 | 462.13 |
| 511 | 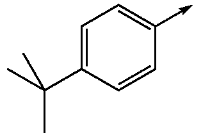 | 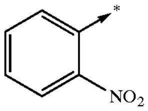 | 96.4 | 4.81 | 473.19 |

-continued
| | | | | | |
|---|---|---|---|---|---|
| 512 | 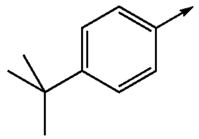 | 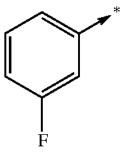 | 96.3 | 4.9 | 446.17 |
| 513 | 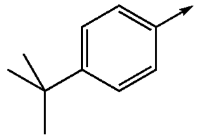 | 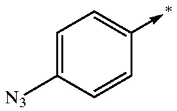 | 94.7 | 4.93 | 469.19 |
| 514 | 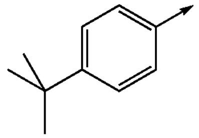 | 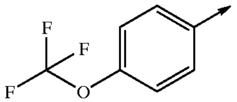 | 96.9 | 5.29 | 512.17 |
| 515 | 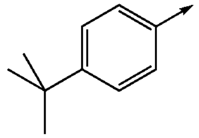 | 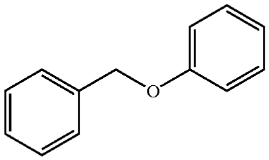 | 90.6 | 5.33 | 534.20 |
| 516 | 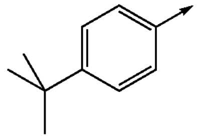 | 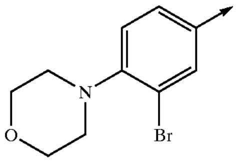 | 96.3 | 5.15 | 591.13 |
| 517 | 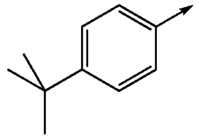 | 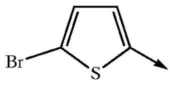 | 93.5 | 5.47 | 512.04 |

-continued
| | | | | | |
|---|---|---|---|---|---|
| 518 | 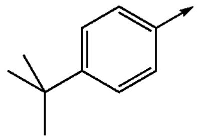 | 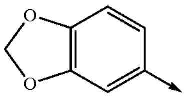 | 95 | 4.65 | 472.19 |
| 519 | 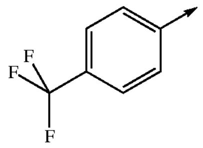 | 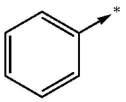 | 95.5 | 5.14 | 420.13 |
| 520 | 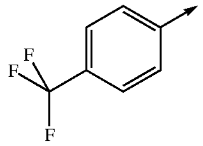 | 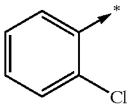 | 95.6 | 5.63 | 474.07 |
| 521 | 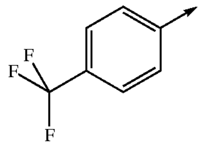 | 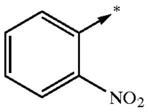 | 93.8 | 5.35 | 485.10 |
| 522 | 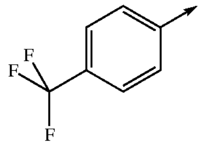 | 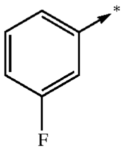 | 95.1 | 5.53 | 458.09 |
| 523 | 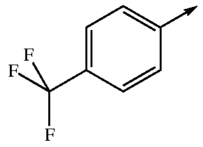 | 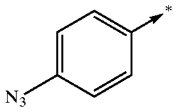 | 94.2 | 5.67 | 481.10 |

-continued
| | | | | | |
|---|---|---|---|---|---|
| 524 | 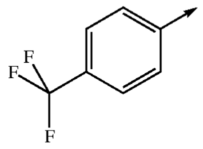 | 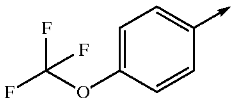 | 94.6 | 5.9 | 524.09 |
| 525 | 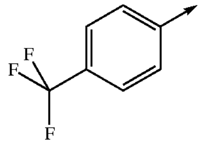 | 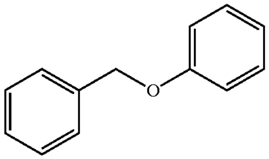 | 88.4 | 6.15 | 546.11 |
| 526 | 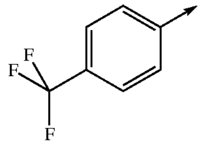 | 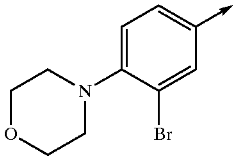 | 92.6 | 5.83 | 603.07 |
| 527 | 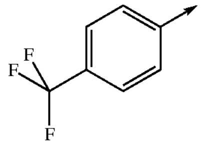 | 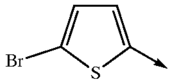 | 89.8 | 5.87 | 523.97 |
| 528 | 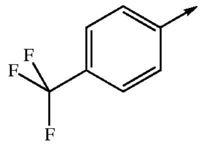 | 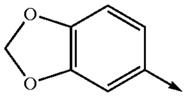 | 92.3 | 5.41 | 484.11 |
| 529 | 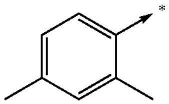 | 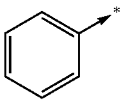 | 98.2 | 3.75 | 380.18 |
| 530 | 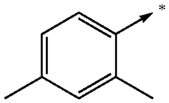 | 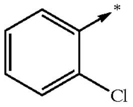 | 96.4 | 4.35 | 434.11 |

-continued
| | | | | | |
|---|---|---|---|---|---|
| 531 | 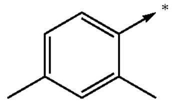 | 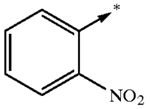 | 96.5 | 4.19 | 445.13 |
| 532 | 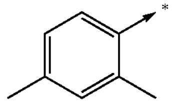 | 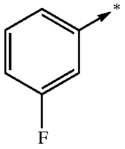 | 95.7 | 4.25 | 418.14 |
| 533 | 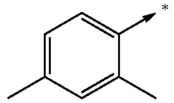 | 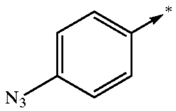 | 94.4 | 4.33 | 441.13 |
| 534 | 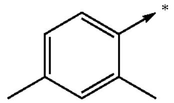 | 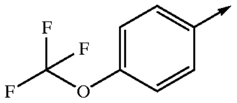 | 95.5 | 4.69 | 484.14 |
| 535 | 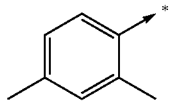 | 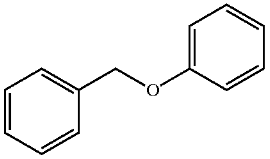 | 89.5 | 4.81 | 506.18 |
| 536 | 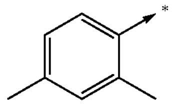 | 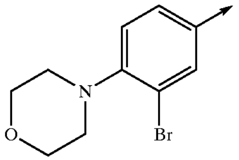 | 95.5 | 4.54 | 563.08 |
| 537 | 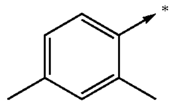 | 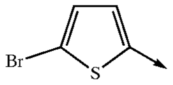 | 92.2 | 4.79 | 484.03 |

-continued
| | | | | | |
|---|---|---|---|---|---|
| 538 | 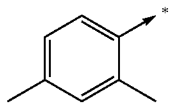 | 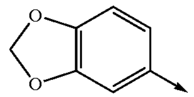 | 93.7 | 4.07 | 444.14 |
| 539 | 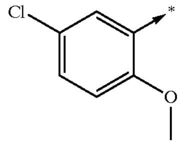 | 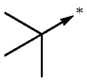 | 95.4 | 4.25 | 416.10 |
| 540 | 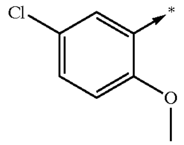 | 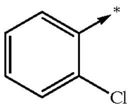 | 95.7 | 5.05 | 470.07 |
| 541 | 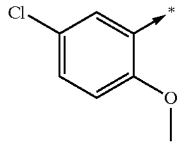 | 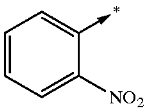 | 95.6 | 4.81 | 481.05 |
| 542 | 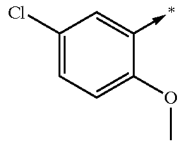 | 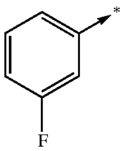 | 95.4 | 4.96 | 454.07 |
| 543 | 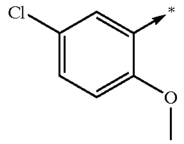 | 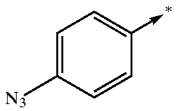 | 94.4 | 5.05 | 477.10 |
| 544 | 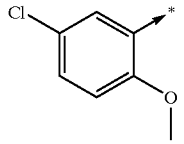 | 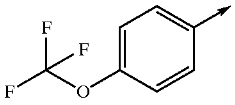 | 95.9 | 5.4 | 520.04 |

-continued
| | | | | | |
|---|---|---|---|---|---|
| 545 | 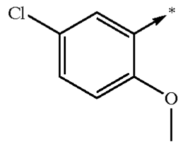 | 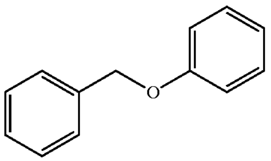 | 89.5 | 5.51 | 542.11 |
| 546 | 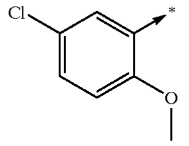 | 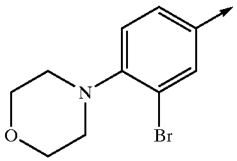 | 94 | 5.26 | 599.02 |
| 547 | 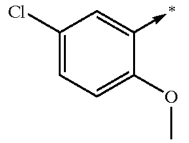 | 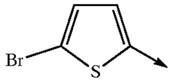 | 92.9 | 5.4 | 519.93 |
| 548 | 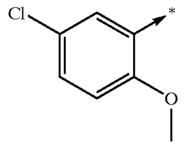 | 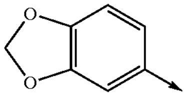 | 92.3 | 4.72 | 480.08 |
| 549 | 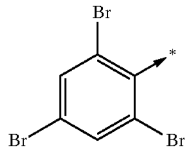 | 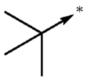 | 92 | 6.01 | 585.84 |
| 550 | 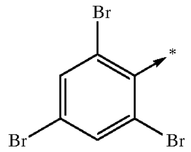 | 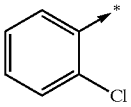 | 96.7 | 6.18 | 639.79 |

-continued
| | | | | | |
|---|---|---|---|---|---|
| 551 | 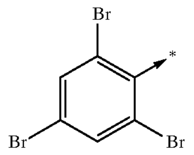 | 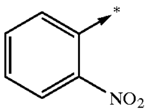 | 95.8 | 5.84 | 650.83 |
| 552 | 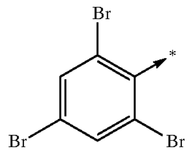 | 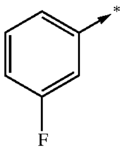 | 96 | 6.04 | 623.81 |
| 553 | 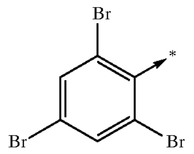 | 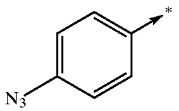 | 94.7 | 6.22 | 646.85 |
| 554 | 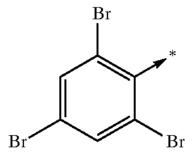 | 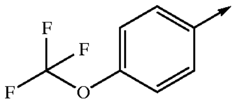 | 95 | 6.39 | 689.82 |
| 555 | 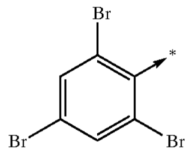 | 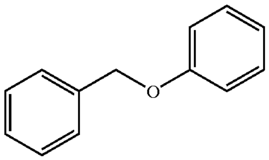 | 88.8 | 6.7 | 711.88 |
| 556 | 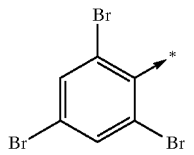 | 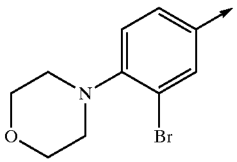 | 94.9 | 6.4 | 768.76 |

-continued
| | | | | | |
|---|---|---|---|---|---|
| 557 | 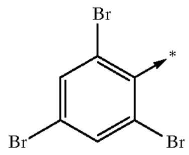 | 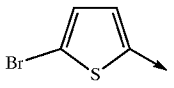 | 95 | 6.35 | 689.71 |
| 558 | 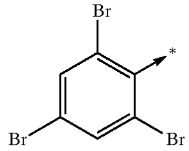 | 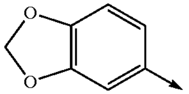 | 93.7 | 6.01 | 649.83 |
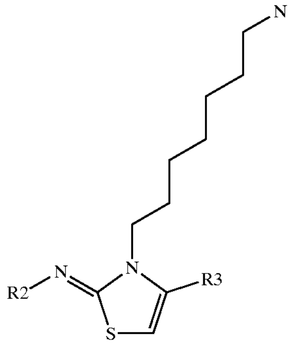
| | | | | | |
|---|---|---|---|---|---|
| 559 | 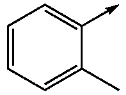 | 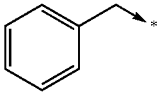 | 87.5 | 4.07 | 408.18 |
| 560 | 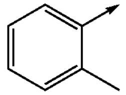 | 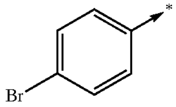 | 89.6 | 4.15 | 458.09 |
| 561 | 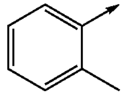 | 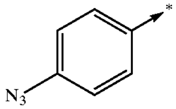 | 89.5 | 4.04 | 421.17 |

-continued
| | | | | | |
|---|---|---|---|---|---|
| 562 | 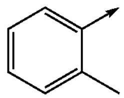 | 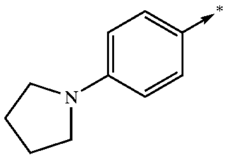 | 54.6 | 4.37 | 449.23 |
| 563 | 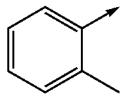 | 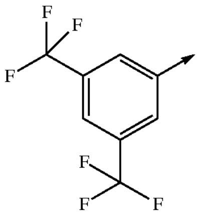 | 92.7 | 4.85 | 516.14 |
| 564 | 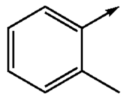 | 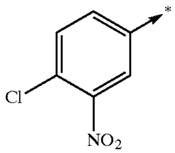 | 92.5 | 4.27 | 459.14 |
| 565 | 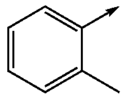 | 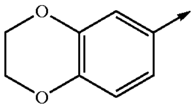 | 94.2 | 3.87 | 438.18 |
| 566 | 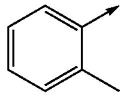 | 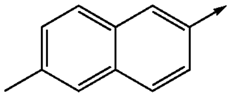 | 92.6 | 4.41 | 444.2 |
| 567 | 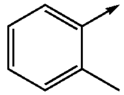 | 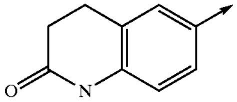 | 92.2 | 3.5 | 449.21 |
| 568 | 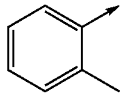 | 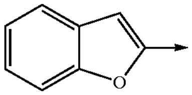 | 92.4 | 4.53 | 420.17 |

-continued
| | | | | | |
|---|---|---|---|---|---|
| 569 | 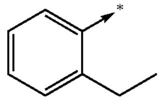 | 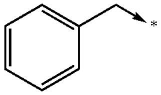 | 86.7 | 4.23 | 422.21 |
| 570 | 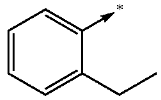 | 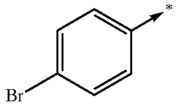 | 93.7 | 4.38 | 472.12 |
| 571 | 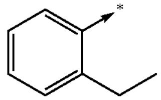 | 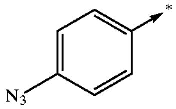 | 88.7 | 4.27 | 435.19 |
| 572 | 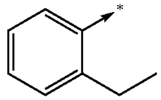 | 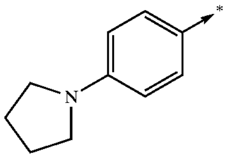 | 64.2 | 4.53 | 463.25 |
| 573 | 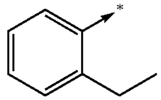 | 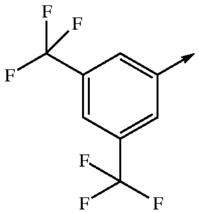 | 93.8 | 5.15 | 530.18 |
| 574 | 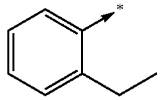 | 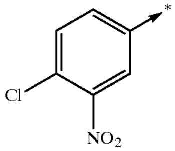 | 93.6 | 4.55 | 473.17 |
| 575 | 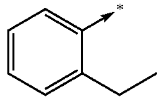 | 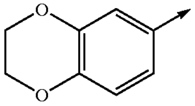 | 86.8 | 4.07 | 452.21 |

-continued
| | | | | | |
|---|---|---|---|---|---|
| 576 | 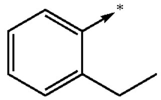 | 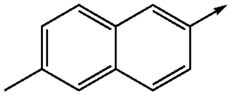 | 93.4 | 4.65 | 458.24 |
| 577 | 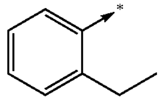 | 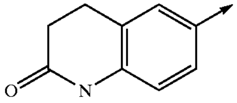 | 91.8 | 3.71 | 463.23 |
| 578 | 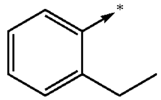 | 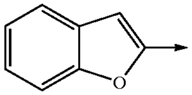 | 91.6 | 4.85 | 434.20 |
| 579 | 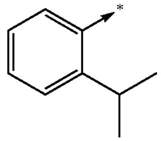 | 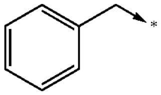 | 83.1 | 4.38 | 436.23 |
| 580 | 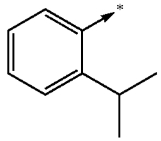 | 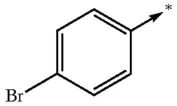 | 92.7 | 4.56 | 486.14 |
| 581 | 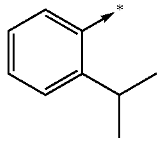 | 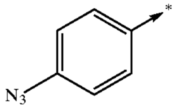 | 88.9 | 4.43 | 449.24 |
| 582 | 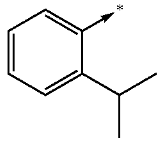 | 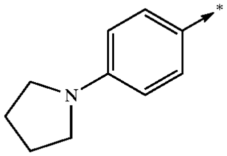 | 80.4 | 4.65 | 477.25 |

-continued
| | | | | | |
|---|---|---|---|---|---|
| 583 | 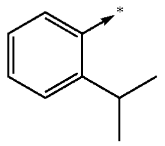 | 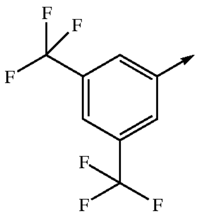 | 93 | 5.34 | 544.19 |
| 584 | 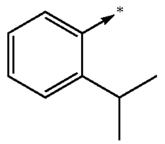 | 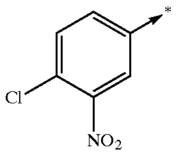 | 94.3 | 4.75 | 487.20 |
| 585 | 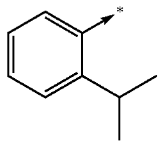 | 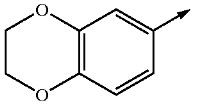 | 93.2 | 4.23 | 466.23 |
| 586 | 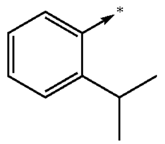 | 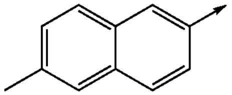 | 94 | 4.82 | 472.28 |
| 587 | 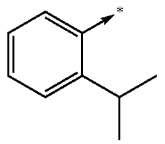 | 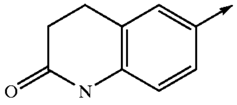 | 92.1 | 3.88 | 477.28 |
| 588 | 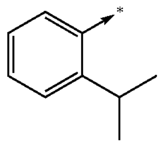 | 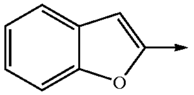 | 91.7 | 5.06 | 448.23 |

-continued
| | | | | | |
|---|---|---|---|---|---|
| 589 | 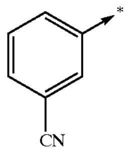 | 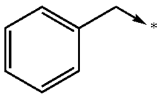 | 83.1 | 4.62 | 419.20 |
| 590 | 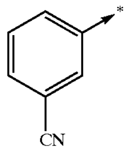 | 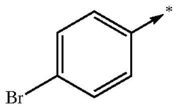 | 93 | 5.06 | 469.09 |
| 591 | 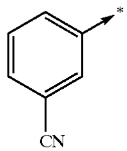 | 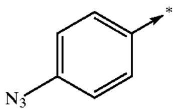 | 88 | 4.89 | 432.18 |
| 592 | 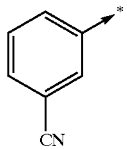 | 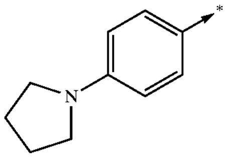 | 88.5 | 5.02 | 460.23 |
| 593 | 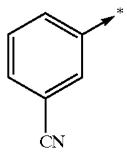 | 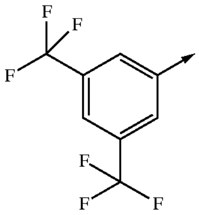 | 93.2 | 5.69 | 527.16 |
| 594 | 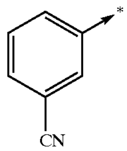 | 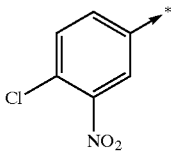 | 91.6 | 5.11 | 470.15 |

-continued
| | | | | | |
|---|---|---|---|---|---|
| 595 | 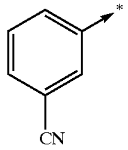 | 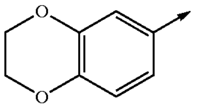 | 90.2 | 4.53 | 449.19 |
| 596 | 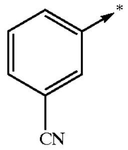 | 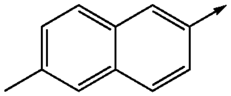 | 91.9 | 5.4 | 455.19 |
| 597 | 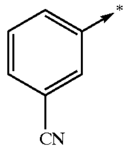 | 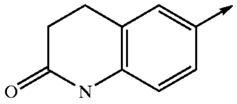 | 90.2 | 3.99 | 460.20 |
| 598 | 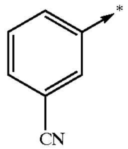 | 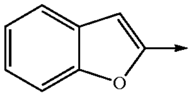 | 93 | 5.41 | 431.16 |
| 599 | 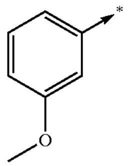 | 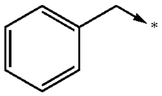 | 86.1 | 4.05 | 424.22 |
| 600 | 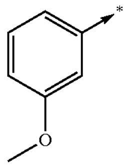 | 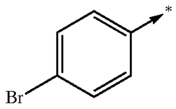 | 91.8 | 4.17 | 474.12 |

-continued
| | | | | | |
|---|---|---|---|---|---|
| 601 | 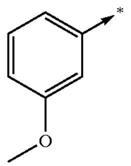 | 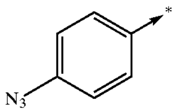 | 90.2 | 4.04 | 437.19 |
| 602 | 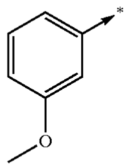 | 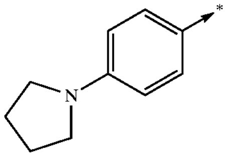 | 86.4 | 4.34 | 465.24 |
| 603 | 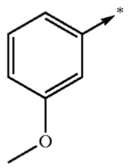 | 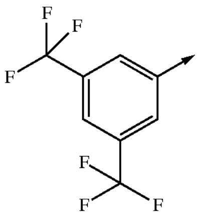 | 93.5 | 4.91 | 532.19 |
| 604 | 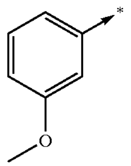 | 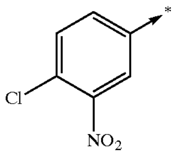 | 93.4 | 4.3 | 475.16 |
| 605 | 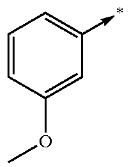 | 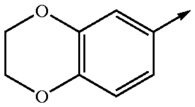 | 87.9 | 3.86 | 454.20 |

-continued
| | | | | | |
|---|---|---|---|---|---|
| 606 | 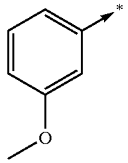 | 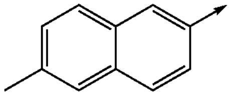 | 91.8 | 4.47 | 460.25 |
| 607 | 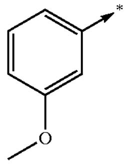 | 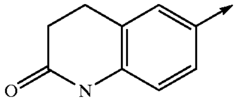 | 90.7 | 3.48 | 465.21 |
| 608 | 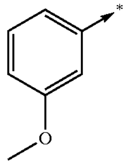 | 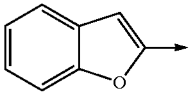 | 92 | 4.55 | 436.19 |
| 609 | 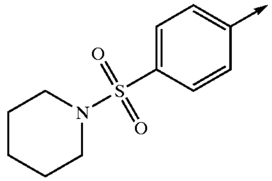 | 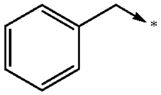 | 85.9 | 5.19 | 541.25 |
| 610 | 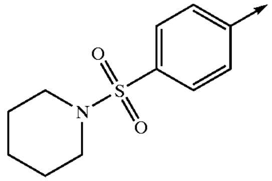 | 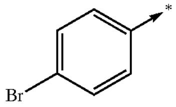 | 92.4 | 5.6 | 591.13 |

-continued
| | | | | | |
|---|---|---|---|---|---|
| 611 | 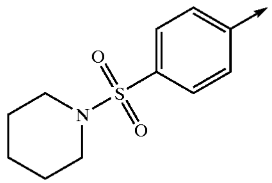 | 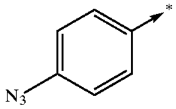 | 89.7 | 5.45 | 554.23 |
| 612 | 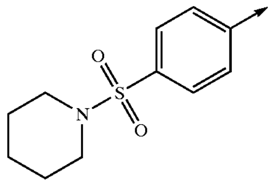 | 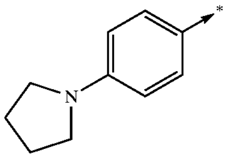 | 88.7 | 5.58 | 582.28 |
| 613 | 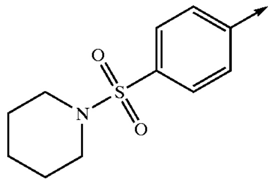 | 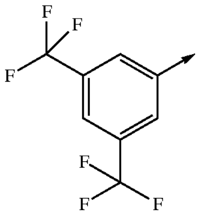 | 93.2 | 6.06 | 649.24 |
| 614 | 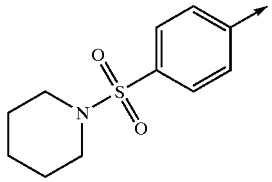 | 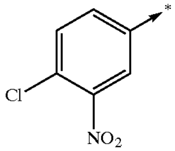 | 94.1 | 5.55 | 592.18 |
| 615 | 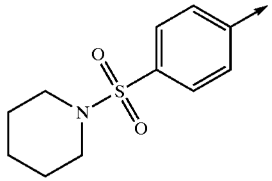 | 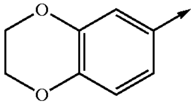 | 90 | 5.09 | 571.23 |

-continued
| | | | | | |
|---|---|---|---|---|---|
| 616 | 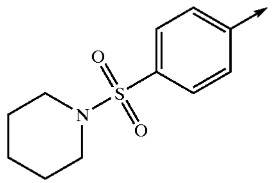 | 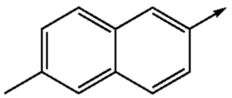 | 93.3 | 5.91 | 577.26 |
| 617 | 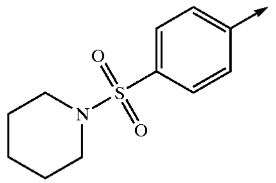 | 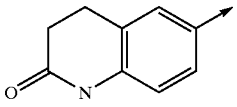 | 91.4 | 4.53 | 582.24 |
| 618 | 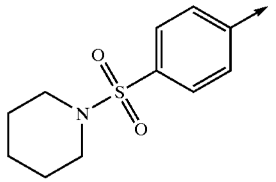 | 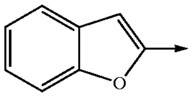 | 92.1 | 5.84 | 553.22 |
| 619 | 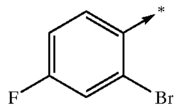 | 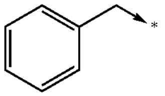 | 76.6 | 5.06 | 490.15 |
| 620 | 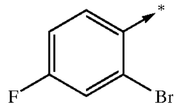 | 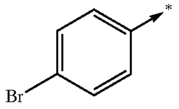 | 91.2 | 5.56 | 539.99 |
| 621 | 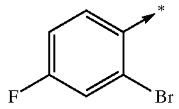 | 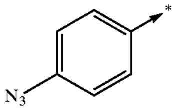 | 86.7 | 5.39 | 503.12 |

-continued
| | | | | | |
|---|---|---|---|---|---|
| 622 | 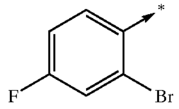 | 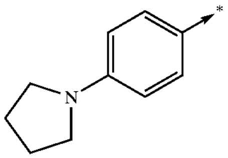 | 81 | 5.47 | 531.15 |
| 623 | 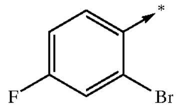 | 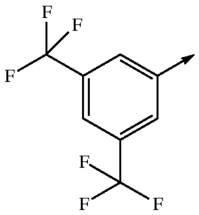 | 92.2 | 6.13 | 598.06 |
| 624 | 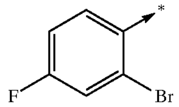 | 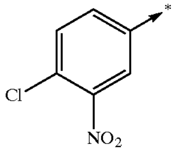 | 84.8 | 5.59 | 541.03 |
| 625 | 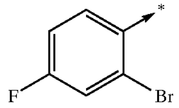 | 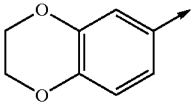 | 88 | 5.04 | 520.11 |
| 626 | 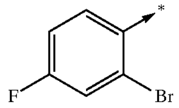 | 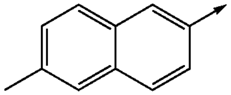 | 91.6 | 5.91 | 526.14 |
| 627 | 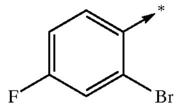 | 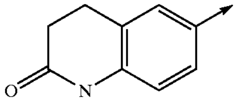 | 89.4 | 4.49 | 531.11 |
| 628 | 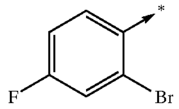 | 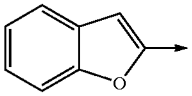 | 90.3 | 5.89 | 502.10 |

-continued
| | | | | | |
|---|---|---|---|---|---|
| 629 | 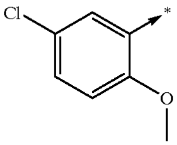 | 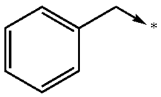 | 83.3 | 4.41 | 458.20 |
| 630 | 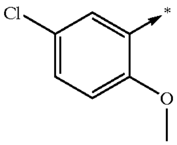 | 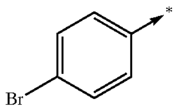 | 91.5 | 4.72 | 508.08 |
| 631 | 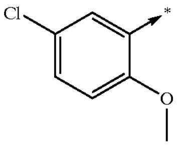 | 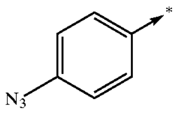 | 87.8 | 4.57 | 471.18 |
| 632 | 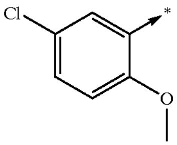 | 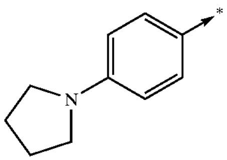 | 57.7 | 4.71 | 499.23 |
| 633 | 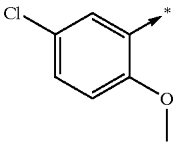 | 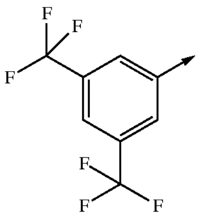 | 92.8 | 5.54 | 566.12 |
| 634 | 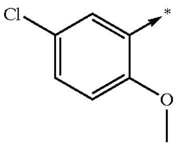 | 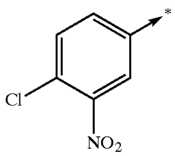 | 93.5 | 4.93 | 509.13 |

-continued
| | | | | | |
|---|---|---|---|---|---|
| 635 | 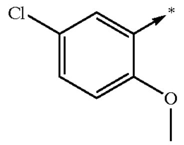 | 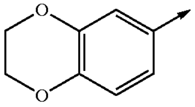 | 89.3 | 4.29 | 488.19 |
| 636 | 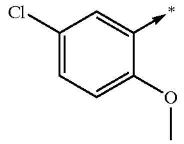 | 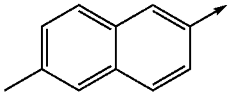 | 93.6 | 4.99 | 494.21 |
| 637 | 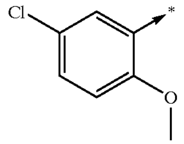 | 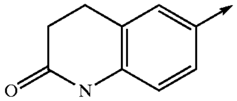 | 91.7 | 3.88 | 499.21 |
| 638 | 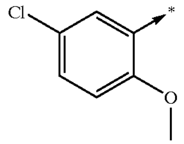 | 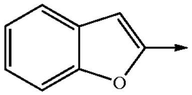 | 91.9 | 5.22 | 470.18 |
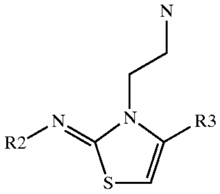
| | | | | | |
|---|---|---|---|---|---|
| 639 | 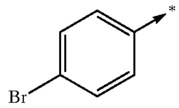 | 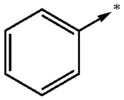 | 95 | 7.28 | 374.10 |
| 640 | 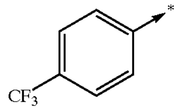 | 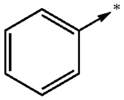 | 87 | 7.62 | 364.24 |

-continued
| | | | | | |
|---|---|---|---|---|---|
| 641 | 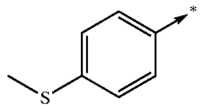 | 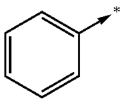 | 84 | 6.75 | 342.23 |
| 642 | 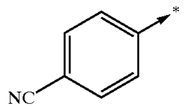 | 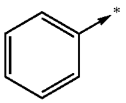 | 79 | 6.6 | 321.24 |
| 643 | 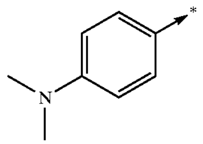 | 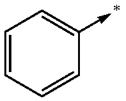 | 81 | 4.96 | 339.29 |
| 644 | 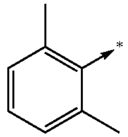 | 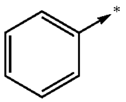 | 82 | 6.44 | 324.28 |
| 645 | 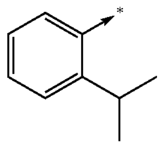 | 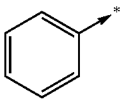 | 83 | 7.16 | 338.30 |
| 646 | 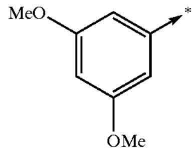 | 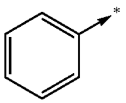 | 59 | 6.6 | 356.25 |
| 647 | 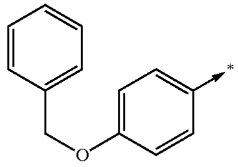 | 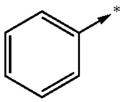 | 86 | 7.28 | 402.23 |

-continued
| | | | | | |
|---|---|---|---|---|---|
| 648 | 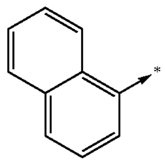 | 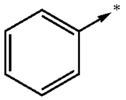 | 84 | 7.29 | 346.26 |
| 649 | 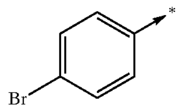 | 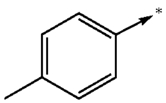 | 85 | 7.66 | 388.1 |
| 650 | 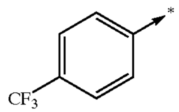 | 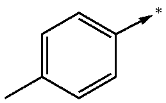 | 84 | 7.96 | 378.21 |
| 651 | 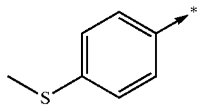 | 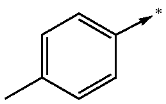 | 85 | 7.14 | 356.23 |
| 652 | 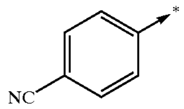 | 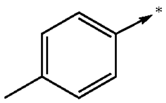 | 73 | 7.02 | 335.26 |
| 653 | 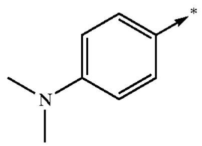 | 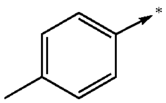 | 76 | 5.37 | 353.29 |
| 654 | 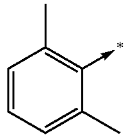 | 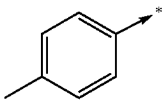 | 83 | 6.84 | 338.30 |

-continued
| | | | | | |
|---|---|---|---|---|---|
| 655 | 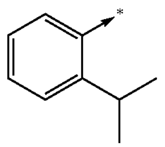 | 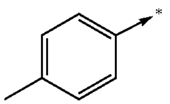 | 81 | 7.51 | 352.29 |
| 656 | 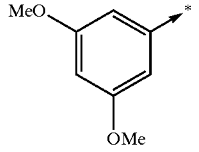 | 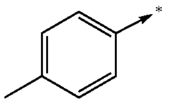 | 75 | 6.99 | 370.27 |
| 657 | 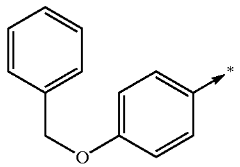 | 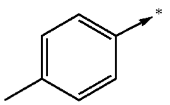 | 77 | 7.6 | 416.26 |
| 658 | 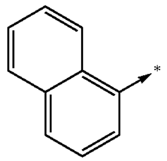 | 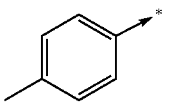 | 80 | 7.65 | 360.25 |
| 659 | 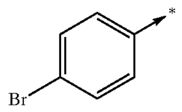 | 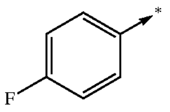 | 87 | 7.37 | 392.10 |
| 660 | 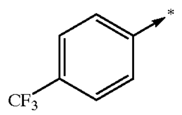 | 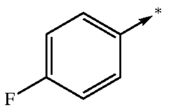 | 71 | 7.7 | 382.16 |
| 661 | 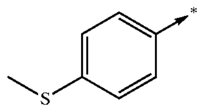 | 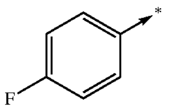 | 63 | 6.9 | 360.21 |

-continued
| | | | | | |
|---|---|---|---|---|---|
| 662 | 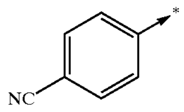 | 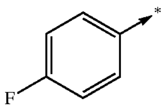 | 59 | 6.7 | 339.23 |
| 663 | 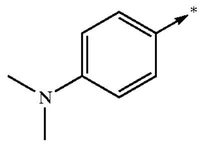 | 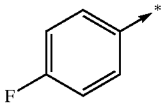 | 80 | 5.06 | 357.26 |
| 664 | 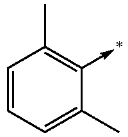 | 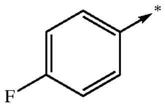 | 63 | 6.61 | 342.26 |
| 665 | 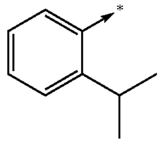 | 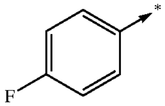 | 82 | 7.28 | 356.25 |
| 666 | 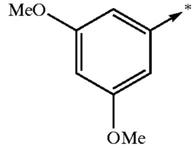 | 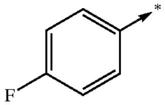 | 39 | 6.74 | 374.22 |
| 667 | 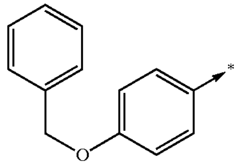 | 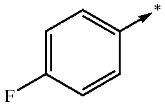 | 85 | 7.42 | 420.24 |

-continued
| | | | | | |
|---|---|---|---|---|---|
| 668 | 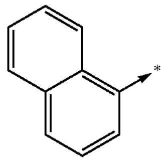 | 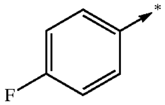 | 81 | 7.39 | 364.26 |
| 669 | 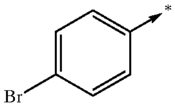 | 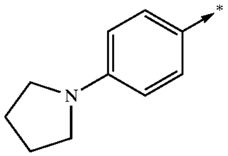 | 93 | 8.28 | 443.2 |
| 670 | 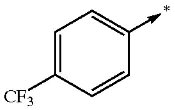 | 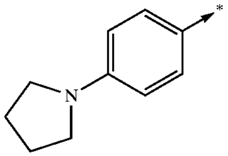 | 88 | 8.61 | 433.2 |
| 671 | 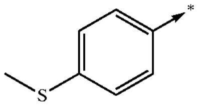 | 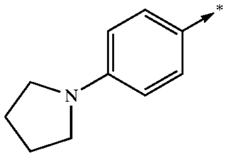 | 88 | 7.7 | 411.2 |
| 672 | 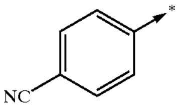 | 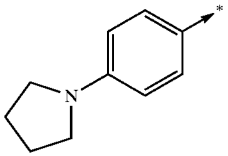 | 80 | 7.76 | 390.26 |
| 673 | 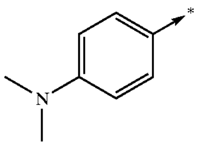 | 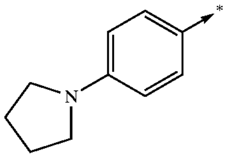 | 85 | 6.08 | 408.3 |

-continued
| | | | | | |
|---|---|---|---|---|---|
| 674 | 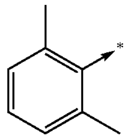 | 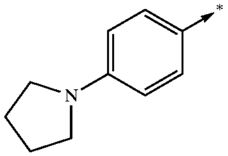 | 89 | 7.36 | 393.3 |
| 675 | 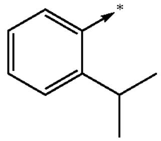 | 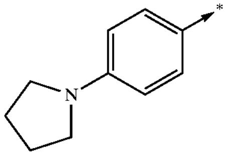 | 84 | 8.03 | 407.3 |
| 676 | 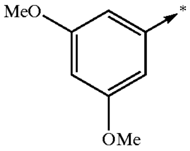 | 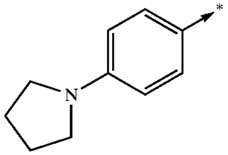 | 81 | 7.59 | 425.3 |
| 677 | 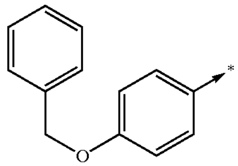 | 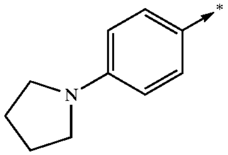 | 83 | 8.03 | 471.3 |
| 678 | 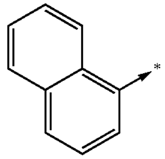 | 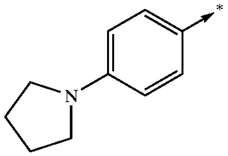 | 91 | 8.24 | 415.2 |
| 679 | 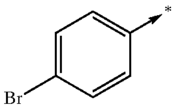 | 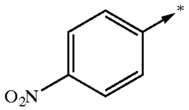 | 78 | 7.41 | 419.09 |

-continued
| | | | | | |
|---|---|---|---|---|---|
| 680 | 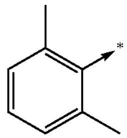 | 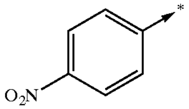 | 75 | 6.98 | 369.23 |
| 681 | 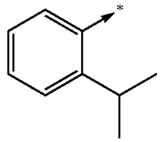 | 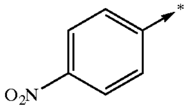 | 81 | 7.51 | 383.23 |
| 682 | 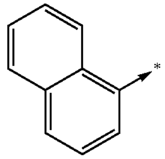 | 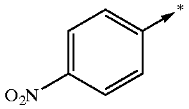 | 85 | 7.46 | 391.20 |
| 683 | 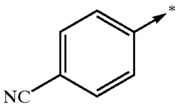 | 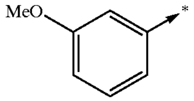 | 74 | 6.79 | 351.21 |
| 684 | 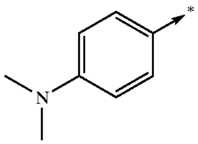 | 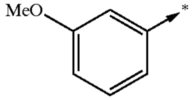 | 81 | 5.18 | 369.26 |
| 685 | 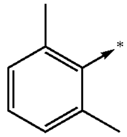 | 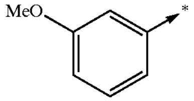 | 76 | 6.73 | 354.26 |
| 686 | 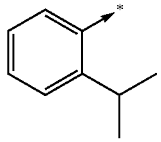 | 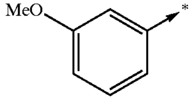 | 87 | 7.39 | 368.27 |

-continued
| | | | | | |
|---|---|---|---|---|---|
| 687 | 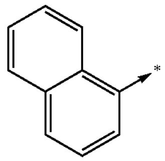 | 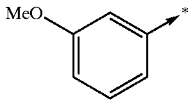 | 80 | 7.48 | 376.22 |
| 688 | 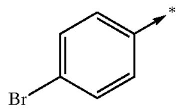 | 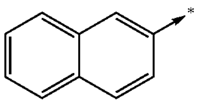 | 83 | 8.14 | 424.11 |
| 689 | 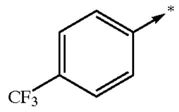 | 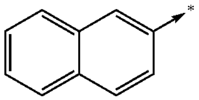 | 83 | 8.37 | 414.14 |
| 690 | 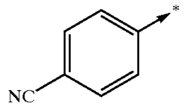 | 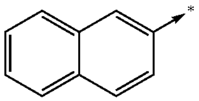 | 78 | 7.48 | 371.21 |
| 691 | 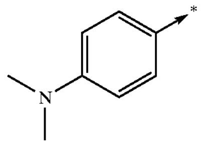 | 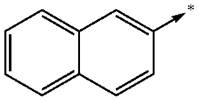 | 85 | 5.88 | 389.24 |
| 692 | 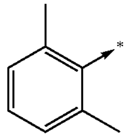 | 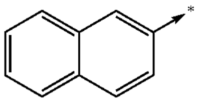 | 79 | 7.53 | 374.24 |
| 693 | 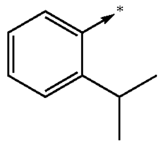 | 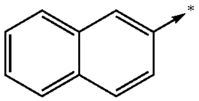 | 83 | 8.1 | 388.23 |

-continued
| | | | | | |
|---|---|---|---|---|---|
| 694 | 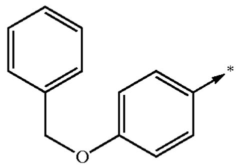 | 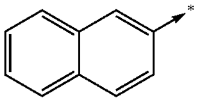 | 77 | 8.18 | 452.23 |
| 695 | 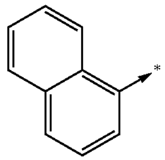 | 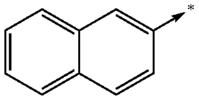 | 81 | 8.14 | 396.20 |
| 696 | 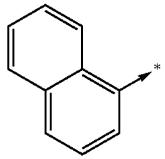 | 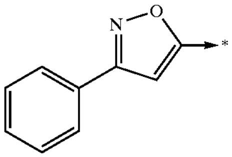 | 76 | 7.94 | 413.16 |
| 697 | 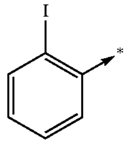 | 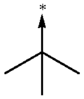 | 86 | 7.41 | 402.01 |
| 698 | 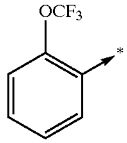 | 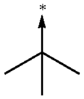 | 93 | 7.57 | 360.16 |
| 699 | 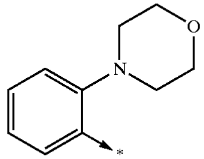 | 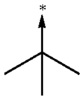 | 74 | 6.32 | 361.23 |

-continued
| | | | | | |
|---|---|---|---|---|---|
| 700 | 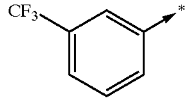 | 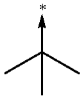 | 88 | 7.75 | 344.19 |
| 701 | 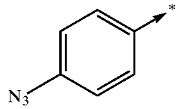 | 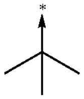 | 83 | 6.88 | 317.22 |
| 702 | 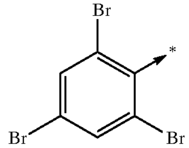 | 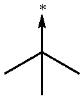 | 93 | 8.33 | 509.9 |
| 703 | 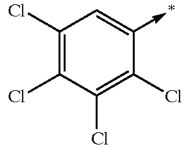 | 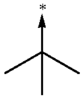 | 90 | 8.69 | 411.99 |
| 704 | 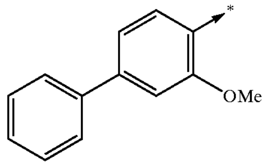 | 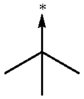 | 72 | 8.16 | 382.21 |
| 705 | 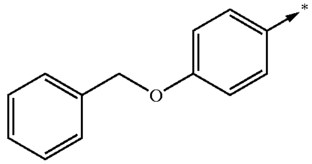 | 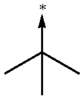 | 81 | 7.27 | 382.2 |
| 706 | 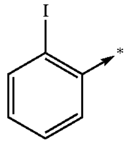 | 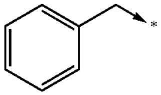 | 82 | 7.7 | 436.05 |

-continued
| | | | | | |
|---|---|---|---|---|---|
| 707 | 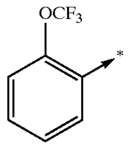 | 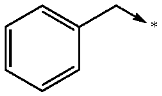 | 91 | 7.85 | 394.16 |
| 708 | 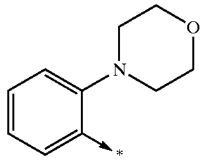 | 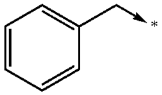 | 80 | 6.59 | 395.19 |
| 709 | 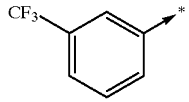 | 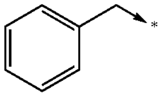 | 87 | 7.99 | 378.16 |
| 710 | 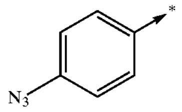 | 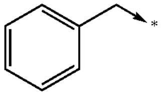 | 83 | 7.3 | 351.2 |
| 711 | 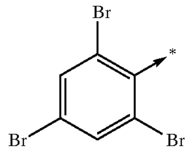 | 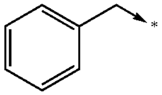 | 89 | 8.58 | 543.85 |
| 712 | 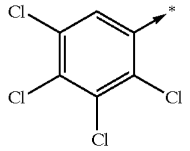 | 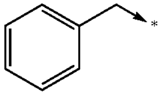 | 89 | 8.9 | 446.01 |

-continued
| | | | | | |
|---|---|---|---|---|---|
| 713 | 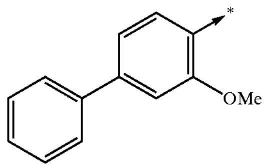 | 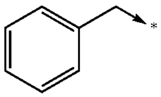 | 72 | 8.35 | 416.19 |
| 714 | 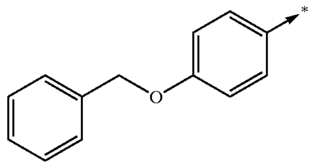 | 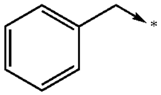 | 82 | 7.62 | 416.19 |
| 715 | 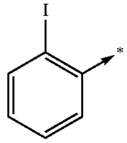 | 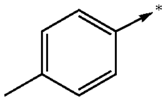 | 85 | 7.84 | 436.05 |
| 716 | 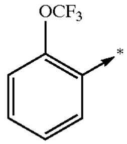 | 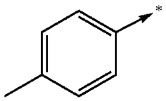 | 88 | 7.97 | 394.14 |
| 717 | 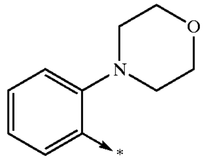 | 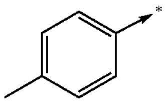 | 75 | 6.82 | 395.21 |
| 718 | 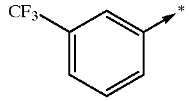 | 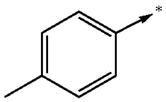 | 88 | 8.13 | 378.13 |

-continued
| | | | | | |
|---|---|---|---|---|---|
| 719 | 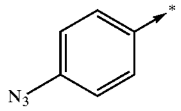 | 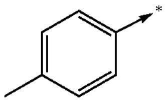 | 78 | 7.5 | 351.2 |
| 720 | 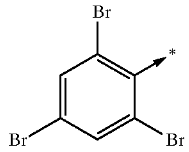 | 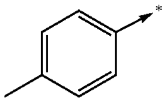 | 91 | 8.65 | 543.86 |
| 721 | 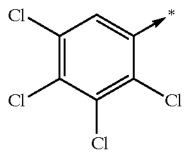 | 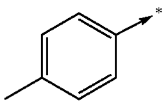 | 89 | 8.97 | 446.0 |
| 722 | 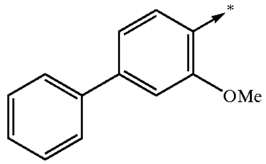 | 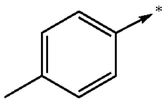 | 75 | 8.55 | 416.19 |
| 723 | 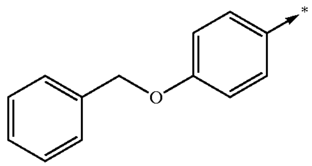 | 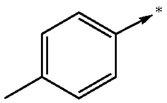 | 83 | 7.84 | 416.19 |
| 724 | 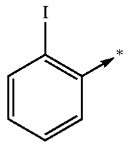 | 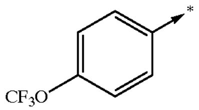 | 90 | 8.24 | 506.01 |

-continued
| | | | | | |
|---|---|---|---|---|---|
| 725 | 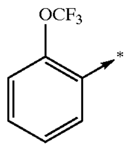 | 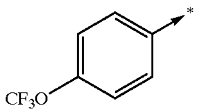 | 88 | 8.37 | 464.1 |
| 726 | 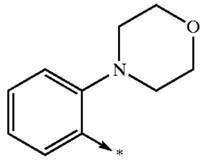 | 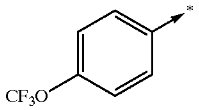 | 76 | 7.43 | 465.17 |
| 727 | 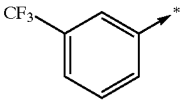 | 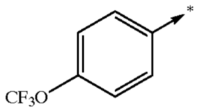 | 86 | 8.52 | 448.1 |
| 728 | 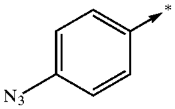 | 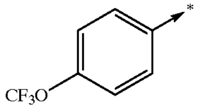 | 84 | 8.11 | 421.11 |
| 729 | 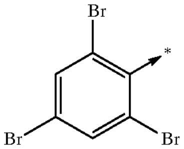 | 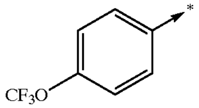 | 89 | 8.97 | 613.8 |
| 730 | 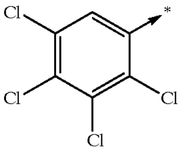 | 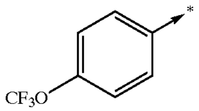 | 90 | 9.24 | 515.94 |

-continued
| | | | | | |
|---|---|---|---|---|---|
| 731 | 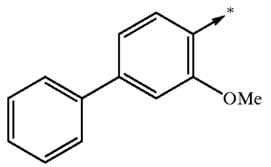 | 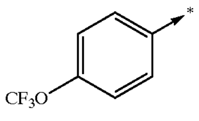 | 74 | 8.94 | 486.17 |
| 732 | 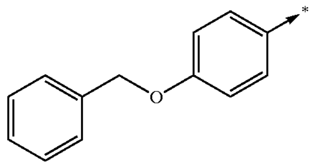 | 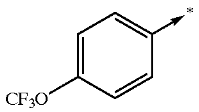 | 81 | 8.51 | 486.16 |
| 733 | 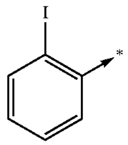 | 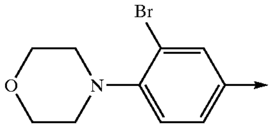 | 82 | 8.15 | 584.93 |
| 734 | 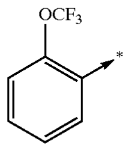 | 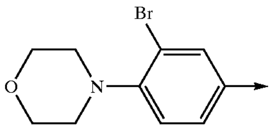 | 81 | 8.26 | 543.05 |
| 735 | 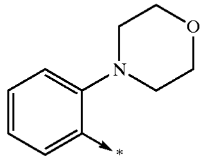 | 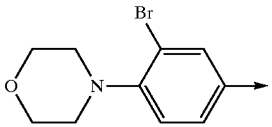 | 69 | 7.31 | 544.1 |
| 736 | 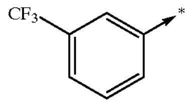 | 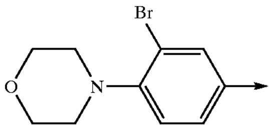 | 80 | 8.43 | 527.07 |

-continued
| | | | | | |
|---|---|---|---|---|---|
| 737 | 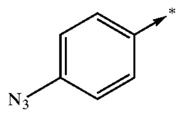 | 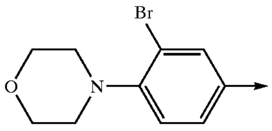 | 82 | 7.99 | 500.1 |
| 738 | 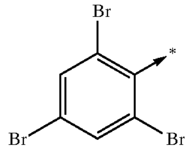 | 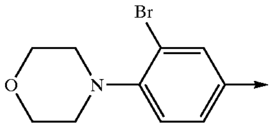 | 88 | 8.92 | 692.79 |
| 739 | 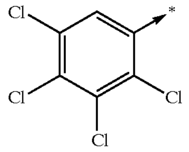 | 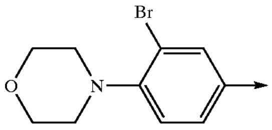 | 85 | 9.23 | 594.87 |
| 740 | 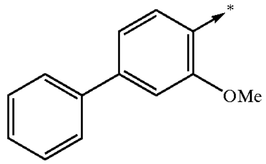 | 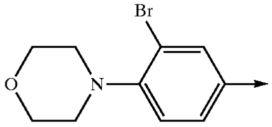 | 71 | 8.84 | 565.1 |
| 741 | 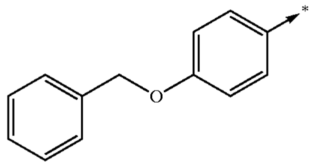 | 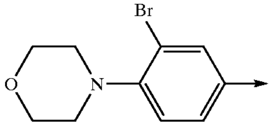 | 79 | 8.36 | 565.08 |
| 742 | 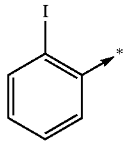 | 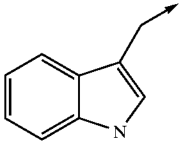 | 82 | 7.77 | 475.06 |

-continued
| | | | | | |
|---|---|---|---|---|---|
| 743 | 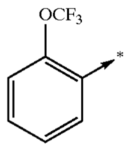 | 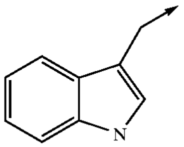 | 81 | 7.91 | 433.13 |
| 744 | 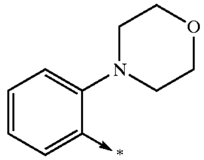 | 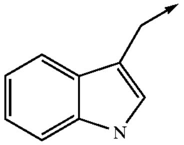 | 86 | 6.72 | 434.21 |
| 745 | 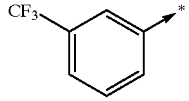 | 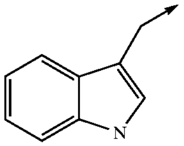 | 82 | 8.03 | 417.15 |
| 746 | 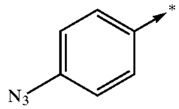 | 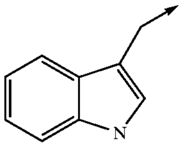 | 74 | 7.32 | 390.17 |
| 747 | 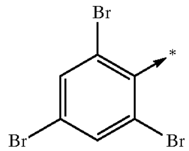 | 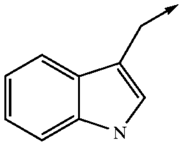 | 86 | 8.61 | 582.85 |
| 748 | 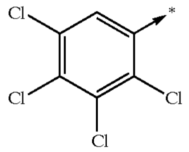 | 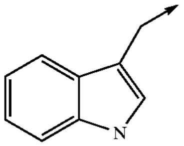 | 76 | 8.94 | 485.01 |

-continued
| | | | | | |
|---|---|---|---|---|---|
| 749 | 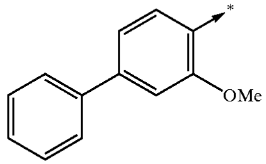 | 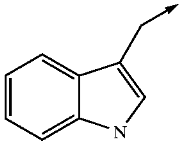 | 73 | 8.33 | 455.19 |
| 750 | 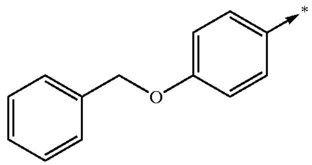 | 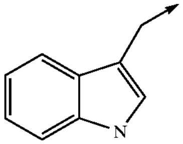 | 84 | 7.59 | 455.2 |
| 751 | 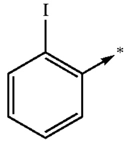 | 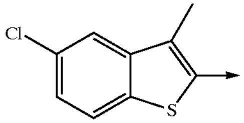 | 67 | 8.82 | 525.96 |
| 752 | 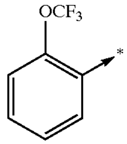 | 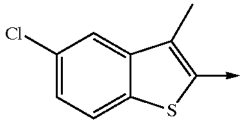 | 75 | 8.93 | 484.08 |
| 753 | 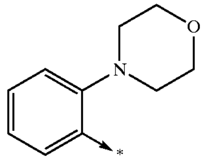 | 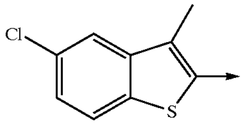 | 68 | 8.08 | 485.14 |
| 754 | 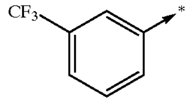 | 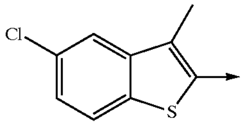 | 75 | 9.08 | 468.06 |

-continued
| | | | | | |
|---|---|---|---|---|---|
| 755 | 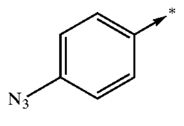 | 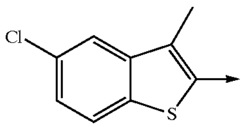 | 78 | 8.77 | 441.06 |
| 756 | 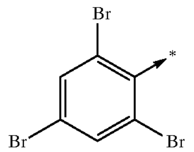 | 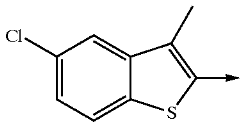 | 81 | 9.56 | 633.79 |
| 757 | 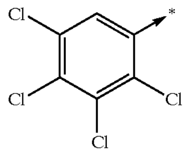 | 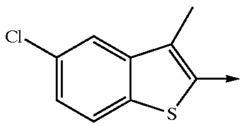 | 81 | 9.77 | 535.91 |
| 758 | 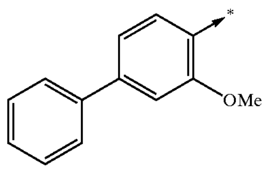 | 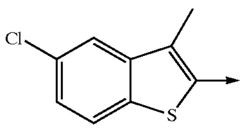 | 70 | 9.55 | 506.12 |
| 759 | 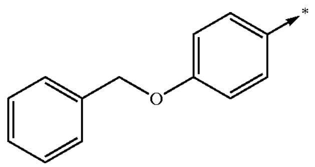 | 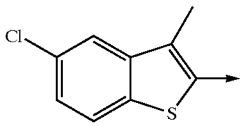 | 78 | 9.21 | 506.13 |

-continued
| | | | | | |
|---|---|---|---|---|---|
| | | 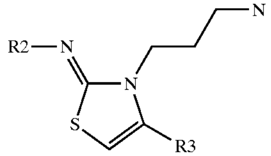 | | | |
| 760 | 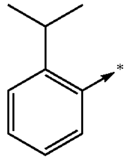 | 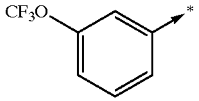 | 92.9 | 5.03 | 436.23 |
| 761 | 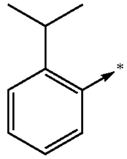 | 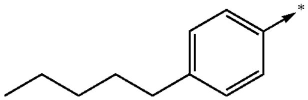 | 90.4 | 5.56 | 422.33 |
| 762 | 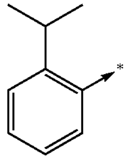 | 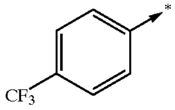 | 94.36 | 4.94 | 420.26 |
| 763 | 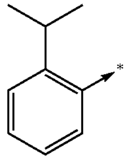 | 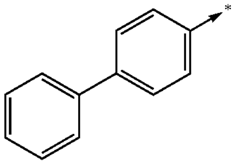 | 88.08 | 5.09 | 428.30 |
| 764 | 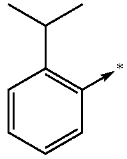 | 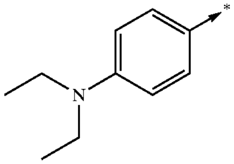 | 77.6 | 4.42 | 423.34 |

-continued
| | | | | | |
|---|---|---|---|---|---|
| 765 | 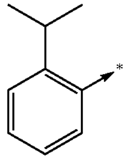 | 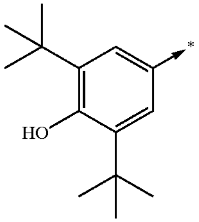 | 92.4 | 5.52 | 480.38 |
| 766 | 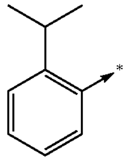 | 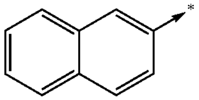 | 84.6 | 4.8 | 402.25 |
| 767 | 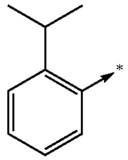 | 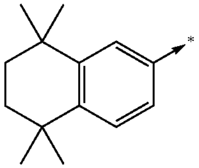 | 89.8 | 5.79 | 462.37 |
| 768 | 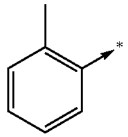 | 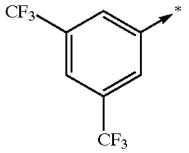 | 91.9 | 5.12 | 460.20 |
| 769 | 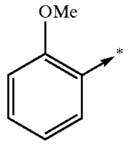 | 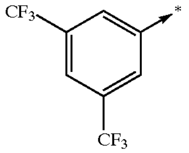 | 91.4 | 5.14 | 476.21 |

-continued
| | | | | | |
|---|---|---|---|---|---|
| 770 | 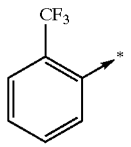 | 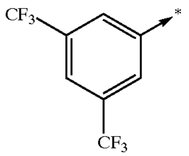 | 94.2 | 5.67 | 514.18 |
| 771 | 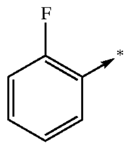 | 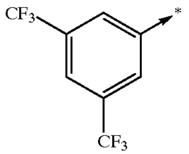 | 93.0 | 5.37 | 464.18 |
| 772 | 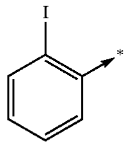 | 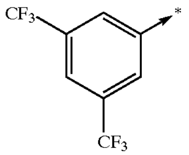 | 94.5 | 5.64 | 572.07 |
| 773 | 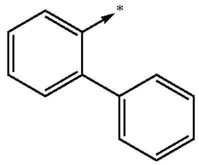 | 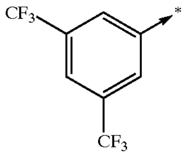 | 87.9 | 5.76 | 522.21 |
| 774 | 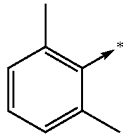 | 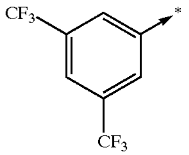 | 91.2 | 5.12 | 474.23 |
| 775 | 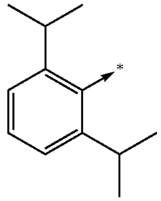 | 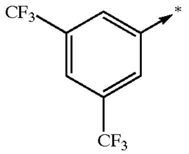 | 78.1 | 5.82 | 530.27 |

-continued
| | | | | | |
|---|---|---|---|---|---|
| 776 | 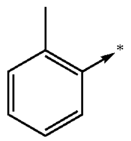 | 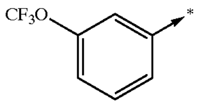 | 88.8 | 4.55 | 408.22 |
| 777 | 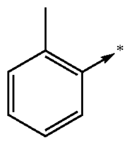 | 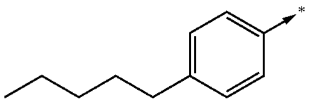 | 90.7 | 5.13 | 394.34 |
| 778 | 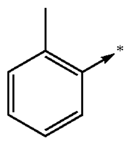 | 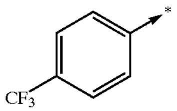 | 92.6 | 4.45 | 392.23 |
| 779 | 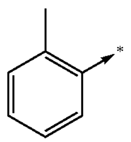 | 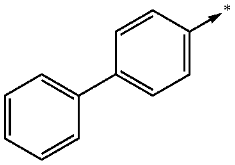 | 88.8 | 4.65 | 400.30 |
| 780 | 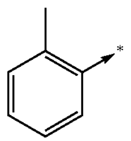 | 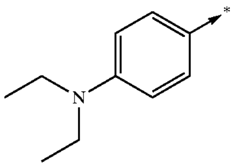 | 76.5 | 3.94 | 395.33 |
| 781 | 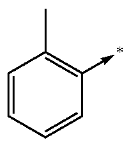 | 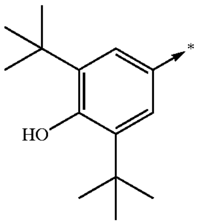 | 90.8 | 5.11 | 452.38 |

-continued
| | | | | | |
|---|---|---|---|---|---|
| 782 | 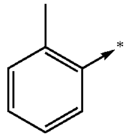 | 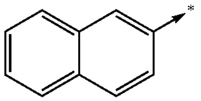 | 87.7 | 4.33 | 374.29 |
| 783 | 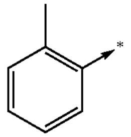 | 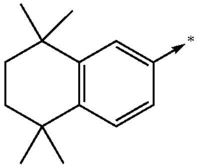 | 91.5 | 5.35 | 434.38 |
| 784 | 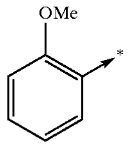 | 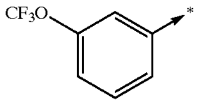 | 92.1 | 4.61 | 424.25 |
| 785 | 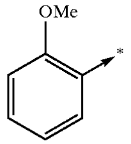 | 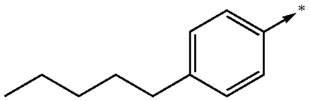 | 89.3 | 5.28 | 410.33 |
| 786 | 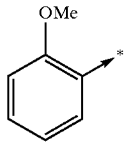 | 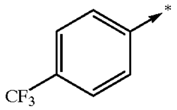 | 95 | 4.49 | 408.22 |
| 787 | 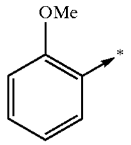 | 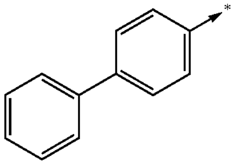 | 82.4 | 4.74 | 416.27 |

-continued
| | | | | | |
|---|---|---|---|---|---|
| 788 | 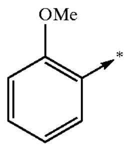 | 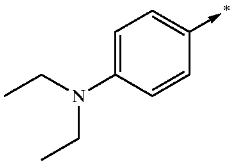 | 73.8 | 3.95 | 411.30 |
| 789 | 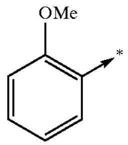 | 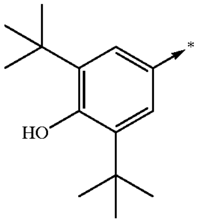 | 92.9 | 5.27 | 468.36 |
| 790 | 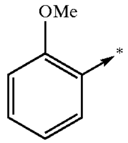 | 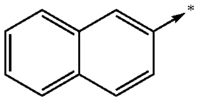 | 84.9 | 4.39 | 390.28 |
| 791 | 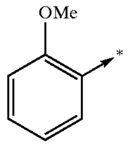 | 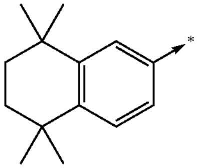 | 91.5 | 5.53 | 450.37 |
| 792 | 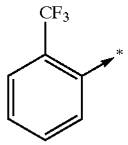 | 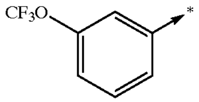 | 90 | 5.5 | 462.19 |
| 793 | 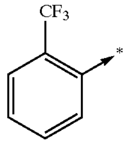 | 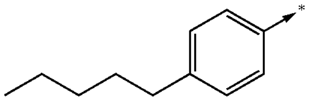 | 93.9 | 6.25 | 448.31 |

-continued
| | | | | | |
|---|---|---|---|---|---|
| 794 | 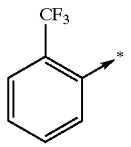 | 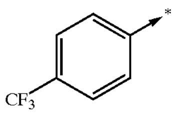 | 94.9 | 5.41 | 446.22 |
| 795 | 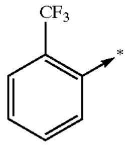 | 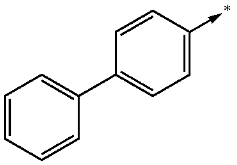 | 93.5 | 5.76 | 454.26 |
| 796 | 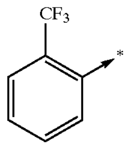 | 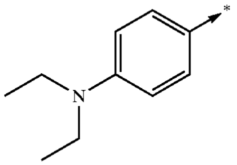 | 89.8 | 4.95 | 449.30 |
| 797 | 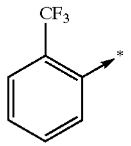 | 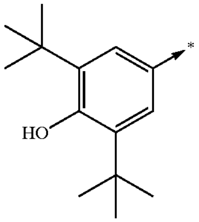 | 92.4 | 6.22 | 506.34 |
| 798 | 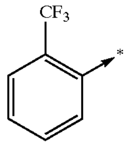 | 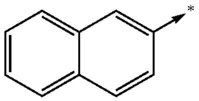 | 93 | 5.52 | 428.245 |
| 799 | 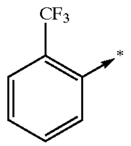 | 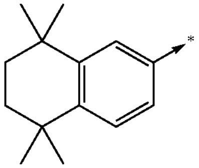 | 92.8 | 6.39 | 488.34 |

-continued
| | | | | | |
|---|---|---|---|---|---|
| 800 | 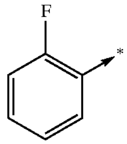 | 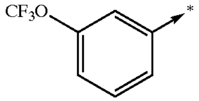 | 87.6 | 5.11 | 412.20 |
| 801 | 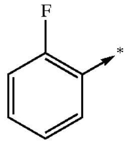 | 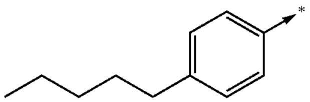 | 92.5 | 5.9 | 398.30 |
| 802 | 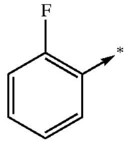 | 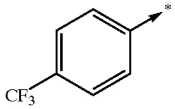 | 93.5 | 5 | 396.20 |
| 803 | 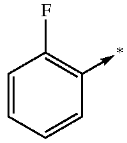 | 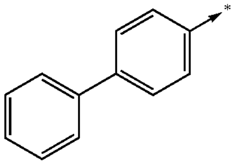 | 92.2 | 5.35 | 404.26 |
| 804 | 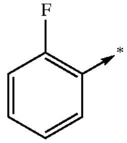 | 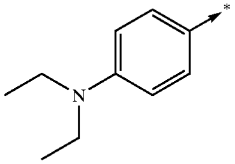 | 90.7 | 4.41 | 399.28 |
| 805 | 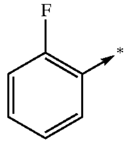 | 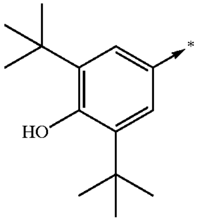 | 94.2 | 5.87 | 456.34 |

-continued
| | | | | | |
|---|---|---|---|---|---|
| 806 | 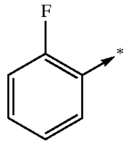 | 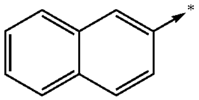 | 89.3 | 5.05 | 378.23 |
| 807 | 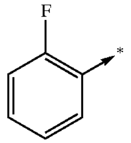 | 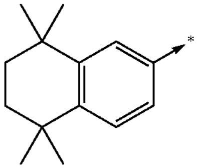 | 90.9 | 6.07 | 438.33 |
| 808 | 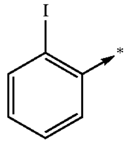 | 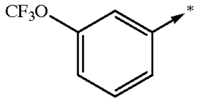 | 88.8 | 5.43 | 520.09 |
| 809 | 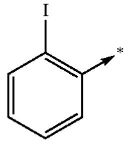 | 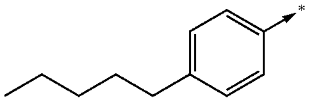 | 94 | 6.19 | 506.19 |
| 810 | 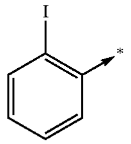 | 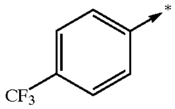 | 95.9 | 5.33 | 504.12 |
| 811 | 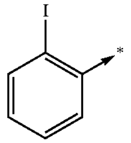 | 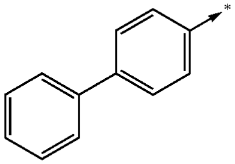 | 92.9 | 5.68 | 512.15 |

-continued
| | | | | | |
|---|---|---|---|---|---|
| 812 | 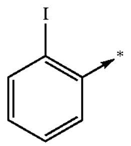 | 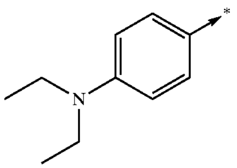 | 88.9 | 4.8 | 507.18 |
| 813 | 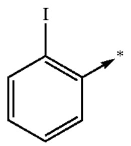 | 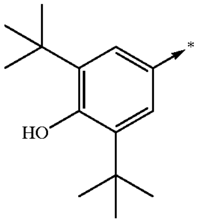 | 92.3 | 6.17 | 564.20 |
| 814 | 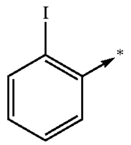 | 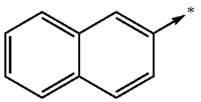 | 93.9 | 5.41 | 486.14 |
| 815 | 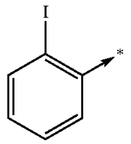 | 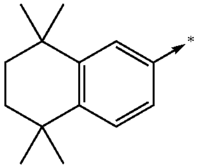 | 93.5 | 6.35 | 546.18 |
| 816 | 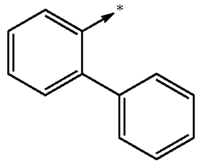 | 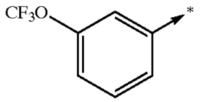 | 91.9 | 5.41 | 470.25 |

-continued
| | | | | | |
|---|---|---|---|---|---|
| 817 | 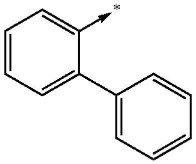 | 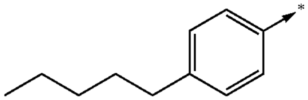 | 93 | 5.98 | 456.34 |
| 818 | 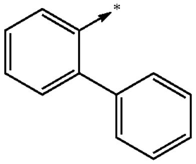 | 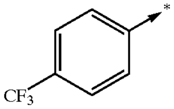 | 91.4 | 5.29 | 454.24 |
| 819 | 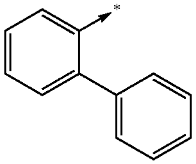 | 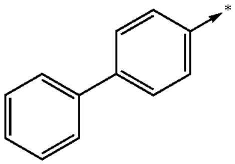 | 90.4 | 5.49 | 462.29 |
| 820 | 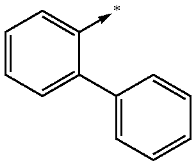 | 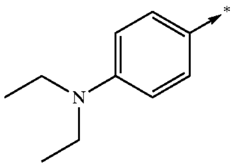 | 86.5 | 4.75 | 457.34 |
| 821 | 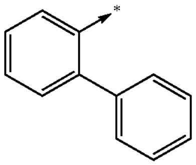 | 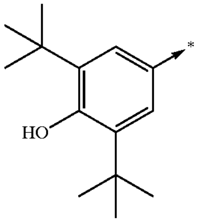 | 90.5 | 5.94 | 514.34 |

-continued
| | | | | | |
|---|---|---|---|---|---|
| 822 | 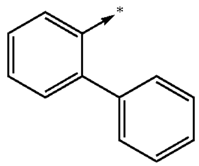 | 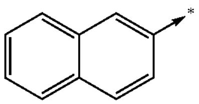 | 90.1 | 5.21 | 436.26 |
| 823 | 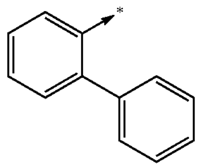 | 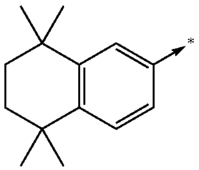 | 89.7 | 6.18 | 496.37 |
| 824 | 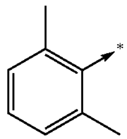 | 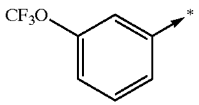 | 79.4 | 4.56 | 422.22 |
| 825 | 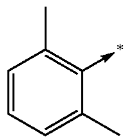 | 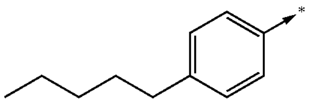 | 92.5 | 5.08 | 408.32 |
| 826 | 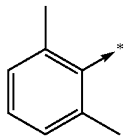 | 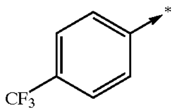 | 93 | 4.45 | 406.23 |
| 827 | 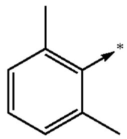 | 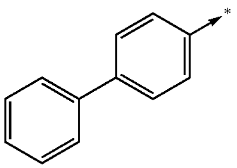 | 90.2 | 4.63 | 414.26 |

-continued
| | | | | | |
|---|---|---|---|---|---|
| 828 | 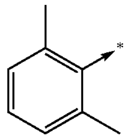 | 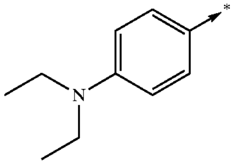 | 76.3 | 4.01 | 409.31 |
| 829 | 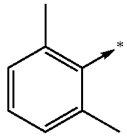 | 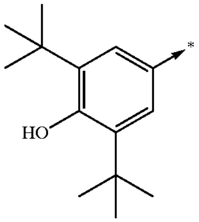 | 94 | 5.08 | 466.36 |
| 830 | 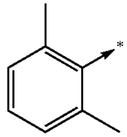 | 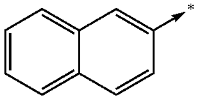 | 90.7 | 4.34 | 388.25 |
| 831 | 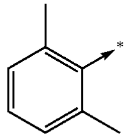 | 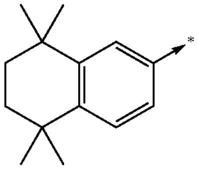 | 92.9 | 5.29 | 448.36 |
| 832 | 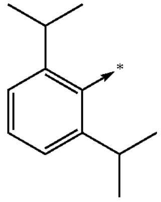 | 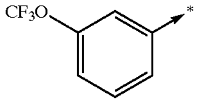 | 56 | 5.3 | 478.29 |

-continued
| | | | | | |
|---|---|---|---|---|---|
| 833 | 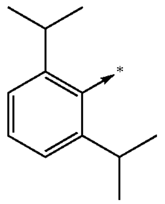 | 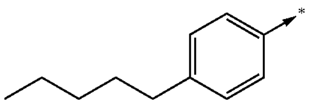 | 83.9 | 5.7 | 464.38 |
| 834 | 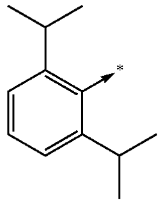 | 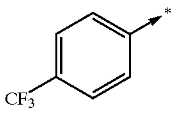 | 82.1 | 5.19 | 462.29 |
| 835 | 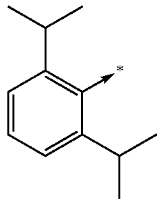 | 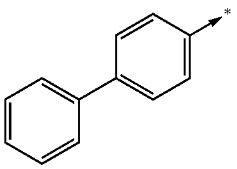 | 80.5 | 5.31 | 470.35 |
| 836 | 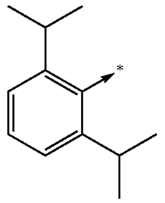 | 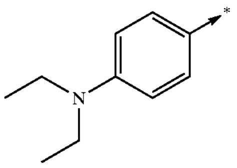 | 70.6 | 4.8 | 465.39 |
| 837 | 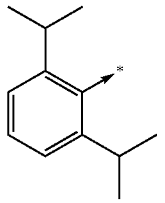 | 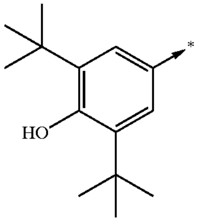 | 82.9 | 5.67 | 522.41 |

-continued
| | | | | | |
|---|---|---|---|---|---|
| 838 | 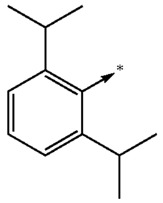 | 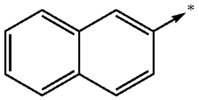 | 81 | 5.07 | 444.33 |
| 839 | 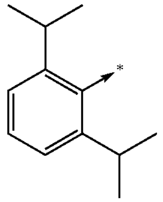 | 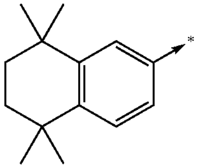 | 83.5 | 5.91 | 504.41 |
| | | 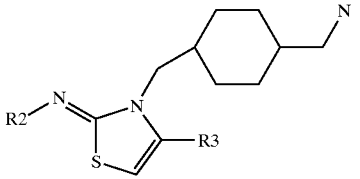 | | | |
| 840 | 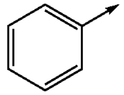 | 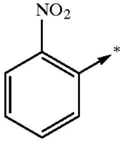 | 35 + 64 | 3.68 + 3.73 | 423.2 |
| 841 | 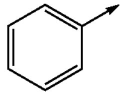 | 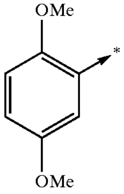 | 98 | 3.7 | 438.3 |

-continued
| | | | | | |
|---|---|---|---|---|---|
| 842 | 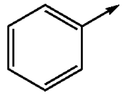 | 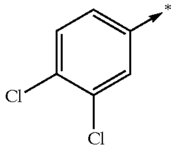 | 35 + 63 | 4.3 + 4.4 | 446.2 |
| 843 | 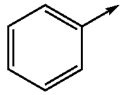 | 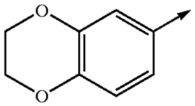 | 97 | 3.71 | 436.3 |
| 844 | 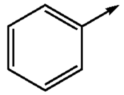 | 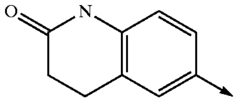 | 32 + 65 | 3.28 + 3.34 | 447.3 |
| 845 | 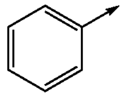 | 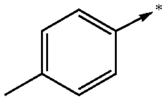 | 96 | 3.84 | 392.3 |
| 846 | 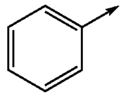 | 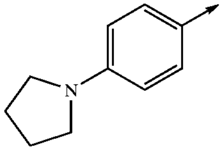 | 96 | 4.18 | 447.3 |
| 847 | 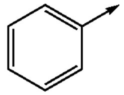 | 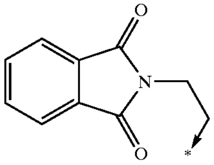 | 30 + 64 | 3.62 + 3.64 | 475.3 |
| 848 | 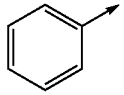 | 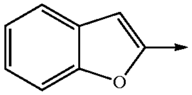 | 36 + 61 | 4.46 + 4.61 | 418.3 |

-continued
| | | | | | |
|---|---|---|---|---|---|
| 849 | 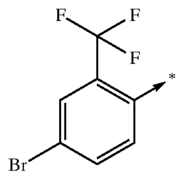 | 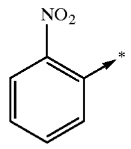 | 96 | 5.89 | 569.1 |
| 850 | 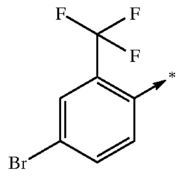 | 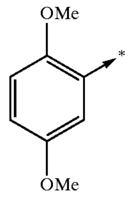 | 94 | 6.09 | 584.2 |
| 851 | 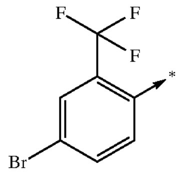 | 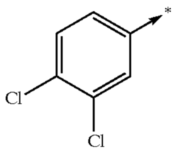 | 57 + 39 | 6.55 + 6.6 | 592.1 |
| 852 | 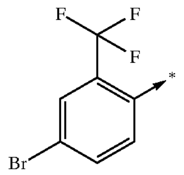 | 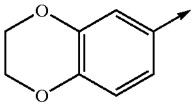 | 96 | 6.16 | 582.2 |
| 853 | 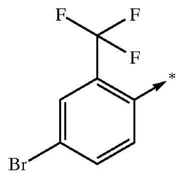 | 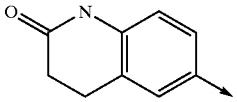 | 28 + 59 | 5.53 + 5.61 | 593.2 |

-continued
| | | | | | |
|---|---|---|---|---|---|
| 854 | 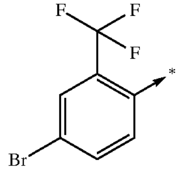 | 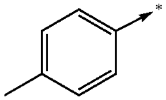 | 95 | 6.35 | 538.2 |
| 855 | 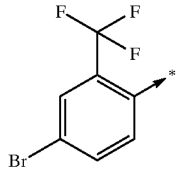 | 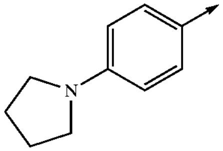 | 54 + 41 | 6.8 + 6.88 | 593.3 |
| 856 | 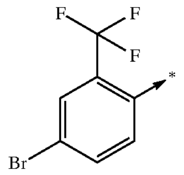 | 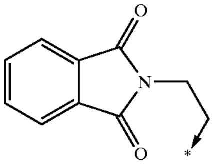 | 94 | 5.96 | 621.2 |
| 857 | 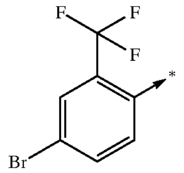 | 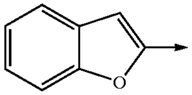 | 56 + 39 | 6.46 + 6.55 | 564.2 |
| 858 | 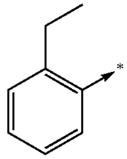 | 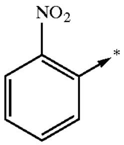 | 34 + 63 | 4.09 + 4.2 | 451.3 |

-continued
| | | | | | |
|---|---|---|---|---|---|
| 859 | 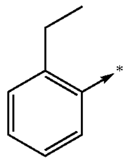 | 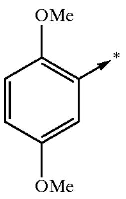 | 96 | 4.03 | 466.4 |
| 860 | 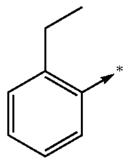 | 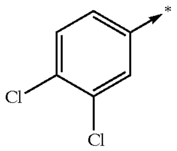 | 33 + 64 | 4.69 + 4.76 | 474.3 |
| 861 | 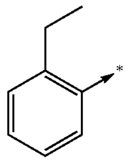 | 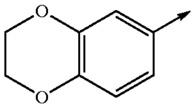 | 27 + 70 | 4.04 + 4.07 | 464.4 |
| 862 | 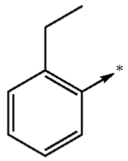 | 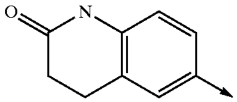 | 33 + 63 | 3.63 + 3.71 | 475.4 |
| 863 | 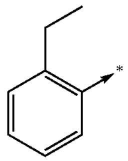 | 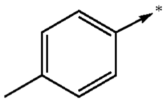 | 95 | 4.18 | 420.4 |
| 864 | 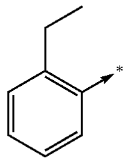 | 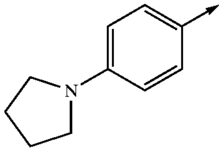 | 89 | 4.46 | 475.4 |

-continued
| | | | | | |
|---|---|---|---|---|---|
| 865 | 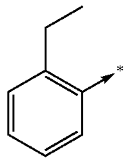 | 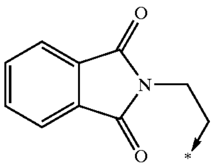 | 22 + 68 | 3.94 + 3.98 | 503.4 |
| 866 | 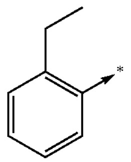 | 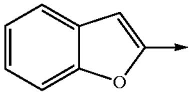 | 35 + 62 | 4.9 + 5.01 | 446.4 |
| 867 | 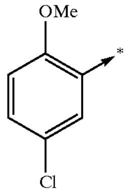 | 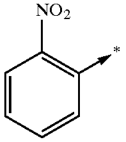 | 35 + 61 | 4.39 + 4.52 | 487.3 |
| 868 | 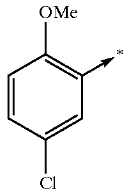 | 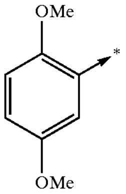 | 33 + 63 | 4.22 + 4.29 | 502.3 |
| 869 | 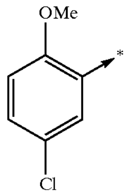 | 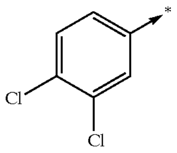 | 35 + 62 | 5.08 + 5.2 | 510.2 |

-continued
| | | | | | |
|---|---|---|---|---|---|
| 870 | 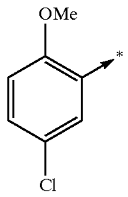 | 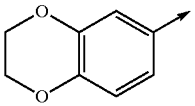 | 31 + 63 | 4.26 + 4.34 | 500.3 |
| 871 | 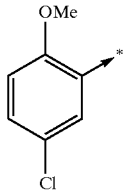 | 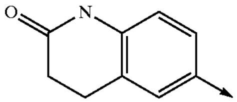 | 33 + 62 | 3.82 + 3.91 | 511.3 |
| 872 | 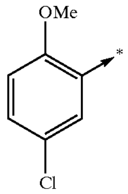 | 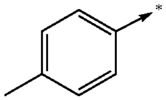 | 31 + 62 | 4.42 + 4.51 | 456.3 |
| 873 | 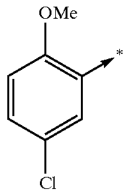 | 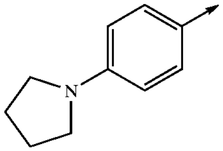 | 29 + 64 | 4.66 + 4.72 | 511.4 |
| 874 | 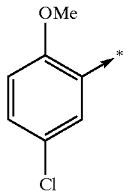 | 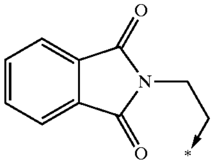 | 33 + 57 | 4.11 + 4.2 | 539.3 |

-continued
| | | | | | |
|---|---|---|---|---|---|
| 875 | 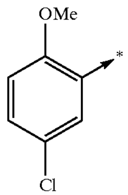 | 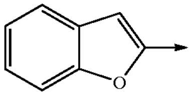 | 35 + 62 | 5.26 + 5.39 | 482.3 |
| 876 | 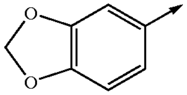 | 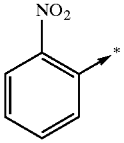 | 32 + 65 | 3.63 + 3.7 | 467.3 |
| 877 | 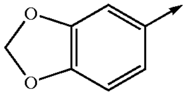 | 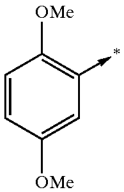 | 97 | 3.69 | 482.4 |
| 878 | 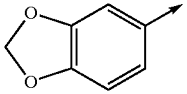 | 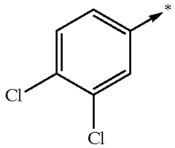 | 35 + 62 | 4.2 + 4.28 | 490.3 |
| 879 | 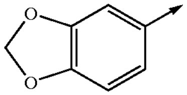 | 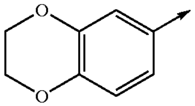 | 94 | 3.69 | 480.3 |
| 880 | 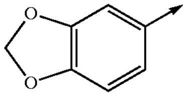 | 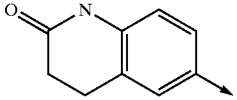 | 28 + 68 | 3.3 + 3.33 | 491.3 |

-continued
| | | | | | |
|---|---|---|---|---|---|
| 881 | 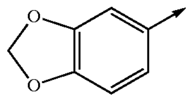 | 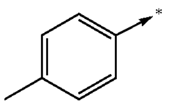 | 96 | 3.8 | 436.3 |
| 882 | 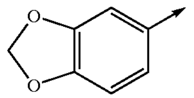 | 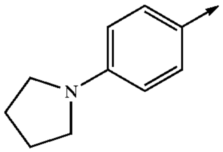 | 96 | 4.18 | 491.4 |
| 883 | 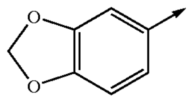 | 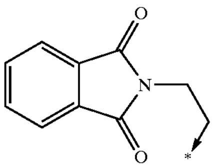 | 94 | 3.63 | 519.3 |
| 884 | 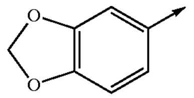 | 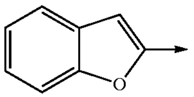 | 36 + 61 | 4.28 + 4.42 | 462.3 |
| 885 | 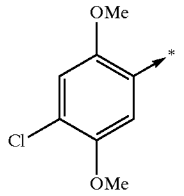 | 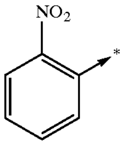 | 36 + 62 | 4.24 + 4.36 | 517.3 |
| 886 | 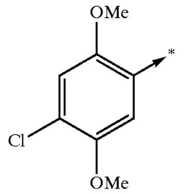 | 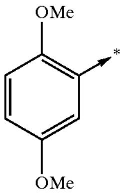 | 28 + 69 | 4.15 + 4.21 | 532.3 |

-continued
| | | | | | |
|---|---|---|---|---|---|
| 887 | 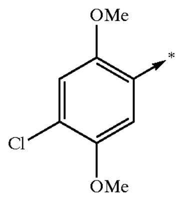 | 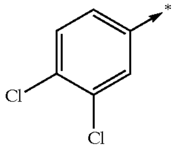 | 35 + 62 | 4.84 + 4.96 | 540.2 |
| 888 | 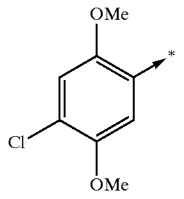 | 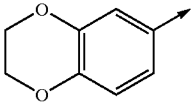 | 33 + 64 | 4.15 + 4.22 | 530.3 |
| 889 | 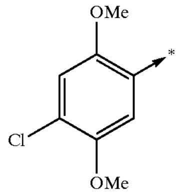 | 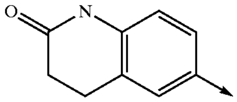 | 32 + 63 | 3.76 + 3.84 | 541.3 |
| 890 | 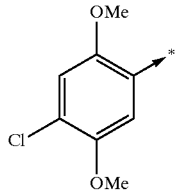 | 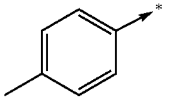 | 32 + 63 | 4.28 + 4.36 | 486.3 |
| 891 | 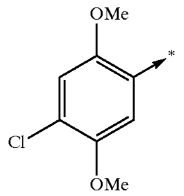 | 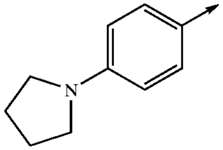 | 24 + 73 | 4.56 + 4.6 | 541.3 |

-continued
| | | | | | |
|---|---|---|---|---|---|
| 892 | 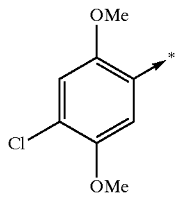 | 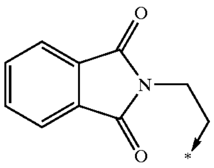 | 31 + 59 | 4.05 + 4.11 | 569.3 |
| 893 | 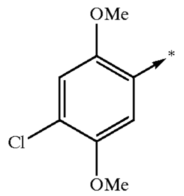 | 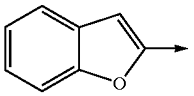 | 35 + 61 | 4.99 + 5.14 | 512.3 |
| 894 | 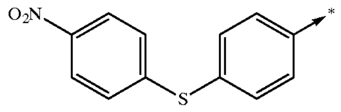 | 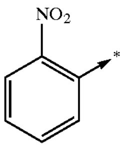 | 33 + 64 | 5.59 + 5.7 | 576.3 |
| 895 | 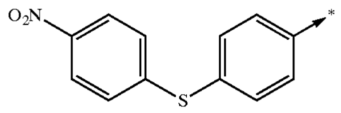 | 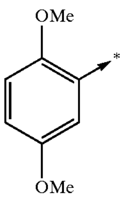 | 35 + 61 | 5.29 + 5.39 | 591.3 |
| 896 | 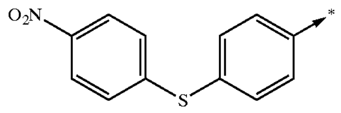 | 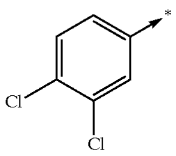 | 26 + 71 | 6.32 + 6.35 | 599.2 |
| 897 | 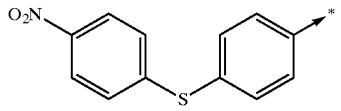 | 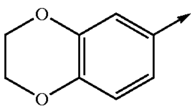 | 34 + 63 | 5.41 + 5.5 | 589.3 |

-continued
| | | | | | |
|---|---|---|---|---|---|
| 898 | 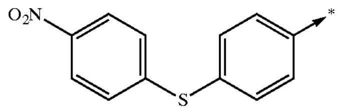 | 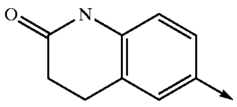 | 35 + 61 | 4.88 + 4.99 | 600.3 |
| 899 | 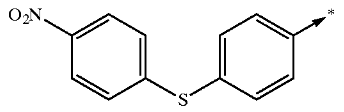 | 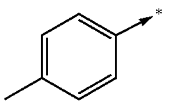 | 35 + 62 | 5.63 + 5.72 | 545.3 |
| 900 | 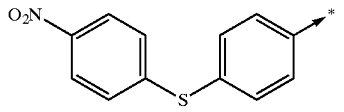 | 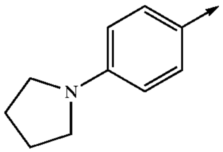 | 34 + 61 | 5.76 + 5.86 | 600.3 |
| 901 | 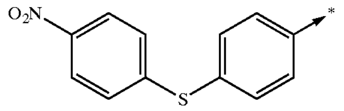 | 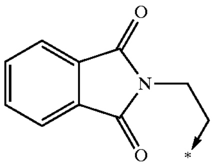 | 34 + 68 | 5.16 + 5.28 | 628.3 |
| 902 | 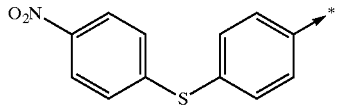 | 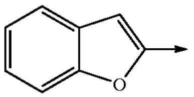 | 98 | 6.45 | 571.3 |
| 903 | 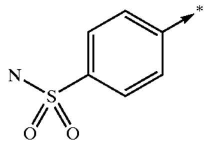 | 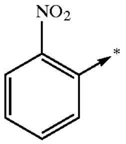 | 35 + 60 | 3.84 + 3.93 | 502.3 |
| 904 | 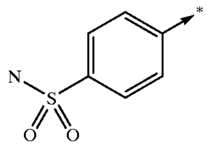 | 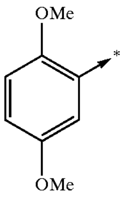 | 32 + 62 | 3.72 + 3.79 | 517.3 |

-continued
| | | | | | |
|---|---|---|---|---|---|
| 905 | 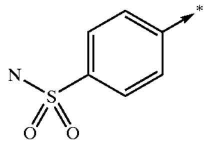 | 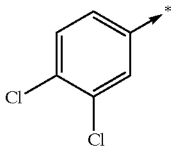 | 32 + 62 | 4.59 + 4.68 | 525.2 |
| 906 | 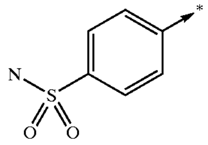 | 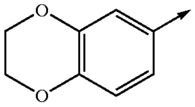 | 33 + 61 | 3.75 + 3.82 | 515.3 |
| 907 | 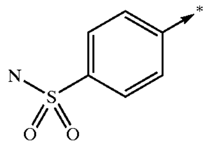 | 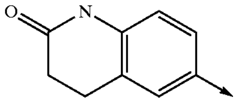 | 29 + 64 | 3.18 + 3.26 | 526.3 |
| 908 | 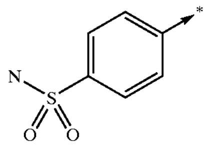 | 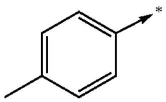 | 32 + 59 | 4 + 4.09 | 471.3 |
| 909 | 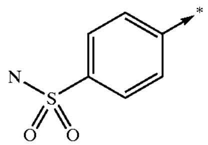 | 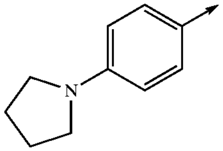 | 32 + 60 | 4.28 + 4.38 | 526.3 |
| 910 | 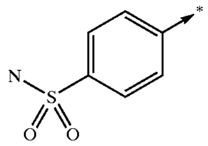 | 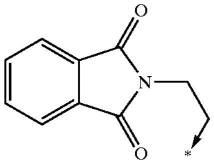 | 34 + 56 | 3.62 + 3.71 | 554.3 |

-continued
| | | | | | |
|---|---|---|---|---|---|
| 911 | 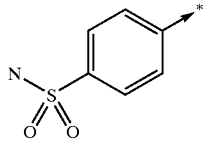 | 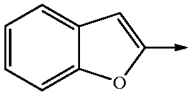 | 31 + 63 | 4.58 + 4.66 | 497.3 |

| Ex. | R1 | R3 | Purity (%) | rt (min.) | [M + H]+ |
|---|---|---|---|---|---|
| | | 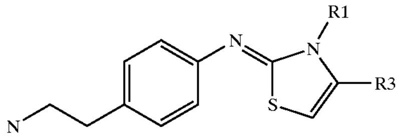 | | | |
| 912 | 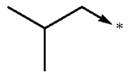 | 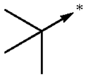 | 6.8 + 91.2 | 3.6 + 3.76 | 332.22 |
| 913 | 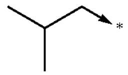 | 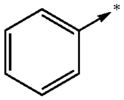 | 88.1 | 3.94 | 352.19 |
| 914 | 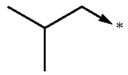 | 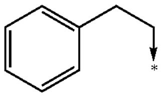 | 89.6 | 4.22 | 380.22 |
| 915 | 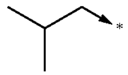 | 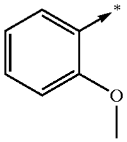 | 61.6 | 3.95 | 382.17 |
| 916 | 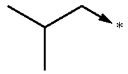 | 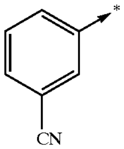 | 83.5 | 3.8 | 377.19 |
| 917 | 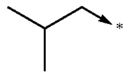 | 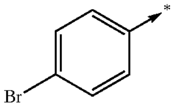 | 84.2 | 4.41 | 430.10 |

-continued
| | | | | | |
|---|---|---|---|---|---|
| 918 | 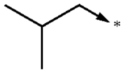 | 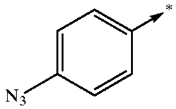 | 70.9 | 4.24 | 393.18 |
| 919 | 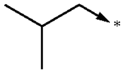 | 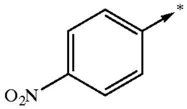 | 84.1 | 4.1 | 397.16 |
| 920 | 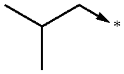 | 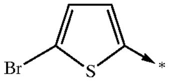 | 82.2 | 4.55 | 436.05 |
| 921 | 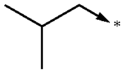 | 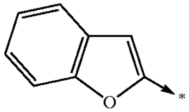 | 82.8 | 4.66 | 392.17 |
| 922 | 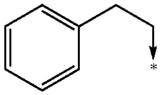 | 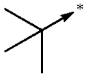 | 98 | 4.25 | 380.22 |
| 923 | 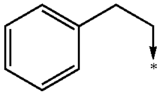 | 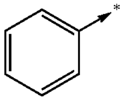 | 91.1 | 4.26 | 400.17 |
| 924 | 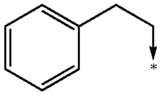 | 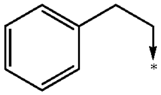 | 92.4 | 4.46 | 428.21 |
| 925 | 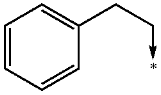 | 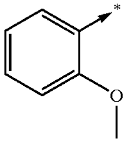 | 93.8 | 4.23 | 430.20 |

-continued
| | | | | | |
|---|---|---|---|---|---|
| 926 | 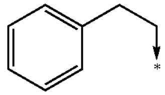 | 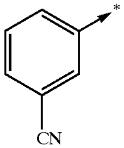 | 86.4 | 4.14 | 425.17 |
| 927 | 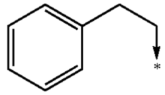 | 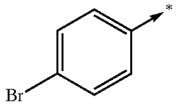 | 92.3 | 4.7 | 478.11 |
| 928 | 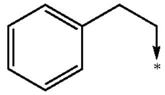 | 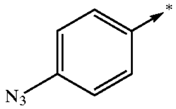 | 82 | 4.56 | 441.18 |
| 929 | 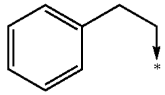 | 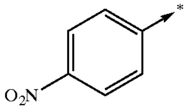 | 90.9 | 4.44 | 445.18 |
| 930 | 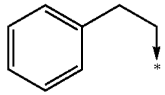 | 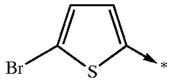 | 89.8 | 4.9 | 484.07 |
| 931 | 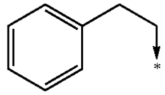 | 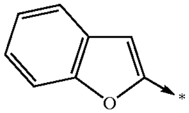 | 86.4 | 5.0 | 440.17 |
| 932 | 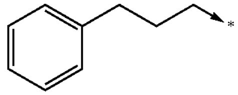 | 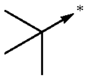 | 97.2 | 4.38 | 394.22 |
| 933 | 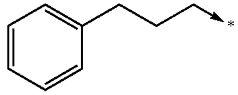 | 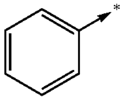 | 86.3 | 4.48 | 414.18 |

-continued
| | | | | | |
|---|---|---|---|---|---|
| 934 | 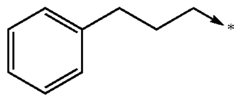 | 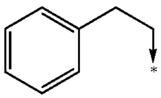 | 92.6 | 4.68 | 442.22 |
| 935 | 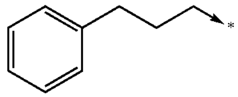 | 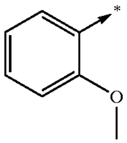 | 91 | 4.44 | 444.22 |
| 936 | 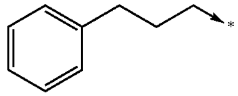 | 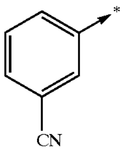 | 85.9 | 4.34 | 439.18 |
| 937 | 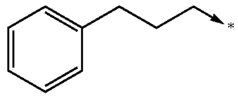 | 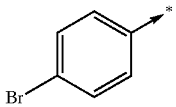 | 88.2 | 4.86 | 492.12 |
| 938 | 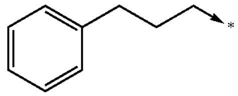 | 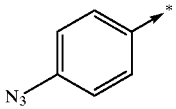 | 83.6 | 4.71 | 455.2 |
| 939 | 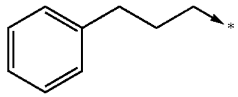 | 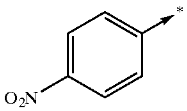 | 87.8 | 4.59 | 459.19 |
| 940 | 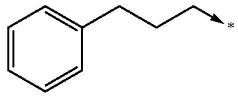 | 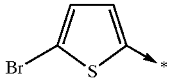 | 89.8 | 5.0 | 498.09 |
| 941 | 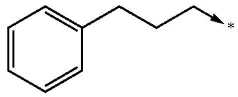 | 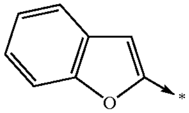 | 83.9 | 5.14 | 454.20 |

-continued
| | | | | | |
|---|---|---|---|---|---|
| 942 | 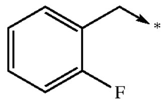 | 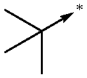 | 87.7 | 4.26 | 384.17 |
| 943 | 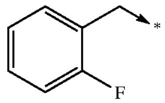 | 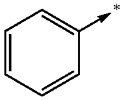 | 94.7 | 4.5 | 404.15 |
| 944 | 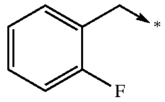 | 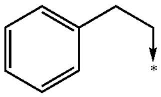 | 18.6 + 76.4 | 4.2 + 4.64 | 432.18 |
| 945 | 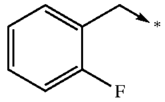 | 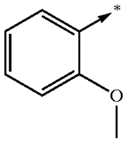 | 95.2 | 4.32 | 434.16 |
| 946 | 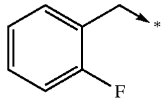 | 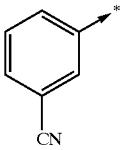 | 92 | 4.46 | 429.15 |
| 947 | 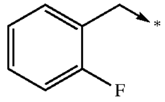 | 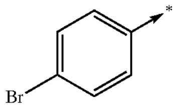 | 94.4 | 5.08 | 482.06 |
| 948 | 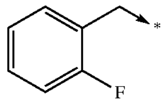 | 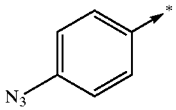 | 93 | 4.86 | 445.16 |
| 949 | 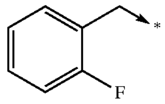 | 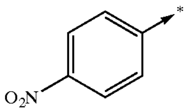 | 94.2 | 4.82 | 449.13 |

-continued
| | | | | | |
|---|---|---|---|---|---|
| 950 | 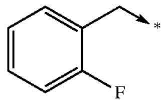 | 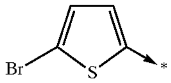 | 93.1 | 5.34 | 488.03 |
| 951 | 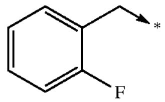 | 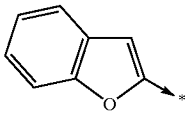 | 93.7 | 5.47 | 444.16 |
| 952 | 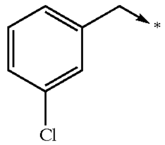 | 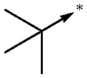 | 91.5 | 4.43 | 400.13 |
| 953 | 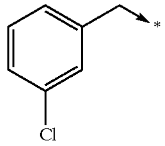 | 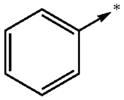 | 95 | 4.82 | 420.12 |
| 954 | 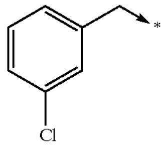 | 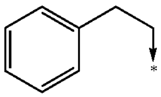 | 14.8 + 81.2 | 4.38 + 4.88 | 448.15 |
| 955 | 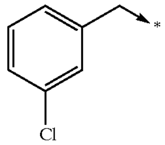 | 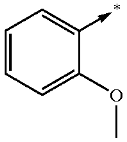 | 95.8 | 4.64 | 450.13 |
| 956 | 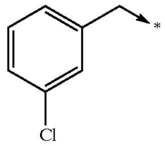 | 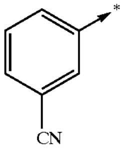 | 95 | 4.79 | 445.11 |

-continued
| | | | | | |
|---|---|---|---|---|---|
| 957 | 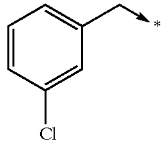 | 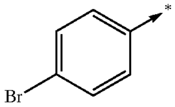 | 95.4 | 5.4 | 498.06 |
| 958 | 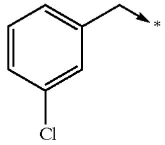 | 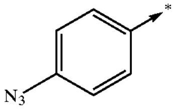 | 93.9 | 5.14 | 461.12 |
| 959 | 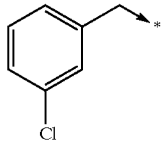 | 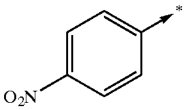 | 94.5 | 5.12 | 465.10 |
| 960 | 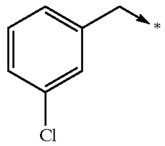 | 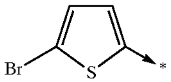 | 94.6 | 5.62 | 504.00 |
| 961 | 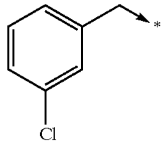 | 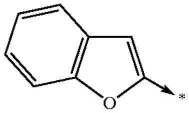 | 96.4 | 5.74 | 460.13 |
| 962 | 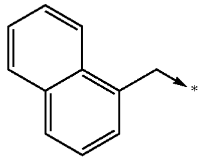 | 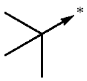 | 6.5 + 87.5 | 4.2 + 4.54 | 416.19 |

-continued
| | | | | | |
|---|---|---|---|---|---|
| 963 | 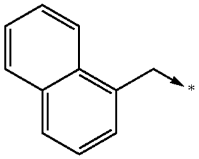 | 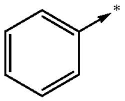 | 92.9 | 4.76 | 436.17 |
| 964 | 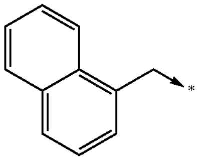 | 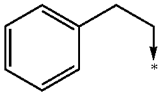 | 17.3 + 6.2 | 4.5 + 4.9 | 464.21 |
| 965 | 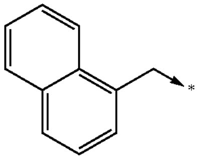 | 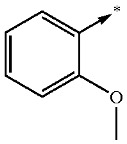 | 92.6 | 4.64 | 466.17 |
| 966 | 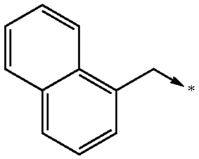 | 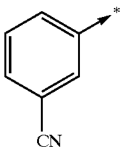 | 89 | 4.76 | 461.16 |
| 967 | 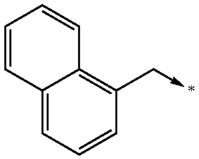 | 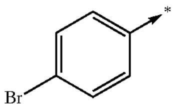 | 94.1 | 5.32 | 514.09 |
| 968 | 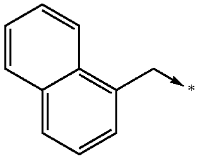 | 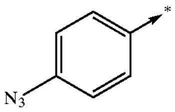 | 92.1 | 5.09 | 477.19 |

-continued
| | | | | | |
|---|---|---|---|---|---|
| 969 | 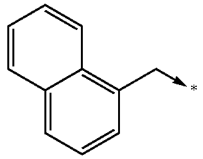 | 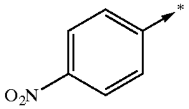 | 90.5 | 5.1 | 481.16 |
| 970 | 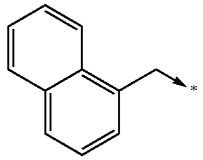 | 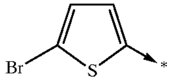 | 92 | 5.56 | 520.02 |
| 971 | 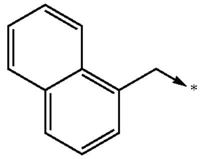 | 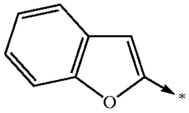 | 93 | 5.72 | 476.17 |
| 972 | 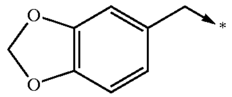 | 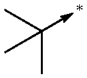 | 91.6 | 4 | 410.16 |
| 973 | 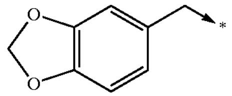 | 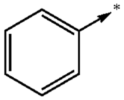 | 89.7 | 4.28 | 430.15 |
| 974 | 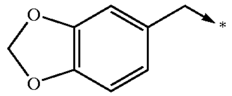 | 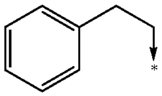 | 83.4 | 4.46 | 458.19 |
| 975 | 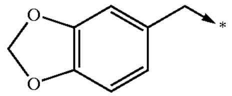 | 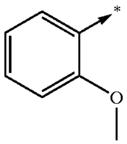 | 96.9 | 4.19 | 460.16 |

-continued
| | | | | | |
|---|---|---|---|---|---|
| 976 | 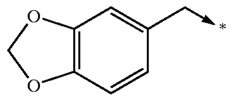 | 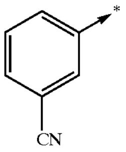 | 58.2 | 4.29 | 455.12 |
| 977 | 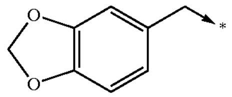 | 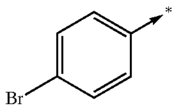 | 81.4 | 4.84 | 508.06 |
| 978 | 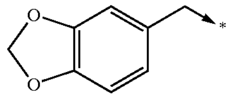 | 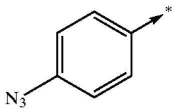 | 85.8 | 4.64 | 471.15 |
| 979 | 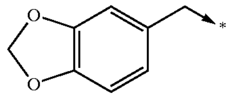 | 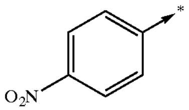 | 46.8 | 4.62 | 475.14 |
| 980 | 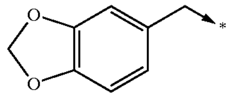 | 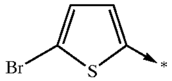 | 77.4 | 5.06 | 514.02 |
| 981 | 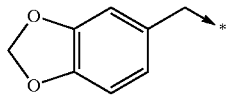 | 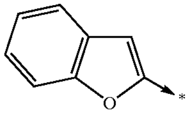 | 61.7 | 5.24 | 470.16 |
| 982 | 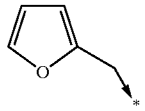 | 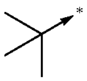 | 4.8 | 3.54 | 356.15 |
| 983 | 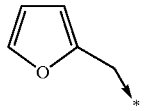 | 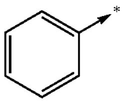 | 71.4 | 4.1 | 376.14 |

-continued
| | | | | | |
|---|---|---|---|---|---|
| 984 | 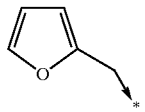 | 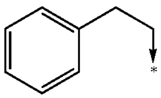 | 79 | 4.3 | 404.17 |
| 985 | 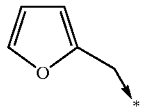 | 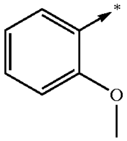 | 88.3 | 4.0 | 406.13 |
| 986 | 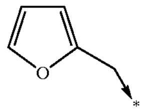 | 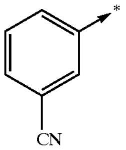 | 12.2 | 5.32 | 401.11 |
| 987 | 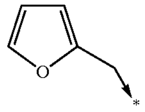 | 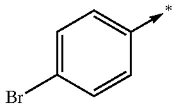 | 46.5 | 4.72 | 454.04 |
| 988 | 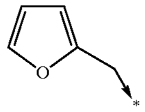 | 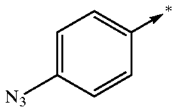 | 56.3 | 4.49 | 417.15 |
| 989 | 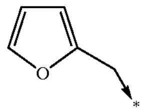 | 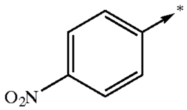 | 13.8 | 5.52 | 421.12 |
| 990 | 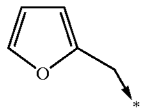 | 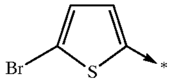 | 35.3 | 4.95 | 460.02 |

-continued
| | | | | | |
|---|---|---|---|---|---|
| 991 | 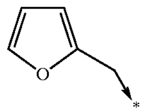 | 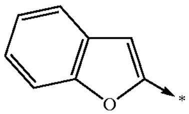 | 9.1 | 5.71 | 416.11 |
| | | 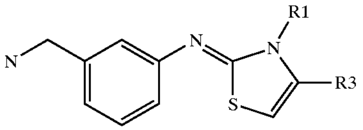 | | | |
| 992 | 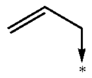 | 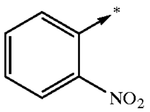 | 95.3 | 3.33 | 367.12 |
| 993 | 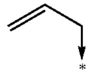 | 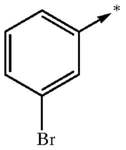 | 91.9 | 3.97 | 400.03 |
| 994 | 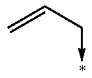 | 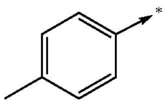 | 92.5 | 3.64 | 336.17 |
| 995 | 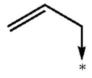 | 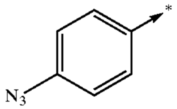 | 83.7 | 3.75 | 363.13 |
| 996 | 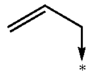 | 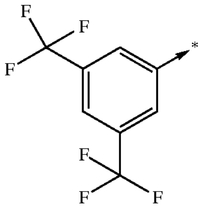 | 94.7 | 4.88 | 458.11 |

-continued
| | | | | | |
|---|---|---|---|---|---|
| 997 | 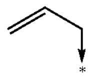 | 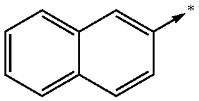 | 93.1 | 4.03 | 372.14 |
| 998 | 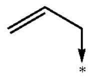 | 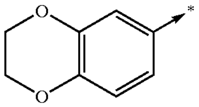 | 92.6 | 3.37 | 380.14 |
| 999 | 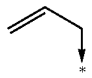 | 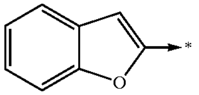 | 92.1 | 4.36 | 362.12 |
| 1000 | 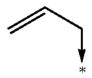 | 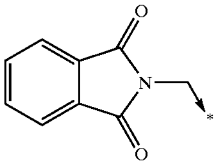 | 91 | 3.32 | 405.11 |
| 1001 | 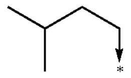 | 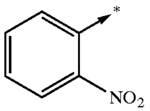 | 87.8 | 3.9 | 397.14 |
| 1002 | 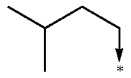 | 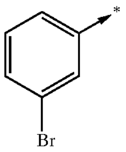 | 64.2 | 4.46 | 430.09 |
| 1003 | 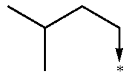 | 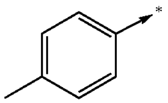 | 61.6 | 4.18 | 366.23 |
| 1004 | 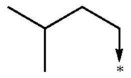 | 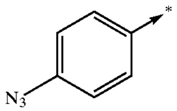 | 45.6 | 4.26 | 393.16 |

-continued
| | | | | | |
|---|---|---|---|---|---|
| 1005 | 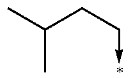 | 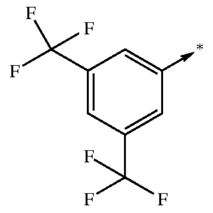 | 72.4 | 5.28 | 488.17 |
| 1006 | 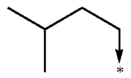 | 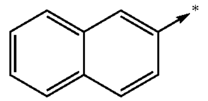 | 67 | 4.47 | 402.17 |
| 1007 | 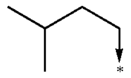 | 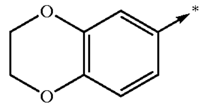 | 51.1 | 3.86 | 410.16 |
| 1008 | 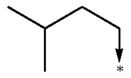 | 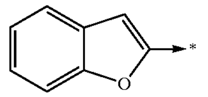 | 57.6 | 4.86 | 392.16 |
| 1009 | 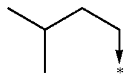 | 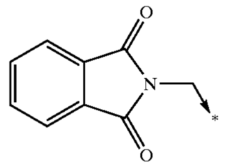 | 75.1 | 3.92 | 435.16 |
| 1010 | 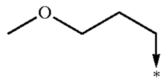 | 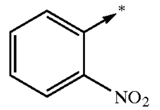 | 90.7 | 3.24 | 399.13 |
| 1011 | 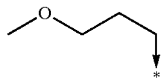 | 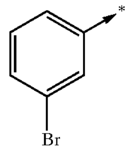 | 79.6 | 3.79 | 432.06 |

-continued
| | | | | | |
|---|---|---|---|---|---|
| 1012 | 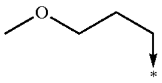 | 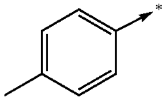 | 74.5 | 3.55 | 368.16 |
| 1013 | 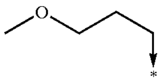 | 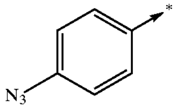 | 58.8 | 3.62 | 395.15 |
| 1014 | 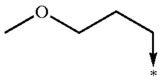 | 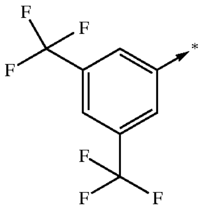 | 81 | 4.65 | 490.15 |
| 1015 | 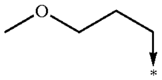 | 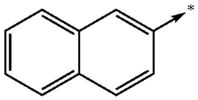 | 86.8 | 3.88 | 404.17 |
| 1016 | 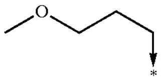 | 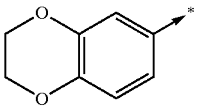 | 71.4 | 3.3 | 412.13 |
| 1017 | 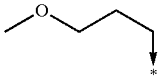 | 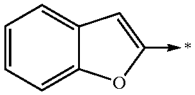 | 73.7 | 4.13 | 394.15 |
| 1018 | 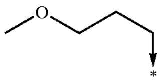 | 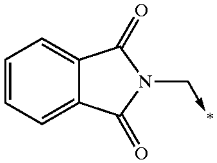 | 80.5 | 3.3 | 437.15 |

-continued
| | | | | | |
|---|---|---|---|---|---|
| 1019 | 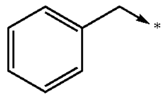 | 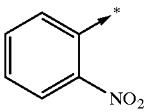 | 94.6 | 4.19 | 417.10 |
| 1020 | 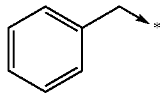 | 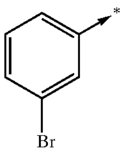 | 94.8 | 4.76 | 450.07 |
| 1021 | 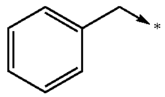 | 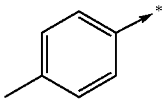 | 92.9 | 4.42 | 386.13 |
| 1022 | 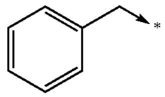 | 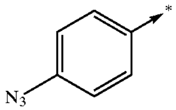 | 88.8 | 4.56 | 413.11 |
| 1023 | 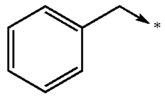 | 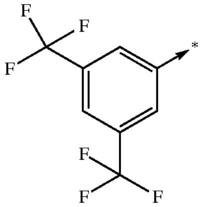 | 94.1 | 5.48 | 508.13 |
| 1024 | 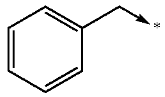 | 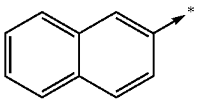 | 93.8 | 4.79 | 422.13 |
| 1025 | 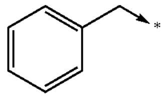 | 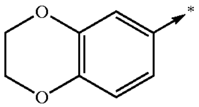 | 92.3 | 4.04 | 430.15 |

-continued
| | | | | | |
|---|---|---|---|---|---|
| 1026 | 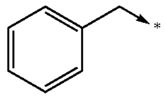 | 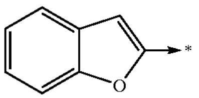 | 90 | 5.08 | 412.10 |
| 1027 | 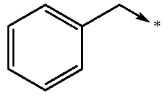 | 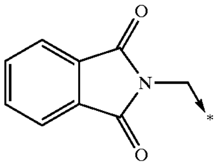 | 93.2 | 3.95 | 455.13 |
| 1028 | 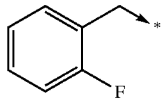 | 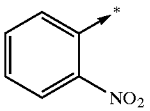 | 92.6 | 4.3 | 435.1 |
| 1029 | 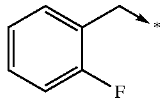 | 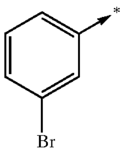 | 92.8 | 4.9 | 470.1 |
| 1030 | 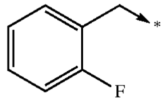 | 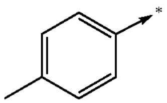 | 89.2 | 4.6 | 404.1 |
| 1031 | 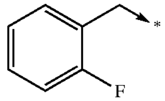 | 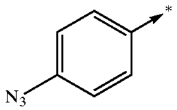 | 89.2 | 4.76 | 431.1 |
| 1032 | 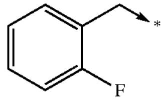 | 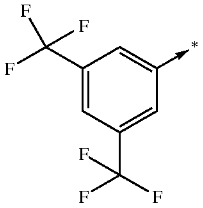 | 94.3 | 5.6 | 526.1 |

-continued
| | | | | | |
|---|---|---|---|---|---|
| 1033 | 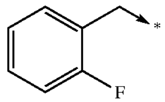 | 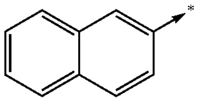 | 93.5 | 5 | 440.2 |
| 1034 | 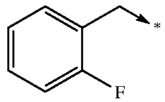 | 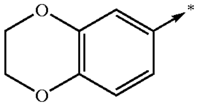 | 92.4 | 4.2 | 448.1 |
| 1035 | 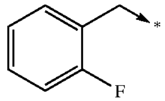 | 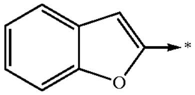 | 87.9 | 5.2 | 430.1 |
| 1036 | 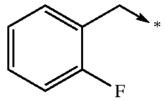 | 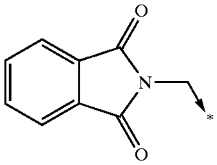 | 93.6 | 4.1 | 473.2 |
| 1037 | 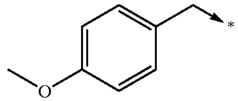 | 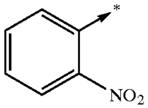 | 80.4 | 4.16 | 447.14 |
| 1038 | 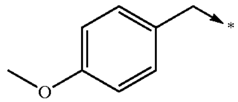 | 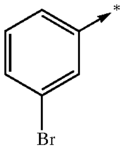 | 72.7 | 4.72 | 480.08 |
| 1039 | 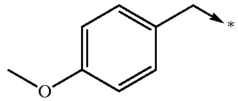 | 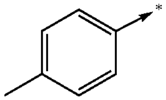 | 77 | 4.39 | 416.14 |
| 1040 | 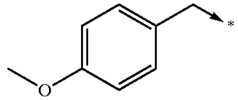 | 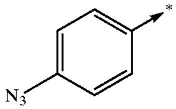 | 59.2 | 4.5 | 443.16 |

-continued
| | | | | | |
|---|---|---|---|---|---|
| 1041 | 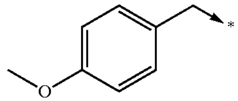 | 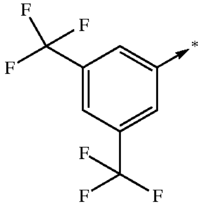 | 16.8 | 5.98 | 538.12 |
| 1042 | 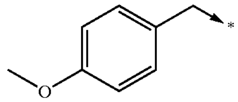 | 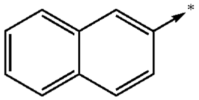 | 59.5 | 4.74 | 452.16 |
| 1043 | 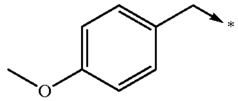 | 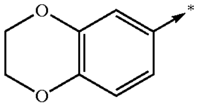 | 74 | 4.02 | 460.16 |
| 1044 | 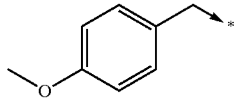 | 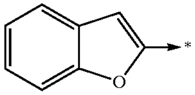 | 26.3 | 5.52 | 442.13 |
| 1045 | 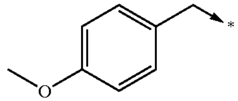 | 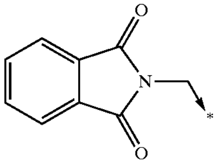 | 91 | 3.82 | 485.17 |
| 1046 | 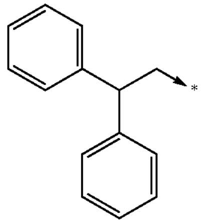 | 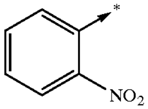 | 89.8 | 5.09 | 507.19 |

-continued
| | | | | | |
|---|---|---|---|---|---|
| 1047 | 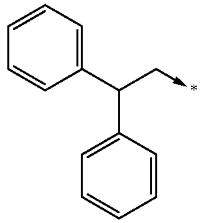 | 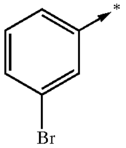 | 84.5 | 5.52 | 540.09 |
| 1048 | 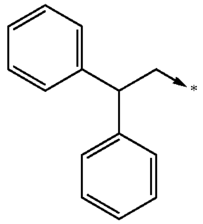 | 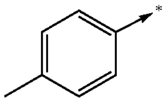 | 86 | 5.06 | 476.21 |
| 1049 | 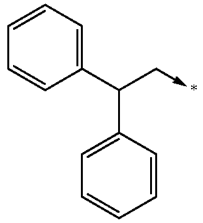 | 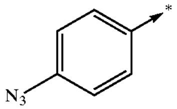 | 75.6 | 5.22 | 503.21 |
| 1050 | 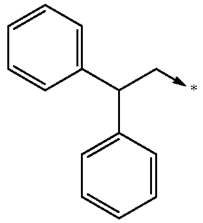 | 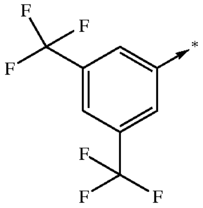 | 90.3 | 6.14 | 598.15 |

-continued
| | | | | | |
|---|---|---|---|---|---|
| 1051 | 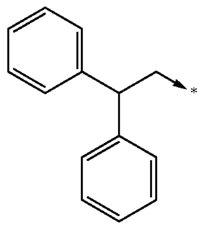 | 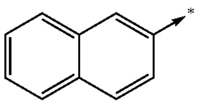 | 85.9 | 5.38 | 512.22 |
| 1052 | 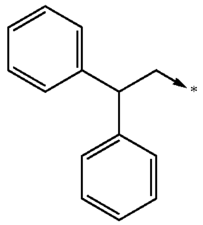 | 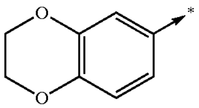 | 81.3 | 4.68 | 520.19 |
| 1053 | 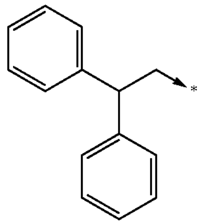 | 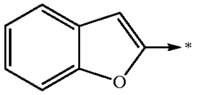 | 83.3 | 5.66 | 502.20 |
| 1054 | 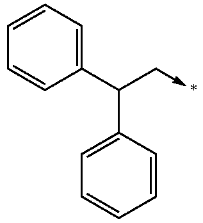 | 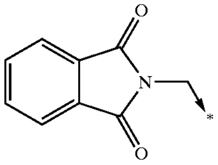 | 82 | 4.92 | 545.17 |
| 1055 | 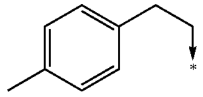 | 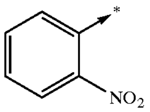 | 93.1 | 4.34 | 445.16 |

-continued
| | | | | | |
|---|---|---|---|---|---|
| 1056 | 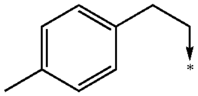 | 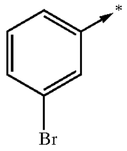 | 81.5 | 4.77 | 478.10 |
| 1057 | 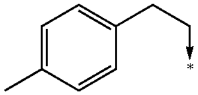 | 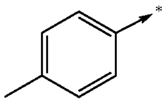 | 79.9 | 4.46 | 414.17 |
| 1058 | 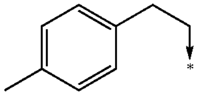 | 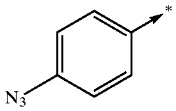 | 70.2 | 4.56 | 441.15 |
| 1059 | 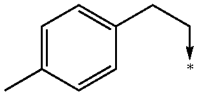 | 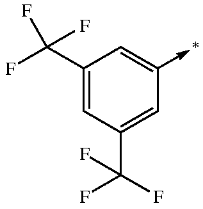 | 85.8 | 5.56 | 536.11 |
| 1060 | 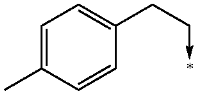 | 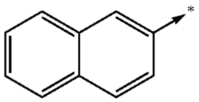 | 84.1 | 4.73 | 450.19 |
| 1061 | 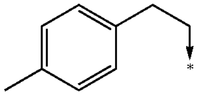 | 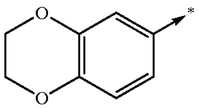 | 78.4 | 4.12 | 458.20 |
| 1062 | 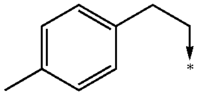 | 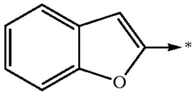 | 83.3 | 5.13 | 440.16 |

-continued
| | | | | | |
|---|---|---|---|---|---|
| 1063 | 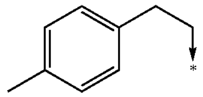 | 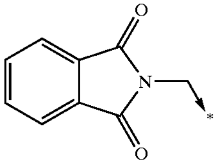 | 83.1 | 4.22 | |
| | | 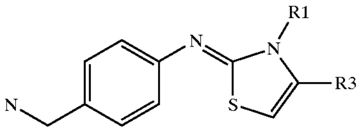 | | | |
| 1064 | 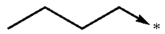 | 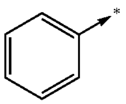 | 86.6 | 3.52 | 338.12 |
| 1065 | 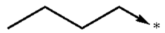 | 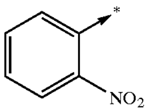 | 90.4 | 3.44 | 383.09 |
| 1066 | 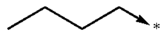 | 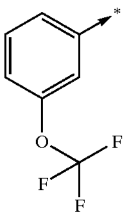 | 87.3 | 4.25 | 422.10 |
| 1067 | 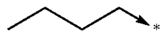 | 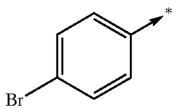 | 85.9 | 4.04 | 416.04 |

-continued
| | | | | | |
|---|---|---|---|---|---|
| 1068 | 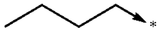 | 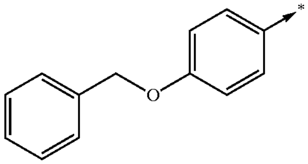 | 70.5 | 4.4 | 444.18 |
| 1069 | 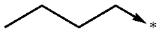 | 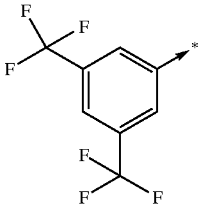 | 80.1 | 4.83 | 474.13 |
| 1070 | 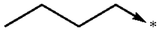 | 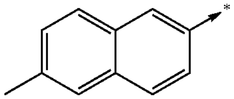 | 80.6 | 4.34 | 402.16 |
| 1071 | 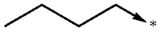 | 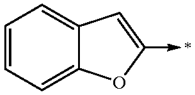 | 80.8 | 4.37 | 378.14 |
| 1072 | 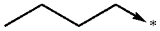 | 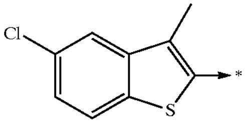 | 86.5 | 4.77 | 442.06 |
| 1073 | 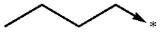 | 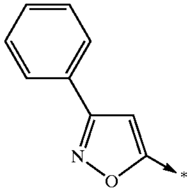 | 83.4 | 4.72 | 405.12 |
| 1074 | 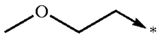 | 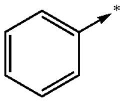 | 90.5 | 3.02 | 340.15 |

-continued
| | | | | | |
|---|---|---|---|---|---|
| 1075 | 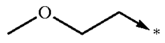 | 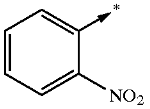 | 93.5 | 2.98 | 385.10 |
| 1076 | 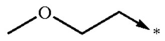 | 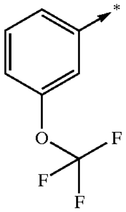 | 91.7 | 3.9 | 424.12 |
| 1077 | 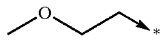 | 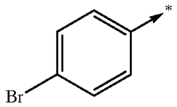 | 90.8 | 3.62 | 418.04 |
| 1078 | 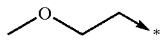 | 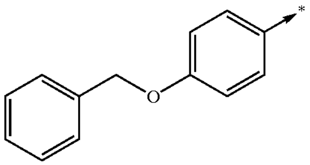 | 80.8 | 4.09 | 446.18 |
| 1079 | 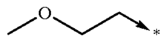 | 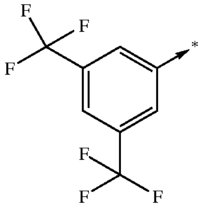 | 88.1 | 4.6 | 476.12 |
| 1080 | 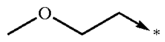 | 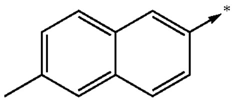 | 91.5 | 3.98 | 404.16 |

-continued
| | | | | | |
|---|---|---|---|---|---|
| 1081 | 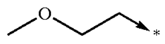 | 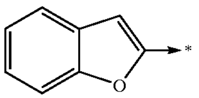 | 89.2 | 3.87 | 380.13 |
| 1082 | 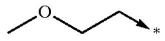 | 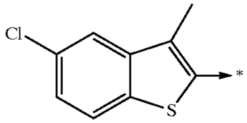 | 87.3 | 4.36 | 444.10 |
| 1083 | 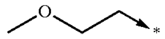 | 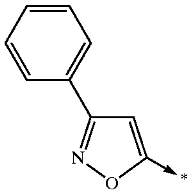 | 90.6 | 4.24 | 407.13 |
| 1084 | 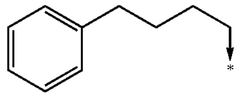 | 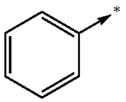 | 86.4 | 4.24 | 414.15 |
| 1085 | 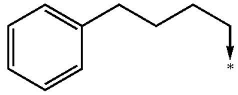 | 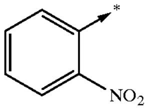 | 91.8 | 4.21 | 459.17 |
| 1086 | 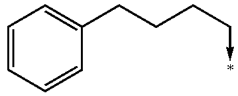 | 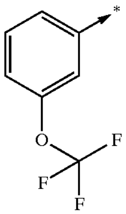 | 88.2 | 4.89 | 498.19 |
| 1087 | 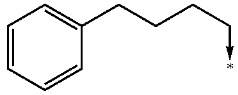 | 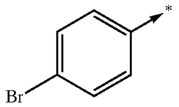 | 85.8 | 4.71 | 492.12 |

-continued
| | | | | | |
|---|---|---|---|---|---|
| 1088 | 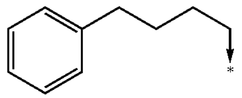 | 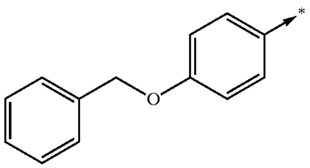 | 76.1 | 4.9 | 520.21 |
| 1089 | 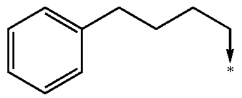 | 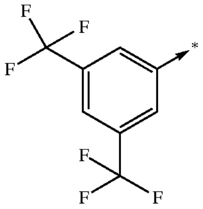 | 83.3 | 5.45 | 550.17 |
| 1090 | 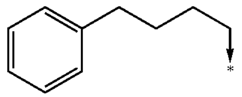 | 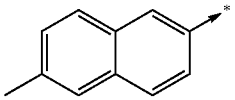 | 84.9 | 4.9 | 478.24 |
| 1091 | 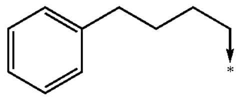 | 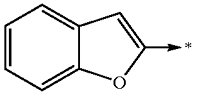 | 86.1 | 5.08 | 454.19 |
| 1092 | 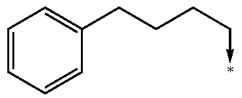 | 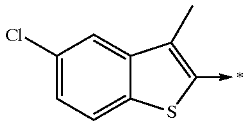 | 78 | 5.38 | 518.14 |
| 1093 | 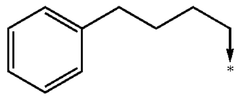 | 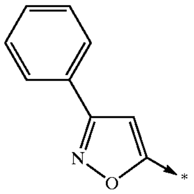 | 84.5 | 5.38 | 481.21 |

-continued
| | | | | | |
|---|---|---|---|---|---|
| 1094 | 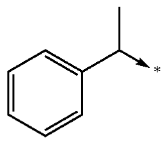 | 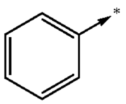 | 37.5 | 3.36 | 386.14 |
| 1095 | 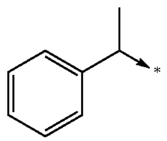 | 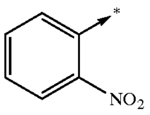 | 57.1 | 3.35 | 431.14 |
| 1096 | 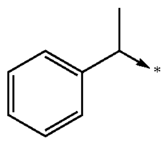 | 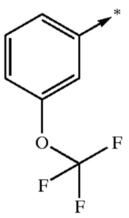 | 44 | 3.78 | 470.17 |
| 1097 | 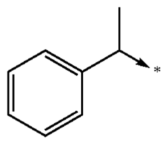 | 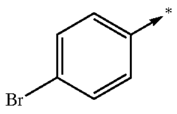 | 42 | 3.62 | 464.09 |
| 1098 | 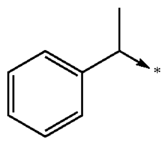 | 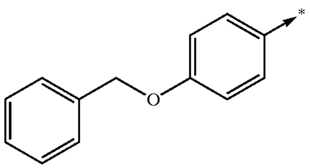 | 38.8 | 4.14 | 492.21 |
| 1099 | 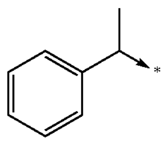 | 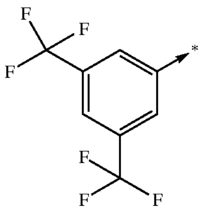 | 45.2 | 3.98 | 522.14 |

-continued
| | | | | | |
|---|---|---|---|---|---|
| 1100 | 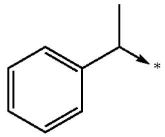 | 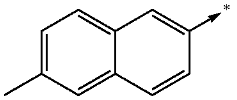 | 33.4 | 3.99 | 450.20 |
| 1101 | 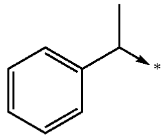 | 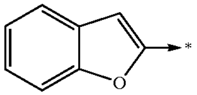 | 44.7 | 3.68 | 426.14 |
| 1102 | 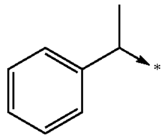 | 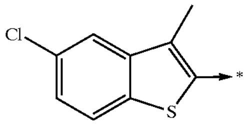 | 33.4 | 4.08 | 490.12 |
| 1103 | 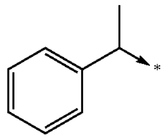 | 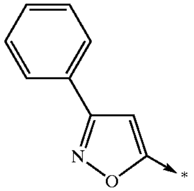 | 42.4 | 3.67 | 453.17 |
| 1104 | 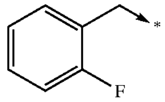 | 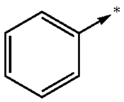 | 92.6 | 4.23 | 390.14 |
| 1105 | 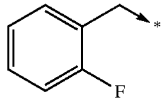 | 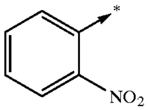 | 91.9 | 4.1 | 439.1 |

-continued
| | | | | | |
|---|---|---|---|---|---|
| 1106 | 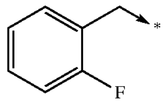 | 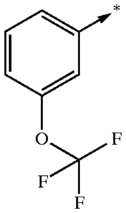 | 92.1 | 5 | 474.13 |
| 1107 | 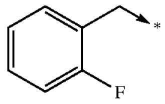 | 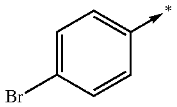 | 93 | 4.85 | 468.04 |
| 1108 | 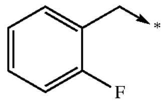 | 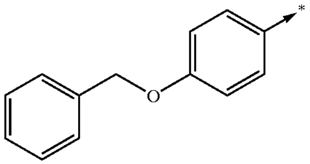 | 86.5 | 5.04 | 496.18 |
| 1109 | 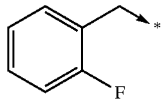 | 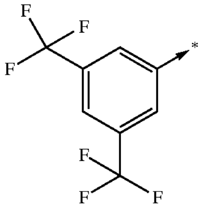 | 92.8 | 5.5 | 526.13 |
| 1110 | 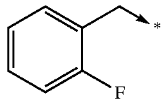 | 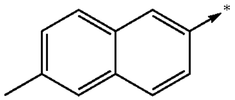 | 92.8 | 5.1 | 454.17 |
| 1111 | 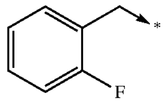 | 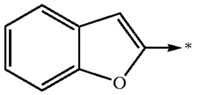 | 92 | 5.1 | 430.10 |

-continued
| | | | | | |
|---|---|---|---|---|---|
| 1112 | 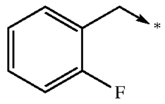 | 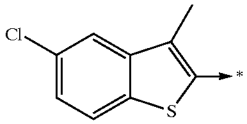 | 92.8 | 5.48 | 494.08 |
| 1113 | 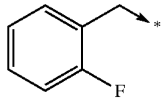 | 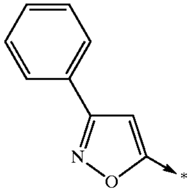 | 92.8 | 5.1 | 457.18 |
| 1114 | 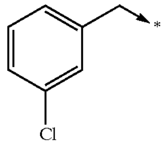 | 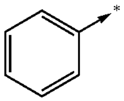 | 93.8 | 4.6 | 406.10 |
| 1115 | 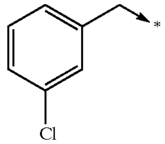 | 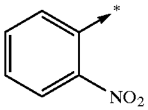 | 93.6 | 4.5 | 451.03 |
| 1116 | 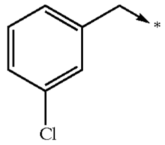 | 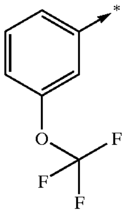 | 93.1 | 5.2 | 490.10 |
| 1117 | 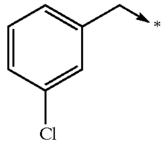 | 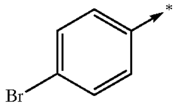 | 94.5 | 5.1 | 483.99 |

-continued
| | | | | | |
|---|---|---|---|---|---|
| 1118 | 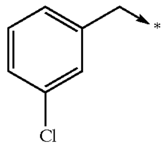 | 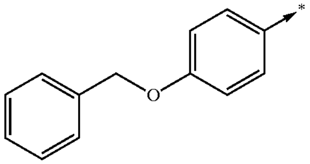 | 89.54 | 5.29 | 512.13 |
| 1119 | 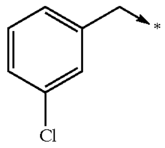 | 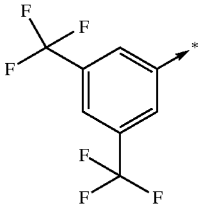 | 95.2 | 5.6 | 542.1 |
| 1120 | 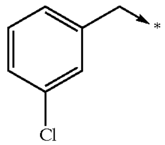 | 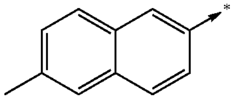 | 92.8 | 5.38 | 470.15 |
| 1121 | 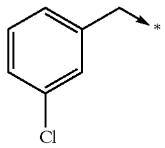 | 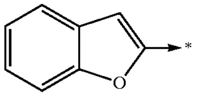 | 93.4 | 5.3 | 445.94 |
| 1122 | 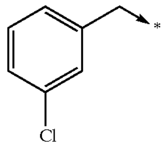 | 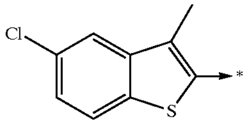 | 94.7 | 5.7 | 510.05 |
| 1123 | 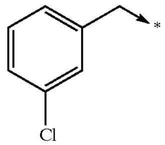 | 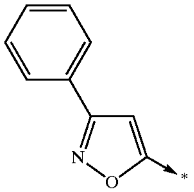 | 94.3 | 5.3 | 473.04 |

-continued
| | | | | | |
|---|---|---|---|---|---|
| 1124 | 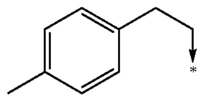 | 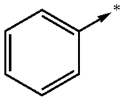 | 89.5 | 4.06 | 400.12 |
| 1125 | 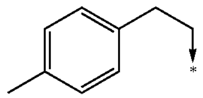 | 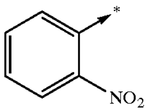 | 92.1 | 4.13 | 445.13 |
| 1126 | 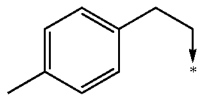 | 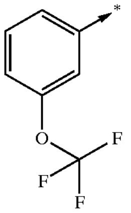 | 88.9 | 4.81 | 484.15 |
| 1127 | 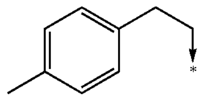 | 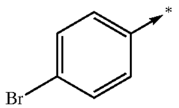 | 88.8 | 4.56 | 478.09 |
| 1128 | 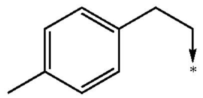 | 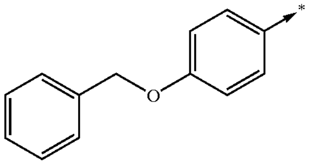 | 82.4 | 4.76 | 506.20 |
| 1129 | 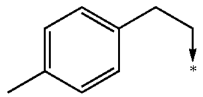 | 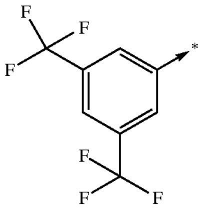 | 88.6 | 5.36 | 536.12 |

-continued
| | | | | | |
|---|---|---|---|---|---|
| 1130 | 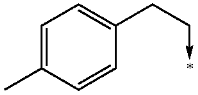 | 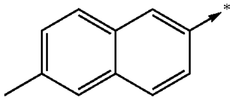 | 85.7 | 4.78 | 464.18 |
| 1131 | 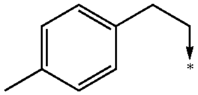 | 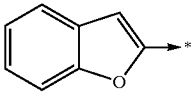 | 84 | 4.94 | 440.15 |
| 1132 | 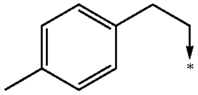 | 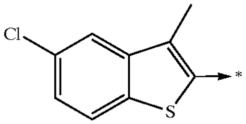 | 64.3 | 5.38 | 504.10 |
| 1133 | 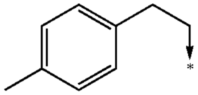 | 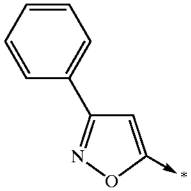 | 88.4 | 5.16 | 467.17 |
| 1134 | 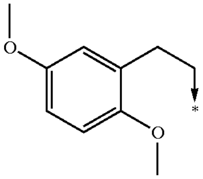 | 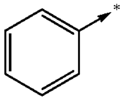 | 82.7 | 3.76 | 446.16 |
| 1135 | 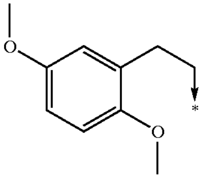 | 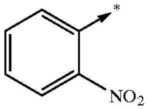 | 89 | 3.77 | 491.14 |

-continued
| | | | | | |
|---|---|---|---|---|---|
| 1136 | 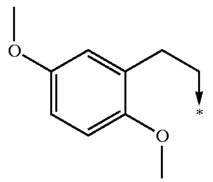 | 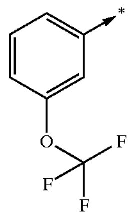 | 87.1 | 4.4 | 530.13 |
| 1137 | 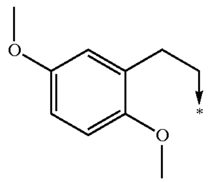 | 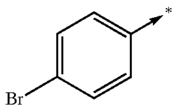 | 84.6 | 4.21 | 524.08 |
| 1138 | 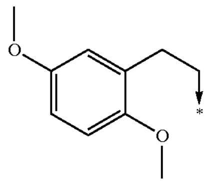 | 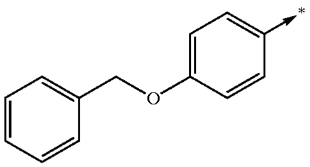 | 76 | 4.52 | 552.19 |
| 1139 | 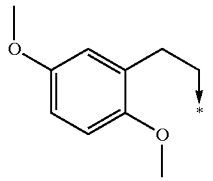 | 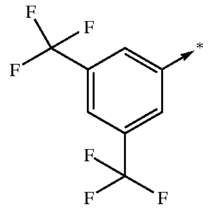 | 85.6 | 4.98 | 582.12 |
| 1140 | 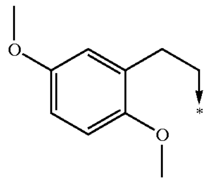 | 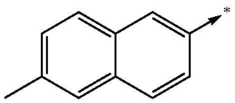 | 83.1 | 4.44 | 510.21 |

-continued
| | | | | | |
|---|---|---|---|---|---|
| 1141 | 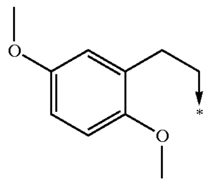 | 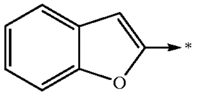 | 88.3 | 4.6 | 486.19 |
| 1142 | 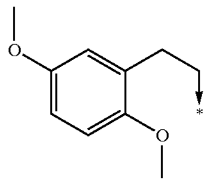 | 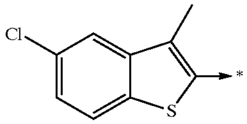 | 1.5 | 5.07 | 550.12 |
| 1143 | 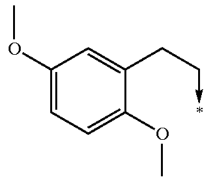 | 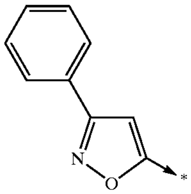 | 84 | 4.75 | 513.16 |
| | | 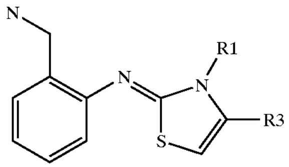 | | | |
| 1144 | 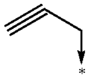 | 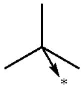 | 75 | 4.48 | 300.16 |
| 1145 | 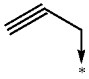 | 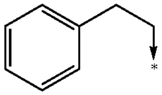 | 82 | 4.89 | 348.16 |

-continued
| | | | | | |
|---|---|---|---|---|---|
| 1146 | 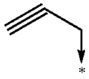 | 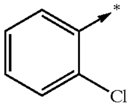 | 86.7 | 4.72 | 354.09 |
| 1147 | 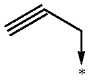 | 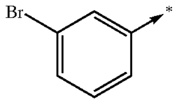 | 89 | 4.96 | 398.01 |
| 1148 | 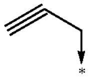 | 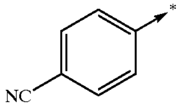 | 87 | 4.37 | 345.18 |
| 1149 | 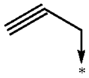 | 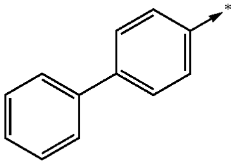 | 90 | 5.4 | 396.1 |
| 1150 | 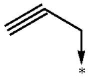 | 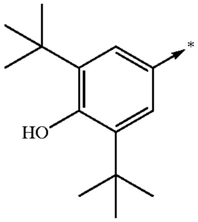 | 89 | 5.9 | 448.2 |
| 1151 | 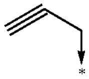 | 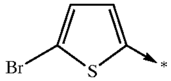 | 85 | 5 | 404 |
| 1152 | 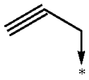 | 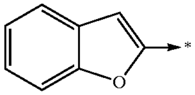 | 85 | 4.96 | 360.10 |

-continued
| | | | | | |
|---|---|---|---|---|---|
| 1153 | 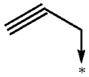 | 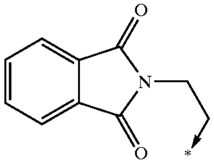 | 91 | 4.39 | 417.14 |
| 1154 | 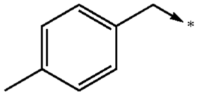 | 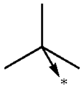 | 95 | 5.14 | 366.21 |
| 1155 | 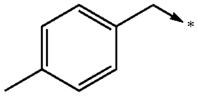 | 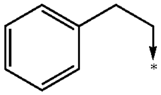 | 92 | 5.52 | 414.17 |
| 1156 | 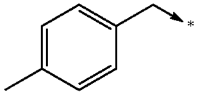 | 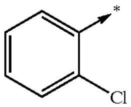 | 95 | 5.37 | 420.13 |
| 1157 | 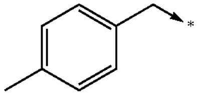 | 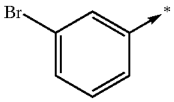 | 93 | 5.6 | 464.08 |
| 1158 | 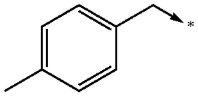 | 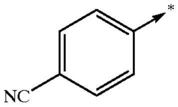 | 94 | 5 | 411.2 |
| 1159 | 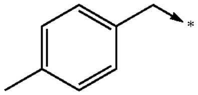 | 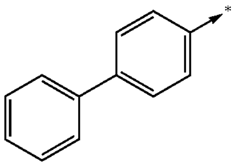 | 91 | 6.04 | 462.19 |

-continued
| | | | | | |
|---|---|---|---|---|---|
| 1160 | 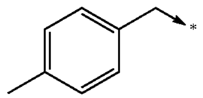 | 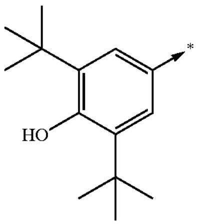 | 91.5 | 6.4 | 514.2 |
| 1161 | 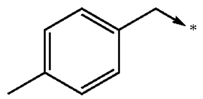 | 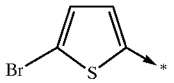 | 92.6 | 5.7 | 470.1 |
| 1162 | 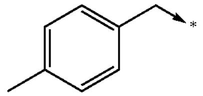 | 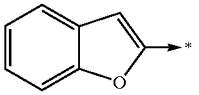 | 93.8 | 5.6 | 426.14 |
| 1163 | 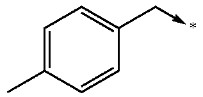 | 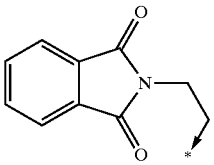 | 91.4 | 5.02 | 483.21 |
| 1164 | 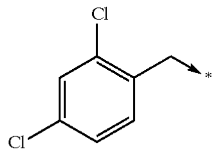 | 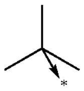 | 96.3 | 5.55 | 420.10 |
| 1165 | 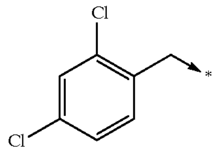 | 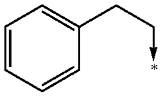 | 78.2 | 5.81 | 468.10 |

-continued
| | | | | | |
|---|---|---|---|---|---|
| 1166 | 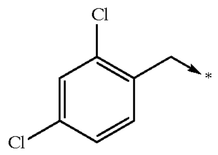 | 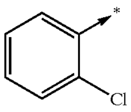 | 96.7 | 5.6 | 474.06 |
| 1167 | 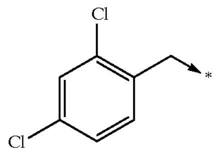 | 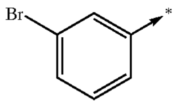 | 96.9 | 5.8 | 517.97 |
| 1168 | 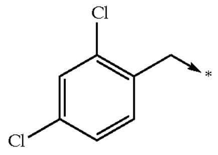 | 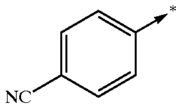 | 94.2 | 5.18 | 465.06 |
| 1169 | 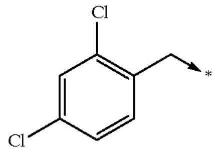 | 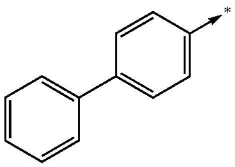 | 94 | 6.25 | 516.10 |
| 1170 | 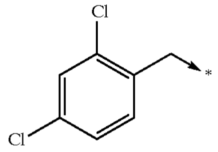 | 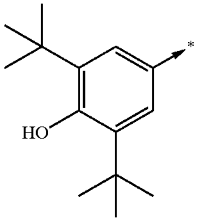 | 96.4 | 6.52 | 568.2 |
| 1171 | 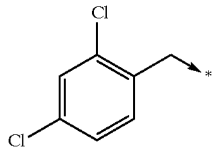 | 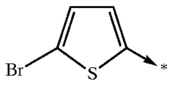 | 94.6 | 5.9 | 524.0 |

-continued
| | | | | | |
|---|---|---|---|---|---|
| 1172 | 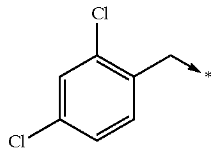 | 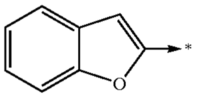 | 94.9 | 5.81 | 480.07 |
| 1173 | 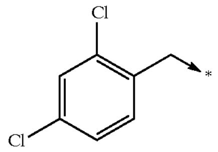 | 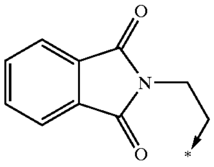 | 91.9 | 5.25 | 537.09 |
| 1174 | 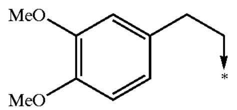 | 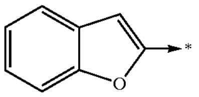 | 77.4 | 5.24 | 486.16 |
| 1175 | 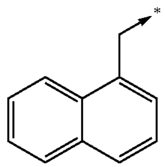 | 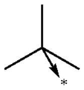 | 96.8 | 5.36 | 402.15 |
| 1176 | 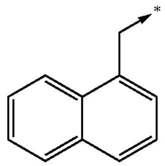 | 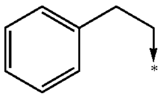 | 92.4 | 5.66 | 450.19 |
| 1177 | 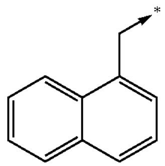 | 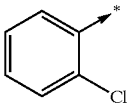 | 93.3 | 5.48 | 456.12 |

-continued
| | | | | | |
|---|---|---|---|---|---|
| 1178 | 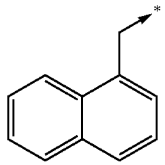 | 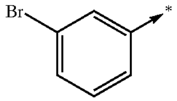 | 93.3 | 5.7 | 500.08 |
| 1179 | 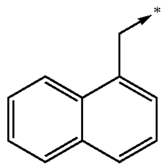 | 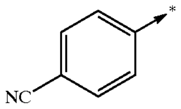 | 90.7 | 5.12 | 447.15 |
| 1180 | 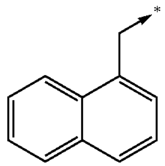 | 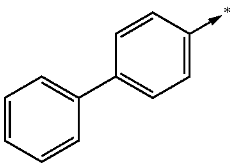 | 91.9 | 6.12 | 498.21 |
| 1181 | 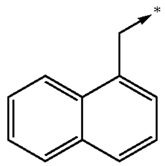 | 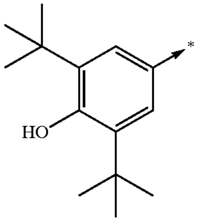 | 95.1 | 6.5 | 550.3 |
| 1182 | 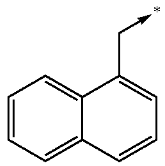 | 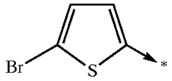 | 92.8 | 5.7 | 506.0 |

-continued
| | | | | | |
|---|---|---|---|---|---|
| 1183 | 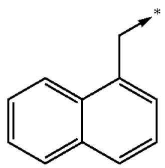 | 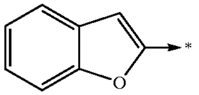 | 94.9 | 5.74 | 462.15 |
| 1184 | 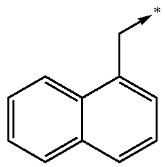 | 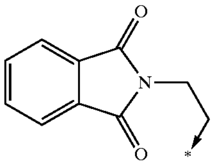 | 91.4 | 5.13 | 519.17 |
| 1185 | 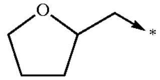 | 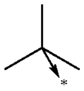 | 73.6 | 3.52 | 346.19 |
| 1186 | 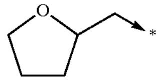 | 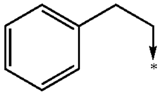 | 71.5 | 4.5 | 394.17 |
| 1187 | 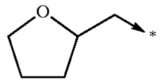 | 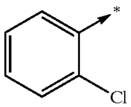 | 82.2 | 4.58 | 400.10 |
| 1188 | 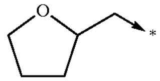 | 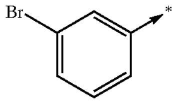 | 78.6 | 4.86 | 444.09 |
| 1189 | 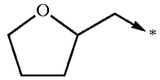 | 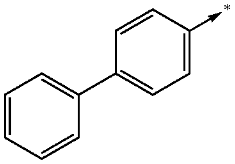 | 70.5 | 5.3 | 442.17 |

-continued
| | | | | | |
|---|---|---|---|---|---|
| 1190 | 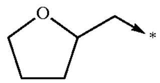 | 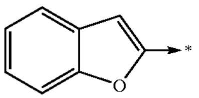 | 76.8 | 5 | 406.13 |
| 1191 | 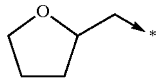 | 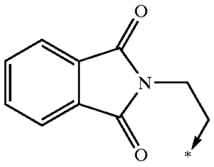 | 80.5 | 4.1 | 463.19 |
| Ex. | R2 | R5 | Purity (%) | rt (min.) | [M + H]+ |
|---|---|---|---|---|---|
| | | 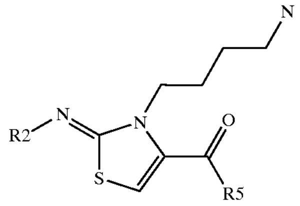 | | | |
| 1192 | 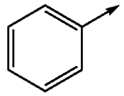 | 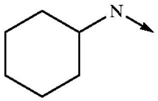 | 28.3 | 3.61 | 373.15 |
| 1193 | 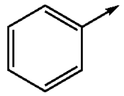 | 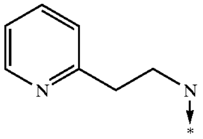 | 64.3 | 2.55 | 396.15 |
| 1194 | 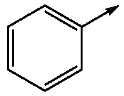 | 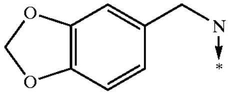 | 66.8 | 3.58 | 425.13 |
| 1195 | 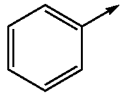 | 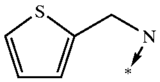 | 51.9 | 3.47 | 387.07 |

-continued
| | | | | | |
|---|---|---|---|---|---|
| 1196 | 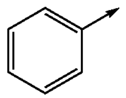 | 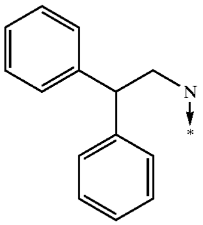 | 75.8 | 4.43 | 471.21 |
| 1197 | 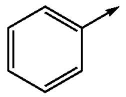 | 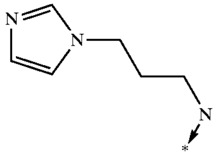 | 66.4 | 2.38 | 399.15 |
| 1198 | 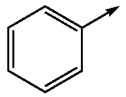 | 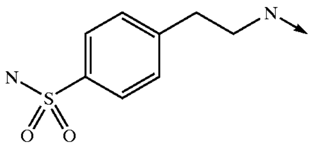 | 42.6 | 3.11 | 474.14 |
| 1199 | 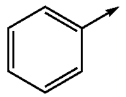 | 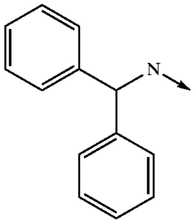 | 45.3 | 4.39 | 457.18 |
| 1200 | 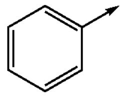 | 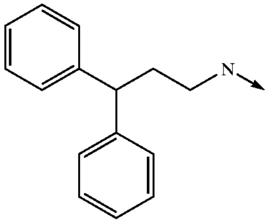 | 64 | 4.62 | 485.21 |

-continued
| | | | | | |
|---|---|---|---|---|---|
| 1201 | 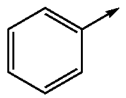 | 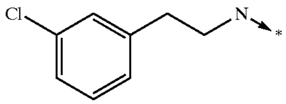 | 55.1 | 4.09 | 429.12 |
| 1202 | 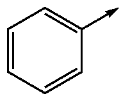 | 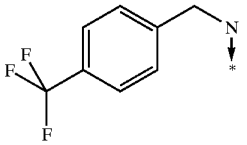 | 75 | 4.22 | 449.13 |
| 1203 | 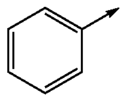 | 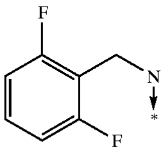 | 67.9 | 3.64 | 417.11 |
| 1204 | 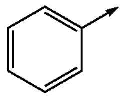 | 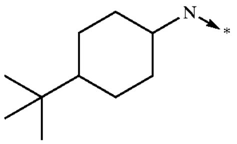 | 31.7 + 17.3 | 4.65 + 4.8 | 429.24 |
| 1205 | 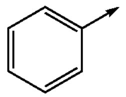 | 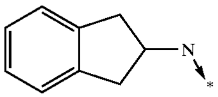 | 41.8 | 3.86 | 407.14 |
| 1206 | 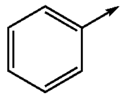 | 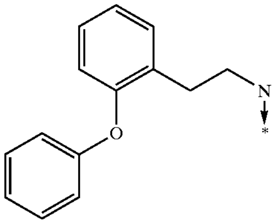 | 67.8 | 4.58 | 487.20 |

-continued
| | | | | | |
|---|---|---|---|---|---|
| 1207 | 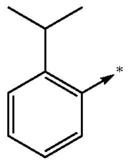 | 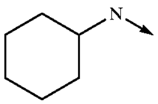 | 33.2 | 4.31 | 415.20 |
| 1208 | 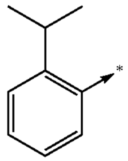 | 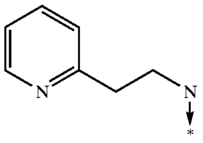 | 60.9 | 3.29 | 438.21 |
| 1209 | 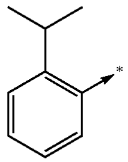 | 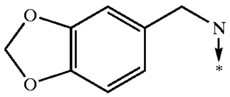 | 58 | 4.29 | 467.18 |
| 1210 | 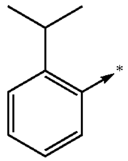 | 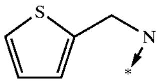 | 51.9 | 4.21 | 429.15 |
| 1211 | 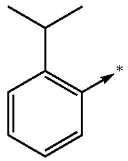 | 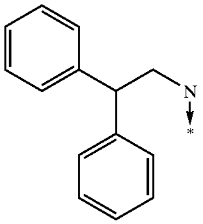 | 70 | 5.03 | 513.24 |

-continued
| | | | | | |
|---|---|---|---|---|---|
| 1212 | 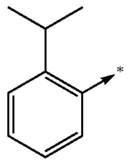 | 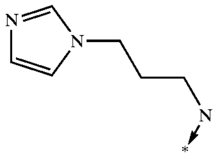 | 22.9 | 3.17 | 441.19 |
| 1213 | 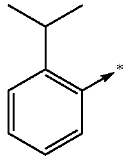 | 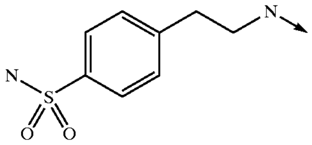 | 71.8 | 3.81 | 516.16 |
| 1214 | 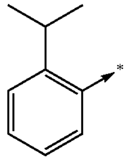 | 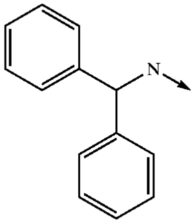 | 35.4 | 5.03 | 499.23 |
| 1215 | 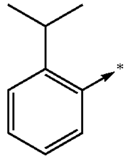 | 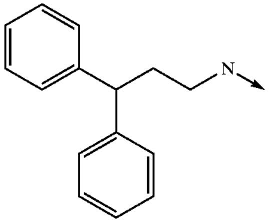 | 64 | 5.18 | 527.25 |
| 1216 | 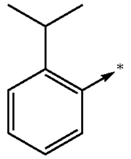 | 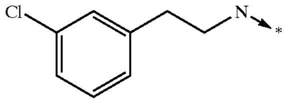 | 68.2 | 4.71 | 471.19 |

-continued
| | | | | | |
|---|---|---|---|---|---|
| 1217 | 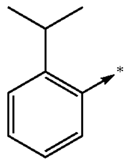 | 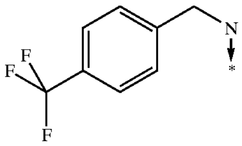 | 76.5 | 4.84 | 491.18 |
| 1218 | 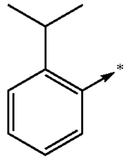 | 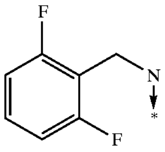 | 67.8 | 4.35 | 459.16 |
| 1219 | 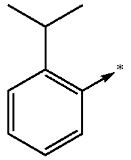 | 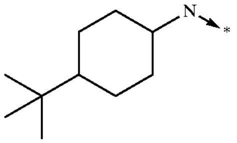 | 28.7 + 14.2 | 5.27 + 5.4 | 471.30 |
| 1220 | 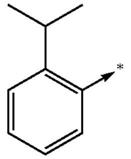 | 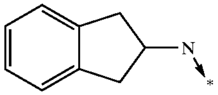 | 66.9 | 4.52 | 449.21 |
| 1221 | 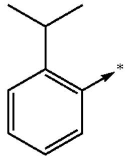 | 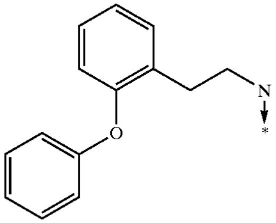 | 64.1 | 5.17 | 529.21 |
| 1222 | 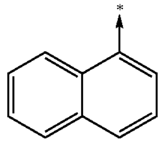 | 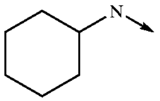 | 49.7 | 4.55 | 423.19 |

-continued
| | | | | | |
|---|---|---|---|---|---|
| 1223 | 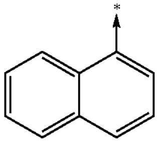 | 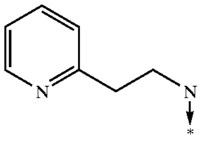 | 78.8 | 3.41 | 446.17 |
| 1224 | 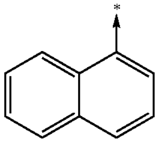 | 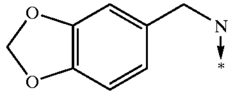 | 76.2 | 4.48 | 475.15 |
| 1225 | 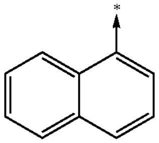 | 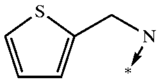 | 68.3 | 4.42 | 437.12 |
| 1226 | 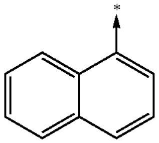 | 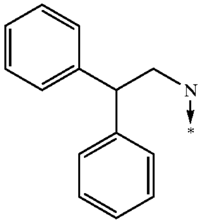 | 79.6 | 5.24 | 521.17 |
| 1227 | 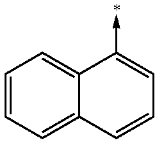 | 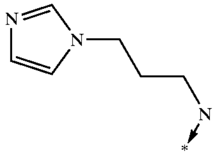 | 49.1 | 3.29 | 449.20 |
| 1228 | 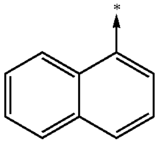 | 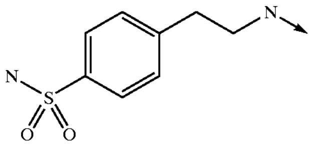 | 72.2 | 4 | 524.15 |

-continued
| | | | | | |
|---|---|---|---|---|---|
| 1229 | 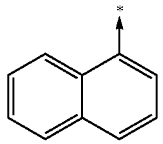 | 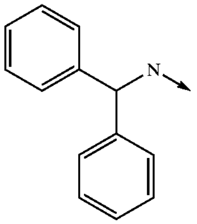 | 69.7 | 5.22 | 507.20 |
| 1230 | 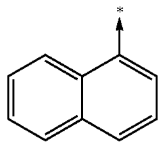 | 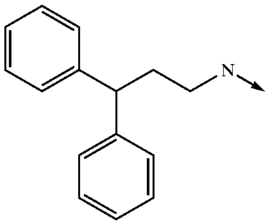 | 75 | 5.42 | 535.20 |
| 1231 | 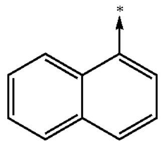 | 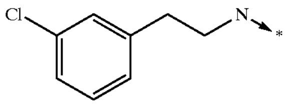 | 78 | 4.93 | 479.13 |
| 1232 | 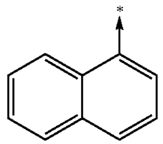 | 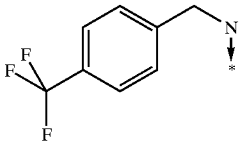 | 79.1 | 5.04 | 499.16 |
| 1233 | 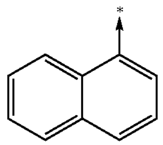 | 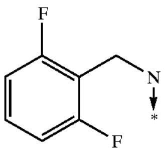 | 82.6 | 4.56 | 467.13 |

-continued
| | | | | | |
|---|---|---|---|---|---|
| 1234 | 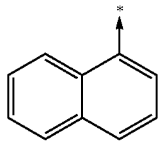 | 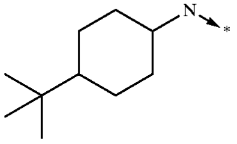 | 45 + 24.6 | 5.53 + 5.7 | 479.26 |
| 1235 | 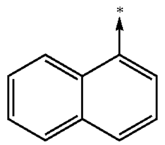 | 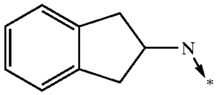 | 77 | 4.75 | 457.18 |
| 1236 | 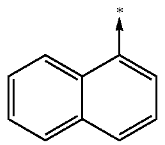 | 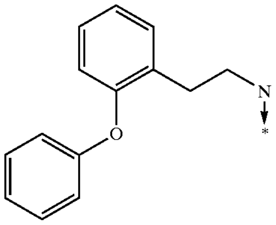 | 70.4 | 5.41 | 537.18 |
| 1237 | 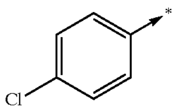 | 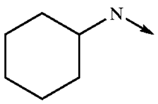 | 47.7 | 4.38 | 407.12 |
| 1238 | 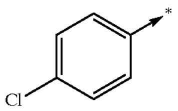 | 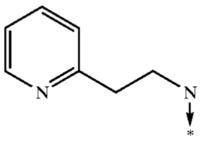 | 71.3 | 3.27 | 430.12 |
| 1239 | 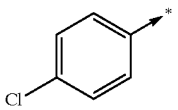 | 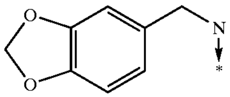 | 70.2 | 4.35 | 459.10 |
| 1240 | 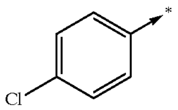 | 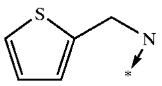 | 68.1 | 4.27 | 421.06 |

-continued
| | | | | | |
|---|---|---|---|---|---|
| 1241 | 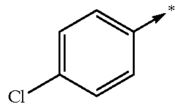 | 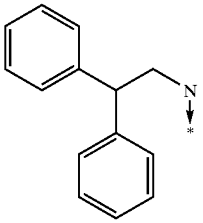 | 78.8 | 5.13 | 505.13 |
| 1242 | 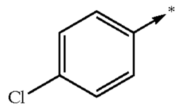 | 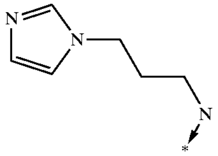 | 24 | 3.17 | 433.11 |
| 1243 | 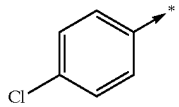 | 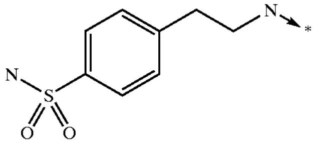 | 74.2 | 3.86 | 508.08 |
| 1244 | 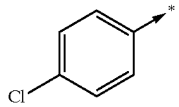 | 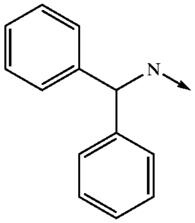 | 43 | 5.16 | 491.08 |
| 1245 | 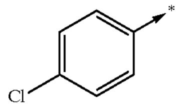 | 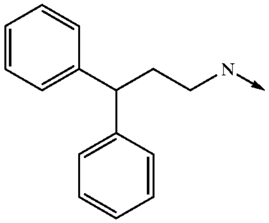 | 71.8 | 5.38 | 519.12 |

-continued
| | | | | | |
|---|---|---|---|---|---|
| 1246 | 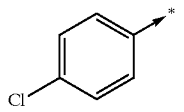 | 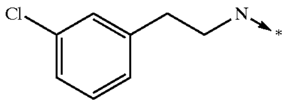 | 69.9 | 4.85 | 463.05 |
| 1247 | 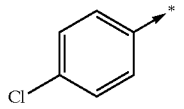 | 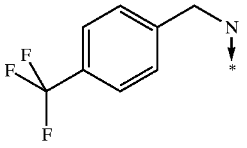 | 79.2 | 4.96 | 483.10 |
| 1248 | 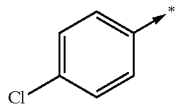 | 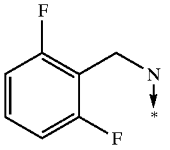 | 77.9 | 4.45 | 451.07 |
| 1249 | 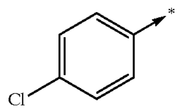 | 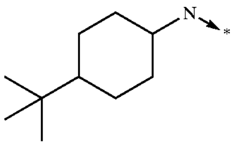 | 42.6 + 23.5 | 5.42 + 5.6 | 463.20 |
| 1250 | 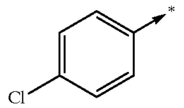 | 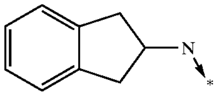 | 70 | 4.65 | 441.11 |
| 1251 | 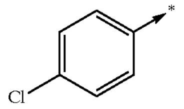 | 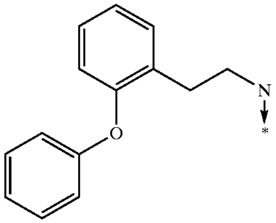 | 72 | 5.36 | 521.12 |

-continued
| | | | | | |
|---|---|---|---|---|---|
| 1252 | 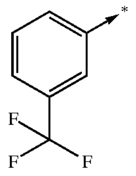 | 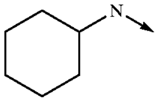 | 28.2 | 4.96 | 441.14 |
| 1253 | 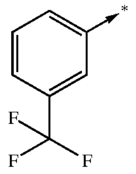 | 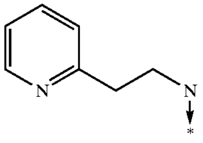 | 65.8 | 3.69 | 464.14 |
| 1254 | 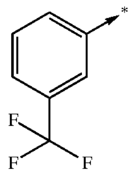 | 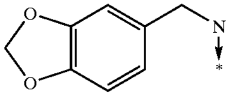 | 51 | 4.86 | 493.14 |
| 1255 | 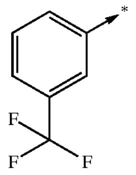 | 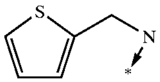 | 64.5 | 4.79 | 455.08 |
| 1256 | 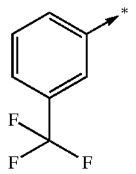 | 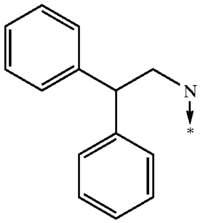 | 72.2 | 5.55 | 539.16 |

-continued
| | | | | | |
|---|---|---|---|---|---|
| 1257 | 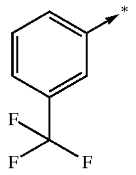 | 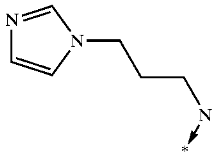 | 27.2 | 3.59 | 467.16 |
| 1258 | 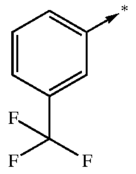 | 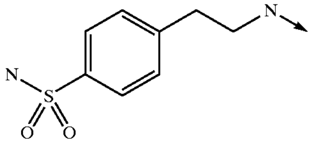 | 38.6 | 4.38 | 542.12 |
| 1259 | 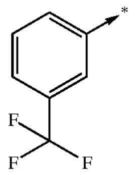 | 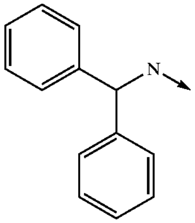 | 49.4 | 5.53 | 525.16 |
| 1260 | 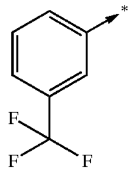 | 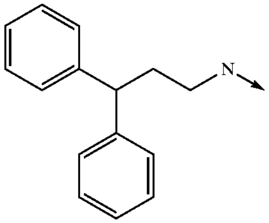 | 60.6 | 5.73 | 553.20 |
| 1261 | 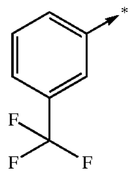 | 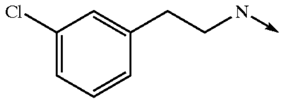 | 67.7 | 5.27 | 497.13 |

-continued
| | | | | | |
|---|---|---|---|---|---|
| 1262 | 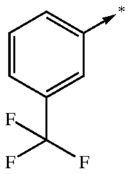 | 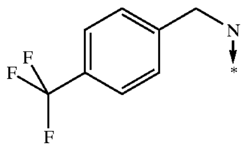 | 80.8 | 5.34 | 517.12 |
| 1263 | 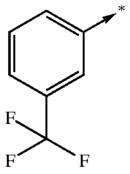 | 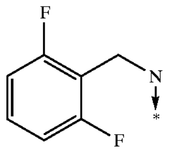 | 78 | 4.92 | 485.13 |
| 1264 | 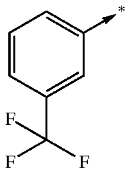 | 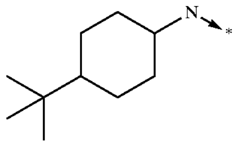 | 28.5 + 14.4 | 5.87 + 6.0 | 497.26 |
| 1265 | 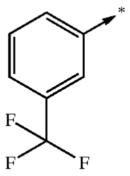 | 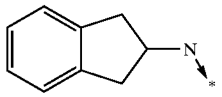 | 60.5 | 5.13 | 475.16 |
| 1266 | 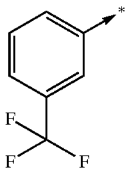 | 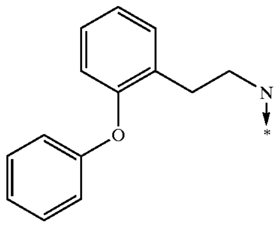 | 65.7 | 5.73 | 555.14 |

-continued
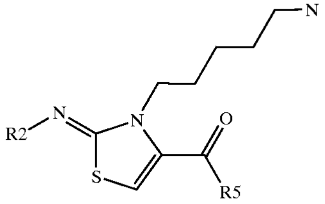
| | | | | | |
|---|---|---|---|---|---|
| 1267 | 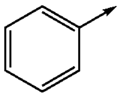 | 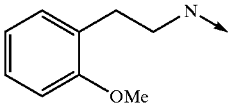 | 60 | 3.86 | 439.18 |
| 1268 | 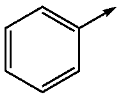 | 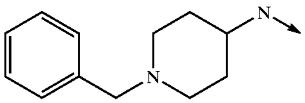 | 88.1 | 2.89 | 478.24 |
| 1269 | 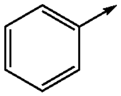 | 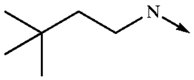 | 89.1 | 3.83 | 389.20 |
| 1270 | 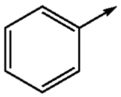 | 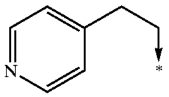 | 94.3 | 2.41 | 396.14 |
| 1271 | 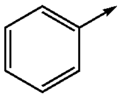 | 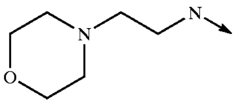 | 94 | 2.33 | 418.20 |
| 1272 | 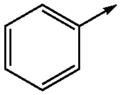 | 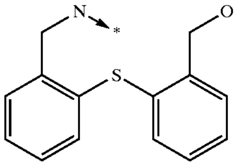 | 80.3 | 4.05 | 533.17 |

-continued
| | | | | | |
|---|---|---|---|---|---|
| 1273 | 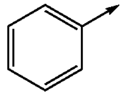 | 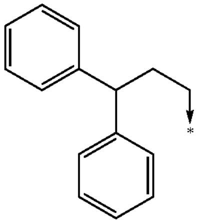 | 93 | 4.33 | 485.23 |
| 1274 | 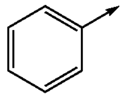 | 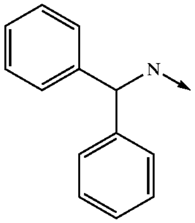 | 90.5 | 4.27 | 471.22 |
| 1275 | 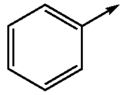 | 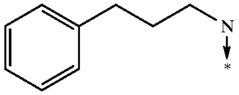 | 82.4 | 3.94 | 423.20 |
| 1276 | 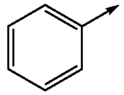 | 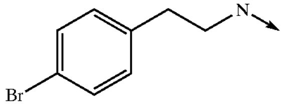 | 92.8 | 4.07 | 487.10 |
| 1277 | 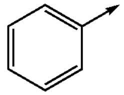 | 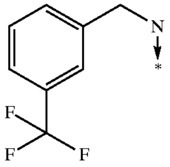 | 92.3 | 4.09 | 463.16 |
| 1278 | 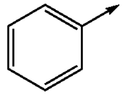 | 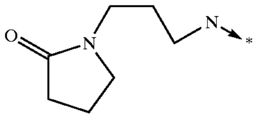 | 90.6 | 2.9 | 430.20 |

-continued
| | | | | | |
|---|---|---|---|---|---|
| 1279 | 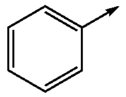 | 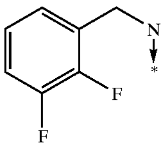 | 94.7 | 3.69 | 431.14 |
| 1280 | 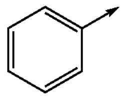 | 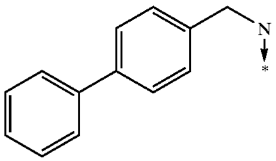 | 90.6 | 4.37 | 471.21 |
| 1281 | 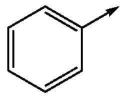 | 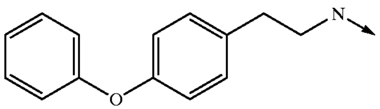 | 86.4 | 4.51 | 501.20 |
| 1282 | 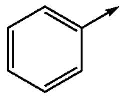 | 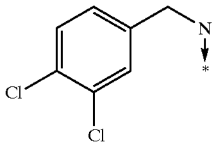 | 93.1 | 4.16 | 463.09 |
| 1283 | 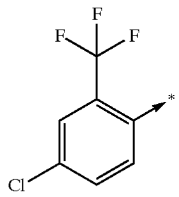 | 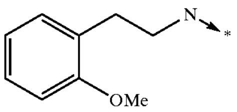 | 63.6 | 5.58 | 541.11 |
| 1284 | 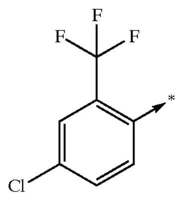 | 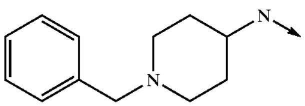 | 82.4 | 4.23 | 580.17 |

-continued
| | | | | | |
|---|---|---|---|---|---|
| 1285 | 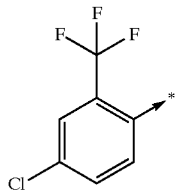 | 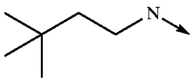 | 87.6 | 5.63 | 491.16 |
| 1286 | 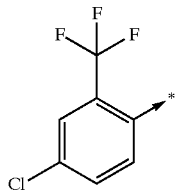 | 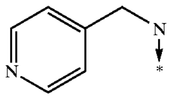 | 91.5 | 4.03 | 498.13 |
| 1287 | 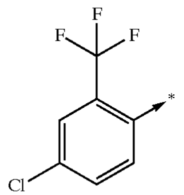 | 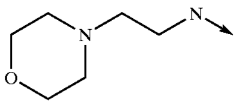 | 89.5 | 3.91 | 520.13 |
| 1288 | 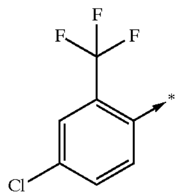 | 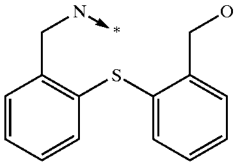 | 82.2 | 5.61 | 635.14 |
| 1289 | 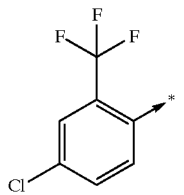 | 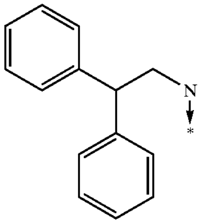 | 92.3 | 5.9 | 587.14 |

-continued
| | | | | | |
|---|---|---|---|---|---|
| 1290 | 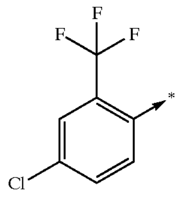 | 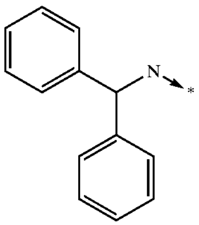 | 89.9 | 5.86 | 573.11 |
| 1291 | 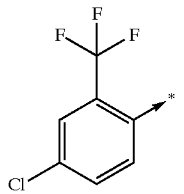 | 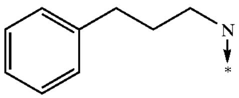 | 90 | 5.66 | 525.14 |
| 1292 | 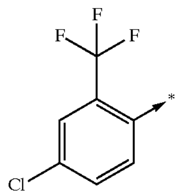 | 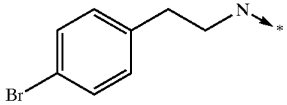 | 90.9 | 5.73 | 589.02 |
| 1293 | 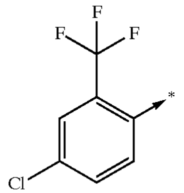 | 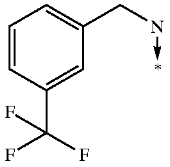 | 91.2 | 5.69 | 565.07 |
| 1294 | 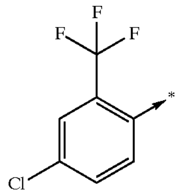 | 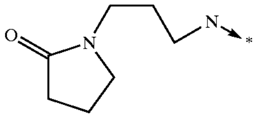 | 89.4 | 4.72 | 532.13 |

-continued
| | | | | | |
|---|---|---|---|---|---|
| 1295 | 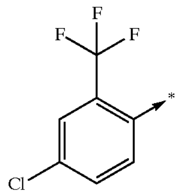 | 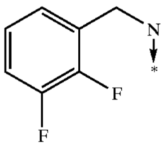 | 93.3 | 5.44 | 533.08 |
| 1296 | 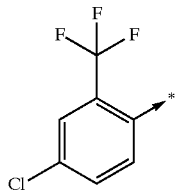 | 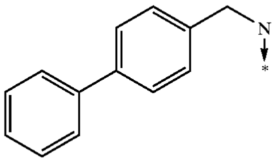 | 93.1 | 5.95 | 573.11 |
| 1297 | 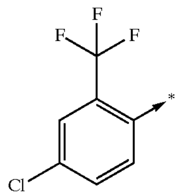 | 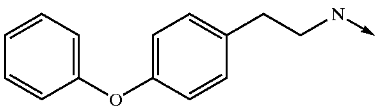 | 90.1 | 6.06 | 603.16 |
| 1298 | 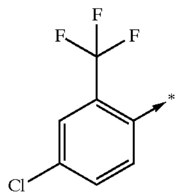 | 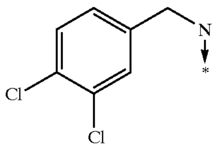 | 90.3 | 5.79 | 565.00 |
| 1299 | 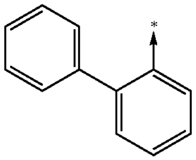 | 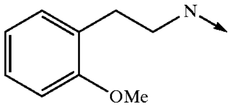 | 63.6 | 4.65 | 515.20 |

-continued
| | | | | | |
|---|---|---|---|---|---|
| 1300 | 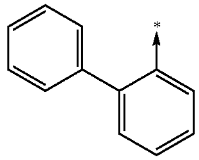 | 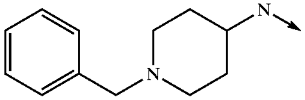 | 82.9 | 3.63 | 554.24 |
| 1301 | 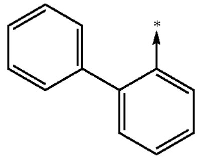 | 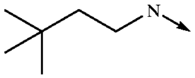 | 85.9 | 4.67 | 465.23 |
| 1302 | 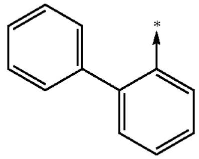 | 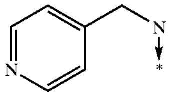 | 85.4 | 3.41 | 472.20 |
| 1303 | 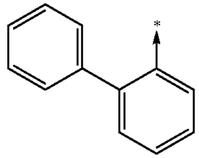 | 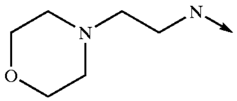 | 83.7 | 3.31 | 494.23 |
| 1304 | 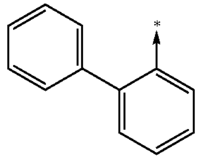 | 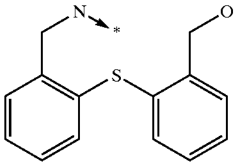 | 84.2 | 4.79 | 609.20 |

-continued
| | | | | | |
|---|---|---|---|---|---|
| 1305 | 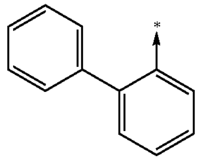 | 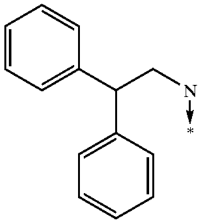 | 86.5 | 5.11 | 561.20 |
| 1306 | 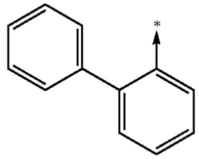 | 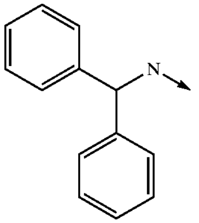 | 84.2 | 5.11 | 547.19 |
| 1307 | 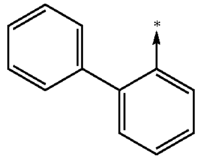 | 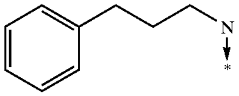 | 84.8 | 4.75 | 499.23 |
| 1308 | 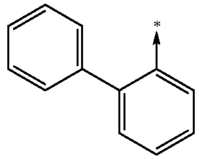 | 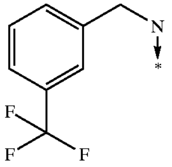 | 89 | 4.89 | 539.15 |
| 1309 | 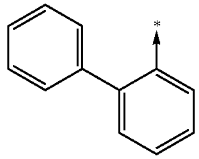 | 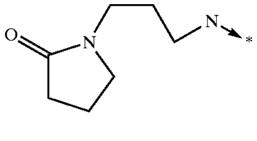 | 85.9 | 3.76 | 506.23 |

-continued
| | | | | | |
|---|---|---|---|---|---|
| 1310 | 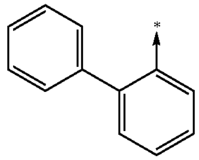 | 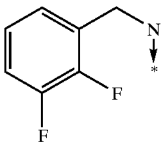 | 88.5 | 4.59 | 507.17 |
| 1311 | 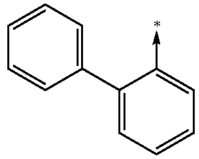 | 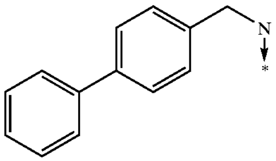 | 87.8 | 5.16 | 547.20 |
| 1312 | 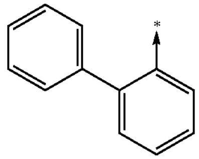 | 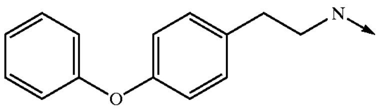 | 1.5 | 5.6 | 577.22 |
| 1313 | 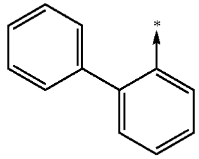 | 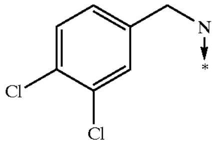 | 89.7 | 4.99 | 539.10 |
| 1314 | 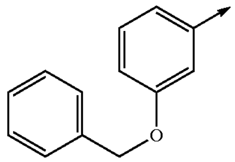 | 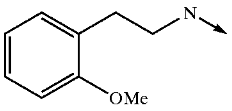 | 65.3 | 4.81 | 545.20 |
| 1315 | 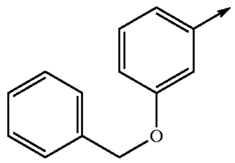 | 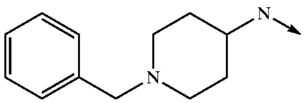 | 86.7 | 3.82 | 584.25 |

-continued
| | | | | | |
|---|---|---|---|---|---|
| 1316 | 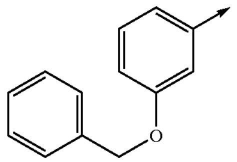 | 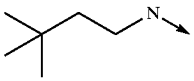 | 87.6 | 4.81 | 495.24 |
| 1317 | 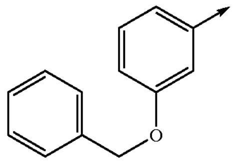 | 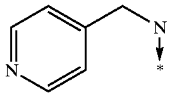 | 91 | 3.63 | 502.20 |
| 1318 | 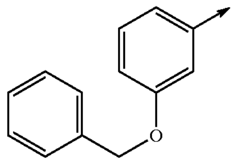 | 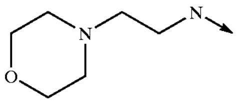 | 90.2 | 3.54 | 524.24 |
| 1319 | 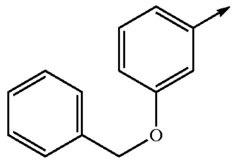 | 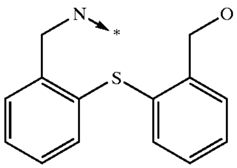 | 85.4 | 4.91 | 639.22 |
| 1320 | 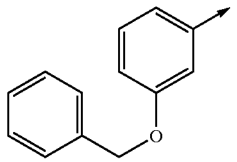 | 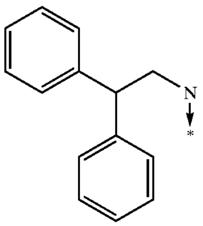 | 85.7 | 5.21 | 591.23 |

-continued
| | | | | | |
|---|---|---|---|---|---|
| 1321 | 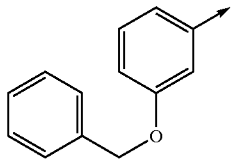 | 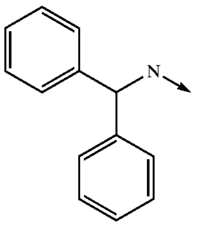 | 90 | 5.19 | 577.22 |
| 1322 | 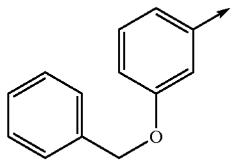 | 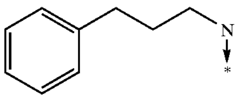 | 87.9 | 4.87 | 529.22 |
| 1323 | 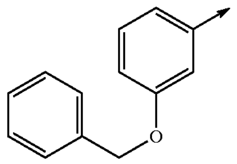 | 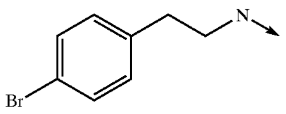 | 86.4 | 5 | 593.12 |
| 1324 | 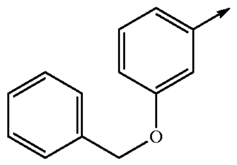 | 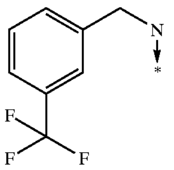 | 87.5 | 5.01 | 569.16 |
| 1325 | 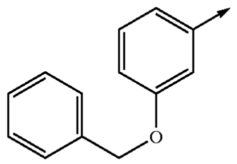 | 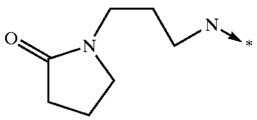 | 89.7 | 4 | 536.23 |

-continued
| | | | | | |
|---|---|---|---|---|---|
| 1326 | 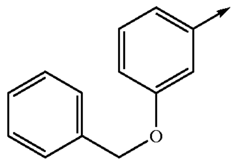 | 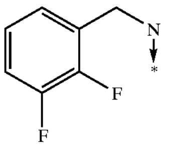 | 89.6 | 4.73 | 537.18 |
| 1327 | 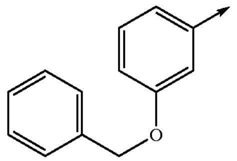 | 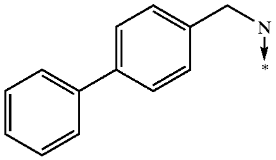 | 89.6 | 5.24 | 577.24 |
| 1328 | 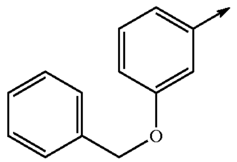 | 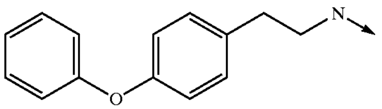 | 86.7 | 5.33 | 607.24 |
| 1329 | 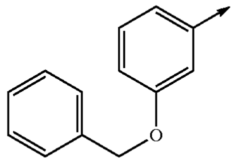 | 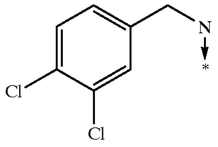 | 90.6 | 5.1 | 569.10 |
| 1330 | 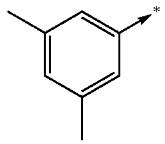 | 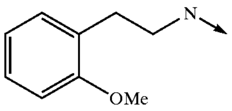 | 62.1 | 4.17 | 467.23 |
| 1331 | 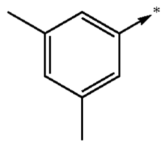 | 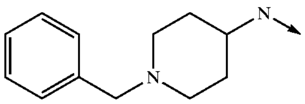 | 92.8 | 3.23 | 506.28 |

-continued
| | | | | | |
|---|---|---|---|---|---|
| 1332 | 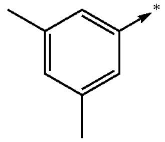 | 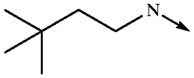 | 81.3 | 4.14 | 417.24 |
| 1333 | 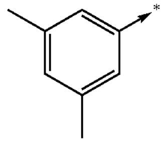 | 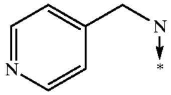 | 91.9 | 2.95 | 424.19 |
| 1334 | 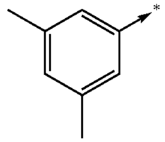 | 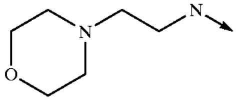 | 91.8 | 2.87 | 446.24 |
| 1335 | 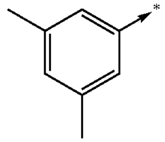 | 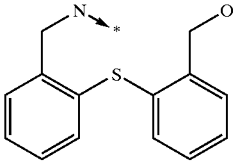 | 78.7 | 4.31 | 561.19 |
| 1336 | 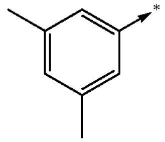 | 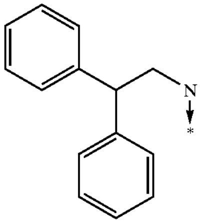 | 89.5 | 4.58 | 513.25 |

-continued
| | | | | | |
|---|---|---|---|---|---|
| 1337 | 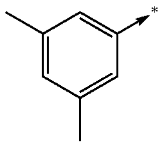 | 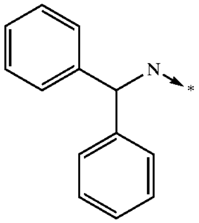 | 91.3 | 4.54 | 499.24 |
| 1338 | 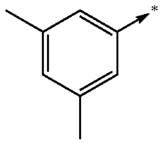 | 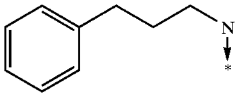 | 80.3 | 4.24 | 451.23 |
| 1339 | 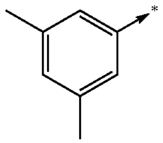 | 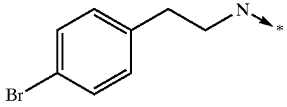 | 77.6 | 4.37 | 515.12 |
| 1340 | 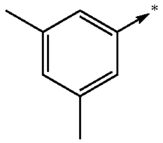 | 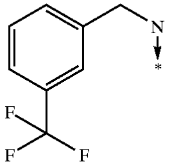 | 85.7 | 4.37 | 491.18 |
| 1341 | 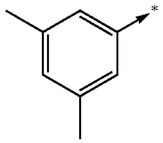 | 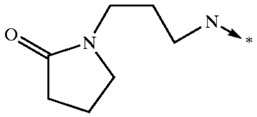 | 92.3 | 3.34 | 458.25 |
| 1342 | 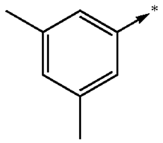 | 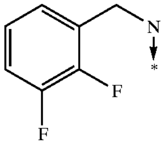 | 90.8 | 4.05 | 459.19 |

-continued
| | | | | | |
|---|---|---|---|---|---|
| 1343 | 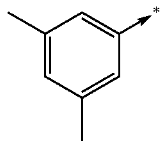 | 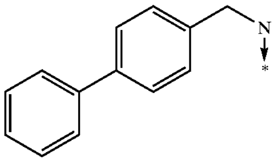 | 79.9 | 4.63 | 499.25 |
| 1344 | 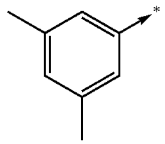 | 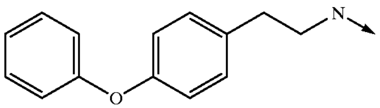 | 76.6 | 4.75 | 529.24 |
| 1345 | 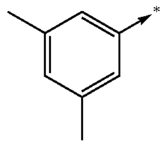 | 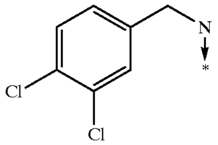 | 91.9 | 4.45 | 491.13 |
| | | 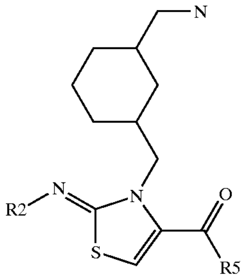 | | | |
| 1346 | 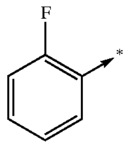 | 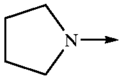 | 56.9 + 24.5 | 4.07 + 4.2 | 417.23 |
| 1347 | 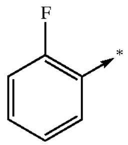 | 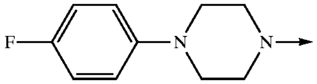 | 64.6 + 24.4 | 4.98 + 5.1 | 526.30 |

-continued
| | | | | | |
|---|---|---|---|---|---|
| 1348 | 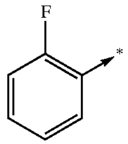 | 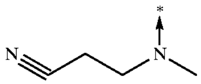 | 62.4 + 25.1 | 3.96 + 4.1 | 430.25 |
| 1349 | 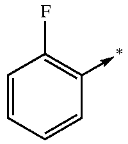 | 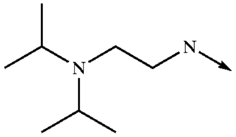 | 80.5 | 3.44 | 490.37 |
| 1350 | 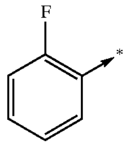 | 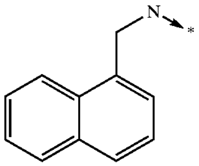 | 65.4 + 27.8 | 4.9 + 5.0 | 503.31 |
| 1351 | 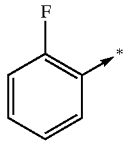 | 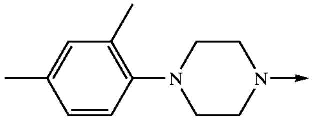 | 64.5 + 25.5 | 5.6 + 5.7 | 536.35 |
| 1352 | 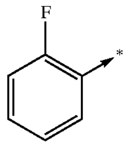 | 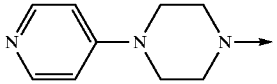 | 86.8 | 3.3 | 509.30 |
| 1353 | 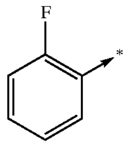 | 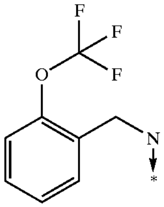 | 64.1 + 29.8 | 5.02 + 5.1 | 537.26 |

-continued
| | | | | | |
|---|---|---|---|---|---|
| 1354 | 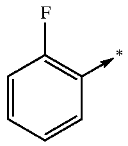 | 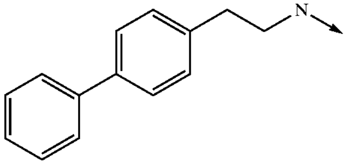 | 60.8 + 32.2 | 5.37 + 5.5 | 543.32 |
| 1355 | 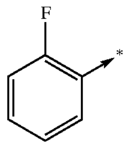 | 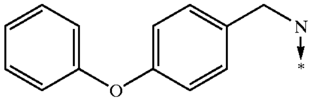 | 59.6 + 31.5 | 5.24 + 5.3 | 545.30 |
| 1356 | 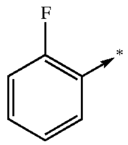 | 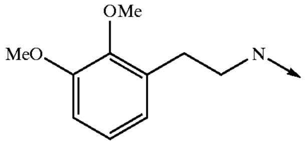 | 61.6 + 24.8 | 4.69 + 4.8 | 527.31 |
| 1357 | 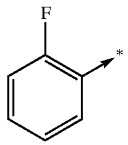 | 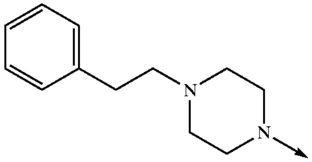 | 88.7 | 38 | 536.36 |
| 1358 | 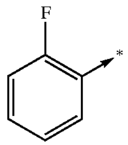 | 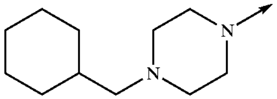 | 87.5 | 3.8 | 528.38 |
| 1359 | 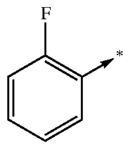 | 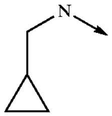 | 58 + 25.2 | 4.12 + 4.3 | 417.27 |

-continued
| | | | | | |
|---|---|---|---|---|---|
| 1360 | 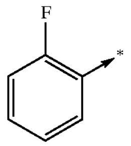 | 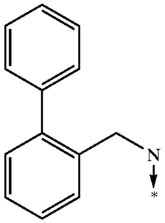 | 68.1 + 24.5 | 5.22 + 5.3 | 529.31 |
| 1361 | 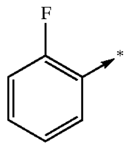 | 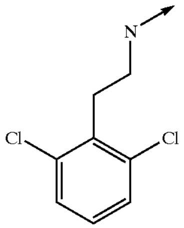 | 64.8 + 23.1 | 5.12 + 5.2 | 535.19 |
| 1362 | 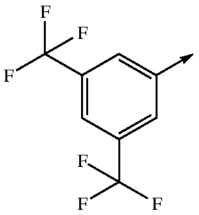 | 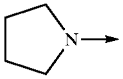 | 61.9 + 21.6 | 5.46 + 5.5 | 535.23 |
| 1363 | 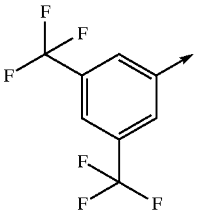 | 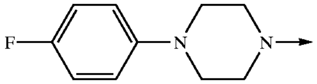 | 90.4 | 6.06 | 644.33 |

-continued
| | | | | | |
|---|---|---|---|---|---|
| 1364 | 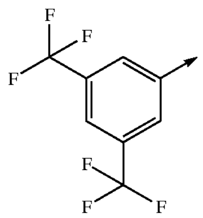 | 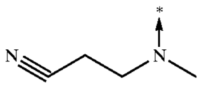 | 89.7 | 5.31 | 548.24 |
| 1365 | 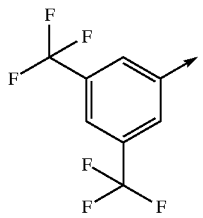 | 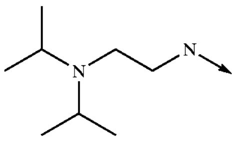 | 84.3 | 4.5 | 608.34 |
| 1366 | 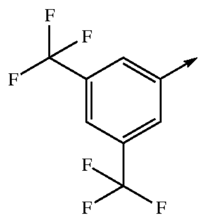 | 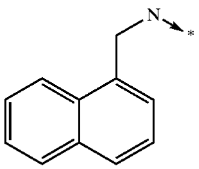 | 95.2 | 6.06 | 621.27 |
| 1367 | 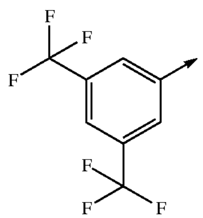 | 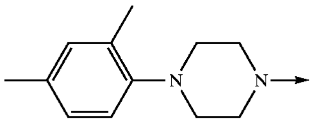 | 90.9 | 6.6 | 654.4 |

-continued
| | | | | | |
|---|---|---|---|---|---|
| 1368 | 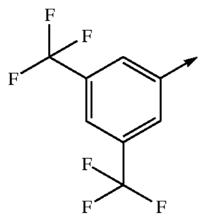 | 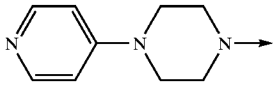 | 84.2 | 4.41 | 627.29 |
| 1369 | 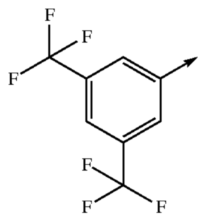 | 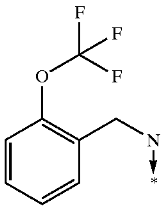 | 92.8 | 6.12 | 655.27 |
| 1370 | 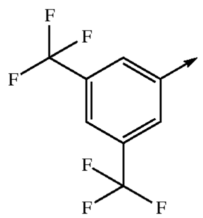 | 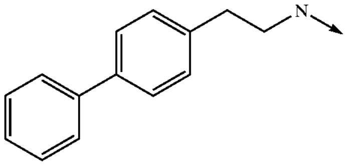 | 91.9 | 6.4 | 661.33 |
| 1371 | 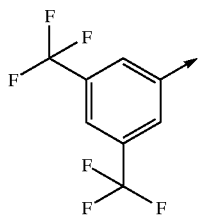 | 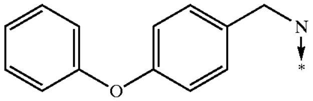 | 93.2 | 6.3 | 663.32 |

-continued
| | | | | | |
|---|---|---|---|---|---|
| 1372 | 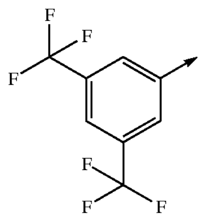 | 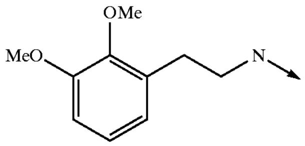 | 87.3 | 5.9 | 645.32 |
| 1373 | 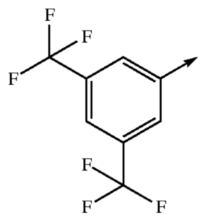 | 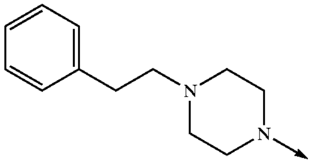 | 87.5 | 4.7 | 654.4 |
| 1374 | 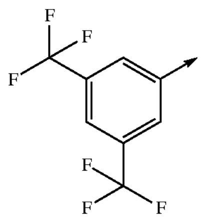 | 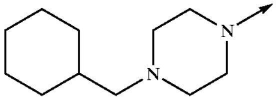 | 84.8 | 4.7 | 646.38 |
| 1375 | 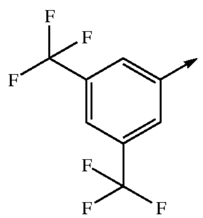 | 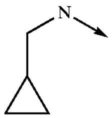 | 71.8 | 5.53 | 535.23 |

-continued
| | | | | | |
|---|---|---|---|---|---|
| 1376 | 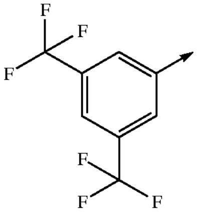 | 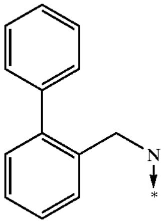 | 94.2 | 6.28 | 647.32 |
| 1377 | 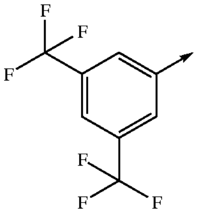 | 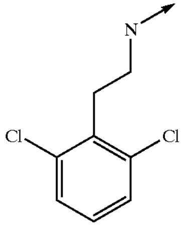 | 91.6 | 6.25 | 653.22 |
| 1378 | 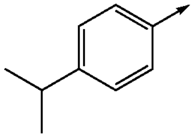 | 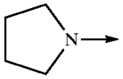 | 63 + 26.1 | 3.98 + 4.2 | 441.30 |
| 1379 | 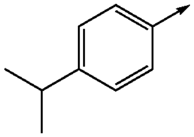 | 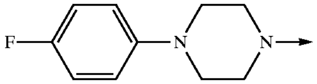 | 64.5 + 28 | 4.8 + 5.0 | 550.36 |
| 1380 | 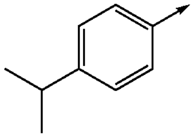 | 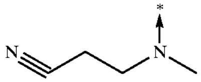 | 65.1 + 26.9 | 3.93 + 4.1 | 454.30 |
| 1381 | 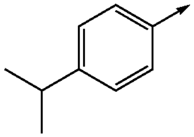 | 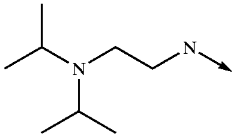 | 56.6 + 30.1 | 3.54 + 3.6 | 514.40 |

-continued
| | | | | | |
|---|---|---|---|---|---|
| 1382 | 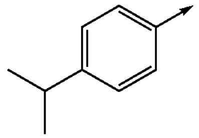 | 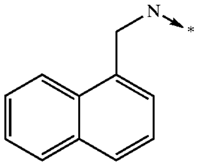 | 64.8 + 30.3 | 4.64 + 4.9 | 527.34 |
| 1383 | 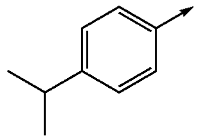 | 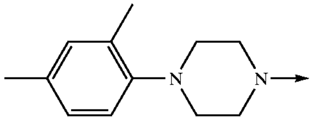 | 64.3 + 28.3 | 5.33 + 5.6 | 560.39 |
| 1384 | 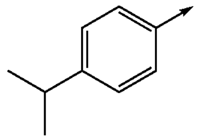 | 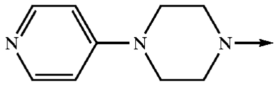 | 64.5 + 24.8 | 3.5 + 3.6 | 533.35 |
| 1385 | 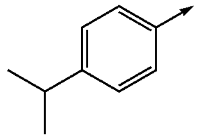 | 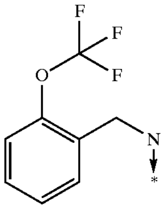 | 62.9 + 27.5 | 4.77 + 5.0 | 561.29 |
| 1386 | 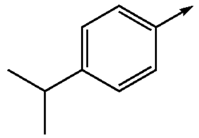 | 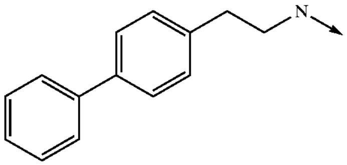 | 48.5 + 20.8 | 5.08 + 5.3 | 567.36 |
| 1387 | 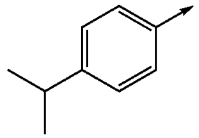 | 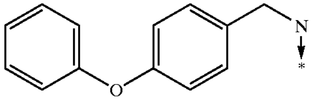 | 61.2 + 27.5 | 4.98 + 5.2 | 569.33 |

-continued
| | | | | | |
|---|---|---|---|---|---|
| 1388 | 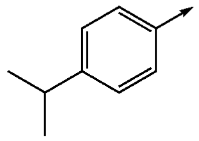 | 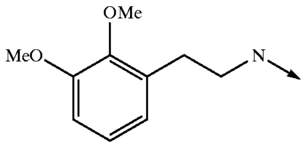 | 58.4 + 22.7 | 4.5 + 4.7 | 551.36 |
| 1389 | 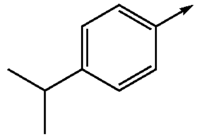 | 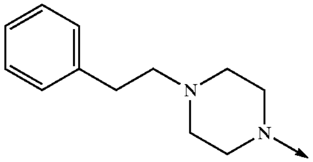 | 65.1 + 26.4 | 3.92 + 4.0 | 560.38 |
| 1390 | 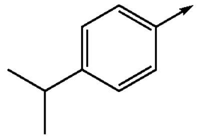 | 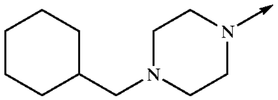 | 63.6 + 26.1 | 3.92 + 4.1 | 552.43 |
| 1391 | 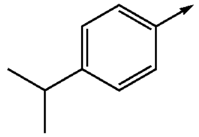 | 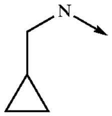 | 64 + 27.3 | 4.01 + 4.2 | 441.30 |
| 1392 | 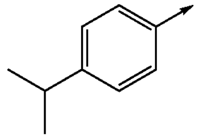 | 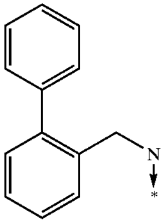 | 66.2 + 28.9 | 4.96 + 5.2 | 553.35 |

-continued
| | | | | | |
|---|---|---|---|---|---|
| 1393 | 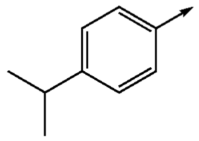 | 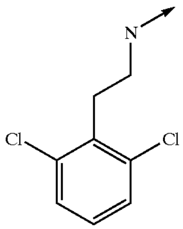 | 62.8 + 26.6 | 4.84 + 5.0 | 559.23 |
| 1394 | 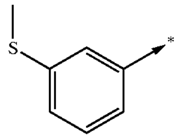 | 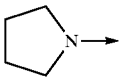 | 59.4 + 26.3 | 3.95 + 4.1 | 445.26 |
| 1395 | 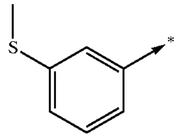 | 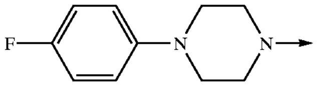 | 63.7 + 28.7 | 4.89 + 5.1 | 554.28 |
| 1396 | 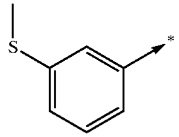 | 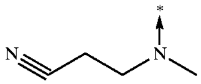 | 62 + 27.9 | 3.9 + 4.1 | 458.27 |
| 1397 | 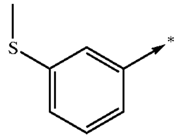 | 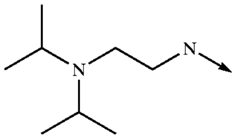 | 58.9 + 28.7 | 3.48 + 3.5 | 518.35 |
| 1398 | 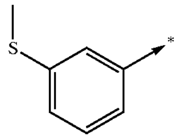 | 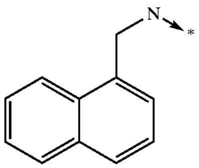 | 62.9 + 29.3 | 4.75 + 5.0 | 531.28 |

-continued
| | | | | | |
|---|---|---|---|---|---|
| 1399 | 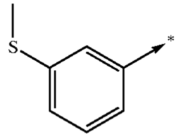 | 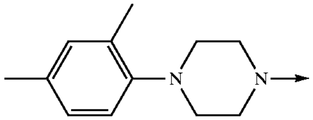 | 63.2 + 28.4 | 5.46 + 5.7 | 564.32 |
| 1400 | 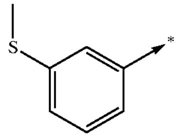 | 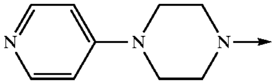 | 58.3 + 30.4 | 3.39 + 3.5 | 537.30 |
| 1401 | 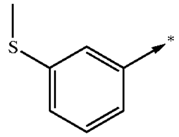 | 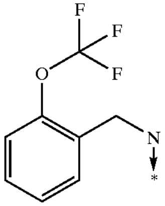 | 61.8 + 28.3 | 4.88 + 5.0 | 565.23 |
| 1402 | 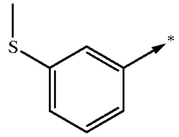 | 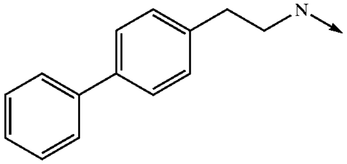 | 61.5 + 27.9 | 5.2 + 5.4 | 571.28 |
| 1403 | 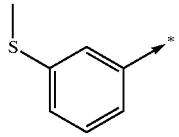 | 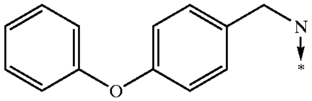 | 62.2 + 29.5 | 5.09 + 5.3 | 573.28 |
| 1404 | 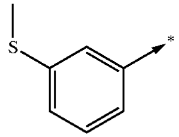 | 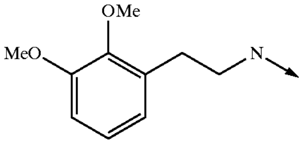 | 60.6 + 26.7 | 4.54 + 4.7 | 555.30 |

-continued
| | | | | | |
|---|---|---|---|---|---|
| 1405 | 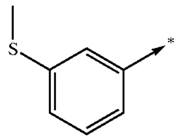 | 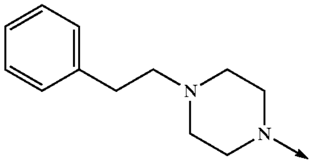 | 59.2 + 31.8 | 3.86 + 4.0 | 564.32 |
| 1406 | 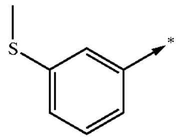 | 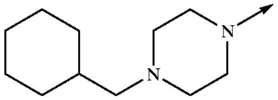 | 59.3 + 31.2 | 3.86 + 4.0 | 556.37 |
| 1407 | 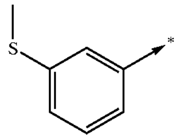 | 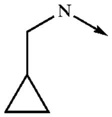 | 49.3 + 21.7 | 4 + 4.2 | 445.26 |
| 1408 | 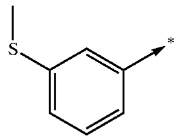 | 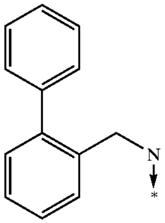 | 64.4 + 29.7 | 5.07 + 5.3 | 557.28 |
| 1409 | 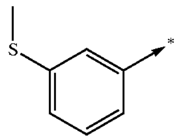 | 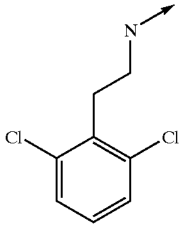 | 61.7 + 27.9 | 4.96 + 5.1 | 563.20 |
| 1410 | 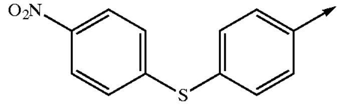 | 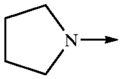 | 62.4 + 25.4 | 5.24 + 5.4 | 552.27 |

-continued
| | | | | | |
|---|---|---|---|---|---|
| 1411 | 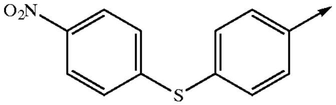 | 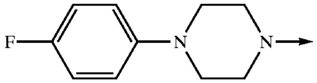 | 63.6 + 28.1 | 5.91 + 6.0 | 661.33 |
| 1412 | 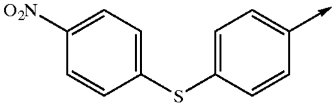 | 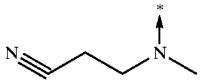 | 60.5 + 30.2 | 5.14 + 5.2 | 565.25 |
| 1413 | 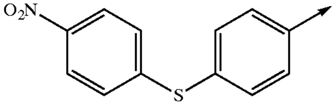 | 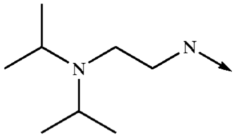 | 87.2 | 4.43 | 625.36 |
| 1414 | 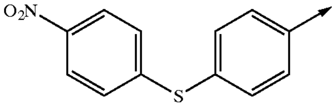 | 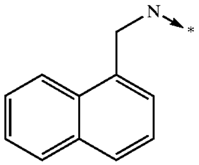 | 60.9 + 31.9 | 5.88 + 6.0 | 638.30 |
| 1415 | 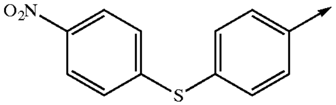 | 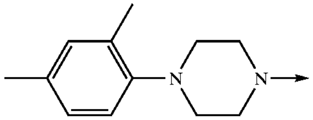 | 61.1 + 31.2 | 6.47 + 6.6 | 671.37 |
| 1416 | 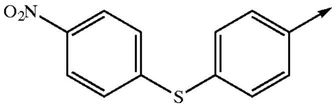 | 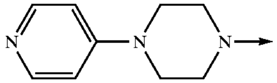 | 89.3 | 4.34 | 644.35 |
| 1417 | 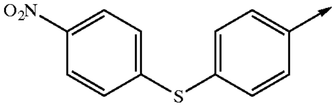 | 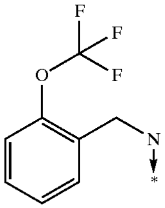 | 66.6 + 25.7 | 5.96 + 6.0 | 672.28 |

-continued
| | | | | | |
|---|---|---|---|---|---|
| 1418 | 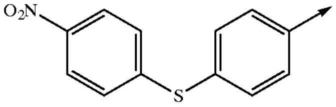 | 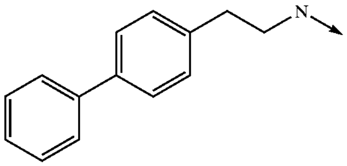 | 65.1 + 25.4 | 6.25 + 6.3 | 678.35 |
| 1419 | 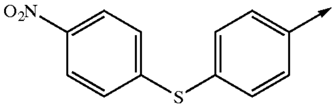 | 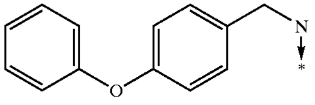 | 63 + 27.5 | 6.13 + 6.2 | 680.32 |
| 1420 | 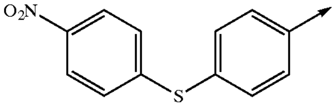 | 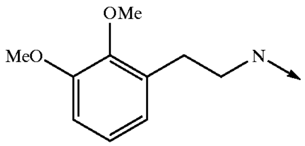 | 54.7 + 29.8 | 5.75 + 5.8 | 662.33 |
| 1421 | 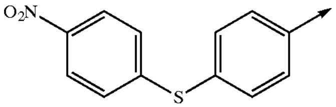 | 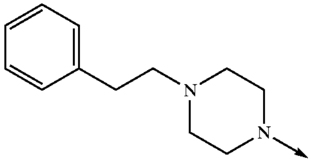 | 91.7 | 4.71 | 671.38 |
| 1422 | 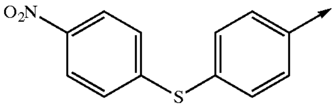 | 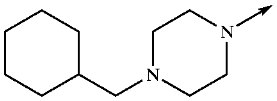 | 89.3 | 4.72 | 663.41 |
| 1423 | 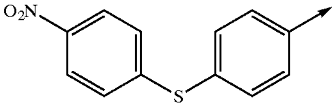 | 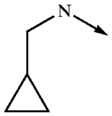 | 49 + 23.9 | 5.34 + 5.4 | 552.26 |

-continued
| | | | | | |
|---|---|---|---|---|---|
| | | 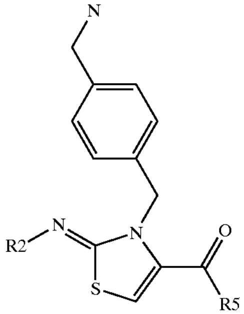 | | | |
| 1424 | 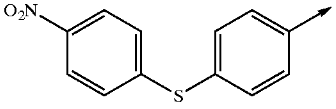 | 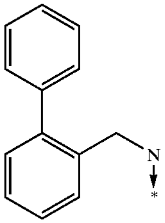 | 64.1 + 27.2 | 6.18 + 6.2 | 664.34 |
| 1425 | 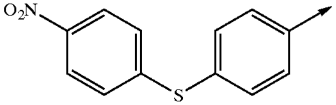 | 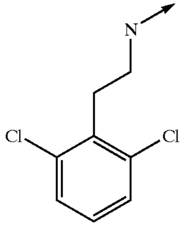 | 62.3 + 27.3 | 6.13 + 6.2 | 670.25 |
| 1426 | 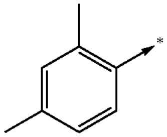 | 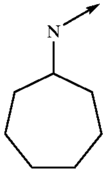 | 78.4 | 4.58 | 463.27 |

-continued
| | | | | | |
|---|---|---|---|---|---|
| 1427 | 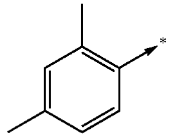 | 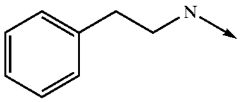 | 53.4 | 4.48 | 471.23 |
| 1428 | 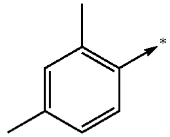 | 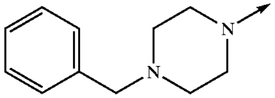 | 86.2 | 3.67 | 526.29 |
| 1429 | 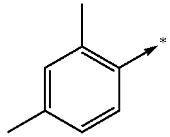 | 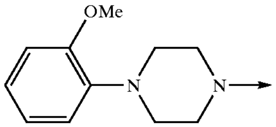 | 86 | 4.58 | 542.25 |
| 1430 | 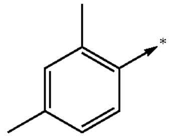 | 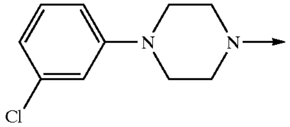 | 84.9 | 4.98 | 546.21 |
| 1431 | 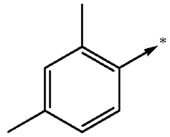 | 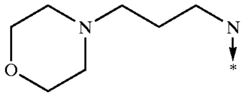 | 42.9 | 3.26 | 494.27 |
| 1432 | 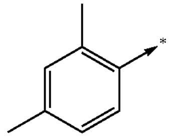 | 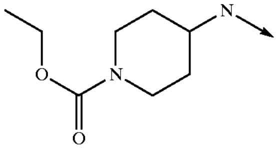 | 84.4 | 4.14 | 522.26 |

-continued
| | | | | | |
|---|---|---|---|---|---|
| 1433 | 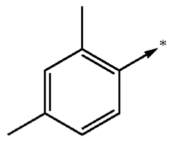 | 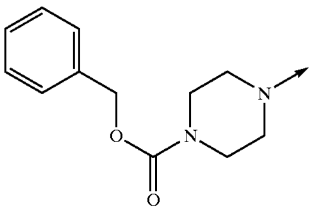 | 83.2 | 4.72 | 570.25 |
| 1434 | 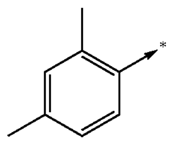 | 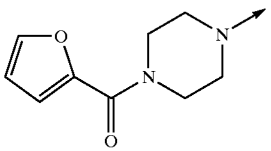 | 87.1 | 4.04 | 530.22 |
| 1435 | 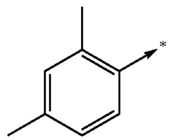 | 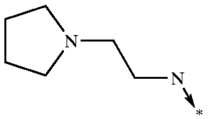 | 45.6 | 3.16 | 464.25 |
| 1436 | 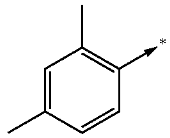 | 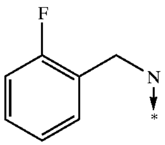 | 85.6 | 4.4 | 475.20 |
| 1437 | 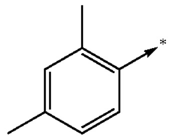 | 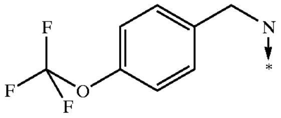 | 84.2 | 4.96 | 541.18 |
| 1438 | 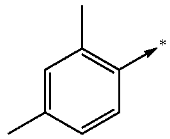 | 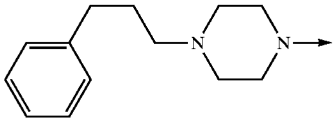 | 87.2 | 3.88 | 554.28 |

-continued
| | | | | | |
|---|---|---|---|---|---|
| 1439 | 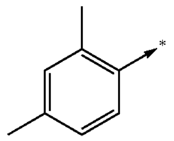 | 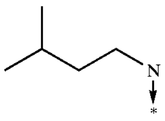 | 84.5 | 4.39 | 437.23 |
| 1440 | 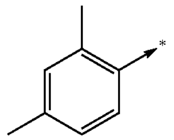 | 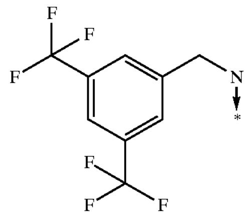 | 33.8 | 5.34 | 593.17 |
| 1441 | 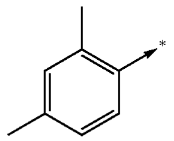 | 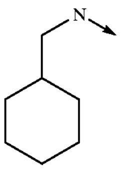 | 9.5 | 4.7 | 463.24 |
| 1442 | 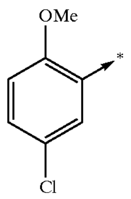 | 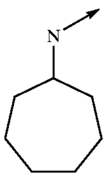 | 78.8 | 5.11 | 499.20 |
| 1443 | 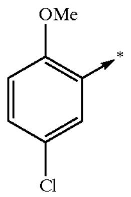 | 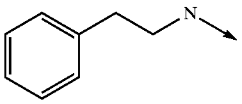 | 46.9 | 4.98 | 507.17 |

-continued
| | | | | | |
|---|---|---|---|---|---|
| 1444 | 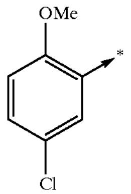 | 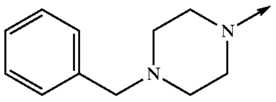 | 87.9 | 3.88 | 562.19 |
| 1445 | 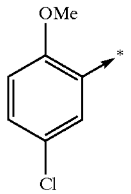 | 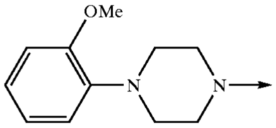 | 85.6 | 4.95 | 578.19 |
| 1446 | 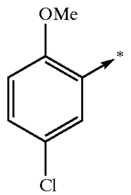 | 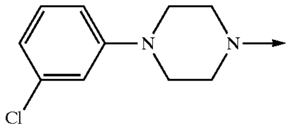 | 84.9 | 5.3 | 582.14 |
| 1447 | 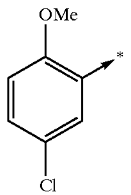 | 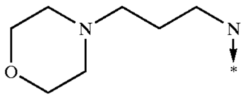 | 49 | 3.45 | 530.19 |
| 1448 | 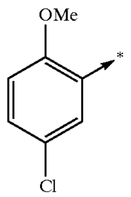 | 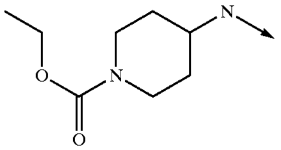 | 81.4 | 4.62 | 558.18 |

-continued
| | | | | | |
|---|---|---|---|---|---|
| 1449 | 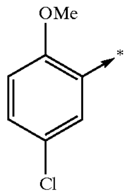 | 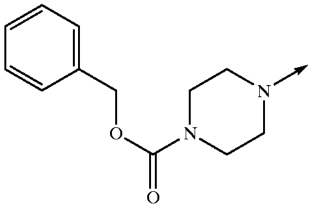 | 83 | 5.06 | 606.20 |
| 1450 | 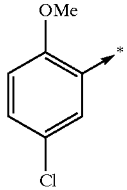 | 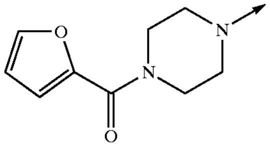 | 84.9 | 4.42 | 566.15 |
| 1451 | 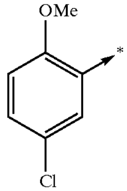 | 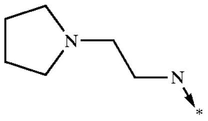 | 40.7 | 3.5 | 500.19 |
| 1452 | 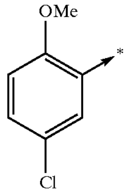 | 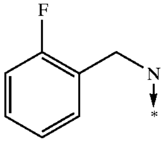 | 85.1 | 4.87 | 511.13 |
| 1453 | 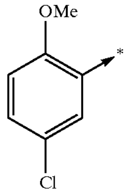 | 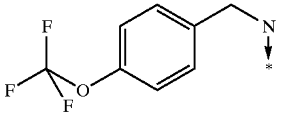 | 87.4 | 5.33 | 577.13 |

-continued
| | | | | | |
|---|---|---|---|---|---|
| 1454 | 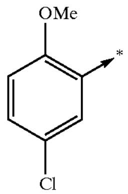 | 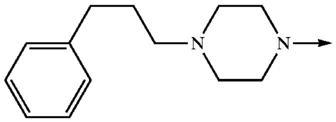 | 85.6 | 4.08 | 590.24 |
| 1455 | 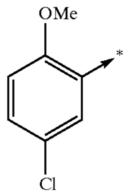 | 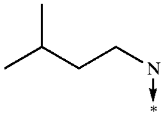 | 54.9 | 4.92 | 473.21 |
| 1456 | 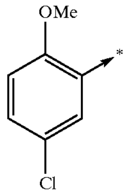 | 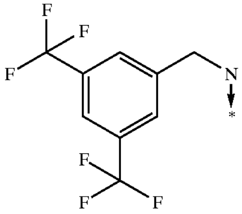 | 43 | 5.66 | 629.13 |
| 1457 | 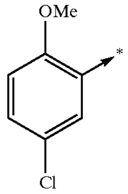 | 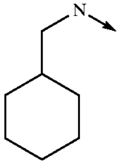 | 17.2 | 5.2 | 499.20 |
| 1458 | 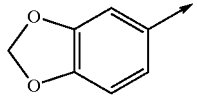 | 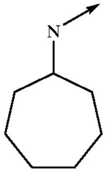 | 77.6 | 4.3 | 479.20 |

-continued
| | | | | | |
|---|---|---|---|---|---|
| 1459 | 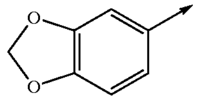 | 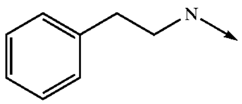 | 55.3 | 4.2 | 487.18 |
| 1460 | 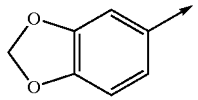 | 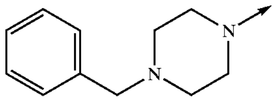 | 85.2 | 3.32 | 542.22 |
| 1461 | 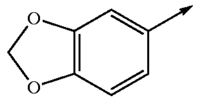 | 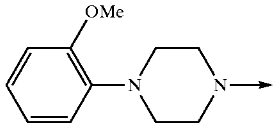 | 87 | 4.22 | 558.19 |
| 1462 | 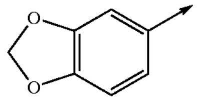 | 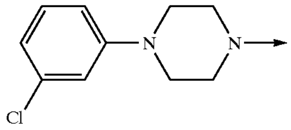 | 85.9 | 4.64 | 562.14 |
| 1463 | 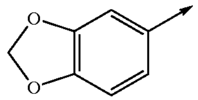 | 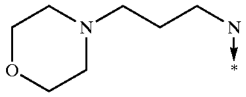 | 82.9 | 2.74 | 510.23 |
| 1464 | 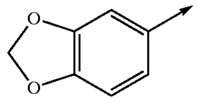 | 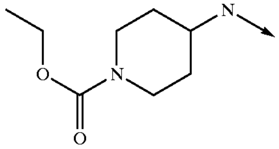 | 81.6 | 3.84 | 538.20 |
| 1465 | 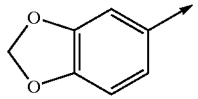 | 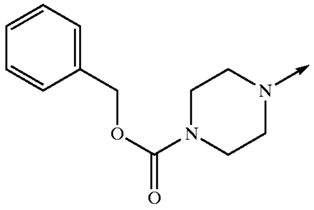 | 84.1 | 4.41 | 586.21 |

-continued
| | | | | | |
|---|---|---|---|---|---|
| 1466 | 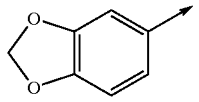 | 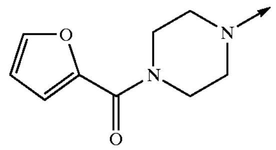 | 85.5 | 3.66 | 546.16 |
| 1467 | 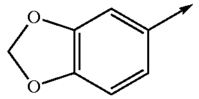 | 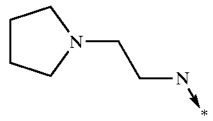 | 49.3 | 2.8 | 480.20 |
| 1468 | 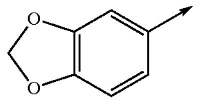 | 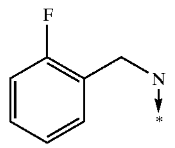 | 81.7 | 4.11 | 491.15 |
| 1469 | 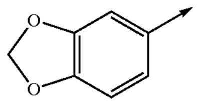 | 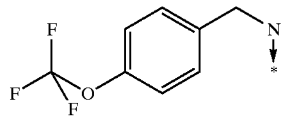 | 83.7 | 4.71 | 557.14 |
| 1470 | 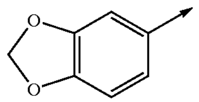 | 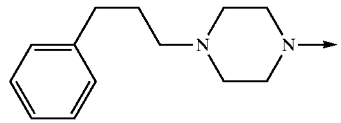 | 82.2 | 3.59 | 570.24 |
| 1471 | 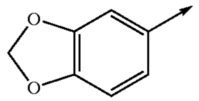 | 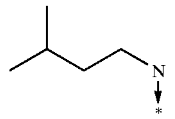 | 66.1 | 4.11 | 453.19 |
| 1472 | 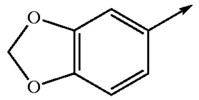 | 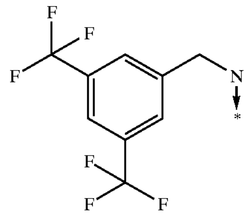 | 29.5 | 5.12 | 609.14 |

-continued
| | | | | | |
|---|---|---|---|---|---|
| 1473 | 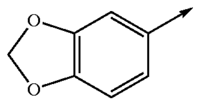 | 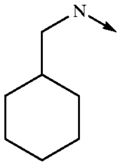 | 9.9 | 4.44 | 479.20 |
| 1474 | 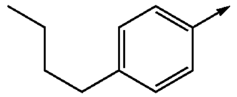 | 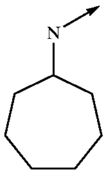 | 82.8 | 5.36 | 491.28 |
| 1475 | 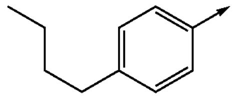 | 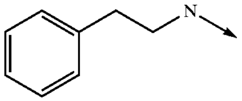 | 58.2 | 5.29 | 499.26 |
| 1476 | 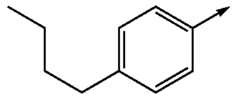 | 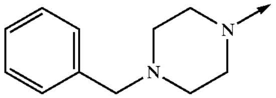 | 86.5 | 4.37 | 554.27 |
| 1477 | 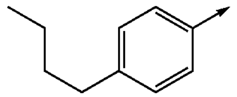 | 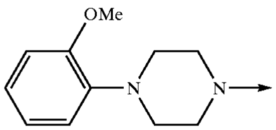 | 86.6 | 5.33 | 570.26 |
| 1478 | 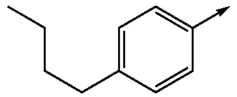 | 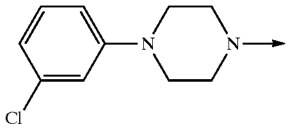 | 84.1 | 5.67 | 574.20 |
| 1479 | 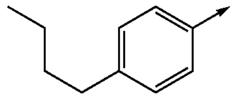 | 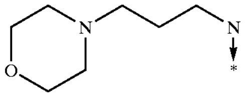 | 70.3 | 3.89 | 522.29 |

-continued
| | | | | | |
|---|---|---|---|---|---|
| 1480 | 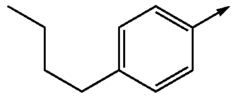 | 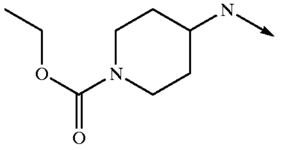 | 84.2 | 4.94 | 550.28 |
| 1481 | 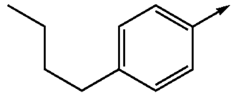 | 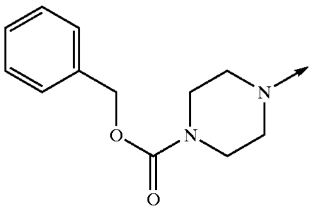 | 84.5 | 5.44 | 598.26 |
| 1482 | 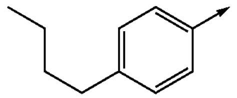 | 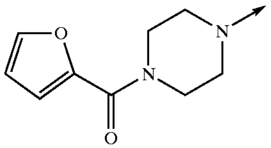 | 86 | 4.84 | 558.24 |
| 1483 | 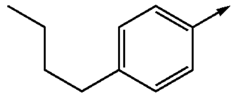 | 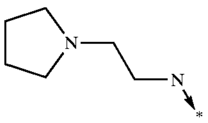 | 50.1 | 3.93 | 492.29 |
| 1484 | 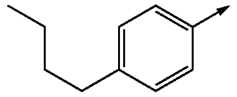 | 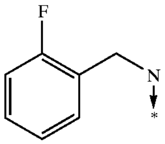 | 82.5 | 5.23 | 503.25 |
| 1485 | 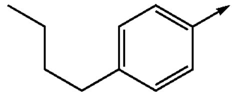 | 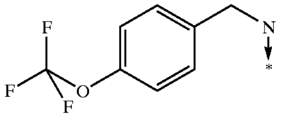 | 79.3 | 5.68 | 569.19 |

-continued
| | | | | | |
|---|---|---|---|---|---|
| 1486 | 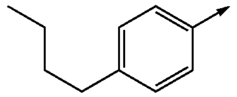 | 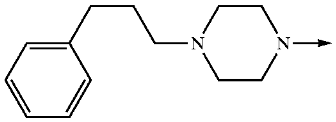 | 87.3 | 4.51 | 582.31 |
| 1487 | 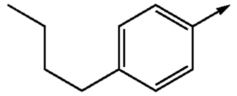 | 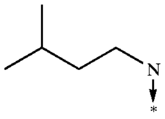 | 79.7 | 5.22 | 465.25 |
| 1488 | 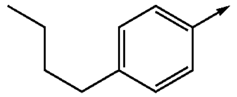 | 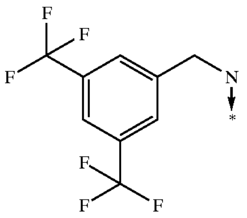 | 26.1 | 6.06 | 621.20 |
| 1489 | 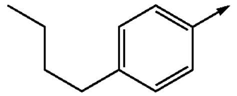 | 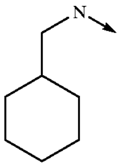 | 16.1 | 5.51 | 491.28 |
| 1490 | 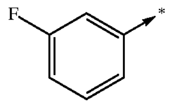 | 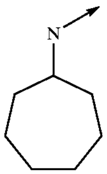 | 77 | 5.02 | 453.22 |
| 1491 | 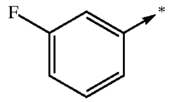 | 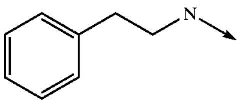 | 48.4 | 4.88 | 461.16 |

-continued
| | | | | | |
|---|---|---|---|---|---|
| 1492 | 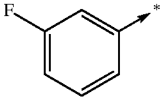 | 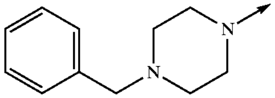 | 83.3 | 3.74 | 516.22 |
| 1493 | 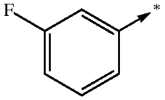 | 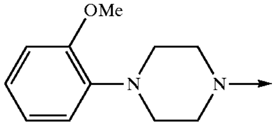 | 84.6 | 4.85 | 532.2 |
| 1494 | 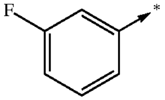 | 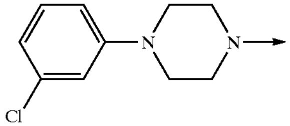 | 84.4 | 5.23 | 536.15 |
| 1495 | 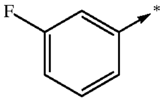 | 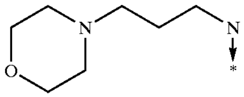 | 69.9 | 3.29 | 484.23 |
| 1496 | 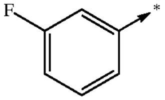 | 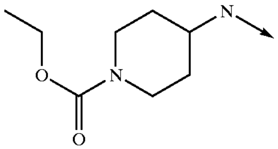 | 79.5 | 4.51 | 512.22 |
| 1497 | 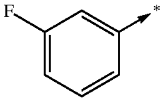 | 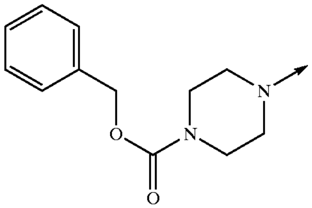 | 81.9 | 4.96 | 560.17 |
| 1498 | 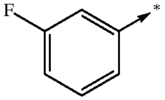 | 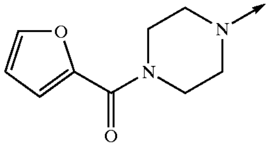 | 85.5 | 4.29 | 520.16 |

-continued
| | | | | | |
|---|---|---|---|---|---|
| 1499 | 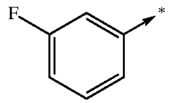 | 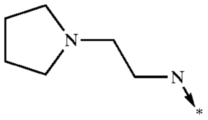 | 67.7 | 3.32 | 454.19 |
| 1500 | 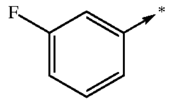 | 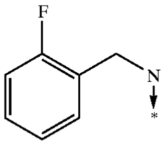 | 82.7 | 4.78 | 465.14 |
| 1501 | 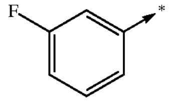 | 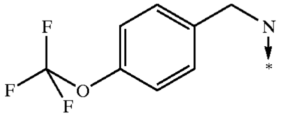 | 82.1 | 5.26 | 531.13 |
| 1502 | 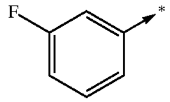 | 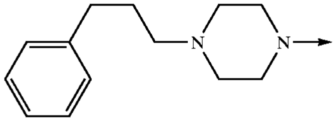 | 84.8 | 3.95 | 544.22 |
| 1503 | 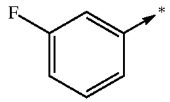 | 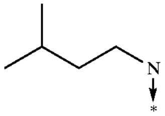 | 77.5 | 4.83 | 427.16 |
| 1504 | 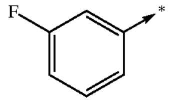 | 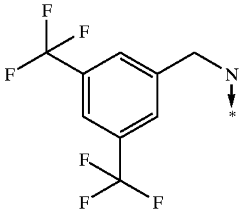 | 24 | 5.6 | 583.11 |

-continued
| | | | | | |
|---|---|---|---|---|---|
| 1505 | 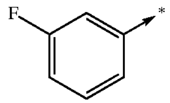 | 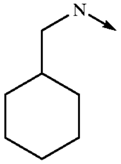 | 17.7 | 5.12 | 453.21 |
| | | 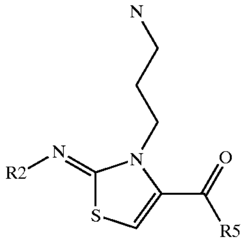 | | | |
| 1506 | 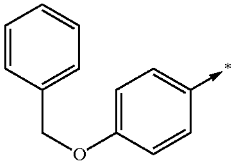 | 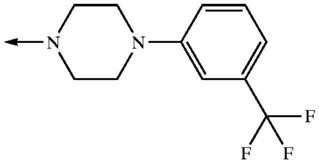 | 89.7 | 5.52 | 596.26 |
| 1507 | 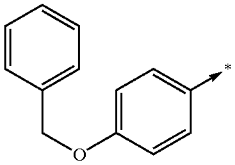 | 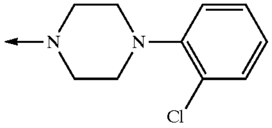 | 87.2 | 5.37 | 562.23 |
| 1508 | 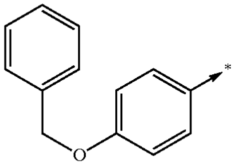 | 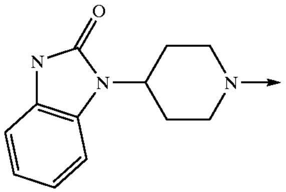 | 77 | 4.62 | 583.26 |

-continued
| | | | | | |
|---|---|---|---|---|---|
| 1509 | 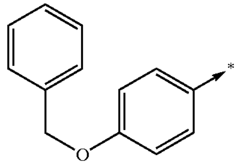 | 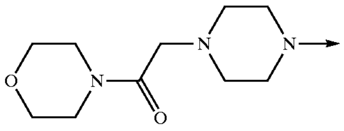 | 89.1 | 3.7 | 579.25 |
| 1510 | 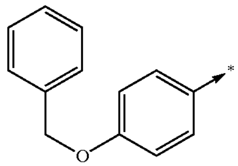 | 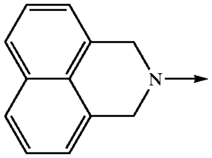 | 88.6 | 5.32 | 535.23 |
| 1511 | 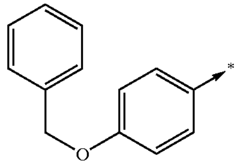 | 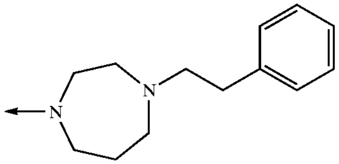 | 87.6 | 4 | 570.27 |
| 1512 | 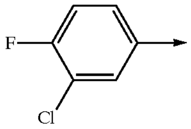 | 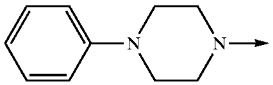 | 88 | 5.12 | 474.19 |
| 1513 | 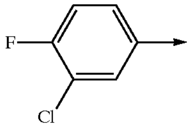 | 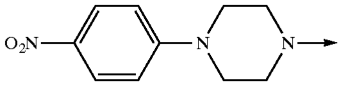 | 90.5 | 5.09 | 519.14 |
| 1514 | 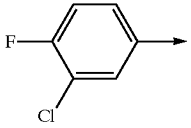 | 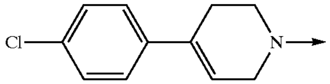 | 91.2 | 5.7 | 505.1 |

-continued
| | | | | | |
|---|---|---|---|---|---|
| 1515 | 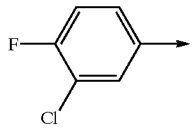 | 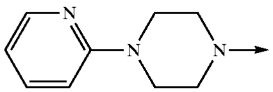 | 88 | 3.74 | 475.17 |
| 1516 | 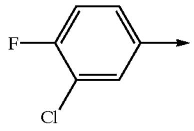 | 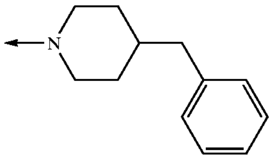 | 86.7 | 5.58 | 487.20 |
| 1517 | 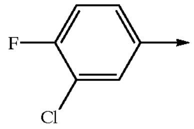 | 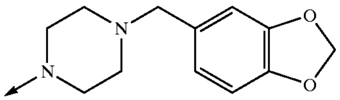 | 88.3 | 3.88 | 532.18 |
| 1518 | 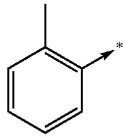 | 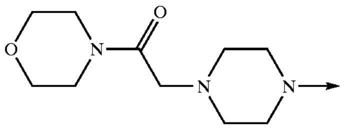 | 90.4 | 3 | 487.27 |
| 1519 | 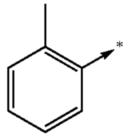 | 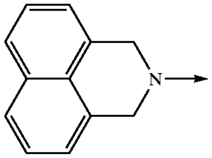 | 92.8 | 4.86 | 443.21 |
| 1520 | 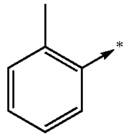 | 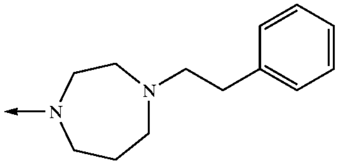 | 87.8 | 3.58 | 478.28 |
| 1521 | 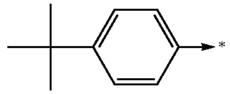 | 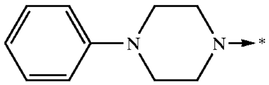 | 90.4 | 5.2 | 478.28 |

-continued
| | | | | | |
|---|---|---|---|---|---|
| 1522 | 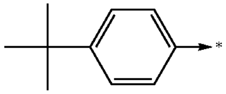 | 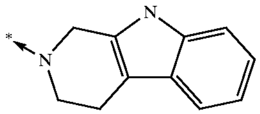 | 79.8 | 5.37 | 488.26 |
| 1523 | 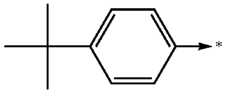 | 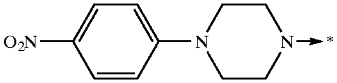 | 90.3 | 5.13 | 523.27 |
| 1524 | 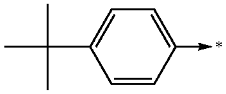 | 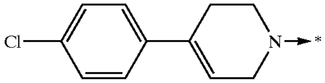 | 81.2 | 5.7 | 509.2 |
| 1525 | 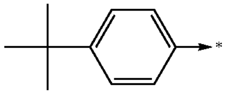 | 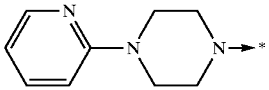 | 91 | 3.88 | 479.26 |
| 1526 | 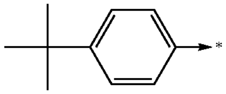 | 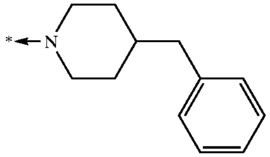 | 91.5 | 5.62 | 491.29 |
| 1527 | 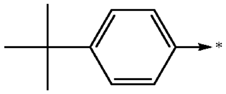 | 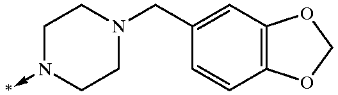 | 91.1 | 4.1 | 536.28 |
| 1528 | 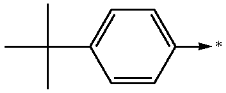 | 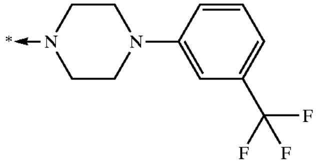 | 91.9 | 5.68 | 546.25 |
| 1529 | 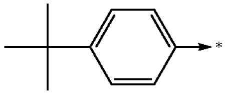 | 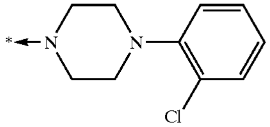 | 92 | 5.54 | 512.24 |

-continued
| | | | | | |
|---|---|---|---|---|---|
| 1530 | 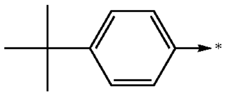 | 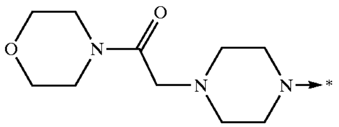 | 91.4 | 3.7 | 529.3 |
| 1531 | 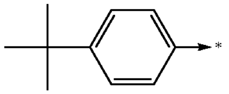 | 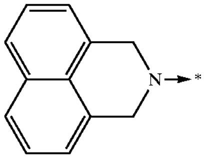 | 92.4 | 5.49 | 485.23 |
| 1532 | 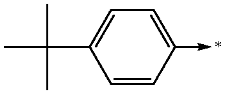 | 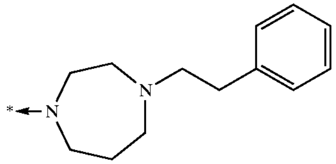 | 89.4 | 4.2 | 520.28 |
| 1533 | 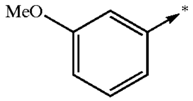 | 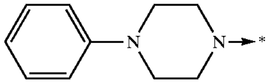 | 90.1 | 4.56 | 452.20 |
| 1534 | 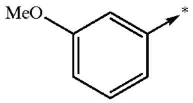 | 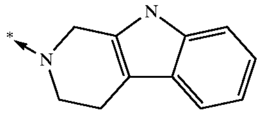 | 76.8 | 4.76 | 462.18 |
| 1535 | 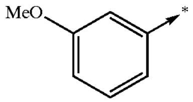 | 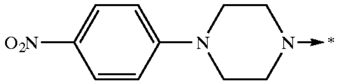 | 92.5 | 4.58 | 497.22 |
| 1536 | 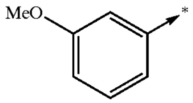 | 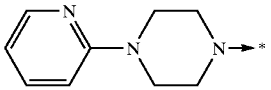 | 93.4 | 3.21 | 453.21 |

-continued
| | | | | | |
|---|---|---|---|---|---|
| 1537 | 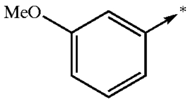 | 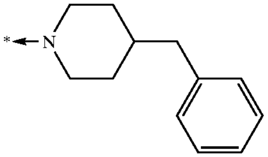 | 91.2 | 5.04 | 465.22 |
| 1538 | 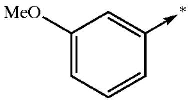 | 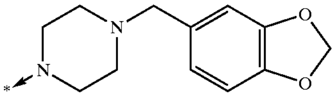 | 92.7 | 3.44 | 510.22 |
| 1539 | 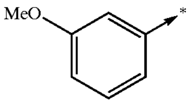 | 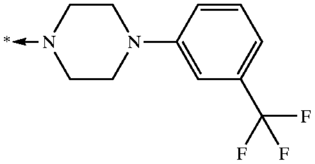 | 89.6 | 5.14 | 520.18 |
| 1540 | 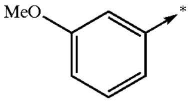 | 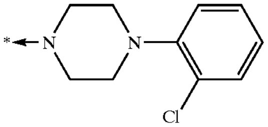 | 90.2 | 4.93 | 486.17 |
| 1541 | 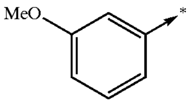 | 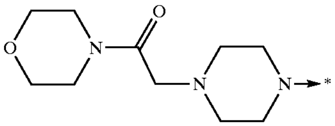 | 89.4 | 2.98 | 503.26 |
| 1542 | 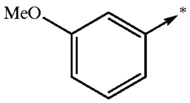 | 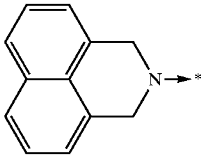 | 90.9 | 4.84 | 459.18 |

-continued
| | | | | | |
|---|---|---|---|---|---|
| 1543 | 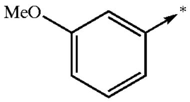 | 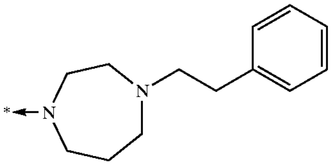 | 89.1 | 3.55 | 494.26 |
| | | 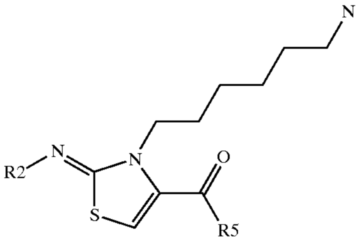 | | | |
| 1544 | 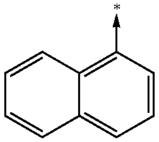 | 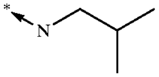 | 83.5 | 4.19 | 425.25 |
| 1545 | 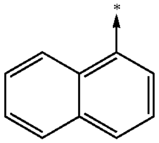 | 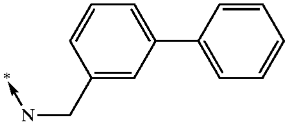 | 78.8 | 5.1 | 535.25 |
| 1546 | 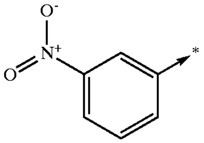 | 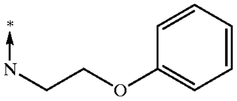 | 79.7 | 4.67 | 484.23 |
| 1547 | 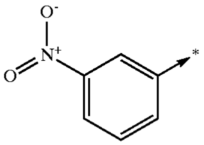 | 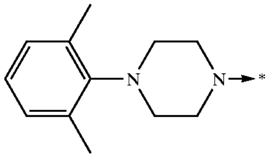 | 88 | 5.46 | 537.27 |

-continued
| | | | | | |
|---|---|---|---|---|---|
| 1548 | 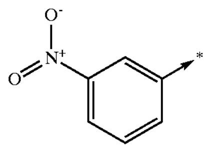 | 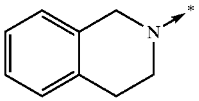 | 87.4 | 4.72 | 480.22 |
| 1549 | 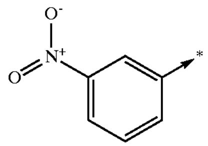 | 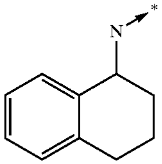 | 82 | 4.94 | 494.23 |
| 1550 | 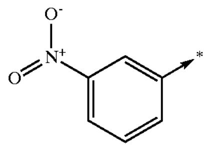 | 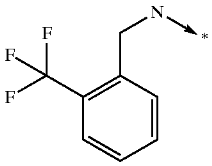 | 89.6 | 4.92 | 522.18 |
| 1551 | 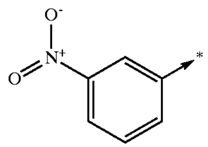 | 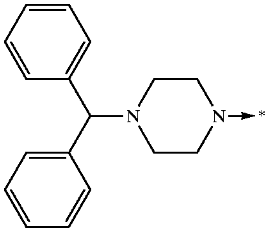 | 86.9 | 5.03 | 599.27 |
| 1552 | 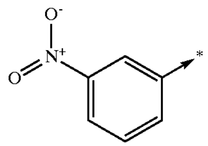 | 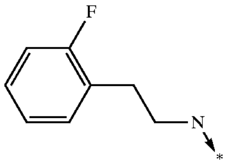 | 84.3 | 4.7 | 486.20 |

-continued
| | | | | | |
|---|---|---|---|---|---|
| 1553 | 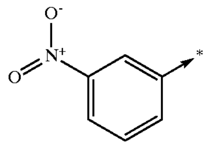 | 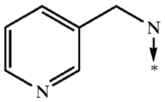 | 82.7 | 3.36 | 455.18 |
| 1554 | 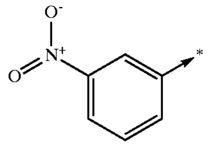 | 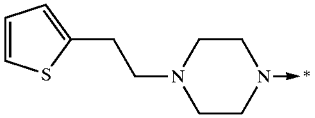 | 82 | 3.68 | 543.20 |
| 1555 | 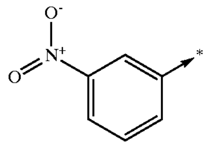 | 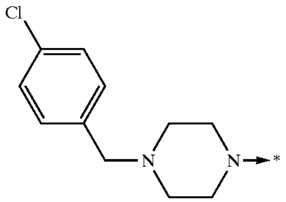 | 86.7 | 3.91 | 557.20 |
| 1556 | 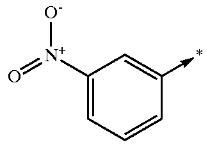 | 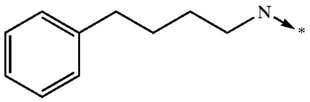 | 80.9 | 5.06 | 496.26 |
| 1557 | 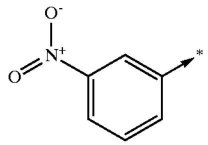 | 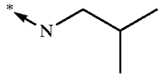 | 83.1 | 4.35 | 420.21 |
| 1558 | 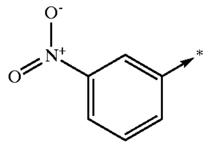 | 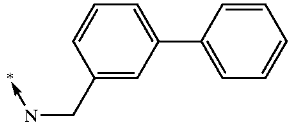 | 87.5 | 5.2 | 530.22 |

-continued
| | | | | | |
|---|---|---|---|---|---|
| 1559 | 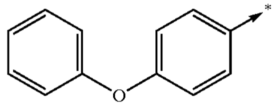 | 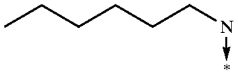 | 76.7 | 4.62 | 495.27 |
| 1560 | 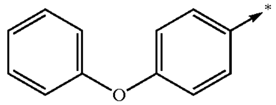 | 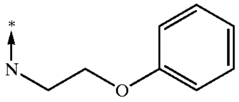 | 80.9 | 4.44 | 531.25 |
| 1561 | 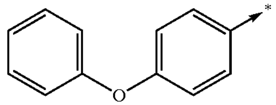 | 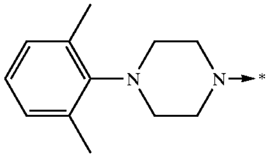 | 85.7 | 5.16 | 584.30 |
| 1562 | 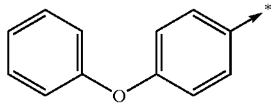 | 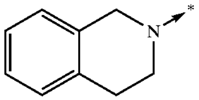 | 85.4 | 4.51 | 527.25 |
| 1563 | 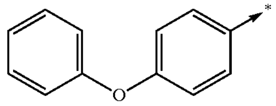 | 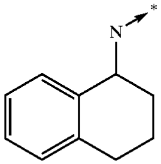 | 82.1 | 4.66 | 541.25 |
| 1564 | 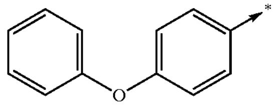 | 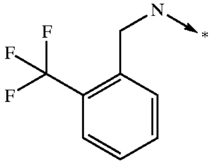 | 87.4 | 4.66 | 569.19 |

-continued
| | | | | | |
|---|---|---|---|---|---|
| 1565 | 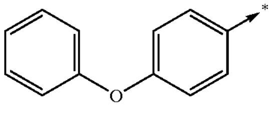 | 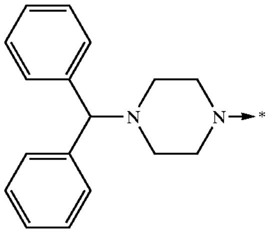 | 82.9 | 5.03 | 646.34 |
| 1566 | 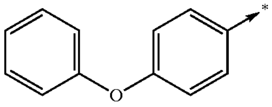 | 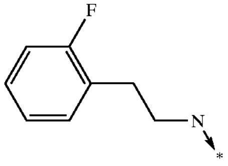 | 82.7 | 4.44 | 533.23 |
| 1567 | 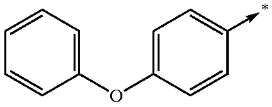 | 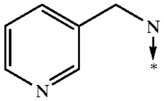 | 85 | 3.46 | 502.24 |
| 1568 | 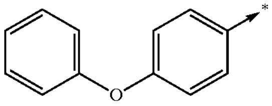 | 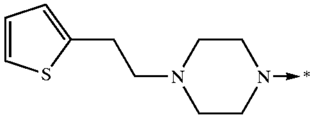 | 81.8 | 3.82 | 590.27 |
| 1569 | 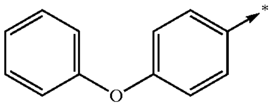 | 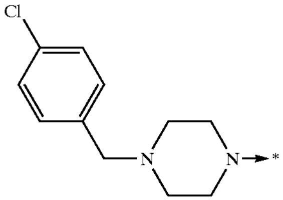 | 84.5 | 4.03 | 604.26 |
| 1570 | 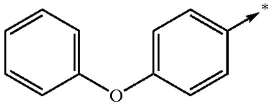 | 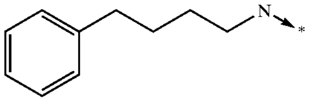 | 81.9 | 4.74 | 543.27 |

-continued
| | | | | | |
|---|---|---|---|---|---|
| 1571 | 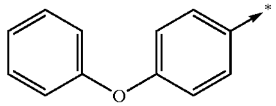 | 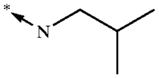 | 84.3 | 4.13 | 467.25 |
| 1572 | 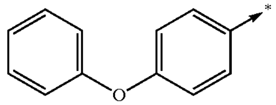 | 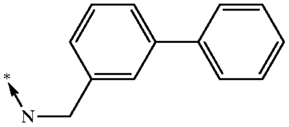 | 77.4 | 4.9 | 577.2 |
| 1573 | 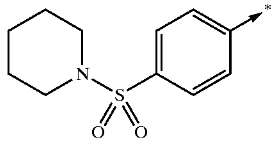 | 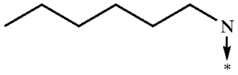 | 77.7 | 5.15 | 550.3 |
| 1574 | 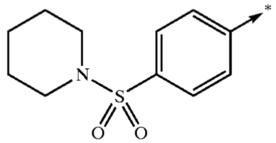 | 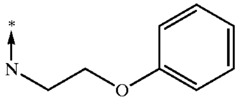 | 80.7 | 4.9 | 586.24 |
| 1575 | 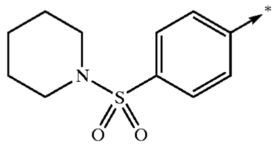 | 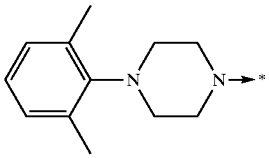 | 86.4 | 5.6 | 639.34 |
| 1576 | 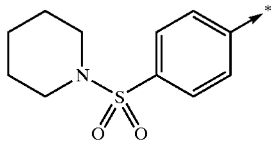 | 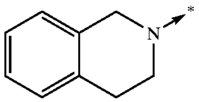 | 86.2 | 4.94 | 582.25 |
| 1577 | 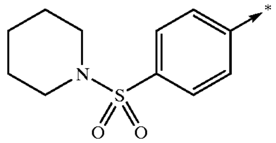 | 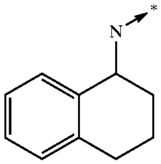 | 82 | 5.17 | 596.28 |

-continued
| | | | | | |
|---|---|---|---|---|---|
| 1578 | 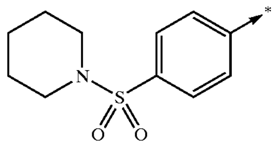 | 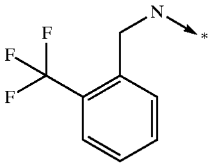 | 89.7 | 5.14 | 624.22 |
| 1579 | 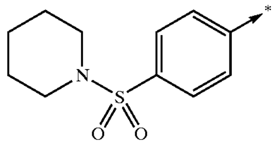 | 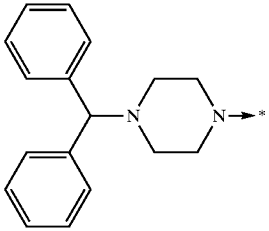 | 86.1 | 5.22 | 701.35 |
| 1580 | 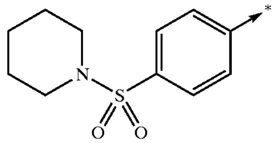 | 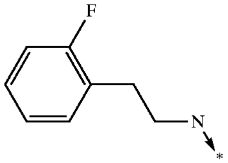 | 85.1 | 4.92 | 588.23 |
| 1581 | 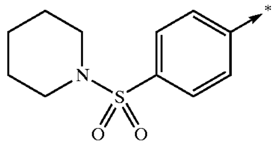 | 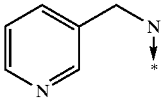 | 81.7 | 3.67 | 557.23 |
| 1582 | 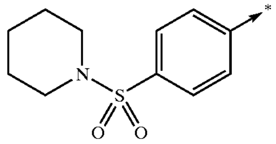 | 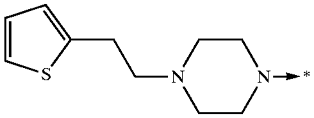 | 81 | 3.9 | 645.32 |

-continued
| | | | | | |
|---|---|---|---|---|---|
| 1583 | 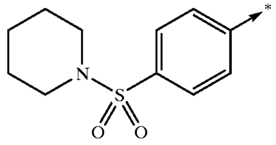 | 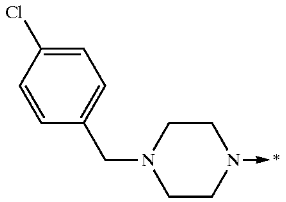 | 85.2 | 4.12 | 659.31 |
| 1584 | 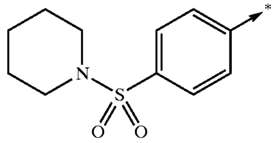 | 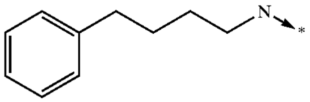 | 82.4 | 5.26 | 598.26 |
| 1585 | 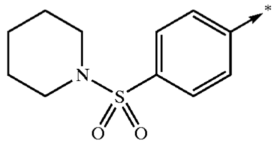 | 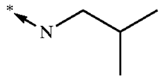 | 83.6 | 4.62 | 522.25 |
| 1586 | 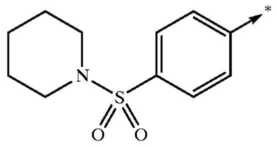 | 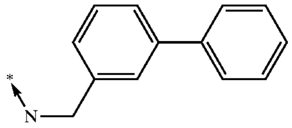 | 85.3 | 5.39 | 632.29 |
| 1587 | 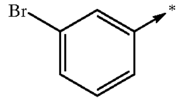 | 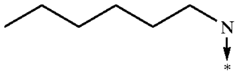 | 82.8 | 4.94 | 481.16 |
| 1588 | 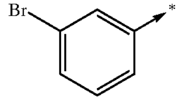 | 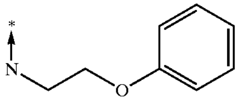 | 84.3 | 4.71 | 517.16 |

-continued
| | | | | | |
|---|---|---|---|---|---|
| 1589 | 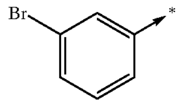 | 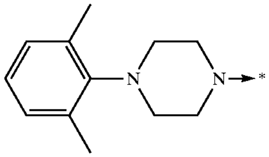 | 89.6 | 5.54 | 570.16 |
| 1590 | 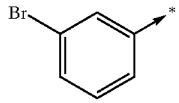 | 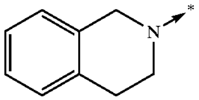 | 87.8 | 4.78 | 513.13 |
| 1591 | 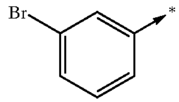 | 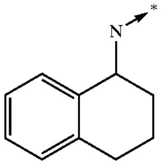 | 85.2 | 4.99 | 527.15 |
| 1592 | 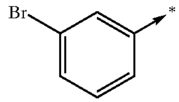 | 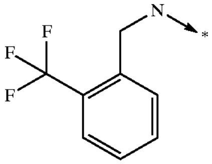 | 90.9 | 4.98 | 555.07 |
| 1593 | 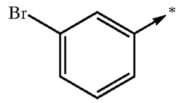 | 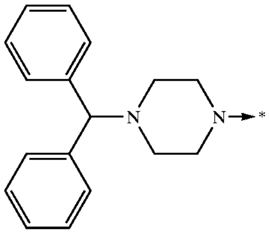 | 88.1 | 5.21 | 632.22 |
| 1594 | 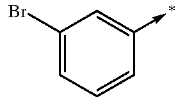 | 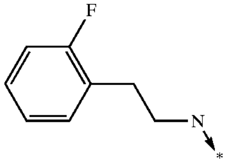 | 86.9 | 4.72 | 519.10 |

-continued
| | | | | | |
|---|---|---|---|---|---|
| 1595 | 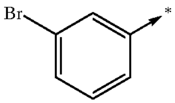 | 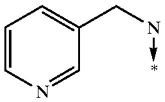 | 87.4 | 3.47 | 488.12 |
| 1596 | 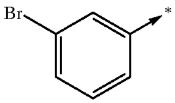 | 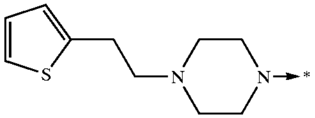 | 82.5 | 3.82 | 576.16 |
| 1597 | 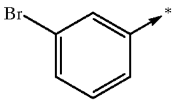 | 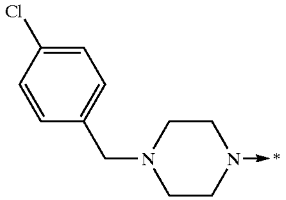 | 86.1 | 4.06 | 590.12 |
| 1598 | 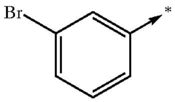 | 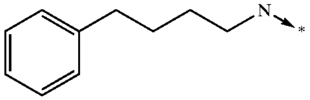 | 85.1 | 5.08 | 529.16 |
| 1599 | 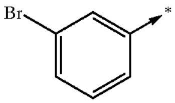 | 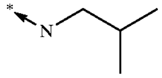 | 84.8 | 4.34 | 453.13 |
| 1600 | 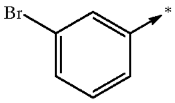 | 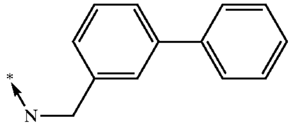 | 74.9 | 5.26 | 563.13 |

-continued
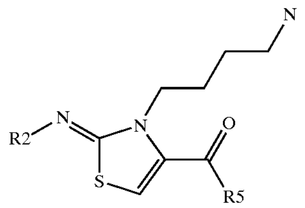
| | | | | | |
|---|---|---|---|---|---|
| 1601 | 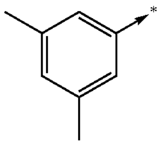 | 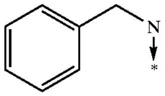 | 88.1 | 3.87 | 409.24 |
| 1602 | 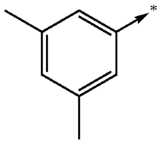 | 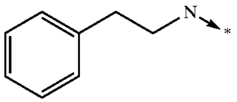 | 90.1 | 4.0 | 423.26 |
| 1603 | 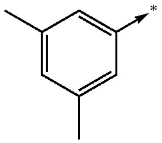 | 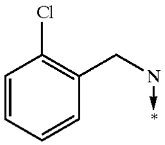 | 60.2 | 4.1 | 443.21 |
| 1604 | 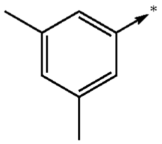 | 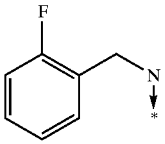 | 91 | 3.9 | 427.24 |
| 1605 | 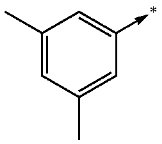 | 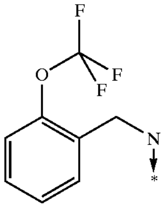 | 57.6 | 4.4 | 493.23 |

-continued
| | | | | | |
|---|---|---|---|---|---|
| 1606 | 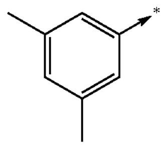 | 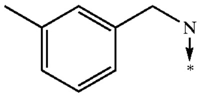 | 48.1 | 4.12 | 423.27 |
| 1607 | 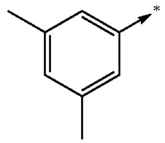 | 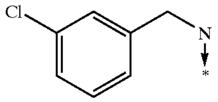 | 45.1 | 4.2 | 443.22 |
| 1608 | 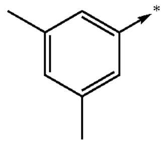 | 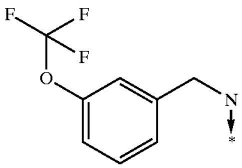 | 60.8 | 4.49 | 493.24 |
| 1609 | 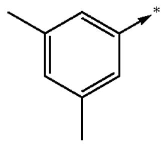 | 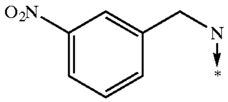 | 54.5 | 3.98 | 454.26 |
| 1610 | 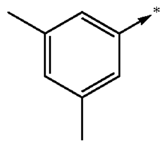 | 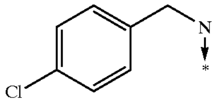 | 84 | 4.19 | 443.23 |
| 1611 | 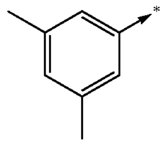 | 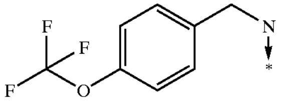 | 92.8 | 4.49 | 493.25 |

-continued
| | | | | | |
|---|---|---|---|---|---|
| 1612 | 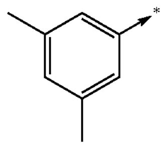 | 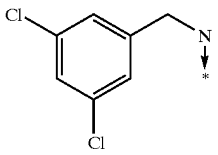 | 86.2 | 4.51 | 477.21 |
| 1613 | 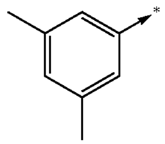 | 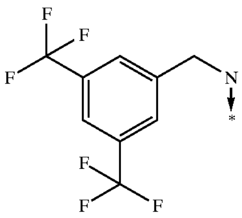 | 84.1 | 4.84 | 545.22 |
| 1614 | 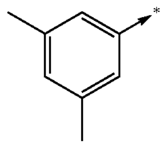 | 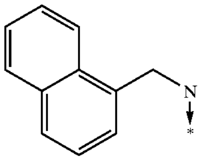 | 77.7 | 4.34 | 459.30 |
| 1615 | 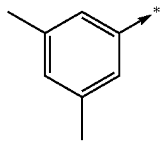 | 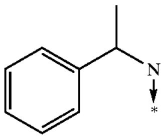 | 90.6 | 3.95 | 423.29 |
| 1616 | 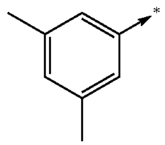 | 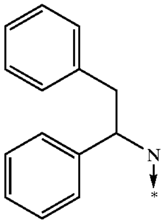 | 91.8 | 4.6 | 499.35 |

-continued
| | | | | | |
|---|---|---|---|---|---|
| 1617 | 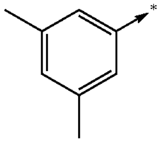 | 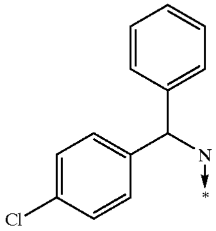 | 91.9 | 4.86 | 519.27 |
| 1618 | 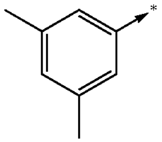 | 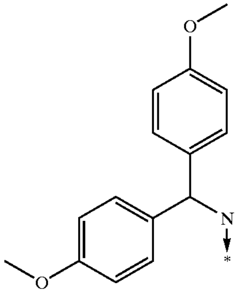 | 62 | 4.6 | 545.3 |
| 1619 | 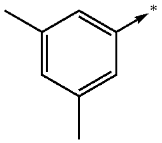 | 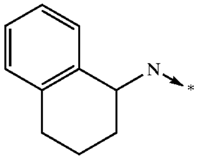 | 91.7 | 4.28 | 449.32 |
| 1620 | 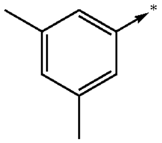 | 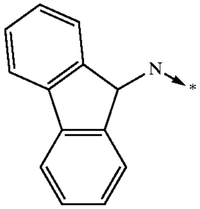 | 63.1 | 4.62 | 483.29 |

-continued
| | | | | | |
|---|---|---|---|---|---|
| 1621 | 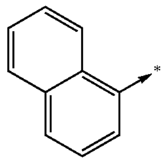 | 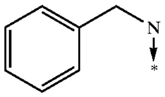 | 83.8 | 4.41 | 431.26 |
| 1622 | 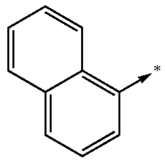 | 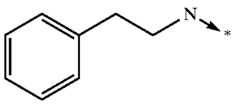 | 64.2 | 4.55 | 445.26 |
| 1623 | 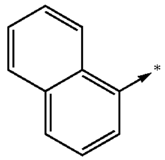 | 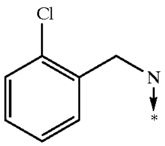 | 48.9 | 4.66 | 465.21 |
| 1624 | 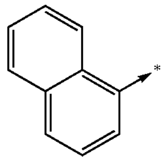 | 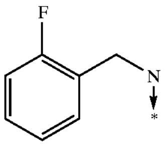 | 89 | 4.46 | 449.27 |
| 1625 | 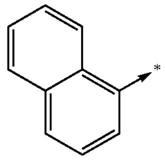 | 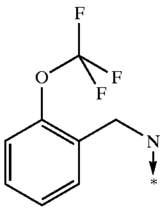 | 56.7 | 4.94 | 515.24 |
| 1626 | 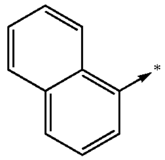 | 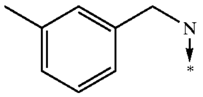 | 78.4 | 4.65 | 445.25 |

-continued
| | | | | | |
|---|---|---|---|---|---|
| 1627 | 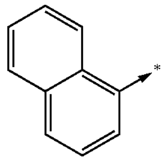 | 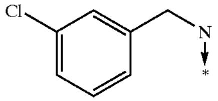 | 44.5 | 4.72 | 465.21 |
| 1628 | 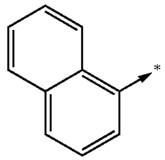 | 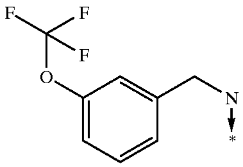 | 84.7 | 5.01 | 515.24 |
| 1629 | 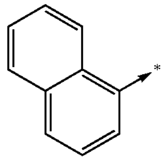 | 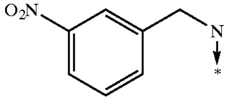 | 73.9 | 4.5 | 476.27 |
| 1630 | 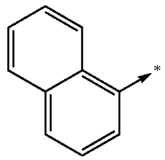 | 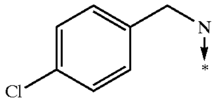 | 76.8 | 4.74 | 465.21 |
| 1631 | 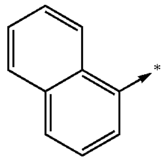 | 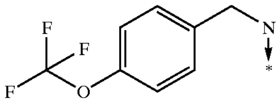 | 88.6 | 5.02 | 515.24 |
| 1632 | 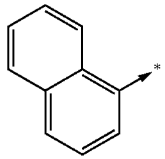 | 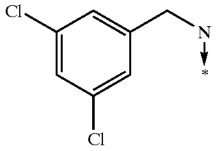 | 90.6 | 5.05 | 499.19 |

-continued
| | | | | | |
|---|---|---|---|---|---|
| 1633 | 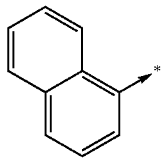 | 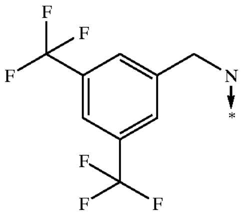 | 89.4 | 5.35 | 567.21 |
| 1634 | 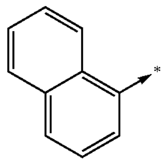 | 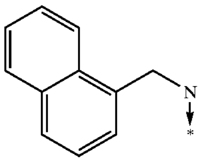 | 80.6 | 4.88 | 481.28 |
| 1635 | 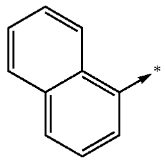 | 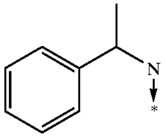 | 90.6 | 4.49 | 445.26 |
| 1636 | 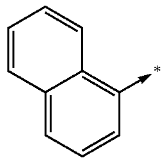 | 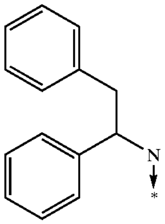 | 91.1 | 5.14 | 521.28 |
| 1637 | 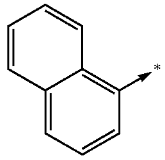 | 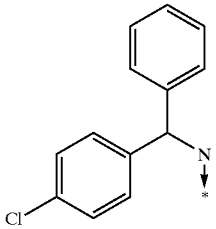 | 91.2 | 5.38 | 541.23 |

-continued
| | | | | | |
|---|---|---|---|---|---|
| 1638 | 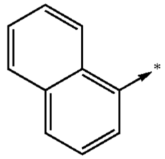 | 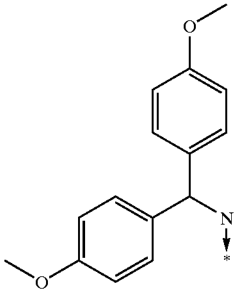 | 90 | 5.1 | 567.3 |
| 1639 | 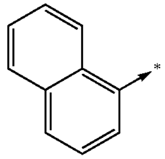 | 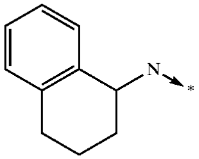 | 92.9 | 4.84 | 471.28 |
| 1640 | 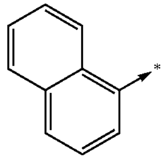 | 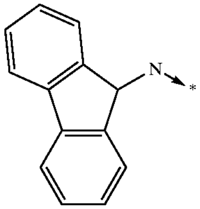 | 88.3 | 5.13 | 505.28 |
| | | 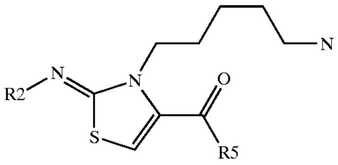 | | | |
| 1641 | 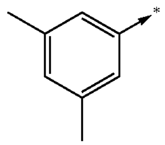 | 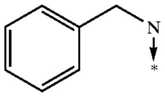 | 83.5 | 3.86 | 423.29 |

-continued
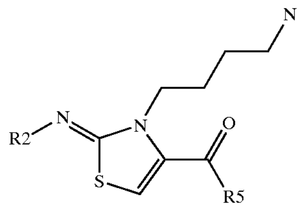
| | | | | | |
|---|---|---|---|---|---|
| 1642 | 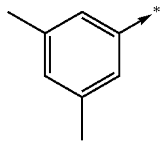 | 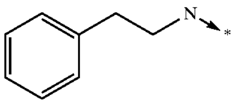 | 81.9 | 4 | 437.30 |
| 1643 | 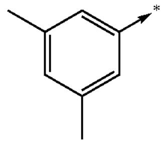 | 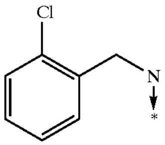 | 81.1 | 4.07 | 457.25 |
| 1644 | 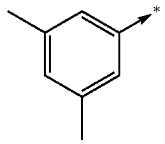 | 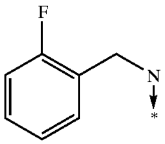 | 89.9 | 3.89 | 441.27 |
| 1645 | 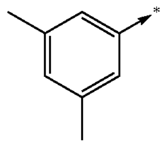 | 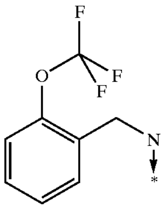 | 91.5 | 4.35 | 507.27 |
| 1646 | 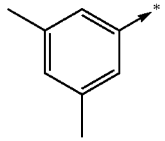 | 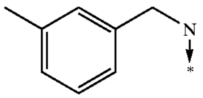 | 70.6 | 4.08 | 437.31 |

-continued
| | | | | | |
|---|---|---|---|---|---|
| 1647 | 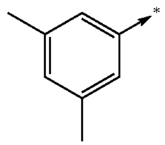 | 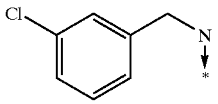 | 73.2 | 4.14 | 457.26 |
| 1648 | 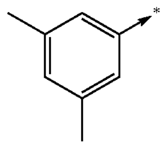 | 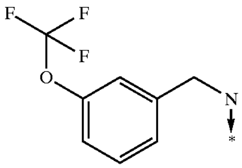 | 91.7 | 4.42 | 507.27 |
| 1649 | 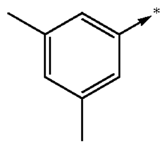 | 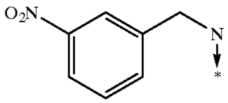 | 61.9 | 3.96 | 468.26 |
| 1650 | 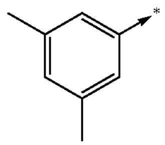 | 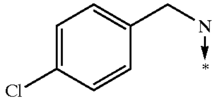 | 82.6 | 4.16 | 457.25 |
| 1651 | 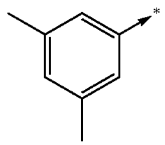 | 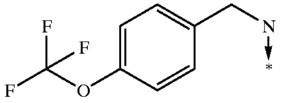 | 78.5 | 4.46 | 507.26 |
| 1652 | 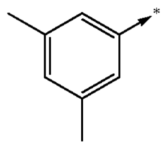 | 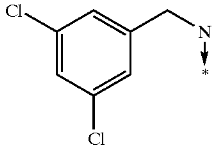 | 80 | 4.46 | 491.21 |

-continued
| | | | | | |
|---|---|---|---|---|---|
| 1653 | 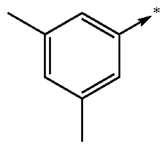 | 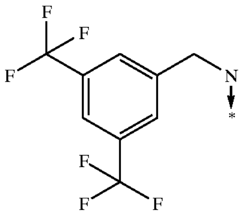 | 80.7 | 4.78 | 559.24 |
| 1654 | 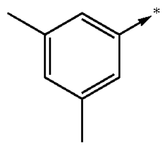 | 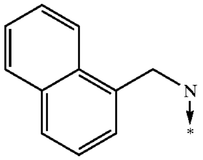 | 90.3 | 4.28 | 473.33 |
| 1655 | 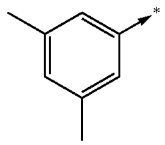 | 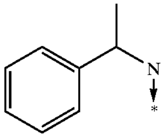 | 91.4 | 3.93 | 437.30 |
| 1656 | 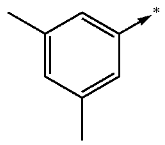 | 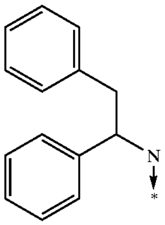 | 93.5 | 4.55 | 513.33 |
| 1657 | 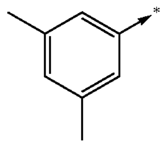 | 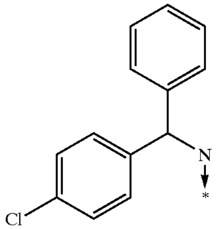 | 92.8 | 4.82 | 533.27 |

-continued
| | | | | | |
|---|---|---|---|---|---|
| 1658 | 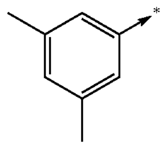 | 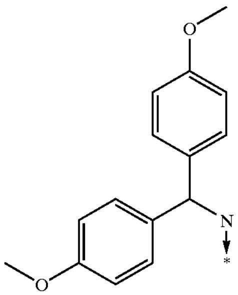 | 58 | 4.5 | 559.3 |
| 1659 | 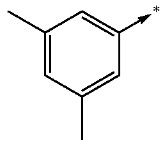 | 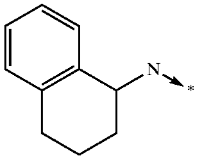 | 92.1 | 4.24 | 463.32 |
| 1660 | 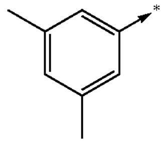 | 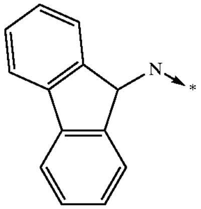 | 92.2 | 4.53 | 497.29 |
| 1661 | 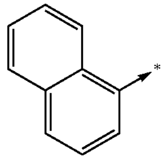 | 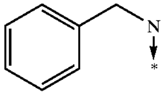 | 36.9 | 4.42 | 445.25 |
| 1662 | 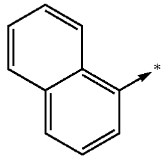 | 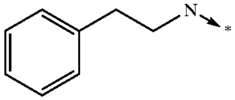 | 31 | 4.56 | 459.28 |

-continued
| | | | | | |
|---|---|---|---|---|---|
| 1663 | 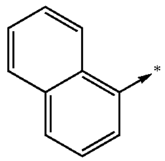 | 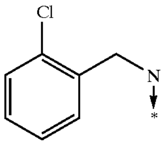 | 38.9 | 4.67 | 479.24 |
| 1664 | 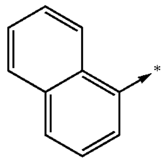 | 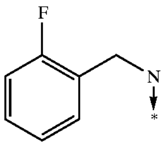 | 43.4 | 4.47 | 463.27 |
| 1665 | 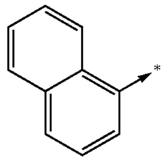 | 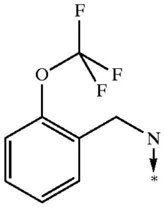 | 47.9 | 4.98 | 529.2 |
| 1666 | 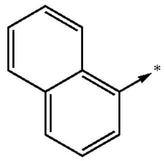 | 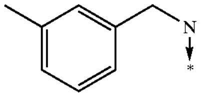 | 32.1 | 4.66 | 459.28 |
| 1667 | 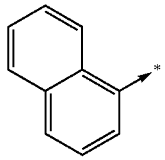 | 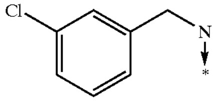 | 23 | 4.74 | 479.23 |
| 1668 | 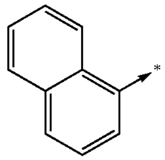 | 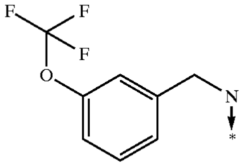 | 38.1 | 5.02 | 529.25 |

-continued
| | | | | | |
|---|---|---|---|---|---|
| 1669 | 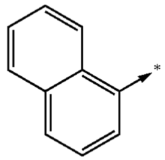 | 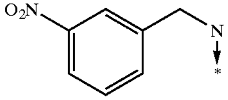 | 35.5 | 4.51 | 490.27 |
| 1670 | 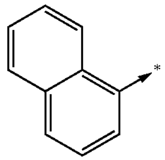 | 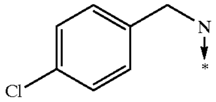 | 47.1 | 4.74 | 479.23 |
| 1671 | 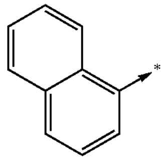 | 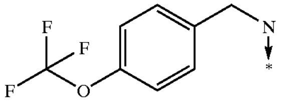 | 37.1 | 5.04 | 529.25 |
| 1672 | 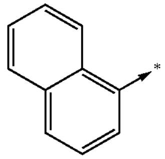 | 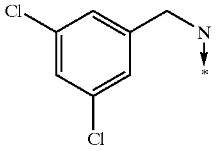 | 60.9 | 5.07 | 513.19 |
| 1673 | 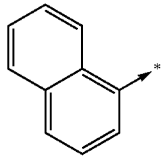 | 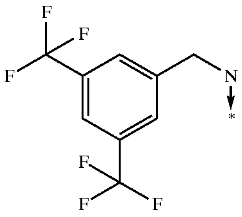 | 82.8 | 5.34 | 581.23 |

-continued
| | | | | | |
|---|---|---|---|---|---|
| 1674 | 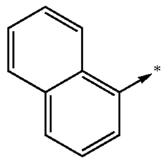 | 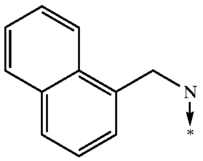 | 20.5 | 4.91 | 495.27 |
| 1675 | 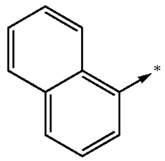 | 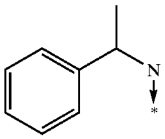 | 72 | 4.52 | 459.28 |
| 1676 | 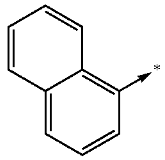 | 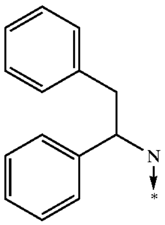 | 91.1 | 5.14 | 535.30 |
| 1677 | 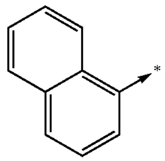 | 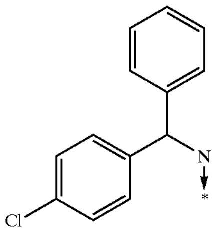 | 89.3 | 5.4 | 555.23 |

-continued
| | | | | | |
|---|---|---|---|---|---|
| 1678 | 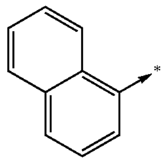 | 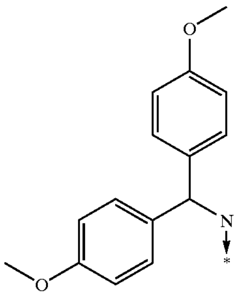 | 52 | 5.1 | 581.3 |
| 1679 | 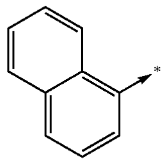 | 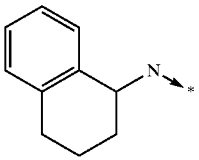 | 91.3 | 4.84 | 485.31 |
| 1680 | 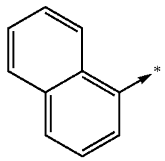 | 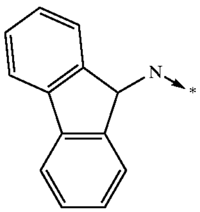 | 71.7 | 5.14 | 519.29 |
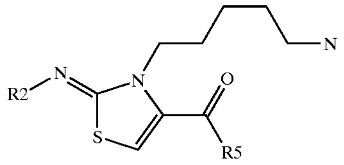
| | | | | | |
|---|---|---|---|---|---|
| 1681 | 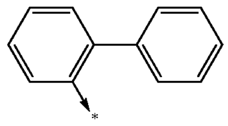 | 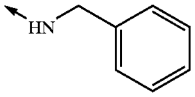 | 72.7 | 4.26 | 471.34 |

-continued
| | | | | | |
|---|---|---|---|---|---|
| 1682 | 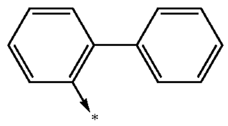 | 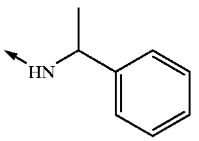 | 76.3 | 4.36 | 485.34 |
| 1683 | 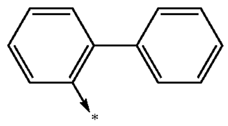 | 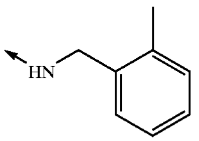 | 51.6 | 4.47 | 485.33 |
| 1684 | 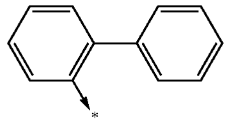 | 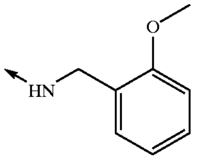 | 33.6 | 4.39 | 501.32 |
| 1685 | 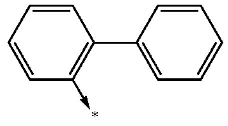 | 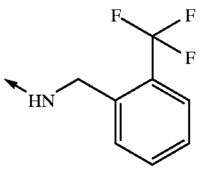 | 79.9 | 4.7 | 539.29 |
| 1686 | 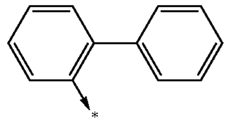 | 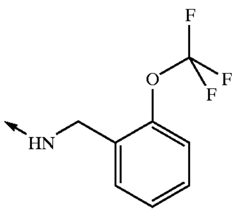 | 76 | 4.77 | 555.28 |
| 1687 | 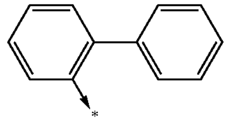 | 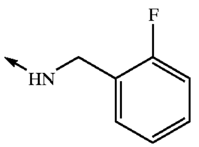 | 53.2 | 4.34 | 489.30 |

-continued
| | | | | | |
|---|---|---|---|---|---|
| 1688 | 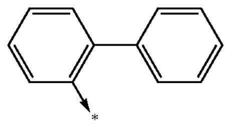 | 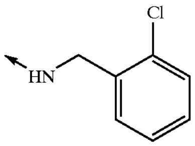 | 59.2 | 4.51 | 505.27 |
| 1689 | 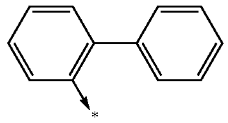 | 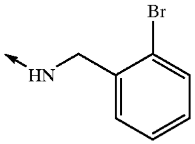 | 74.7 | 4.57 | 549.21 |
| 1690 | 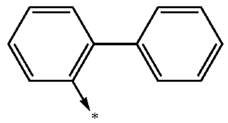 | 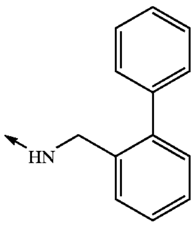 | 82 | 4.84 | 547.34 |
| 1691 | 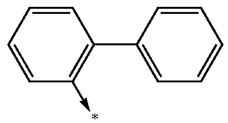 | 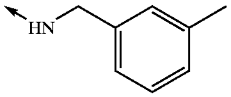 | 68.8 | 4.49 | 485.32 |
| 1692 | 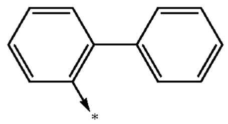 | 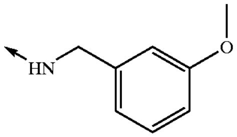 | 73.4 | 4.25 | 501.37 |
| 1693 | 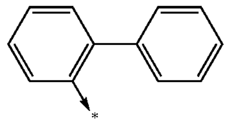 | 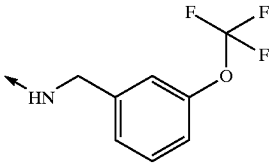 | 75.0 | 4.83 | 555.27 |

-continued
| | | | | | |
|---|---|---|---|---|---|
| 1694 | 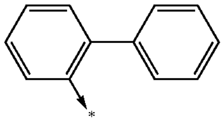 | 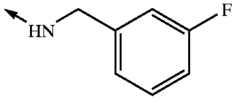 | 44.5 | 4.39 | 489.30 |
| 1695 | 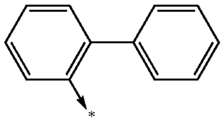 | 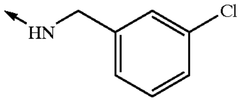 | 42.7 | 4.57 | 505.25 |
| 1696 | 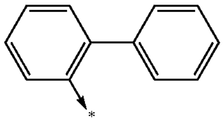 | 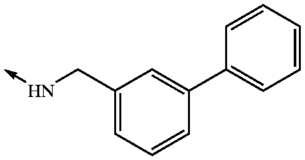 | 79.8 | 4.97 | 547.32 |
| 1697 | 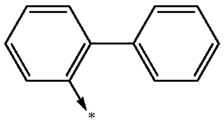 | 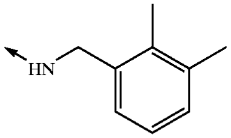 | 78.9 | 4.56 | 499.39 |
| 1698 | 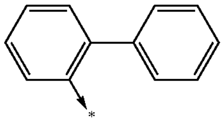 | 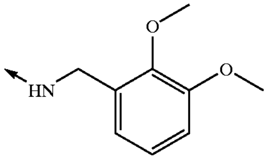 | 70.8 | 4.27 | 531.36 |
| 1699 | 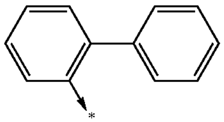 | 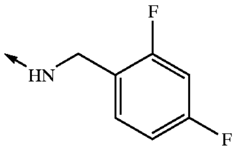 | 77.5 | 4.35 | 507.33 |

-continued
| | | | | | |
|---|---|---|---|---|---|
| 1700 | 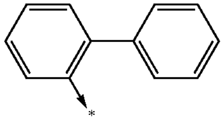 | 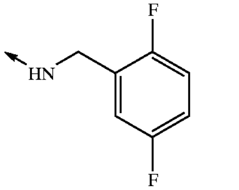 | 78.9 | 4.34 | 507.33 |
| 1701 | 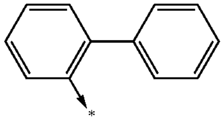 | 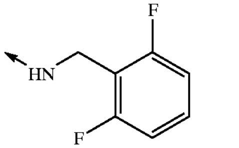 | 75.8 | 4.27 | 507.32 |
| 1702 | 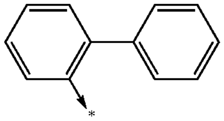 | 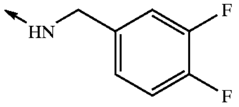 | 74.9 | 4.41 | 507.32 |
| 1703 | 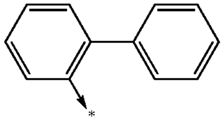 | 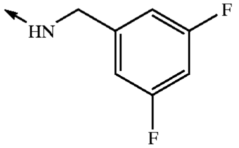 | 75.3 | 4.49 | 507.29 |
| 1704 | 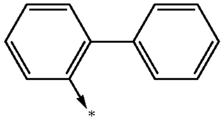 | 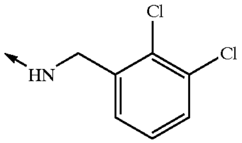 | 73.5 | 4.75 | 539.22 |
| 1705 | 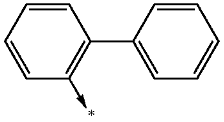 | 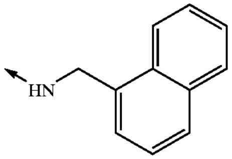 | 82.9 | 4.7 | 521.31 |

-continued
| Ex. | R1 | R5 | Purity (%) | rt (min.) | [M + H]$^+$ |
|---|---|---|---|---|---|
| | | 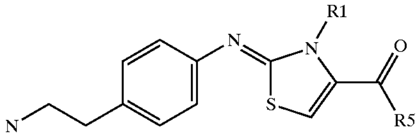 | | | |
| 1706 | 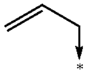 | 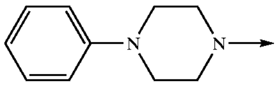 | 87.3 | 3.8 | 448.31 |
| 1707 | 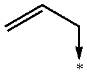 | 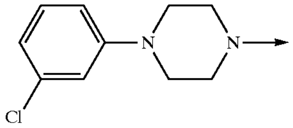 | 86.0 | 4.3 | 482.24 |
| 1708 | 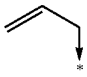 | 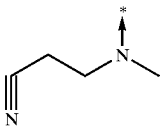 | 90.0 | 2.4 | 370.24 |
| 1709 | 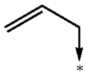 | 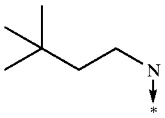 | 76.6 | 3.88 | 387.26 |
| 1710 | 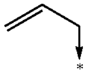 | 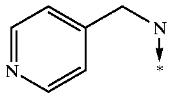 | 53.2 | 3.0 | 394.2 |
| 1711 | 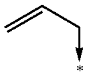 | 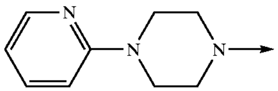 | 91.2 | 2.3 | 449.29 |

-continued
| | | | | | |
|---|---|---|---|---|---|
| 1712 | 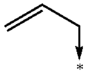 | 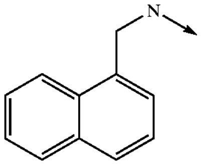 | 87.7 | 4.13 | 443.29 |
| 1713 | 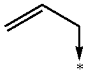 | 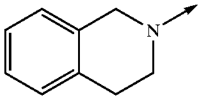 | 88.3 | 3.7 | 419.28 |
| 1714 | 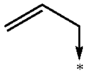 | 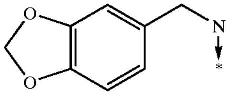 | 70.8 | 3.5 | 437.25 |
| 1715 | 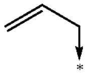 | 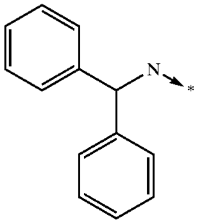 | 87.0 | 4.4 | 469.30 |
| 1716 | 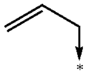 | 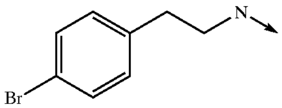 | 82.5 | 4.12 | 485.20 |
| 1717 | 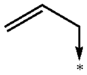 | 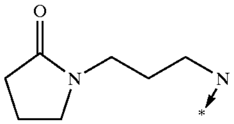 | 88.1 | 2.59 | 428.29 |
| 1718 | 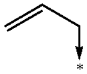 | 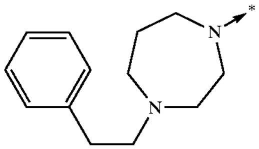 | 88.7 | 2.8 | 490.35 |

-continued
| | | | | | |
|---|---|---|---|---|---|
| 1719 | 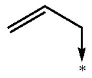 | 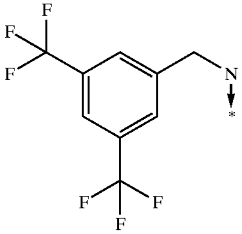 | 79.0 | 4.68 | 529.23 |
| 1720 | 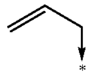 | 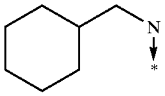 | 78.0 | 3.94 | 399.29 |
| 1721 | 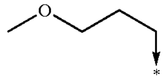 | 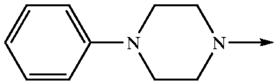 | 87.4 | 3.7 | 480.32 |
| 1722 | 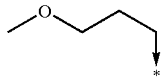 | 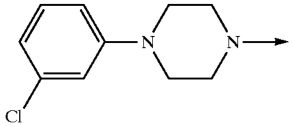 | 83.1 | 4.14 | 514.28 |
| 1723 | 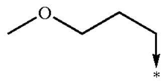 | 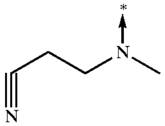 | 89.1 | 2.44 | 402.24 |
| 1724 | 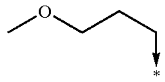 | 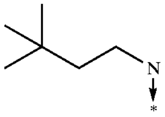 | 81.5 | 3.73 | 419.3 |
| 1725 | 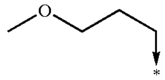 | 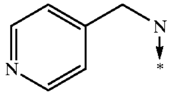 | 56.1 | 3.0 | 416.2 |

-continued
| | | | | | |
|---|---|---|---|---|---|
| 1726 | 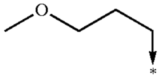 | 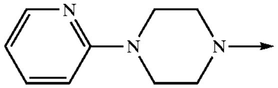 | 90.1 | 2.3 | 481.33 |
| 1727 | 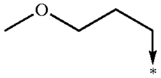 | 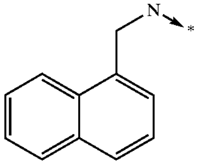 | 87.3 | 3.96 | 475.31 |
| 1728 | 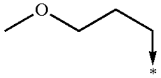 | 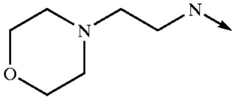 | 75.2 | 2.9 | 448.3 |
| 1729 | 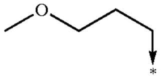 | 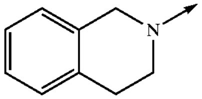 | 85.7 | 3.61 | 451.29 |
| 1730 | 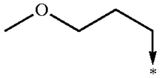 | 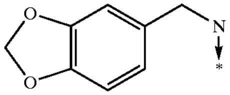 | 74.5 | 3.37 | 469.28 |
| 1731 | 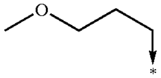 | 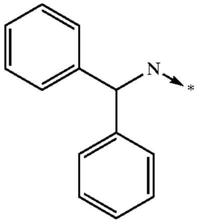 | 83.7 | 4.22 | 501.32 |
| 1732 | 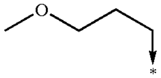 | 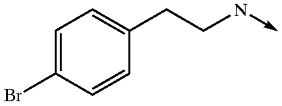 | 86.7 | 3.95 | 517.20 |

-continued
| | | | | | |
|---|---|---|---|---|---|
| 1733 | 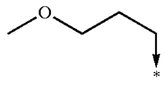 | 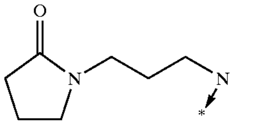 | 80.6 | 2.61 | 460.32 |
| 1734 | 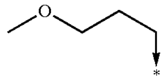 | 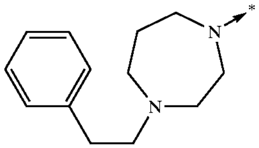 | 80.8 | 2.8 | 522.35 |
| 1735 | 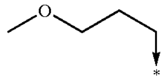 | 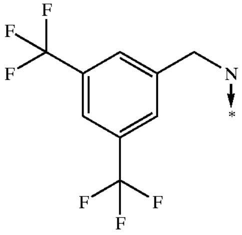 | 74.0 | 4.48 | 561.23 |
| 1736 | 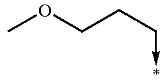 | 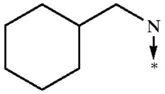 | 81.2 | 3.8 | 431.31 |
| 1737 | 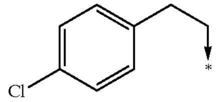 | 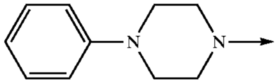 | 87.1 | 4.76 | 546.27 |
| 1738 | 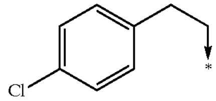 | 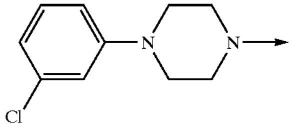 | 85.5 | 5.16 | 580.24 |
| 1739 | 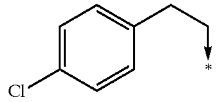 | 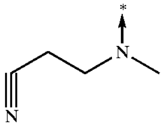 | 85.5 | 3.72 | 468.24 |

-continued
| | | | | | |
|---|---|---|---|---|---|
| 1740 | 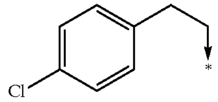 | 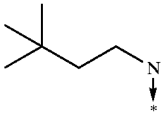 | 82.1 | 4.74 | 485.29 |
| 1741 | 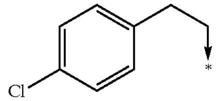 | 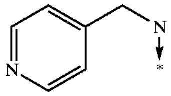 | 80.7 | 3.04 | 492.24 |
| 1742 | 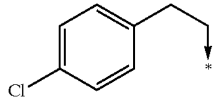 | 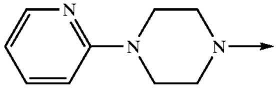 | 87.7 | 3.4 | 547.28 |
| 1743 | 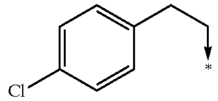 | 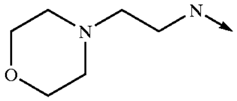 | 81.9 | 4.96 | 541.23 |
| 1744 | 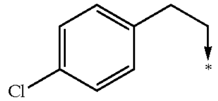 | 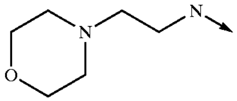 | 55.2 | 2.9 | 514.27 |
| 1745 | 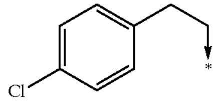 | 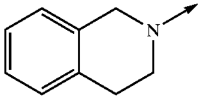 | 87.2 | 4.7 | 517.25 |
| 1746 | 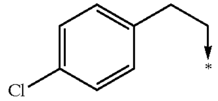 | 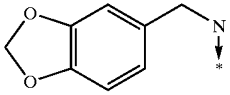 | 73.7 | 4.39 | 535.21 |
| 1747 | 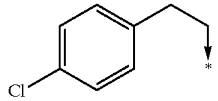 | 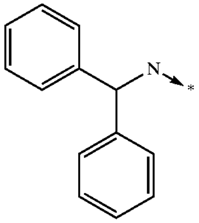 | 84.3 | 5.22 | 567.25 |

-continued
| | | | | | |
|---|---|---|---|---|---|
| 1748 | 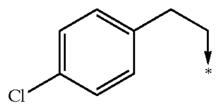 | 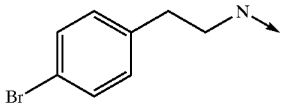 | 74.7 | 4.9 | 583.16 |
| 1749 | 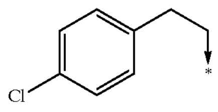 | 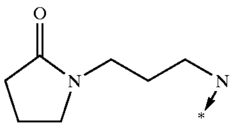 | 76.8 | 3.53 | 526.28 |
| 1750 | 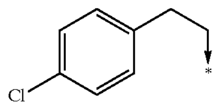 | 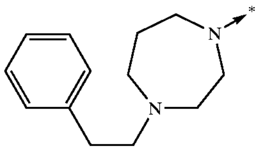 | 84.3 | 3.7 | 588.34 |
| 1751 | 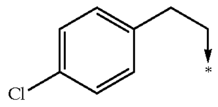 | 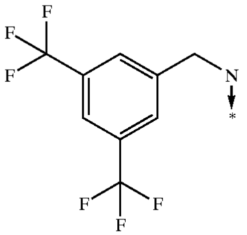 | 74.4 | 5.41 | 627.20 |
| 1752 | 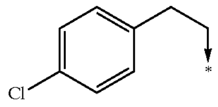 | 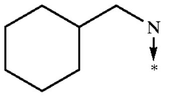 | 80.9 | 4.88 | 497.31 |
| 1753 | 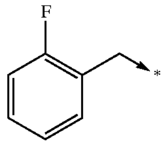 | 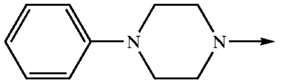 | 83.4 | 4.53 | 516.2 |

-continued
| | | | | | |
|---|---|---|---|---|---|
| 1754 | 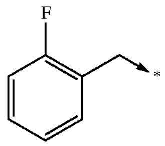 | 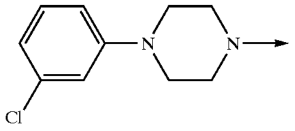 | 83.2 | 4.96 | 550.24 |
| 1755 | 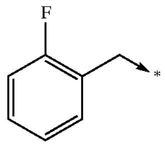 | 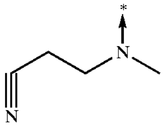 | 84.1 | 3.39 | 438.25 |
| 1756 | 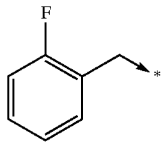 | 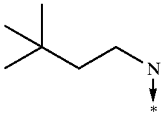 | 84.7 | 4.71 | 455.28 |
| 1757 | 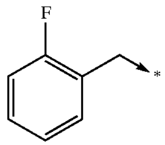 | 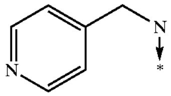 | 56.6 | 2.8 | 462.24 |
| 1758 | 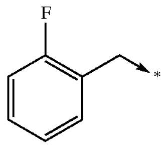 | 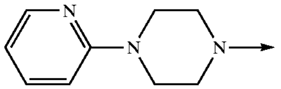 | 85.0 | 3.0 | 517.30 |
| 1759 | 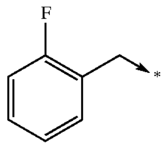 | 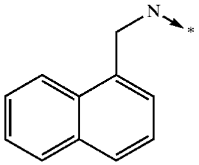 | 84.6 | 4.9 | 511.26 |

-continued
| | | | | | |
|---|---|---|---|---|---|
| 1760 | 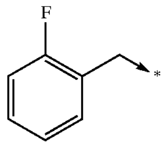 | 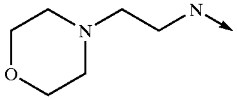 | 82.1 | 2.8 | 484.3 |
| 1761 | 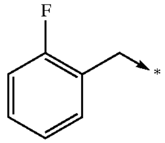 | 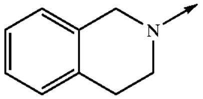 | 84.4 | 4.44 | 487.27 |
| 1762 | 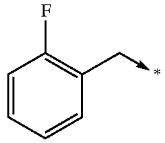 | 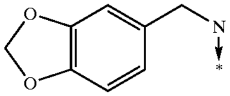 | 52.0 | 4.3 | 505.23 |
| 1763 | 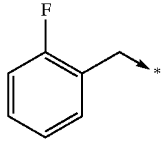 | 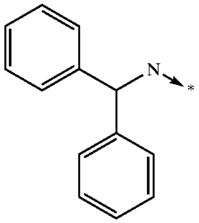 | 84.5 | 5.12 | 537.28 |
| 1764 | 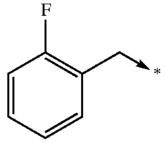 | 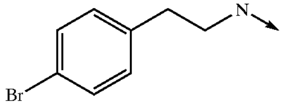 | 81.5 | 4.93 | 553.17 |
| 1765 | 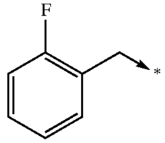 | 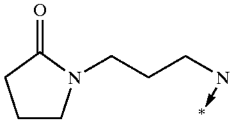 | 80.2 | 3.34 | 496.29 |

-continued
| | | | | | |
|---|---|---|---|---|---|
| 1766 | 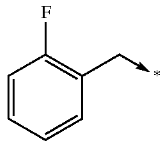 | 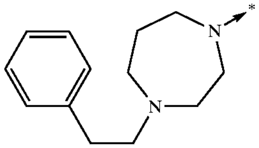 | 85.9 | 3.5 | 558.31 |
| 1767 | 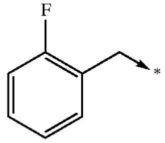 | 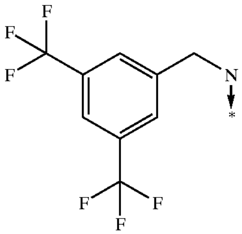 | 53.4 | 5.39 | 597.22 |
| 1768 | 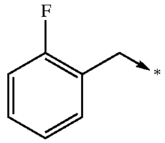 | 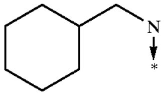 | 81.6 | 4.81 | 467.29 |
| 1769 | 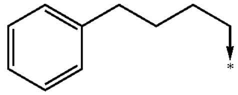 | 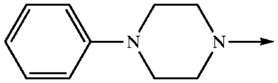 | 83.5 | 3.5 | 540.32 |
| 1770 | 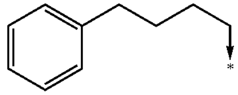 | 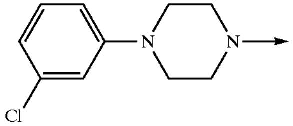 | 82.4 | 5.01 | 574.27 |
| 1771 | 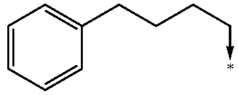 | 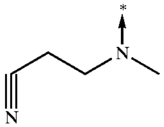 | 80.9 | 3.72 | 462.30 |

-continued
| | | | | | |
|---|---|---|---|---|---|
| 1772 | 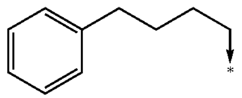 | 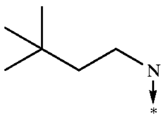 | 77.9 | 4.78 | 479.36 |
| 1773 | 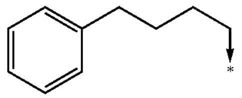 | 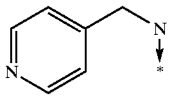 | 79.3 | 3.11 | 486.32 |
| 1774 | 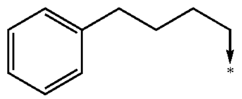 | 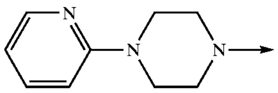 | 85.0 | 3.4 | 541.35 |
| 1775 | 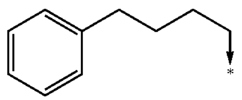 | 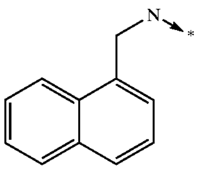 | 85.3 | 4.9 | 535.31 |
| 1776 | 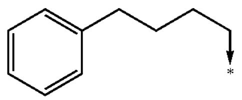 | 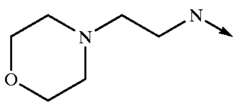 | 74.9 | 3.0 | 508.34 |
| 1777 | 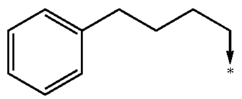 | 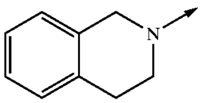 | 83.9 | 4.58 | 511.33 |
| 1778 | 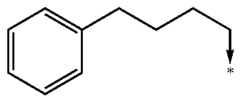 | 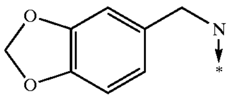 | 69.1 | 4.4 | 529.3 |

-continued
| | | | | | |
|---|---|---|---|---|---|
| 1779 | 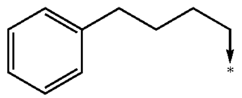 | 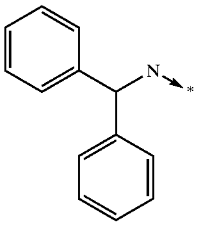 | 83.1 | 5.1 | 561.3 |
| 1780 | 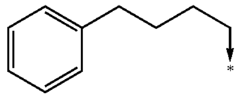 | 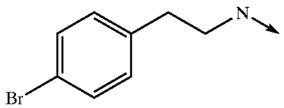 | 81.8 | 4.9 | 577.23 |
| 1781 | 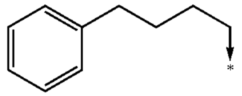 | 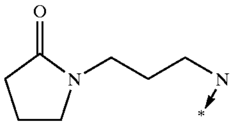 | 83.6 | 3.64 | 520.34 |
| 1782 | 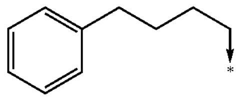 | 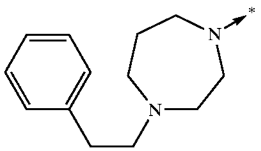 | 80.9 | 3.7 | 582.4 |
| 1783 | 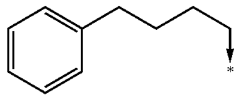 | 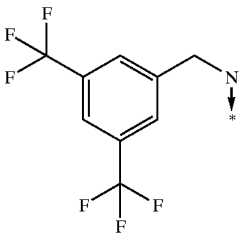 | 68.0 | 5.34 | 621.28 |
| 1784 | 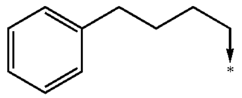 | 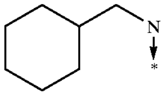 | 76.3 | 4.85 | 491.36 |

-continued
| | | 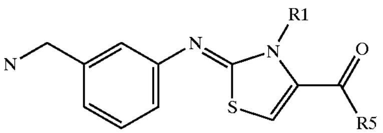 | | | |
|---|---|---|---|---|---|
| 1785 | 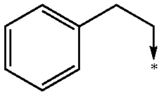 | 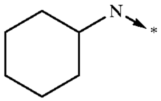 | 77.9 | 4.44 | 435.25 |
| 1786 | 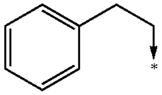 | 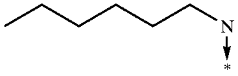 | 78.8 | 4.83 | 437.30 |
| 1787 | 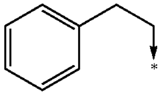 | 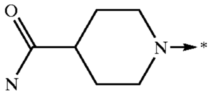 | 79.5 | 3.13 | 464.27 |
| 1788 | 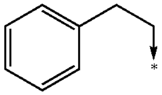 | 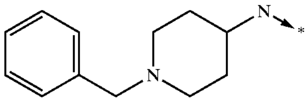 | 80.3 | 3.28 | 526.38 |
| 1789 | 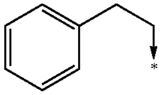 | 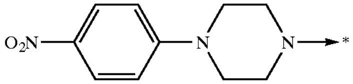 | 86.6 | 4.67 | 543.32 |
| 1790 | 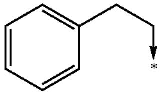 | 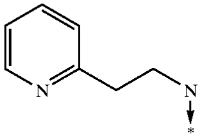 | 74.8 | 2.9 | 458.32 |
| 1791 | 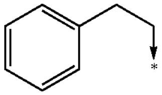 | 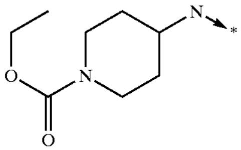 | 81.7 | 3.99 | 508.34 |

-continued
| | | | | | |
|---|---|---|---|---|---|
| 1792 | 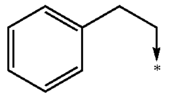 | 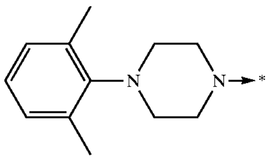 | 86.9 | 5.41 | 526.38 |
| 1793 | 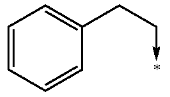 | 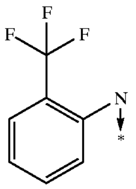 | 86.4 | 4.85 | 511.27 |
| 1794 | 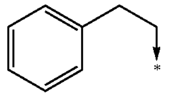 | 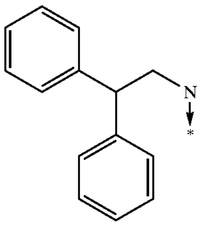 | 82.2 | 5.07 | 533.35 |
| 1795 | 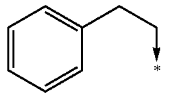 | 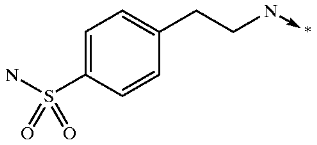 | 83.1 | 3.55 | 536.28 |
| 1796 | 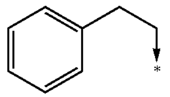 | 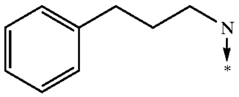 | 82.3 | 4.66 | 471.3 |
| 1797 | 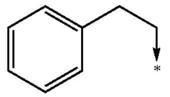 | 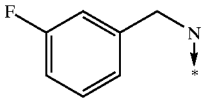 | 86.3 | 4.41 | 461.31 |

-continued
| | | | | | |
|---|---|---|---|---|---|
| 1798 | 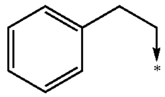 | 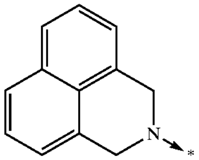 | 85.1 | 4.95 | 505.33 |
| 1799 | 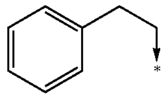 | 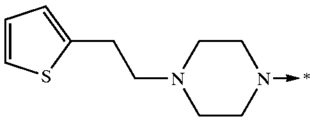 | 76.0 | 3.5 | 532.3 |
| 1800 | 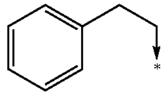 | 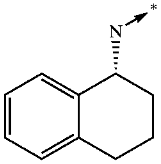 | 81.1 | 4.87 | 483.34 |
| 1801 | 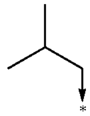 | 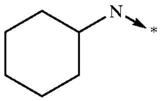 | 68.62 | 3.96 | 387.33 |
| 1802 | 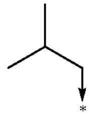 | 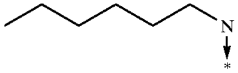 | 73.4 | 4.39 | 389.33 |
| 1803 | 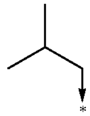 | 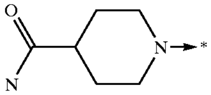 | 81.2 | 2.57 | 416.32 |
| 1804 | 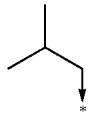 | 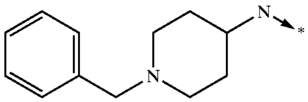 | 79.2 | 2.9 | 478.3 |

-continued
| | | | | | |
|---|---|---|---|---|---|
| 1805 | 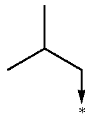 | 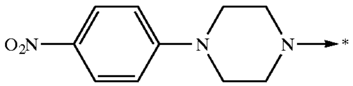 | 83.2 | 4.26 | 495.34 |
| 1806 | 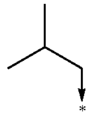 | 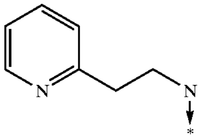 | 70.2 | 2.5 | 410.3 |
| 1807 | 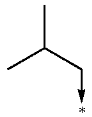 | 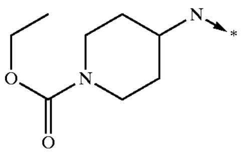 | 73.3 | 3.6 | 460.37 |
| 1808 | 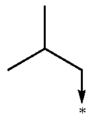 | 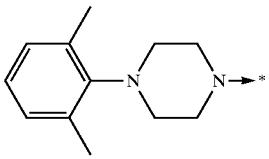 | 75.0 | 5.01 | 478.39 |
| 1809 | 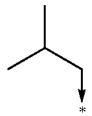 | 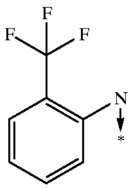 | 70.3 | 4.45 | 463.31 |
| 1810 | 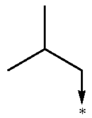 | 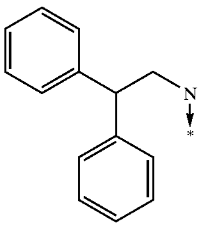 | 83.9 | 4.73 | 485.37 |

-continued
| | | | | | |
|---|---|---|---|---|---|
| 1811 | 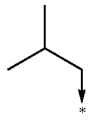 | 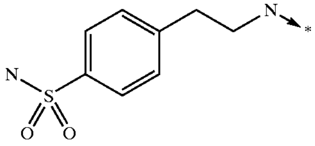 | 76.5 | 3.14 | 488.31 |
| 1812 | 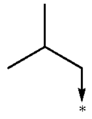 | 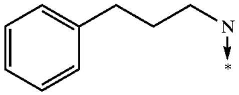 | 79.1 | 4.28 | 423.35 |
| 1813 | 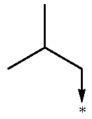 | 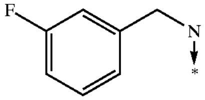 | 79.2 | 3.99 | 413.29 |
| 1814 | 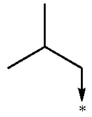 | 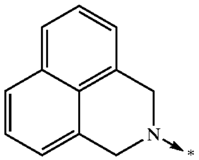 | 75.5 | 4.55 | 457.33 |
| 1815 | 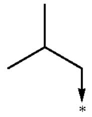 | 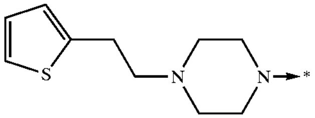 | 67.7 | 3.1 | 484.3 |
| 1816 | 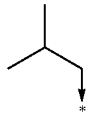 | 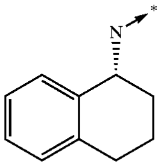 | 62.7 | 4.44 | 435.33 |

-continued
| | | | | | |
|---|---|---|---|---|---|
| 1817 | 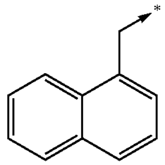 | 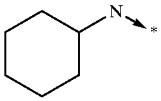 | 85.7 | 5.02 | 471.33 |
| 1818 | 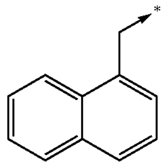 | 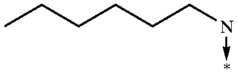 | 70.2 | 5.31 | 473.37 |
| 1819 | 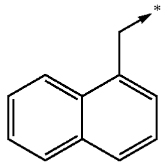 | 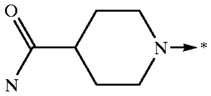 | 86.6 | 3.59 | 500.35 |
| 1820 | 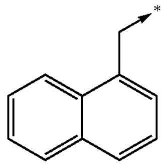 | 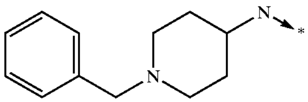 | 83.8 | 3.7 | 562.4 |
| 1821 | 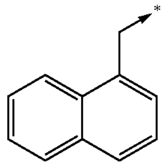 | 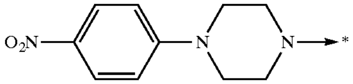 | 88.5 | 5.04 | 579.32 |
| 1822 | 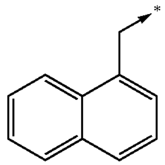 | 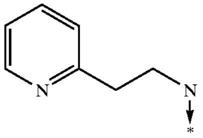 | 39.8 | 3.3 | 494.3 |

-continued
| | | | | | |
|---|---|---|---|---|---|
| 1823 | 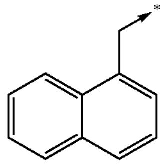 | 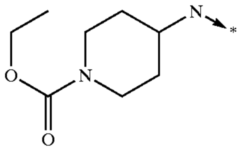 | 85.8 | 4.55 | 544.33 |
| 1824 | 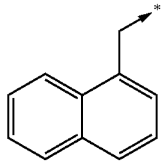 | 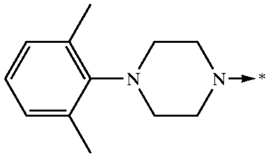 | 86.4 | 5.78 | 562.36 |
| 1825 | 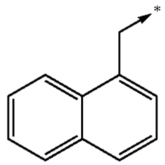 | 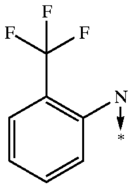 | 84.3 | 5.27 | 547.25 |
| 1826 | 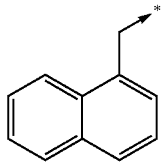 | 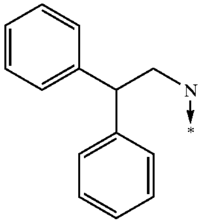 | 69.7 | 5.58 | 569.32 |
| 1827 | 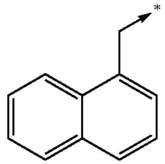 | 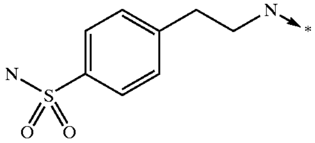 | 70.3 | 4.17 | 572.27 |

-continued
| | | | | | |
|---|---|---|---|---|---|
| 1828 | 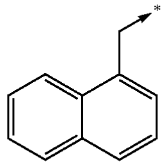 | 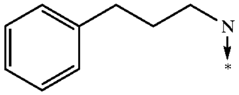 | 85.4 | 5.17 | 507.34 |
| 1829 | 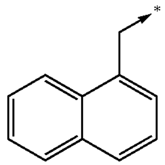 | 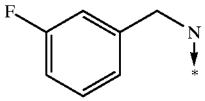 | 82.3 | 4.91 | 497.28 |
| 1830 | 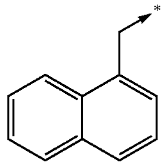 | 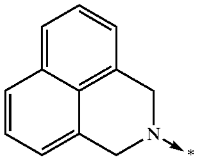 | 82.4 | 5.41 | 541.29 |
| 1831 | 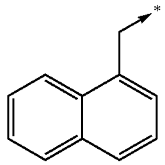 | 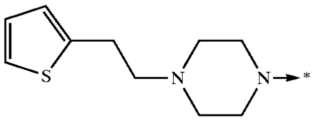 | 79.4 | 3.8 | 568.3 |
| 1832 | 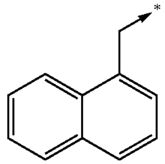 | 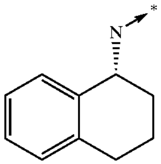 | 86.9 | 5.31 | 519.33 |
| 1833 | 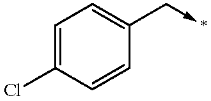 | 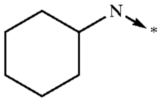 | 86.3 | 4.99 | 455.27 |

-continued
| | | | | | |
|---|---|---|---|---|---|
| 1834 | 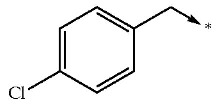 | 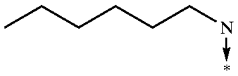 | 84.5 | 5.3 | 457.30 |
| 1835 | 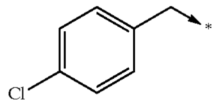 | 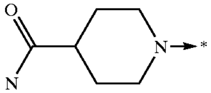 | 88.3 | 3.42 | 484.27 |
| 1836 | 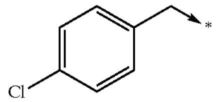 | 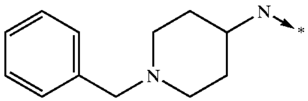 | 83.6 | 3.65 | 546.29 |
| 1837 | 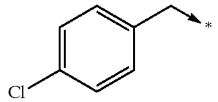 | 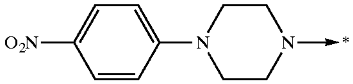 | 88.8 | 4.91 | 563.24 |
| 1838 | 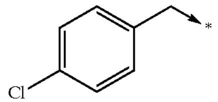 | 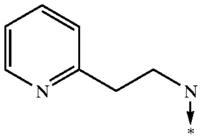 | 65.2 | 3.3 | 478.24 |
| 1839 | 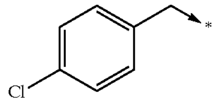 | 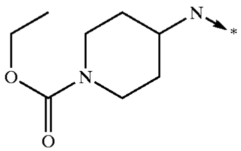 | 87.6 | 4.5 | 528.30 |
| 1840 | 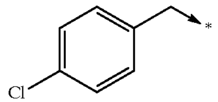 | 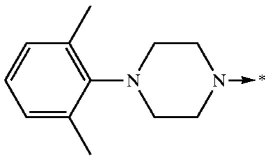 | 90.4 | 5.68 | 546.30 |

-continued
| | | | | | |
|---|---|---|---|---|---|
| 1841 | 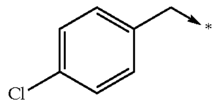 | 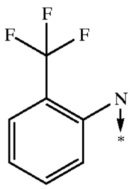 | 82.8 | 5.31 | 531.23 |
| 1842 | 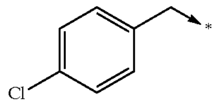 | 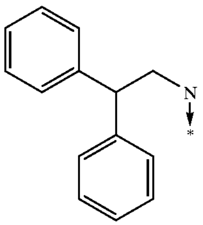 | 68.2 | 5.57 | 553.28 |
| 1843 | 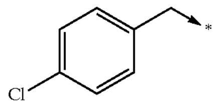 | 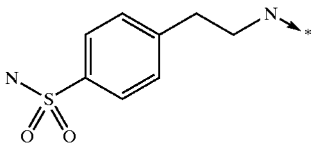 | 72.4 | 4.11 | 556.21 |
| 1844 | 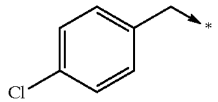 | 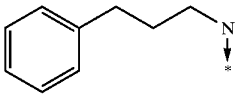 | 83.9 | 5.15 | 491.29 |
| 1845 | 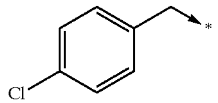 | 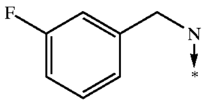 | 86.4 | 4.93 | 481.27 |
| 1846 | 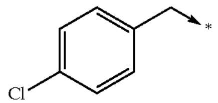 | 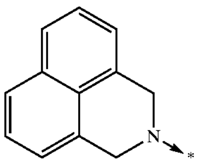 | 86.3 | 5.29 | 525.25 |

-continued
| | | | | | |
|---|---|---|---|---|---|
| 1847 | 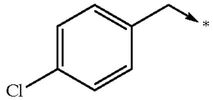 | 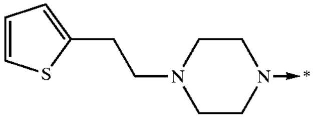 | 82.6 | 3.7 | 552.3 |
| 1848 | 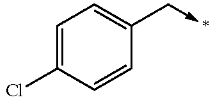 | 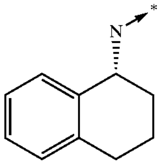 | 88.1 | 5.3 | 503.29 |
| 1849 | 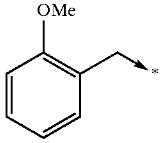 | 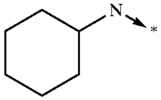 | 82.9 | 4.25 | 451.32 |
| 1850 | 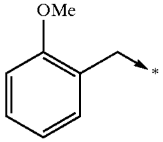 | 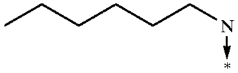 | 82.1 | 4.64 | 453.35 |
| 1851 | 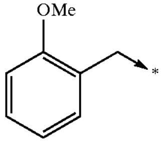 | 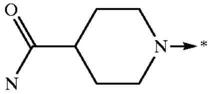 | 85.6 | 2.72 | 480.33 |
| 1852 | 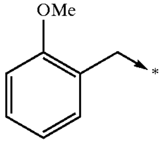 | 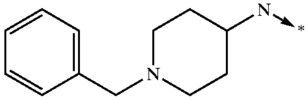 | 82.9 | 3.16 | 542.35 |

-continued
| | | | | | |
|---|---|---|---|---|---|
| 1853 | 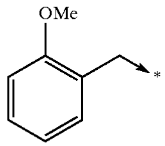 | 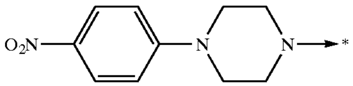 | 87.7 | 4.28 | 559.29 |
| 1854 | 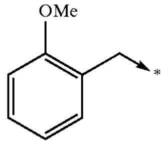 | 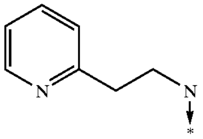 | 75.3 | 2.82 | 474.33 |
| 1855 | 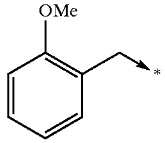 | 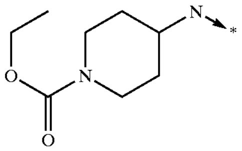 | 84.4 | 3.83 | 524.32 |
| 1856 | 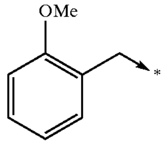 | 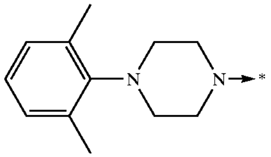 | 87.0 | 5.0 | 542.36 |
| 1857 | 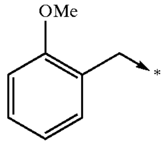 | 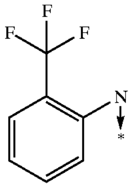 | 82.6 | 4.73 | 527.28 |
| 1858 | 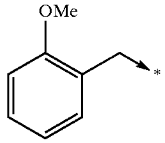 | 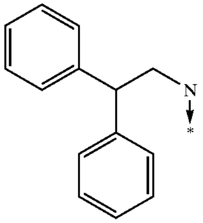 | 65.8 | 5.01 | 549.31 |

-continued
| | | | | | |
|---|---|---|---|---|---|
| 1859 | 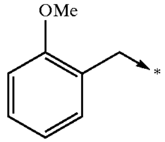 | 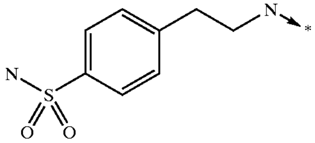 | 76.4 | 3.49 | 552.26 |
| 1860 | 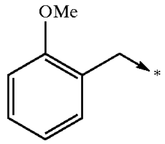 | 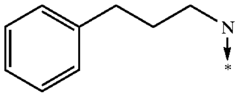 | 80.4 | 4.54 | 487.35 |
| 1861 | 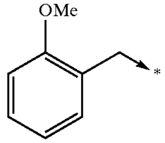 | 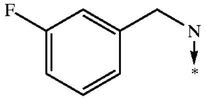 | 81.3 | 4.28 | 477.30 |
| 1862 | 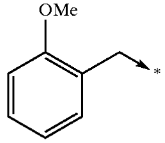 | 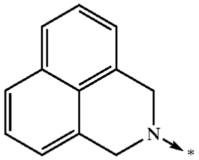 | 79.9 | 4.59 | 521.29 |
| 1863 | 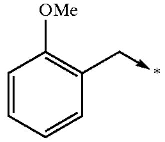 | 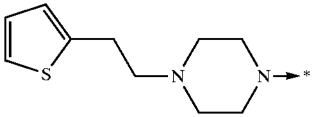 | 77.5 | 3.2 | 548.3 |
| 1864 | 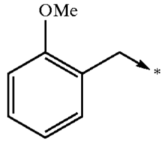 | 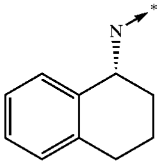 | 86.5 | 4.65 | 499.32 |

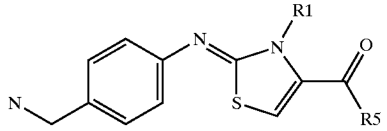
| Ex. | R1 | R5 | Purity (%) | rt (min) | $[M + H]^+$ |
|---|---|---|---|---|---|
| 1865 | 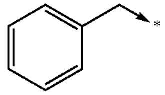 | 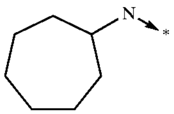 | 84.7 | 4.94 | 435.29 |
| 1866 | 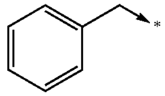 | 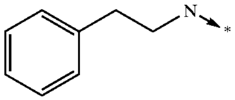 | 85.0 | 4.66 | 443.26 |
| 1867 | 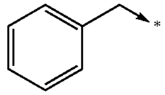 | 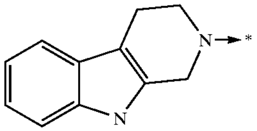 | 26.2 | 4.82 | 494.26 |
| 1868 | 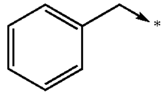 | 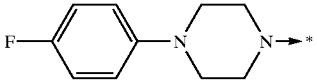 | 88.4 | 4.8 | 502.28 |
| 1869 | 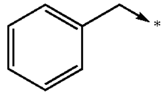 | 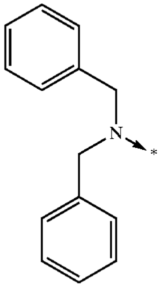 | 83.6 | 5.48 | 519.28 |

-continued
| | | | | | |
|---|---|---|---|---|---|
| 1870 | 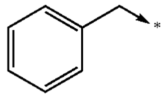 | 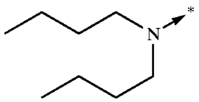 | 63.17 | 5.3 | 451.33 |
| 1871 | 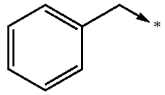 | 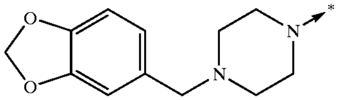 | 91.1 | 3.4 | 542.3 |
| 1872 | 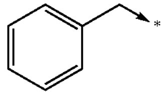 | 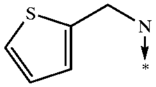 | 35.7 | 4.48 | 435.20 |
| 1873 | 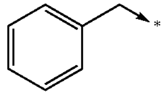 | 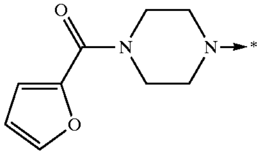 | 88.8 | 3.8 | 502.26 |
| 1874 | 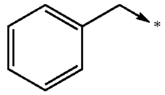 | 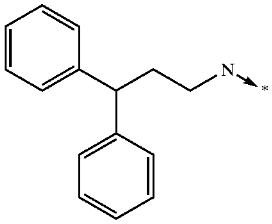 | 87.1 | 5.41 | 533.29 |
| 1875 | 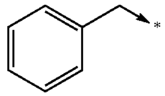 | 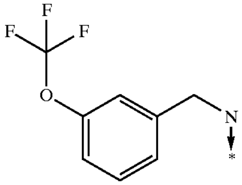 | 89.5 | 5.14 | 513.22 |
| 1876 | 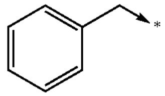 | 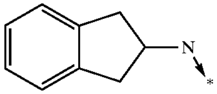 | 47.8 | 4.82 | 455.24 |

-continued
| | | | | | |
|---|---|---|---|---|---|
| 1877 | 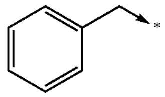 | 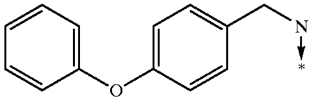 | 77.1 | 5.32 | 521.24 |
| 1878 | 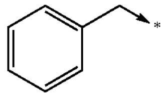 | 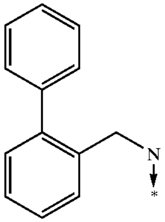 | 81.8 | 5.31 | 505.26 |
| 1879 | 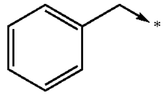 | 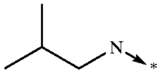 | 19.7 | 4.37 | 395.24 |
| 1880 | 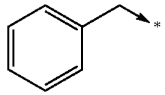 | 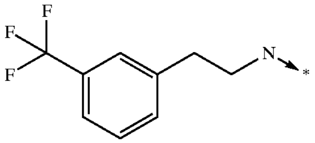 | 61.4 | 5.14 | 511.22 |
| 1881 | 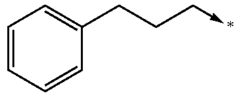 | 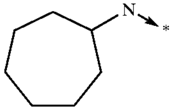 | 82.7 | 4.95 | 463.31 |
| 1882 | 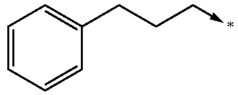 | 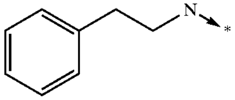 | 82.2 | 4.71 | 471.27 |
| 1883 | 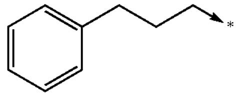 | 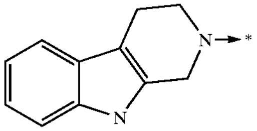 | 67.2 | 4.84 | 522.26 |

-continued
| | | | | | |
|---|---|---|---|---|---|
| 1884 | 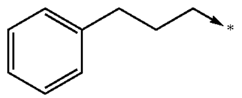 | 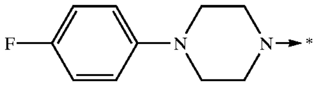 | 87.7 | 4.9 | 530.28 |
| 1885 | 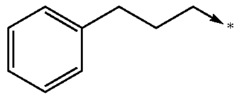 | 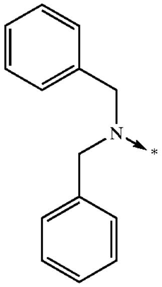 | 79.4 | 5.54 | 547.28 |
| 1886 | 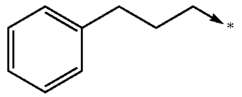 | 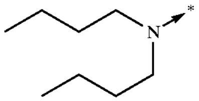 | 80.8 | 5.3 | 479.34 |
| 1887 | 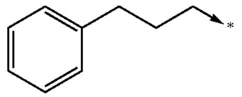 | 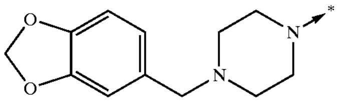 | 88.9 | 3.6 | 570.24 |
| 1888 | 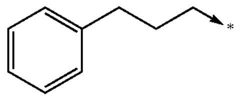 | 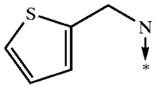 | 30.2 | 4.53 | 463.23 |
| 1889 | 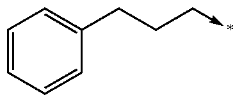 | 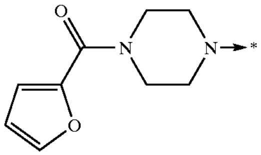 | 88.9 | 3.98 | 530.26 |

-continued
| | | | | | |
|---|---|---|---|---|---|
| 1890 | 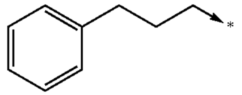 | 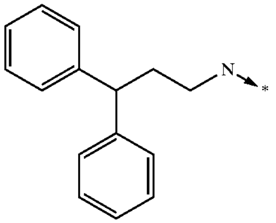 | 84.2 | 5.42 | 561.30 |
| 1891 | 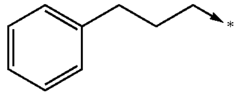 | 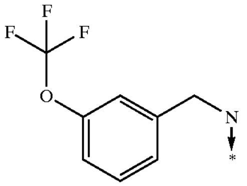 | 75.8 | 5.17 | 541.22 |
| 1892 | 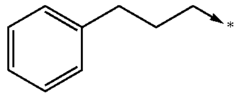 | 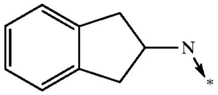 | 85.8 | 4.86 | 483.28 |
| 1893 | 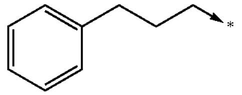 | 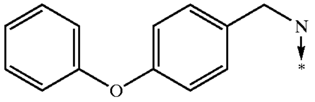 | 71.7 | 5.33 | 549.26 |
| 1894 | 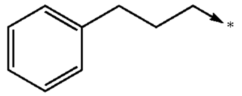 | 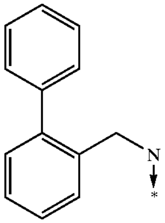 | 86.6 | 5.34 | 533.29 |
| 1895 | 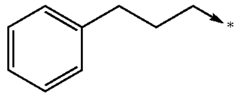 | 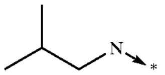 | 54.1 | 4.43 | 423.28 |

-continued
| | | | | | |
|---|---|---|---|---|---|
| 1896 | 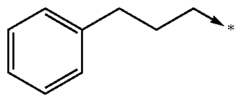 | 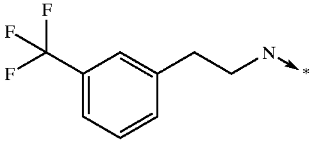 | 47.7 | 5.16 | 539.26 |
| 1897 | 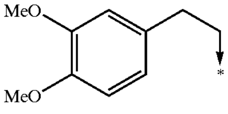 | 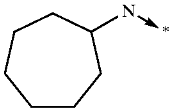 | 74.6 | 4.44 | 509.30 |
| 1898 | 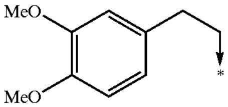 | 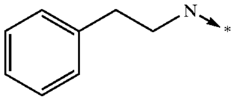 | 77.6 | 4.2 | 517.27 |
| 1899 | 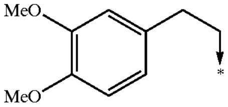 | 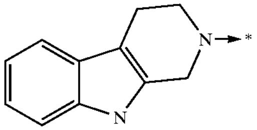 | 38.8 | 4.53 | 568.26 |
| 1900 | 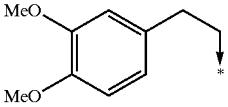 | 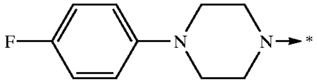 | 80.1 | 4.5 | 576.3 |
| 1901 | 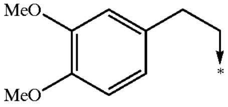 | 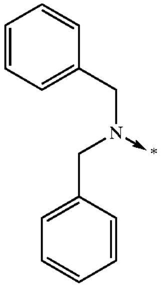 | 72.3 | 5.17 | 593.30 |

-continued
| | | | | | |
|---|---|---|---|---|---|
| 1902 | 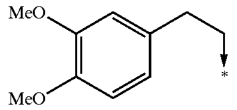 | 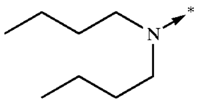 | 77.0 | 4.88 | 525.34 |
| 1903 | 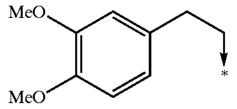 | 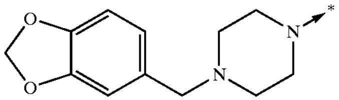 | 80.5 | 3.3 | 616.3 |
| 1904 | 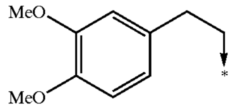 | 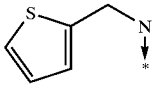 | 34.6 | 4.03 | 509.21 |
| 1905 | 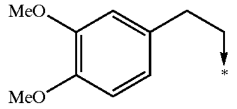 | 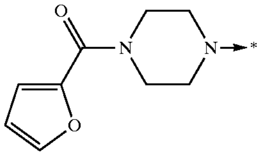 | 81.3 | 3.6 | 576.2 |
| 1906 | 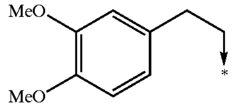 | 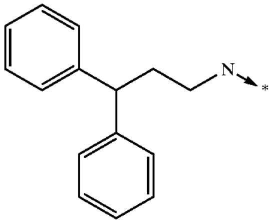 | 77.1 | 5.04 | 607.31 |
| 1907 | 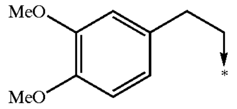 | 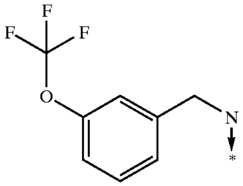 | 79.6 | 4.76 | 587.24 |

-continued
| | | | | | |
|---|---|---|---|---|---|
| 1908 | 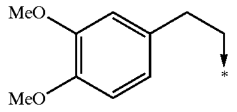 | 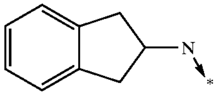 | 77.8 | 4.38 | 529.28 |
| 1909 | 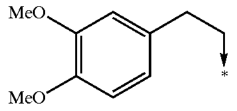 | 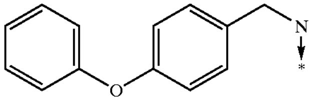 | 78.0 | 4.95 | 595.28 |
| 1910 | 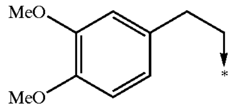 | 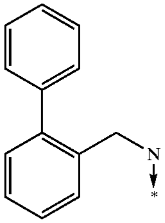 | 81.1 | 4.88 | 579.29 |
| 1911 | 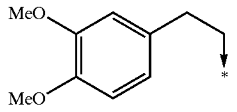 | 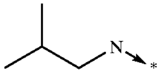 | 32.4 | 3.89 | 469.29 |
| 1912 | 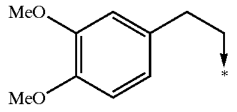 | 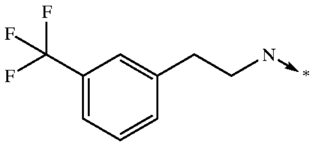 | 49.3 | 4.7 | 585.26 |
| 1913 | 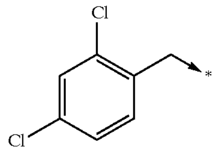 | 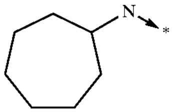 | 87.0 | 5.59 | 503.20 |
| 1914 | 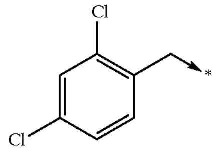 | 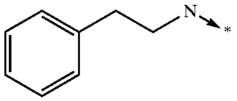 | 88.5 | 5.3 | 511.15 |

-continued
| | | | | | |
|---|---|---|---|---|---|
| 1915 | 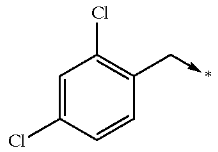 | 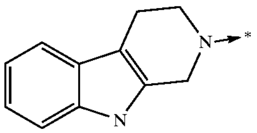 | 69.5 | 5.28 | 562.16 |
| 1916 | 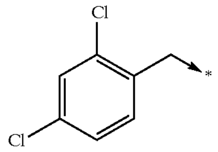 | 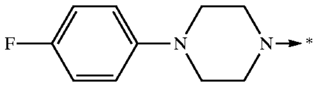 | 89.4 | 5.3 | 570.1 |
| 1917 | 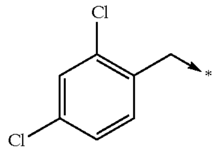 | 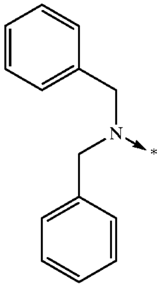 | 79.1 | 5.98 | 587.17 |
| 1918 | 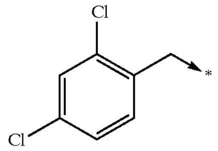 | 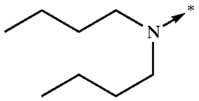 | 82.4 | 5.84 | 519.23 |
| 1919 | 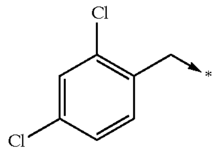 | 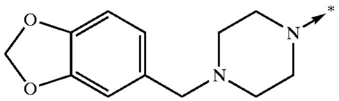 | 89.5 | 3.9 | 610.1 |

-continued
| | | | | | |
|---|---|---|---|---|---|
| 1920 | 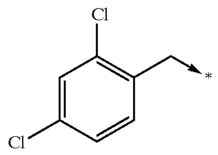 | 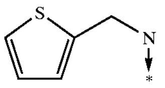 | 27.2 | 5.12 | 503.11 |
| 1921 | 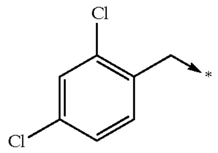 | 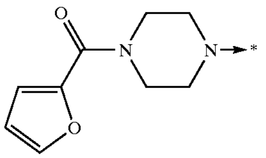 | 88.6 | 4.41 | 570.13 |
| 1922 | 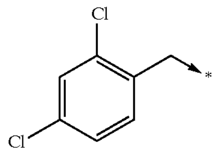 | 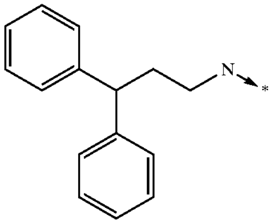 | 86.4 | 5.91 | 601.19 |
| 1923 | 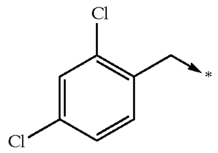 | 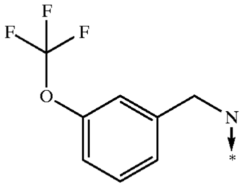 | 84.9 | 5.66 | 581.11 |
| 1924 | 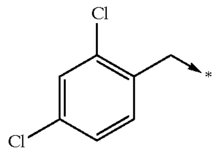 | 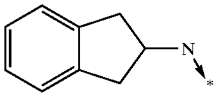 | 86.4 | 5.44 | 523.13 |
| 1925 | 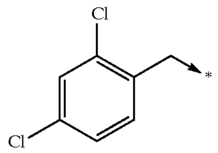 | 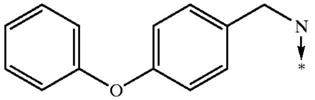 | 61.9 | 5.81 | 589.16 |

-continued
| | | | | | |
|---|---|---|---|---|---|
| 1926 | 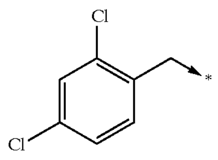 | 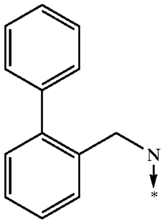 | 84.7 | 5.85 | 573.15 |
| 1927 | 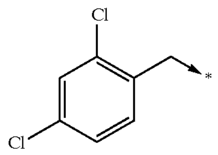 | 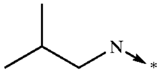 | 36.8 | 5.1 | 463.16 |
| 1928 | 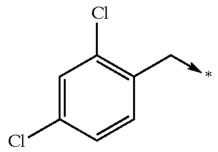 | 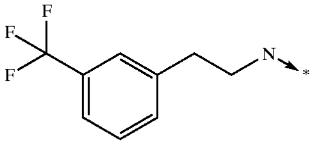 | 76.4 | 5.68 | 579.13 |
| 1929 | 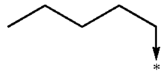 | 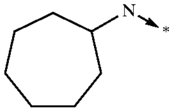 | 79.4 | 4.65 | 415.30 |
| 1930 | 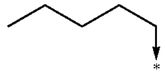 | 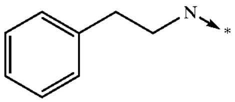 | 84.5 | 4.41 | 423.29 |
| 1931 | 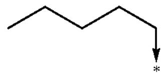 | 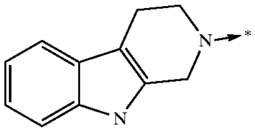 | 44.0 | 4.62 | 474.29 |
| 1932 | 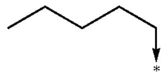 | 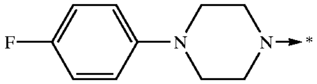 | 86.1 | 4.65 | 482.3 |

-continued
| | | | | | |
|---|---|---|---|---|---|
| 1933 | 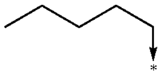 | 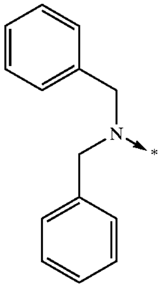 | 78.5 | 5.33 | 499.31 |
| 1934 | 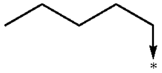 | 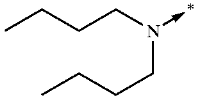 | 79.6 | 5.06 | 431.33 |
| 1935 | 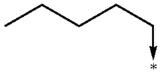 | 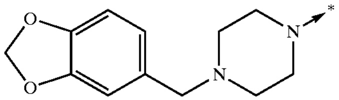 | 84.6 | 3.4 | 522.30 |
| 1936 | 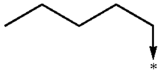 | 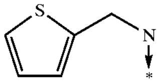 | 54.6 | 4.2 | 415.21 |
| 1937 | 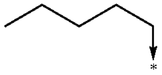 | 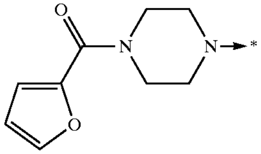 | 85.4 | 3.7 | 482.29 |
| 1938 | 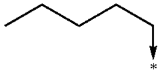 | 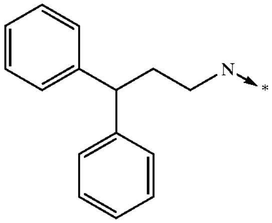 | 83.5 | 5.21 | 513.32 |

-continued
| | | | | | |
|---|---|---|---|---|---|
| 1939 | 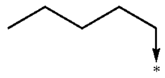 | 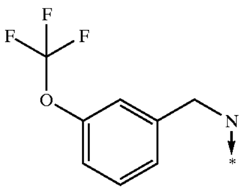 | 85.7 | 4.92 | 493.24 |
| 1940 | 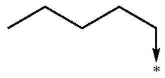 | 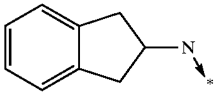 | 83.0 | 4.58 | 435.29 |
| 1941 | 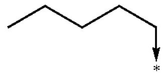 | 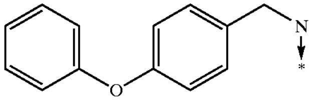 | 75.1 | 5.1 | 501.31 |
| 1942 | 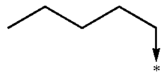 | 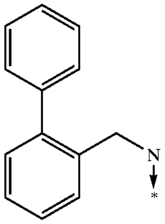 | 88.2 | 5.1 | 485.31 |
| 1943 | 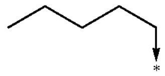 | 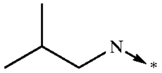 | 76.1 | 4.08 | 375.28 |
| 1944 | 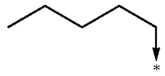 | 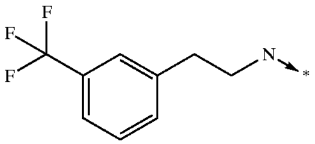 | 81.1 | 4.9 | 491.28 |

-continued
| | | 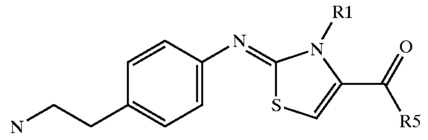 | | | |
|---|---|---|---|---|---|
| 1945 | 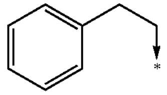 | 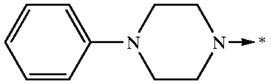 | 84.3 | 4.24 | 512.26 |
| 1946 | 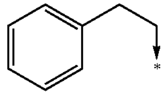 | 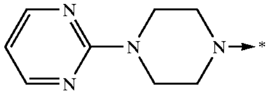 | 85.4 | 3.63 | 514.25 |
| 1947 | 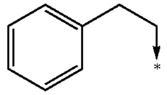 | 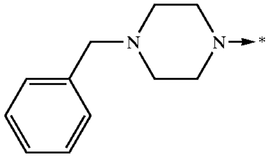 | 86.8 | 3.1 | 526.27 |
| 1948 | 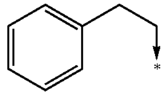 | 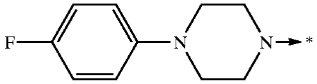 | 87.7 | 4.32 | 530.23 |
| 1949 | 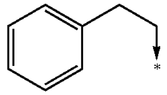 | 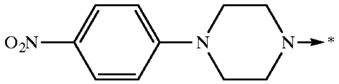 | 87.5 | 4.24 | 557.23 |
| 1950 | 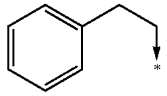 | 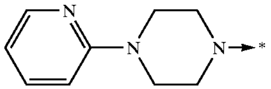 | 88.8 | 2.9 | 513.26 |
| 1951 | 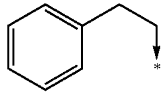 | 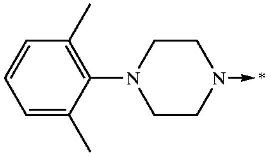 | 84.5 | 4.92 | 540.28 |

-continued
| | | | | | |
|---|---|---|---|---|---|
| 1952 | 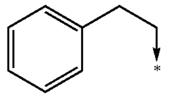 | 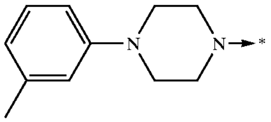 | 87.7 | 4.49 | 526.27 |
| 1953 | 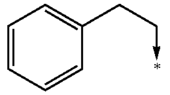 | 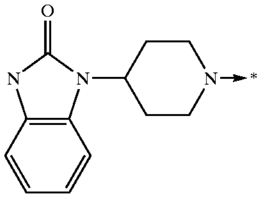 | 62.5 | 3.66 | 567.26 |
| 1954 | 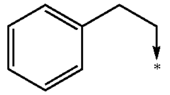 | 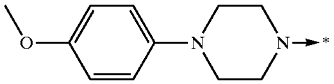 | 89 | 4.08 | 542.26 |
| 1955 | 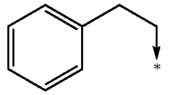 | 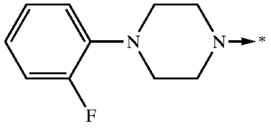 | 87.7 | 4.38 | 530.24 |
| 1956 | 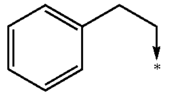 | 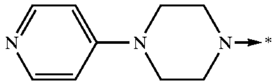 | 82.4 | 2.7 | 513.28 |
| 1957 | 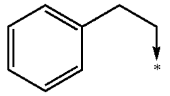 | 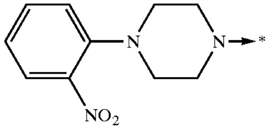 | 87.7 | 4.31 | 557.23 |
| 1958 | 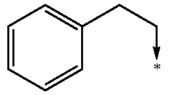 | 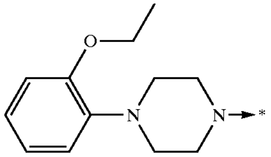 | 91.0 | 4.44 | 556.27 |

-continued
| | | | | | |
|---|---|---|---|---|---|
| 1959 | 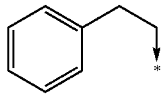 | 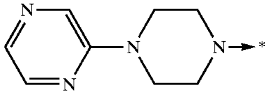 | 80.7 | 3.44 | 514.25 |
| 1960 | 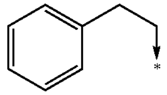 | 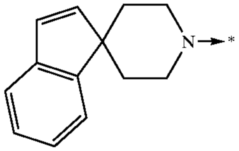 | 68.6 | 4.67 | 535.24 |
| 1961 | 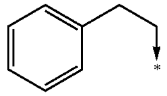 | 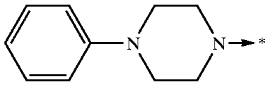 | 85.3 | 4.32 | 526.27 |
| 1962 | 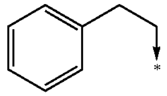 | 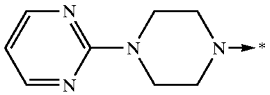 | 83.0 | 3.75 | 528.25 |
| 1963 | 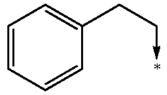 | 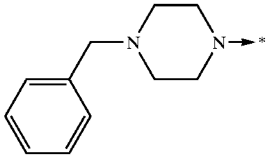 | 88.7 | 3.28 | 540.28 |
| 1964 | 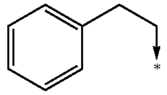 | 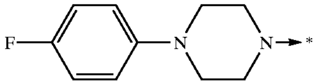 | 86.8 | 4.37 | 544.25 |
| 1965 | 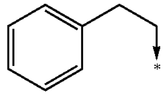 | 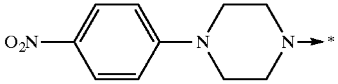 | 89.4 | 4.29 | 571.24 |
| 1966 | 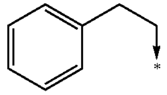 | 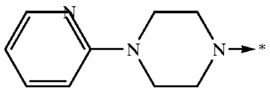 | 86.9 | 3.1 | 527.25 |

-continued
| | | | | | |
|---|---|---|---|---|---|
| 1967 | 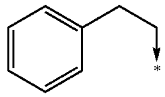 | 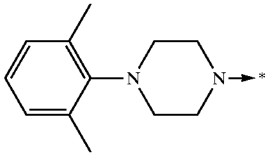 | 86.1 | 4.94 | 554.29 |
| 1968 | 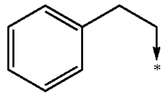 | 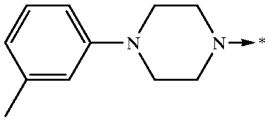 | 87.6 | 4.54 | 540.27 |
| 1969 | 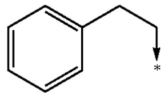 | 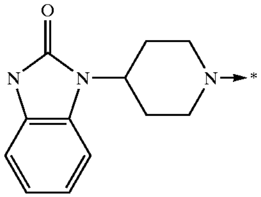 | 65.4 | 3.76 | 581.27 |
| 1970 | 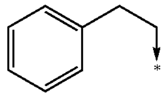 | 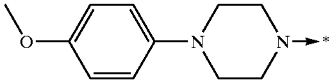 | 86.3 | 4.16 | 556.28 |
| 1971 | 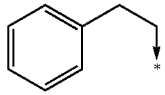 | 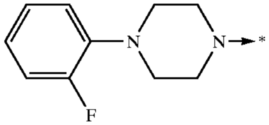 | 86.0 | 4.43 | 544.25 |
| 1972 | 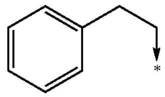 | 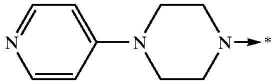 | 83.2 | 2.8 | 527.3 |
| 1973 | 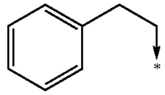 | 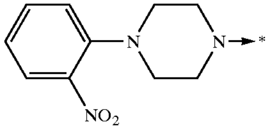 | 84.8 | 4.38 | 571.24 |

-continued
| | | | | | |
|---|---|---|---|---|---|
| 1974 | 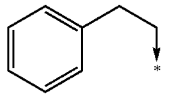 | 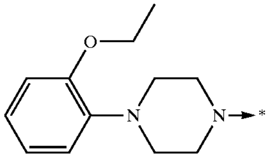 | 87.8 | 4.5 | 570.28 |
| 1975 | 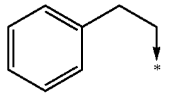 | 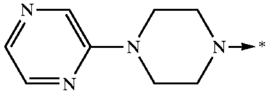 | 80.9 | 3.55 | 528.26 |
| 1976 | 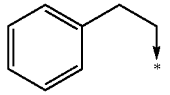 | 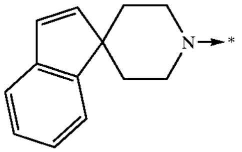 | 62.7 | 4.71 | 549.27 |
| 1977 | 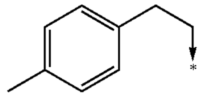 | 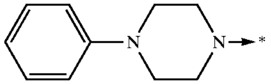 | 85.7 | 4.41 | 526.29 |
| 1978 | 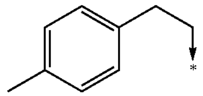 | 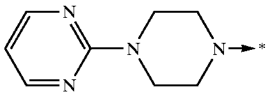 | 84.2 | 3.82 | 528.27 |
| 1979 | 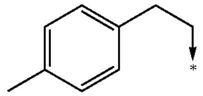 | 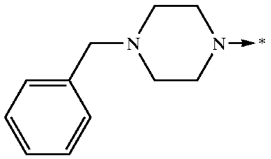 | 87.4 | 3.28 | 540.28 |
| 1980 | 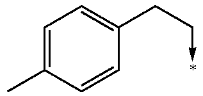 | 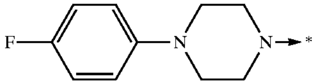 | 86.6 | 4.47 | 544.24 |
| 1981 | 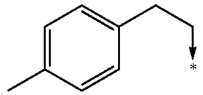 | 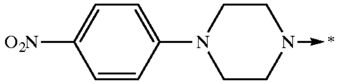 | 86.4 | 4.38 | 571.24 |

-continued
| | | | | | |
|---|---|---|---|---|---|
| 1982 | 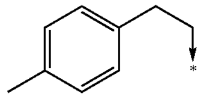 | 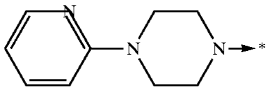 | 85.9 | 3.1 | 527.27 |
| 1983 | 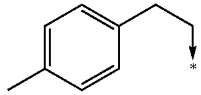 | 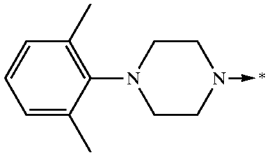 | 85.3 | 5.06 | 554.28 |
| 1984 | 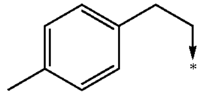 | 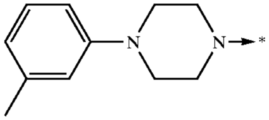 | 85.3 | 4.66 | 540.28 |
| 1985 | 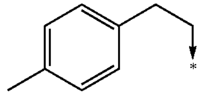 | 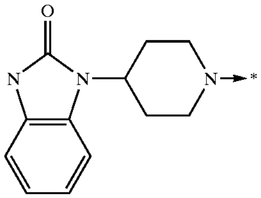 | 60.8 | 3.8 | 581.28 |
| 1986 | 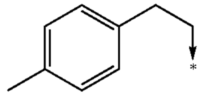 | 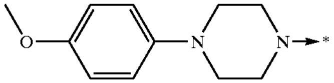 | 86.1 | 4.25 | 556.28 |
| 1987 | 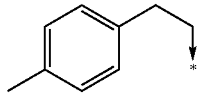 | 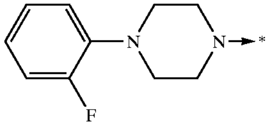 | 86.4 | 4.54 | 544.25 |
| 1988 | 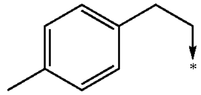 | 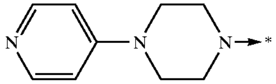 | 75.9 | 2.86 | 527.28 |

-continued
| | | | | | |
|---|---|---|---|---|---|
| 1989 | 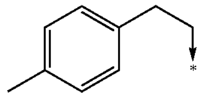 | 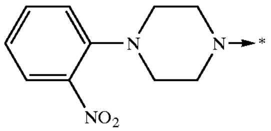 | 86.5 | 4.46 | 571.24 |
| 1990 | 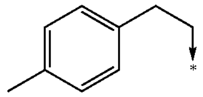 | 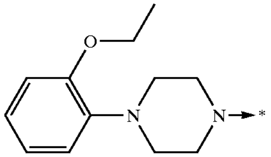 | 88.4 | 4.6 | 570.29 |
| 1991 | 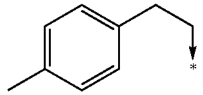 | 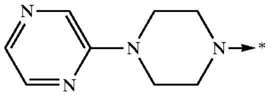 | 79.8 | 3.62 | 528.27 |
| 1992 | 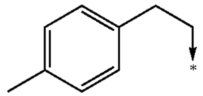 | 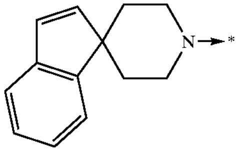 | 63.2 | 4.82 | 549.26 |
| 1993 | 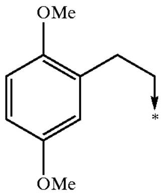 | 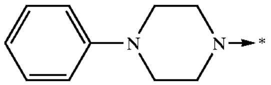 | 81.8 | 4.15 | 572.25 |
| 1994 | 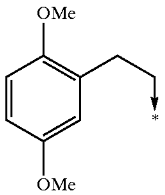 | 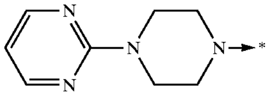 | 81.0 | 3.58 | 574.25 |

-continued
| | | | | | |
|---|---|---|---|---|---|
| 1995 | 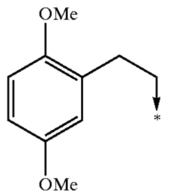 | 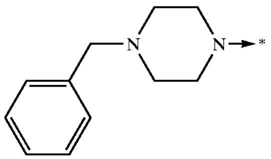 | 83.5 | 3.08 | 586.3 |
| 1996 | 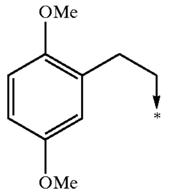 | 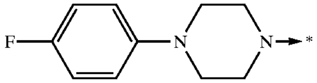 | 84.3 | 4.2 | 590.27 |
| 1997 | 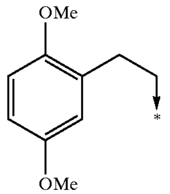 | 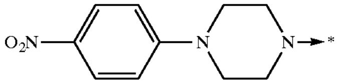 | 85.3 | 4.12 | 617.26 |
| 1998 | 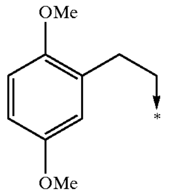 | 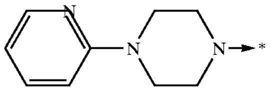 | 86.1 | 2.91 | 573.28 |
| 1999 | 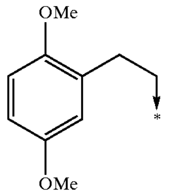 | 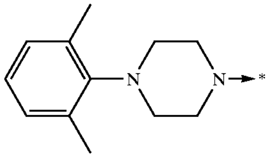 | 85.5 | 4.74 | 600.31 |

-continued
| | | | | | |
|---|---|---|---|---|---|
| 2000 | 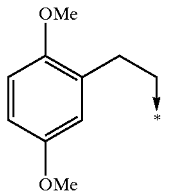 | 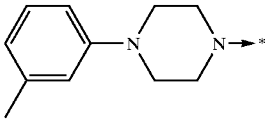 | 87.3 | 4.37 | 586.28 |
| 2001 | 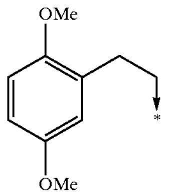 | 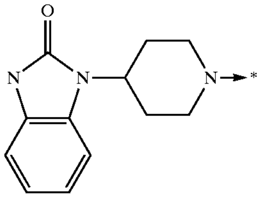 | 68.4 | 3.6 | 627.28 |
| 2002 | 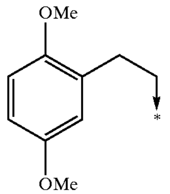 | 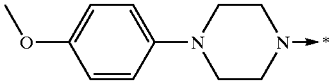 | 85.4 | 3.98 | 602.28 |
| 2003 | 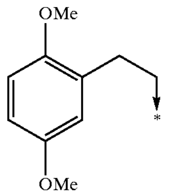 | 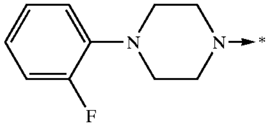 | 83.1 | 4.26 | 590.27 |
| 2004 | 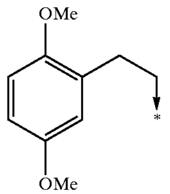 | 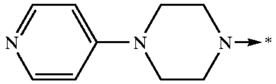 | 84.5 | 2.7 | 573.26 |

-continued
| | | | | | |
|---|---|---|---|---|---|
| 2005 | 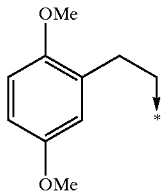 | 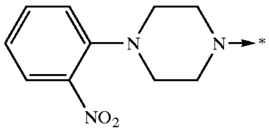 | 85.9 | 4.2 | 617.27 |
| 2006 | 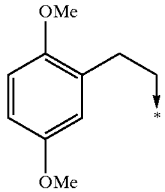 | 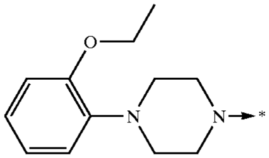 | 86.9 | 4.32 | 616.31 |
| 2007 | 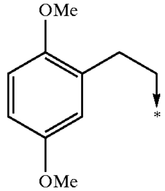 | 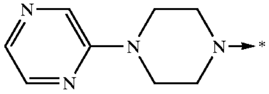 | 81.2 | 3.4 | 574.24 |
| 2008 | 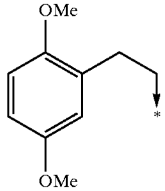 | 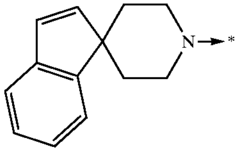 | 69.0 | 4.54 | 595.29 |
| 2009 | 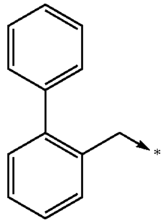 | 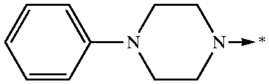 | 82.1 | 4.72 | 574.25 |

-continued
| | | | | | |
|---|---|---|---|---|---|
| 2010 | 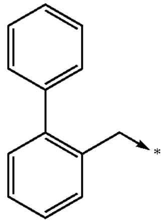 | 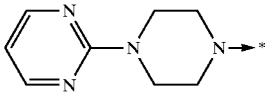 | 80.1 | 4.15 | 576.27 |
| 2011 | 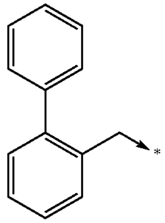 | 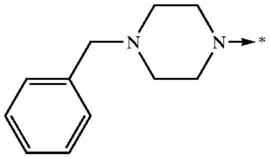 | 83.9 | 3.53 | 588.27 |
| 2012 | 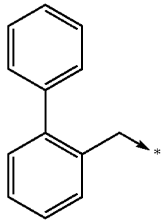 | 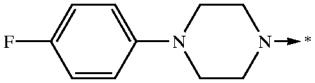 | 80.8 | 4.78 | 592.26 |
| 2013 | 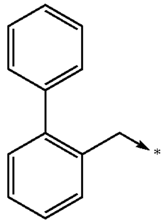 | 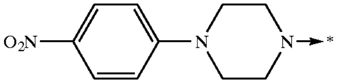 | 83.0 | 4.68 | 619.26 |

-continued
| | | | | | |
|---|---|---|---|---|---|
| 2014 | 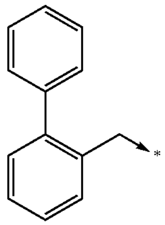 | 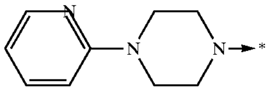 | 85.6 | 3.35 | 575.25 |
| 2015 | 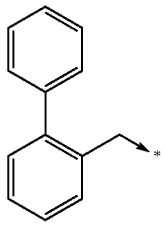 | 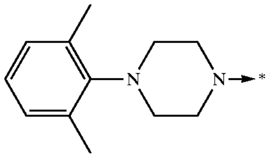 | 82.9 | 5.41 | 602.30 |
| 2016 | 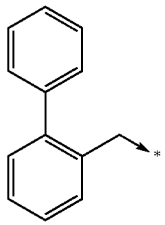 | 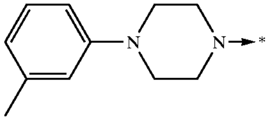 | 81.9 | 4.96 | 588.26 |
| 2017 | 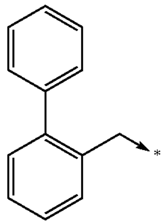 | 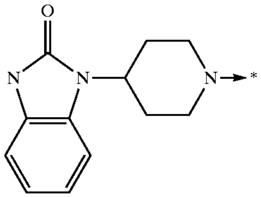 | 58.6 | 4.09 | 629.29 |

-continued
| | | | | | |
|---|---|---|---|---|---|
| 2018 | 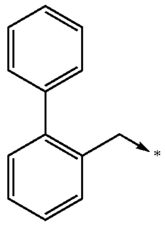 | 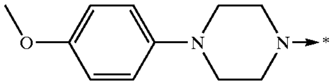 | 81.7 | 4.53 | 604.27 |
| 2019 | 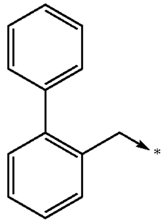 | 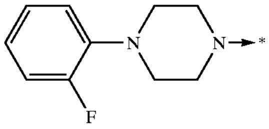 | 81.4 | 4.84 | 592.26 |
| 2020 | 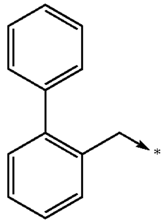 | 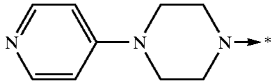 | 78.7 | 3.06 | 575.31 |
| 2021 | 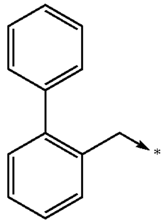 | 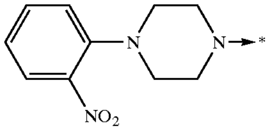 | 83.9 | 4.74 | 619.25 |

-continued
| | | | | | |
|---|---|---|---|---|---|
| 2022 | 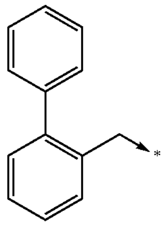 | 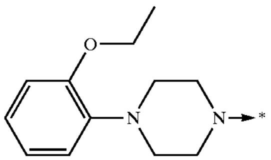 | 82.6 | 4.89 | 618.29 |
| 2023 | 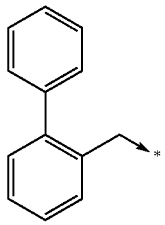 | 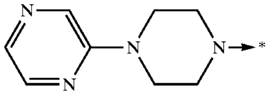 | 79.5 | 3.9 | 576.27 |
| 2024 | 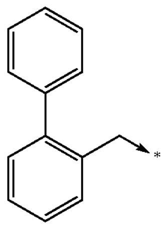 | 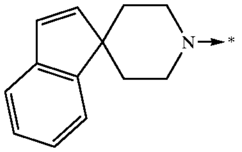 | 64.2 | 5.15 | 597.27 |
| 2025 | 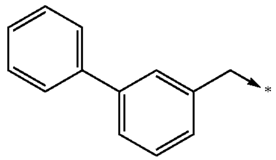 | 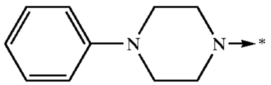 | 88.8 | 4.94 | 574.23 |
| 2026 | 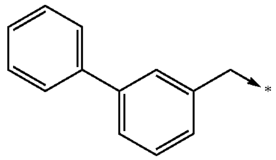 | 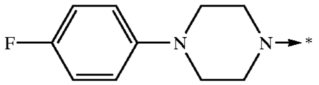 | 88.4 | 4.96 | 592.25 |

-continued
| | | | | | |
|---|---|---|---|---|---|
| 2027 | 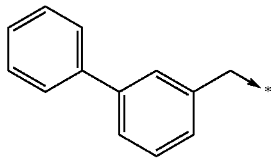 | 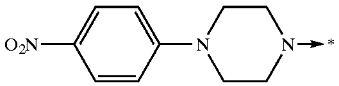 | 87.7 | 4.86 | 619.24 |
| 2028 | 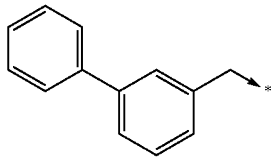 | 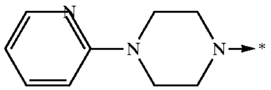 | 89.7 | 3.61 | 575.2 |
| 2029 | 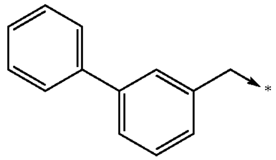 | 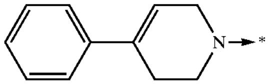 | 70.4 | 5.13 | 571.25 |
| 2030 | 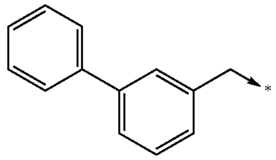 | 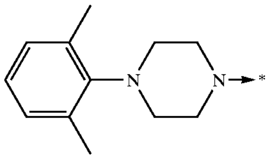 | 88.0 | 5.58 | 602.28 |
| 2031 | 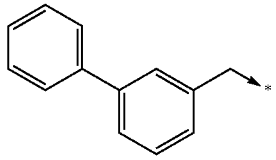 | 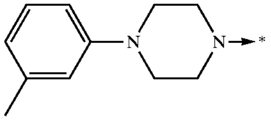 | 87.8 | 5.15 | 588.26 |
| 2032 | 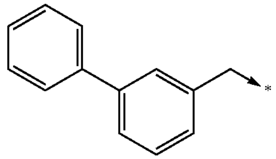 | 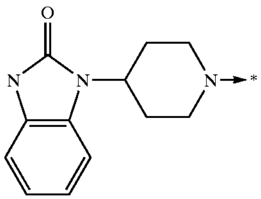 | 76.5 | 4.24 | 629.28 |

-continued
| | | | | | |
|---|---|---|---|---|---|
| 2033 | 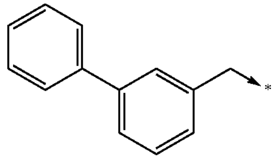 | 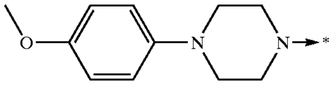 | 88.8 | 4.7 | 604.27 |
| 2034 | 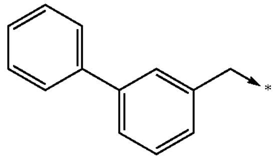 | 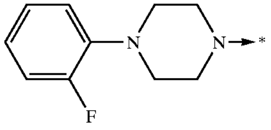 | 88.3 | 5.04 | 592.25 |
| 2035 | 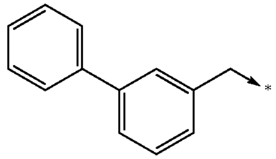 | 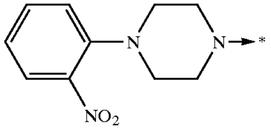 | 89.5 | 4.96 | 619.24 |
| 2036 | 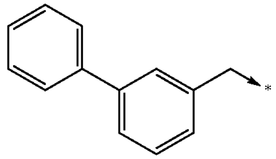 | 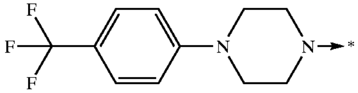 | 87.5 | 5.41 | 642.26 |
| 2037 | 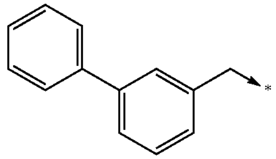 | 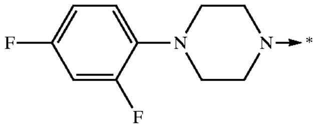 | 88.9 | 5.12 | 610.24 |
| 2038 | 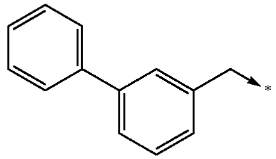 | 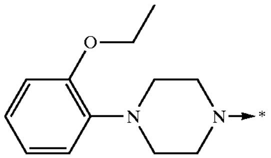 | 89.4 | 5.07 | 618.27 |

-continued
| | | | | | |
|---|---|---|---|---|---|
| 2039 | 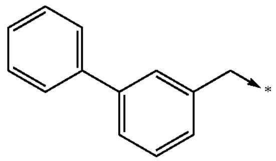 | 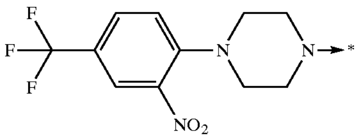 | 88.7 | 5.42 | 687.24 |
| 2040 | 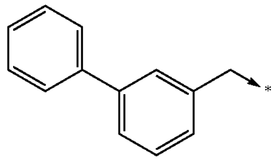 | 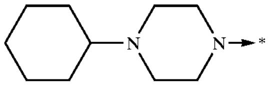 | 87.7 | 3.68 | 580.30 |
| 2041 | 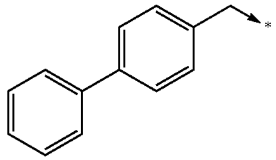 | 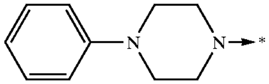 | 85.2 | 4.89 | 574.23 |
| 2042 | 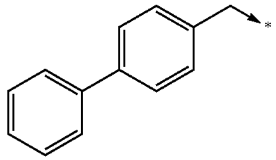 | 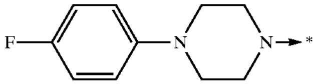 | 84.4 | 4.9 | 592.25 |
| 2043 | 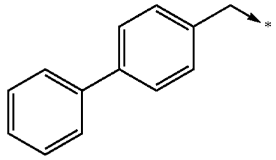 | 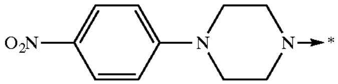 | 84.7 | 4.78 | 619.23 |
| 2044 | 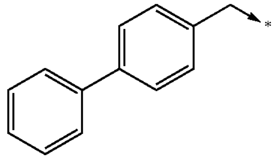 | 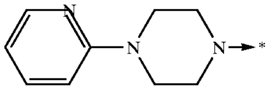 | 89.0 | 3.58 | 575.25 |

-continued
| | | | | | |
|---|---|---|---|---|---|
| 2045 | 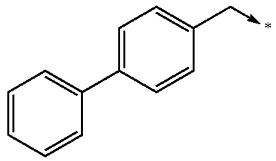 | 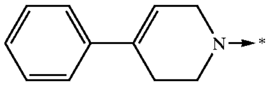 | 61.5 | 5.16 | 571.22 |
| 2046 | 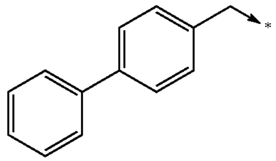 | 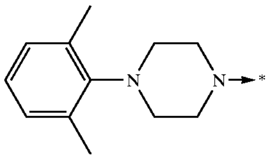 | 83.2 | 5.57 | 602.28 |
| 2047 | 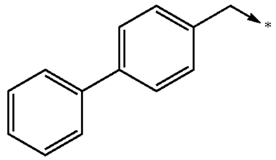 | 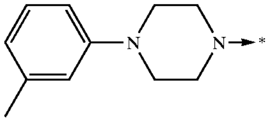 | 84.4 | 5.1 | 588.25 |
| 2048 | 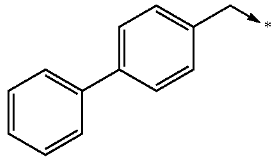 | 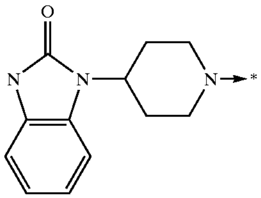 | 73.2 | 4.25 | 629.27 |
| 2049 | 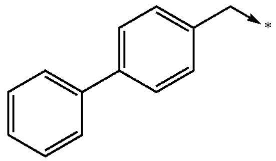 | 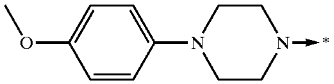 | 85.5 | 4.64 | 604.26 |
| 2050 | 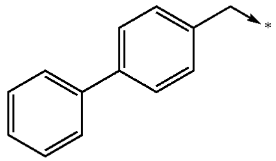 | 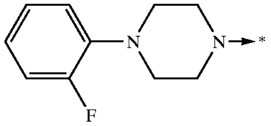 | 85.6 | 4.99 | 592.2 |

-continued
| | | | | | |
|---|---|---|---|---|---|
| 2051 | 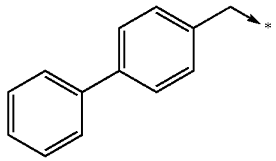 | 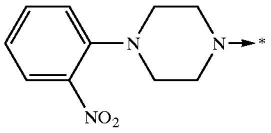 | 85.7 | 4.93 | 619.24 |
| 2052 | 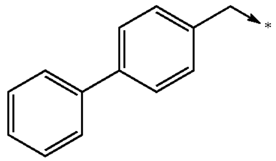 | 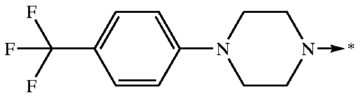 | 86.2 | 5.34 | 642.25 |
| 2053 | 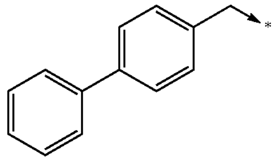 | 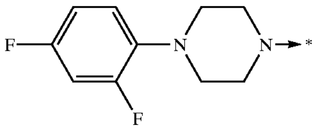 | 85.1 | 5.06 | 610.23 |
| 2054 | 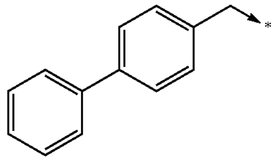 | 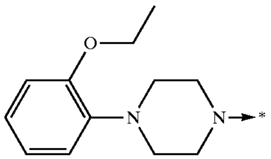 | 84.6 | 5.06 | 618.27 |
| 2055 | 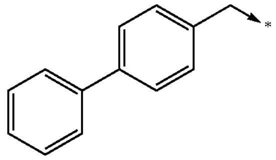 | 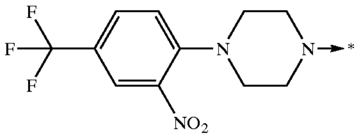 | 85.4 | 5.37 | 687.23 |
| 2056 | 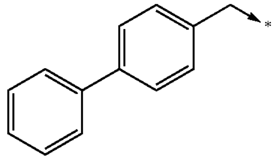 | 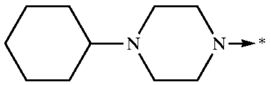 | 85.8 | 3.68 | 580.30 |

-continued
| | | | | | |
|---|---|---|---|---|---|
| 2057 | 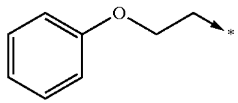 | 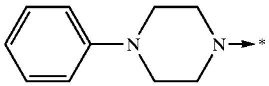 | 68.0 | 4.37 | 528.26 |
| 2058 | 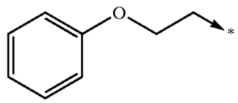 | 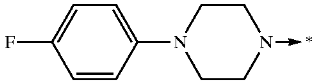 | 86.3 | 4.41 | 546.22 |
| 2059 | 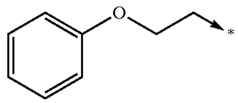 | 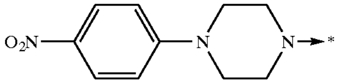 | 88.1 | 4.32 | 573.19 |
| 2060 | 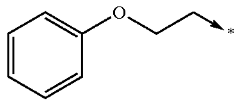 | 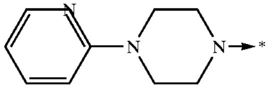 | 86.1 | 3 | 529.25 |
| 2061 | 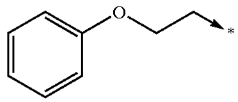 | 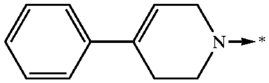 | 67.2 | 4.56 | 525.25 |
| 2062 | 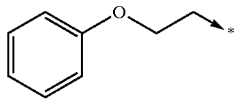 | 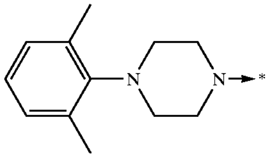 | 91.2 | 4.98 | 556.26 |
| 2063 | 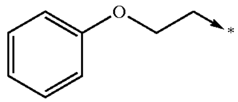 | 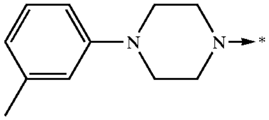 | 87.8 | 4.56 | 542.26 |

-continued
| | | | | | |
|---|---|---|---|---|---|
| 2064 | 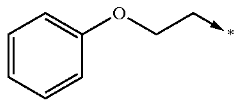 | 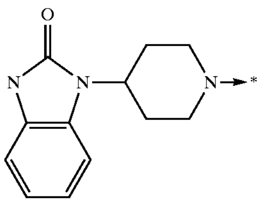 | 75.6 | 3.73 | 583.23 |
| 2065 | 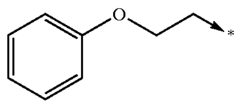 | 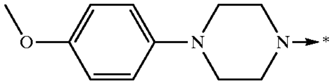 | 88.7 | 4.16 | 558.23 |
| 2066 | 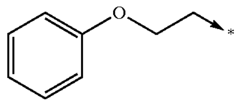 | 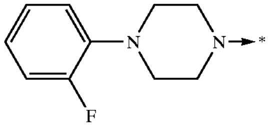 | 88.4 | 4.46 | 546.22 |
| 2067 | 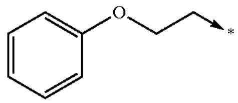 | 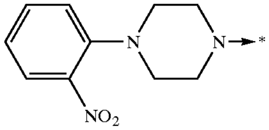 | 87.4 | 4.4 | 573.20 |
| 2068 | 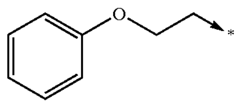 | 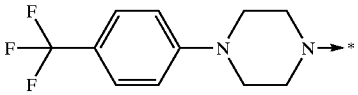 | 87.7 | 4.88 | 596.21 |
| 2069 | 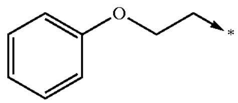 | 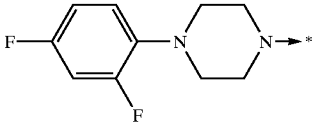 | 87.9 | 4.56 | 564.21 |
| 2070 | 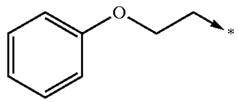 | 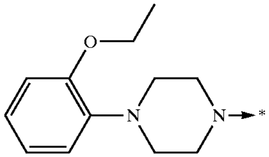 | 87.5 | 4.51 | 572.26 |

-continued
| | | | | | |
|---|---|---|---|---|---|
| 2071 | 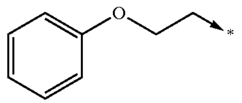 | 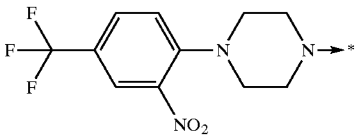 | 88.8 | 4.91 | 641.20 |
| 2072 | 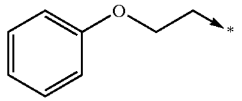 | 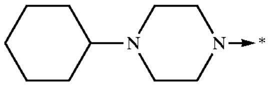 | 86.2 | 3.08 | 534.27 |
| 2073 | 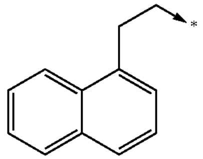 | 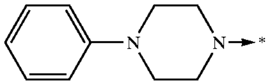 | 71.7 | 4.78 | 562.25 |
| 2074 | 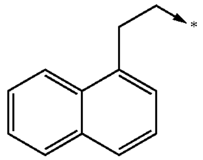 | 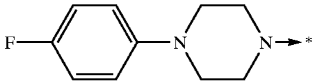 | 82.1 | 4.8 | 580.23 |
| 2075 | 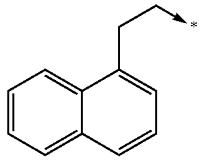 | 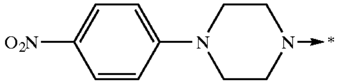 | 82.6 | 4.68 | 607.23 |
| 2076 | 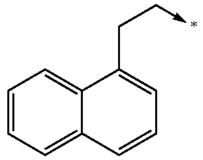 | 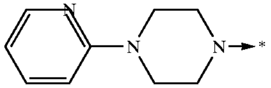 | 79.5 | 3.4 | 563.21 |

-continued
| | | | | | |
|---|---|---|---|---|---|
| 2077 | 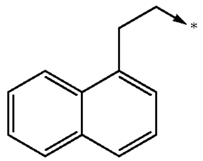 | 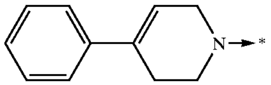 | 67.5 | 4.92 | 559.23 |
| 2078 | 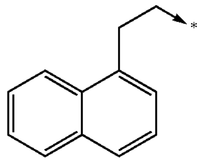 | 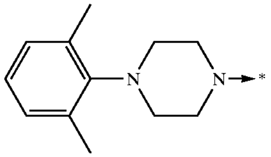 | 83.0 | 5.39 | 590.27 |
| 2079 | 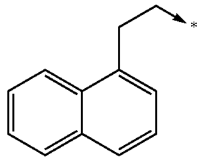 | 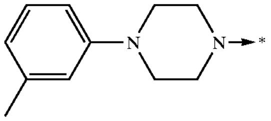 | 82.5 | 4.98 | 576.26 |
| 2080 | 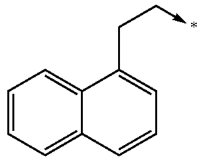 | 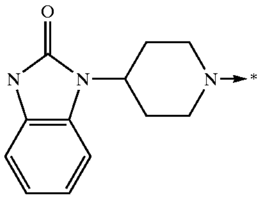 | 42.5 | 4.1 | 617.23 |
| 2081 | 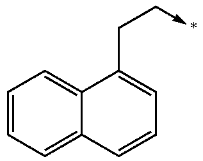 | 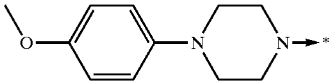 | 86.9 | 4.58 | 592.26 |
| 2082 | 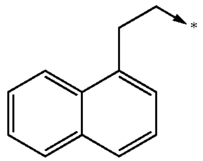 | 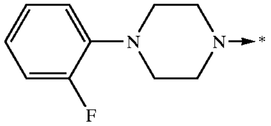 | 82.5 | 4.88 | 580.23 |

-continued
| | | | | | |
|---|---|---|---|---|---|
| 2083 | 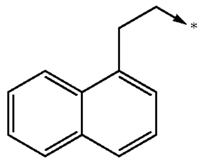 | 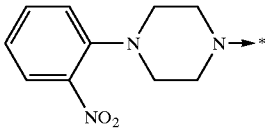 | 81.4 | 4.77 | 607.23 |
| 2084 | 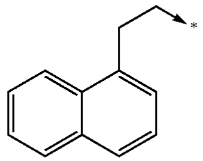 | 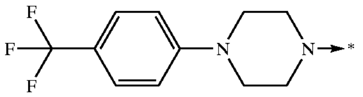 | 82.3 | 5.24 | 630.26 |
| 2085 | 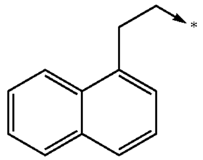 | 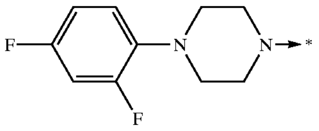 | 83.5 | 4.97 | 598.20 |
| 2086 | 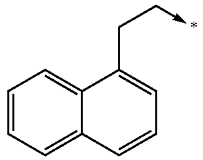 | 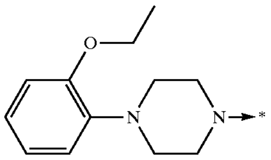 | 81.6 | 4.93 | 606.28 |
| 2087 | 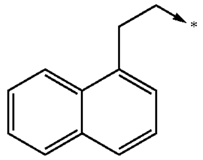 | 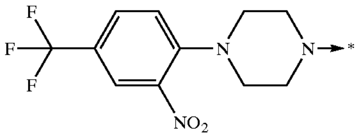 | 82.7 | 5.25 | 675.23 |
| 2088 | 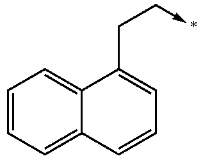 | 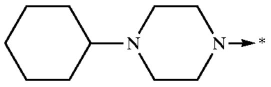 | 84.4 | 3.4 | 568.26 |

-continued
| | | | | | |
|---|---|---|---|---|---|
| 2089 | 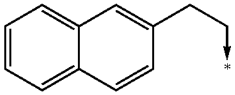 | 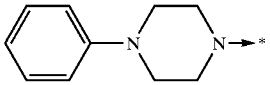 | 67.0 | 4.64 | 562.24 |
| 2090 | 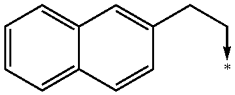 | 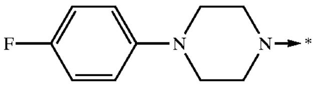 | 83.0 | 83.0 | 4.66 |
| 2091 | 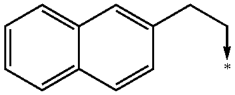 | 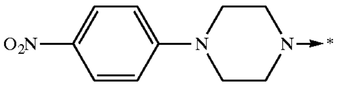 | 83.6 | 4.54 | 607.22 |
| 2092 | 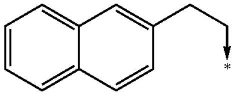 | 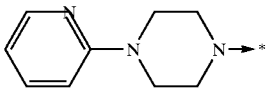 | 82.5 | 3.3 | 563.25 |
| 2093 | 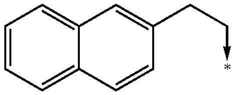 | 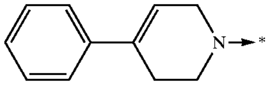 | 84.2 | 4.8 | 559.22 |
| 2094 | 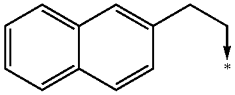 | 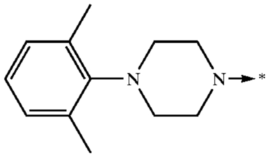 | 86.2 | 5.21 | 590.29 |
| 2095 | 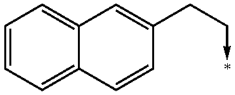 | 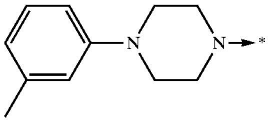 | 83.2 | 4.82 | 576.28 |
| 2096 | 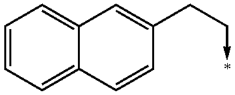 | 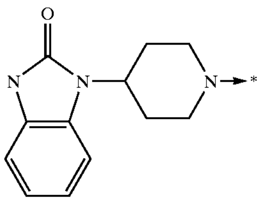 | 62.8 | 3.99 | 617.26 |

-continued
| | | | | | |
|---|---|---|---|---|---|
| 2097 | 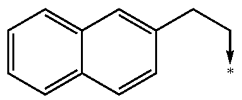 | 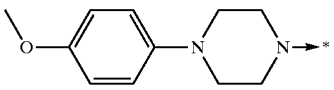 | 86.0 | 4.44 | 592.2 |
| 2098 | 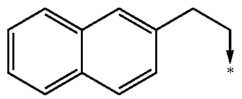 | 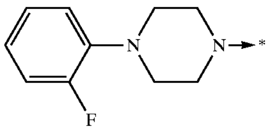 | 85.8 | 4.72 | 580.25 |
| 2099 | 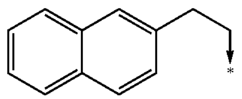 | 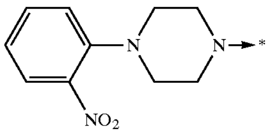 | 84.0 | 4.62 | 607.23 |
| 2100 | 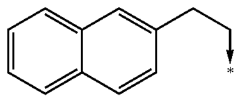 | 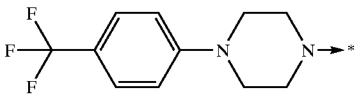 | 83.4 | 5.09 | 630.26 |
| 2101 | 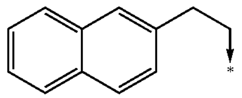 | 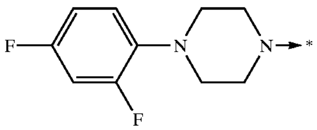 | 84.8 | 4.8 | 598.21 |
| 2102 | 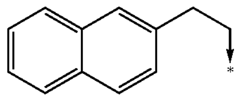 | 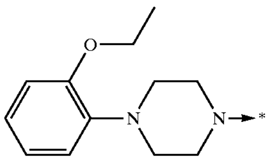 | 83.7 | 4.78 | 606.29 |
| 2103 | 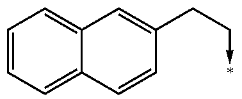 | 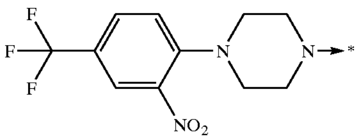 | 83.6 | 5.1 | 675.24 |

-continued
| | | | | | |
|---|---|---|---|---|---|
| 2104 | 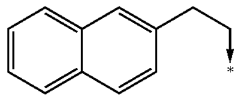 | 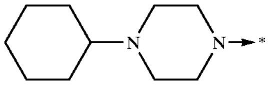 | 5.6 | 3.05 | 568.28 |
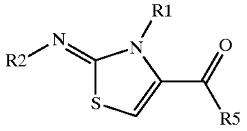
| Ex. | R5 | R2 | R1 | Purity (%) | rt (min.) | $[M + H]^+$ |
|---|---|---|---|---|---|---|
| 2105 | 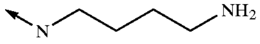 | 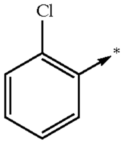 | 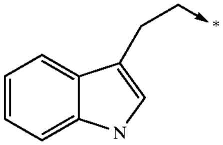 | 81.5 | 4.9 | 468.27 |
| 2106 | 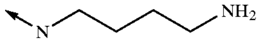 | 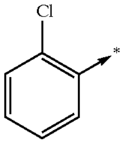 | 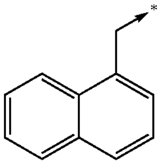 | 81.4 | 5.01 | 465.28 |
| 2107 | 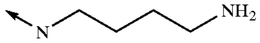 | 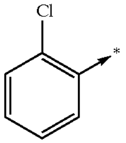 | 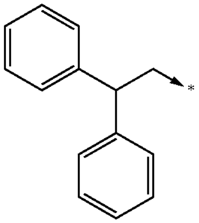 | 77.3 | 5.34 | 505.31 |
| 2108 | 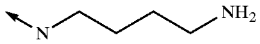 | 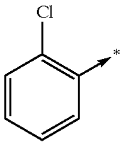 | 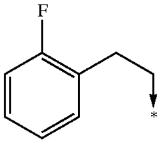 | 73.5 | 4.7 | 447.29 |

-continued
| | | | | | | |
|---|---|---|---|---|---|---|
| 2109 | 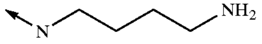 | 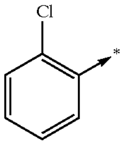 | 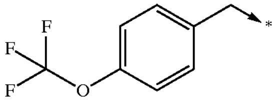 | 70.5 | 5.28 | 499.26 |
| 2110 | 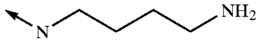 | 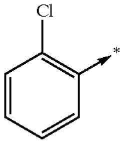 | 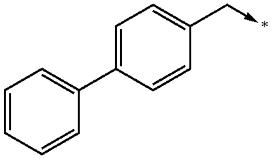 | 73.9 | 5.38 | 491.30 |
| 2111 | 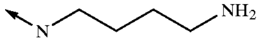 | 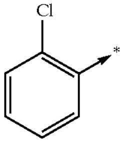 | 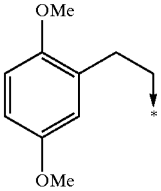 | 72.0 | 4.5 | 489.31 |
| 2112 | 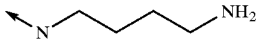 | 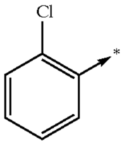 | 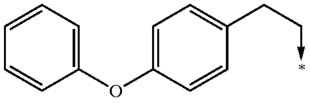 | 73.0 | 5.5 | 521.29 |
| 2113 | 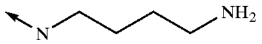 | 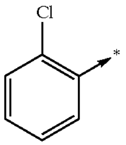 | 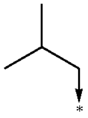 | 90.0 | 4.23 | 381.29 |
| 2114 | 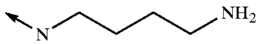 | 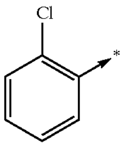 | 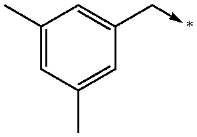 | 76.1 | 5.02 | 443.30 |

-continued
| | | | | | | |
|---|---|---|---|---|---|---|
| 2115 | 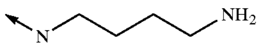 | 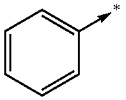 | 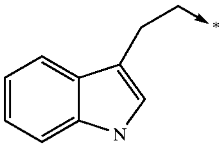 | 56.9 | 4.2 | 434.32 |
| 2116 | 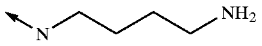 | 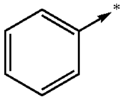 | 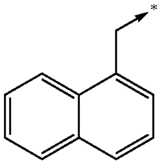 | 79.8 | 4.29 | 431.31 |
| 2117 | 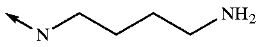 | 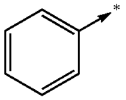 | 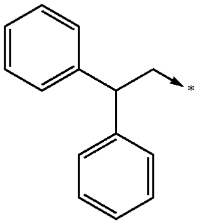 | 79.1 | 4.45 | 471.35 |
| 2118 | 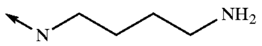 | 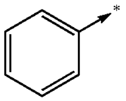 | 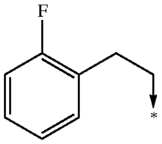 | 70.2 | 3.56 | 413.29 |
| 2119 | 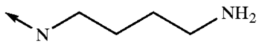 | 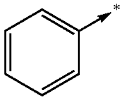 | 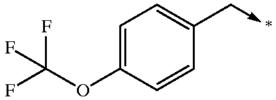 | 72.4 | 4.68 | 465.27 |
| 2120 | 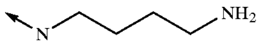 | 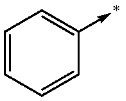 | 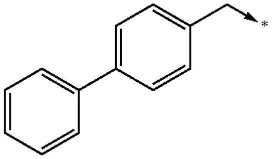 | 78.3 | 4.66 | 457.33 |

-continued
| | | | | | | |
|---|---|---|---|---|---|---|
| 2121 | 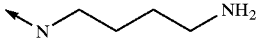 | 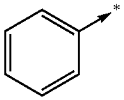 | 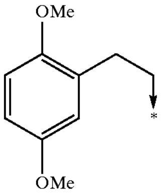 | 90.1 | 3.41 | 455.33 |
| 2122 | 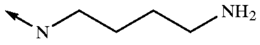 | 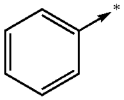 | 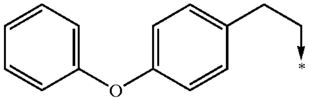 | 82.2 | 4.38 | 487.36 |
| 2123 | 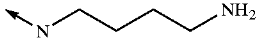 | 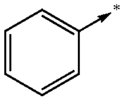 | 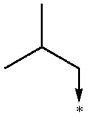 | 68.8 | 2.99 | 347.34 |
| 2124 | 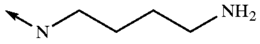 | 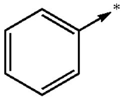 | 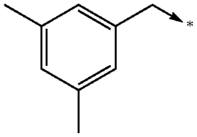 | 75.2 | 4.13 | 409.33 |
| 2125 | 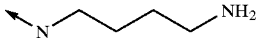 | 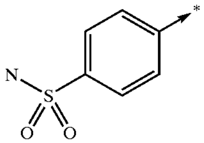 | 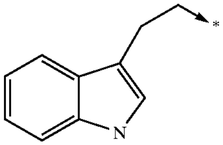 | 56.9 | 4.01 | 513.30 |
| 2126 | 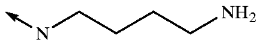 | 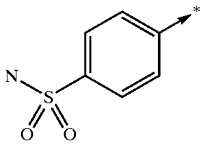 | 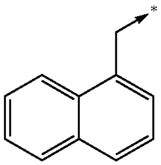 | 70.1 | 3.88 | 510.29 |

-continued
| | | | | | | |
|---|---|---|---|---|---|---|
| 2127 | 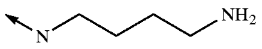 | 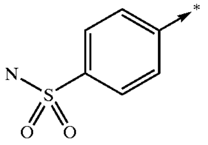 | 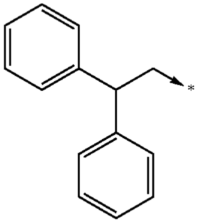 | 77.8 | 4.16 | 550.29 |
| 2128 | 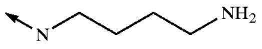 | 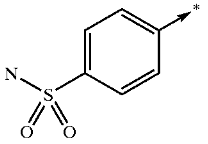 | 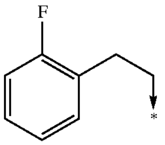 | 67.7 | 3.49 | 492.28 |
| 2129 | 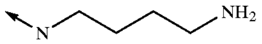 | 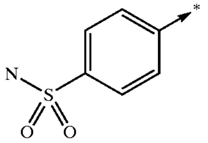 | 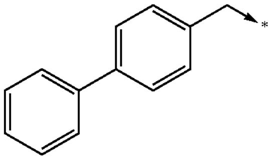 | 71 | 4.27 | 536.28 |
| 2130 | 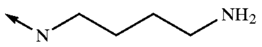 | 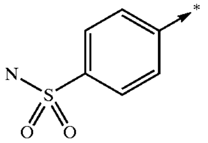 | 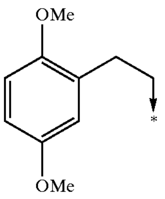 | 71.4 | 3.38 | 534.30 |
| 2131 | 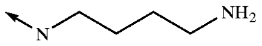 | 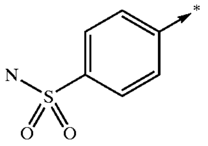 | 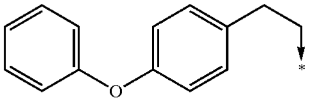 | 67.7 | 4.29 | 566.30 |

-continued
| | | | | | | |
|---|---|---|---|---|---|---|
| 2132 | 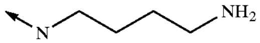 | 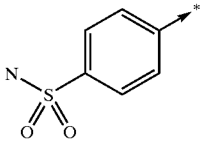 | 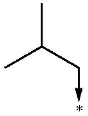 | 54.5 | 2.98 | 426.29 |
| 2133 | 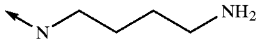 | 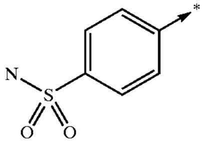 | 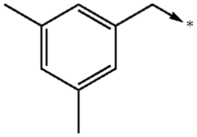 | 70.1 | 3.85 | 488.31 |
| 2134 | 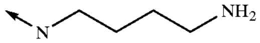 | 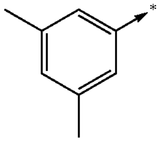 | 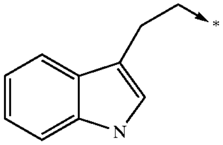 | 57.1 | 4.5 | 462.36 |
| 2135 | 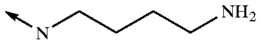 | 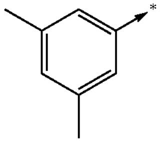 | 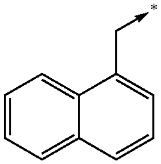 | 83.2 | 4.61 | 459.35 |
| 2136 | 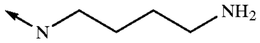 | 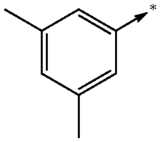 | 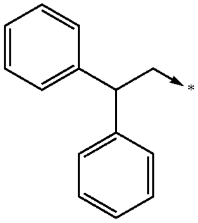 | 91.6 | 4.72 | 499.40 |
| 2137 | 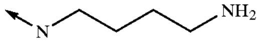 | 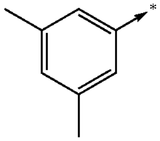 | 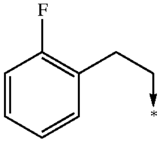 | 80.7 | 3.94 | 441.32 |

-continued
| | | | | | | |
|---|---|---|---|---|---|---|
| 2138 | 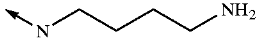 | 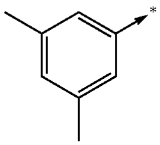 | 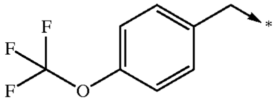 | 73.9 | 4.99 | 493.32 |
| 2139 | 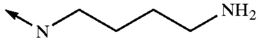 | 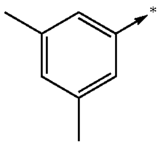 | 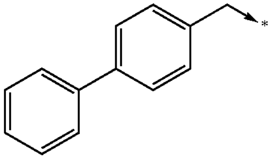 | 77.5 | 4.95 | 485.37 |
| 2140 | 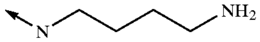 | 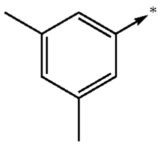 | 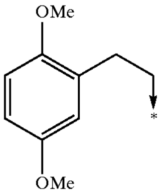 | 77.4 | 3.79 | 483.36 |
| 2141 | 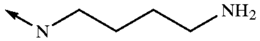 | 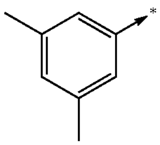 | 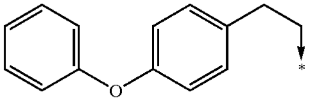 | 66.1 | 4.62 | 515.38 |
| 2142 | 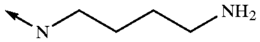 | 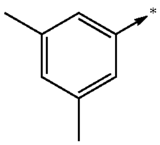 | 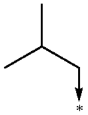 | 70.1 | 3.49 | 375.33 |
| 2143 | 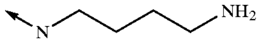 | 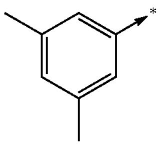 | 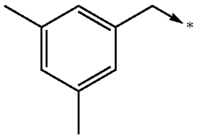 | 74.1 | 4.46 | 437.35 |

-continued
| | | | | | | |
|---|---|---|---|---|---|---|
| 2144 | 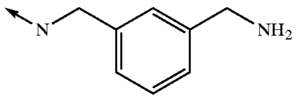 | 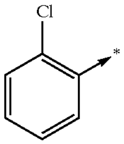 | 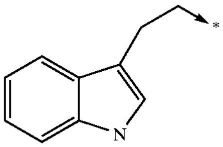 | 93.8 | 5.14 | 516.28 |
| 2145 | 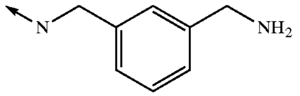 | 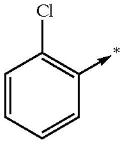 | 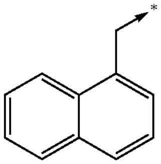 | 90.0 | 5.27 | 513.28 |
| 2146 | 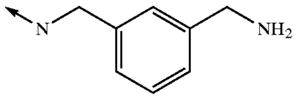 | 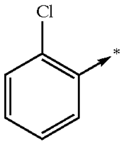 | 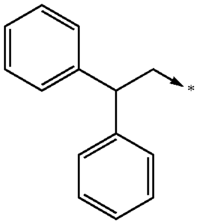 | 81.4 | 5.58 | 553.30 |
| 2147 | 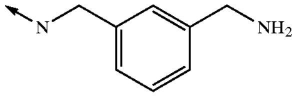 | 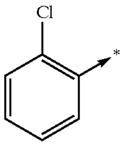 | 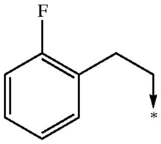 | 78.6 | 5.02 | 495.27 |
| 2148 | 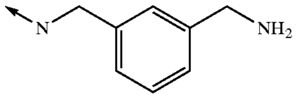 | 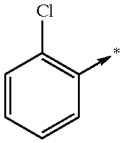 | 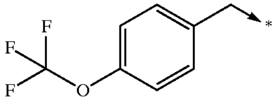 | 81.4 | 5.51 | 547.21 |
| 2149 | 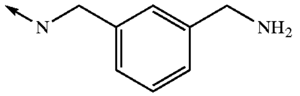 | 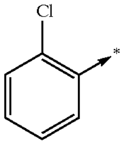 | 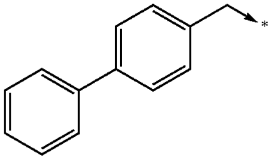 | 85.5 | 5.62 | 539.29 |

-continued
| | | | | | | |
|---|---|---|---|---|---|---|
| 2150 | 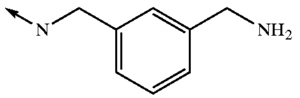 | 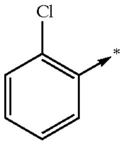 | 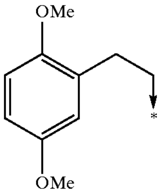 | 78.9 | 4.86 | 537.28 |
| 2151 | 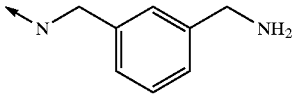 | 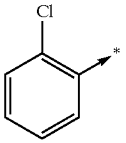 | 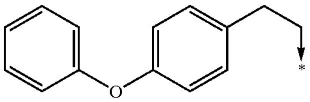 | 83.2 | 5.76 | 569.28 |
| 2152 | 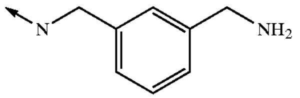 | 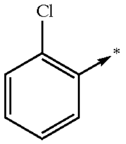 | 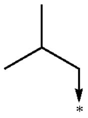 | 90.5 | 4.62 | 429.28 |
| 2153 | 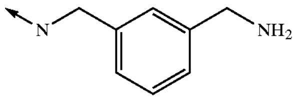 | 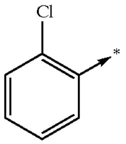 | 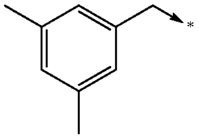 | 91.8 | 5.31 | 491.31 |
| 2154 | 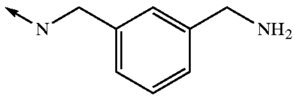 | 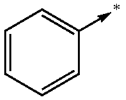 | 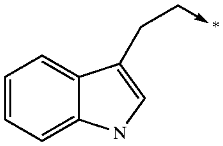 | 60.4 | 4.47 | 482.33 |
| 2155 | 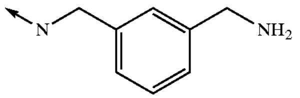 | 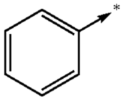 | 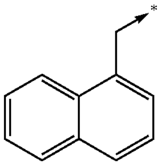 | 83.6 | 4.62 | 479.31 |

-continued
| | | | | | | |
|---|---|---|---|---|---|---|
| 2156 | 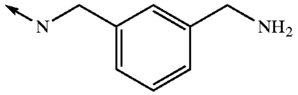 | 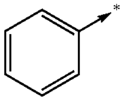 | 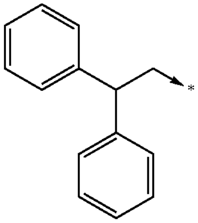 | 79.1 | 4.72 | 519.34 |
| 2157 | 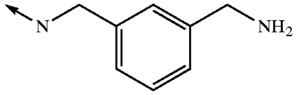 | 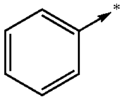 | 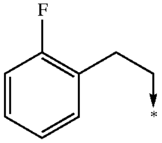 | 72.6 | 3.96 | 461.31 |
| 2158 | 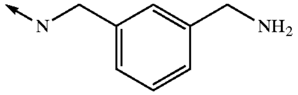 | 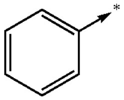 | 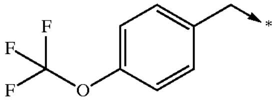 | 75.7 | 5.0 | 513.27 |
| 2159 | 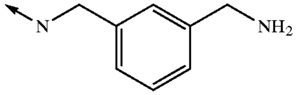 | 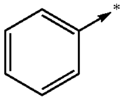 | 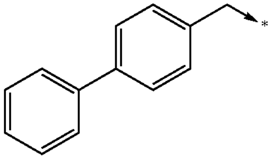 | 79.3 | 4.99 | 505.34 |
| 2160 | 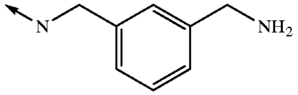 | 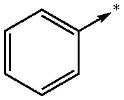 | 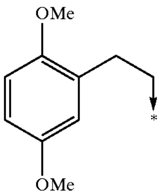 | 89.6 | 3.72 | 503.34 |
| 2161 | 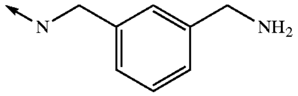 | 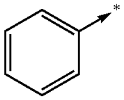 | 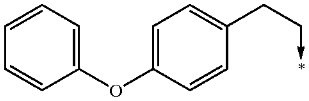 | 89.6 | 4.7 | 535.32 |

-continued
| | | | | | | |
|---|---|---|---|---|---|---|
| 2162 | 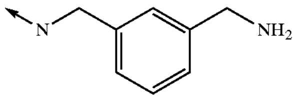 | 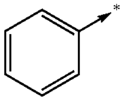 | 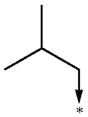 | 73.5 | 3.38 | 395.32 |
| 2163 | 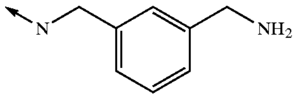 | 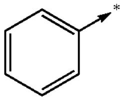 | 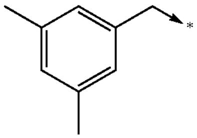 | 80.1 | 4.5 | 457.32 |
| 2164 | 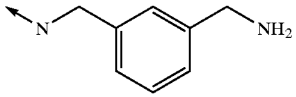 | 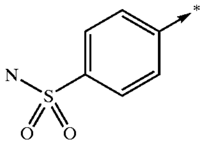 | 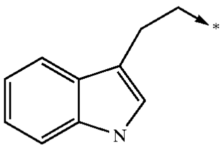 | 58.8 | 4.24 | 561.29 |
| 2165 | 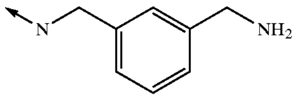 | 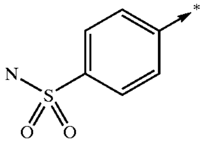 | 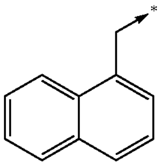 | 77.9 | 4.16 | 558.27 |
| 2166 | 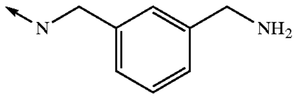 | 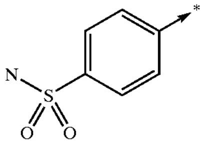 | 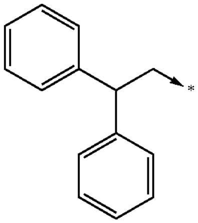 | 85.5 | 4.42 | 598.29 |
| 2167 | 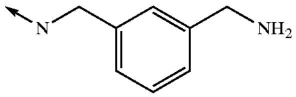 | 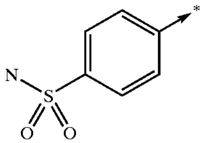 | 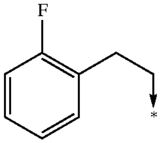 | 82.8 | 3.87 | 540.27 |

-continued
| | | | | | | |
|---|---|---|---|---|---|---|
| 2168 | 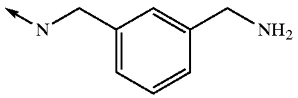 | 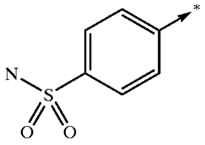 | 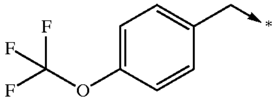 | 1.54 | 4.52 | 592.25 |
| 2169 | 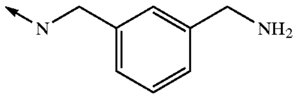 | 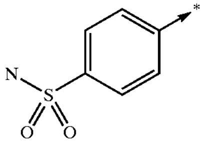 | 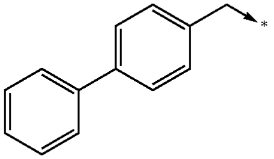 | 58.0 | 4.54 | 584.25 |
| 2170 | 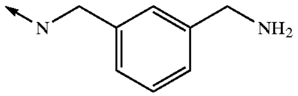 | 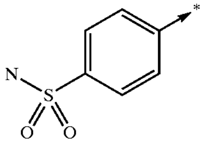 | 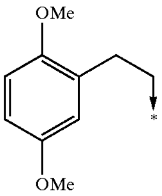 | 82.5 | 3.76 | 582.30 |
| 2171 | 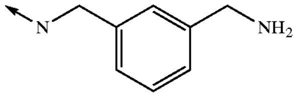 | 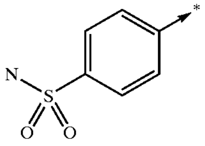 | 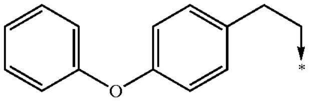 | 71.8 | 4.58 | 614.31 |
| 2172 | 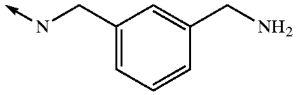 | 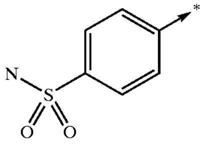 | 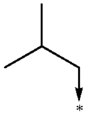 | 71.9 | 3.43 | 474.30 |
| 2173 | 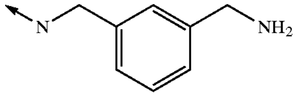 | 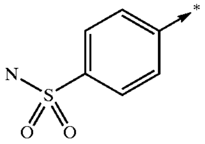 | 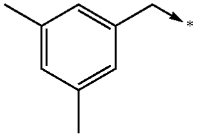 | 80.9 | 4.16 | 536.28 |

-continued
| | | | | | | |
|---|---|---|---|---|---|---|
| 2174 | 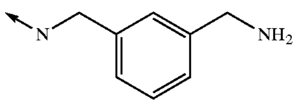 | 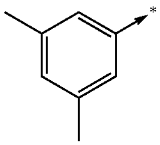 | 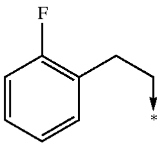 | 61.9 | 4.76 | 510.36 |
| 2175 | 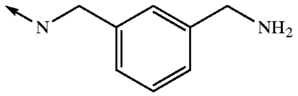 | 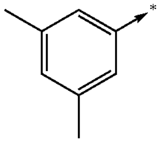 | 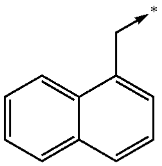 | 83.1 | 4.93 | 507.35 |
| 2176 | 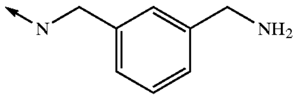 | 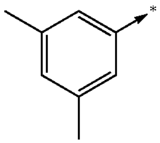 | 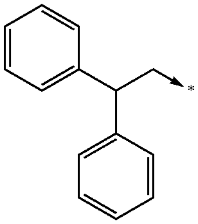 | 92.0 | 499 | 647.36 |
| 2177 | 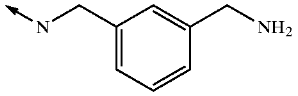 | 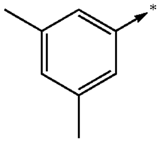 | 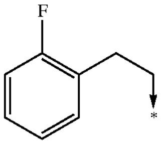 | 88.3 | 4.27 | 489.35 |
| 2178 | 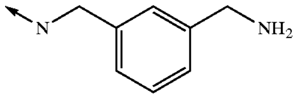 | 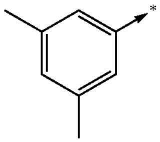 | 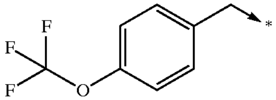 | 86.3 | 541 | 541.29 |
| 2179 | 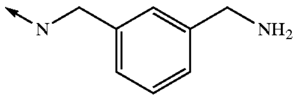 | 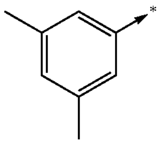 | 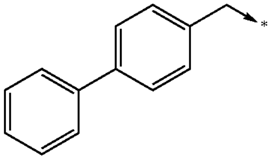 | 79.7 | 5.36 | 533.36 |

-continued
| | | | | | | |
|---|---|---|---|---|---|---|
| 2180 | 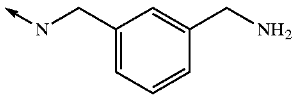 | 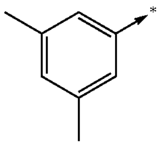 | 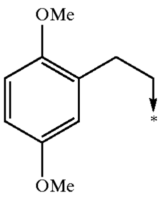 | 82.5 | 4.13 | 531.35 |
| 2181 | 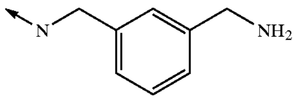 | 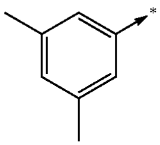 | 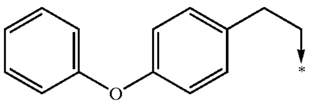 | 74.0 | 4.99 | 563.34 |
| 2182 | 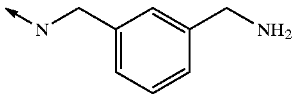 | 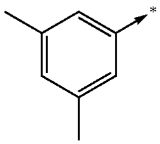 | 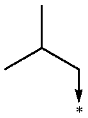 | 76 | 3.89 | 423.35 |
| 2183 | 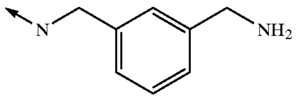 | 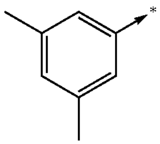 | 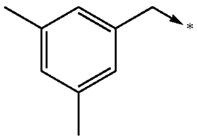 | 79.8 | 4.89 | 485.38 |
| 2184 | 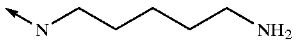 | 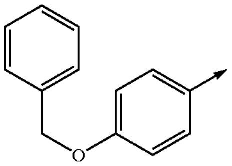 | 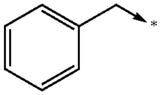 | 80.8 | 4.43 | 501.32 |
| 2185 | 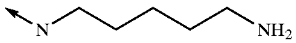 | 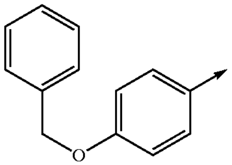 | 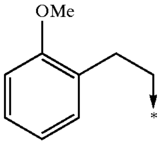 | 66.2 | 4.18 | 545.31 |

-continued
| | | | | | | |
|---|---|---|---|---|---|---|
| 2186 | 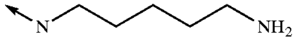 | 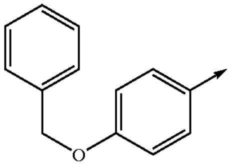 | 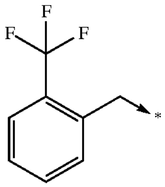 | 64.6 | 5.18 | 569.27 |
| 2187 | 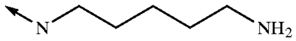 | 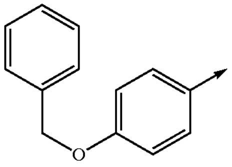 | 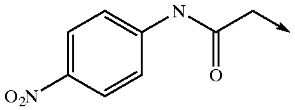 | 57.2 | 4.78 | 589.30 |
| 2188 | 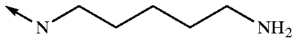 | 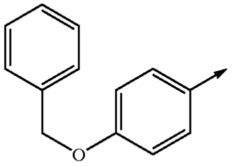 | 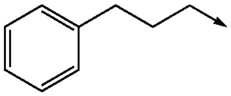 | 65.7 | 4.41 | 529.36 |
| 2189 | 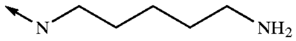 | 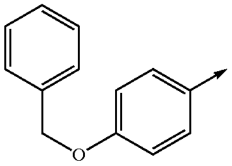 | 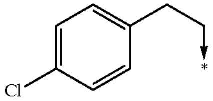 | 65.4 | 4.52 | 549.28 |
| 2190 | 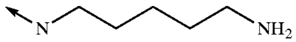 | 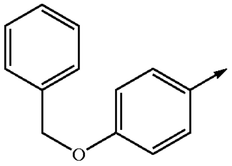 | 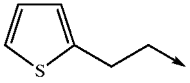 | 65.8 | 4.24 | 521.29 |

-continued
| | | | | | | |
|---|---|---|---|---|---|---|
| 2191 | 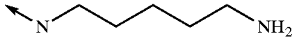 | 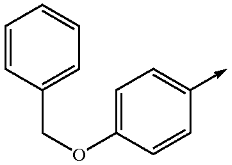 | 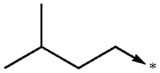 | 71.4 | 4.19 | 481.37 |
| 2192 | 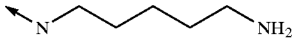 | 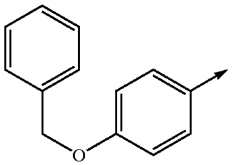 | 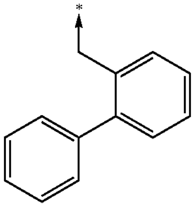 | 83.9 | 4.8 | 577.32 |
| 2193 | 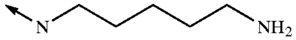 | 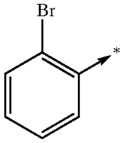 | 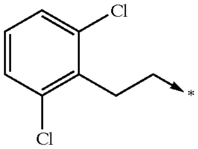 | 76.5 | 4.54 | 583.24 |
| 2194 | 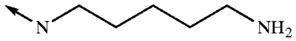 | 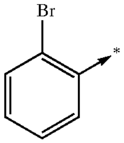 | 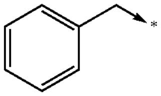 | 67.2 | 4.76 | 473.22 |
| 2195 | 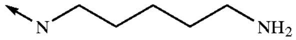 | 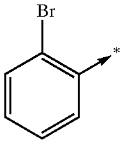 | 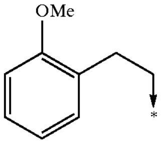 | 66.6 | 4.69 | 517.20 |
| 2196 | 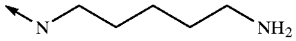 | 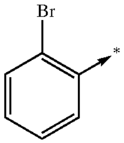 | 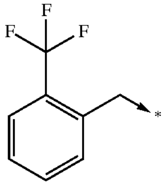 | 71 | 5.2 | 541.18 |

-continued
| | | | | | | |
|---|---|---|---|---|---|---|
| 2197 | 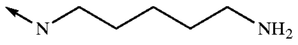 | 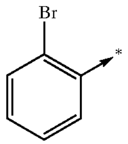 | 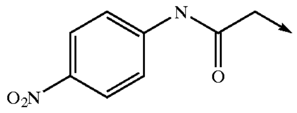 | 69 | 4.73 | 561.15 |
| 2198 | 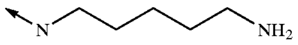 | 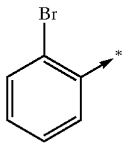 | 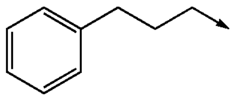 | 74.8 | 5.04 | 501.24 |
| 2199 | 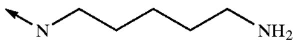 | 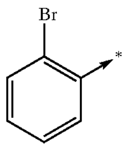 | 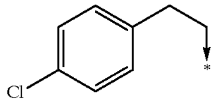 | 69.5 | 5.18 | 521.16 |
| 2200 | 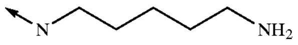 | 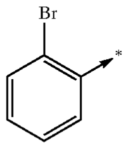 | 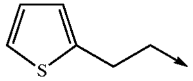 | 79.3 | 4.8 | 493.18 |
| 2201 | 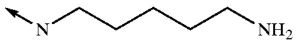 | 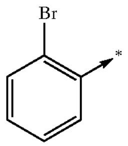 | 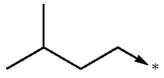 | 74.9 | 4.79 | 453.24 |
| 2202 | 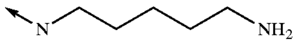 | 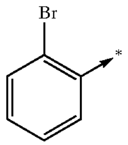 | 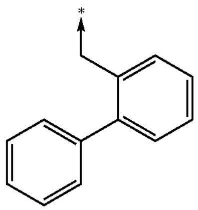 | 68.9 | 5.41 | 549.20 |

-continued
| | | | | | | |
|---|---|---|---|---|---|---|
| 2203 | 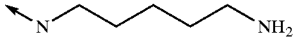 | 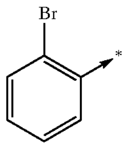 | 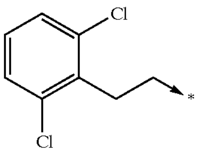 | 68 | 5.2 | 555.11 |
| 2204 | 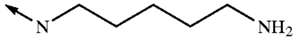 | 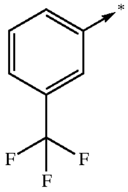 | 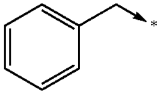 | 66 | 5.02 | 463.27 |
| 2205 | 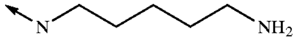 | 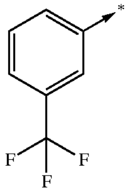 | 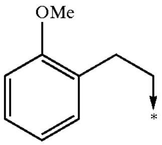 | 62.2 | 4.83 | 507.28 |
| 2206 | 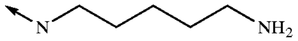 | 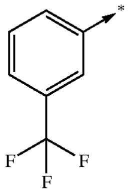 | 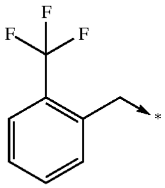 | 65.2 | 5.48 | 531.24 |
| 2207 | 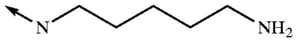 | 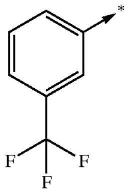 | 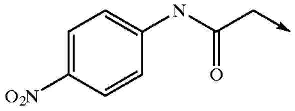 | 66.3 | 4.99 | 551.22 |

-continued
| | | | | | | |
|---|---|---|---|---|---|---|
| 2208 | 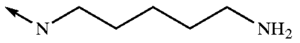 | 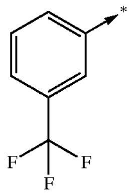 | 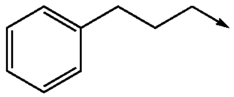 | 72.9 | 5.22 | 491.31 |
| 2209 | 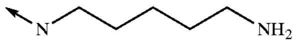 | 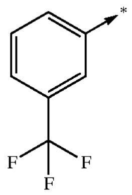 | 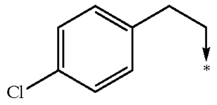 | 77.2 | 5.31 | 511.24 |
| 2210 | 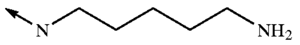 | 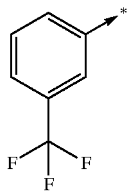 | 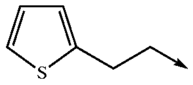 | 62.8 | 4.98 | 483.24 |
| 2211 | 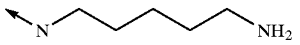 | 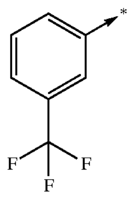 | 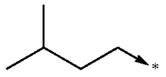 | 62.4 | 4.98 | 443.31 |
| 2212 | 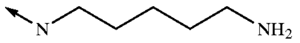 | 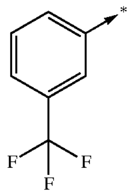 | 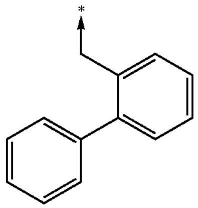 | 69.6 | 5.55 | 539.29 |

-continued
| | | | | | | |
|---|---|---|---|---|---|---|
| 2213 | 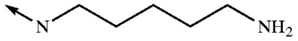 | 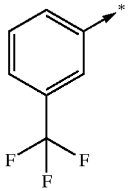 | 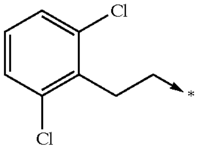 | 63.5 | 5.41 | 545.19 |
| 2214 | 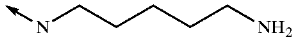 | 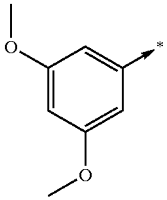 | 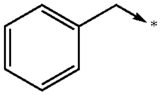 | 41.2 | 4.09 | 455.28 |
| 2215 | 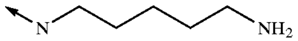 | 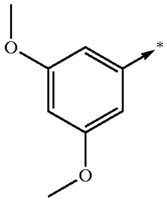 | 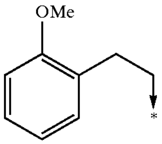 | 58.5 | 3.73 | 499.35 |
| 2216 | 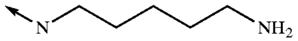 | 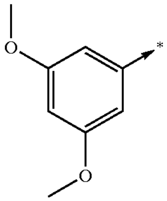 | 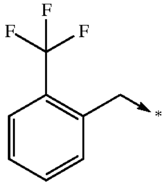 | 68.8 | 4.78 | 523.28 |
| 2217 | 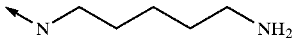 | 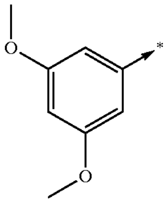 | 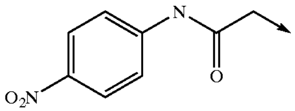 | 36.2 | 4.37 | 543.28 |

-continued
| | | | | | | |
|---|---|---|---|---|---|---|
| 2218 | 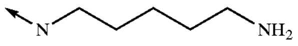 | 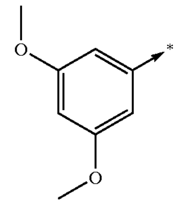 | 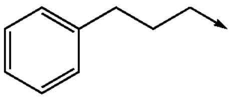 | 42.9 | 4.1 | 483.36 |
| 2219 | 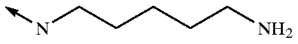 | 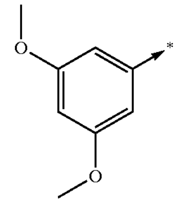 | 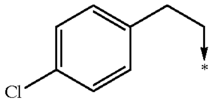 | 46.1 | 4.24 | 503.30 |
| 2220 | 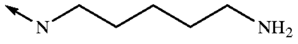 | 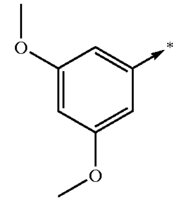 | 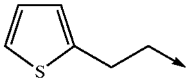 | 48.4 | 3.87 | 475.28 |
| 2221 | 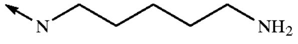 | 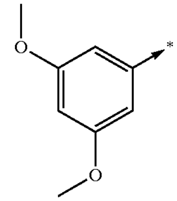 | 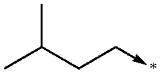 | 39 | 3.8 | 435.34 |
| 2222 | 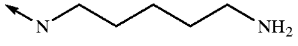 | 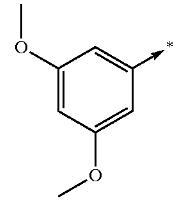 | 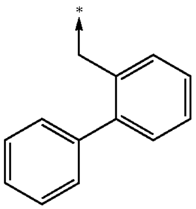 | 48.3 | 4.55 | 531.30 |

-continued
| | | | | | | |
|---|---|---|---|---|---|---|
| 2223 | 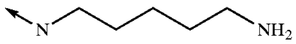 | 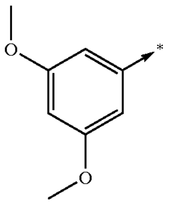 | 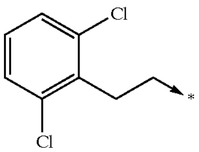 | 47 | 4.33 | 537.20 |
| 2224 | 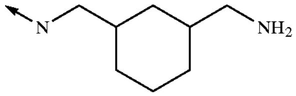 | 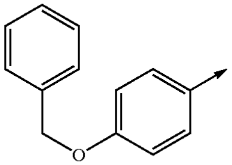 | 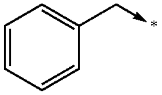 | 57.4 | 4.64 | 541.34 |
| 2225 | 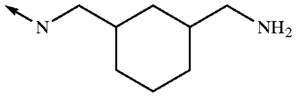 | 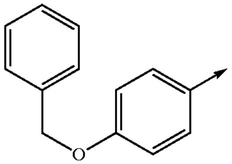 | 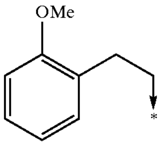 | 69.1 | 4.34 | 585.37 |
| 2226 | 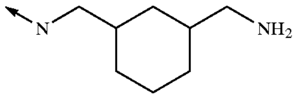 | 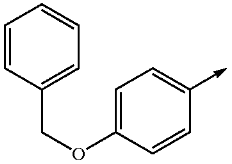 | 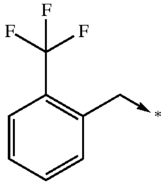 | 64.6 | 5.36 | 609.35 |
| 2227 | 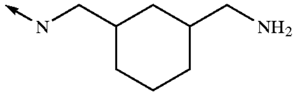 | 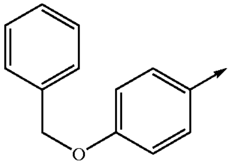 | 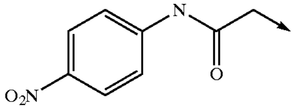 | 40.2 | 4.94 | 629.34 |

-continued
| | | | | | | |
|---|---|---|---|---|---|---|
| 2228 | 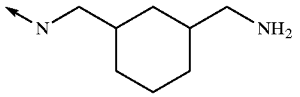 | 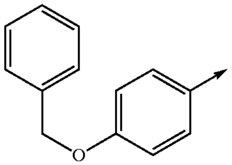 | 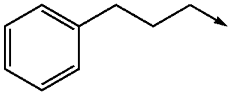 | 62.6 | 4.57 | 569.3 |
| 2229 | 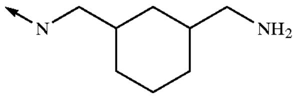 | 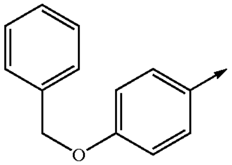 | 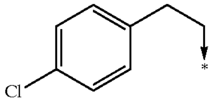 | 68 | 4.72 | 589.31 |
| 2230 | 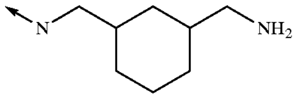 | 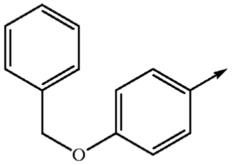 | 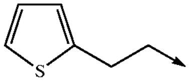 | 61.2 | 4.44 | 561.31 |
| 2231 | 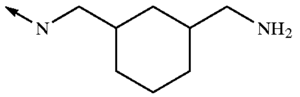 | 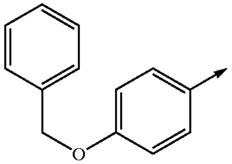 | 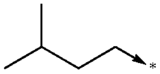 | 61.2 | 4.37 | 521.36 |
| 2232 | 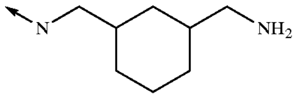 | 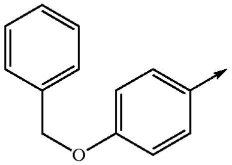 | 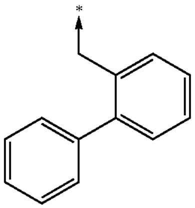 | 80.7 | 5.02 | 617.37 |

-continued
| | | | | | | |
|---|---|---|---|---|---|---|
| 2233 | 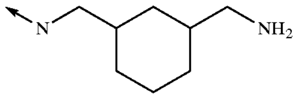 | 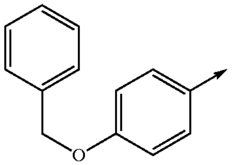 | 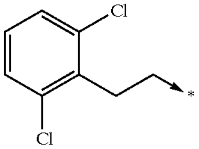 | 74.2 | 4.77 | 623.28 |
| 2234 | 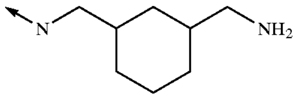 | 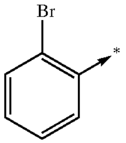 | 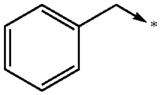 | 68.1 | 4.99 | 513.23 |
| 2235 | 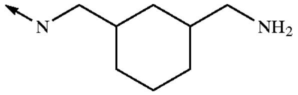 | 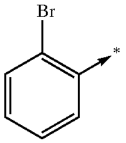 | 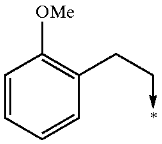 | 66.1 | 4.98 | 557.22 |
| 2236 | 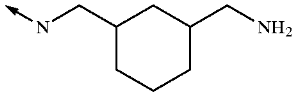 | 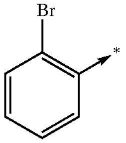 | 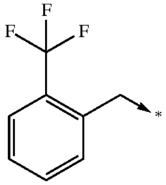 | 68.8 | 5.38 | 581.20 |
| 2237 | 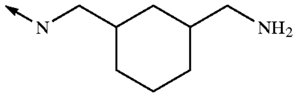 | 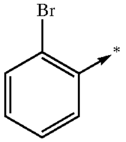 | 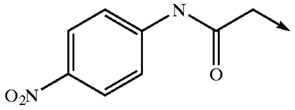 | 69.7 | 4.9 | 601.19 |
| 2238 | 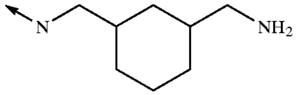 | 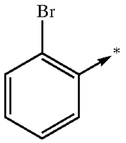 | 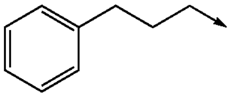 | 67.1 | 5.27 | 541.23 |

-continued
| | | | | | | |
|---|---|---|---|---|---|---|
| 2239 | 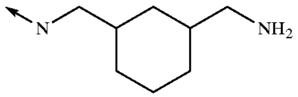 | 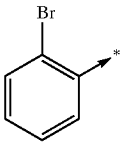 | 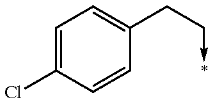 | 72.6 | 5.45 | 561.16 |
| 2240 | 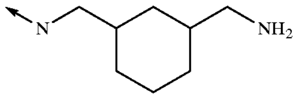 | 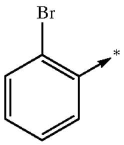 | 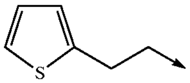 | 75.6 | 5.09 | 533.17 |
| 2241 | 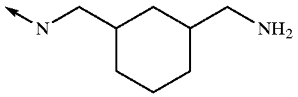 | 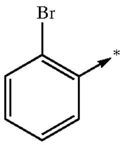 | 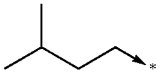 | 74.6 | 5.08 | 493.26 |
| 2242 | 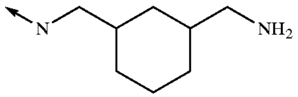 | 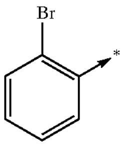 | 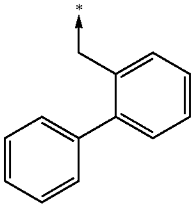 | 74.2 | 5.6 | 589.22 |
| 2243 | 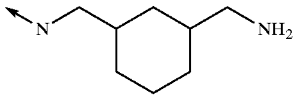 | 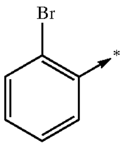 | 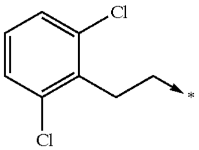 | 70 | 5.48 | 595.14 |
| 2244 | 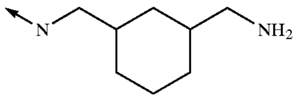 | 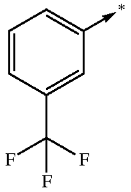 | 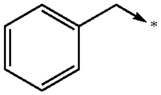 | 63.2 | 5.24 | 503.32 |

-continued
| | | | | | | |
|---|---|---|---|---|---|---|
| 2245 | 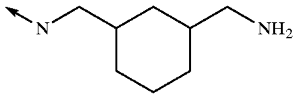 | 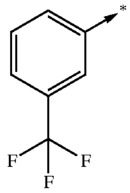 | 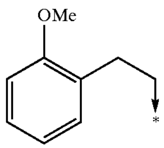 | 61.1 | 5.1 | 547.30 |
| 2246 | 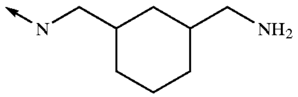 | 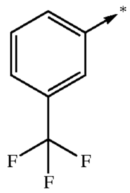 | 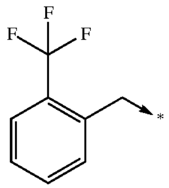 | 63.3 | 5.65 | 571.25 |
| 2247 | 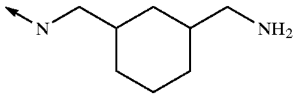 | 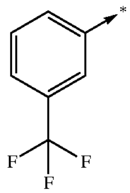 | 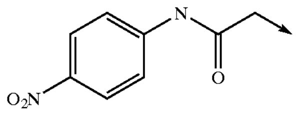 | 63.7 | 5.15 | 591.28 |
| 2248 | 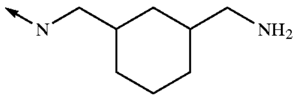 | 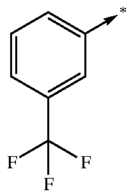 | 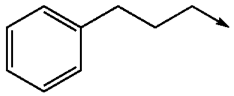 | 67.2 | 5.46 | 531.31 |
| 2249 | 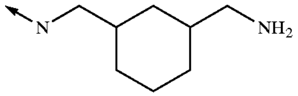 | 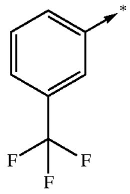 | 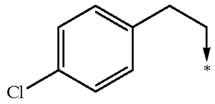 | 76 | 5.58 | 551.24 |

-continued
| | | | | | | |
|---|---|---|---|---|---|---|
| 2250 | 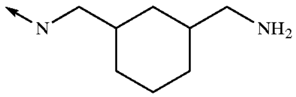 | 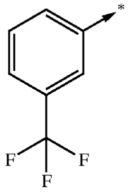 | 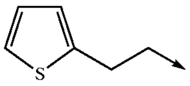 | 60.2 | 5.25 | 523.26 |
| 2251 | 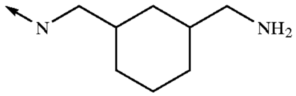 | 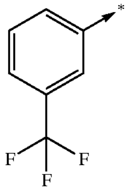 | 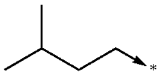 | 58.8 | 5.24 | 483.3 |
| 2252 | 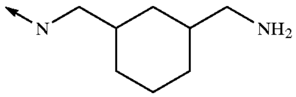 | 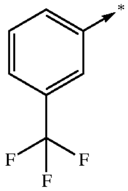 | 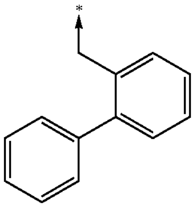 | 72.1 | 5.76 | 579.31 |
| 2253 | 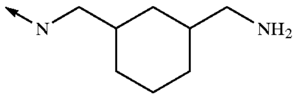 | 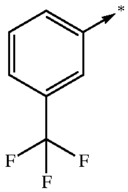 | 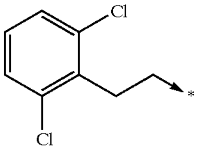 | 65.2 | 5.66 | 585.20 |
| 2254 | 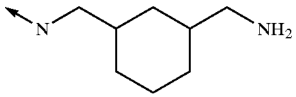 | 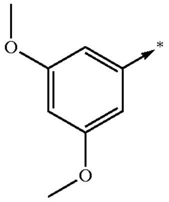 | 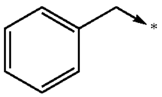 | 36 | 436 | 495.33 |

-continued
| | | | | | | |
|---|---|---|---|---|---|---|
| 2255 | 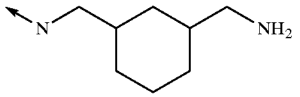 | 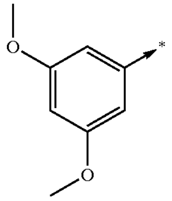 | 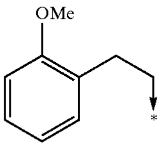 | 58.6 | 3.97 | 539.36 |
| 2256 | 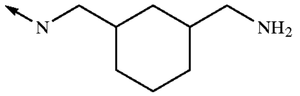 | 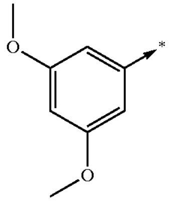 | 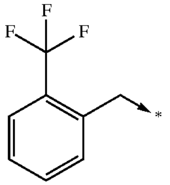 | 70 | 5.0 | 563.28 |
| 2257 | 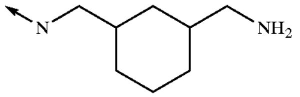 | 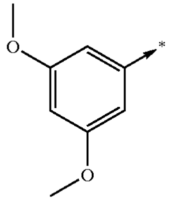 | 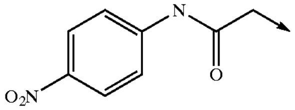 | 50.2 | 4.55 | 583.28 |
| 2258 | 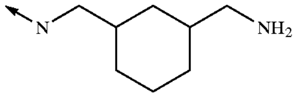 | 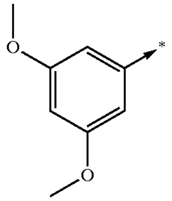 | 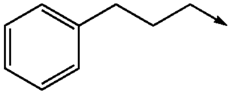 | 43.2 | 4.34 | 523.35 |
| 2259 | 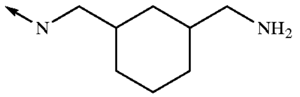 | 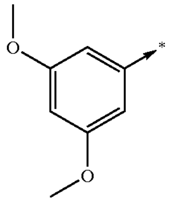 | 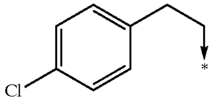 | 52 | 4.53 | 543.29 |

-continued
| | | | | | | |
|---|---|---|---|---|---|---|
| 2260 | 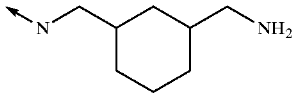 | 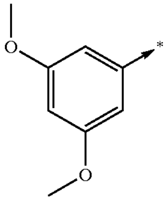 | 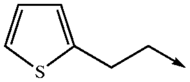 | 52.1 | 4.16 | 515.30 |
| 2261 | 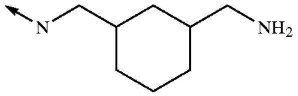 | 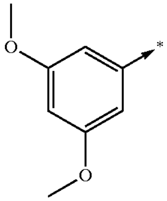 | 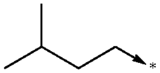 | 46.2 | 4.07 | 475.38 |
| 2262 | 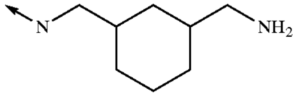 | 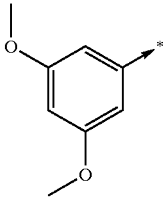 | 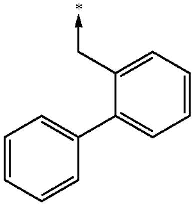 | 55.2 | 4.82 | 571.33 |
| 2263 | 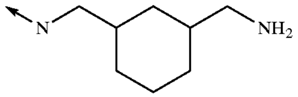 | 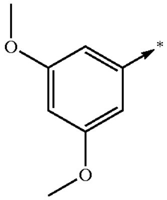 | 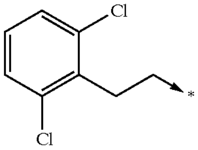 | 51.5 | 4.63 | 577.22 |
| 2264 | 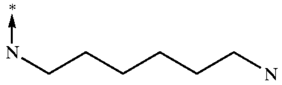 | 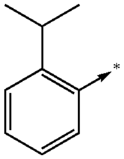 | 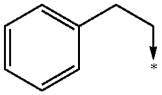 | 81.1 | 4.49 | 465.35 |

-continued
| | | | | | | |
|---|---|---|---|---|---|---|
| 2265 | 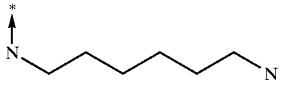 | 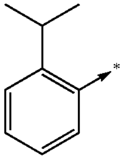 | 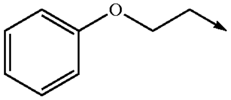 | 84.1 | 4.7 | 481.36 |
| 2266 | 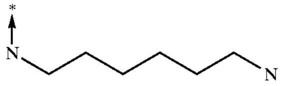 | 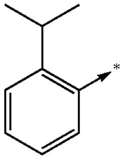 | 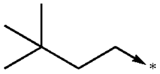 | 65.7 | 4.78 | 445.36 |
| 2267 | 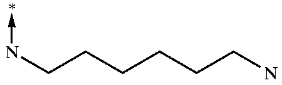 | 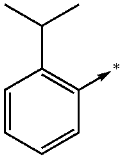 | 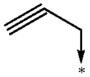 | 63.0 | 4.51 | 399.29 |
| 2268 | 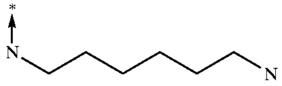 | 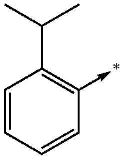 | 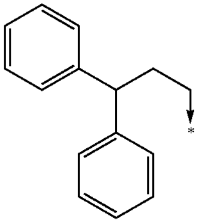 | 77.8 | 5.39 | 555.37 |
| 2269 | 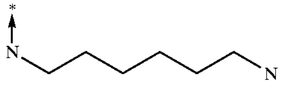 | 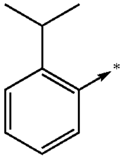 | 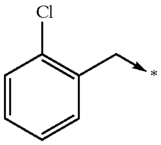 | 78.5 | 5.21 | 485.32 |

-continued
| | | | | | | |
|---|---|---|---|---|---|---|
| 2270 | 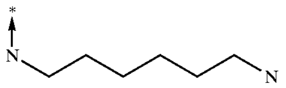 | 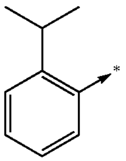 | 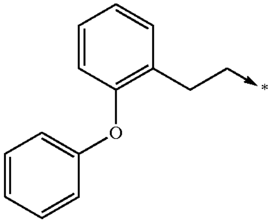 | 74.0 | 5.02 | 557.37 |
| 2271 | 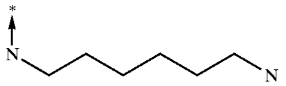 | 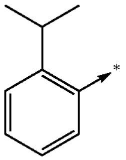 | 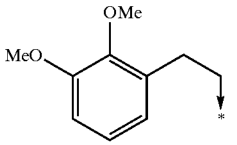 | 78.1 | 4.38 | 525.37 |
| 2272 | 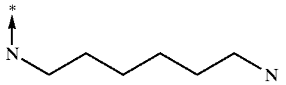 | 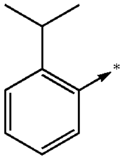 | 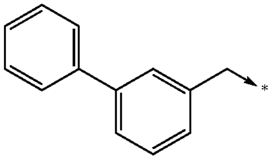 | 89.2 | 5.42 | 527.38 |
| 2273 | 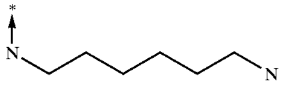 | 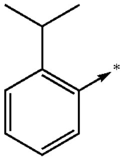 | 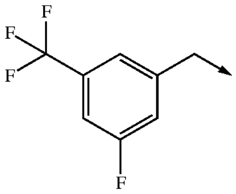 | 83.0 | 5.75 | 537.30 |
| 2274 | 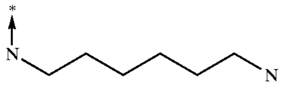 | 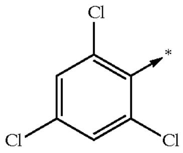 | 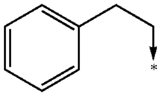 | 67.8 | 5.87 | 525.21 |

-continued
| | | | | | | |
|---|---|---|---|---|---|---|
| 2275 | 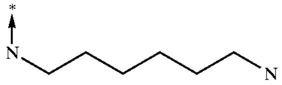 | 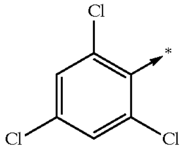 | 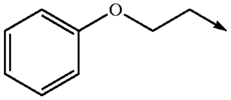 | 83.2 | 5.75 | 541.16 |
| 2276 | 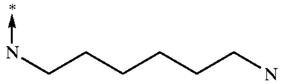 | 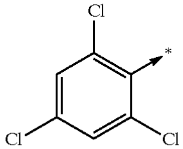 | 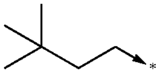 | 71.9 | 6.11 | 505.25 |
| 2277 | 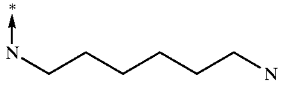 | 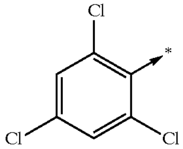 | 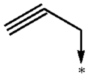 | 70.5 | 5.14 | 459.15 |
| 2278 | 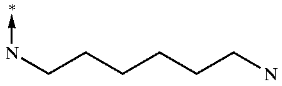 | 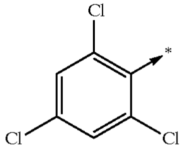 | 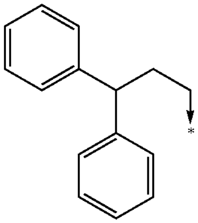 | 74.6 | 6.44 | 615.23 |
| 2279 | 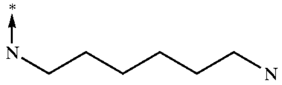 | 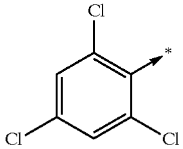 | 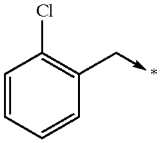 | 71.5 | 5.88 | 545.10 |

-continued
| | | | | | | |
|---|---|---|---|---|---|---|
| 2280 | 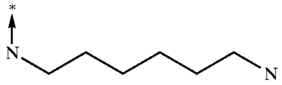 | 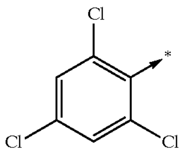 | 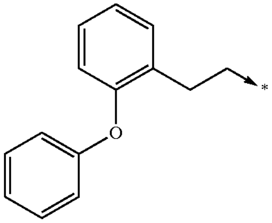 | 80.2 | 643 | 617.19 |
| 2281 | 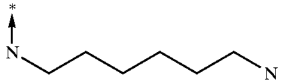 | 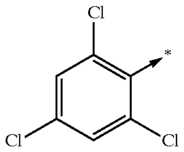 | 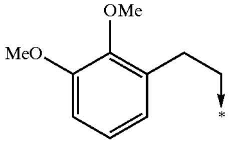 | 93.4 | 5.82 | 585.18 |
| 2282 | 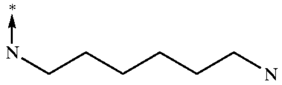 | 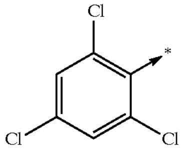 | 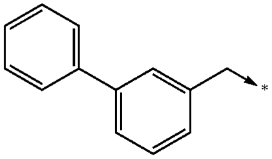 | 74.9 | 6.28 | 587.19 |
| 2283 | 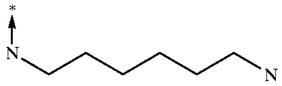 | 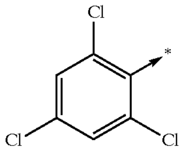 | 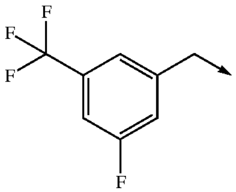 | 68.3 | 6.24 | 597.14 |
| 2284 | 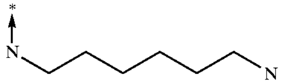 | 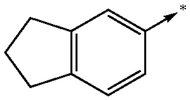 | 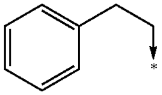 | 65.8 | 4.02 | 463.35 |
| 2285 | 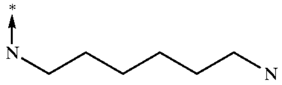 | 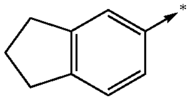 | 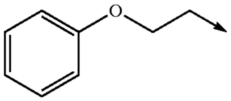 | 75.8 | 4.22 | 479.33 |

-continued
| | | | | | | |
|---|---|---|---|---|---|---|
| 2286 | 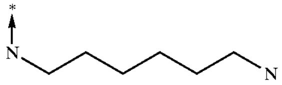 | 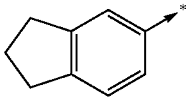 | 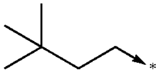 | 69.0 | 4.21 | 443.37 |
| 2287 | 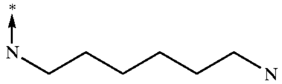 | 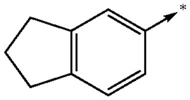 | 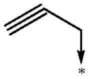 | 4.2 | 4.36 | 397.33 |
| 2288 | 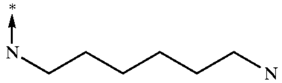 | 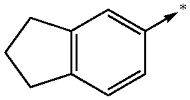 | 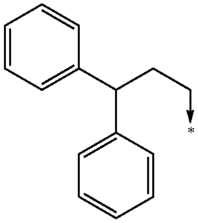 | 82.7 | 4.74 | 553.37 |
| 2289 | 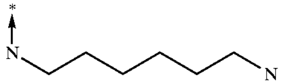 | 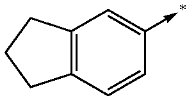 | 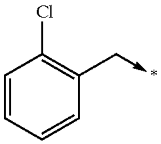 | 89.8 | 4.62 | 483.29 |
| 2290 | 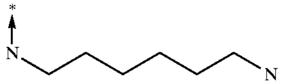 | 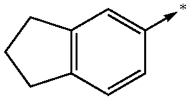 | 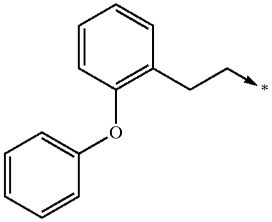 | 77.2 | 4.52 | 555.33 |
| 2291 | 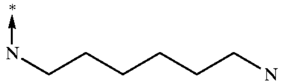 | 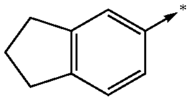 | 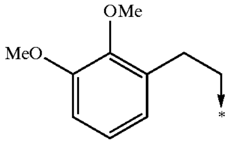 | 69.3 | 3.98 | 523.35 |

-continued
| | | | | | | |
|---|---|---|---|---|---|---|
| 2292 | 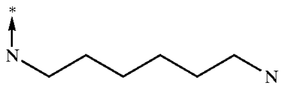 | 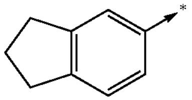 | 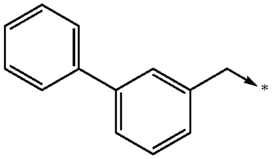 | 73.3 | 4.98 | 525.34 |
| 2293 | 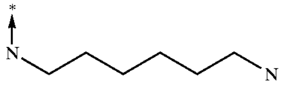 | 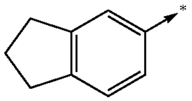 | 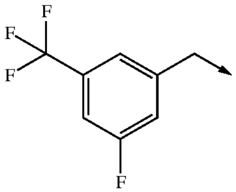 | 73.1 | 5.44 | 535.29 |
| 2294 | 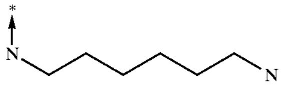 | 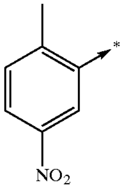 | 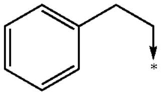 | 59.4 | 5.14 | 482.30 |
| 2295 | 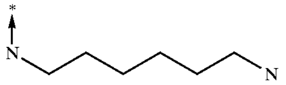 | 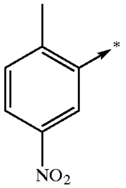 | 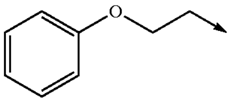 | 76.0 | 5.09 | 498.28 |
| 2296 | 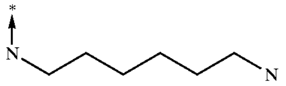 | 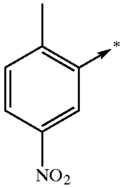 | 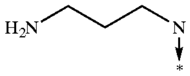 | 62.3 | 5.47 | 462.32 |

-continued
| | | | | | | |
|---|---|---|---|---|---|---|
| 2297 | 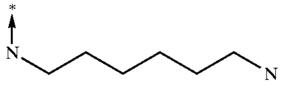 | 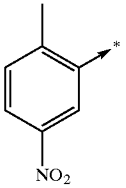 | 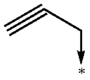 | 58.6 | 4.55 | 416.22 |
| 2298 | 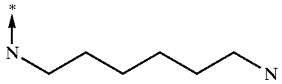 | 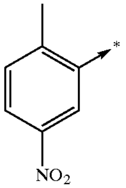 | 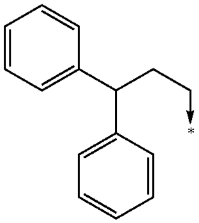 | 79.5 | 5.84 | 572.32 |
| 2299 | 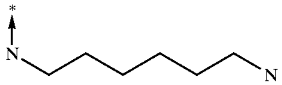 | 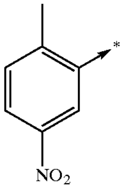 | 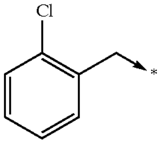 | 74.9 | 5.3 | 502.25 |
| 2300 | 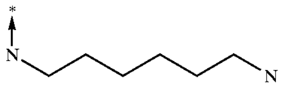 | 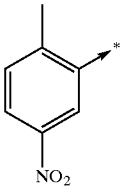 | 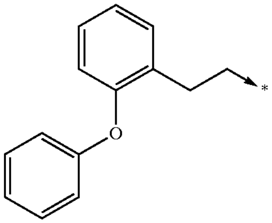 | 72.7 | 5.71 | 574.28 |
| 2301 | 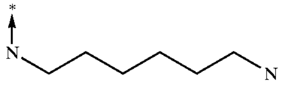 | 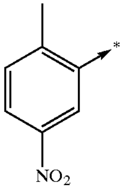 | 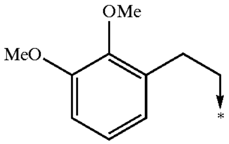 | 71.1 | 5.06 | 542.32 |

-continued
| | | | | | | |
|---|---|---|---|---|---|---|
| 2302 | 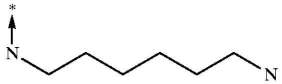 | 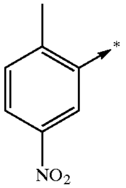 | 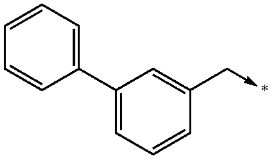 | 73.0 | 5.66 | 544.29 |
| 2303 | 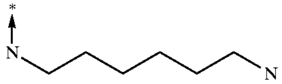 | 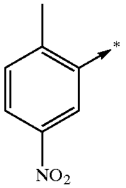 | 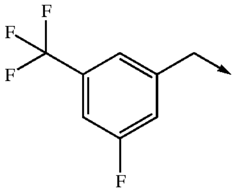 | 64.6 | 5.62 | 554.24 |
| 2304 | 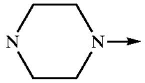 | 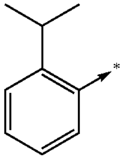 | 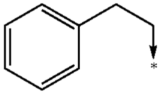 | 92.2 | 4.62 | 435.30 |
| 2305 | 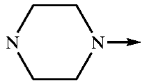 | 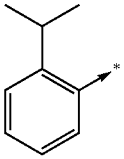 | 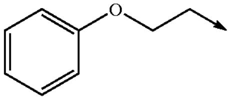 | 90.1 | 4.67 | 451.29 |
| 2306 | 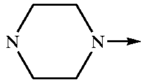 | 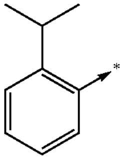 | 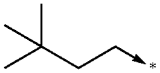 | 84.3 | 4.76 | 415.32 |

-continued
| | | | | | | |
|---|---|---|---|---|---|---|
| 2307 | 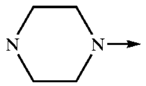 | 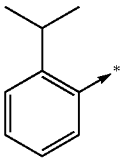 | 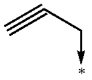 | 43.7 | 4.34 | 369.27 |
| 2308 | 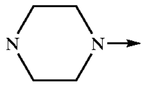 | 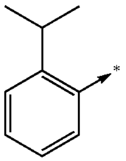 | 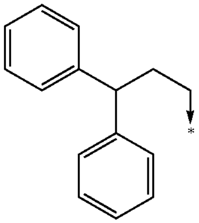 | 83.7 | 5.44 | 525.34 |
| 2309 | 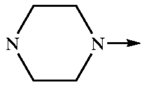 | 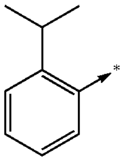 | 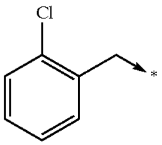 | 80.3 | 4.96 | 455.25 |
| 2310 | 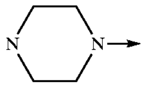 | 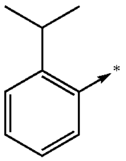 | 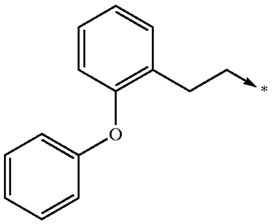 | 83.7 | 5.26 | 527.32 |
| 2311 | 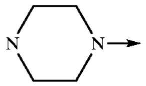 | 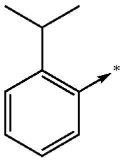 | 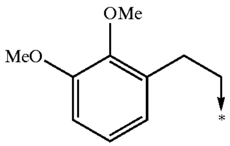 | 82.8 | 4.64 | 495.34 |

-continued
| | | | | | | |
|---|---|---|---|---|---|---|
| 2312 | 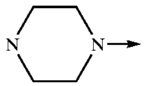 | 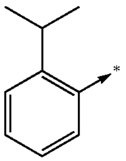 | 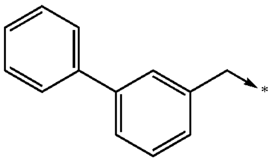 | 94.1 | 5.44 | 497.32 |
| 2313 | 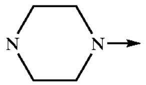 | 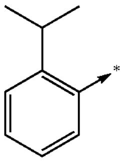 | 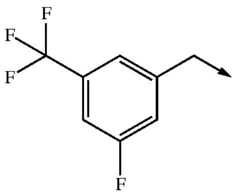 | 90.1 | 5.55 | 507.29 |
| 2314 | 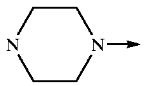 | 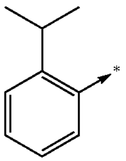 | 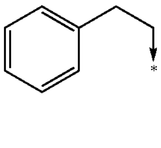 | 64.7 | 5.62 | 495.16 |
| 2315 | 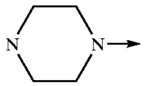 | 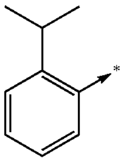 | 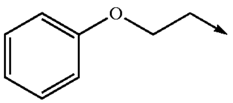 | 50.7 | 5.54 | 511.15 |
| 2316 | 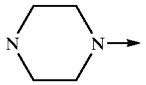 | 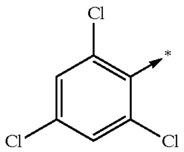 | 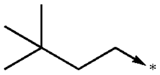 | 78.0 | 5.8 | 475.22 |
| 2317 | 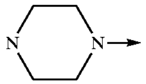 | 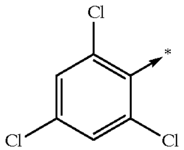 | 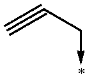 | 20.9 | 4.86 | 429.14 |

-continued
| | | | | | | |
|---|---|---|---|---|---|---|
| 2318 | 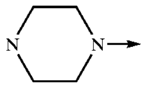 | 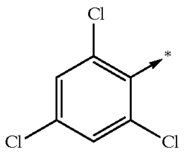 | 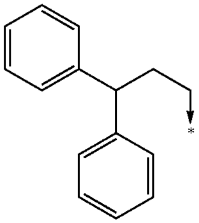 | 79.2 | 6.27 | 585.15 |
| 2319 | 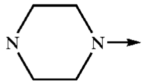 | 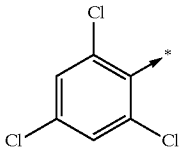 | 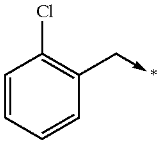 | 46.3 | 5.58 | 515.12 |
| 2320 | 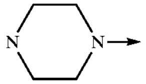 | 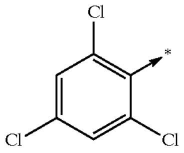 | 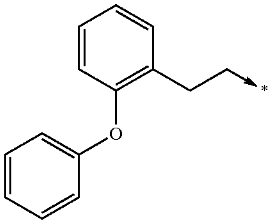 | 84.1 | 6.23 | 587.20 |
| 2321 | 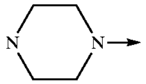 | 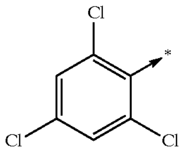 | 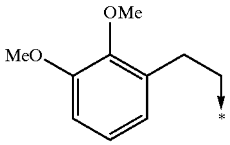 | 91.1 | 5.64 | 555.18 |
| 2322 | 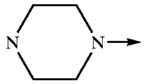 | 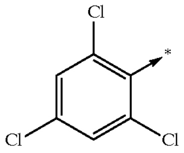 | 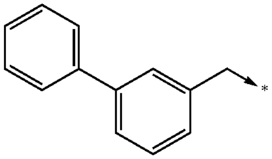 | 67.8 | 6.07 | 557.22 |

-continued
| | | | | | | |
|---|---|---|---|---|---|---|
| 2323 | 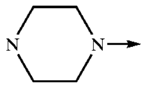 | 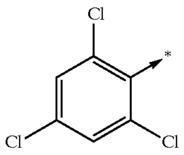 | 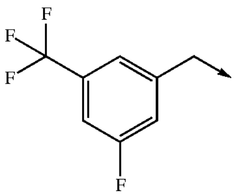 | 23.9 | 5.96 | 567.17 |
| 2324 | 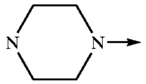 | 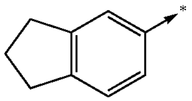 | 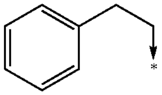 | 68.1 | 4.02 | 433.40 |
| 2325 | 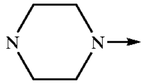 | 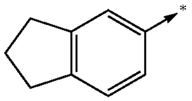 | 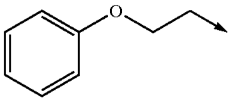 | 65.6 | 4.2 | 449.38 |
| 2326 | 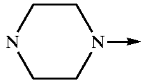 | 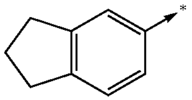 | 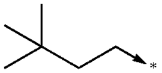 | 83.5 | 4.14 | 413.39 |
| 2327 | 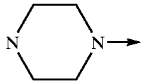 | 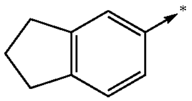 | 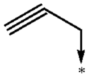 | 36.4 | 3.94 | 367.35 |
| 2328 | 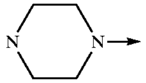 | 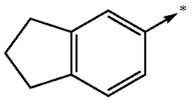 | 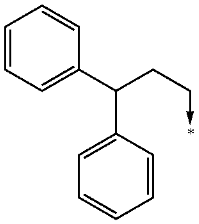 | 87.5 | 4.82 | 523.39 |
| 2329 | 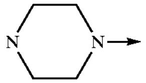 | 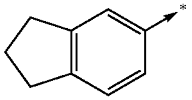 | 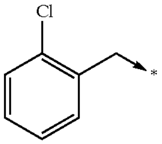 | 65.1 | 4.42 | 453.33 |

-continued
| | | | | | | |
|---|---|---|---|---|---|---|
| 2330 | 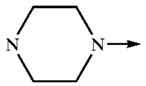 | 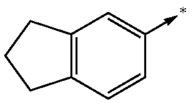 | 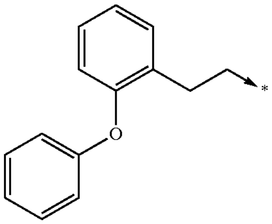 | 91.7 | 4.59 | 525.37 |
| 2331 | 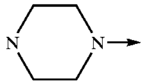 | 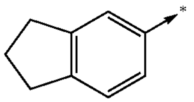 | 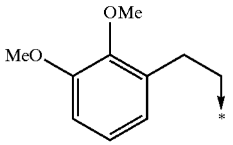 | 81.5 | 4.01 | 493.40 |
| 2332 | 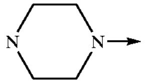 | 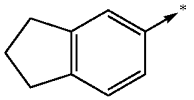 | 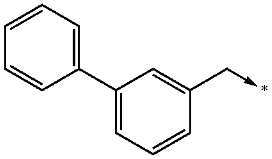 | 73.9 | 4.96 | 495.39 |
| 2333 | 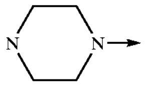 | 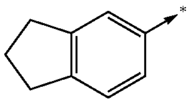 | 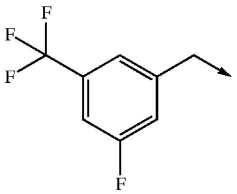 | 72.7 | 5.3 | 505.33 |
| 2334 | 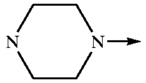 | 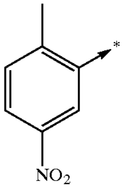 | 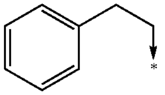 | 79.9 | 4.93 | 452.35 |

-continued
| | | | | | | |
|---|---|---|---|---|---|---|
| 2335 | 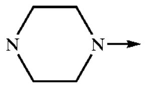 | 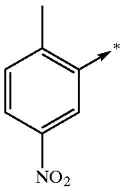 | 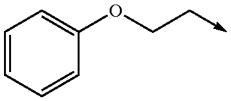 | 81.8 | 4.88 | 468.33 |
| 2336 | 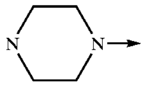 | 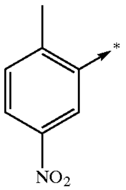 | 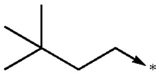 | 85.9 | 5.17 | 432.36 |
| 2337 | 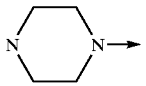 | 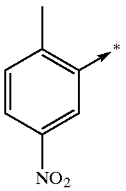 | 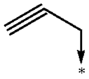 | 36.2 | 4.25 | 386.28 |
| 2338 | 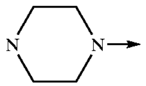 | 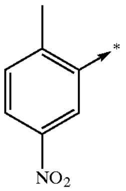 | 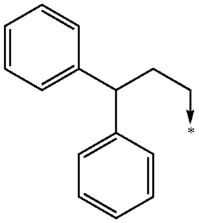 | 93.3 | 5.62 | 542.36 |
| 2339 | 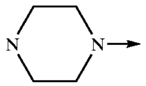 | 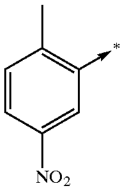 | 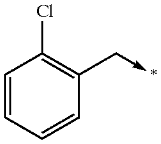 | 76.5 | 4.96 | 472.3 |

-continued
| | | | | | | |
|---|---|---|---|---|---|---|
| 2340 | 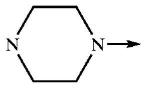 | 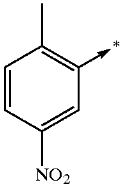 | 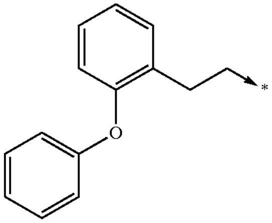 | 84.9 | 5.53 | 544.34 |
| 2341 | 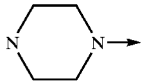 | 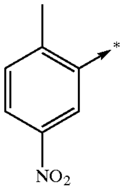 | 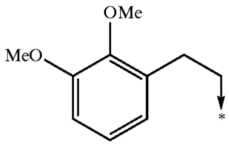 | 80.6 | 4.96 | 512.34 |
| 2342 | 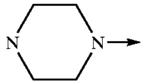 | 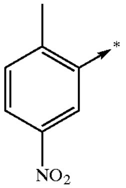 | 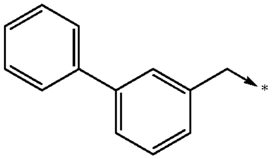 | 79.6 | 5.42 | 514.35 |
| 2343 | 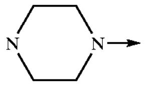 | 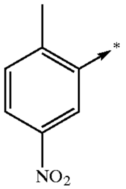 | 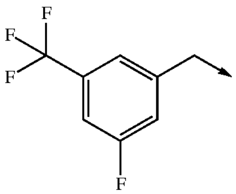 | 64.9 | 5.34 | 524.27 |
| 2344 | 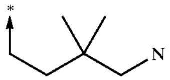 | 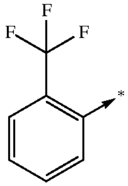 | 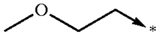 | 76.9 | 4.54 | 431.32 |

-continued
| | | | | | | |
|---|---|---|---|---|---|---|
| 2345 | 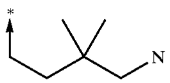 | 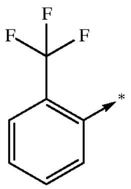 | 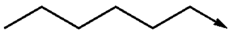 | 80.7 | 5.47 | 457.38 |
| 2346 | 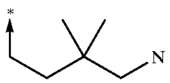 | 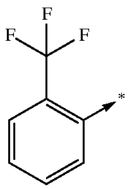 | 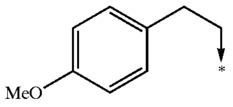 | 82.2 | 5.19 | 507.34 |
| 2347 | 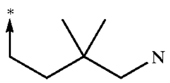 | 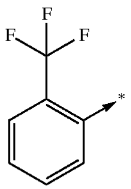 | 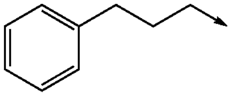 | 82.1 | 5.38 | 491.35 |
| 2348 | 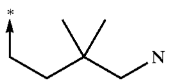 | 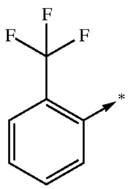 | 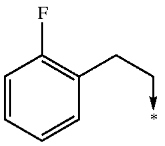 | 76.7 | 5.2 | 495.30 |
| 2349 | 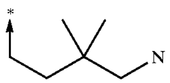 | 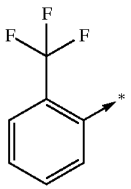 | 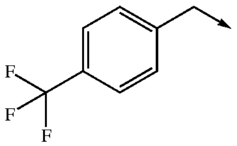 | 83.1 | 5.42 | 531.30 |

-continued
| | | | | | | |
|---|---|---|---|---|---|---|
| 2350 | 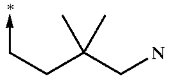 | 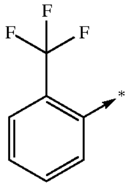 | 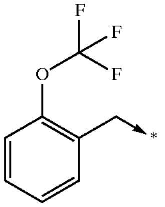 | 78.5 | 5.4 | 547.27 |
| 2351 | 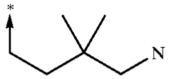 | 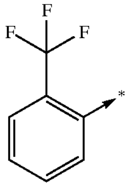 | 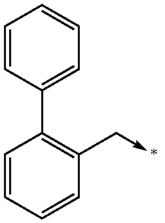 | 86.8 | 5.58 | 539.33 |
| 2352 | 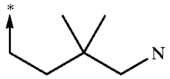 | 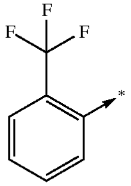 | 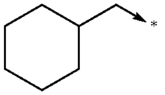 | 79.3 | 5.37 | 469.38 |
| 2353 | 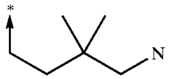 | 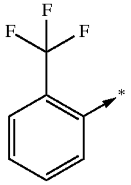 | 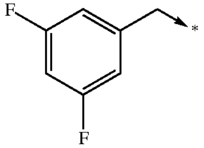 | 83.1 | 5.18 | 499.31 |
| 2354 | 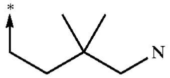 | 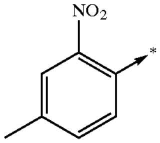 | 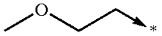 | 82.3 | 4.32 | 422.33 |

-continued
| | | | | | | |
|---|---|---|---|---|---|---|
| 2355 | 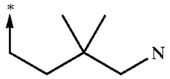 | 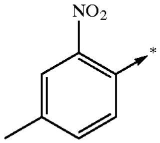 | 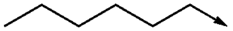 | 78.2 | 5.26 | 448.39 |
| 2356 | 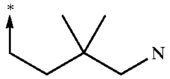 | 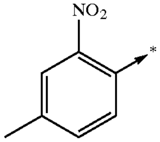 | 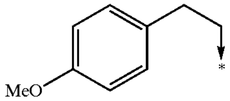 | 79.7 | 4.98 | 498.37 |
| 2357 | 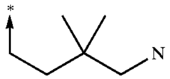 | 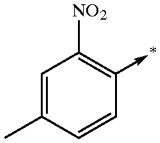 | 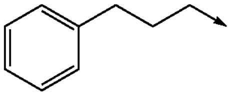 | 80.0 | 5.2 | 482.38 |
| 2358 | 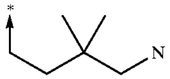 | 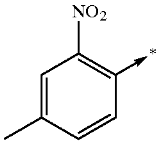 | 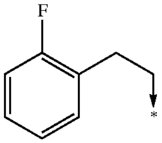 | 75.3 | 5.0 | 486.34 |
| 2359 | 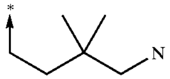 | 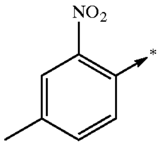 | 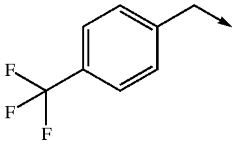 | 81.9 | 5.26 | 522.30 |
| 2360 | 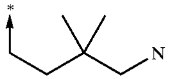 | 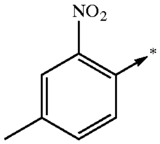 | 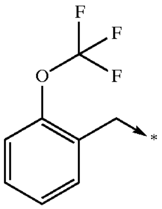 | 77.7 | 5.25 | 538.29 |

-continued
| | | | | | | |
|---|---|---|---|---|---|---|
| 2361 | 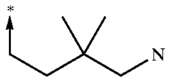 | 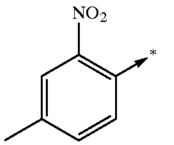 | 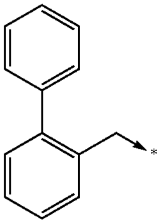 | 83.9 | 5.4 | 530.35 |
| 2362 | 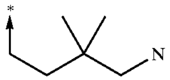 | 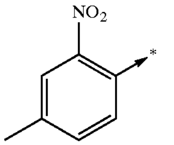 | 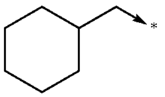 | 81.8 | 5.16 | 460.38 |
| 2363 | 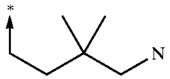 | 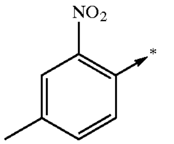 | 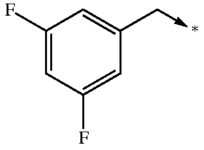 | 79.3 | 5.03 | 490.31 |
| 2364 | 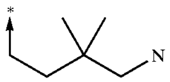 | 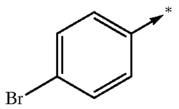 | 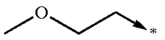 | 82.5 | 4.01 | 441.22 |
| 2365 | 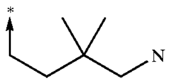 | 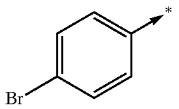 | 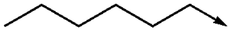 | 80.6 | 4.98 | 467.28 |
| 2366 | 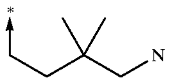 | 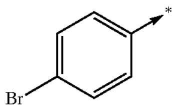 | 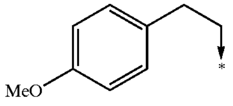 | 82.7 | 4.72 | 517.25 |
| 2367 | 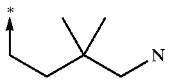 | 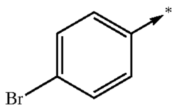 | 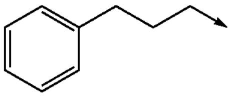 | 83.6 | 5.0 | 501.26 |

-continued
| | | | | | | |
|---|---|---|---|---|---|---|
| 2368 | 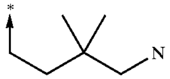 | 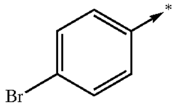 | 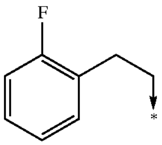 | 84.3 | 4.9 | 505.23 |
| 2369 | 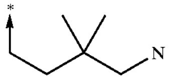 | 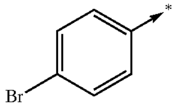 | 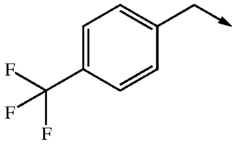 | 82.5 | 5.48 | 541.19 |
| 2370 | 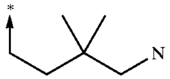 | 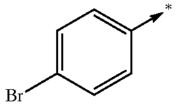 | 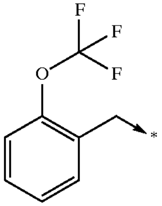 | 86.6 | 5.5 | 557.19 |
| 2371 | 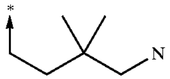 | 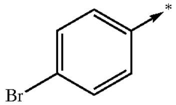 | 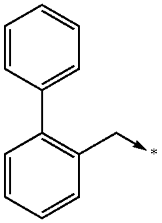 | 85.4 | 5.53 | 549.24 |
| 2372 | 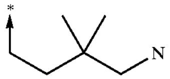 | 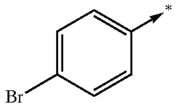 | 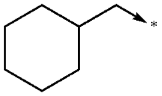 | 82.3 | 4.9 | 479.30 |
| 2373 | 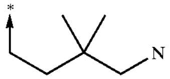 | 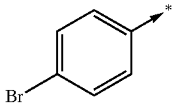 | 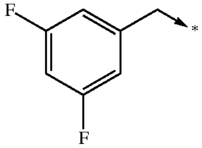 | 81.5 | 5.26 | 509.21 |

-continued
| | | | | | | |
|---|---|---|---|---|---|---|
| 2374 | 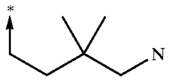 | 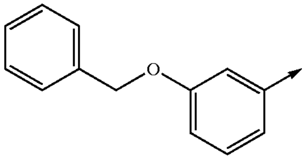 | 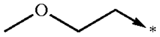 | 83.4 | 4.23 | 469.37 |
| 2375 | 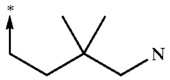 | 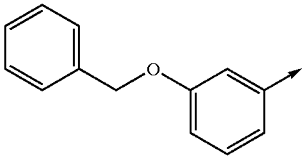 | 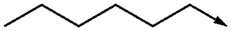 | 82.3 | 4.94 | 495.40 |
| 2376 | 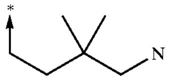 | 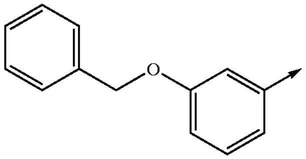 | 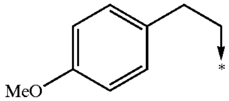 | 88.1 | 4.73 | 545.36 |
| 2377 | 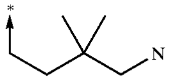 | 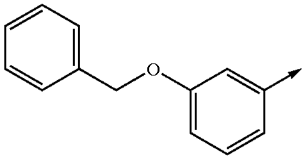 | 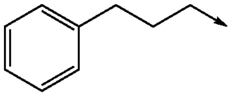 | 90.4 | 4.99 | 529.39 |
| 2378 | 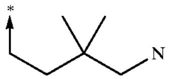 | 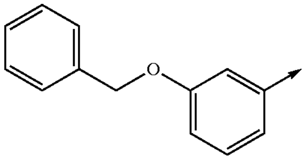 | 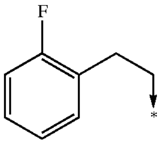 | 90.6 | 4.92 | 533.35 |
| 2379 | 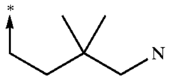 | 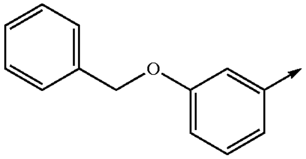 | 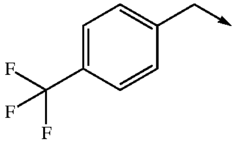 | 85.2 | 5.62 | 569.33 |

-continued
| | | | | | | |
|---|---|---|---|---|---|---|
| 2380 | 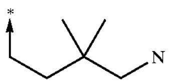 | 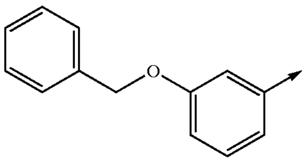 | 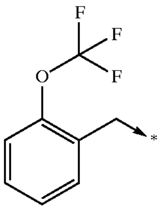 | 84.2 | 5.6 | 585.33 |
| 2381 | 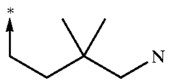 | 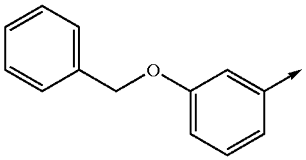 | 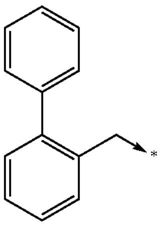 | 85.0 | 5.54 | 577.38 |
| 2382 | 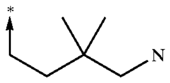 | 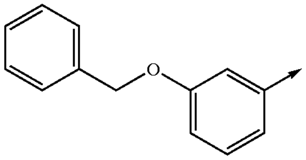 | 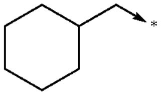 | 80.6 | 4.87 | 507.41 |
| 2383 | 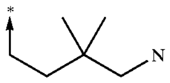 | 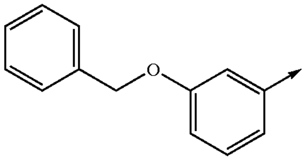 | 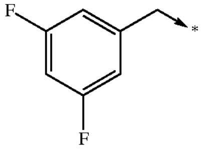 | 85.9 | 5.42 | 537.34 |
| 2384 | 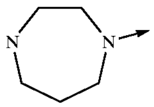 | 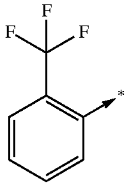 | 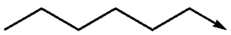 | 74.2 | 5.32 | 455.34 |

-continued
| | | | | | | |
|---|---|---|---|---|---|---|
| 2385 | 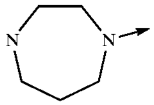 | 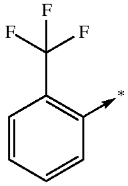 | 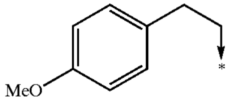 | 92.3 | 5.1 | 505.32 |
| 2386 | 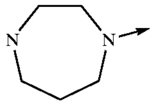 | 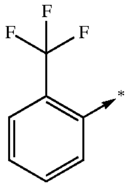 | 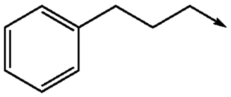 | 78.4 | 5.23 | 489.33 |
| 2387 | 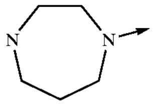 | 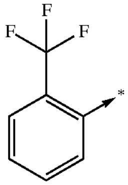 | 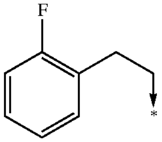 | 71.3 | 5.12 | 493.32 |
| 2388 | 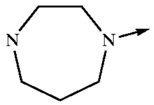 | 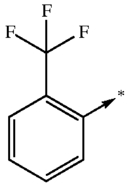 | 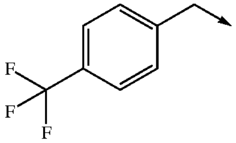 | 74.4 | 5.32 | 529.27 |
| 2389 | 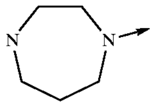 | 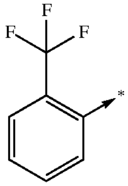 | 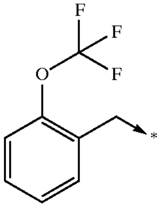 | 68.8 | 5.29 | 545.25 |

-continued
| | | | | | | |
|---|---|---|---|---|---|---|
| 2390 | 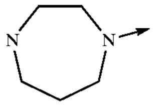 | 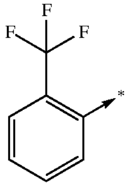 | 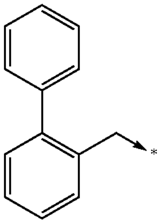 | 77.7 | 5.44 | 537.33 |
| 2391 | 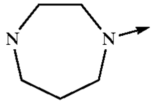 | 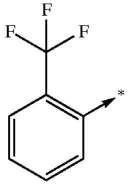 | 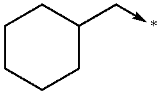 | 80.7 | 5.24 | 467.36 |
| 2392 | 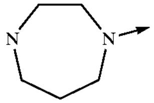 | 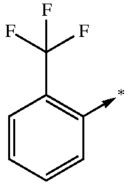 | 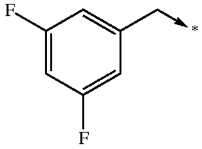 | 63.3 | 5.04 | 497.30 |
| 2393 | 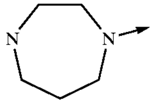 | 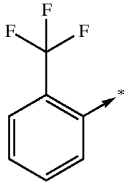 | 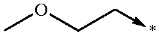 | 87.4 | 4.16 | 420.33 |
| 2394 | 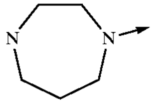 | 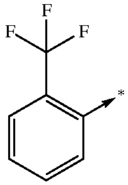 | 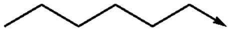 | 82.7 | 5.12 | 446.38 |

-continued
| | | | | | | |
|---|---|---|---|---|---|---|
| 2395 | 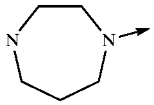 | 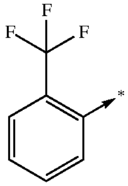 | 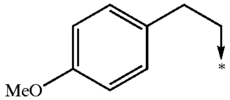 | 82.4 | 4.88 | 496.35 |
| 2396 | 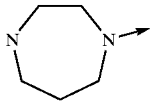 | 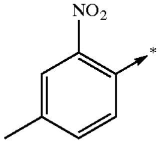 | 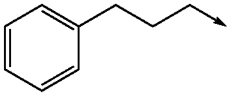 | 78.0 | 5.04 | 480.37 |
| 2397 | 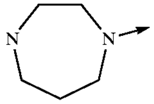 | 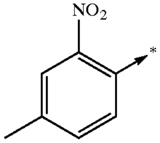 | 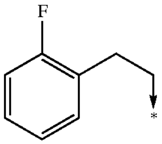 | 75.9 | 4.9 | 484.33 |
| 2398 | 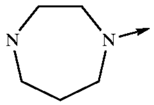 | 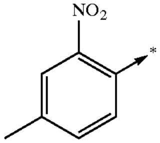 | 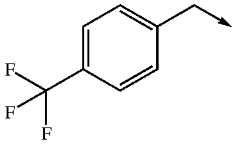 | 71.5 | 5.16 | 520.29 |
| 2399 | 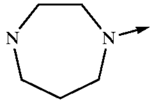 | 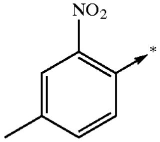 | 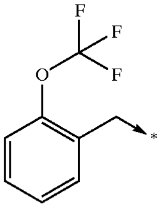 | 65.4 | 5.12 | 536.30 |

-continued
| | | | | | | |
|---|---|---|---|---|---|---|
| 2400 | 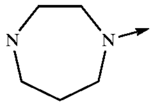 | 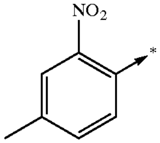 | 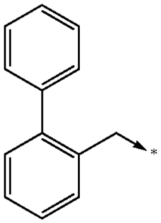 | 76.0 | 5.28 | 528.33 |
| 2401 | 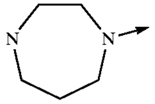 | 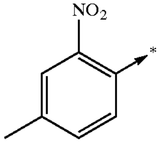 | 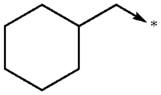 | 93.8 | 5.03 | 458.38 |
| 2402 | 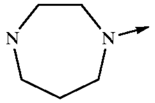 | 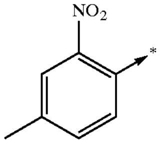 | 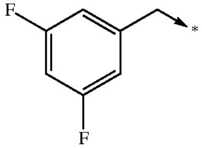 | 69.2 | 4.88 | 488.30 |
| 2403 | 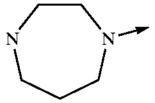 | 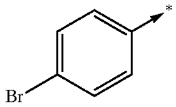 | 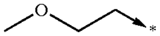 | 68.3 | 3.88 | 439.23 |
| 2404 | 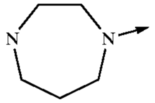 | 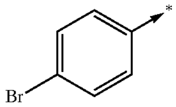 | 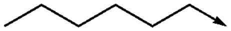 | 70.8 | 4.89 | 465.28 |
| 2405 | 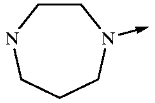 | 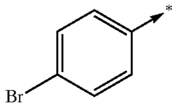 | 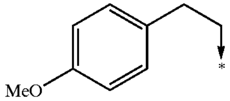 | 76.2 | 4.72 | 515.23 |
| 2406 | 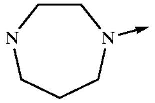 | 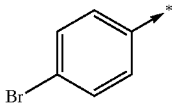 | 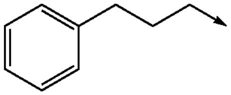 | 76.5 | 4.88 | 499.27 |

-continued
| | | | | | | |
|---|---|---|---|---|---|---|
| 2407 | 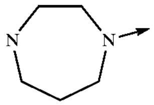 | 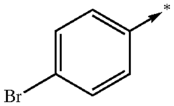 | 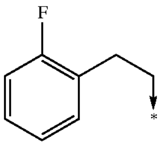 | 90.1 | 4.88 | 503.26 |
| 2408 | 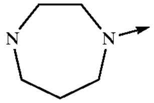 | 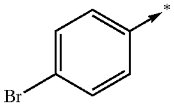 | 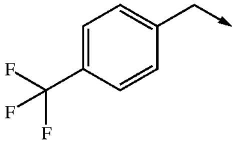 | 78.8 | 5.36 | 539.19 |
| 2409 | 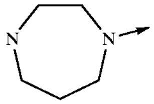 | 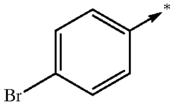 | 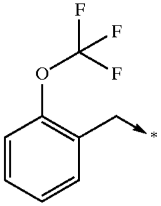 | 76.1 | 5.31 | 555.17 |
| 2410 | 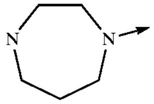 | 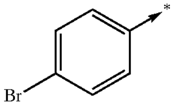 | 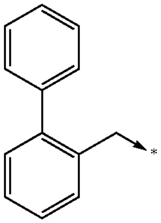 | 80.5 | 5.29 | 547.22 |
| 2411 | 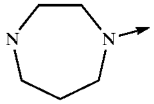 | 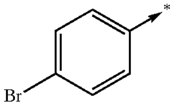 | 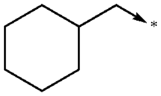 | 68.2 | 4.86 | 477.30 |
| 2412 | 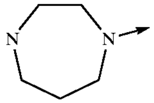 | 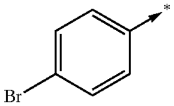 | 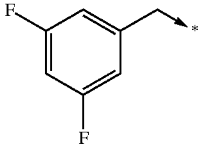 | 55.7 | 5.1 | 507.20 |

-continued
| | | | | | | |
|---|---|---|---|---|---|---|
| 2413 | 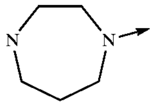 | 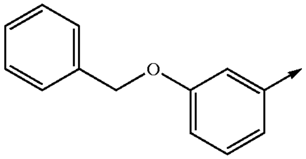 | 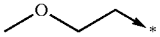 | 69.2 | 412 | 467.36 |
| 2414 | 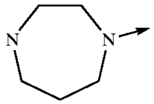 | 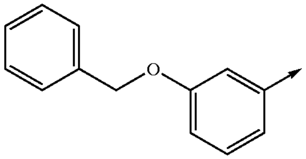 | 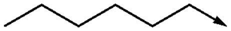 | 73.6 | 4.85 | 493.41 |
| 2415 | 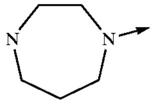 | 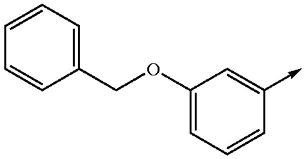 | 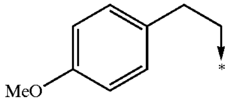 | 73.9 | 4.72 | 543.36 |
| 2416 | 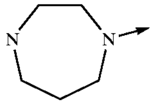 | 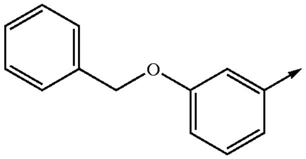 | 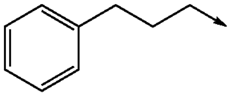 | 73.4 | 4.87 | 527.39 |
| 2417 | 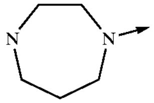 | 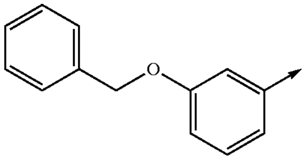 | 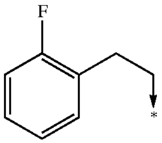 | 90.6 | 4.92 | 531.36 |
| 2418 | 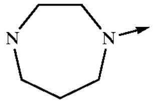 | 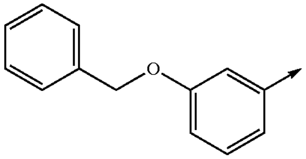 | 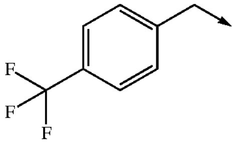 | 71.6 | 5.5 | 567.32 |

-continued
| | | | | | | |
|---|---|---|---|---|---|---|
| 2419 | 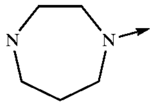 | 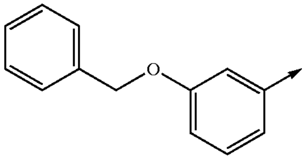 | 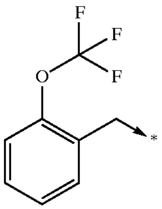 | 60.5 | 5.4 | 583.32 |
| 2420 | 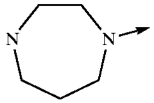 | 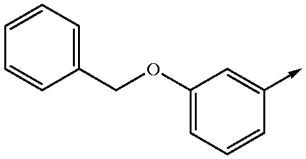 | 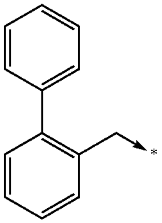 | 60.8 | 5.29 | 575.36 |
| 2421 | 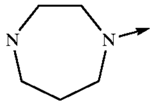 | 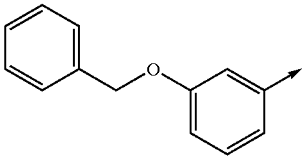 | 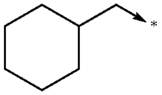 | 58.8 | 4.82 | 505.39 |
| 2422 | 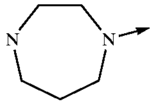 | 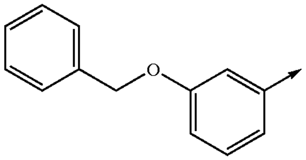 | 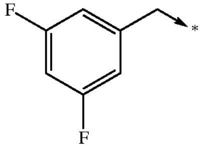 | 54.7 | 5.29 | 535.31 |

-continued
| Ex. | R10 | R2 | R3 | Purity (%) | rt (min.) | [M + H]+ |
|---|---|---|---|---|---|---|
| | | | 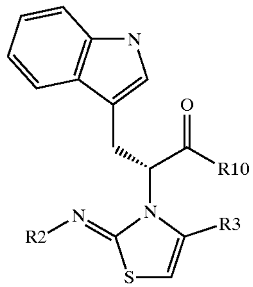 | | | |
| 2423 | 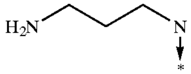 | 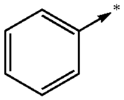 | 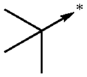 | 79.8 | 3.66 | 476.30 |
| 2424 | 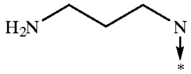 | 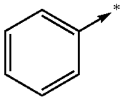 | 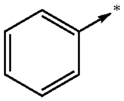 | 59.3 | 3.68 | 496.26 |
| 2425 | 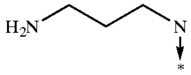 | 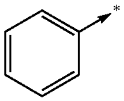 | 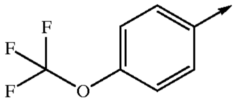 | 60.5 | 4.2 | 580.22 |
| 2426 | 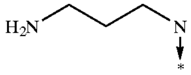 | 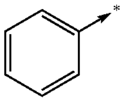 | 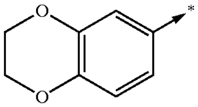 | 52.7 | 3.68 | 554.24 |
| 2427 | 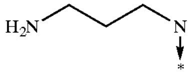 | 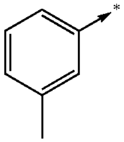 | 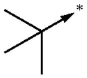 | 72.3 | 3.87 | 490.30 |

-continued
| | | | | | | |
|---|---|---|---|---|---|---|
| 2428 | 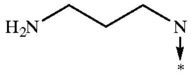 | 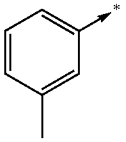 | 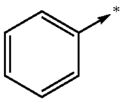 | 63.8 | 3.85 | 510.26 |
| 2429 | 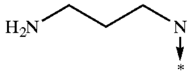 | 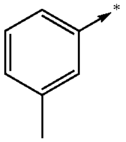 | 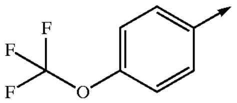 | 63.0 | 4.34 | 594.23 |
| 2430 | 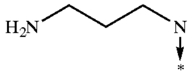 | 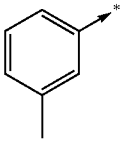 | 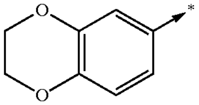 | 54.1 | 3.82 | 568.25 |
| 2431 | 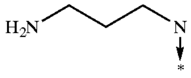 | 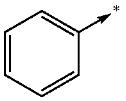 | 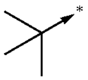 | 76.9 | 3.72 | 490.30 |
| 2432 | 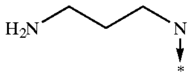 | 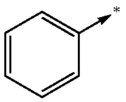 | 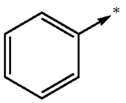 | 70.7 | 3.73 | 510.26 |
| 2433 | 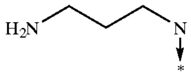 | 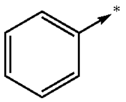 | 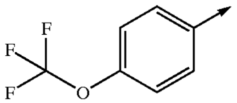 | 69.1 | 4.23 | 594.24 |
| 2434 | 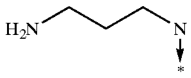 | 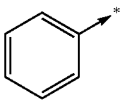 | 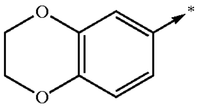 | 52.7 | 3.72 | 568.24 |

-continued
| | | | | | | |
|---|---|---|---|---|---|---|
| 2435 | 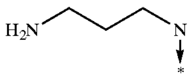 | 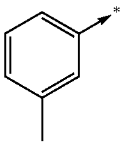 | 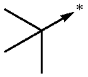 | 76.6 | 3.92 | 504.32 |
| 2436 | 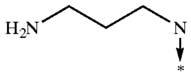 | 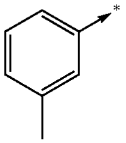 | 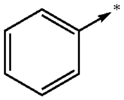 | 64.8 | 3.9 | 524.28 |
| 2437 | 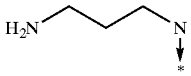 | 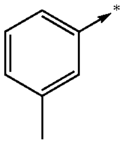 | 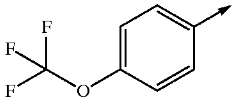 | 66.2 | 4.37 | 608.24 |
| 2438 | 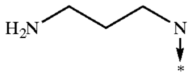 | 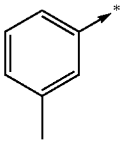 | 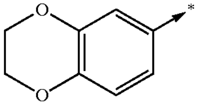 | 59.3 | 3.86 | 582.27 |
| 2439 | 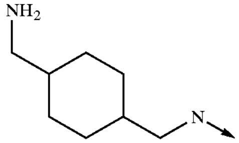 | 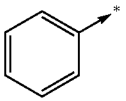 | 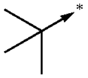 | 74.3 | 3.9 | 544.32 |
| 2440 | 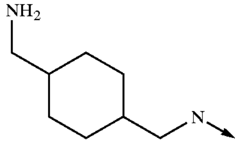 | 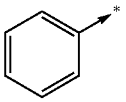 | 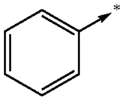 | 65.4 | 3.91 | 564.29 |
| 2441 | 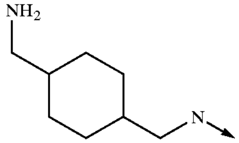 | 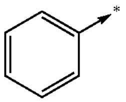 | 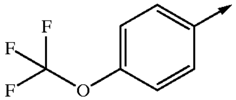 | 63.8 | 4.41 | 648.30 |

-continued
| | | | | | | |
|---|---|---|---|---|---|---|
| 2442 | 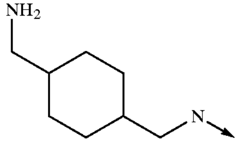 | 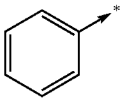 | 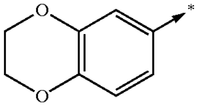 | 57.6 | 3.92 | 622.31 |
| 2443 | 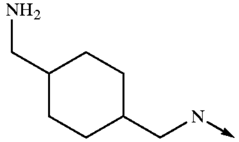 | 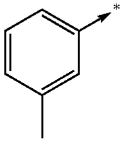 | 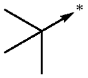 | 77.8 | 4.09 | 558.34 |
| 2444 | 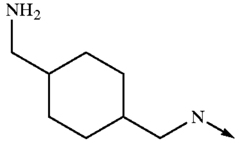 | 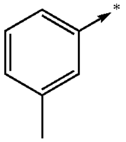 | 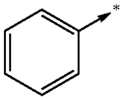 | 65.5 | 4.08 | 578.30 |
| 2445 | 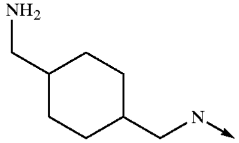 | 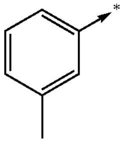 | 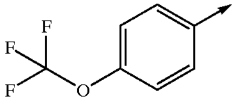 | 64.3 | 4.5 | 662.31 |
| 2446 | 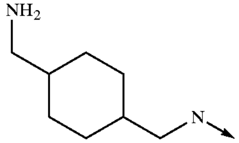 | 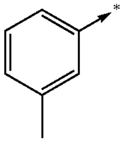 | 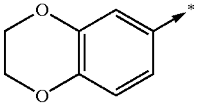 | 47.6 | 4.04 | 636.36 |
| 2447 | 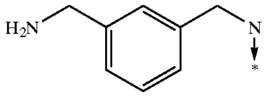 | 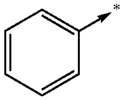 | 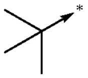 | 78.6 | 3.88 | 538.28 |
| 2448 | 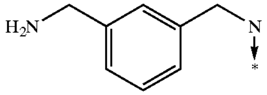 | 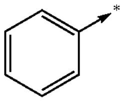 | 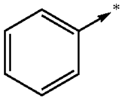 | 61.2 | 3.9 | 558.24 |

-continued
| | | | | | | |
|---|---|---|---|---|---|---|
| 2449 | 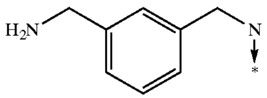 | 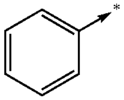 | 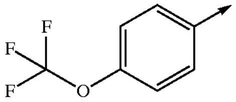 | 59.8 | 4.38 | 642.27 |
| 2450 | 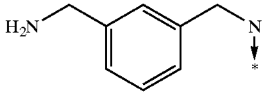 | 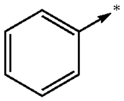 | 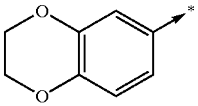 | 48.4 | 3.88 | 616.30 |
| 2451 | 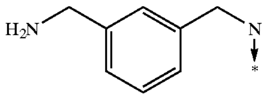 | 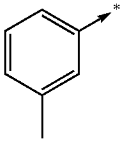 | 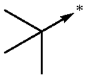 | 79.9 | 4.06 | 552.28 |
| 2452 | 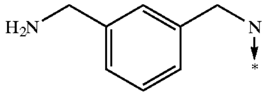 | 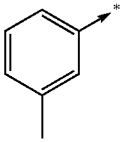 | 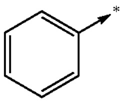 | 59.4 | 4.04 | 572.25 |
| 2453 | 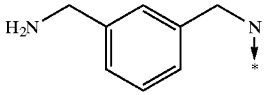 | 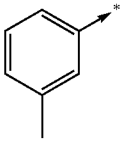 | 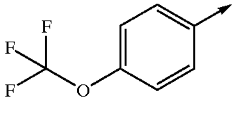 | 61.4 | 4.52 | 656.29 |
| 2454 | 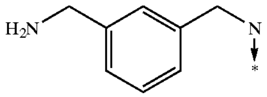 | 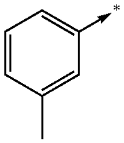 | 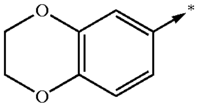 | 50.0 | 4.02 | 630.31 |
| 2455 | 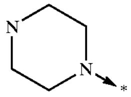 | 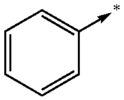 | 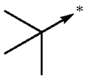 | 76.1 | 3.74 | 488.29 |

-continued
| | | | | | | |
|---|---|---|---|---|---|---|
| 2456 | 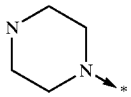 | 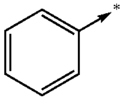 | 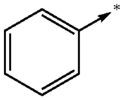 | 88.3 | 3.72 | 508.25 |
| 2457 | 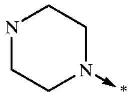 | 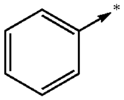 | 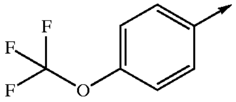 | 84.2 | 4.21 | 592.22 |
| 2458 | 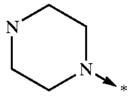 | 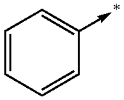 | 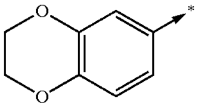 | 82.1 | 3.71 | 586.24 |
| 2459 | 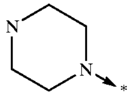 | 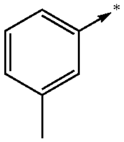 | 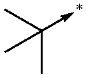 | 72.4 | 3.96 | 502.32 |
| 2460 | 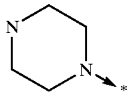 | 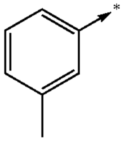 | 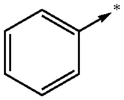 | 88.5 | 3.89 | 522.27 |
| 2461 | 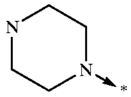 | 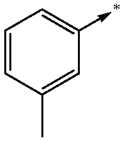 | 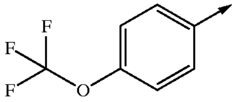 | 86.6 | 4.37 | 606.26 |
| 2462 | 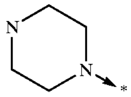 | 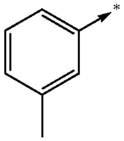 | 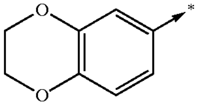 | 77.2 | 3.8 | 580.26 |

-continued
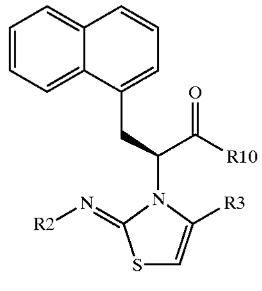
Chiral
| | | | | | | |
|---|---|---|---|---|---|---|
| 2463 | 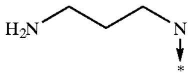 | 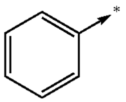 | 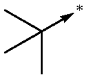 | 86.6 | 3.96 | 487.31 |
| 2464 | 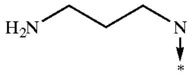 | 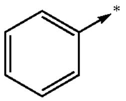 | 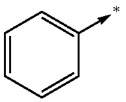 | 58.7 | 4 | 507.27 |
| 2465 | 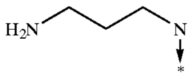 | 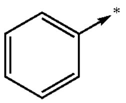 | 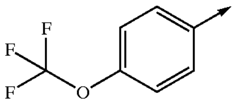 | 64.9 | 4.48 | 591.22 |
| 2466 | 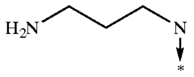 | 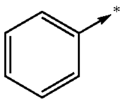 | 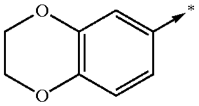 | 40.3 | 4 | 565.25 |
| 2467 | 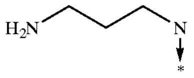 | 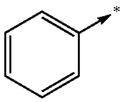 | 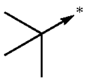 | 91.3 | 4.12 | 501.31 |

-continued
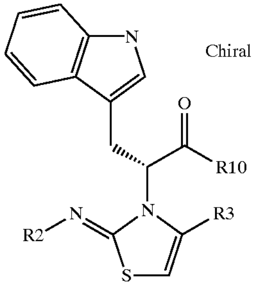
Chiral
| | | | | | | |
|---|---|---|---|---|---|---|
| 2468 | 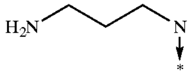 | 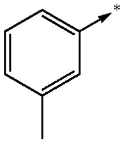 | 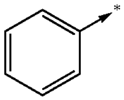 | 61.2 | 4.14 | 521.25 |
| 2469 | 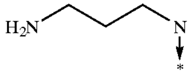 | 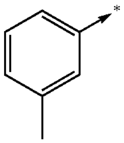 | 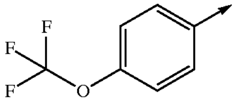 | 62.4 | 4.62 | 605.25 |
| 2470 | 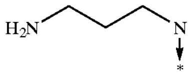 | 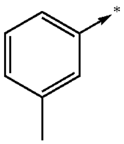 | 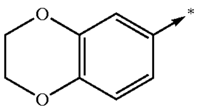 | 33.1 | 4.13 | 579.27 |
| 2471 | 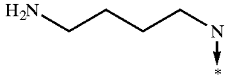 | 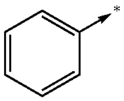 | 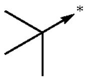 | 87.3 | 4.01 | 501.31 |
| 2472 | 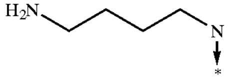 | 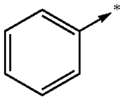 | 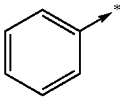 | 54.0 | 4.05 | 521.25 |

-continued
| | | | | | | |
|---|---|---|---|---|---|---|
| 2473 | 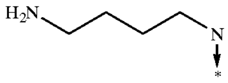 | 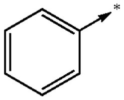 | 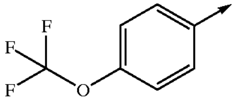 | 69.1 | 4.51 | 605.26 |
| 2474 | 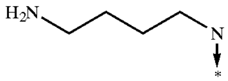 | 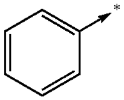 | 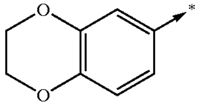 | 35.4 | 4.04 | 579.27 |
| 2475 | 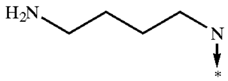 | 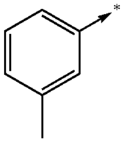 | 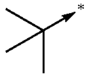 | 88.4 | 4.18 | 515.31 |
| 2476 | 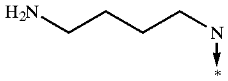 | 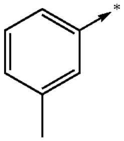 | 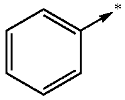 | 68.0 | 4.19 | 535.28 |
| 2477 | 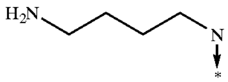 | 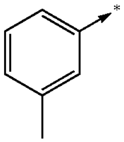 | 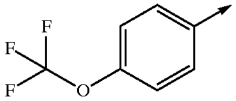 | 72.9 | 4.64 | 619.25 |
| 2478 | 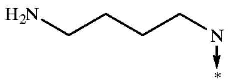 | 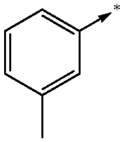 | 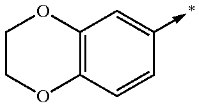 | 32.6 | 4.17 | 593.28 |
| 2479 | 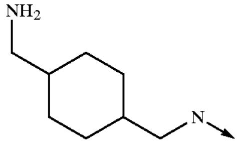 | 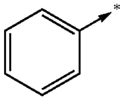 | 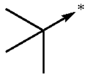 | 92.7 | 4.18 | 555.33 |

-continued
| | | | | | | |
|---|---|---|---|---|---|---|
| 2480 | 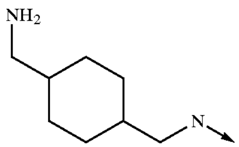 | 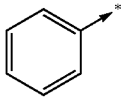 | 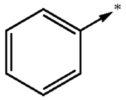 | 59.4 | 4.24 | 575.29 |
| 2481 | 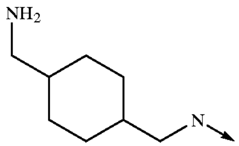 | 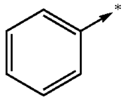 | 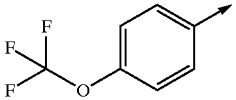 | 71.8 | 4.72 | 659.33 |
| 2482 | 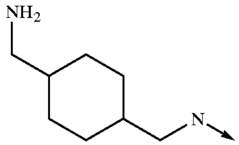 | 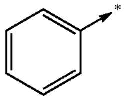 | 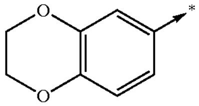 | 36.4 | 4.2 | 633.44 |
| 2483 | 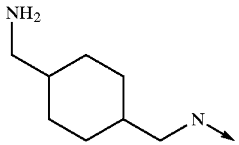 | 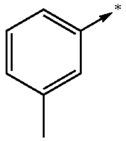 | 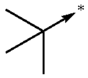 | 92.4 | 4.36 | 569.34 |
| 2484 | 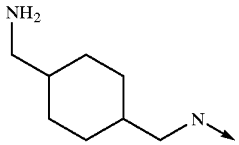 | 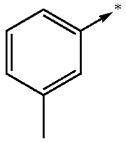 | 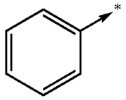 | 62.9 | 4.38 | 589.32 |
| 2485 | 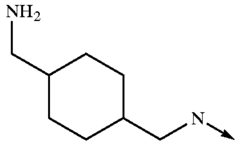 | 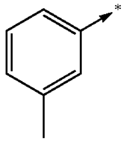 | 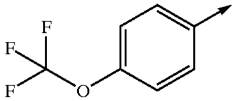 | 71.9 | 4.82 | 673.33 |

-continued
| | | | | | | |
|---|---|---|---|---|---|---|
| 2486 | 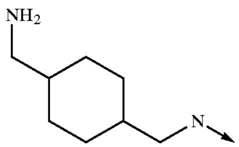 | 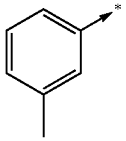 | 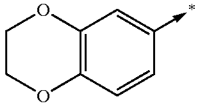 | 32.2 | 4.36 | 647.19 |
| 2487 | 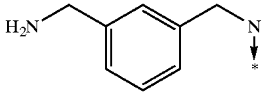 | 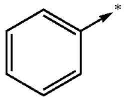 | 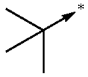 | 90.2 | 4.14 | 549.28 |
| 2488 | 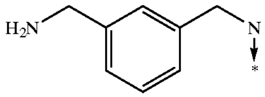 | 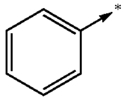 | 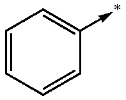 | 59.7 | 4.22 | 569.24 |
| 2489 | 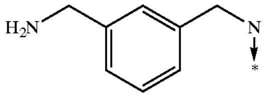 | 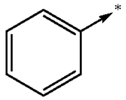 | 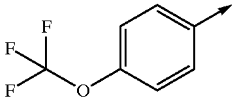 | 66.6 | 4.7 | 653.25 |
| 2490 | 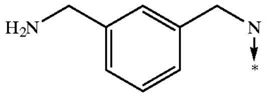 | 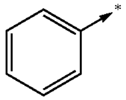 | 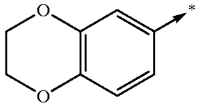 | 34.5 | 4.22 | 627.27 |
| 2491 | 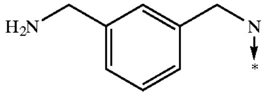 | 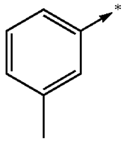 | 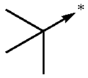 | 91.3 | 4.32 | 563.30 |
| 2492 | 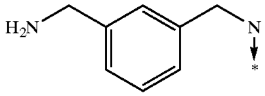 | 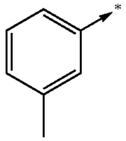 | 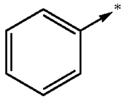 | 60.8 | 4.35 | 583.26 |

-continued
| | | | | | | |
|---|---|---|---|---|---|---|
| 2493 | 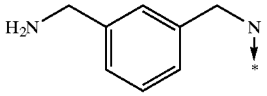 | 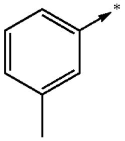 | 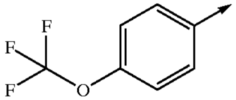 | 73.3 | 4.8 | 667.27 |
| 2494 | 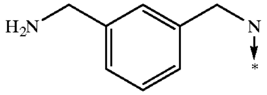 | 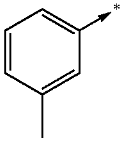 | 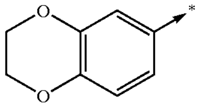 | 32.9 | 4.34 | 641.29 |
| 2495 | 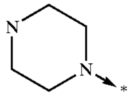 | 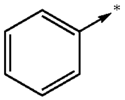 | 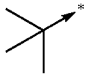 | 60.4 | 3.94 | 499.30 |
| 2496 | 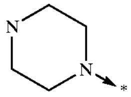 | 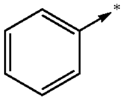 | 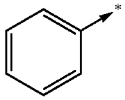 | 87.0 | 3.92 | 519.24 |
| 2497 | 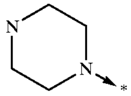 | 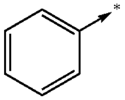 | 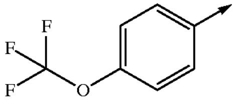 | 84.4 | 4.41 | 603.24 |
| 2498 | 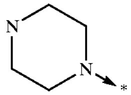 | 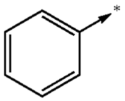 | 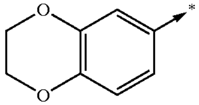 | 81.4 | 3.94 | 577.26 |
| 2499 | 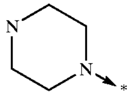 | 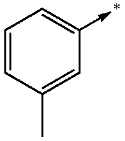 | 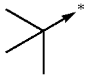 | 73.9 | 4.12 | 513.31 |

-continued
| | | | | | | |
|---|---|---|---|---|---|---|
| 2500 | 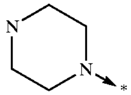 | 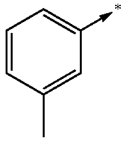 | 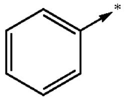 | 91.5 | 4.09 | 533.26 |
| 2501 | 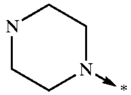 | 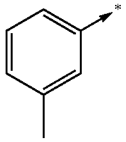 | 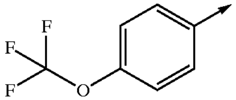 | 89.6 | 4.54 | 617.26 |
| 2502 | 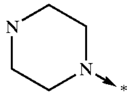 | 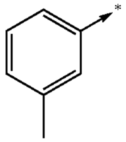 | 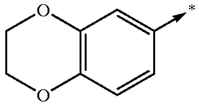 | 85.4 | 4.09 | 591.27 |
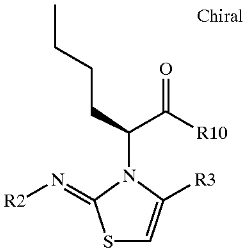
Chiral
| | | | | | | |
|---|---|---|---|---|---|---|
| 2503 | 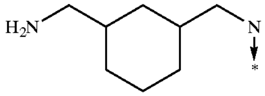 | 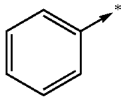 | 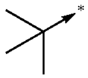 | 77.7 | 3.8 | 471.39 |
| 2504 | 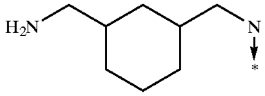 | 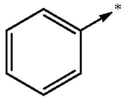 | 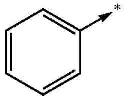 | 37.7 | 3.82 | 491.34 |

-continued
| | | | | | | |
|---|---|---|---|---|---|---|
| 2505 | 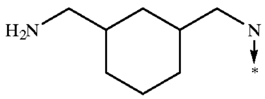 | 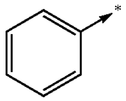 | 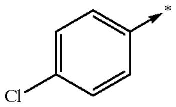 | 79.7 | 4.09 | 525.28 |
| 2506 | 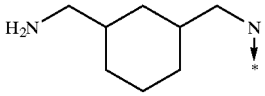 | 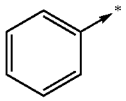 | 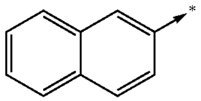 | 58.5 | 4.23 | 541.33 |
| 2507 | 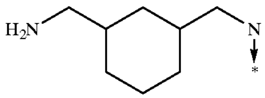 | 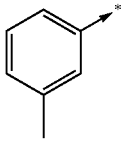 | 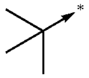 | 84.6 | 4.0 | 485.38 |
| 2508 | 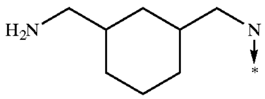 | 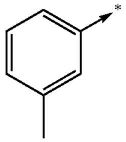 | 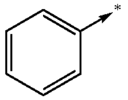 | 73.2 | 4.0 | 505.34 |
| 2509 | 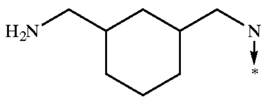 | 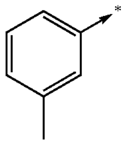 | 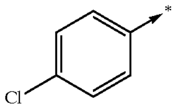 | 82.3 | 4.25 | 539.29 |
| 2510 | 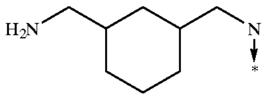 | 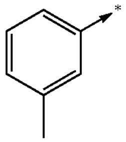 | 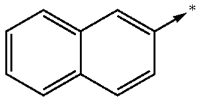 | 74.2 | 4.37 | 555.34 |
| 2511 | 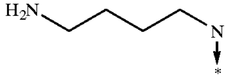 | 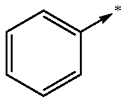 | 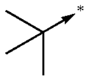 | 57.5 | 3.56 | 417.32 |

-continued
| | | | | | | |
|---|---|---|---|---|---|---|
| 2512 | 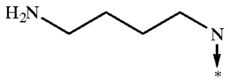 | 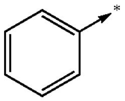 | 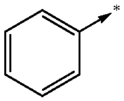 | 66.9 | 3.56 | 437.27 |
| 2513 | 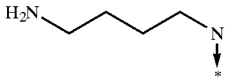 | 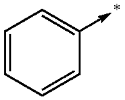 | 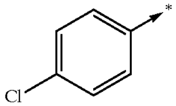 | 69.0 | 3.85 | 471.26 |
| 2514 | 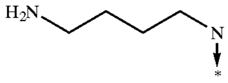 | 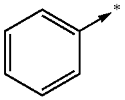 | 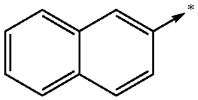 | 71.1 | 4.0 | 487.33 |
| 2515 | 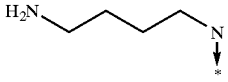 | 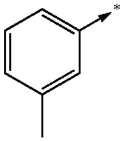 | 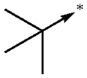 | 76.4 | 3.76 | 431.34 |
| 2516 | 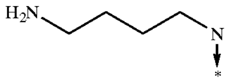 | 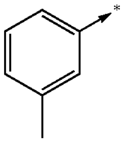 | 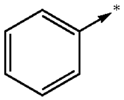 | 67.8 | 3.75 | 451.30 |
| 2517 | 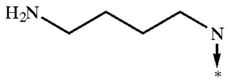 | 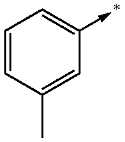 | 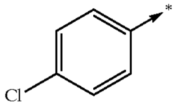 | 75.2 | 4.02 | 485.27 |
| 2518 | 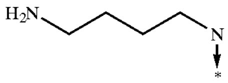 | 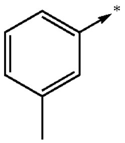 | 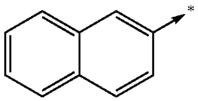 | 70.4 | 4.16 | 501.32 |

-continued
Chiral
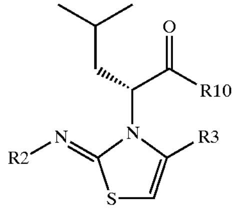
| | | | | | | |
|---|---|---|---|---|---|---|
| 2519 | 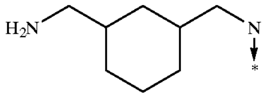 | 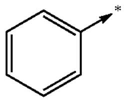 | 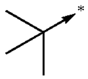 | 76.4 | 3.73 | 471.38 |
| 2520 | 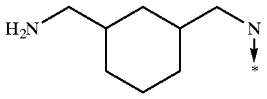 | 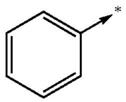 | 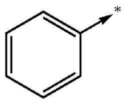 | 67.9 | 3.76 | 491.33 |
| 2521 | 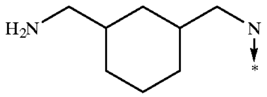 | 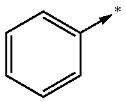 | 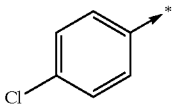 | 75.0 | 4.04 | 525.28 |
| 2522 | 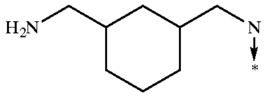 | 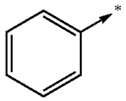 | 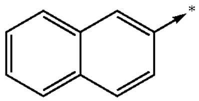 | 71.2 | 4.17 | 541.34 |
| 2523 | 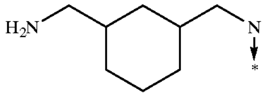 | 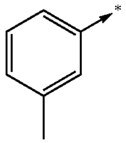 | 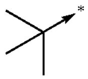 | 87.9 | 3.94 | 485.39 |
| 2524 | 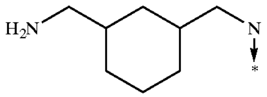 | 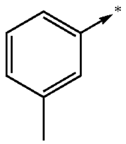 | 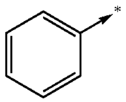 | 72.2 | 3.94 | 505.34 |

-continued
| | | | | | | |
|---|---|---|---|---|---|---|
| 2525 | 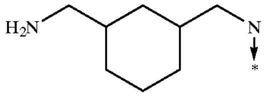 | 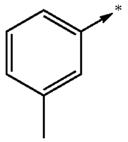 | 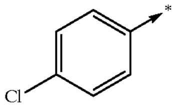 | 82.1 | 4.2 | 539.30 |
Chiral
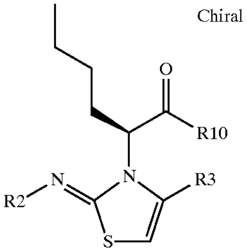
| | | | | | | |
|---|---|---|---|---|---|---|
| 2526 | 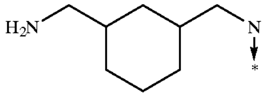 | 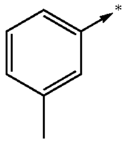 | 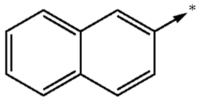 | 80.9 | 4.33 | 555.34 |
| 2527 | 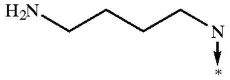 | 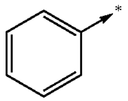 | 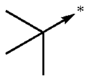 | 70.7 | 3.51 | 417.32 |
| 2528 | 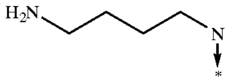 | 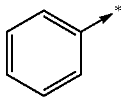 | 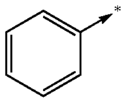 | 50.3 | 3.52 | 437.28 |
| 2529 | 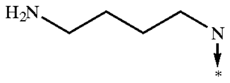 | 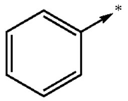 | 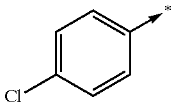 | 72.4 | 3.8 | 471.26 |

-continued
| | | | | | | |
|---|---|---|---|---|---|---|
| 2530 | 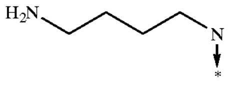 | 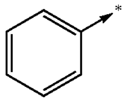 | 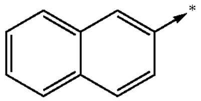 | 74.5 | 3.96 | 487.32 |
| 2531 | 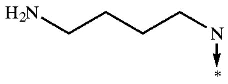 | 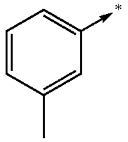 | 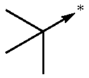 | 84.4 | 3.72 | 431.32 |
| 2532 | 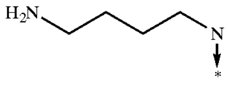 | 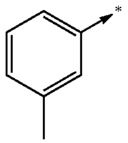 | 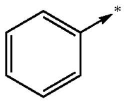 | 68 | 3.71 | 451.29 |
| 2533 | 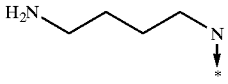 | 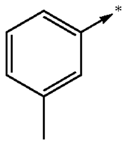 | 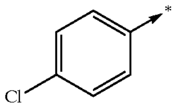 | 89.6 | 3.98 | 485.26 |
| 2534 | 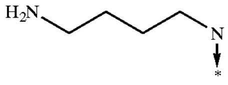 | 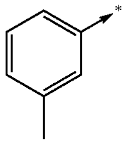 | 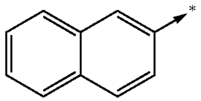 | 77.9 | 4.12 | 501.32 |

-continued
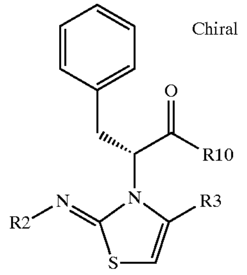
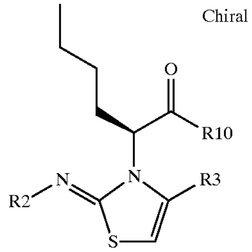
| | | | | | | |
|---|---|---|---|---|---|---|
| 2535 | 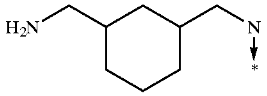 | 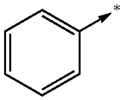 | 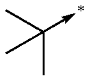 | 84.7 | 3.83 | 505.34 |
| 2536 | 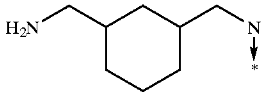 | 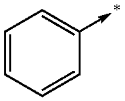 | 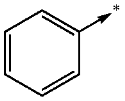 | 75.2 | 3.89 | 525.30 |
| 2537 | 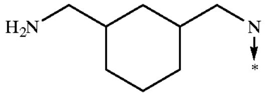 | 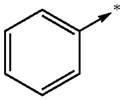 | 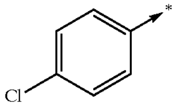 | 75.9 | 4.17 | 559.25 |
| 2538 | 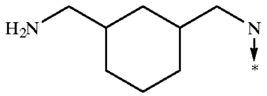 | 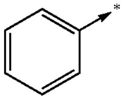 | 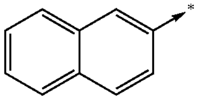 | 70.4 | 4.29 | 575.30 |

-continued
| | | | | | | |
|---|---|---|---|---|---|---|
| 2539 | 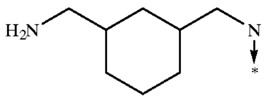 | 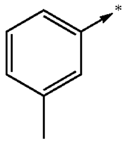 | 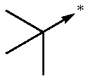 | 90.9 | 4.03 | 519.35 |
| 2540 | 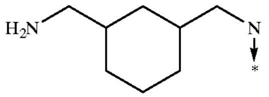 | 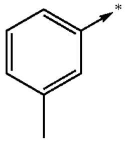 | 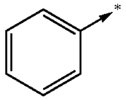 | 71.5 | 4.04 | 539.31 |
| 2541 | 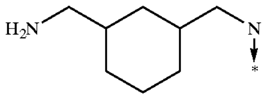 | 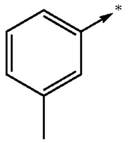 | 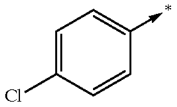 | 79.2 | 4.31 | 573.25 |
| 2542 | 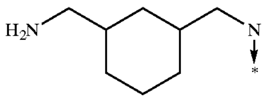 | 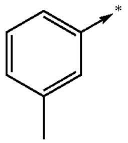 | 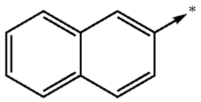 | 80.6 | 4.43 | 589.33 |
| 2543 | 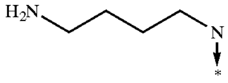 | 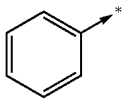 | 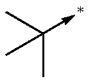 | 77.2 | 3.62 | 451.30 |
| 2544 | 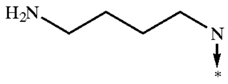 | 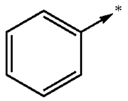 | 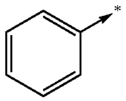 | 69.9 | 3.65 | 471.27 |
| 2545 | 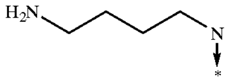 | 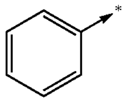 | 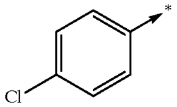 | 74.8 | 3.92 | 505.22 |

-continued
| | | | | | | |
|---|---|---|---|---|---|---|
| 2546 | 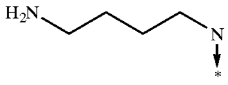 | 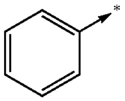 | 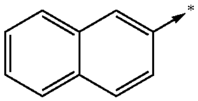 | 66.7 | 4.06 | 521.26 |
| 2547 | 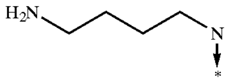 | 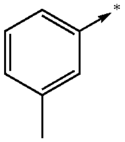 | 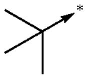 | 83.5 | 3.82 | 465.31 |
| 2548 | 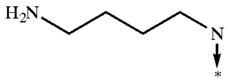 | 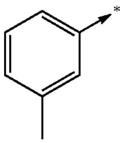 | 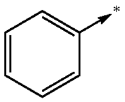 | 72.9 | 3.82 | 485.28 |
| 2549 | 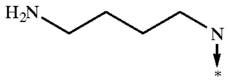 | 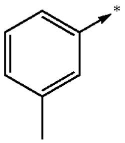 | 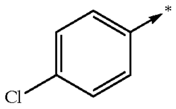 | 33.1 | 4.1 | 519.23 |
| 2550 | 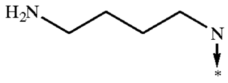 | 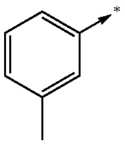 | 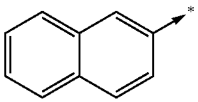 | 51.2 | 4.22 | 535.28 |

-continued
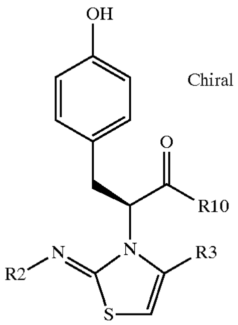
| | | | | | | |
|---|---|---|---|---|---|---|
| 2551 | 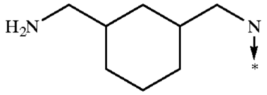 | 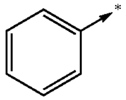 | 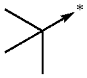 | 79.8 | 3.45 | 521.33 |
| 2552 | 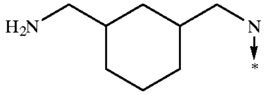 | 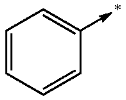 | 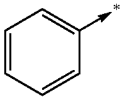 | 72.6 | 4.14 | 541.29 |
| 2553 | 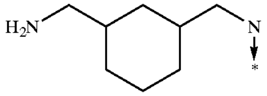 | 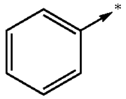 | 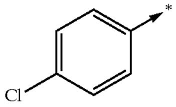 | 63.7 | 3.79 | 575.24 |
| 2554 | 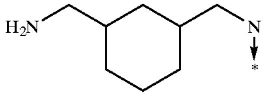 | 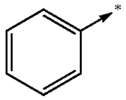 | 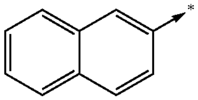 | 73.8 | 3.93 | 591.31 |
| 2555 | 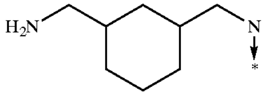 | 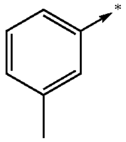 | 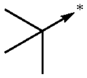 | 91.2 | 3.65 | 535.35 |

-continued
| | | | | | | |
|---|---|---|---|---|---|---|
| 2556 | 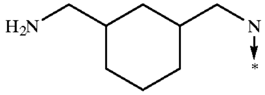 | 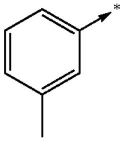 | 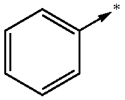 | 75.6 | 3.66 | 555.29 |
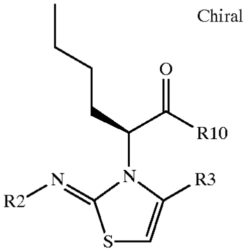
Chiral
| | | | | | | |
|---|---|---|---|---|---|---|
| 2557 | 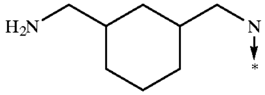 | 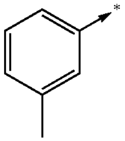 | 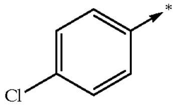 | 78.3 | 3.94 | 589.26 |
| 2558 | 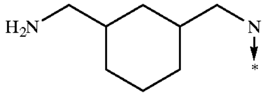 | 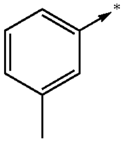 | 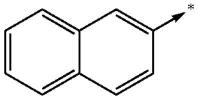 | 69.7 | 4.06 | 605.35 |
| 2559 | 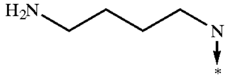 | 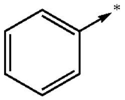 | 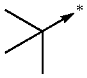 | 69.1 | 3.22 | 467.29 |
| 2560 | 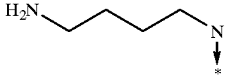 | 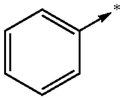 | 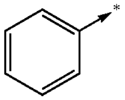 | 73.7 | 3.26 | 487.27 |

-continued
| | | | | | | |
|---|---|---|---|---|---|---|
| 2561 | 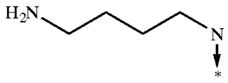 | 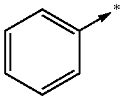 | 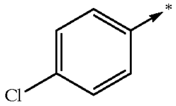 | 79.6 | 3.56 | 521.20 |
| 2562 | 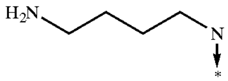 | 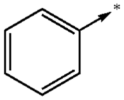 | 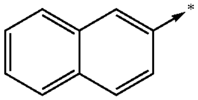 | 73.5 | 3.72 | 537.27 |
| 2563 | 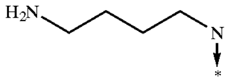 | 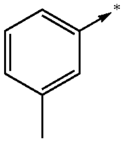 | 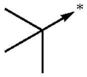 | 86.1 | 3.42 | 481.31 |
| 2564 | 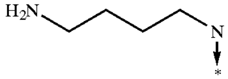 | 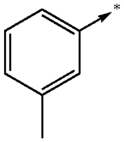 | 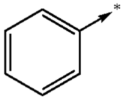 | 77.1 | 3.43 | 501.29 |
| 2565 | 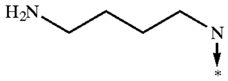 | 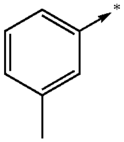 | 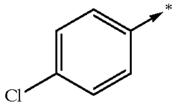 | 83.0 | 3.73 | 535.22 |
| 2566 | 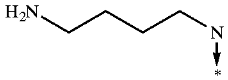 | 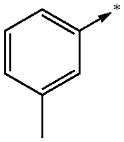 | 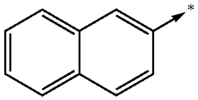 | 71.9 | 3.86 | 551.28 |

-continued
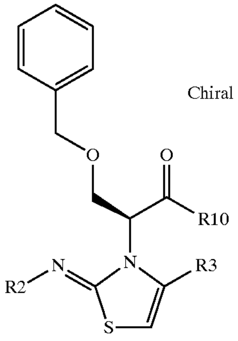
Chiral
| | | | | | | |
|---|---|---|---|---|---|---|
| 2567 | 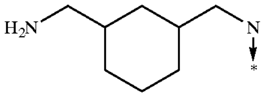 | 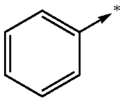 | 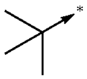 | 82.0 | 3.99 | 535.3 |
| 2568 | 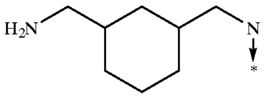 | 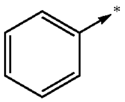 | 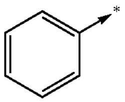 | 40.6 | 4.04 | 555.31 |
| 2569 | 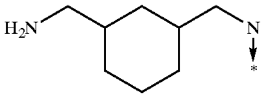 | 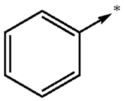 | 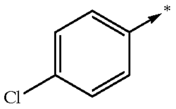 | 47.5 | 4.31 | 589.26 |
| 2570 | 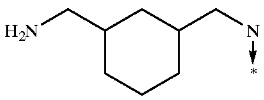 | 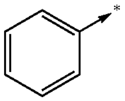 | 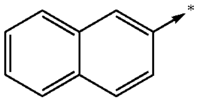 | 37.4 | 4.43 | 605.33 |
| 2571 | 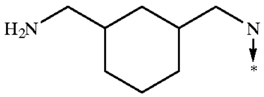 | 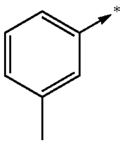 | 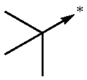 | 79.3 | 4.18 | 549.35 |

-continued
| | | | | | | |
|---|---|---|---|---|---|---|
| 2572 | 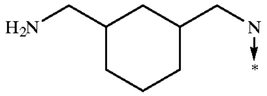 | 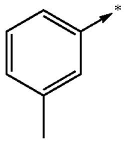 | 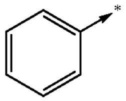 | 38.8 | 4.19 | 569.30 |
| 2573 | 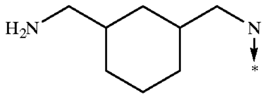 | 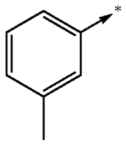 | 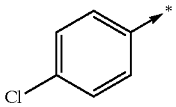 | 51.6 | 4.46 | 603.28 |
| 2574 | 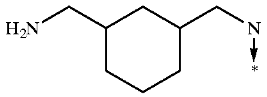 | 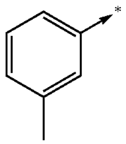 | 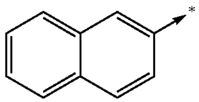 | 36 | 4.55 | 619.35 |
| 2575 | 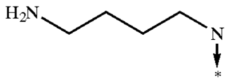 | 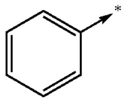 | 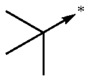 | 61.4 | 3.77 | 481.30 |
Chiral
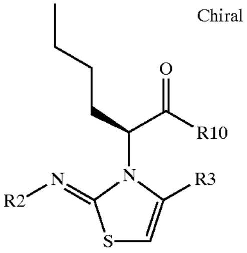
| | | | | | | |
|---|---|---|---|---|---|---|
| 2576 | 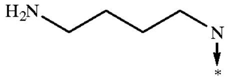 | 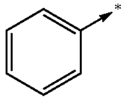 | 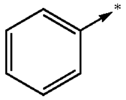 | 37.9 | 3.81 | 501.28 |

-continued
| | | | | | | |
|---|---|---|---|---|---|---|
| 2577 | 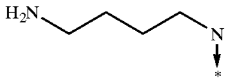 | 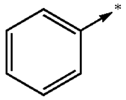 | 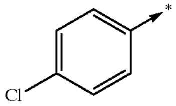 | 45.6 | 4.08 | 535.21 |
| 2578 | 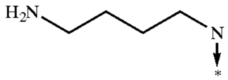 | 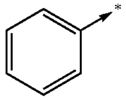 | 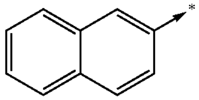 | 34.9 | 4.2 | 551.27 |
| 2579 | 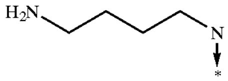 | 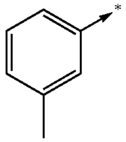 | 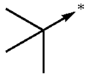 | 66.2 | 3.95 | 495.31 |
| 2580 | 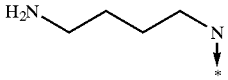 | 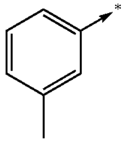 | 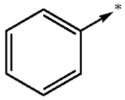 | 44.8 | 3.96 | 515.25 |
| 2581 | 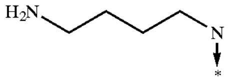 | 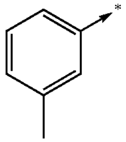 | 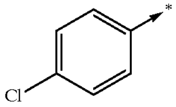 | 54.4 | 4.23 | 549.24 |
| 2582 | 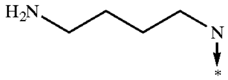 | 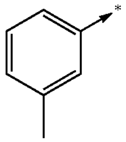 | 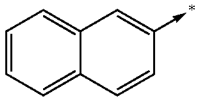 | 36.5 | 4.34 | 565.28 |

-continued
Chiral
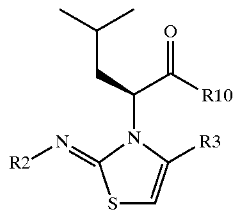
| | | | | | | |
|---|---|---|---|---|---|---|
| 2583 | 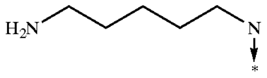 | 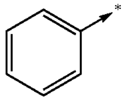 | 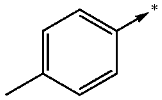 | 52.2 | 3.91 | 465.24 |
| 2584 | 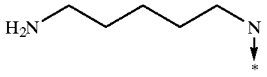 | 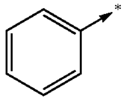 | 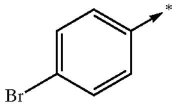 | 55.9 | 4 | 529.14 |
| 2585 | 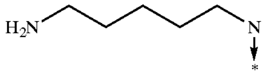 | 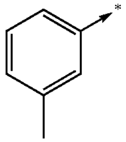 | 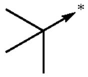 | 51.3 | 3.9 | 445.29 |
| 2586 | 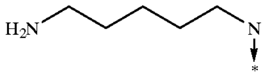 | 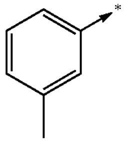 | 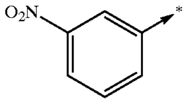 | 57.4 | 3.9 | 510.24 |
| 2587 | 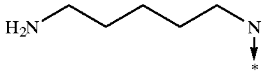 | 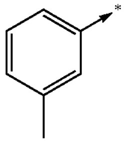 | 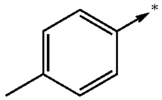 | 54.3 | 4.04 | 479.28 |

-continued
| | | | | | | |
|---|---|---|---|---|---|---|
| 2588 | 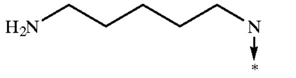 | 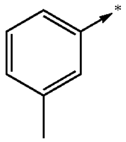 | 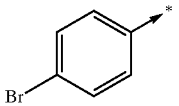 | 61.7 | 4.12 | 543.15 |
| 2589 | 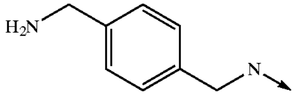 | 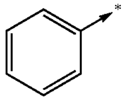 | 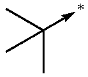 | 80.0 | 3.82 | 465.25 |
| 2590 | 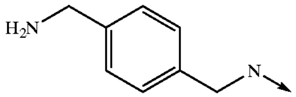 | 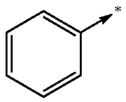 | 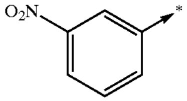 | 61.6 | 3.85 | 530.20 |
| 2591 | 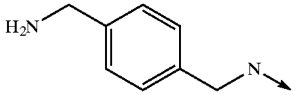 | 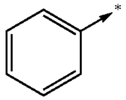 | 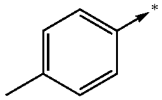 | 61.1 | 3.97 | 499.25 |
| 2592 | 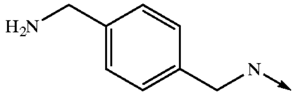 | 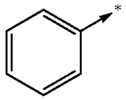 | 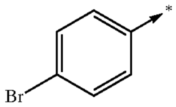 | 61.3 | 4.06 | 563.1 |
| 2593 | 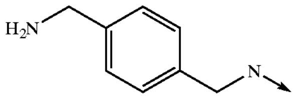 | 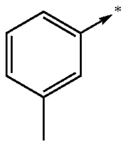 | 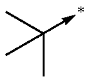 | 84.2 | 3.96 | 479.29 |
| 2594 | 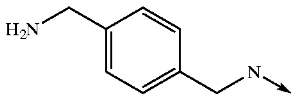 | 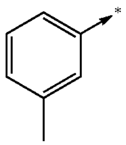 | 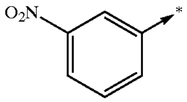 | 58.8 | 3.98 | 544.20 |

-continued
| | | | | | | |
|---|---|---|---|---|---|---|
| 2595 | 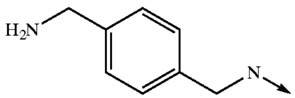 | 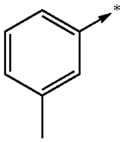 | 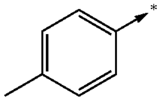 | 61.5 | 4.1 | 513.26 |
| 2596 | 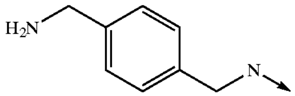 | 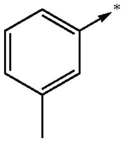 | 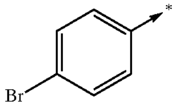 | 65.5 | 4.19 | 577.1 |
Chiral
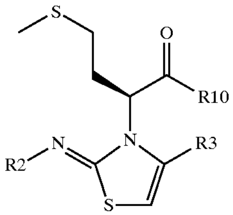
| | | | | | | |
|---|---|---|---|---|---|---|
| 2597 | 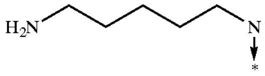 | 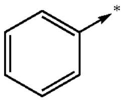 | 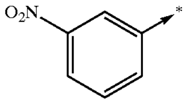 | 28.6 | 3.7 | 514.16 |
| 2598 | 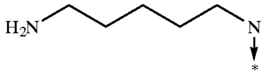 | 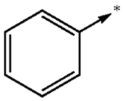 | 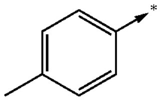 | 39.0 | 3.83 | 483.24 |
| 2599 | 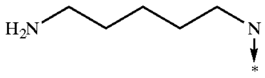 | 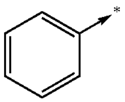 | 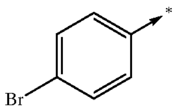 | 39.9 | 3.92 | 547.1 |

-continued
| | | | | | | |
|---|---|---|---|---|---|---|
| 2600 | 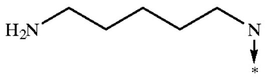 | 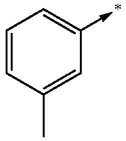 | 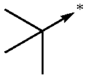 | 53.5 | 3.8 | 463.26 |
| 2601 | 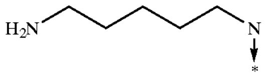 | 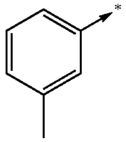 | 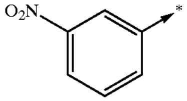 | 28.8 | 3.83 | 528.19 |
| 2602 | 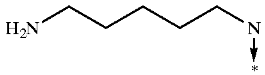 | 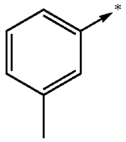 | 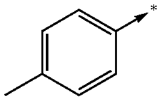 | 31.0 | 3.96 | 497.24 |
| 2603 | 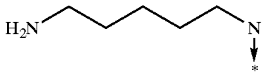 | 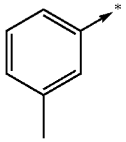 | 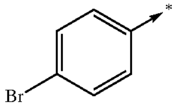 | 34.0 | 4.05 | 561.1 |
Chiral
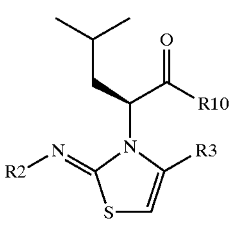
| | | | | | | |
|---|---|---|---|---|---|---|
| 2604 | 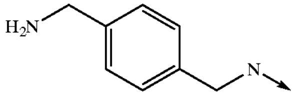 | 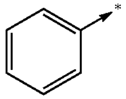 | 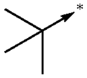 | 64.5 | 3.72 | 483.24 |

-continued
| | | | | | | |
|---|---|---|---|---|---|---|
| 2605 | 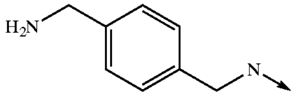 | 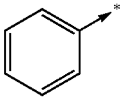 | 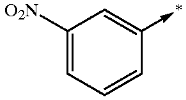 | 25.4 | 3.78 | 548.12 |
| 2606 | 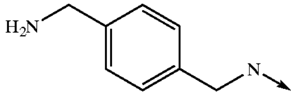 | 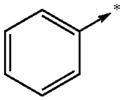 | 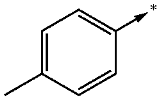 | 36.8 | 3.9 | 517.20 |
| 2607 | 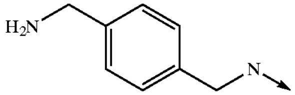 | 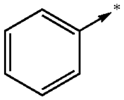 | 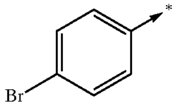 | 31.2 | 4 | 581.1 |
| 2608 | 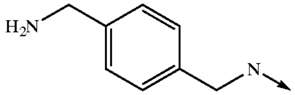 | 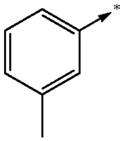 | 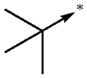 | 72.8 | 3.86 | 497.24 |
| 2609 | 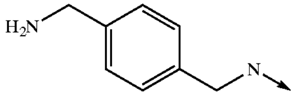 | 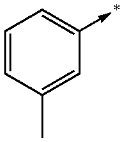 | 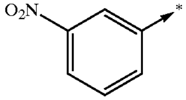 | 31.7 | 3.9 | 562.17 |
| 2610 | 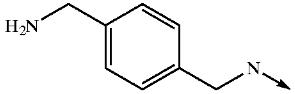 | 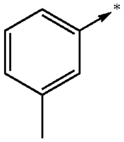 | 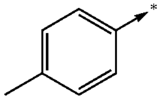 | 40.1 | 4.02 | 531.21 |
| 2611 | 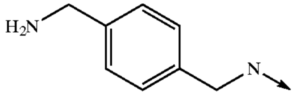 | 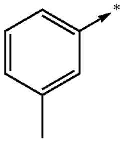 | 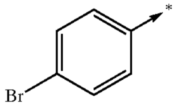 | 38.2 | 4.12 | 595.1 |

-continued
| | | | | | | |
|---|---|---|---|---|---|---|
| | | | Chiral 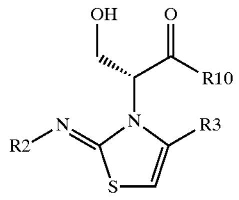 | | | |
| 2612 | 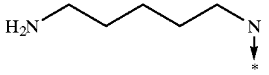 | 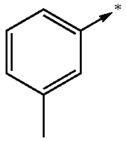 | 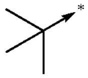 | 45.2 | 3.49 | 419.24 |
| | | | Chiral 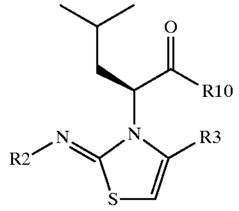 | | | |
| 2613 | 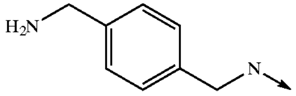 | 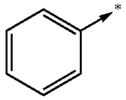 | 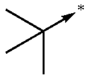 | 56.6 | 3.39 | 439.21 |
| 2614 | 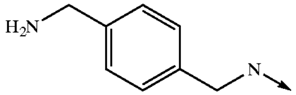 | 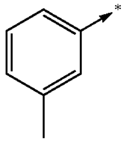 | 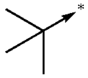 | 58.6 | 3.56 | 453.23 |

-continued
| | | | | | | |
|---|---|---|---|---|---|---|
| | | 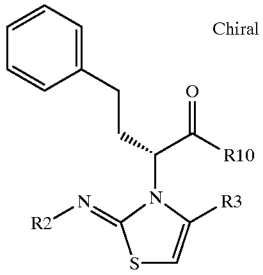 Chiral | | | | |
| 2615 | 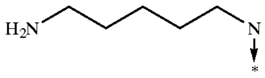 | 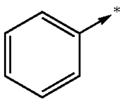 | 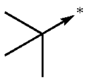 | 65.5 | 3.96 | 479.28 |
| 2616 | 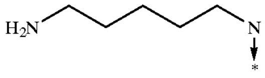 | 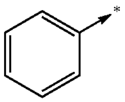 | 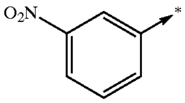 | 50.5 | 4 | 544.19 |
| 2617 | 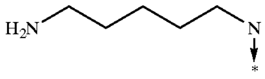 | 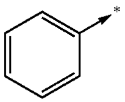 | 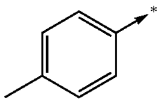 | 55.7 | 4.11 | 513.26 |
| 2618 | 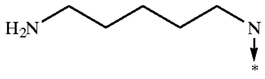 | 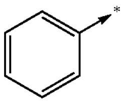 | 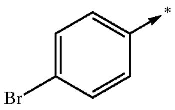 | 55.5 | 4.2 | 577.13 |
| 2619 | 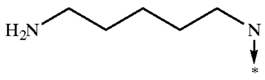 | 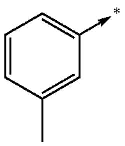 | 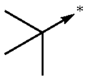 | 67.1 | 4.09 | 493.30 |
| 2620 | 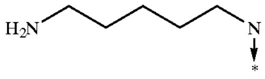 | 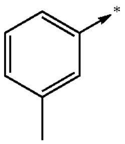 | 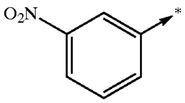 | 53.7 | 4.11 | 558.20 |

-continued
| | | | | | | |
|---|---|---|---|---|---|---|
| 2621 | 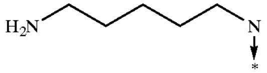 | 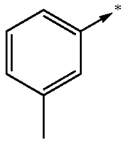 | 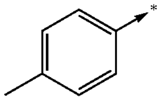 | 55.5 | 4.22 | 527.27 |
| | | | Chiral 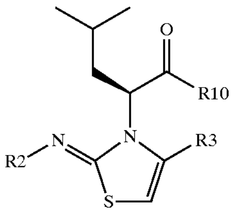 | | | |
| 2622 | 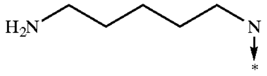 | 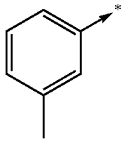 | 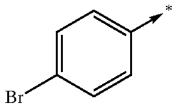 | 72.1 | 4.3 | 591.13 |
| 2623 | 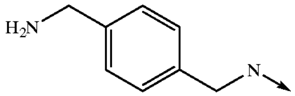 | 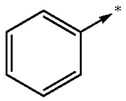 | 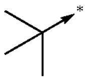 | 81.1 | 4.02 | 513.26 |
| 2624 | 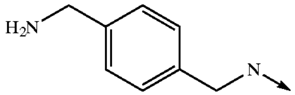 | 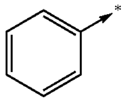 | 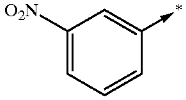 | 51.0 | 4.08 | 578.18 |
| 2625 | 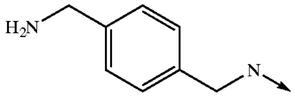 | 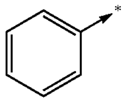 | 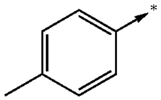 | 54.1 | 4.17 | 547.21 |
| 2626 | 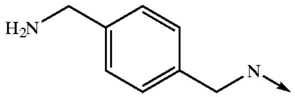 | 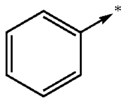 | 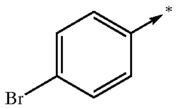 | 65.2 | 4.26 | 611.11 |

-continued
| | | | | | | |
|---|---|---|---|---|---|---|
| 2627 | 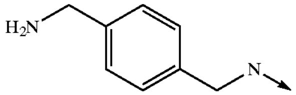 | 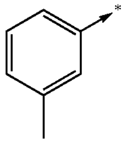 | 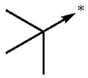 | 83.9 | 4.16 | 527.27 |
| 2628 | 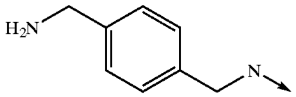 | 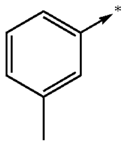 | 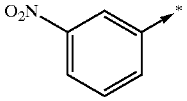 | 60.2 | 4.18 | 592.21 |
| 2629 | 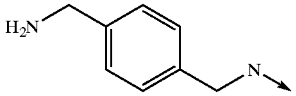 | 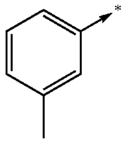 | 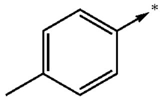 | 63 | 4.3 | 561.21 |
| 2630 | 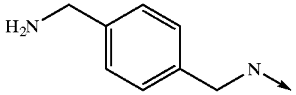 | 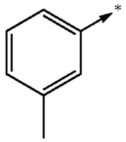 | 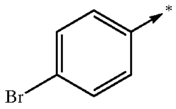 | 74.0 | 4.36 | 625.11 |

-continued
Chiral
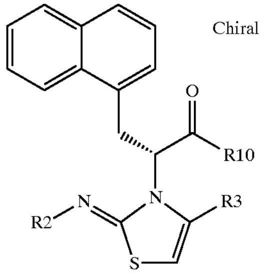
Chiral
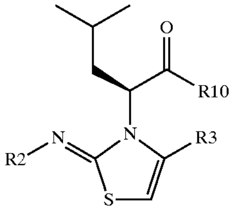
| | | | | | | |
|---|---|---|---|---|---|---|
| 2631 | 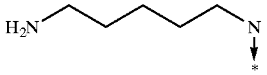 | 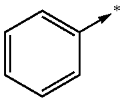 | 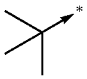 | 83.1 | 4.06 | 515.26 |
| 2632 | 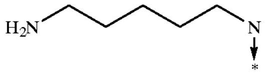 | 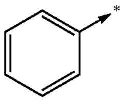 | 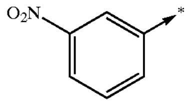 | 57.8 | 4.13 | 580.20 |
| 2633 | 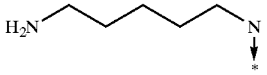 | 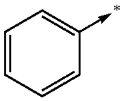 | 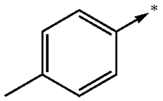 | 37.4 | 4.22 | 549.23 |
| 2634 | 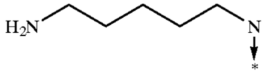 | 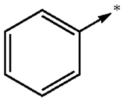 | 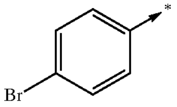 | 43.3 | 4.31 | 613.12 |

-continued
| | | | | | | |
|---|---|---|---|---|---|---|
| 2635 | 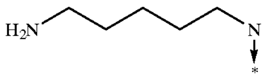 | 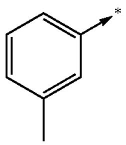 | 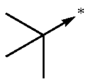 | 86.7 | 4.18 | 529.27 |
| 2636 | 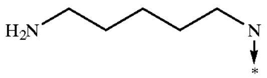 | 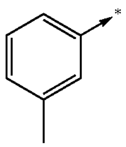 | 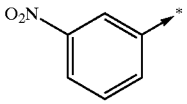 | 64.3 | 4.22 | 594.19 |
| 2637 | 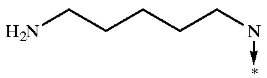 | 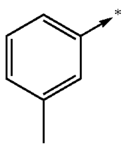 | 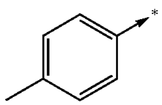 | 37.0 | 4.32 | 563.25 |
| 2638 | 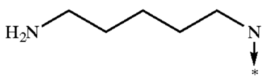 | 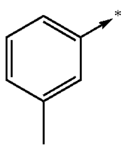 | 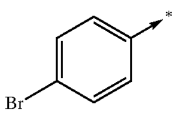 | 44.3 | 4.4 | 627.15 |
| 2639 | 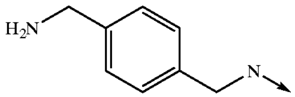 | 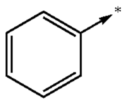 | 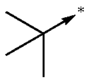 | 86.9 | 4.14 | 549.23 |
| 2640 | 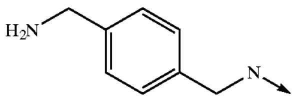 | 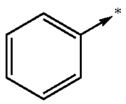 | 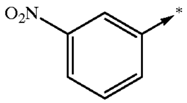 | 53.4 | 4.23 | 614.17 |
| 2641 | 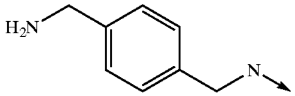 | 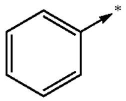 | 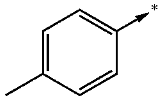 | 37 | 4.3 | 583.21 |

-continued
| | | | | | | |
|---|---|---|---|---|---|---|
| 2642 | 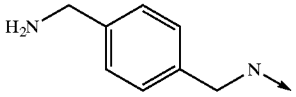 | 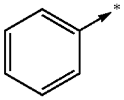 | 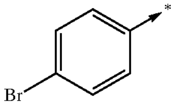 | 45.7 | 4.4 | 647.11 |
| 2643 | 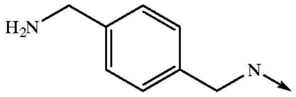 | 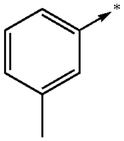 | 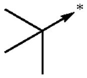 | 88.9 | 4.24 | 563.25 |
| 2644 | 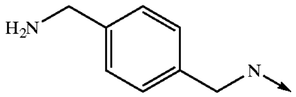 | 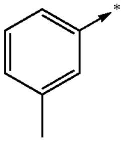 | 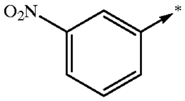 | 57.3 | 4.3 | 628.19 |
| 2645 | 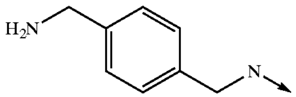 | 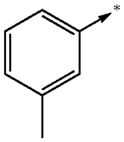 | 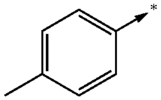 | 39.4 | 4.39 | 597.22 |
| 2646 | 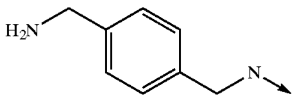 | 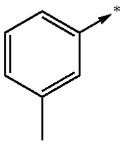 | 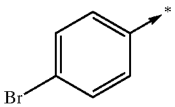 | 44.1 | 4.48 | 661.15 |

-continued
| | | | | | | |
|---|---|---|---|---|---|---|
| | | 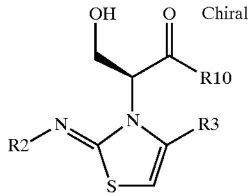 | | | | |
| 2647 | 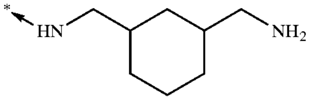 | 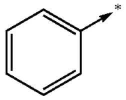 | 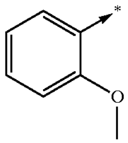 | 25.6 | 3.18 | 495.23 |
| 2648 | 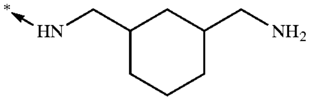 | 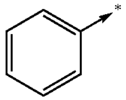 | 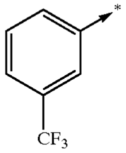 | 33.1 | 3.59 | 533.15 |
| 2649 | 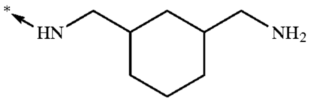 | 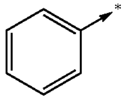 | 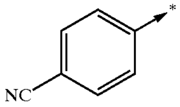 | 27.0 | 3 | 490.2 |
| 2650 | 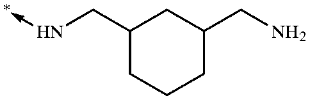 | 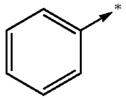 | 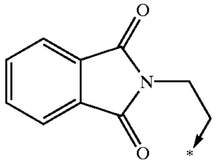 | 33.6 | 3.14 | 562.16 |
| 2651 | 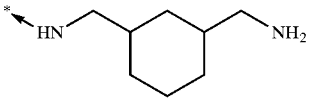 | 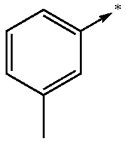 | 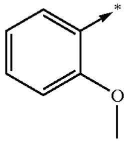 | 27.2 | 3.36 | 509.21 |

-continued
| | | | | | | |
|---|---|---|---|---|---|---|
| 2652 | 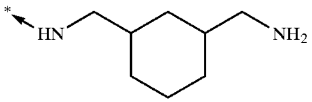 | 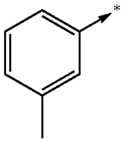 | 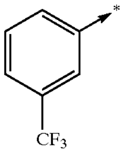 | 32.5 | 3.76 | 547.16 |
| 2653 | 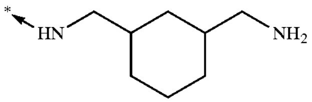 | 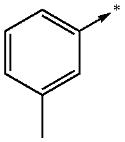 | 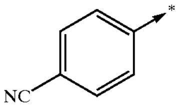 | 29.7 | 3.2 | 504.2 |
| 2654 | 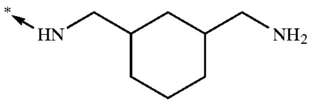 | 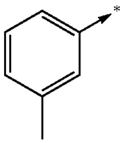 | 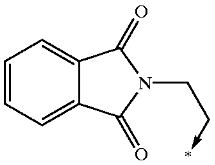 | 34.8 | 3.32 | 576.21 |
| 2655 | 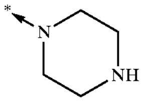 | 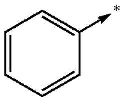 | 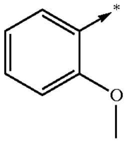 | 73.7 | 2.93 | 439.15 |
| 2656 | 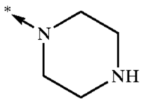 | 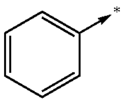 | 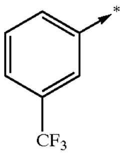 | 60.6 | 3.37 | 477.14 |
| 2657 | 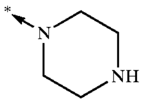 | 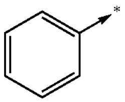 | 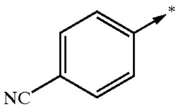 | 65.1 | 2.7 | 434.1 |

-continued
| | | | | | | |
|---|---|---|---|---|---|---|
| 2658 | 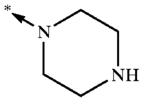 | 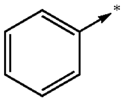 | 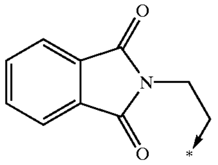 | 69.3 | 2.92 | 506.14 |
| 2659 | 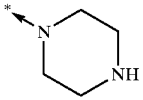 | 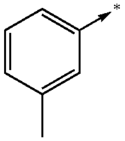 | 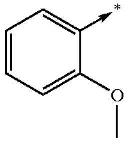 | 72.5 | 3.14 | 453.17 |
| 2660 | 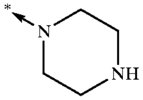 | 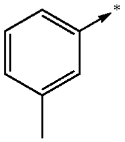 | 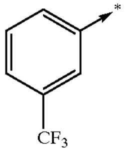 | 77.2 | 3.55 | 491.14 |
| 2661 | 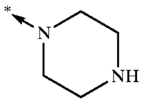 | 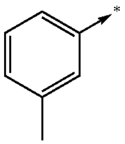 | 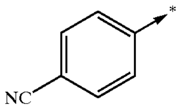 | 66.4 | 2.9 | 448.1 |
| 2662 | 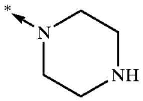 | 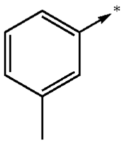 | 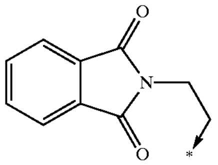 | 65.9 | 3.14 | 520.15 |

-continued
| | | | | | | |
|---|---|---|---|---|---|---|
| 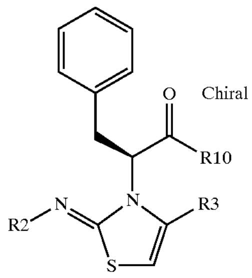 | | | | | | |
| 2663 | 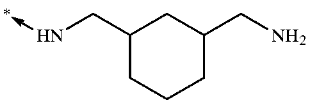 | 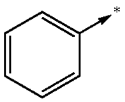 | 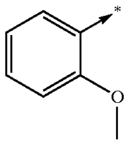 | 63.3 | 3.82 | 555.21 |
| 2664 | 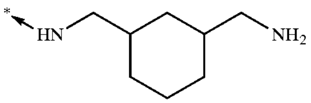 | 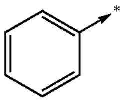 | 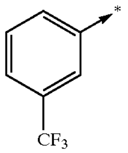 | 85.8 | 4.24 | 593.19 |
| 2665 | 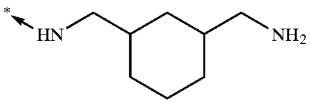 | 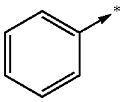 | 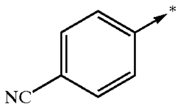 | 87.5 | 3.8 | 550.2 |
| 2666 | 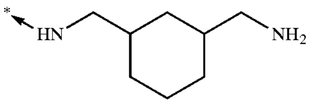 | 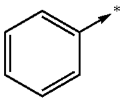 | 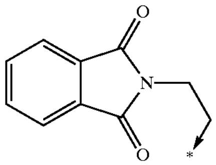 | 75.1 | 3.78 | 622.22 |
| 2667 | 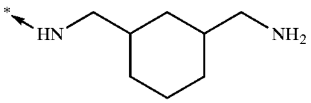 | 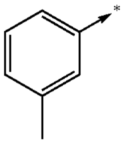 | 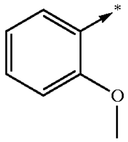 | 66.1 | 3.98 | 569.21 |

-continued
| | | | | | | |
|---|---|---|---|---|---|---|
| 2668 | 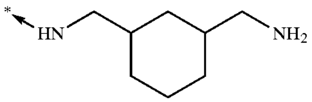 | 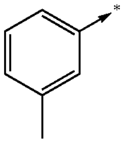 | 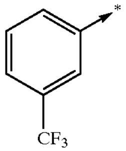 | 87.2 | 4.35 | 607.21 |
| 2669 | 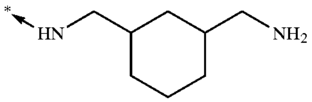 | 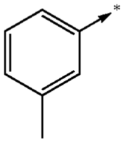 | 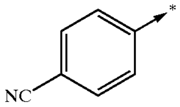 | 82.9 | 3.9 | 564.2 |
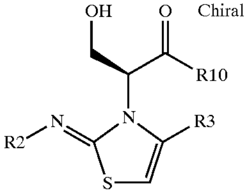
Chiral
| | | | | | | |
|---|---|---|---|---|---|---|
| 2670 | 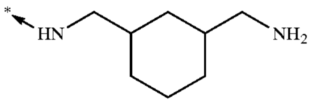 | 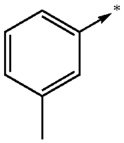 | 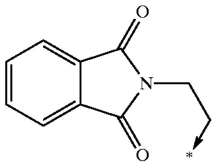 | 79.1 | 3.94 | 636.25 |
| 2671 | 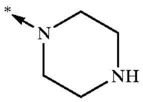 | 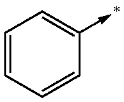 | 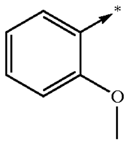 | 82.0 | 3.55 | 499.18 |
| 2672 | 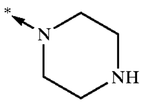 | 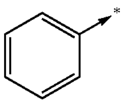 | 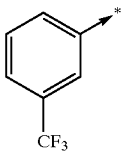 | 82.2 | 3.93 | 537.14 |

-continued
| | | | | | | |
|---|---|---|---|---|---|---|
| 2673 | 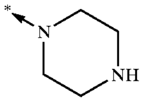 | 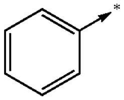 | 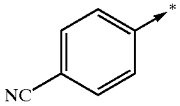 | 86.4 | 3.4 | 494.2 |
| 2674 | 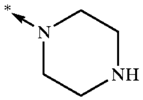 | 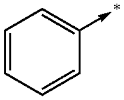 | 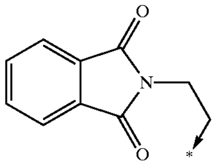 | 90.4 | 3.52 | 566.15 |
| 2675 | 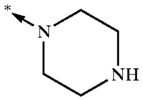 | 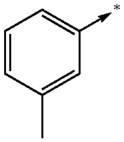 | 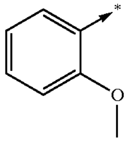 | 88.0 | 3.72 | 513.19 |
| 2676 | 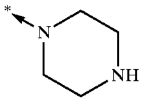 | 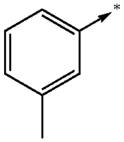 | 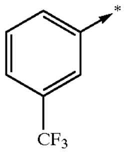 | 88.8 | 4.08 | 551.15 |
| 2677 | 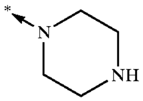 | 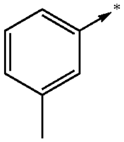 | 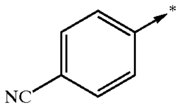 | 88.9 | 3.6 | 508.2 |
| 2678 | 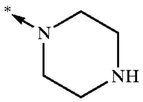 | 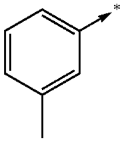 | 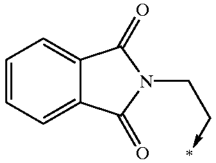 | 93.6 | 3.7 | 580.17 |

-continued
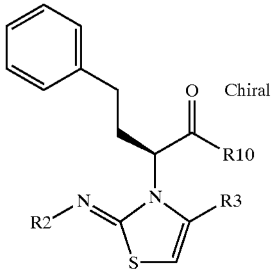
| | | | | | | |
|---|---|---|---|---|---|---|
| 2679 | 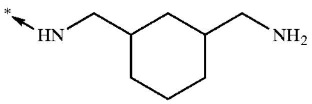 | 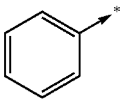 | 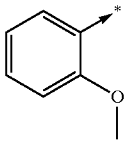 | 59.5 | 4 | 569.20 |
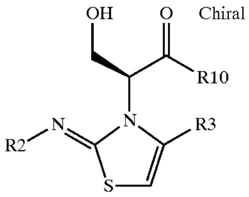
| | | | | | | |
|---|---|---|---|---|---|---|
| 2680 | 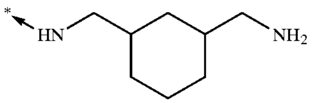 | 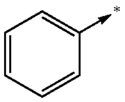 | 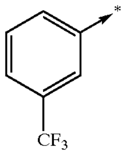 | 82.6 | 4.37 | 607.21 |
| 2681 | 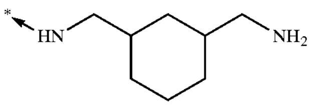 | 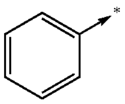 | 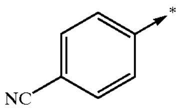 | 74.9 | 3.9 | 564.2 |

-continued
| | | | | | | |
|---|---|---|---|---|---|---|
| 2682 | 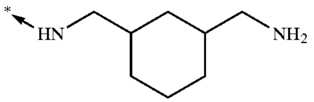 | 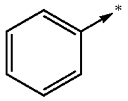 | 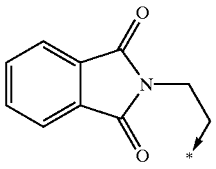 | 70.6 | 3.94 | 636.26 |
| 2683 | 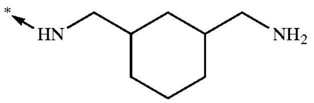 | 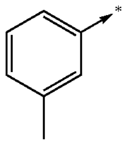 | 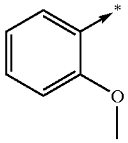 | 55.3 | 4.14 | 583.24 |
| 2684 | 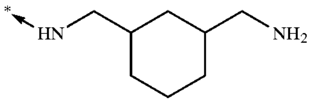 | 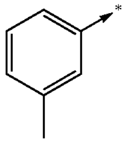 | 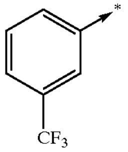 | 85.3 | 4.49 | 621.22 |
| 2685 | 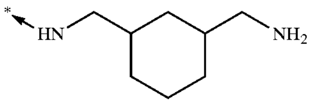 | 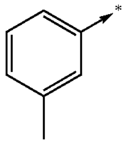 | 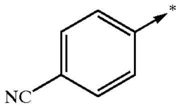 | 86.1 | 4.1 | 578.2 |
| 2686 | 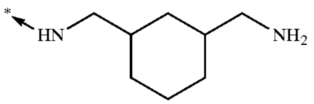 | 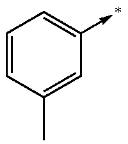 | 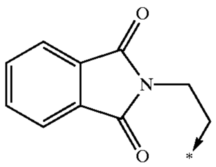 | 72.7 | 4.09 | 650.26 |
| 2687 | 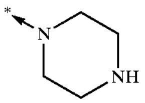 | 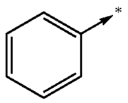 | 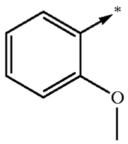 | 87.5 | 3.74 | 513.20 |

-continued
| | | | | | | |
|---|---|---|---|---|---|---|
| 2688 | 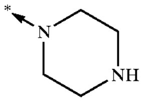 | 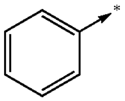 | 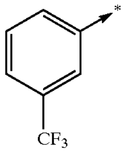 | 86.1 | 4.1 | 551.16 |
| 2689 | 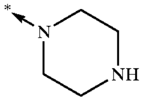 | 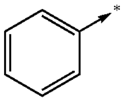 | 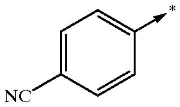 | 87.4 | 3.6 | 508.2 |
| 2690 | 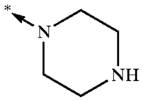 | 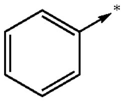 | 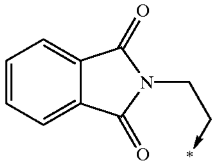 | 87.9 | 3.73 | 580.18 |
| 2691 | 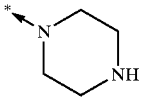 | 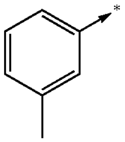 | 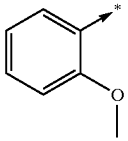 | 87.2 | 3.89 | 527.21 |
| 2692 | 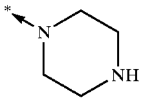 | 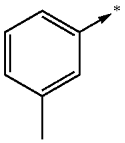 | 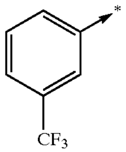 | 88.3 | 4.24 | 565.15 |
| 2693 | 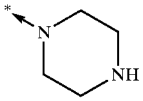 | 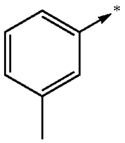 | 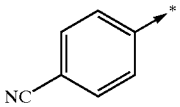 | 89.8 | 3.8 | 522.2 |

-continued
| | | | | | | |
|---|---|---|---|---|---|---|
| 2694 | 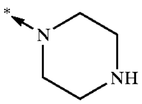 | 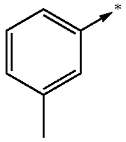 | 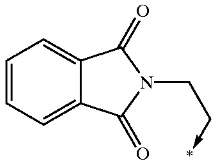 | 92.5 | 3.86 | 594.17 |
| | | | 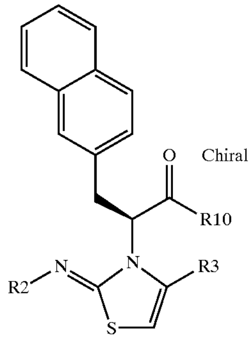 | | | |
| 2695 | 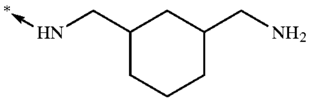 | 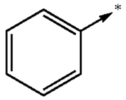 | 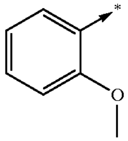 | 69.9 | 4.14 | 605.25 |
| 2696 | 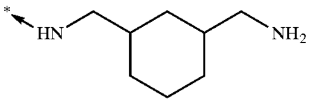 | 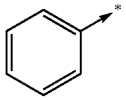 | 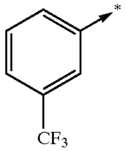 | 81.8 | 4.55 | 643.21 |
| 2697 | 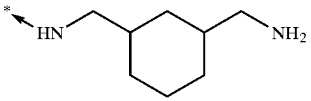 | 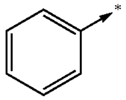 | 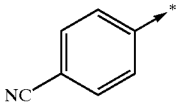 | 65.3 | 4.1 | 600.2 |

-continued
| | | | | | | |
|---|---|---|---|---|---|---|
| 2698 | 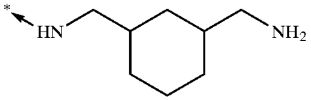 | 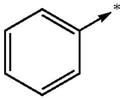 | 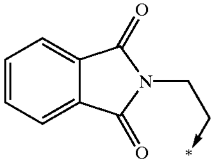 | 69.2 | 4.11 | 672.25 |
| 2699 | 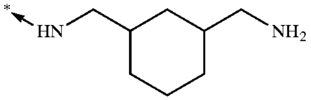 | 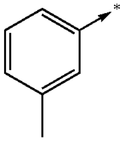 | 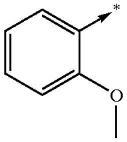 | 74.0 | 4.28 | 619.24 |
| 2700 | 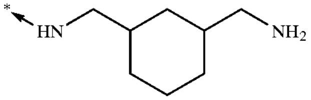 | 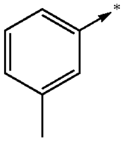 | 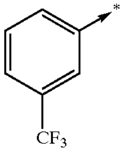 | 69.3 | 4.67 | 657.24 |
| 2701 | 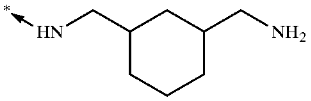 | 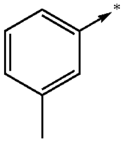 | 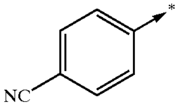 | 75.9 | 4.3 | 614.2 |
| 2702 | 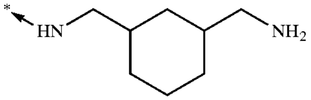 | 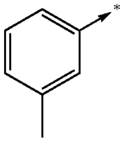 | 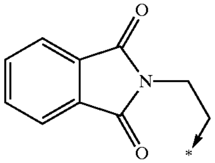 | 84.8 | 4.27 | 686.27 |

-continued
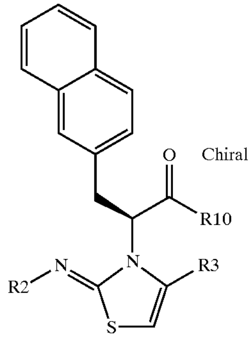
| | | | | | | |
|---|---|---|---|---|---|---|
| 2703 | 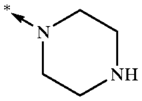 | 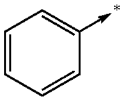 | 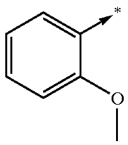 | 86.6 | 3.91 | 549.16 |
| 2704 | 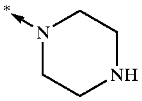 | 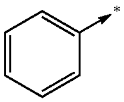 | 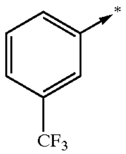 | 77.7 | 4.26 | 587.13 |
| 2705 | 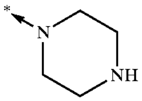 | 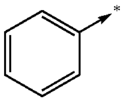 | 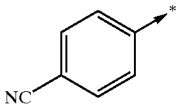 | 69.4 | 3.8 | 544.1 |
| 2706 | 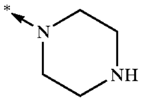 | 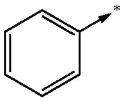 | 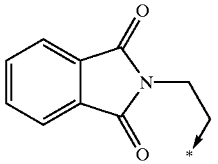 | 88.0 | 3.9 | 616.19 |

-continued
| | | | | | | |
|---|---|---|---|---|---|---|
| 2707 | 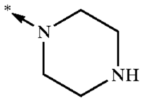 | 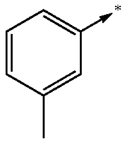 | 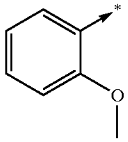 | 79.9 | 4.06 | 563.18 |
| 2708 | 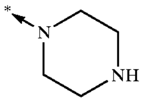 | 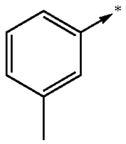 | 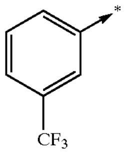 | 75.9 | 4.38 | 601.14 |
| 2709 | 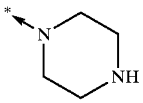 | 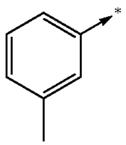 | 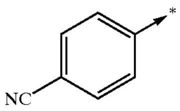 | 62 | 3.9 | 603.2 |
| 2710 | 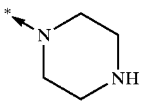 | 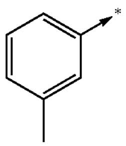 | 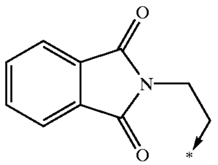 | 87.7 | 4.05 | 630.21 |

-continued
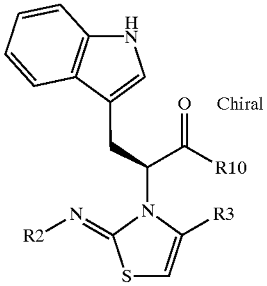
| | | | | | | |
|---|---|---|---|---|---|---|
| 2711 | 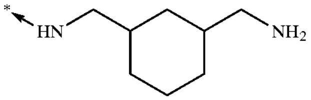 | 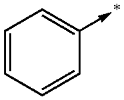 | 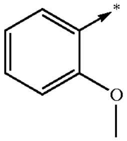 | 56.8 | 3.85 | 594.20 |
| 2712 | 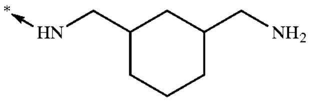 | 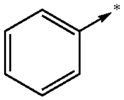 | 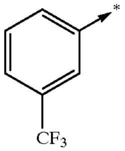 | 69.7 | 4.18 | 632.22 |
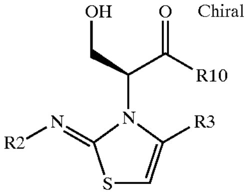
| | | | | | | |
|---|---|---|---|---|---|---|
| 2713 | 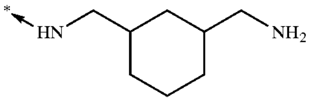 | 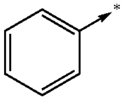 | 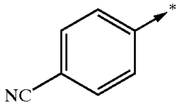 | 62.2 | 3.7 | 589.2 |

-continued
| | | | | | | |
|---|---|---|---|---|---|---|
| 2714 | 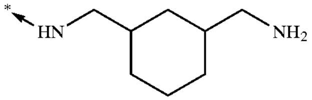 | 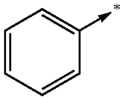 | 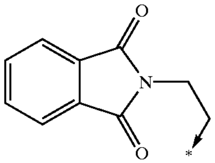 | 79.2 | 3.76 | 661.23 |
| 2715 | 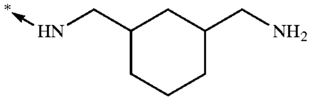 | 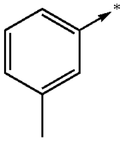 | 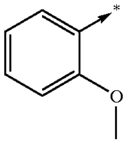 | 56.8 | 4 | 608.23 |
| 2716 | 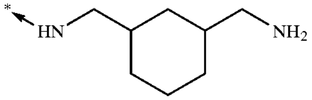 | 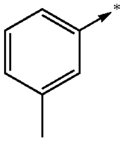 | 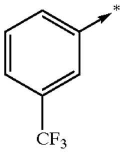 | 70.5 | 4.31 | 646.23 |
| 2717 | 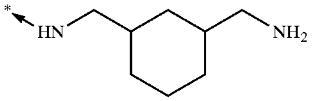 | 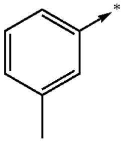 | 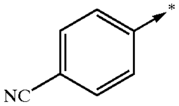 | 62 | 3.9 | 603.2 |
| 2718 | 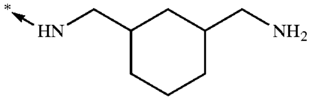 | 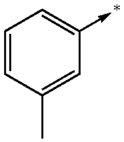 | 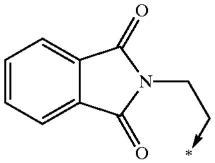 | 76.9 | 3.92 | 675.26 |
| 2719 | 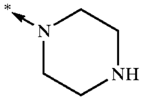 | 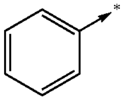 | 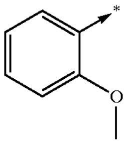 | 75.5 | 3.63 | 538.18 |

-continued
| | | | | | | |
|---|---|---|---|---|---|---|
| 2720 | 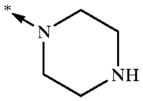 | 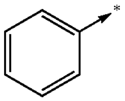 | 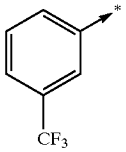 | 79.4 | 3.96 | 576.13 |
| 2721 | 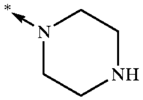 | 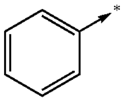 | 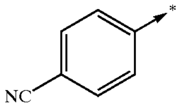 | 73 | 3.5 | 533.2 |
| 2722 | 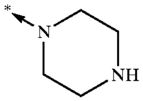 | 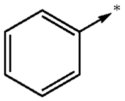 | 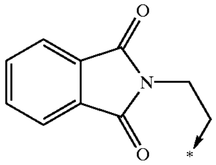 | 87.0 | 3.56 | 605.17 |
| 2723 | 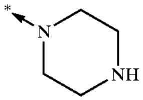 | 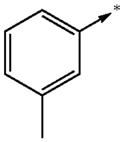 | 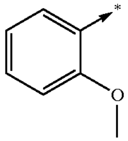 | 81.8 | 3.8 | 552.18 |
| 2724 | 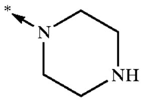 | 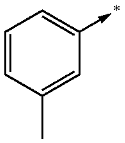 | 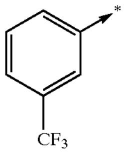 | 80.1 | 4.11 | 590.15 |
| 2725 | 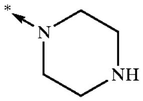 | 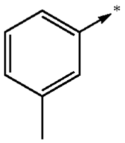 | 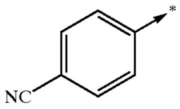 | 79.4 | 3.6 | 547.2 |

-continued
| | | | | | | |
|---|---|---|---|---|---|---|
| 2726 | 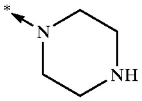 | 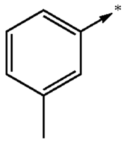 | 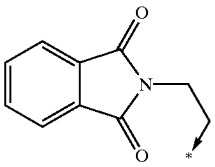 | 86.3 | 3.73 | 619.18 |
| Ex. | R2 | R3 | Purity (%) | rt (min.) | $[M + H]^+$ |
|---|---|---|---|---|---|
| | | 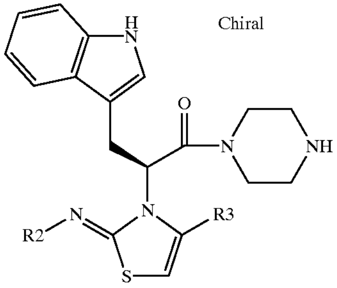 Chiral | | | |
| 2727 | 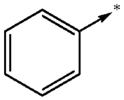 | 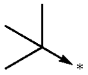 | 73.7 | 4.7 | 488.3 |
| 2728 | 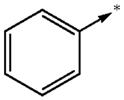 | 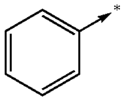 | 87.1 | 4.2 | 508.2 |
| 2729 | 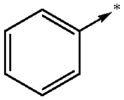 | 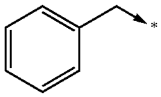 | 90.3 | 4.3 | 522.3 |
| 2730 | 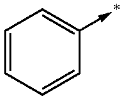 | 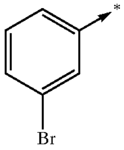 | 78.2 | 4.5 | 586.1 |

-continued
| | | | | | |
|---|---|---|---|---|---|
| 2731 | 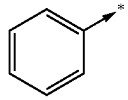 | 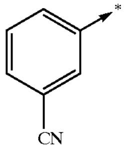 | 73 | 4.1 | 533.2 |
| 2732 | 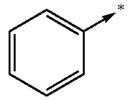 | 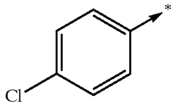 | 86.4 | 4.5 | 542.2 |
| 2733 | 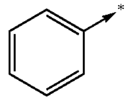 | 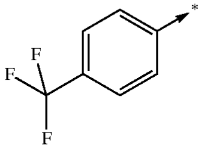 | 77.7 | 4.6 | 576.2 |
| 2734 | 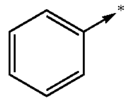 | 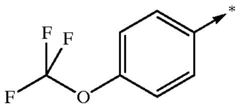 | 80 | 4.7 | 592.2 |
| 2735 | 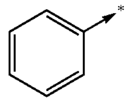 | 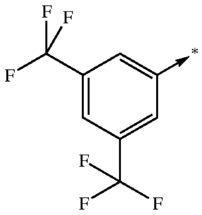 | 76.4 | 4.9 | 644.2 |
| 2736 | 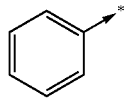 | 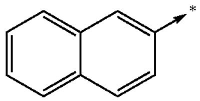 | 81.4 | 4.6 | 558.2 |
| 2737 | 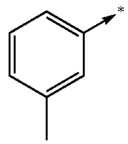 | 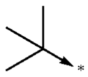 | 79.8 | 4.4 | 502.3 |

-continued
| | | | | | |
|---|---|---|---|---|---|
| 2738 | 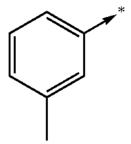 | 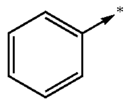 | 87.5 | 4.4 | 522.3 |
| 2739 | 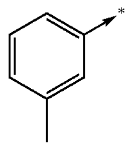 | 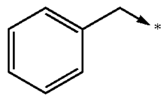 | 91.4 | 4.5 | 536.3 |
| 2740 | 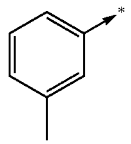 | 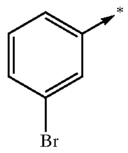 | 83.3 | 4.6 | 600.1 |
| 2741 | 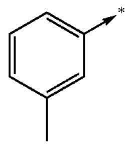 | 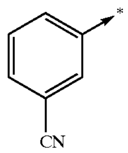 | 82 | 4.3 | 547.2 |
| 2742 | 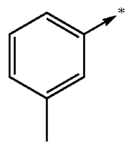 | 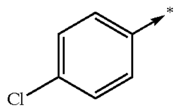 | 83.9 | 4.6 | 556.2 |
| 2743 | 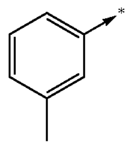 | 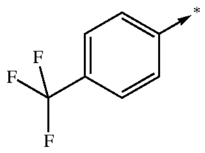 | 85.4 | 4.7 | 590.2 |

-continued
| | | | | | |
|---|---|---|---|---|---|
| 2744 | 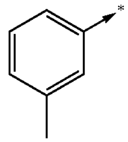 | 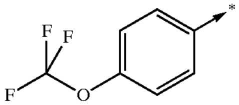 | 85.2 | 4.8 | 606.2 |
| 2745 | 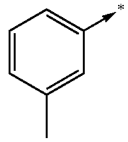 | 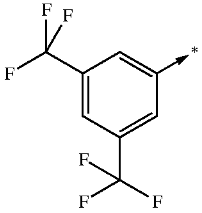 | 82 | 4.3 | 658.2 |
| 2746 | 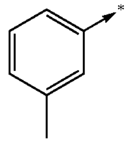 | 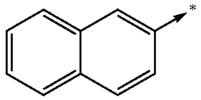 | 86.7 | 4.7 | 572.2 |
| 2747 | 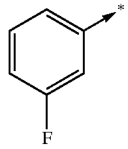 | 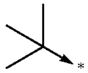 | 31.6 | 4.3 | 506.3 |
| 2748 | 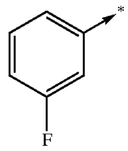 | 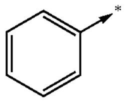 | 71.1 | 4.3 | 526.2 |
| 2749 | 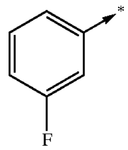 | 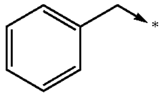 | 89.5 | 4.4 | 540.2 |

-continued
| | | | | | |
|---|---|---|---|---|---|
| 2750 | 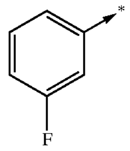 | 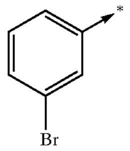 | 59.6 | 4.5 | 604.1 |
| 2751 | 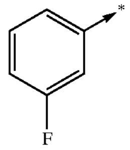 | 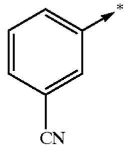 | 51.3 | 4.2 | 551.2 |
| 2752 | 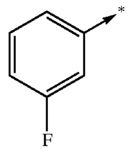 | 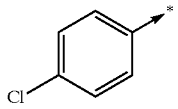 | 62.2 | 4.5 | 560.2 |
| 2753 | 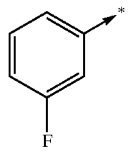 | 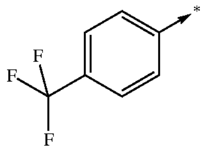 | 59.6 | 4.7 | 594.2 |
| 2754 | 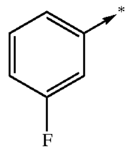 | 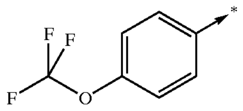 | 63 | 4.7 | 610.2 |
| 2755 | 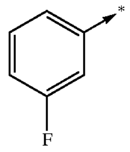 | 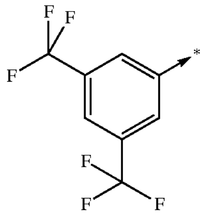 | 52.5 | 4.9 | 662.2 |

-continued
| | | | | | |
|---|---|---|---|---|---|
| 2756 | 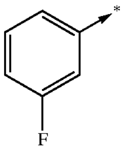 | 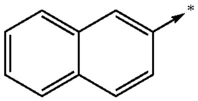 | 67.8 | 4.6 | 576.1 |
| 2757 | 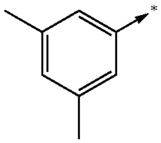 | 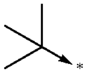 | 81.1 | 4.6 | 516.3 |
| 2758 | 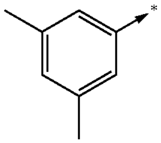 | 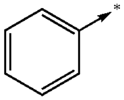 | 85.8 | 4.5 | 536.3 |
| 2759 | 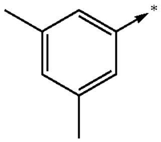 | 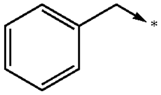 | 85.4 | 4.7 | 550.3 |
| 2760 | 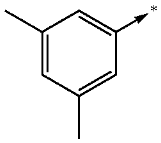 | 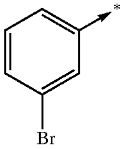 | 76.6 | 4.7 | 614.1 |
| 2761 | 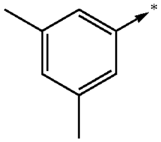 | 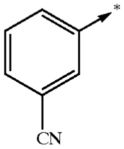 | 77.2 | 4.4 | 561.2 |

-continued
| | | | | | |
|---|---|---|---|---|---|
| 2762 | 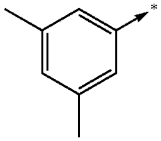 | 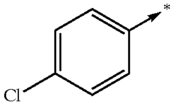 | 85.4 | 4.7 | 570.2 |
| 2763 | 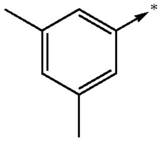 | 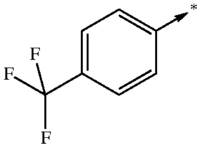 | 79.7 | 4.8 | 604.2 |
| 2764 | 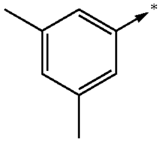 | 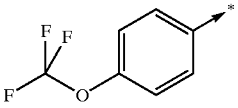 | 81.1 | 4.9 | 620.2 |
| 2765 | 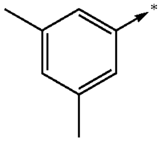 | 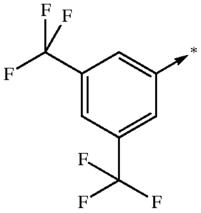 | 79.2 | 5.1 | 672.2 |
| 2766 | 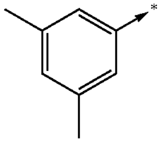 | 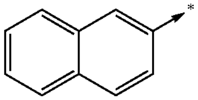 | 82 | 4.8 | 586.3 |

-continued
| Ex. | R2 | R10 | R3 | Purity (%) | rt (min.) | $[M + H]^+$ |
|---|---|---|---|---|---|---|
| | | 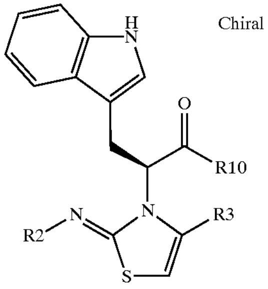 | Chiral | | | |
| 2767 | 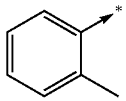 | 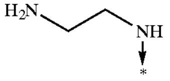 | 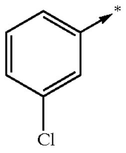 | 64.3 | 3.91 | 530.20 |
| 2768 | 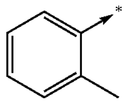 | 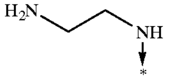 | 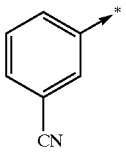 | 58.3 | 3.57 | 521.22 |
| 2769 | 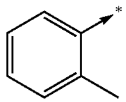 | 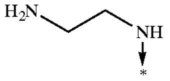 | 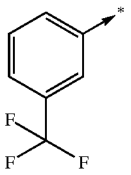 | 66.7 | 4.03 | 564.20 |
| 2770 | 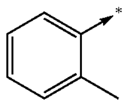 | 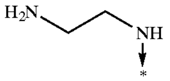 | 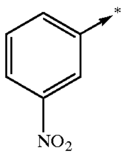 | 65.1 | 3.71 | 541.19 |

-continued
| | | | | | | |
|---|---|---|---|---|---|---|
| 2771 | 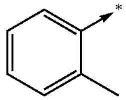 | 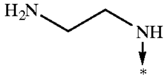 | 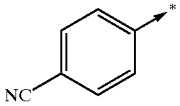 | 56.1 | 3.58 | 521.21 |
| 2772 | 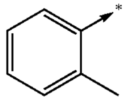 | 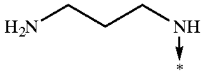 | 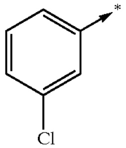 | 42.1 | 3.93 | 544.19 |
| 2773 | 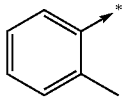 | 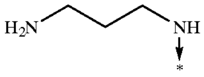 | 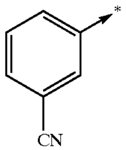 | 34.6 | 3.59 | 535.22 |
| 2774 | 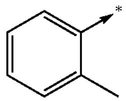 | 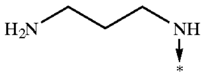 | 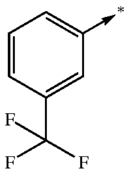 | 46.9 | 4.05 | 578.21 |
| 2775 | 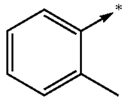 | 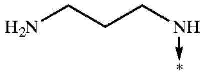 | 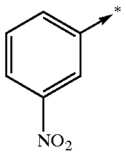 | 33.3 | 3.73 | 555.19 |
| 2776 | 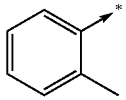 | 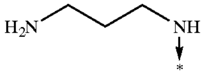 | 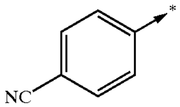 | 33.4 | 3.6 | 535.22 |
| 2777 | 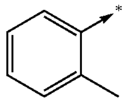 | 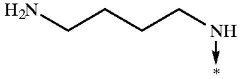 | 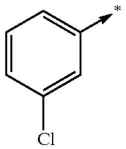 | 39.6 | 3.97 | 558.22 |

-continued
| | | | | | | |
|---|---|---|---|---|---|---|
| 2778 | 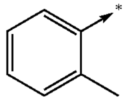 | 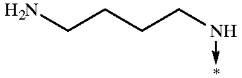 | 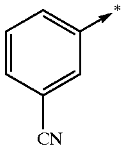 | 47.5 | 3.63 | 549.23 |
| 2779 | 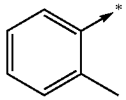 | 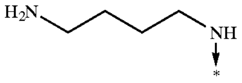 | 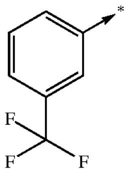 | 50.3 | 4.09 | 592.23 |
| 2780 | 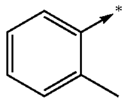 | 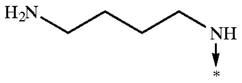 | 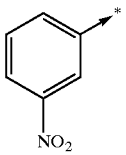 | 40.6 | 3.76 | 569.19 |
| 2781 | 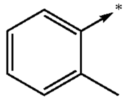 | 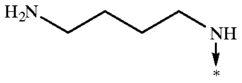 | 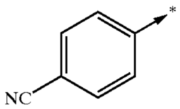 | 42.7 | 3.63 | 549.25 |
| 2782 | 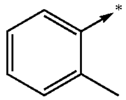 | 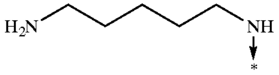 | 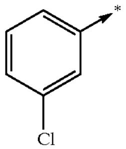 | 35.5 | 4.0 | 572.17 |
| 2783 | 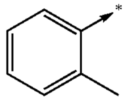 | 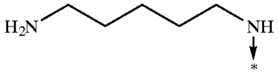 | 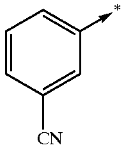 | 33.2 | 3.69 | 563.26 |

-continued
| | | | | | | |
|---|---|---|---|---|---|---|
| 2784 | 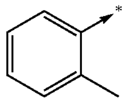 | 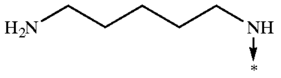 | 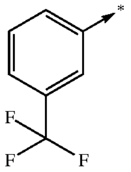 | 45 | 4.1 | 606.27 |
| 2785 | 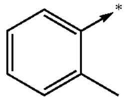 | 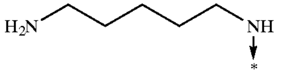 | 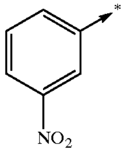 | 36.0 | 3.82 | 583.23 |
| 2786 | 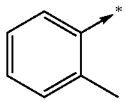 | 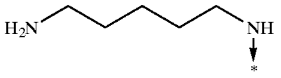 | 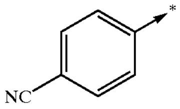 | 27.1 | 3.7 | 563.26 |
| 2787 | 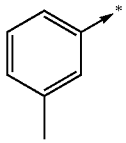 | 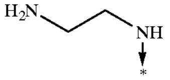 | 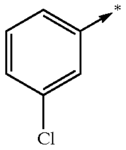 | 73.6 | 3.98 | 530.19 |
| 2788 | 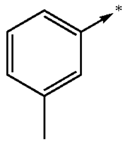 | 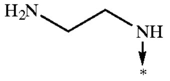 | 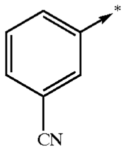 | 62.5 | 3.64 | 521.21 |
| 2789 | 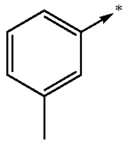 | 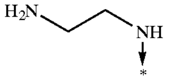 | 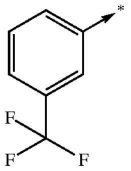 | 74.8 | 4.09 | 564.2 |

-continued
| | | | | | | |
|---|---|---|---|---|---|---|
| 2790 | 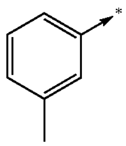 | 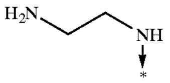 | 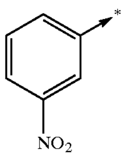 | 67.7 | 3.77 | 541.20 |
| 2791 | 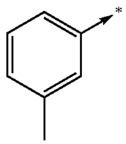 | 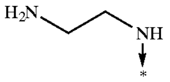 | 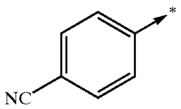 | 71.3 | 3.65 | 521.21 |
| 2792 | 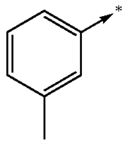 | 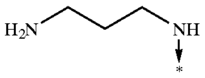 | 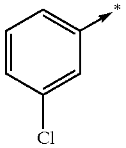 | 52.4 | 4.0 | 544.18 |
| 2793 | 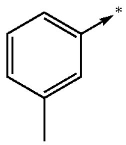 | 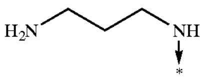 | 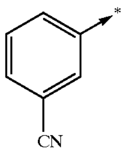 | 47.0 | 3.65 | 535.22 |
| 2794 | 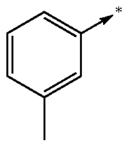 | 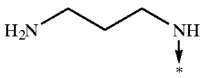 | 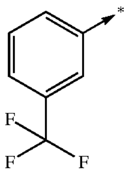 | 54.7 | 4.11 | 578.22 |
| 2795 | 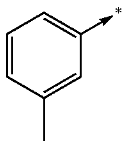 | 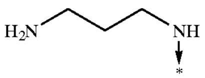 | 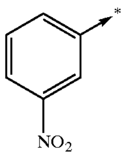 | 43.7 | 3.79 | 555.20 |

-continued
| | | | | | | |
|---|---|---|---|---|---|---|
| 2796 | 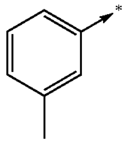 | 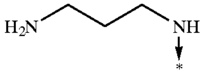 | 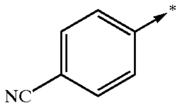 | 44.6 | 3.67 | 535.22 |
| 2797 | 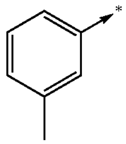 | 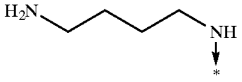 | 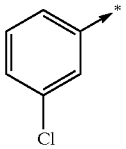 | 53.7 | 4.03 | 558.20 |
| 2798 | 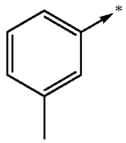 | 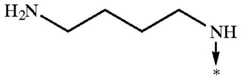 | 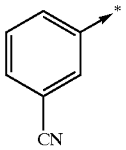 | 51.0 | 3.69 | 549.23 |
| 2799 | 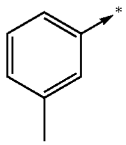 | 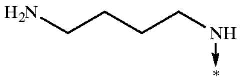 | 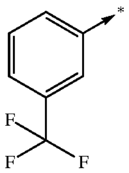 | 56.5 | 4.15 | 592.23 |
| 2800 | 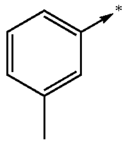 | 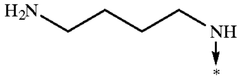 | 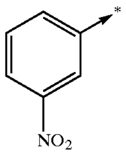 | 48.9 | 3.83 | 569.20 |
| 2801 | 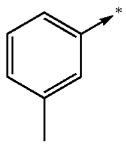 | 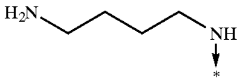 | 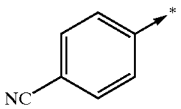 | 46.0 | 3.7 | 549.24 |

-continued
| | | | | | | |
|---|---|---|---|---|---|---|
| 2802 | 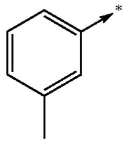 | 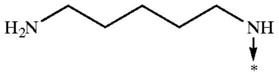 | 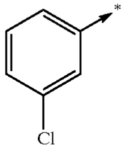 | 41.2 | 4.1 | 572.21 |
| 2803 | 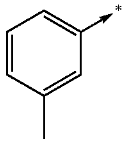 | 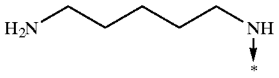 | 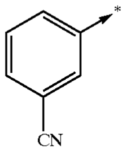 | 36.7 | 3.76 | 563.26 |
| 2804 | 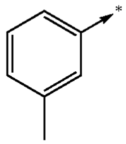 | 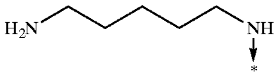 | 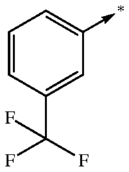 | 47.4 | 4.2 | 606.26 |
| 2805 | 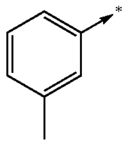 | 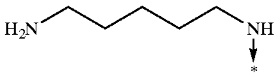 | 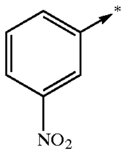 | 37.0 | 3.89 | 583.22 |
| 2806 | 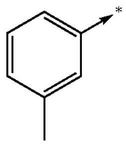 | 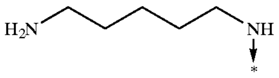 | 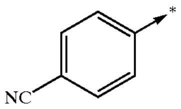 | 37.3 | 3.76 | 563.26 |

-continued
| Ex. | R3 | R2 | Purity (%) | rt (min.) | [M + H]$^+$ |
|---|---|---|---|---|---|
| | | 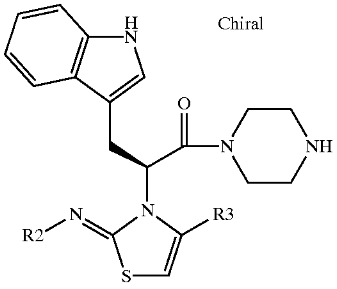 | | | |
| 2807 | 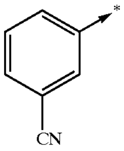 | 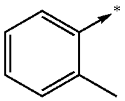 | 52.1 | 3.65 | 547.22 |
| 2808 | 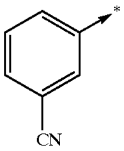 | 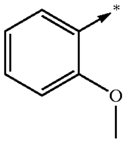 | 61.7 | 3.61 | 563.24 |
| 2809 | 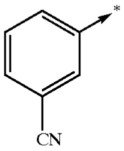 | 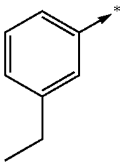 | 54.1 | 3.91 | 561.26 |
| 2810 | 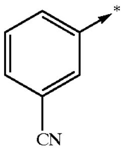 | 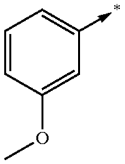 | 56.7 | 3.69 | 563.23 |

-continued
| | | | | | |
|---|---|---|---|---|---|
| 2811 | 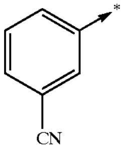 | 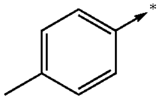 | 54.7 | 3.65 | 547.23 |
| 2812 | 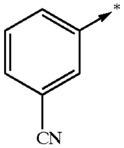 | 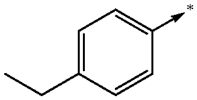 | 63.6 | 3.96 | 561.25 |
| 2813 | 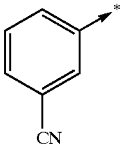 | 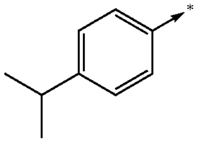 | 66.1 | 4.13 | 575.26 |
| 2814 | 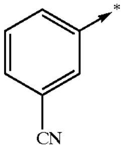 | 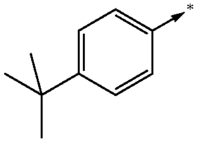 | 34.9 | 4.29 | 589.29 |
| 2815 | 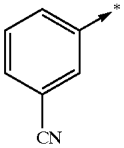 | 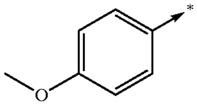 | 69.3 | 3.66 | 563.24 |
| 2816 | 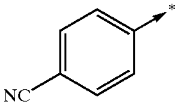 | 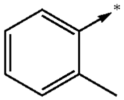 | 47.6 | 3.66 | 547.23 |

-continued
| | | | | | |
|---|---|---|---|---|---|
| 2817 | 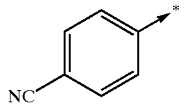 | 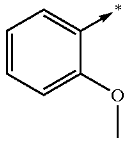 | 41.4 | 3.61 | 563.23 |
| 2818 | 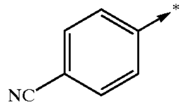 | 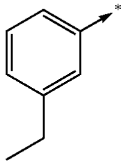 | 28.5 | 3.97 | 561.24 |
| 2819 | 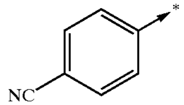 | 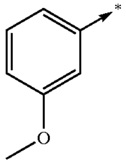 | 56.4 | 3.71 | 563.23 |
| 2820 | 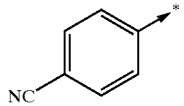 | 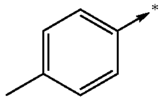 | 45.6 | 3.65 | 547.22 |
| 2821 | 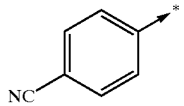 | 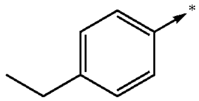 | 62.6 | 3.99 | 561.24 |
| 2822 | 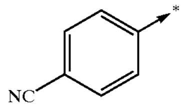 | 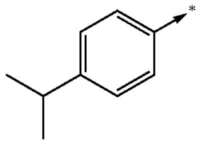 | 42.0 | 4.17 | 575.26 |
| 2823 | 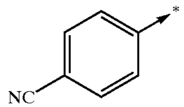 | 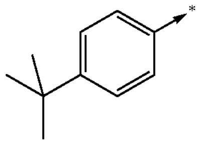 | 45.7 | 4.32 | 589.28 |

-continued
| | | | | | |
|---|---|---|---|---|---|
| 2824 | 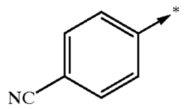 | 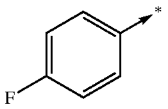 | 23.5 | 3.65 | 551.21 |
| 2825 | 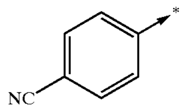 | 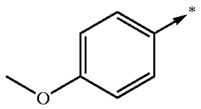 | 70.9 | 3.67 | 563.22 |

Pharmacological Properties of the Products of the Invention

The compounds of the present invention can and have been tested as regards their affinity for different sub-types of somatostatin receptors according to the procedures described below.

Study of the affinity for the sub-types of human somatostatin receptors:

The affinity of a compound of the invention on sub-types of human somatostatin receptors 1 to 5 ($sst_1$, $sst_2$, $sst_3$, $sst_4$ and $sst_5$, respectively) is determined by measurement of the inhibition of the bond of [$^{125}$I-Tyr$^{11}$]SRIF-14 to transfected CHO-K1 cells.

The gene of the $sst_1$ receptor of human somatostatin has been cloned in the form of a genomic fragment. A segment PstI-XmnI of 1.5 Kb containing 100 bp of the non transcribed 5' region, 1.17 Kb of the coding region in totality, and 230 bp of the non transcribed 3' region is modified by the addition of the linker Bg1II. The resulting DNA fragment is subcloned in the BamHI site of a pCMV-81 in order to produce the expression plasmid in mammals (provided by Dr. Graeme Bell, Univ. Chicago). A cloned cell line expressing in a stable fashion the $sst_1$ receptor is obtained by transfection in CHO-K1 cells (ATCC) using the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The gene of the $sst_2$ receptor of human somatostatin, isolated in the form of a genomic fragment of DNA of 1.7 Kb BamHI-HindIII and subdcloned in a plasmid vector pGEM3Z (Promega), was provided by Dr. G. Bell (Univ. of Chicago). The expression vector of the mammalian cells is constructed by inserting the BamH1-HindII fragment of 1.7 Kb in endonuclease restriction sites compatible with the plasmid pCMV5. A cloned cell line is obtained by transfection in CHO-K1 cells using the calcium phosphate co-precipitation method. The plasmid pRSV-neo is included as selection marker.

The $sst_3$ receptor is isolated as a genomic fragment, and the complete coding sequence is contained in a BamHI/HindIII fragment of 2.4 Kb. The expression plasmid in mammals, pCMV-h3, is constructed by insertion of the NcoI-HindIII fragment of 2.0 Kb in the EcoR1 site of the vector pCMV after modification of the terminations and addition of EcoR1 linkers. A cloned cell line expressing in a stable fashion the $sst_3$ receptor is obtained by transfection in CHO-K1 cells (ATCC) by the calcium phosphate co-precipitation method. The plasmid pRSV-neo (ATCC) is included as selection marker. Cloned cell lines were selected in an RPMI 1640 medium containing 0.5 mg/ml of G418 (Gibco), followed by circular cloning and multiplication in culture.

The expression plasmid of the human $sst_4$ receptor, pCMV-HX, was provided by Dr. Graeme Bell (Univ. Chicago). This vector contains the genomic fragment coding for the human sst4 receptor of 1.4 Kb NheI-NheI, 456 pb of the non transcribed 5' region, and 200 pb of the non transcribed 3' region, cloned in the XbaI/EcoR1 sites of PCMV-HX. A cloned cell line expressing in a stable fashion the $sst_4$ receptor is obtained by transfection in CHO-K1 (ATCC) cells by the calcium phosphate co-precipitation method. The plasmid pRSV-neo (ATCC) is included as selection marker. The cloned cell lines were selected in an RPMI 1640 medium containing 0.5 mg/ml of G418 (Gibco), followed by circular cloning and multiplication in culture.

The gene corresponding to the human $sst_5$ receptor, obtained by the PCR method using a genomic λ clone as probe, was provided by Dr. Graeme Bell (Univ. Chicago). The resulting PCR fragment of 1.2 Kb contains 21 base pairs of the non transcribed 5' region, the coding region in totality, and 55 pb of the non transcribed 3' region. The clone is inserted in an EcoR1 site of the plasmid pBSSK(+). The insert is recovered in the form of a HindIII-XbaI fragment of 1.2 Kb for subcloning in an expression vector in mammals, pCVM5. A cloned cell lines expressing in a stable fashion the $sst_5$ receptor is obtained by transfection in CHO-K1 cells (ATCC) by the calcium phosphate co-precipitation method. The plasmid pRSV-neo (ATCC) is included as selection marker. The cloned cell lines were selected in an RPMI 1640 medium containing 0.5 mg/ml of G418 (Gibco), followed by circular cloning and multiplication in culture.

The CHO-K1 cells which express in a stable fashion the human sst receptors are cultured in an RPMI 1640 medium containing 10% of foetal calf serum and 0.4 mg/ml of geneticin. The cells are collected with EDTA at 0.5 mM and centrifuged at 500 g for approximately 5 minutes at approximately 4° C. The pellet is resuspended in Tris 50 mM at pH 7.4 and centrifuged twice at 500 g for approximately 5 minutes at approximately 4° C. The cells are lysed by sonication then centrifuged at 39000 g for approximately 10 minutes at 4° C. The pellet is resuspended in the same buffer and centrifuged at 50000 g for approximately 10 minutes at approximately 4° C. and the cell membranes in the pellet obtained are stored at −80° C.

The competitive inhibition experiments of the bond with [$^{125}$I-Tyr$^{11}$]SRIF-14 are carried out in duplicate in 96-well polypropylene plates. The cell membranes (10 μg protein/well) are incubated with [$^{125}$I-Tyr$^{11}$]SRIF-14 (0.05 nM) for approximately 60 min. at approximately 37° C. in a HEPES 50 mM buffer (pH 7.4) containing BSA 0.2%, $MgCl_2$ 5 mM, Trasylol 200 KIU/ml, bacitricin 0.02 mg/ml, phenylmethylsulphonyl fluoride 0.02 mg/ml.

The bound [$^{125}$I-Tyr$^{11}$]SRIF-14 is separated from the free [125I-Tyr$^{11}$]SRIF-14 by immediate filtration through GF/C glass fibre filter plates (Unifilter, Packard) pre-impregnated with 0.1% of polyethylenimine (P.E.I.), using a Filtermate 196 (Packard). The filters are washed with 50 mM HEPES buffer at approximately 0–4° C. for approximately 4 seconds and their radioactivity is determined using a counter (Packard Top Count).

The specific bond is obtained by subtracting the non-specific bond (determined in the presence of 0.1 μM of SRIF-14) from the total bond. The data relative to the bond are analyzed by computer-aided non-linear regression analysis (MDL) and the values of the inhibition constants (Ki) are determined.

Determination of the agonist or antagonist character of a compound of the present invention is carried out using the test described below.

Functional test: Inhibition of production of intracellular cAMP:

CHO-K1 cells expressing the sub-types of human somatostatin receptors (SRIF-14) are cultured in 24-well plates in an RPMI 1640 medium with 10% of foetal calf serum and 0.4 mg/ml of geneticin. The medium is changed the day preceding the experiment.

The cells at a rate of $10^5$ cells/well are washed twice with 0.5 ml of new RPMI medium comprising 0.2% BSA completed by 0.5 mM of 3-isobutyl-1-methylxanthine (IBMX) and incubated for approximately 5 min at approximately 37° C.

The production of cyclic AMP is stimulated by the addition of 1 mM of forskolin (FSK) for 15–30 minutes at approximately 37° C.

The inhibitor effect of the somatostatin of an agonist compound is measured by the simultaneous addition of FSK (1 μM), SRIF-14 ($10^{-12}$ M to $10^{-6}$ M) and of the compound to be tested ($10^{-10}$ M to $10^{-5}$ M).

The antagonist effect of a compound is measured by the simultaneous addition of FSK (1 μM), SRIF-14 (1 to 10 nM) and of the compound to be tested ($10^{-10}$ M to $10^{-5}$ M).

The reaction medium is eliminated and 200 ml of 0.1 N HCl are added. The quantity of cAMP is measured by a radioimmunological test (FlashPlate SMP001A kit, New England Nuclear).

Results:

The tests carried out according to the protocols described above have demonstrated that the products of general formula (I) defined in the present Application have a good affinity for at least one of the sub-types of somatostatin receptors, the inhibition constant $K_i$ being lower than micromolar for certain exemplified compounds, and in particular for the products shown in the table below.

| Formula of compound | $K_i$ (nM) |
|---|---|
| 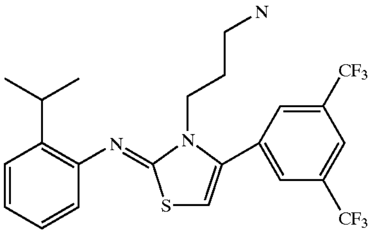 | <200 |
| 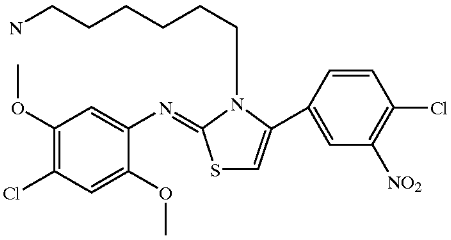 | <200 |
| 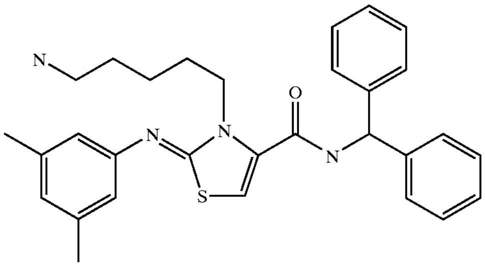 | <200 |
| 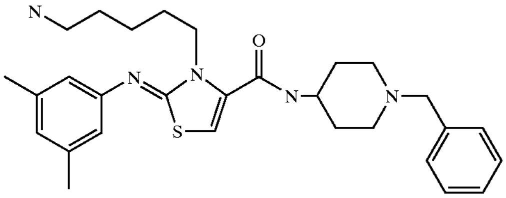 | <200 |

-continued

| Formula of compound | $K_i$ (nM) |
|---|---|
| 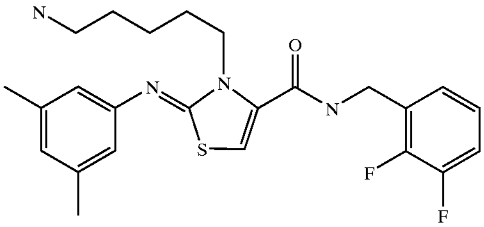 | <200 |
| 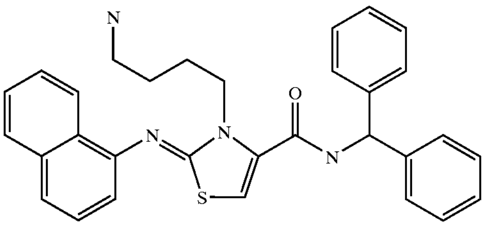 | <200 |
| 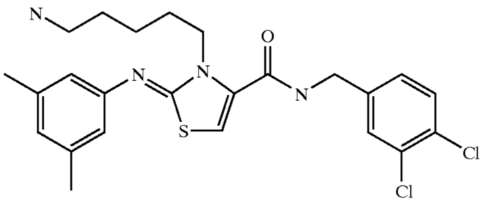 | <200 |
| 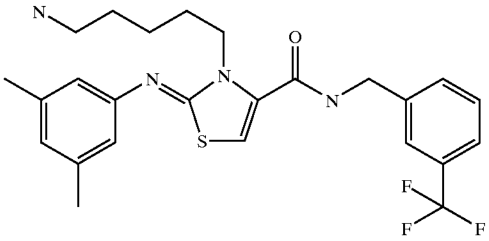 | <200 |
| 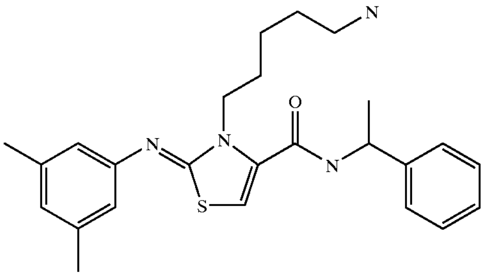 | <200 |
| 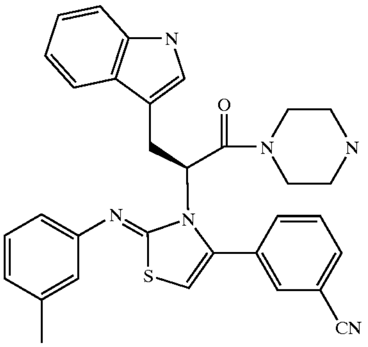 | <200 |

What is claimed is:

1. A compound of the formula (I)

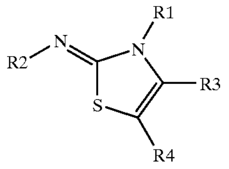

(I)

in racemic, enantiomeric form or any combination of these forms, in which:

R1 is selected from the group consisting of an amino (C2-C7)alkyl, aminoalkylarylalkyll, aminoalkylcycloalkylalkyl, (C1-C-15)alkyl, (C3–C7) cycloalkyl, (C1–C6)alkyl(C3–C6)cycloalkyl, (C3–C6) cycalkylalkyl, R2 represents an optionally substituted carbocyclic aryl consisting of a system of rings at least one of which is aromatic or R2 represents one of the radicals represented below:

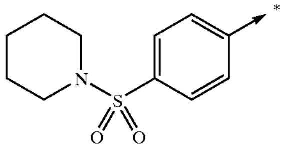

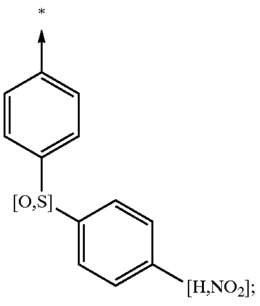

R3 represents a linear or branched alkyl radical containing 1 to 6 carbon atoms or R3 represents an optionally substituted carbocyclic aryl radical, said carbocyclic aryl radical consisting of a system of rings at least one of which is aromatic, or R3 is

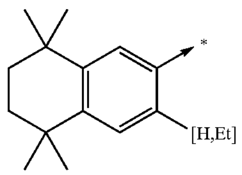

R4 is H or alkyl of 1 to 6 carbon atoms, i)for R2, when the group is substituted, it is substituted 1 to 5 times (apart from the bond which connects it to the rest of the molecule) by at least one member of the group consisting of halogen, alkyl of 1 to 6 atoms, linear or branched alkoxy containing 1 to 6 carbon atoms, linear or branched alkythio of 1 to 6 carbon atoms, haloalkyl of 1 to 6 carbon atoms alkenyl, haloalkoxy of 1 to 6 carbon atoms, nitro, cyano, azido, $So_2N$, mono- or di-alkylamino the alkyl of which have 1 to 6 carbon atoms, aminoalkyl alkyl of which has 1 to 6 carbon atoms, aralkoxy of which the araloxy has 1 to 6 carbon atoms, or aryl, which two substituents can, if appropriate, be connected together and form a ring, ii) for R3, when aryl group(s) (originating from an aryl or aralkyl) is the carbocyclic aryl or aralkyl radicals have 1 to 5 substituents selected from the group consisting of a halogen, alkyl of 1 to 6 carbon atoms, hydroxy, alkoxy of 1 to 6 carbon atoms, haloalkyl of 1 to 6 carbon atoms, haloalkyl of 1 to 6 atoms, haloalkoxy of 1 to 6 carbon atoms, nitro, cyano, azido, mono or di-alkylamino the alkyls have 1 to 6 carbon atoms, pyrrolidinyl, morpholinyl, aralkoxy the alkoxy has 1 to 6 carbon atoms, or aryl, which two substituents can, if appropriate, be connected together and form a ring, or salt of a compound of formula (I).

2. Compound according to claim 1, characterized in that:

R1 is of one of the following radicals:

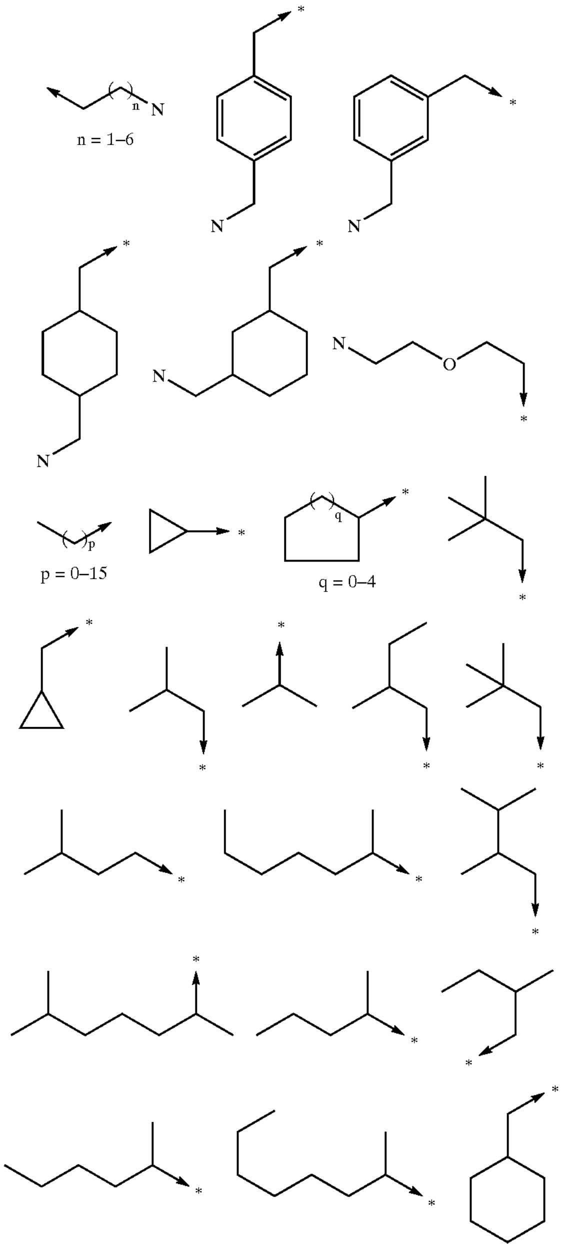

-continued
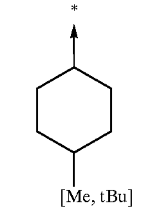
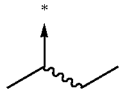
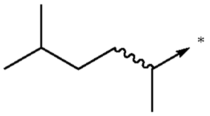
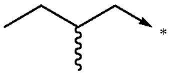
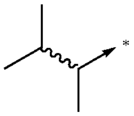
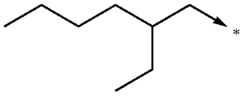
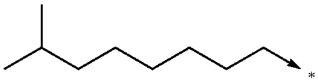
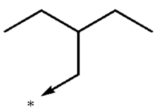
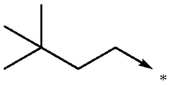
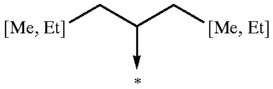
R2 represents one of the following radicals:
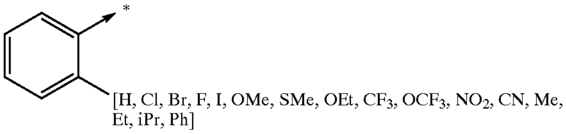
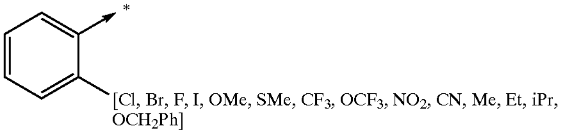
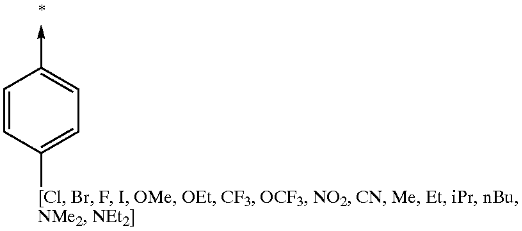
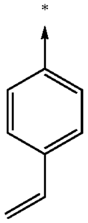
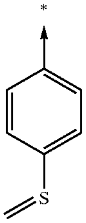
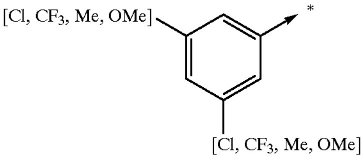
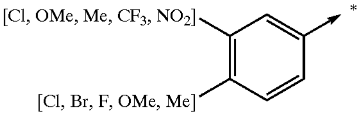
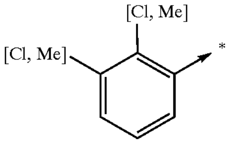
-continued
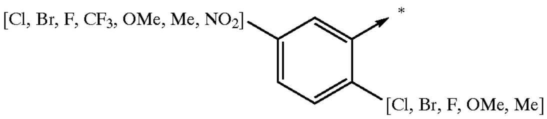
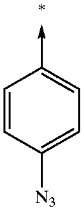
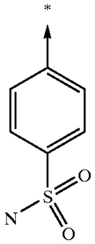
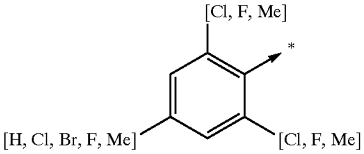
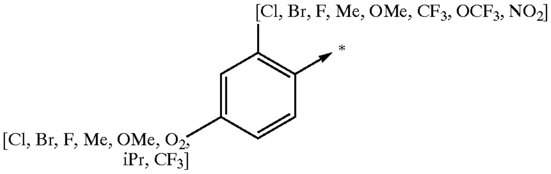
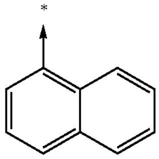
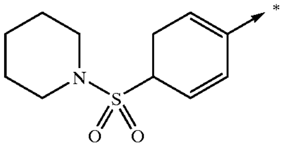
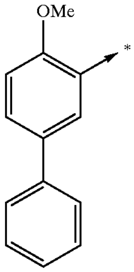
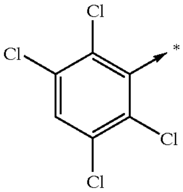
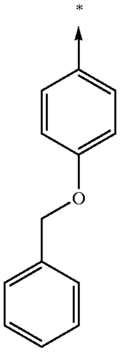
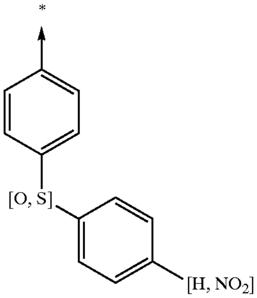
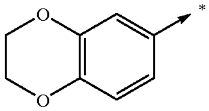
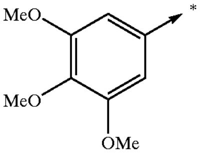

-continued
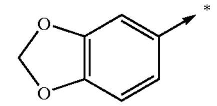
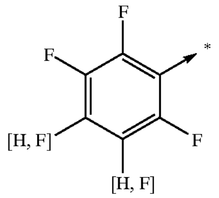
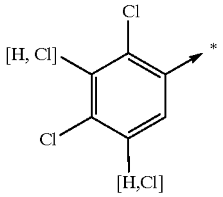
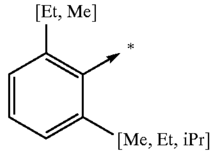
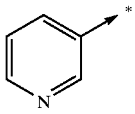
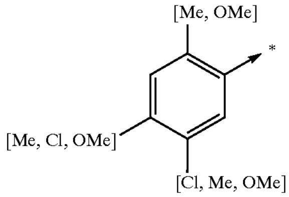
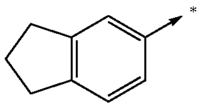
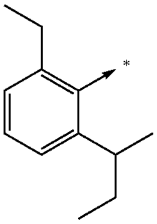
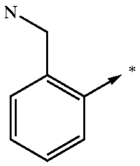
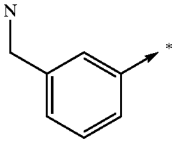
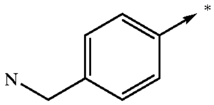
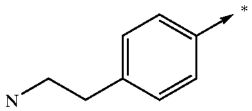
R3 represents one of the following radicals
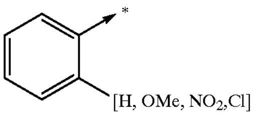
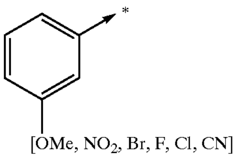
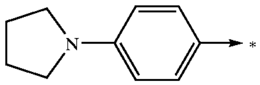
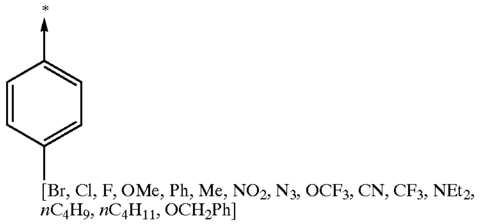
-continued
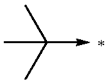
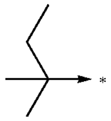
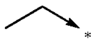
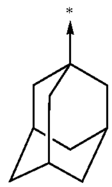
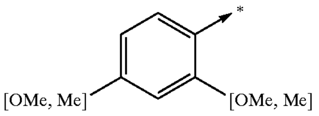
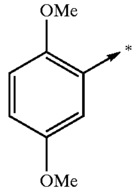
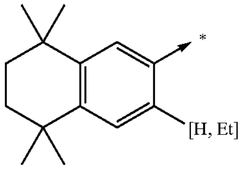
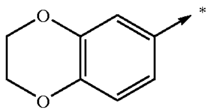
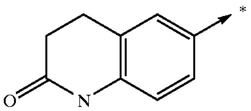
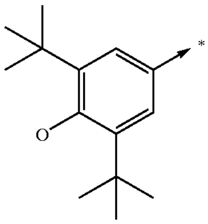
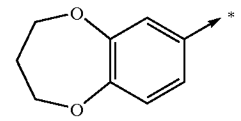
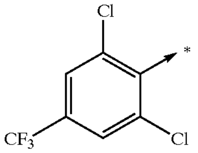
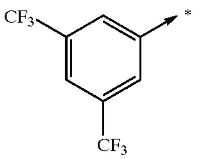
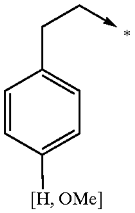
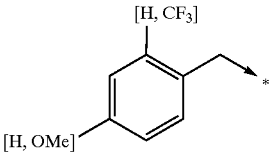
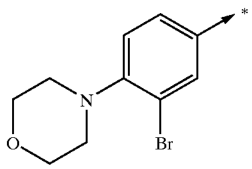
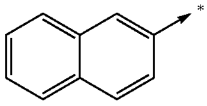
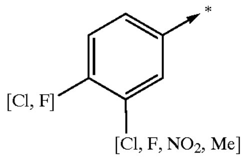
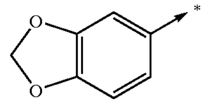
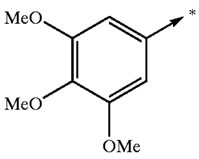

-continued

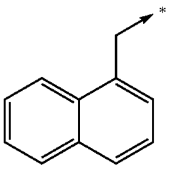
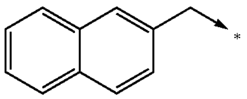
;

R4 represents H, or a linear or branched alkyl radical containing 1 to 6 carbons atoms.

3. A compound of claim 1 having the formula (II)

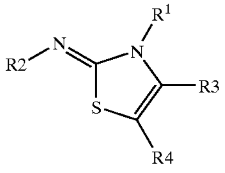

in which:

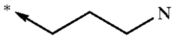 or 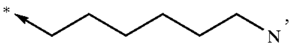,

R2 is

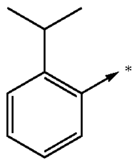 or 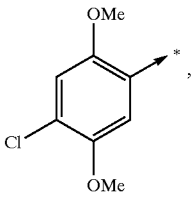,

R3 is

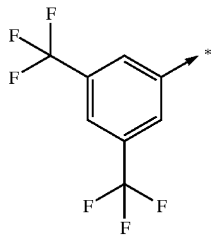 or 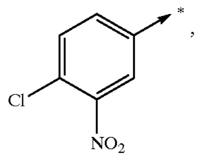, and R4 is H.

4. Process for the preparation of a compound of general formula (I)a (I)a

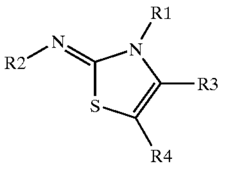

R1 represents a $-CH_2-Al-NH_2$ radical, in which Al represents a $-(CH_2)_n-$, aralkylene or cycloalkylalkylene radical, n and p represent integers from 1 to 6;

R2 and $R_4$ represent the same radicals as in general formula (I) as defined in claim 1;

and R3 represents the same radicals as in general formula (I) as defined in claim 1, said process being characterized in that it comprises the following successive stages:

1) treatment, in an aprotic solvent such as dichloromethane or dimethylformamide, of a p-nitrophenylcarbonate Wang resin with a large excess of $R1-NH_2$ symmetrical diamine;

2) treatment, in an aprotic solvent such as dichloromethane or dimethylformamide, of the resin isolated after stage 1) with an aromatic isothioncyanate of formula R2—N=C=S in which the R2 radical has the same meaning as in general formula (I)a;

3) treatment in an aprotic solvent such as dioxane or dimethylformamide, of the resin obtained in stage 2) with the compound of general formula (III)

(III)

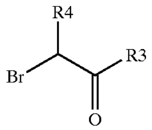

in which the R3 and R4 radicals are identical to those which have been defined in general formula (I)a:

4) cleavage of the resin under acid conditions;

5) treatment under basic conditions of the product obtained after stage 4).

5. Process for the preparation of a compound of general formula (I)b (I)b

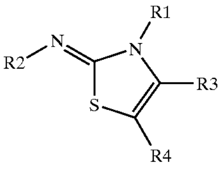

in which:

R1 represents the same radicals as in general formula (I) as defined in claim 1, with the exception of the $-CH_2-Al-NH_2$ type radicals, in which Al represents a $-(CH_2)_n-$, aralkylene or cycloalkylalkylene radical, n and p representing integers from 1 to 6, R2 represents an aminoalkylphenyl radical;

R3 represents the same radicals as in general formula (I) as defined in claim 1, and R4 represents the same radicals as in general formula (I) as defined in claim 1;

said process being characterized in that it comprises the following successive stages:

1) treatment, in an aprotic solvent such as dichloromethane or dimethylformamide, of a p-nitrophenylcarbonate Wang resin with an excess of aminoalkylaniline of formula $R2-NH_2$ in which the R2 radical has the same meaning as in general formula (I)b;

2) treatment, in an aprotic solvent such as dichloromethane or dimethylformamide, if the resin isolated after stage 1) with an isothiocyanate of formula R1—N=C=S in which the R1 radical has the same meaning as in general formula (I)b;

3) treatment, in an aprotic solvent such as dioxane or dimethylformamide, of the resin obtained in stage 2) with the compound of general formula (III)

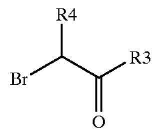

(III)

in which the R3 and R4 radical are identical to those which have been defined in general formula (I)b;

4) cleavage of the resin under acid conditions;

6) treatment under basic conditions of the product obtained after stage 4.

6. A composition for treating pathological disorders are selected from the group consisting of acromegalia, hypophyseal adenomas, gastrointestinal bleeding and endocrinic gastroenteropancreatic tumors caused by somatostatin receptors comprising an amount of a compound of claim 1 sufficient to inactivate somatostatin receptors and a pharmaceutical carrier.

7. A method of treating pathological disorders are selected from the group consisting of acromegalia, hypophyseal adenomas, gastrointestinal bleeding and endocrinic gastroenteropancreatic tumors caused by somatostatin receptors in warm-blooded animals comprising administering to warm-blooded animals in need thereof an amount of a compound of claim 6 sufficient to inactivate somatostating receptors.

* * * * *